(12) United States Patent  
Ruxer et al.

(10) Patent No.: US 8,309,721 B2
(45) Date of Patent: Nov. 13, 2012

(54) HSP90 INHIBITORY CARBAZOLE DERIVATIVES, COMPOSITIONS CONTAINING SAME AND USE THEREOF

(75) Inventors: Jean-Marie Ruxer, Paris (FR); Victor Certal, Paris (FR); Marcel Alasia, Paris (FR); Luc Bertin, Paris (FR); Herve Minoux, Paris (FR); Patrick Mailliet, Paris (FR); Frank Halley, Paris (FR); Maria Mendez-Perez, Frankfurt (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/881,414

(22) Filed: Sep. 14, 2010

(65) Prior Publication Data
US 2011/0166169 A1 Jul. 7, 2011

Related U.S. Application Data

(63) Continuation of application No. PCT/FR2009/000267, filed on Mar. 13, 2009.

(30) Foreign Application Priority Data

Mar. 14, 2008 (FR) ...................................... 08 01394

(51) Int. Cl.
C07D 401/10 (2006.01)
C07D 401/14 (2006.01)
C07D 403/10 (2006.01)
C07D 413/14 (2006.01)
C07D 471/04 (2006.01)

(52) U.S. Cl. ..... 544/331; 546/118; 546/173; 546/273.4; 546/276.7; 548/241; 548/305.1

(58) Field of Classification Search ........................ None
See application file for complete search history.

(56) References Cited

U.S. PATENT DOCUMENTS
2008/0042837 A1 2/2008 Burke

FOREIGN PATENT DOCUMENTS
WO WO02/36597 A1 5/2002
WO WO2006/055760 A1 5/2006
WO WO2007/035620 A2 3/2007

OTHER PUBLICATIONS

O'Boyle et al., Lead identification of b-lactam and related imine inhibitors of the molecular chaperone heat shock protein 90, 19 Bioorg. Med. Chem. 6055-6068 (2011).*
International Search Report dated Oct. 19, 2009 issued in PCT/FR2009/000267.

* cited by examiner

*Primary Examiner* — Janet Andres
*Assistant Examiner* — Timothy R Rozof
(74) *Attorney, Agent, or Firm* — Scully, Scott, Murphy & Presser, P.C.

(57) ABSTRACT

The invention relates to the novel substances in Formula (I): wherein Het is a heterocycle optionally substituted by one or a plurality of radicals R1 or R'1; R is selected from the group comprising Formula (A'), (B), (C), (D), or (E), with R1 and/or R'1 selected from H, halogen, CF3, nitro, cyano, alkyl, hydroxyl, mercapto, amino, alkylamino, dialkylamino, alkoxy, phenylalcoxy, alkylhio, or carboxy that is free or esterified by an alkyl, carboxamide, CO—NH(alkyl), CON(alkyl)2, NH—CO-alkyl, sulfonamide, NH—S02-alkyl, S(0)2-NHalkyl, or S(02)-N(alkyl)2 radical; all these radicals are optionally substituted; W1, W2, and W3 independently are CH or N; X is 0, S, NR2, C(O), S(O), or S(0)2; Z is optionally substituted H, Hal, -0-R2 or —NH—R2 with R2 being H, alkyl, cycloalkyl, or heterocycloalkyl; and these substances are all isomeric forms and salts thereof, used as drugs.

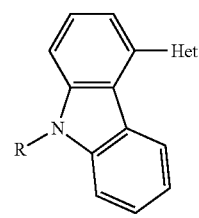

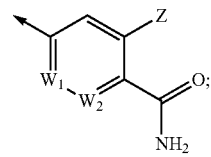

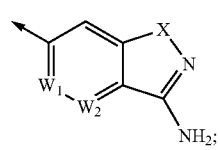

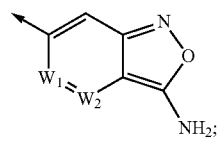

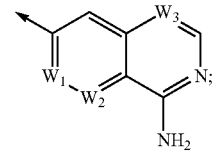

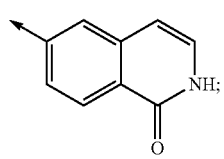

8 Claims, No Drawings

HSP90 INHIBITORY CARBAZOLE DERIVATIVES, COMPOSITIONS CONTAINING SAME AND USE THEREOF

The present invention relates to novel chemical compounds which are heterocyclic derivatives of carbazole, to the compositions which contain them, and to the use thereof as medicaments.

More particularly, according to a first aspect, the invention relates to novel heterocyclic derivatives of carbazole displaying anticancer activity, and in particular Hsp90 chaperone protein-inhibiting activity, and more particularly via inhibition of the ATPase-type catalytic activity of the Hsp90 chaperone protein.

Chaperone Proteins:

The molecular chaperones of the "Heat Shock Protein" (HSP) family, which are classified according to their molecular weight (Hsp27, Hsp70, Hsp90, etc.) are key elements in the equilibrium between the synthesis and the degradation of cellular proteins responsible for correct protein folding. They play a vital role in response to cellular stress. HSPs, and in particular Hsp90, are also involved in the regulation of various very important functions of the cell, via their association with various client proteins involved in cell proliferation or apoptosis (Jolly C. and Morimoto R. I., J. N. Cancer Inst. (2000), 92, 1564-72; Smith D. F. et al., Pharmacological Rev. (1998), 50, 493-513; Smith D. F., Molecular Chaperones in the Cell, 165-178, Oxford University Press 2001).

Hsp90 Chaperone and Hsp90 Inhibitors in Cancer Treatment:

The Hsp90 chaperone, which represents 1 to 2% of the protein content of the cell, has recently been demonstrated as a particularly promising target in anticancer therapy (cf. for review: Moloney A. and Workman P, Expert Opin. Biol. Ther. (2002), 2(1), 3-24; Chiosis et al, Drug Discovery Today (2004), 9, 881-888). This interest relates in particular to the cytoplasmic interactions of Hsp90 with the main client proteins of Hsp90, which proteins are involved in the six mechanisms of tumour progression, as defined by Hanahan D. and Weinberg R. A. (Cell (2002), 100, 57-70), namely:

an ability to proliferate in the absence of growth factors: EGFR-R/HER2, Src, Akt, Raf, MEK, Bcr-Abl, Flt-3, etc.,
an ability to evade apoptosis: mutated form of p53, Akt, survivin, etc.,
an insensitivity to signals to halt proliferation: Cdk4, Plk, Wee1, etc.,
an ability to activate angiogenesis: VEGF-R, FAK, HIF-1, Akt, etc.,
an ability to proliferate without replicative limit: hTert, etc.,
an ability to invade new tissues and to metastasize: c-Met.

Among the other client proteins of Hsp90, steroid hormone receptors, such as the oestrogen receptor or the androgen receptor, are also of considerable interest in the context of anticancer therapies.

It has recently been shown that the alpha form of Hsp90 also has an extracellular role via its interaction with the MMP-2 metalloprotease, which is itself involved in tumour invasion (Eustace B. K. et al, Nature Cell Biology (2004), 6, 507-514).

Hsp90 is made up of two N- and C-terminal domains separated by a highly charged region. The dynamic interaction between these two domains, coordinated by the binding of nucleotides and of co-chaperones, determines the conformation of the chaperone and its state of activation. The association of the client proteins depends mainly on the nature of the co-chaperones Hsp70//Hsp40, Hop60, etc., and on the nature of the ADP or ATP nucleotide bound to the N-terminal domain of Hsp90. Thus, the hydrolysis of ATP to ADP and the ADP/ATP exchange factor control all of the chaperone "machinery", and it has been shown that it is sufficient to prevent the hydrolysis of ATP to ADP—ATPase activity of Hsp90—in order to release client proteins in the cytoplasm, which client proteins will then be degraded by the proteasome (Neckers L and Neckers K, Expert Opin. Emerging Drugs (2002), 7, 277-288; Neckers L, Current Medicinal Chemistry, (2003), 10, 733-739; Piper P. Current Opin. Invest. New Drugs (2001), 2, 1606-1610).

Role of Hsp90 and of Inhibitors Thereof in Pathologies Other than Cancer:

Various human pathologies are the consequence of incorrect folding of key proteins, resulting in particular in neurodegenerative diseases following the aggregation of certain proteins, such as in Alzheimer's disease and Huntington's disease or prion-related diseases (Tytell M. and Hooper P. L., Emerging Ther. Targets (2001), 5, 267-287). In these pathologies, approaches aimed at inhibiting Hsp90 for the purpose of activating the stress pathways (Hsp70, for example) could be beneficial (Nature Reviews Neuroscience 6: 11, 2005). Some examples are mentioned below:

i) Huntington's disease: This neurodegenerative disease is due to an extension of CAG triplets in exon 1 of the gene encoding the huntington protein. It has been shown that geldanamycin inhibits the aggregation of this protein due to the overexpression of the Hsp70 and Hsp40 chaperones (Human Molecular Genetics 10: 1307, 2001).

ii) Parkinson's disease: This disease is due to the progressive loss of dopaminergic neurons and is characterized by aggregation of the alpha-synuclein protein. It has been shown that geldanamycin is capable of protecting *drosophila* against the toxicity of alpha-synuclein on dopaminergic neurons.

iii) Focal cerebral ischaemia: It has been shown, in a rat animal model, that geldanamycin protects the brain against cerebral ischaemia, due to the effect of stimulation of the transcription of genes encoding the heat shock proteins by an Hsp90 inhibitor.

iv) Alzheimer's disease and multiple sclerosis: These diseases are due in part to the expression of pro-inflammatory cytokines and of the inducible form of NOS (Nitric Oxide Synthase) in the brain, and this harmful expression is suppressed by the response to stress. In particular, the Hsp90 inhibitors are capable of garnering this response to stress, and it has been shown, in vitro, that geldanamycin and 17-AAG exhibit anti-inflammatory activity in brain gliale cells (J. Neuroscience Res. 67: 461, 2002).

v) Amyotrophic lateral sclerosis: This neurodegenerative disease is due to the progressive loss of motor neurons. It has been shown that arimoclomol, an inducer of heat-shock proteins, delays the progression of the disease in an animal model (Nature Medicine 10: 402, 2004). Given that an Hsp90 inhibitor is also an inducer of heat-shock proteins (Mol. Cell. Biol. 19: 8033, 1999; Mol. Cell. Biol. 18: 4949, 1998), it is probable that a beneficial effect could also be obtained in this pathology for inhibitors of this type.

Furthermore, an inhibitor of the Hsp90 protein could potentially be of use in various diseases, other than cancer mentioned above, such as parasitic, viral or fungal diseases or neurodegenerative diseases, by virtue of a direct action on Hsp90 and specific client proteins. Some examples are given below:

vi) Malaria: the Hsp90 protein of *Plasmodium falciparum* exhibits 59% identity and 69% similarity with the human Hsp90 protein, and it has been shown that geldanamycin inhibits the growth of the parasite in vitro (Malaria Journal 2: 30, 2003; J. Biol. Chem. 278: 18336, 2003; J. Biol. Chem. 279: 46692, 2004).

vii) *Brugia* filariasis and Bancroft's filariasis: these lymphatic filarial parasites possess an Hsp90 protein which can potentially be inhibited with inhibitors of the human protein. In fact, it has been shown, for another similar parasite, *Brugia pahangi*, that the latter is sensitive to inhibition with geldanamycin. The *B. pahangi* and human sequences are 80% identical and 87% similar (Int. J. for Parasitology 35: 627, 2005).

viii) Toxoplasmosis: *Toxoplasma gondii*, the parasite responsible for toxoplasmosis, has an Hsp90 chaperone protein for which induction has been shown during tachyzoite-bradyzoite conversion, corresponding to passage from chronic infection to active toxoplasmosis. Furthermore, geldanamycin blocks this tachyzoite-bradyzoite conversion in vitro (J. Mol. Biol. 350: 723, 2005).

ix) Treatment-resistant mycoses: It is possible that the Hsp90 protein potentiates the evolution of drug resistance by allowing new mutations to develop. Consequently, an Hsp90 inhibitor, alone or in combination with another antifungal treatment, could prove to be of use in the treatment of certain resistant strains (Science 309: 2185, 2005). Furthermore, the anti-Hsp90 antibody developed by Neu Tec Pharma demonstrates an activity against *C. albicans*, which is sensitive and resistant to fluconazole, *C. krusei*, *C. tropicalis*, *C. glabrata*, *C. lusitaniae* and *C. parapsilosis* in vivo (Current Molecular Medicine 5: 403, 2005).

x) Hepatitis B: Hsp90 is one of the host proteins which interacts with the reverse transcriptase of the hepatitis B virus during the replication cycle of the virus. It has been shown that geldanamycin inhibits replication of the viral DNA and encapsulation of the viral RNA (Proc. Natl. Acad. Sci. USA 93: 1060, 1996).

xi) Hepatitis C: The human Hsp90 protein participates in the step consisting of cleavage between the NS2 and NS3 proteins by the viral protease. Geldanamycin and radicicol are capable of inhibiting this NS2/3 cleavage in vitro (Proc. Natl. Acad. Sci. USA 98: 13931, 2001).

xii) The Herpes virus: Geldanamycin has demonstrated inhibitory activities on HSV-1 virus replication in vitro, with a good therapeutic index (Antimicrobial Agents and Chemotherapy 48: 867, 2004). The authors have also found geldanamycin activity on the other viruses HSV-2, VSV, Cox B3, HIV-1 and the SARS coronavirus (data not shown).

xiii) Dengue (or tropical flu): It has been shown that the human Hsp90 protein participates in the virus entry step, by forming a complex also containing Hsp70 which serves as a receptor for the virus; an anti-Hsp90 antibody decreases the infectious capacity of the virus in vitro (J. of Virology 79: 4557, 2005)

xiv) Spinal and bulbar muscular atrophy (SBMA): A hereditary neurodegenerative disease characterized by an extension of CAG triplets in the androgen receptor gene. It has been shown that 17-AAG, a geldanamycin derivative, exhibits activity in vivo on transgenic animals used as experimental models for this disease (Nature Medicine 11: 1088, 2005).

Hsp90 Inhibitors:

The first known Hsp90 inhibitors are compounds of the amsamycin family, in particular geldanamycin (1) and herbimycin A. X-ray studies have shown that geldanamycin binds to the ATP site of the N-terminal domain of Hsp90, where it inhibits the ATPase activity of the chaperone (Prodromou C. et al, Cell (1997), 90, 65-75).

Currently, the NIH and Kosan BioSciences are carrying out the clinical development of 17-AAG (2), which is an Hsp90 inhibitor derived from geldanamycin (1), which blocks the ATPase activity of Hsp90 by binding to the N-terminal ATP recognition site. The results of phase I clinical trials for 17-AAG (1) have now led to phase II trials being started, but have also directed research towards derivatives which are more soluble, such as analogue 3 (17-DMAG from Kosan BioSciences), which carries a dimethyl amino chain in place of the methoxy residue, and towards optimized formulations of 17AAG (CNF1010 from Conforma Therapeutics):

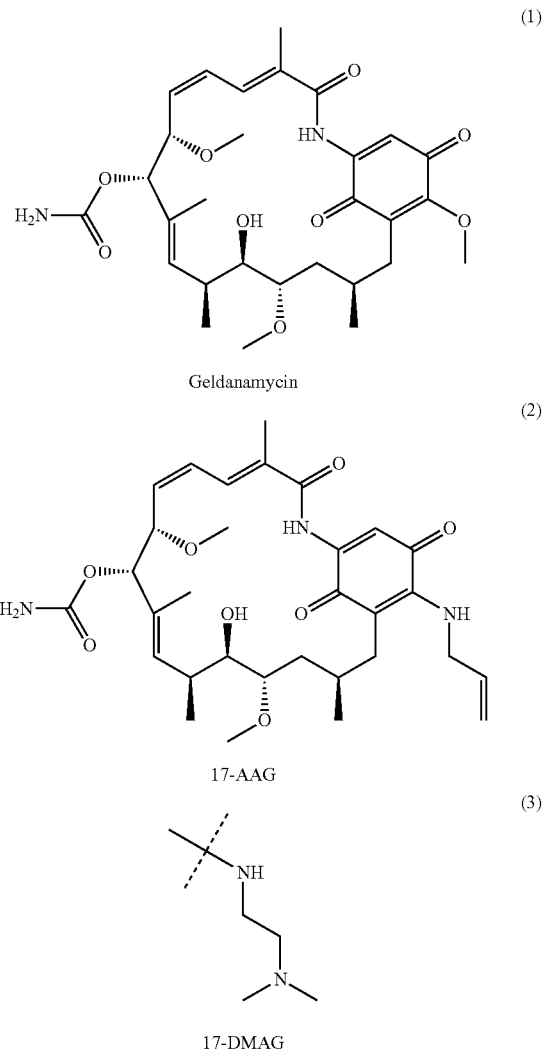

The reduced analogue of 17-AAG (WO 2005/063714/US 2006/019941) has also since relatively recently been undergoing phase I clinical studies by the company Infinity Pharmaceuticals. Novel geldanamycin derivatives or ansamycin derivatives have recently been described (WO2006/016773/ U.S. Pat. No. 6,855,705/US 2005/026894/WO2006/050477/

US2006/205705/WO2007/001049/WO2007/064926/
WO2007/074347/WO2007/098229/WO2007/128827/
WO2007/128829).

Radicicol (4) is also an Hsp90 inhibitor of natural origin (Roe S. M. et al, J. Med. Chem. (1999), 42, 260-66). However, although the latter is by far the best in vitro inhibitor of Hsp90, its metabolic instability with respect to sulphur-containing nucleophiles makes it difficult to use in vivo. Oxime derivatives that are much more stable, such as KF 55823 (5) or KF 25706, have been developed by the company Kyowa Hakko Kogyo (Soga et al, Cancer Research (1999), 59, 2931-2938).

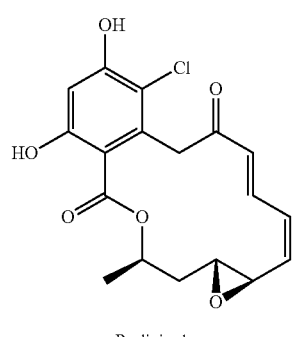

Radicicol (4)

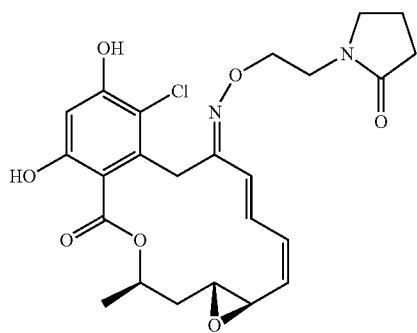

KF 55823 (5)

Structures of natural origin related to radicicol have also recently been described, such as zearalenone (6) by the company Conforma Therapeutics (WO 2003/041643) or compounds (7-9).

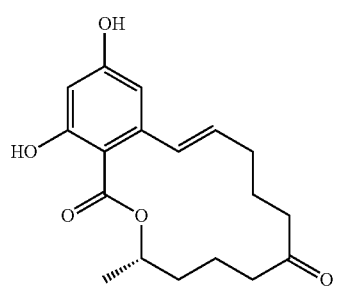

Zearalenone (6)

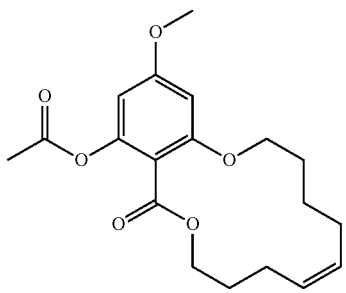

(7)

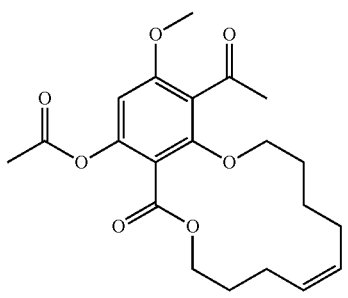

(8)

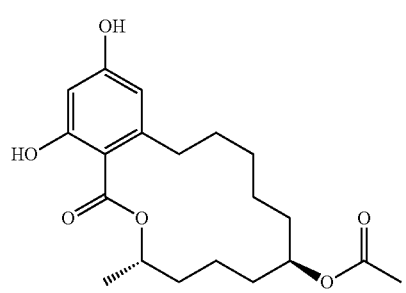

Zearalanol acetate (9)

Patent application US 2006/089495 describes mixed compounds comprising a quinone ring, such as the amsamycin derivatives, and a resorcinol ring, such as the radicicol analogues, as Hsp90 inhibitors.

An Hsp90 inhibitor of natural origin, novobiocin (10), binds to a different ATP site located in the C-terminal domain of the protein (Itoh H. et al, Biochem J. (1999), 343, 697-703). Simplified analogues of novobiocin have recently been identified as more powerful inhibitors of Hsp90 than novobiocin itself (J. Amer. Chem. Soc. (2005), 127(37), 12778-12779).

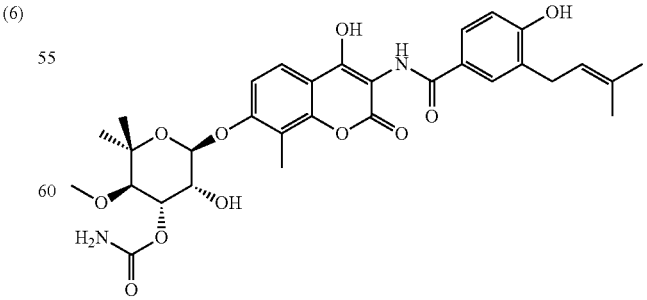

(10)

Patent applications WO2006/050501 and US2007/270452 claim novobiocin analogues as Hsp90 inhibitors.

Patent application WO2007/117466 claims derivatives of celastrol and of gedunine as Hsp90 inhibitors.

A depsipeptide, called pipalamycin or ICI101, has also been described as a non-competitive inhibitor of the ATP site of Hsp90 (J. Pharmacol. Exp. Ther. (2004), 310, 1288-1295).

Sherperdine, a KHSSGCAFL nonapeptide, mimics a part of the K79-K90 sequence (KHSSGCAFLSVK) of survivin and blocks the interaction of proteins of the IAP family with Hsp90 in vitro (WO 2006/014744).

Small peptides, comprising a sequence of otoferlin-type (YSLPGYMVKKLLGA), have recently been described as Hsp90 inhibitors (WO 2005/072766).

Purines, such as the compounds PU3 (11) (Chiosis et al, Chem. Biol. (2001), 8, 289-299) and PU24FCI (12) (Chiosis et al, Curr. Canc. Drug Targets (2003), 3, 371-376; WO 2002/036075) have also been described as Hsp90 inhibitors:

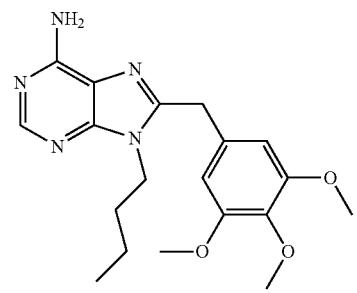

(11)

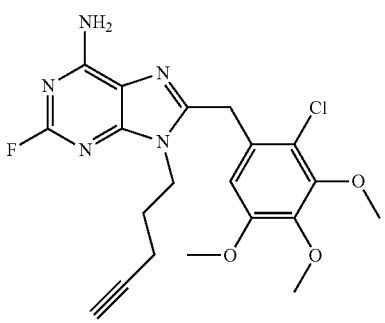

(12)

A purine derivative, CNF2024 (13), has recently been introduced clinically by the company Conforma therapeutics, in collaboration with the Sloan Kettering Memorial Institute for Cancer Research (WO 2006/084030).

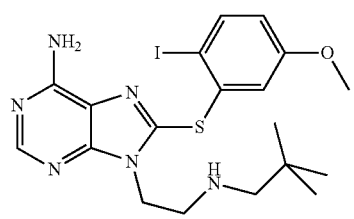

(13)

Patent application FR 2880540 (Aventis) claims another family of Hsp90-inhibiting purines.

Patent application WO 2004/072080 (Cellular Genomics) claims a family of 8-heteroaryl-6-phenylimidazo[1,2-a]pyrazines as modulators of hsp90 activity.

Patent application WO 2004/028434 (Conforma Therapeutics) claims aminopurines, aminopyrrolopyrimidines, aminopyrazolopyrimidines and aminotriazolopyrimidines as Hsp90 inhibitors.

Patent application WO 2004/050087 (Ribotarget/Vernalis) claims a family of pyrazoles that can be used for treating pathologies related to the inhibition of heat-shock proteins such as the Hsp90 chaperone.

Patent application WO 2004/056782 (Vernalis) claims a novel family of pyrazoles that can be used for treating pathologies related to the inhibition of heat-shock proteins such as the Hsp90 chaperone.

Patent application WO 2004/07051 (Vernalis) claims aryl-isoxazole derivatives that can be used for treating pathologies related to the inhibition of heat-shock proteins such as the Hsp90 chaperone.

Patent application WO 2004/096212 (Vernalis) claims a third family of pyrazoles that can be used for treating pathologies related to the inhibition of heat-shock proteins such as the Hsp90 chaperone.

Patent application WO 2005/00300 (Vernalis) claims, more generally, 5-membered heterocycles, substituted with aryl radicals, that can be used for treating pathologies related to the inhibition of heat-shock proteins such as the Hsp90 chaperone.

Patent application JP 2005/225787 (Nippon Kayaku) claims another family of pyrazoles as Hsp90 inhibitors.

Patent application WO2005/00778 (Kyowa Hakko Kogyo) claims a family of benzophenone derivatives as Hsp90 inhibitors, that can be used for the treatment of tumours.

Patent application WO2005/06322 (Kyowa Hakko Kogyo) claims a family of resorcinol derivatives as Hsp90 inhibitors.

Patent application WO2005/051808 (Kyowa Hakko Kogyo) claims a family of resorcinylbenzoic acid derivatives as Hsp90 inhibitors.

Patent applications WO2005/021552, WO2005/0034950, WO2006/08503, WO2006/079789 and WO2006/090094 (Vernalis) claim families of pyrimidothiophenes or of pyridothiophenes, that can be used for treating pathologies related to the inhibition of heat-shock proteins such as the Hsp90 chaperone.

Application WO2006/018082 (Merck) claims another family of pyrazoles as Hsp90 inhibitors.

Application WO2006/010595 (Novartis) claims a family of indazoles as Hsp90 inhibitors.

Application WO2006/010594 (Novartis) claims a family of dihydrobenzimidazolones as Hsp90 inhibitors.

Patent application WO2006/055760 (Synta Pharma) claims a family of diaryltriazoles as Hsp90 inhibitors.

Patent application WO2006/087077 (Merck) claims a family of (s-triazol-3-yl)phenols as Hsp90 inhibitors.

Patent application FR2882361 (Aventis) claims a family of 3-aryl-1,2-benzisoxazoles as Hsp90 inhibitors.

Patent application WO2006/091963 (Serenex) claims families of tetrahydroindolones and of tetrahydroindazolones as Hsp90 inhibitors.

Patent application DE10200509440 (Merck) claims a family of thienopyridines as Hsp90 inhibitors.

Patent application WO2006/095783 (Nippon Kayaku) claims a family of triazoles as Hsp90 inhibitors.

Patent application WO2006/101052 (Nippon Kayaku) claims a family of acetylene derivatives as Hsp90 inhibitors.

Patent application WO2006/105372 (Conforma Therapeutics) claims a family of alkynyl pyrrolo[2,3-d]pyrimidines as Hsp90 inhibitors.

Patent application FR2884252 (Aventis) claims a family of isoindoles as Hsp90 inhibitors.

Patent application WO2006/1009075 (Astex Therapeutics) claims a family of benzamides as Hsp90 inhibitors.

Patent application WO2006/109085 (Astex Therapeutics) claims a family of hydroxybenzamides as Hsp90 inhibitors.

Patent application WO2006/113498 (Chiron) claims a family of 2-aminoquinazolin-5-ones as Hsp90 inhibitors.

Patent application JP200606755 (Nippon Kayaku) claims a family of pyrazoles as Hsp90 inhibitors.

Patent application WO2006/117669 (Pfizer) claims a family of hydroxyarylcarboxamides as Hsp90 inhibitors.

Patent applications WO2006/122631 and DE102006008890 (Merck GmbH) claim a family of amino-2-phenyl-4-quinazolines as Hsp90 inhibitors.

Patent application WO2006/123061 (Aventis) claims a family of azabenzimidazolylfluorene or benzimidazolylfluorene derivatives as Hsp90 inhibitors.

Patent application WO2006/123065 (Astex Therapeutics) claims a family of azinamines (amino-2-pyrimidines or triazines) as Hsp90 inhibitors.

Patent application WO2006/125531 (Merck GmbH) claims a family of thieno[2,3b]pyridines as Hsp90 inhibitors.

Patent applications WO2006/125813 and WO2006/125815 (Altana Pharma) claim a family of tetrahydropyridothiophenes as Hsp90 inhibitors.

Patent application WO2007/017069 (Merck GmbH) claims a family of adenine derivatives as Hsp90 inhibitors.

Patent applications WO2007/021877 and WO2007/01966 (Synta Pharma) claim, respectively, families of arylpyrazoles and of arylimidazoles as Hsp90 inhibitors.

Patent application WO2007/022042 (Novartis) claims a family of pyrimidylaminobenzamides as Hsp90 inhibitors.

Patent application WO2007/034185 (Vernalis) claims a family of heteroarylpurines as Hsp90 inhibitors.

Patent application WO2007/041362 (Novartis) claims a family of 2-amino-7,8-dihydro-6H-pyrido[4,3-d]pyrimidin-5-ones as Hsp90 inhibitors.

Patent application WO2007/104944 (Vernalis) claims a family of pyrrolo[2,3b]pyridines as Hsp90 inhibitors.

Patent application US2007/105862 claims a family of azole derivatives as Hsp90 inhibitors.

Patent application WO2007/129062 (Astex Therapeutics) claims a family of diazoles (aryl pyrazoles) as Hsp90 inhibitors.

Patent application US2007/129334 (Conforma Therapeutics) claims a family of arylthiopurines as Hsp90 inhibitors, which are active orally.

Patent application WO2007/155809 (Synta Pharma) claims families of phenyltriazoles as Hsp90 inhibitors.

Patent application WO2007/092496 (Conforma Therapeutics) claims a family of 7,9-dihydropurin-8-ones as Hsp90 inhibitors.

Patent application WO2007/207984 (Serenex) claims a family of cyclohexylaminobenzene derivatives as Hsp90 inhibitors.

Patent applications DE10206023336 and DE10206023337 (Merck GmbH) claim, respectively, families of 1,5-diphenylpyrazoles and of 1,5-diphenyltriazoles as Hsp90 inhibitors.

Patent application WO2007/134298 (Myriad Genetics) claims a family of purinamines as Hsp90 inhibitors.

Patent application WO2007/138994 (Chugai) claims families of 2-aminopyrimidines or of 2-aminotriazines as Hsp90 inhibitors.

Patent applications WO2007/139951, WO2007/139952, WO2007/139960, WO2007/139967, WO2007/139968, WO2007/139955 and WO2007/140002 (Synta Pharma) claim families of triazoles as Hsp90 inhibitors and agents for treating non-Hodgkin's lymphomas.

The present invention relates to carbazole derivatives which are products of formula (I):

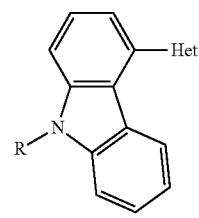

(I)

in which:

Het represents a monocyclic or bicyclic, aromatic or partially unsaturated heterocycle—of dihydro or tetrahydro type—, with from 5 to 11 ring members, containing from 1 to 4 heteroatoms chosen from N, O or S, optionally substituted with one or more radicals R1 or R'1, which may be identical or different, as described below, R is chosen from the group constituted of

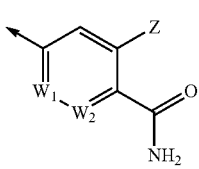

(A)

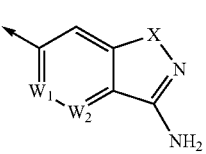

(B)

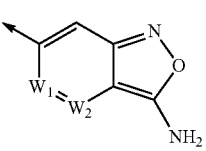

(C)

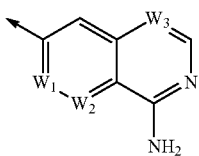

(D)

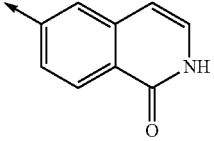

(E)

with R1 and/or R'1, which may be identical or different, being in the group constituted of H, halogen, $CF_3$, nitro, cyano, alkyl, hydroxyl, mercapto, amino, alkylamino, dialkylamino, alkoxy, phenylalkoxy, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, $S(O)_2$—NHalkyl and $S(O_2)$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

W1, W2 and W3 independently represent CH or N;
X represents an oxygen or sulphur atom, or an NR2, C(O), S(O) or S(O)$_2$ radical;
Z represents a hydrogen atom or a halogen atom or an —O—R2 radical or an —NH—R2 radical in which:
R2 represents a hydrogen atom or a C$_1$-C$_6$ alkyl radical, or a C$_3$-C$_8$ cycloalkyl radical or a C$_3$-C$_{10}$ heterocycloalkyl radical, which is monocyclic or bicyclic; these alkyl, cycloalkyl and heterocycloalkyl radicals being optionally substituted with one or more radicals, which may be identical or different, chosen from the radicals:

—O—PO$_3$H$_2$, O—PO$_3$Na$_2$, —O—SO$_3$H$_2$, —O—SO$_3$Na$_2$, —O—CH$_2$—PO$_3$H$_2$, —O—CH$_2$—PO$_3$Na$_2$, O—CO-alanine, O—CO-serine, O—CO-lysine, O—CO-arginine, O—CO-glycine-lysine, —O—CO-alanine-lysine;

halogen, hydroxyl; mercapto; amino; carboxamide (CONH$_2$); carboxyl;

heterocycloalkyl, such as aziridino; azetidino; oxetano; tetrahydrofurano; piperidino; tetrahydropyrano; piperazino; alkylpiperazino; pyrrolidino; morpholino; homopiperidino; homopiperazino; quinuclidino; cycloalkyl, heteroaryl; carboxy esterified with an alkyl radical; CO—NH(alkyl); —O—CO-alkyl, —NH—CO-alkyl; alkyl; alkoxy; hydroxyalkoxy; alkylthio; alkylamino; dialkylamino; in all these radicals, the alkyl, alkoxy and alkylthio radicals being themselves optionally substituted with a hydroxyl, mercapto, amino, alkylamino, dialkylamino, CO$_2$alkyl, NHCO$_2$alkyl; azetidino, oxetano, pyrrolidino, tetrahydrofurano, piperidino, tetrahydropyrano, piperazino, morpholino, homopiperidino, homopiperazino or quinuclidino radical; in all these radicals, all the cyclic, cycloalkyl, heterocycloalkyl and heteroaryl radicals being themselves optionally substituted with one or more radicals, which may be identical or different, chosen from hydroxyl, alkyl, alkoxy, CH$_2$OH; amino, alkylamino, dialkylamino, CO$_2$alkyl or NHCO$_2$alkyl radicals;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

The present invention thus relates in particular to the products of formula (I) as defined above or below in which:
Het is chosen from the group constituted of:

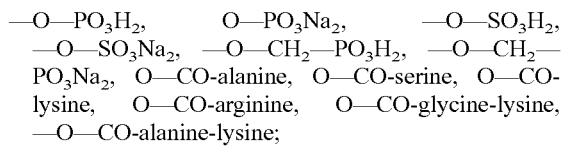

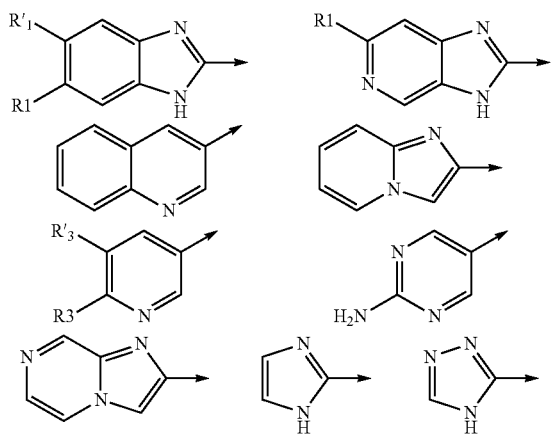

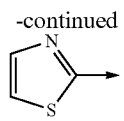

in which R'3 and R3 are such that one represents a hydrogen atom and the other is chosen from the values of R1 and R'1;
R1 and/or R'1, which may be identical or different, are from the group constituted of H, halogen, CF$_3$, nitro, cyano, alkyl, hydroxyl, mercapto, amino, alkylamino, dialkylamino, alkoxy, phenylalkoxy, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NHalkyl and S(O$_2$)—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;
the substituent R of said products of formula (I) being chosen from the values defined above or hereinafter,
said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

The present invention thus relates in particular to the products of formula (I) as defined above or below, in which:
Het is chosen from the group constituted of:

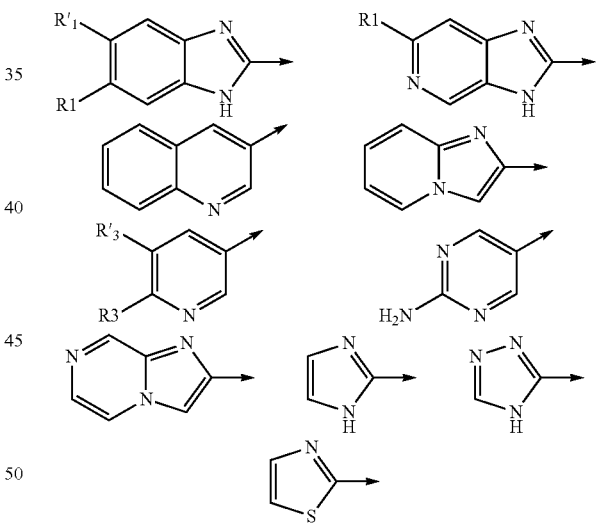

in which R'3 and R3 are such that one represents a hydrogen atom and the other is chosen from the radicals —NH$_2$; —CN, —CH$_2$—OH, —CF$_3$, —OH, —O—CH$_2$-phenyl, —O—CH$_3$, —CO—NH$_2$;
R1 and/or R'1 is from the group constituted of H, halogen, CF$_3$, nitro, cyano, alkyl, hydroxyl, mercapto, amino, alkylamino, dialkylamino, alkoxy, alkylthio, carboxyl in free form or esterified with an alkyl radical, carboxamide, CO—NH(alkyl) and CON(alkyl)$_2$, NH—CO-alkyl, sulphonamide, NH—SO$_2$-alkyl, S(O)$_2$—NH(alkyl) and S(O)$_2$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

the substituent R of said products of formula (I) being chosen from the values defined above or hereinafter,
said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

The present invention thus relates in particular to the products of formula (I) as defined above or below, in which:
Het is chosen from the group constituted of:

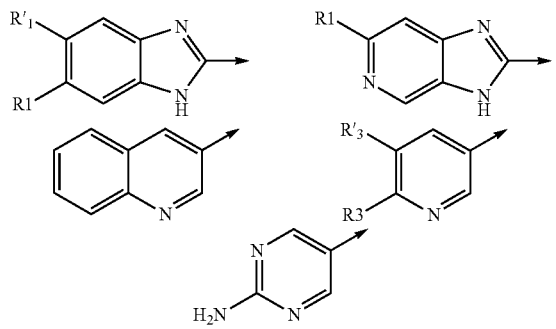

in which R'3 and R3 are such that one represents a hydrogen atom and the other is chosen from the radicals —NH2; —CN, —CH$_2$—OH, —CF$_3$, —OH, —O—CH$_2$-phenyl, —O—CH$_3$ and —CO—NH$_2$;
R is chosen from the group constituted of:

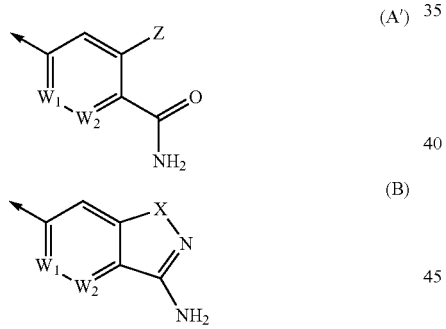

with R1 and/or R'1, which may be identical or different, being in the group constituted of H, halogen, CF$_3$, nitro, cyano, alkyl, hydroxyl, mercapto, amino, alkylamino, dialkylamino, alkoxy, —O—CH$_2$-phenyl, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NHalkyl and S(O$_2$)—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;
W1, W2 and W3 independently represent CH or N;
X represents an oxygen or sulphur atom, or an NR2, C(O), S(O) or S(O)$_2$ radical;
Z represents a hydrogen atom or a halogen atom or an —O—R$_2$ radical or a radical in which:
R2 represents a hydrogen atom or a C$_1$-C$_6$ alkyl radical, or a C$_3$-C$_8$ cycloalkyl radical or a C$_3$-C$_{10}$ heterocycloalkyl radical, which is monocyclic or bicyclic; these alkyl, cycloalkyl and heterocycloalkyl radicals being optionally substituted with one or more radicals, which may be identical or different, chosen from the radicals:
halogen, hydroxyl; mercapto; amino; carboxamide (CONH$_2$); carboxyl;
heterocycloalkyl such as piperidinyl or pyrrolidinyl; cycloalkyl; heteroaryl such as furanyl, pyridyl, pyrazolyl, oxazolyl or imidazolyl; carboxyl esterified with an alkyl radical; CO—NH(alkyl); —O—CO-alkyl, —NH—CO-alkyl; alkyl; alkoxy; hydroxyalkoxy; alkylthio; alkylamino; dialkylamino; in all these radicals, the alkyl, alkoxy and alkylthio radicals being themselves optionally substituted with a hydroxyl, mercapto, amino, alkylamino, dialkylamino, CO$_2$alkyl, NHCO$_2$alkyl; azetidino, oxetano, pyrrolidino, tetrahydrofurano, piperidino, tetrahydropyrano, piperazino, morpholino, homopiperidino, homopiperazino or quinuclidino radical; in all these radicals, all the cyclic, cycloalkyl, heterocycloalkyl and heteroaryl radicals being themselves optionally substituted with one or more radicals, which may be identical or different, chosen from hydroxyl, alkyl, alkoxy, CH$_2$OH; amino, alkylamino, dialkylamino, CO$_2$alkyl or NHCO$_2$alkyl radicals;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

The present invention relates to carbazole derivatives as defined above or hereinafter which are products of formula (I)

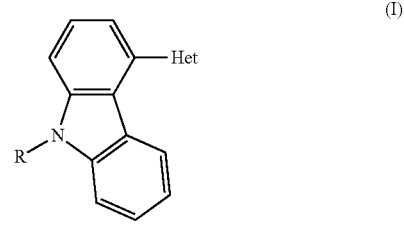

in which:
Het represents a monocyclic or bicyclic, aromatic or partially unsaturated heterocycle—of dihydro or tetrahydro type—, with from 5 to 11 ring members, containing from 1 to 4 heteroatoms chosen from N, O or S, optionally substituted with one or more radicals R1 or R'1, which may be identical or different, as described below,
R is chosen from the group constituted of:

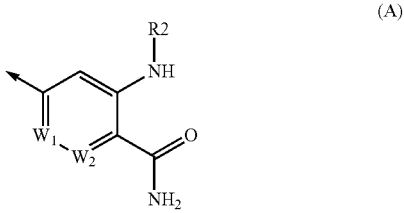

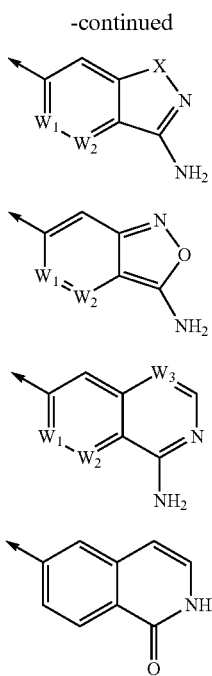

R1 and/or R'1 are in the group constituted of H, halogen, CF$_3$, nitro, cyano, alkyl, hydroxyl, mercapto, amino, alkylamino, dialkylamino, alkoxy, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NHalkyl and S(O$_2$)—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

W1, W2 and W3 independently represent CH or N;

X represents an oxygen or sulphur atom, or an NR2, C(O), S(O) or S(O)$_2$ radical;

R2 represents a hydrogen atom or a C$_1$-C$_6$ alkyl radical, or a C$_3$-C$_8$ cycloalkyl radical or a C$_3$-C$_{10}$ heterocycloalkyl radical, which is monocyclic or bicyclic, these alkyl, cycloalkyl and heterocycloalkyl radicals being optionally substituted with one or more radicals, which may be identical or different, chosen from the radicals:

hydroxyl; mercapto; amino; aziridino; azetidino; oxetano; tetrahydrofurano; piperidino; tetrahydropyrano; piperazino; alkylpiperazino; pyrrolidino; morpholino; homopiperidino; homopiperazino; quinuclidino; carboxamide (CONH$_2$); carboxyl;

carboxyl esterified with an alkyl radical; CO—NH(alkyl); —O—CO-alkyl; NH—CO-alkyl; alkoxy; hydroxyalkoxy; alkylthio; alkylamino; dialkylamino; all the latter alkyl, alkoxy and alkylthio radicals being themselves optionally substituted with a hydroxyl, mercapto, amino, alkylamino, dialkylamino, azetidino, oxetano, pyrrolidino, tetrahydrofurano, piperidino, tetrahydropyrano, piperazino, morpholino, homopiperidino, homopiperazino or quinuclidino radical;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

In the products of formula (I) and in the subsequent text, the terms indicated have the meanings which follow:

The term "halogen" denotes fluorine, chlorine, bromine or iodine atoms, and preferably fluorine, chlorine or bromine.

The term "alkyl radical" denotes a linear or branched radical containing at most 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl and also heptyl, octyl, nonyl, decyl, undecyl and dodecyl radicals, and also the linear or branched positional isomers thereof. Mention may more particularly be made of alkyl radicals having at most 6 carbon atoms, and in particular the following radicals: methyl, ethyl, propyl, isopropyl, n-butyl, isobutyl, tert-butyl, pentyl, which may be linear or branched, and hexyl, which may be linear or branched.

The term "alkoxy radical" denotes a linear or branched radical containing at most 12 carbon atoms, and preferably 6 carbon atoms, chosen, for example, from the following radicals: methoxy, ethoxy, propoxy, isopropoxy, linear, secondary or tertiary butoxy, pentoxy, hexoxy or heptoxy, and also the linear or branched positional isomers thereof.

The term "alkylthio" or "alkyl-S-" denotes a linear or branched radical containing at most 12 carbon atoms and represents in particular methylthio, ethylthio, isopropylthio and heptylthio radicals. In the radicals containing a sulphur atom, the sulphur atom may be oxidized to an SO or S(O)$_2$ radical.

The term "carboxamide" denotes CONH$_2$.

The term "sulphonamide" denotes SO$_2$NH$_2$.

The term "acyl or r-CO— radical" denotes a linear or branched radical containing at most 12 carbon atoms, in which the radical r represents a hydrogen atom or an alkyl, cycloalkyl, cycloalkenyl, heterocycloalkyl or aryl radical, these radicals having the values indicated above and being optionally substituted as indicated: mention is made, for example, of formyl, acetyl, propionyl, butyryl or benzoyl radicals, or else valeryl, hexanoyl, acryloyl, crotonoyl or carbamoyl radicals.

The term "cycloalkyl radical" denotes a monocyclic or bicyclic, carbocyclic radical containing from 3 to 10 ring members and denotes in particular cyclopropyl, cyclobutyl, cyclopentyl and cyclohexyl radicals.

The term "cycloalkylalkyl radical" denotes a radical in which cycloalkyl and alkyl are chosen from the values indicated above: this radical thus denotes, for example, cyclopropylmethyl, cyclopentylmethyl, cyclohexylmethyl and cycloheptylmethyl radicals.

The term "acyloxy radical" is intended to mean acyl-O— radicals in which acyl has the meaning indicated above: mention is made, for example, of acetoxy or propionyloxy radicals.

The term "acylamino radical" is intended to mean acyl-N— radicals in which acyl has the meaning indicated above.

The term "aryl radical" denotes carbocyclic unsaturated radicals which are monocyclic or consist of condensed rings. As examples of such an aryl radical, mention may be made of phenyl or naphthyl radicals.

The term "arylalkyl" is intended to mean radicals resulting from the combination of the alkyl radicals mentioned above, which are optionally substituted, and the aryl radicals also mentioned above, which are optionally substituted: mention is, for example, made of benzyl, phenylethyl, 2-phenethyl, triphenylmethyl or naphthlenemethyl radicals.

The term "heterocyclic radical" denotes a saturated (heterocycloalkyl) or partially or completely unsaturated (heteroaryl) carbocyclic radical consisting of 4 to 10 ring members interrupted with one or more heteroatoms, which may be identical or different, chosen from oxygen, nitrogen or sulphur atoms.

As heterocycloalkyl radicals, mention may in particular be made of dioxolane, dioxane, dithiolane, thiooxolane, thiooxane, oxirannyl, oxolannyl, dioxolannyl, piperazinyl, piperidyl, pyrrolidinyl, imidazolidinyl, imidazolidine-2,4-dione, pyrazolidinyl, morpholinyl, tetrahydrofuryl, hexahydropyran, tetrahydrothienyl, chromanyl, dihydrobenzofuranyl, indolinyl, perhydropyranyl, pyrindolinyl, tetrahydroquinolinyl, tetrahydroisoquinolinyl or thioazolidinyl radicals, all these radicals being optionally substituted.

Among the heterocycloalkyl radicals, mention may in particular be made of optionally substituted piperazinyl, N-methylpiperazinyl, optionally substituted piperidyl, optionally substituted pyrrolidinyl, imidazolidinyl, pyrazolidinyl, morpholinyl, hexahydropyran or thiazolidinyl radicals.

The term "heterocycloalkylalkyl radical" is intended to mean radicals in which the heterocycloalkyl and alkyl residues have the meanings above.

Among the heteroaryl radicals with 5 ring members, mention may be made of furyl, pyrrolyl, tetrazolyl, thiazolyl, isothiazolyl, diazolyl, thiadiazolyl, thiatriazolyl, oxazolyl, oxadiazolyl, isoxazolyl, imidazolyl, pyrazolyl, thienyl and triazolyl radicals.

Among the heteroaryl radicals with 6 ring members, mention may in particular be made of pyridyl radicals such as 2-pyridyl, 3-pyridyl and 4-pyridyl, pyrimidyl radicals, pyridazinyl radicals and pyrazinyl radicals.

As condensed heteroaryl radicals containing at least one heteroatom chosen from sulphur, nitrogen and oxygen, mention may, for example, be made of benzothienyl, benzofuryl, benzopyrrolyl, benzothiazolyl, benzimidazolyl, imidazopyridyl, purinyl, pyrrolopyrimidinyl, pyrolopyridinyl, benzoxazolyl, benzisoxazolyl, benzisothiazolyl, thionaphtyl, chromenyl, indolizinyl, quinazolinyl, quinoxalinyl, indolyl, indazolyl, purinyl, quinolyl, isoquinolyl and naphthyridinyl.

The term "alkylamino radical" is intended to mean radicals in which the alkyl radical is chosen from the alkyl radicals mentioned above. Preference is given to alkyl radicals having at most 4 carbon atoms, and mention may, for example, be made of methylamino, ethylamino, propylamino or linear or branched butylamino radicals.

The term "dialkylamino radical" is intended to mean radicals in which the alkyl radicals, which may be identical or different, are chosen from the alkyl radicals mentioned above. As above, preference is given to alkyl radicals having at most 4 carbon atoms, and mention may, for example, be made of dimethylamino radicals, diethylamino radicals or methylethylamino radicals, which may be linear or branched.

The term "patient" denotes human beings, but also other mammals.

The term "prodrug" denotes a product which can be converted in vivo, by metabolic mechanisms (such as hydrolysis), to a product of formula (I). For example, an ester of a product of formula (I) containing a hydroxyl group can be converted by hydrolysis, in vivo, to its parent molecule. Alternatively, an ester of a product of formula (I) containing a carboxyl group can be converted by hydrolysis, in vivo, to its parent molecule.

By way of examples, mention may be made of esters of products of formula (I) containing a hydroxyl group, such as acetates, citrates, lactates, tartrates, malonates, oxalates, salicylates, propionates, succinates, fumarates, maleates, methylene-bis-beta-hydroxynaphthoates, gentisates, isethionates, di-p-toluoyl tartrates, methanesulphonates, ethanesulphonates, benzenesulphonates, p-toluenesulphonates, camphorsulphonates, cyclohexylsulphamates and quinates.

Particularly useful esters of products of formula (I) containing a hydroxyl group can be prepared from acid residues such as those described by Bundgaard et. al., J. Med. Chem., 1989, 32, page 2503-2507: these esters include, in particular, substituted (aminomethyl)benzoates, dialkylamino-methyl benzoates in which the two alkyl groups can be linked together or can be interrupted with an oxygen atom or with an optionally substituted nitrogen atom, i.e. an alkylated nitrogen atom, or else (morpholinomethyl)benzoates, e.g. 3- or 4-(morpholinomethyl)benzoates, and (4-alkylpiperazin-1-yl)benzoates, e.g. 3- or 4-(4-alkylpiperazin-1-yl)benzoates.

The carboxyl radical(s) of the products of formula (I) can be salified or esterified with the various groups known to those skilled in the art, among which mention may be made, by way of nonlimiting examples, of the following compounds:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, or N-methylglucamine;

among the esterification compounds, alkyl radicals so as to form alkoxycarbonyl groups such as, for example, methoxycarbonyl, ethoxycarbonyl, tert-butoxycarbonyl or benzyloxycarbonyl, it being possible for these alkyl radicals to be substituted with radicals chosen, for example, from halogen atoms and hydroxyl, alkoxy, acyl, acyloxy, alkylthio, amino or aryl radicals, for instance from chloromethyl, hydroxypropyl, methoxymethyl, propionyloxymethyl, methylthiomethyl, dimethylaminoethyl, benzyl or phenethyl groups.

The term "esterified carboxyl" is intended to mean, for example, radicals such as alkyloxycarbonyl radicals, for example methoxycarbonyl, ethoxycarbonyl, propoxycarbonyl, butyl or tert-butyloxycarbonyl, cyclobutyloxycarbonyl, cyclopentyloxycarbonyl or cyclohexyloxycarbonyl radicals.

Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl radicals; alkyloxycarbonyloxy alkyl radicals such as methoxycarbonyloxymethyl or methoxycarbonyloxyethyl radicals, isopropyloxycarbonyloxymethyl radicals or isopropyloxycarbonyloxyethyl radicals.

A list of such ester radicals can be found, for example, in European Patent EP 0 034 536.

The term "amidated carboxyl" is intended to mean radicals of the —CONH$_2$ type, the hydrogen atoms of which are optionally substituted with one or two alkyl radicals so as to form alkylamino or dialkylamino radicals, which are themselves optionally substituted as indicated above or below, it being possible for these radicals to also form, with the nitrogen atom to which they are attached, a cyclic amine as defined above.

The term "salified carboxyl" is intended to mean the salts formed, for example, with an equivalent of sodium, of potassium, of lithium, of calcium, of magnesium or of ammonium. Mention may also be made of the salts formed with organic bases such as methylamine, propylamine, trimethylamine, diethylamine or triethylamine. The sodium salt is preferred.

When the products of formula (I) comprise an amino radical that can be salified with an acid, it is clearly understood that these acid salts are also part of the invention. Mention may be made of the salts provided with hydrochloric acid or methanesulphonic acid, for example.

The addition salts with inorganic or organic acids of the products of formula (I) may, for example, be the salts formed with hydrochloric acid, hydrobromic acid, hydriodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alcoylmonosulphonic acids such as, for example, methanesulphonic acid, ethanesulphonic acid, propanesulphonic acid, alkoyldisulphonic acids such as, for example, methanedisulphonic acid, alpha, beta-ethanedisulphonic acid, arylmonosulphonic acids such as benzenesulphonic acid and aryldisulphonic acids.

It may be recalled that stereoisomerism can be defined, in its broad sense, as the isomerism of compounds having the same structural formulae, but the various groups of which are arranged differently in space, such as, in particular, in monosubstituted cyclohexanes in which the substituent can be in the axial or equatorial position, and the various possible rotational conformations of ethane derivatives. However, another type of stereoisomerism exists, due to the different spatial arrangements of attached substituents, either on double bonds or on rings, which is often referred to as geometric isomerism or cis-trans isomerism. The term "stereoisomer" is used, in the present application, in its broadest sense and therefore relates to all the compounds indicated above.

The present invention thus relates in particular to the products of formula (I) as defined above in which:

Het is chosen from the group constituted of:

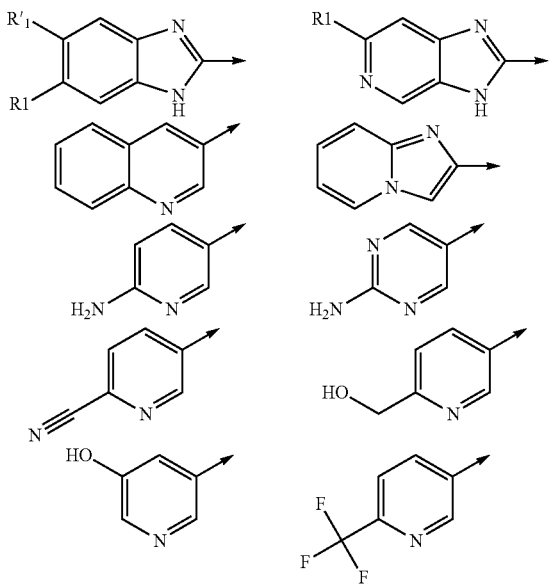

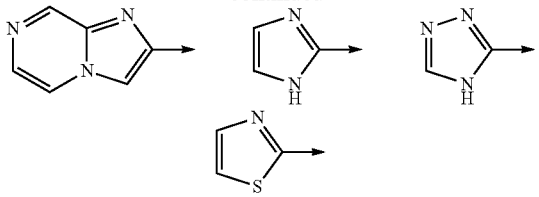

R1 and/or R'1 is (are) in the group constituted of H, halogen, $CF_3$, nitro, cyano, alkyl, hydroxyl, mercapto, amino, alkylamino, dialkylamino, alkoxy, alkylthio (methylthio), carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NH(alkyl) and S(O)$_2$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

the substituent R of said products of formula (I) being chosen from the values defined above or hereinafter, said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above, in which:

R is chosen from the groups constituted of:

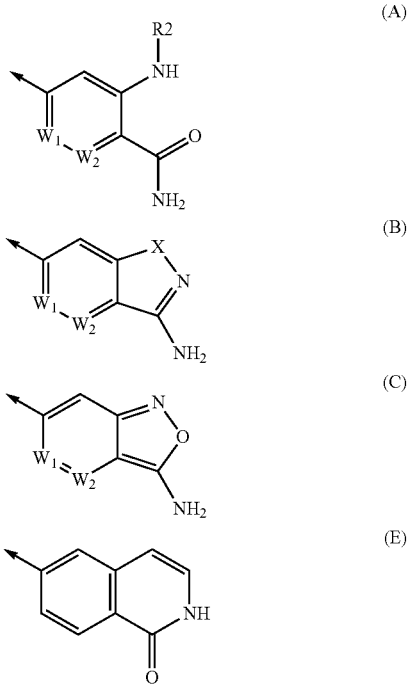

W1 and W2 represent CH or else one represents CH and the other N;

X represents an oxygen atom or an NR2 radical,

R2 represents a hydrogen atom or a $C_1$-$C_6$ alkyl, $C_3$-$C_8$ cycloalkyl or $C_4$-$C_8$ heterocycloalkyl radical, these alkyl, cycloalkyl and heterocycloalkyl radicals being optionally substituted with one or more radicals, which may be identical or different, chosen from the radicals:

hydroxyl; mercapto; amino; azetidino; oxetano; tetrahydrofurano; piperidino; tetrahydropyrano; piperazino; alkylpiperazino; pyrrolidino; morpholino; homopiperidino; homopiperazino; quinuclidino; carboxamide; carboxyl;

carboxyl esterified with an alkyl radical; CO—NH(alkyl); —O—CO-alkyl; NH—CO-alkyl; alkoxy; hydroxyalkoxy; methylthio; alkylamino; dialkylamino; all the latter alkyl and alkoxy radicals being optionally themselves substituted with a hydroxyl, mercapto, amino, alkylamino, dialkylamino, azetidino, oxetano, pyrrolidino, tetrahydrofurano, piperidino, tetrahydropyrano, piperazino, morpholino, homopiperidino, homopiperazino or quinuclidino radical;

the substituent Het of said products of formula (I) being chosen from the values defined above or hereinafter, said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above or hereinafter, in which:
Het is chosen in the group consistuted of:

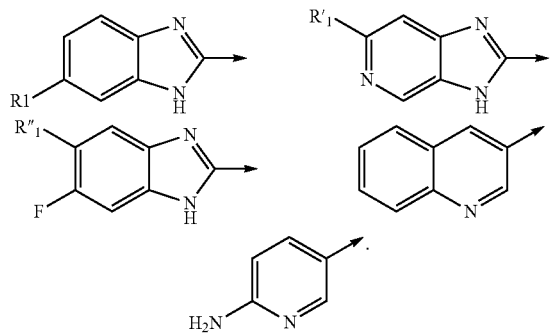

R is chosen from the group constituted of:

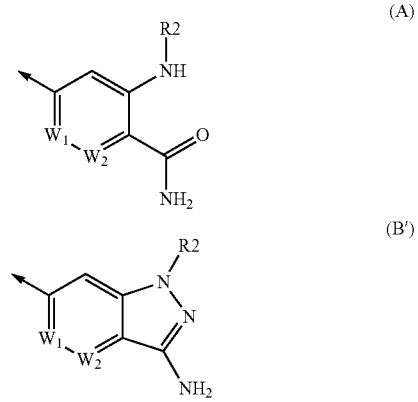

R1 is chosen from the group constituted of H, F, Cl, Br, $CF_3$, $NO_2$, CN, $CH_3$, OH, $OCH_3$, $OCF_3$, $CO_2Me$, $CONH_2$, CON-HMe, CONH—$(CH_2)_3$—OMe, CONH—$(CH_2)_3$—N(Me)$_2$, NHC(O)Me, $SO_2NH_2$ and $SO_2N(Me)_2$;

R'1 is in the group constituted of H, $CONH_2$, CONHMe and OMe;

R"1 is in the group constituted of F, Cl, OH, OMe, CN, O—$(CH_2)_3$—OMe and O—$(CH_2)_3$—N(Me)$_2$;

W1 and W2 represent CH or else one represents CH and the other N;

R2 represents a hydrogen atom or a $C_1$-$C_6$ alkyl, $C_3$-$C_8$ cycloalkyl or $C_4$-$C_8$ heterocycloalkyl radical, all these alkyl, cycloalkyl and heterocycloalkyl radicals being optionally substituted with one or more radicals, which may be identical or different, chosen from the radicals:

hydroxyl; mercapto; amino; azetidino; oxetano; tetrahydrofurano; piperidino; tetrahydropyrano; piperazino; alkylpiperazino; pyrrolidino; morpholino; homopiperidino; homopiperazino; quinuclidino; carboxamide; carboxyl;

carboxyl esterified with an alkyl radical; CO—NH(alkyl); —O—CO-alkyl; NH—CO-alkyl; alkoxy; hydroxyalkoxy; methylthio; alkylamino; dialkylamino; all the latter alkyl and alkoxy radicals being optionally themselves substituted with a hydroxyl, mercapto, amino, alkylamino, dialkylamino, azetidino, oxetano, pyrrolidino, tetrahydrofurano, piperidino, tetrahydropyrano, piperazino, morpholino, homopiperidino, homopiperazino or quinuclidino radical;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above or hereinafter, in which:
Het is chosen from the group constituted of:

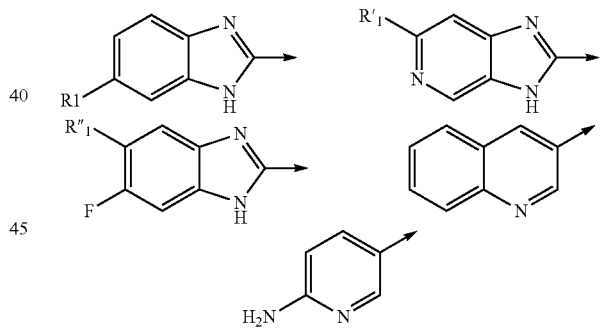

R is chosen from the group constituted of:

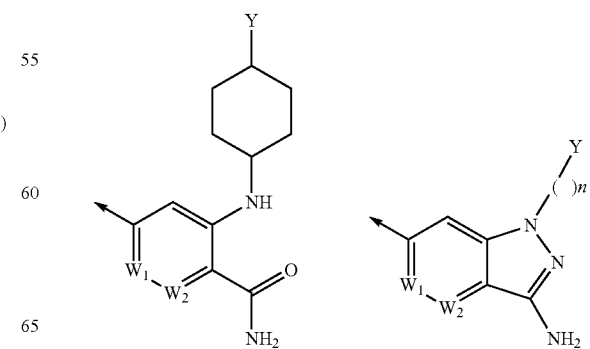

R1 is in the group constituted of H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ and $SO_2N(Me)_2$;

R'1 is in the group constituted of H, $CONH_2$, CONHMe and OMe;

R"1 is in the group constituted of F, Cl, OH, OMe, CN, O—$(CH_2)_3$—OMe and O—$(CH_2)_3$—$N(Me)_2$;

W1 and W2 represent CH or else one represents CH and the other N;

Y represents OH, O—$PO_3H_2$, O—$PO_3Na_2$, O—$SO_3H_2$, O—$SO_3Na_2$, O—$CH_2$—$PO_3H_2$, O—$CH_2$—$PO_3Na_2$, O—CO—$CH_2$—$CO_2tBu$, O—CO—$CH_2$—$NH_2$ or O—CO-glycine, O—CO—$CH_2$—$N(Me)_2$, O—CO—$CH_2$—NHMe, O—CO-alanine, O—CO-serine, O—CO-lysine, O—CO-arginine, O—CO-glycine-lysine, O—CO-alanine-lysine;

n represents 2 or 3;

said products of formula (I) being in all the possible isomeric forms: racemic, enantiomeric and diastereoisomeric; and also the addition salts with inorganic and organic acids or with inorganic and organic bases.

In the radicals —O—CO-glycine, —O—CO—$CH_2$—$N(Me)_2$, —O—CO—$CH_2$—NHMe, —O—CO-alanine, —O—CO-serine, —O—CO-lysine, —O—CO-arginine, —O—CO-glycine-lysine and —O—CO-alanine-lysine as defined above or hereinafter, the terms glycine, -alanine, -serine, -lysine and -arginine represent the amino acid residues as known and described in the conventional manuals of those skilled in the art.

A subject of the invention is in particular the products of formula (I) as defined above, in which:

Het is chosen from the group constituted of:

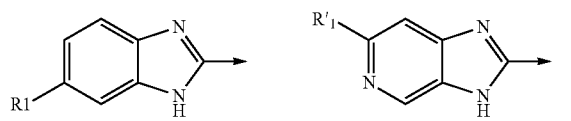

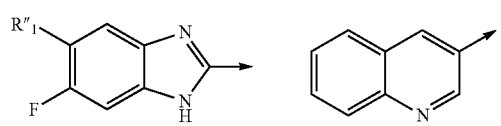

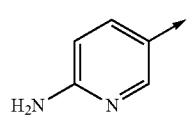

with:
R1 represents H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ or $SO_2N(Me)_2$;

R'1 represents H, $CONH_2$, CONHMe or OMe;

R"1 represents F, Cl, OH, OMe, CN, O—$(CH_2)_3$—OMe or O—$(CH_2)_3$—$N(Me)_2$; and R is chosen from the group constituted of:

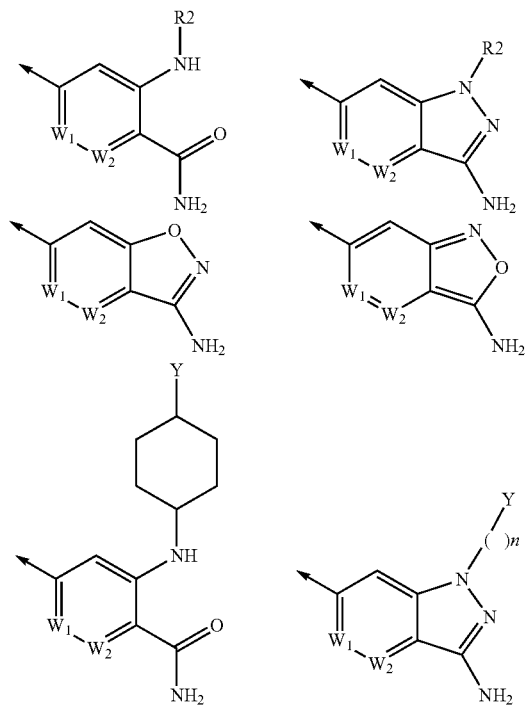

with:
W1 and W2 represent CH or else one represents CH and the other N;

R2 represents hydrogen, or ethyl substituted in the 2-position, n-propyl substituted in the 3-position or cyclohexyl trans-substituted in the 4-position with OH, SH, $NH_2$, OMe, NHMe, $N(Me)_2$, $N(Et)_2$, azetidino, oxetano, prolino, tetrahydrofurano, piperidino, tetrahydropyrano, piperazino, morpholino, homopiperidino, homopiperazino, quinuclidino, $CONH_2$ or COOH;

Y represents OH, O—$PO_3H_2$, O—$PO_3Na_2$, O—$SO_3H_2$, O—$SO_3Na_2$, O—$CH_2$—$PO_3H_2$, O—$CH_2$—$PO_3Na_2$, O—CO—$CH_2$—$CO_2tBu$, O—CO—$CH_2$—$NH_2$ or O—CO-glycine, O—CO—$CH_2$—$N(Me)_2$, O—CO—$CH_2$—NHMe, O—CO-alanine, O—CO-serine, O—CO-lysine, O—CO-arginine, O—CO-glycine-lysine or O—CO-alanine-lysine, with n represents 2 or 3;

and also the prodrugs thereof, said products of formula (I) being in all the possible isomeric forms: tautomeric, racemic, enantiomeric and diastereo-isomeric, and also the addition salts with inorganic and organic acids or with inorganic and organic bases of said products of formula (I).

A subject of the invention is in particular the products of formula (I) as defined above, in which:
R is chosen from the group constituted of:

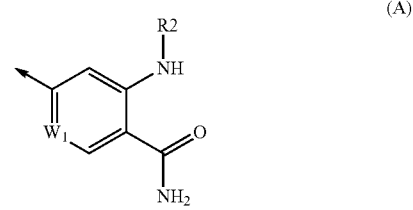

(A)

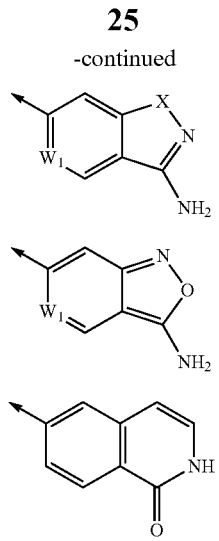

W1 represents CH or N;

X represents an oxygen atom or an NR2 radical;

R2 represents a hydrogen atom or a $C_1$-$C_6$ alkyl, $C_3$-$C_8$ cycloalkyl or $C_4$-$C_8$ heterocycloalkyl radical, these alkyl, cycloalkyl and heterocycloalkyl radicals being optionally substituted with one or more radicals, which may be identical or different, chosen from the radicals:

- hydroxyl; mercapto; amino; azetidino; oxetano; tetrahydrofurano; piperidino; tetrahydropyrano; piperazino; alkylpiperazino; pyrrolidino; morpholino; homopiperidino; homopiperazino; quinuclidino; carboxamide; carboxyl;
- carboxyl esterified with an alkyl radical; CO—NH(alkyl); —O—CO-alkyl; NH—CO-alkyl; alkoxy; hydroxyalkoxy; methylthio; alkylamino; dialkylamino; all these latter alkyl and alkoxy radicals being optionally themselves substituted with a hydroxyl, mercapto, amino, alkylamino, dialkylamino, azetidino, oxetano, pyrrolidino, tetrahydrofurano, piperidino, tetrahydropyrano, piperazino, morpholino, homopiperidino, homopiperazino or quinuclidino radical;

the substituent Het of said products of formula (I) being chosen from the values defined above or hereinafter, said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

A subject of the invention is in particular the products of formula (I) as defined above, in which:

Het is chosen from the group constituted of:

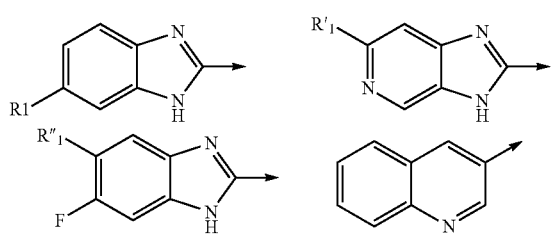

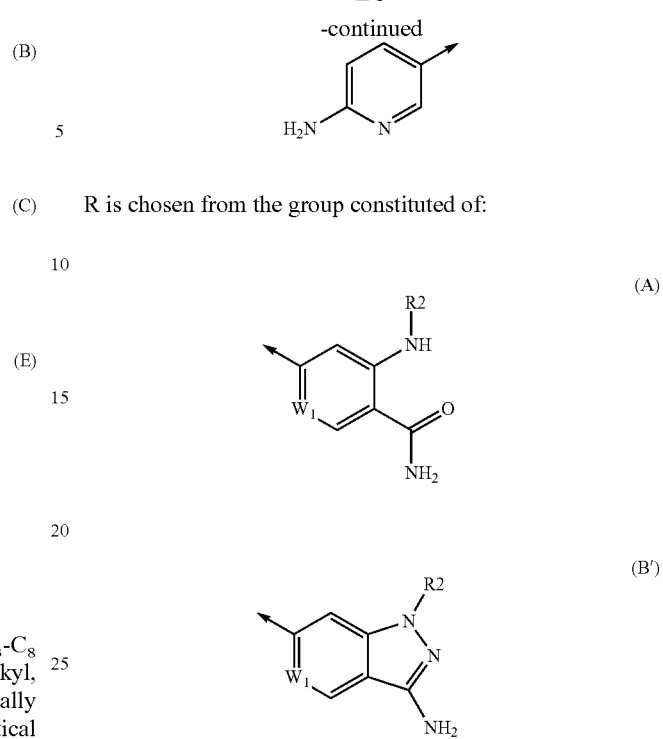

R is chosen from the group constituted of:

R1 is in the group constituted of H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ and $SO_2N(Me)_2$;

R'1 is in the group constituted of H, $CONH_2$, CONHMe and OMe;

R"1 is in the group constituted of F, Cl, OH, OMe, CN, O—$(CH_2)_3$—OMe and O—$(CH_2)_3$—$N(Me)_2$;

W1 represents CH or N;

R2 represents a hydrogen atom or a $C_1$-$C_6$ alkyl, $C_3$-$C_8$ cycloalkyl or $C_4$-$C_8$ heterocycloalkyl radical, all these alkyl, cycloalkyl and heterocycloalkyl radicals being optionally substituted with one or more radicals, which may be identical or different, chosen from the radicals:

- hydroxyl; mercapto; amino; azetidino; oxetano; tetrahydrofurano; piperidino; tetrahydropyrano; piperazino; alkylpiperazino; pyrrolidinyl; morpholino; homopiperidino; homopiperazino; quinuclidino; carboxamide; carboxyl;
- carboxyl esterified with an alkyl radical, CO—NH(alkyl), —O—CO-alkyl, NH—CO-alkyl, alkoxy, hydroxyalkoxy, methylthio, alkylamino, dialkylamino, all the latter alkyl and alkoxy radicals being themselves optionally substituted with a hydroxyl, mercapto, amino, alkylamino, dialkylamino, azetidino, oxetano, prolino, tetrahydrofurano, piperidino, tetrahydropyrano, piperazino, morpholino, homopiperidino, homopiperazino or quinuclidino radical;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of formula (I).

A subject of the invention is in particular the products of formula (I) as defined above, in which:
Het is chosen from the group constituted of:

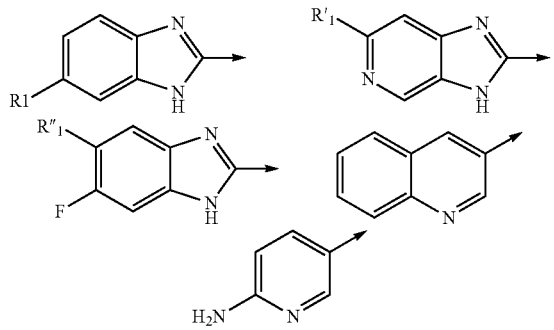

R is chosen from the group constituted of:

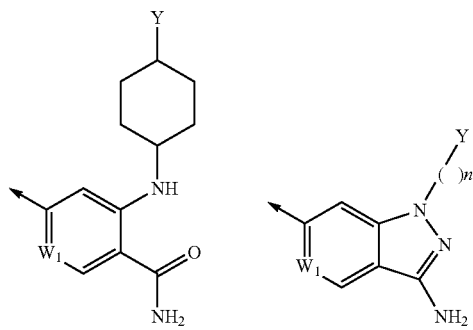

R1 is in the group constituted of H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ and $SO_2N(Me)_2$;
R'1 is in the group constituted of H, $CONH_2$, CONHMe and OMe;
R"1 is in the groupe constituted of F, Cl, OH, OMe, CN, O—$(CH_2)_3$—OMe and O—$(CH_2)_3$—$N(Me)_2$;
W1 represents CH or N;
Y represents OH, O—$PO_3H_2$, O—$PO_3Na_2$, O—$SO_3H_2$, O—$SO_3Na_2$, O—$CH_2$—$PO_3H_2$, O—$CH_2$—$PO_3Na_2$, O—CO—$CH_2$—$CO_2tBu$, O—CO—$CH_2$—$NH_2$, O—CO-glycine, O—CO—$CH_2$—$N(Me)_2$, O—CO—$CH_2$—NHMe, O—CO-alanine, O—CO-serine, O—CO-lysine, O—CO-arginine, O—CO-glycine-lysine or O—CO-alanine-lysine;
n represents 2 or 3;
said products of formula (I) being in all the possible isomeric forms: racemic, enantiomeric and diastereoisomeric, and also the addition salts with inorganic and organic acids or with inorganic and organic bases.

A subject of the invention is in particular the products of formula (I) as defined above, in which:
Het is chosen from the group constituted of:

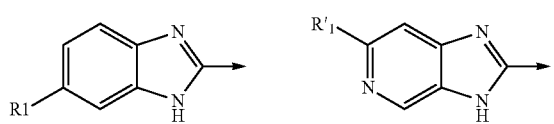

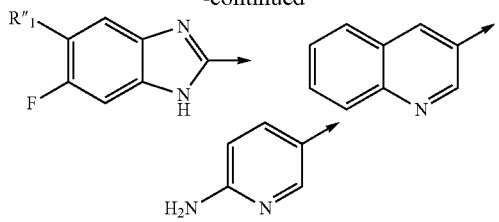

with:
R1 represents H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ or $SO_2N(Me)_2$;
R'1 represents H, $CONH_2$, CONHMe or OMe;
R"1 represents F, Cl, OH, OMe, CN, O—$(CH_2)_3$—OMe or O—$(CH_2)_3$—$N(Me)_2$;
and R is chosen from the group constituted of:

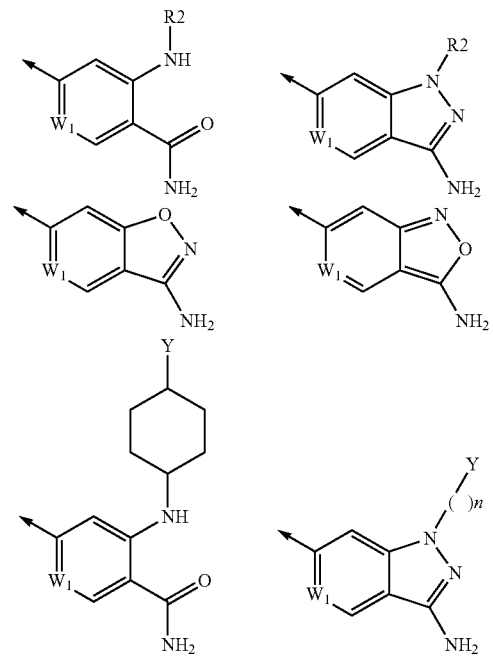

with:
R2 represents hydrogen, or ethyl substituted in the 2-position, n-propyl substituted in the 3-position or cyclohexyl trans-substituted in the 4-position with OH, SH, $NH_2$, OMe, NHMe, $N(Me)_2$, $N(Et)_2$, azetidino, oxetano, pyrrolidino, tetrahydrofurano, piperidino, tetrahydropyrano, piperazino, morpholino, homopiperidino, homopiperazino, quinuclidino, $CONH_2$ or COOH;
Y represents OH, O—$PO_3H_2$, O—$PO_3Na_2$, O—$SO_3H_2$, O—$SO_3Na_2$, O—$CH_2$—$PO_3H_2$, O—$CH_2$—$PO_3Na_2$, O—CO—$CH_2$—$CO_2tBu$, O—CO—$CH_2$—$NH_2$ or O—CO-glycine, O—CO—$CH_2$—$N(Me)_2$, O—CO—$CH_2$—NHMe, O—CO-alanine, O—CO-serine, O—CO-lysine, O—CO-arginine, O—CO-glycine-lysine or O—CO-alanine-lysine, with n represents 2 or 3;
and also the prodrugs thereof, said products of formula (I) being in all the possible isomeric forms: tautomeric, racemic, enantiomeric and diastereoisomeric, and also the pharmaceutically acceptable addition salts with inorganic and organic acids or with inorganic and organic bases of said products of formula (I).

A subject of the present invention is more particularly the products of formula (I) as defined above, the names of which are given below:
4-[4-(6-fluoro-1H-benzimidazol-2-yl)-9H-carbazol-9-yl]-2-(4-trans-hydroxycyclohexylamino)benzamide
2-(4-trans-hydroxycyclohexylamino)-4-[(4-quinolin-3-yl)-9H-carbazol-9-yl]benzamide
2-(2-diethylaminoethylamino)-4-[4-(6-fluoro-1H-benzimidazol-2-yl)-9H-carbazol-9-yl]benzamide
2-(4-trans-hydroxycyclohexylamino)-4-[4-(3H-imidazo[4,5-c]pyridin-2-yl)-9H-carbazol-9-yl]benzamide
acetic acid 4-{2-carbamoyl-5-[4-(6-fluoro-1H-benzimidazol-2-yl)-9H-carbazol-9-yl]phenylamino}cyclohexyl ester
2-cyclohexylamino-4-[4-(6-fluoro-1H-benzimidazol-2-yl)-9H-carbazol-9-yl]benzamide
4-[4-(6-fluoro-1H-benzimidazol-2-yl)-9H-carbazol-9-yl]-2-[2-(2-hydroxyethoxy)ethylamino]benzamide
4-[4-(6-fluoro-1H-benzimidazol-2-yl)-9H-carbazol-9-yl]-2-(3-hydroxypropylamino)benzamide
4-[4-(6-fluoro-1H-benzimidazol-2-yl)-9H-carbazol-9-yl]-2-(4-cis-hydroxycyclohexylamino)benzamide
2-amino-4-[4-(6-fluoro-1H-benzimidazol-2-yl)-9H-carbazol-9-yl]benzamide
4-[4-(6-fluoro-1H-benzimidazol-2-yl)-9H-carbazol-9-yl]-2-(2-pyrrolidin-1-ylethylamino)benzamide
6-[4-(6-fluoro-1H-benzimidazol-2-yl)-9H-carbazol-9-yl]-1H-indazol-3-ylamine
6-[4-(6-fluoro-1H-benzimidazol-2-yl)-9H-carbazol-9-yl]-1,2-benzisoxazol-3-ylamine,
3-(trans-4-hydroxycyclohexylamino)-5-[(4-quinolin-3-yl)-9H-carbazol-9-yl)pyridine-2-carboxamide
4-[4-(6-fluoro-1H-benzimidazol-2-yl)-9H-carbazol-9-yl]-2-(tetrahydro-pyran-4-ylamino)benzamide
4-[4-(6-cyanopyridin-3-yl)-9H-carbazol-9-yl]-2-[(1,2,2,6,6-pentamethylpiperidin-4-yl)amino]benzamide
aminoacetic acid 4-{[2-carbamoyl-5-(quinolin-3-yl)-9H-carbazol-9-yl]-pyridin-3-ylamino}cyclohexyl ester
4-[4-(6-cyanopyridin-3-yl)-9H-carbazol-9-yl]-2-[(8-methyl-8-azabicyclo[3.2.1]oct-3-yl)amino]benzamide
5-[4-(6-fluoro-1H-benzimidazol-2-yl)-9H-carbazol-9-yl]-3-(tetrahydropyran-4-yl)amino)pyridin-2-carboxamide
2-[4-(quinolin-3-yl)-9H-carbazol-9-yl]-4-(tetrahydropyran-4-yl)-amino)pyridin-5-carboxamide
2-(8-methyl-8-azabicyclo[3.2.1]oct-3-yl)amino-4-[4-(quinolin-3-yl)-9H-carbazol-9-yl]benzamide
3-[(2-hydroxy-2-methylpropylamino)-5-[4-(quinolin-3-yl)-9H-carbazol-9-yl]pyridine-2-carboxamide
and also the addition salts with inorganic and organic acids or with inorganic and organic bases of said products of formula (I).

The products of formula (I) according to the present invention can be prepared according to the methods known to those skilled in the art and particularly according to the methods described hereinafter: a subject of the present invention is thus also the methods for synthesizing the products of formula (I) according to the present invention, and in particular the general methods of synthesis described in the schemes hereinafter.

General Methods of Synthesis of Compounds of General Formula (I):

The products of general formula (I) can be prepared from a 4-hydroxy-9H-carbazole derivative, of general formula (II), by first introducing either the heterocycle Het so as to form a compound of general formula (III), or a precursor of the radical R so as to form a product of general formula (IV), according to general scheme (1) below:

Scheme (1)

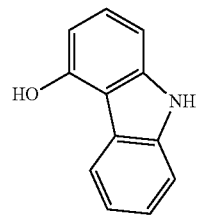

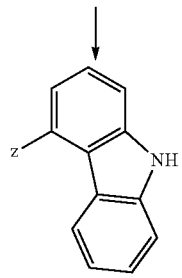

(II)

Z = OTf, I, Br, B(OH)₂ or B(OR)₂* or
C(O)—OMe, C(O)—OH or C(O)—H)
or OH or O—CH₂—PH

*B(OR)₂ being able to form a ring

Z = OTf, I, Br, B(OH)₂ or B(OR)₂
or C(O)—OMe, C(O)—OH
or C(O)—H)

Z = C(O)—OMe or C(O)—OH
or OH or O—CH₂—PH

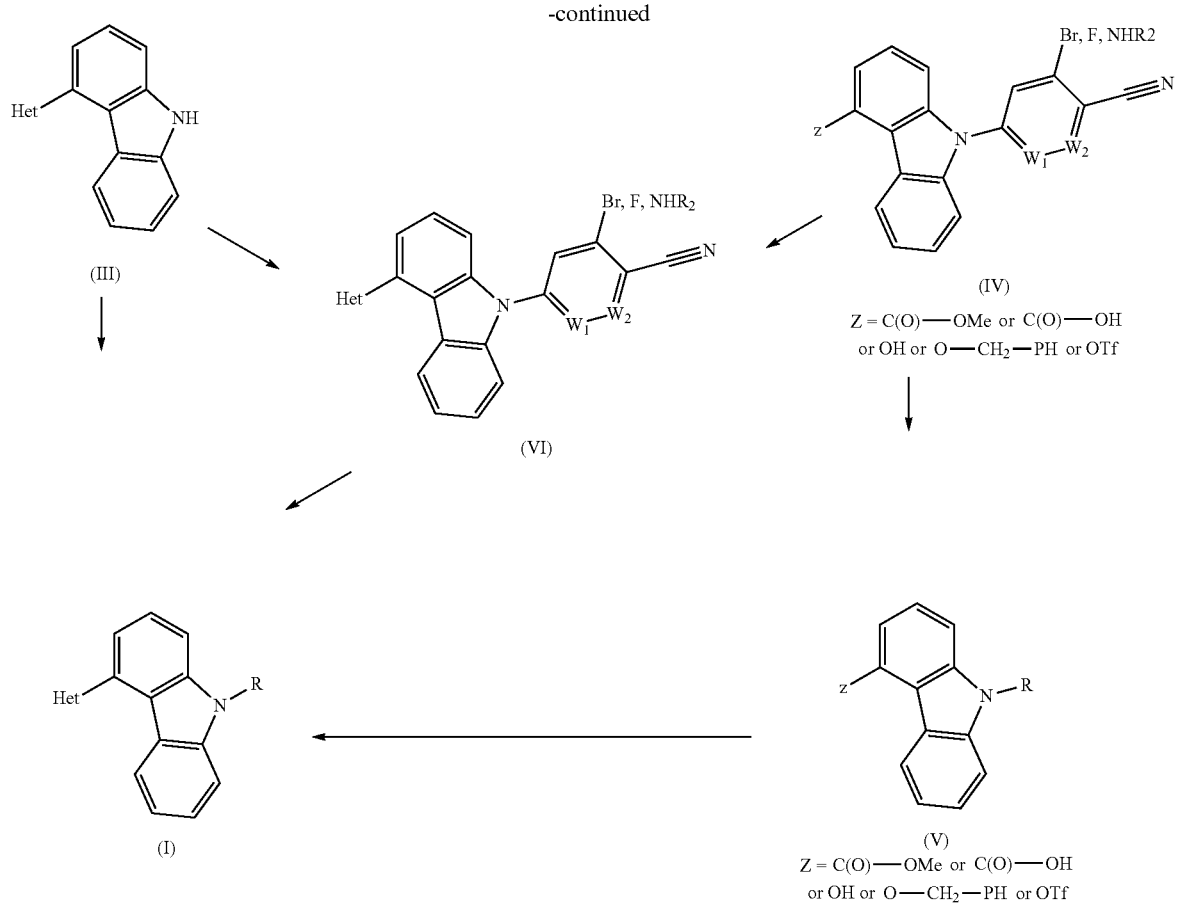

A subject of the present invention is thus in particular Scheme (1) above for synthesizing the products of formula (I) as defined above.

A subject of the present invention is also, as new industrial products, the synthesis intermediates of formulae (III), (IV), (V) and (VI) as defined above, in which the substitutents Het, R, R2, W1 and W2 have the meanings indicated above for the products of formula (I) as defined above and z has the meaning indicated above in Scheme (1).

Preparation of the Compounds of General Formula (II)

A subject of the present invention is thus also the methods for synthesizing the products of formula (II), in which Z represents the triflate radical, a boronic acid or a boronate, which is optionally cyclic.

The product of general formula (II) in which Z represents the benzyloxy radical can be obtained according to Biorg. Med. Chem. 2005, 13(13), 4279.

The product of general formula (II) in which Z represents the trifluoromethanesulphonyloxy radical (also called "triflate" in the rest of the invention) can be obtained by the action of a trifluoromethylsulphonating agent, such as N-phenylbis(trifluoromethanesulphonimide), in an organic solvent such as dichloromethane, in the presence of an organic base such as triethylamine, according to Scheme (2) below.

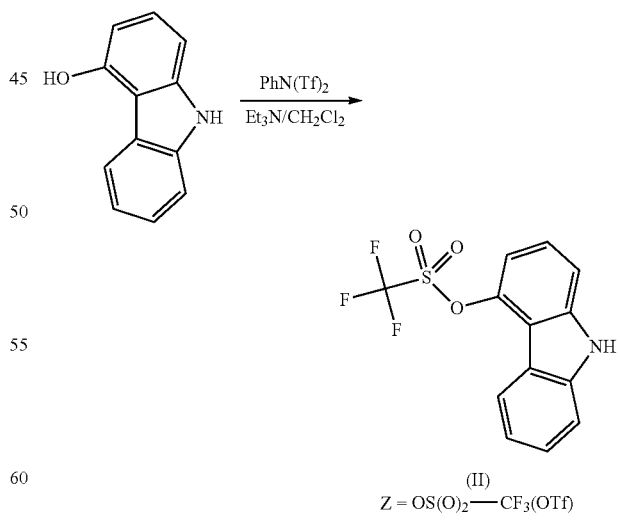

The product of general formula (II) in which Z represents a methyl carboxylate radical can be obtained by carrying out the procedure according to Tetrahedron Letters (1985), 26(13), 1647-50. However, it has been found, in the context of the invention, that this methyl carboxylate can be advantageously obtained by means of a carbonylation reaction in methanol, catalysed by a palladium complex, such as palladium acetate, in the presence of a phosphine-type ligand such as 1,3-diphenylphosphinopropane, according to Scheme (3) below:

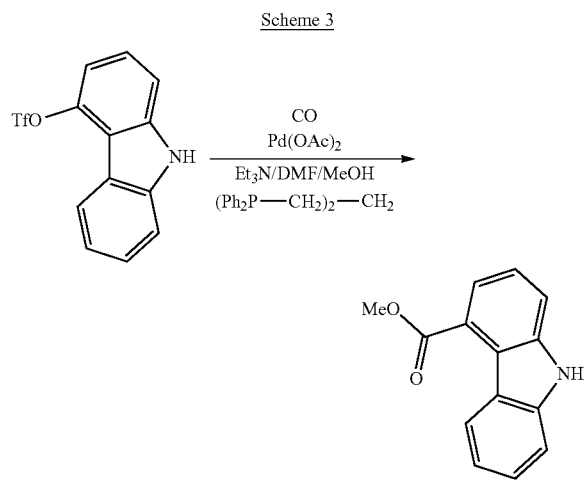

Scheme 3

The product of general formula (II) in which Z represents a carboxyl radical can be obtained by carrying out the process according to Journal of the Chemical Society (1937), 1125-9.

The product of general formula (II) in which Z represents a formyl radical can be obtained by carrying out the process according to Journal of the Chemical Society (1957), 2210-5.

The product of general formula (II) in which Z represents the bromine atom can be obtained by carrying out the process according to Journal of the Chemical Society (1945), 530-3.

The product of general formula (II) in which Z represents the iodine atom can be obtained by the action of n-butyllithium and then of iodine on 4-bromocarbazole at low temperature in an organic solvent such as tetrahydrofuran, according to Scheme (4):

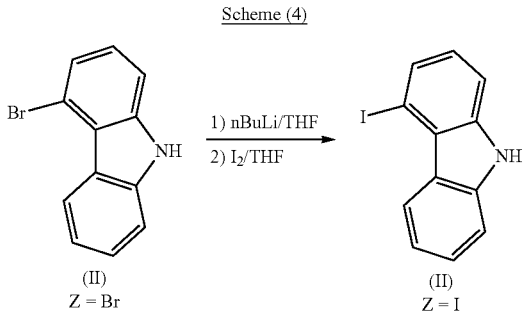

The products of general formula (II) in which Z represents a boronic acid or a boronic ester, which is optionally cyclic, can be advantageously prepared by the action of n-butyllithium and then of a borate, such as dimethyl borate, di-n-butyl borate, diisopropyl borate or pinacolyl borate, on 4-bromocarbazole at low temperature in an organic solvent such as tetrahydrofuran, or else from the 4-iodocarbazole derivative or from the 4-trifluoromethylsulphonyloxy derivative, in the presence of a palladium(0) catalyst, according to Scheme (5).

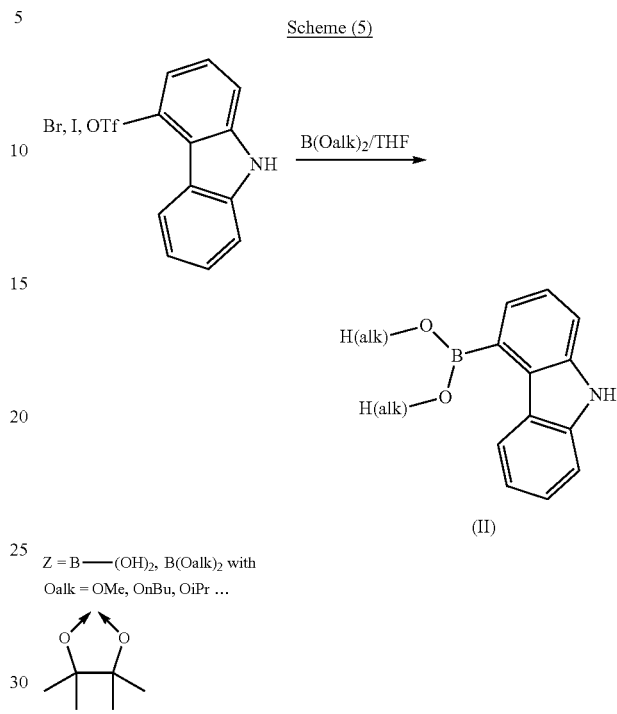

Preparation of the Compounds of General Formula (III)

A subject of the present invention is thus also the methods for synthesizing the products of formula (III), in which, R1 and/or R1 being as defined above, Het is in the group constituted of:

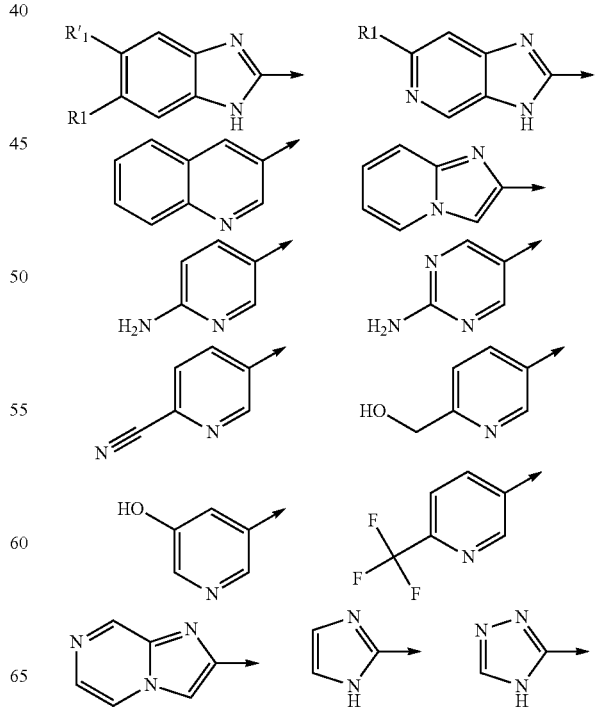

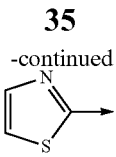

More particularly, when Het does not represent a heterocycle of imidazol-2-yl, triazol-3-yl, benzimidazol-2-yl or azabenzimidazol-2-yl type, and is optionally substituted with one or more radicals R1, as defined above, it is particularly advantageous according to the invention to prepare the compounds of general formula (III)

- either by coupling 4-bromocarbazole, 4-iodocarbazole or 4-trifluoromethylsulphonyloxycarbazole with a heterocyclic boronic derivative, which may be an acid or an ester,
- or by coupling carbazole-4-boronic acid, or an ester thereof, such as the methyl, n-butyl, isopropyl or pinacol ester, with a bromo or an iodo heterocycle, under the Suzuki reaction conditions, in the presence of a palladium(0) derivative as catalyst, by carrying out the process according to Scheme (6):

Scheme (6)

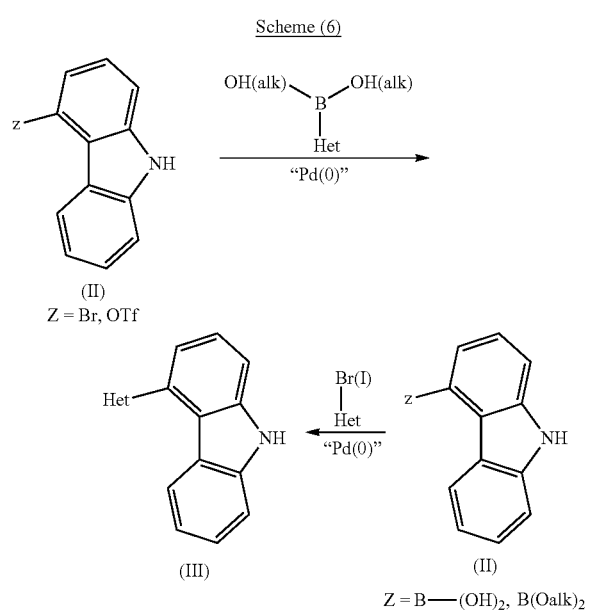

More particularly, when the heterocycle Het is of benzimidazole or azabenzimidazole type—or alternatively of benzoxazole or azabenzoxazole, benzothiazole or azabenzothiazole type, linked via its 2-position to the 4-position of the carbazole, it is particularly advantageous to form said heterocycle by coupling a derivative of ortho-phenylenediamine or of diaminopyridine, or else of ortho-aminophenol, of ortho-aminothiophenol or of aminohydroxypyridine or of aminomercaptopyridine which is ortho-disubstituted, with an acid, an acid chloride, a methyl or ethyl ester, or an aldehyde, in the 4-position of a carbazole N-protected with a protective group such as a tert-butyloxycarbonyl (Boc) radical or a tert-butyldimethylsilyl (TBDMS) radical or a 2-(trimethylsilyl)ethoxymethyl (SEM) radical, followed by cyclization in an acidic medium, which allows cleavage of the Boc or TBDMS protective group borne by the nitrogen atom of the carbazole, by carrying out the process according to Scheme (7):

Scheme (7)

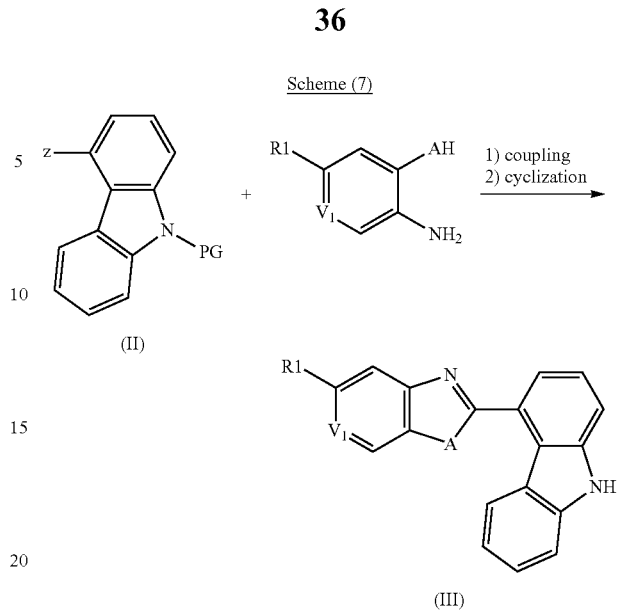

A = NH, O, S
Z = COOH, COCl, COOMe, COOEt, CHO
V1 = N, CR1
PG = TBDMS or Boc
R1 as defined above In the context of the invention, it is advantageous to protect the nitrogen of a carbazole derivative bearing an acid, ester or aldehyde radical in the 4-position, with a tert-butyloxycarbonyl (Boc) group—through the action of $Boc_2O$, of BocCl or of BocON in an organic solvent such as dichloromethane or tetrahydrofuran in the presence of an organic or inorganic base—or with a tert-butyldimethylsilyl (TBDMS) group—through the action of tert-butyldimethylsilane chloride (TBDMSCl) in an organic solvent such as dichloromethane or tetrahydrofuran in the presence of an organic or inorganic base—or with a 2-(trimethylsilyl)ethoxymethyl (SEM) group—through the action of 2-(trimethylsilyl)ethoxymethyl chloride (SEMCl) in an organic solvent such as dichloromethane or tetrahydrofuran in the presence of an organic or inorganic base.

When an N-protected derivative of carbazole-4-carboxylic acid is used, it is particularly advantageous to activate this acid using a coupling agent known to those skilled in the art, such as 1-(3-dimethylaminopropyl)-3-ethylcarbodiimide hydrochloride (EDCI) in the presence of 1-hydroxybenzotriazole (HOBT), or of O-((ethoxycarbonyl)cyanomethyleneamino)-N,N, N',N'-tetramethyluronium tetrafluoroborate (TOTU).

When an N-protected derivative of a methyl or ethyl ester of carbazole-4-carboxylic acid is used, it is advantageous, in the context of the invention, to carry out the process in the presence of trimethylaluminium in a halogenated organic solvent, such as dichloromethane or dichloroethane.

When an N-protected derivative of carbazole-4-carboxaldehyde is used, it is advantageous, in the context of the invention, to carry out the process:

- either by microwave heating in the presence of silica, according to Tetrahedron Lett. 1998, 39, 4481-84;
- or in the presence of dichlorodicyanobenzoquinone (DDQ), according to Tetrahedron 1995, 51, 5813-18;
- or in the presence of a mixture of thionyl chloride and of pyridine, according to E.P. 511187;
- or in the presence of ferric chloride, according to Eur. J. Med. Chem. 2006, 31, 635-42.

Various conditions for cyclization of the mixture of intermediate amides can be used in the context of the invention, such as acetic acid or a mixture of trifluoroacetic acid and trifluoroacetic anhydride. It is also particularly advantageous, in the context of the invention, to carry out this type of thermal cyclization in an acidic medium by heating in a microwave reactor.

More particularly, when said heterocycle is of imidazole, oxazole or thiazole type, linked via its 2-position to the 4-position of the carbazole, it is particularly advantageous to form said heterocycle using an acid, an acid chloride, an ester or an aldehyde in the 4-position of an N-protected derivative of carbazole, by carrying out the process according to Scheme (8):

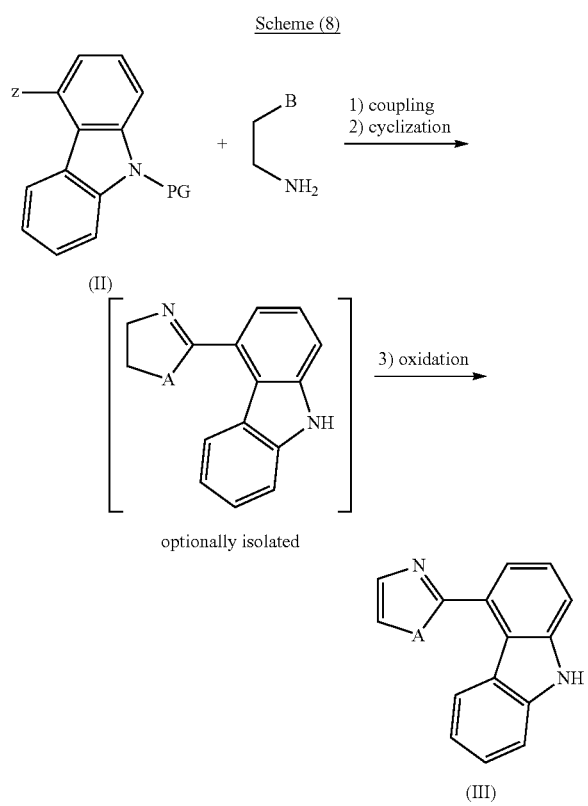

A = NH, O, S
B = AH or a reactive group which is a precursor of A
z = COOH, COCl, COOMe, COOEtCHO In the context of the invention, it is advantageous to protect the nitrogen of a carbazole derivative bearing an acid, ester or aldehyde radical in the 4-position, with a tert-butyloxycarbonyl (Boc) group—through the action of Boc₂O, of BocCl or of BocON in an organic solvent such as dichloromethane or tetrahydrofuran in the presence of an organic or inorganic base—or with a tert-butyldimethylsilyl (TBDMS) group—through the action of tert-butyldimethylsilane chloride (TBDMSCl) in an organic solvent such as dichloromethane or tetrahydrofuran in the presence of an organic or inorganic base—or with a 2-(trimethylsilyl)ethoxymethyl (SEM) group—through the action of 2-(trimethylsilyl)ethoxymethyl chloride (SEMCl) in an organic solvent such as dichloromethane or tetrahydrofuran in the presence of an organic or inorganic base.

In the context of the invention, it is particularly advantageous to carry out the process:

1. in the case where said heterocycle is an imidazole or an imidazoline:
   using a 2-azidoethylamine, according to Tetrahedron, 47(38), 1991, 8177-94,
   using an ethylenediamine, according to Biorg. Med. Chem. Lett. 12(3), 2002, 471-75,
   using glyoxal and aqueous ammonia, according to J. Med. Chem., 46(25), 2003, 5416-27;

2. in the case where said heterocycle is an oxazole or an oxazoline:
   using a 2-azidoethanol, according to J. Org. Chem., 61(7), 1996, 2487-96,
   using a 2-aminoethanol, according to J. Med. Chem. 47(8), 2004, 1969-86 or Khim. Geterosikl. Soed. 1984(7), 881-4,
   using 2-aminoacetaldehyde diethylacetal, according to Heterocycles, 39(2), 1994, 767-78;

3. in the case where said heterocycle is a thiazole or a thiazoline:
   using a 2-chloroethylamine and Lawesson's reagent, according to Helv. Chim. Acta, 88(2), 2005, 187-95,
   using a 2-aminoethanethiol, according to J. Org. Chem. 69(3), 2004, 811-4, or Tetrahedron Lett., 41(18), 2000, 3381-4.

More generally, it is advantageous, in the context of the invention, to form the heterocycle of a product of general formula (III) using a triflate, a brominated or iodinated derivative, a boronic acid or ester, a carboxylic acid, an acid chloride of an ester of a carboxylic acid, or an aldehyde, in the 4-position of a carbazole, by any one of the methods of synthesis known to those skilled in the art, such as those described in Comprehensive Organic Chemistry, by D. H. R. Barton et al. (Pergamon Press) or Advances in Heterocyclic Chemistry (Academic Press) or Heterocyclic Compounds (Wiley Intersciences).

Preparation of the Compounds of General Formula (IV)

A subject of the present invention is thus also the methods for synthesizing the products of formula (IV), in which Z represents a carboxylic ester group, in particular methyl or ethyl ester, or a benzyloxy radical.

The products of general formula (IV) in which Z represents a carboxylic ester or a benzyloxy radical can be advantageously prepared in the context of the invention by reacting a product of general formula (II), in which Z represents a carboxylic ester or a benzyloxy radical, 1) either by carrying out the process according to Scheme (9):

by means of a reaction of aromatic nucleophilic substitution of 2-bromo-4-fluorobenzonitrile or of 4-bromo-5-cyano-2-fluoropyridine or of 5-bromo-2-cyano-3-fluoropyridine, in a solvent such as dimethylformamide (DMF), dimethyl sulphoxide (DMSO) or N-methylpyrrolidone (NMP), after having pretreated the carbazole derivative of general formula (II) with a strong base, for instance sodium hydride, followed by Buchwald-Hartwig amination with an amine R2-NH₂, in which R2 is as defined above, in the presence of a base such as potassium tent-butoxide, and of a palladium(0) derivative, such as "Palladium-dppf", formed from palladium acetate and 1,1'-bis(diphenylphosphino)ferrocene, in a solvent such as toluene.

Scheme (9)

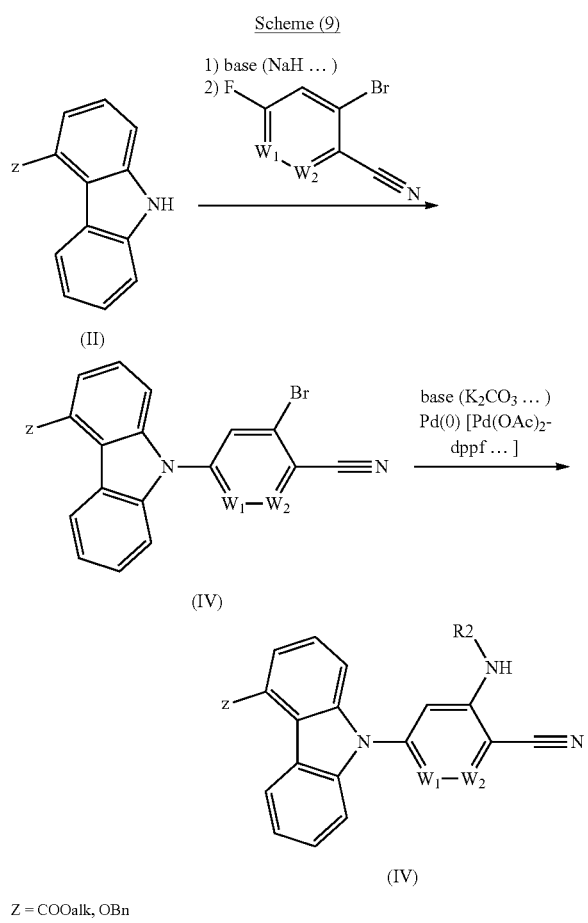

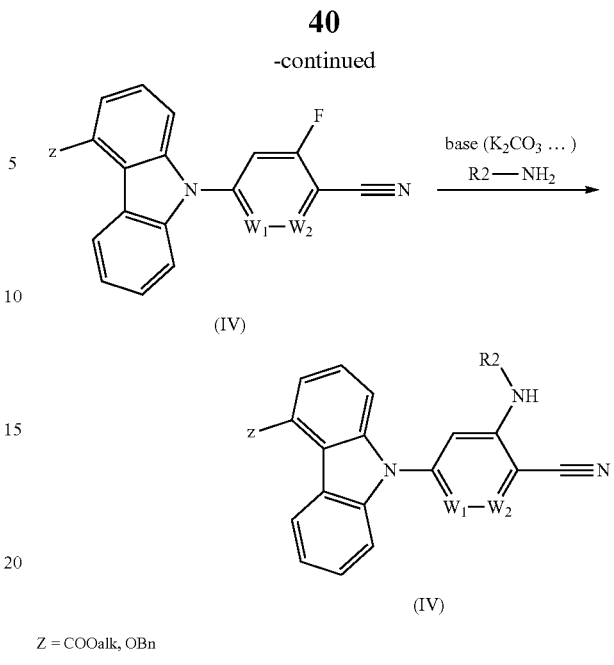

2) or by carrying out the process according to Scheme (10)

by Buchwald-Hartwig reaction between 4-bromo-2-fluorobenzonitrile or 2-bromo-5-cyano-4-fluoropyridine or 5-bromo-2-cyano-3-fluoropyridine and a carbazole of general formula (II), in the presence of a base such as caesium carbonate and a palladium(0) derivative, such as "Palladium-Xanthphos", formed from palladium acetate and 4,5-bis(diphenylphosphino)-9,9-dimethylxanthene, in a solvent such as dioxane, followed by a reaction of aromatic nucleophilic substitution with an amine R2—NH$_2$, in which R2 is as defined above, in the presence of a base such as potassium carbonate, in a solvent such as DMSO.

The products of general formula (IV) in which Z represents a carboxylic acid or a hydroxyl radical, can be respectively prepared by alkaline hydrolysis of the corresponding esters or by hydrogenolysis of the corresponding benzyloxy derivatives, according to the conventional methods known to those skilled in the art.

The products of general formula (IV) in which Z represents a trifluoromethanesulphonyloxy radical can be obtained as described above in Scheme (2), through the action of N-phenylbis(trifluoromethanesulphonimide), in an organic solvent such as dichloromethane, in the presence of an organic base such as triethylamine, on a product of general formula (IV) in which Z represents a hydroxyl radical.

Preparation of the Compounds of General Formula (V)

A subject of the present invention is thus also the methods for synthesizing the products of formula (V), in which Z represents a carboxylic ester group, in particular methyl or ethyl ester, or a benzyloxy radical.

The compounds of general formula (V) in which R is of type A can be prepared by hydrolysis of the cyano radical of a compound of general formula (IV). This hydrolysis can be carried out, advantageously in the context of the invention, through the action of an aqueous solution of hydrogen peroxide, according to Scheme (11):

Scheme (10)

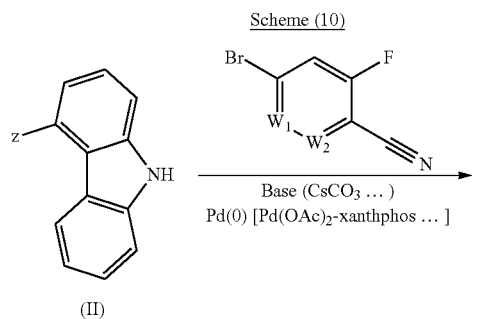

Scheme (11)

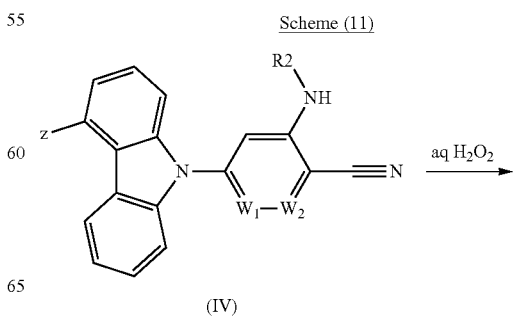

-continued

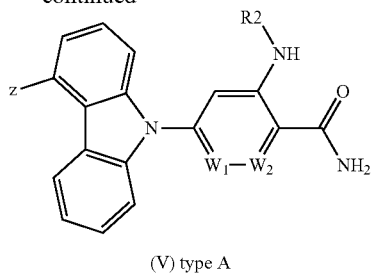

(V) type A

Z = COOalk, COOH, OH, OBn

-continued

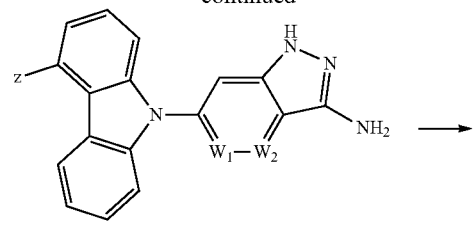

(V) type B
X = NH
Z = OH, OBn

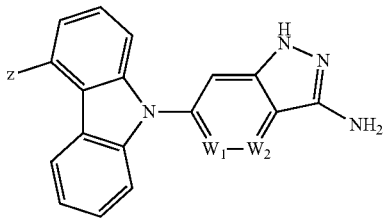

(V) type B
X = NH
Z = COOalk, COOH, OTf, B(OR)$_2$

The compounds of general formula (V) in which R is of type B and X is an NH radical, can be prepared, advantageously in the context of the invention, by means of an aromatic nucleophilic substitution reaction, followed by intramolecular cyclization, through the action of hydrazine hydrate in a polar solvent, such as n-butanol, on a nitrile of general formula (IV), ortho-substituted with a halogen atom, very preferably a fluorine atom, according to Scheme (12):

Scheme (12)

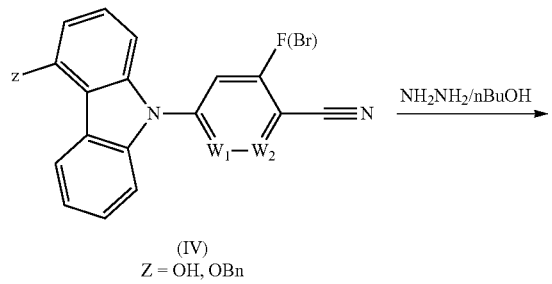

(IV)
Z = OH, OBn

The compounds of general formula (V), in which R is of type B and X is an NR2 radical, with R2 as defined above, can be prepared according to Scheme (13):
  either, advantageously in the context of the invention, through the action of a hydrazine monosubstituted with a radical R2, in a polar solvent, such as n-butanol, on a nitrile of general formula (IV), ortho-substituted with a halogen atom, very preferably a fluorine atom,
  or by N-alkylation of a product of general formula (V) of type B with X=NH. This alkylation can be carried out according to the methods known to those skilled in the art, in particular by treatment with a base such as sodium hydride, followed by the action of a halogenated derivative R2-Hal.

By carrying out the process in this way, a mixture of N1-N3-alkylated regioisomers is generally obtained, it being possible for these regioisomers to be separated using conventional methods known to those skilled in the art.

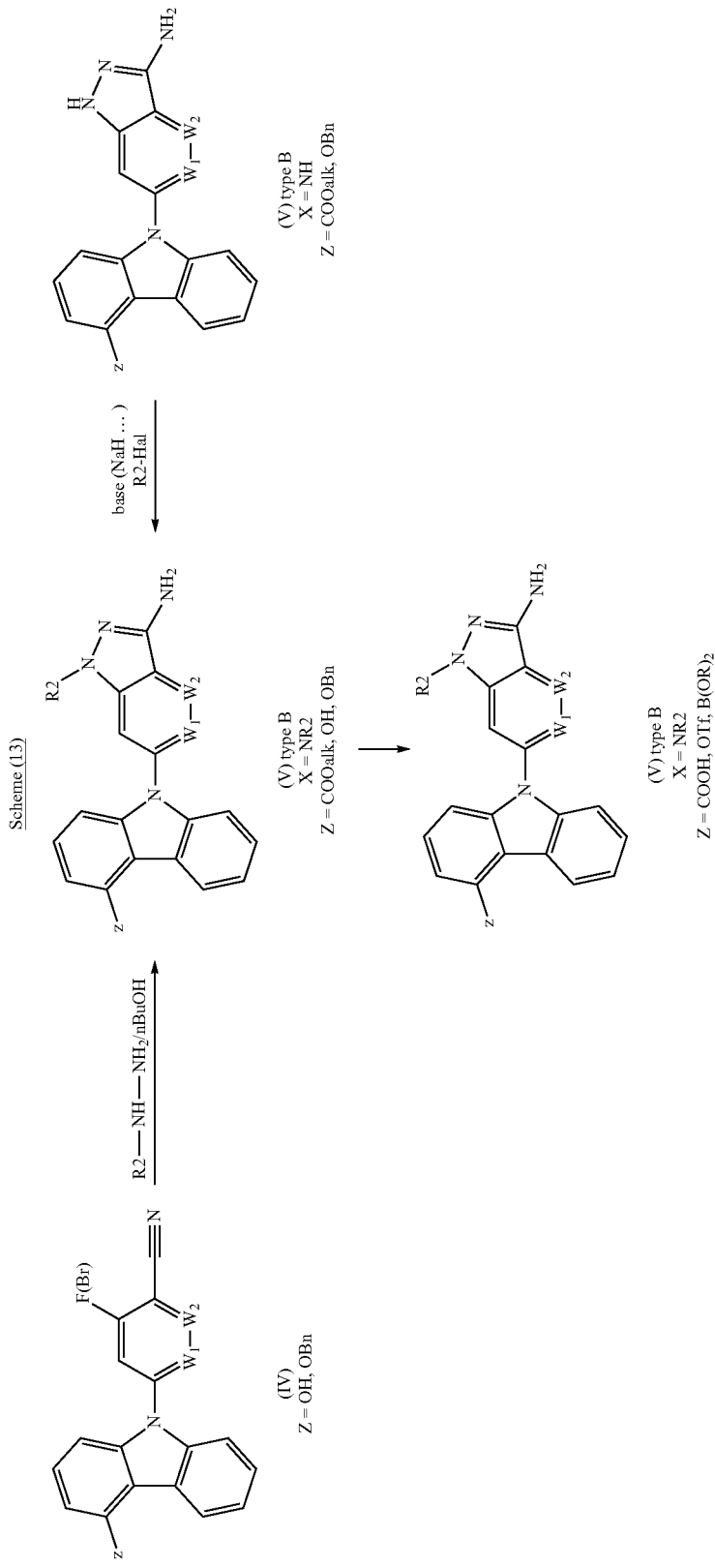
Scheme (13)

The compounds of general formula (V), in which R is of type B and X is an oxygen atom, can be prepared, advantageously in the context of the invention, through the action of an N-protected hydroxylamine, such as N-tert-butyloxycarbonylhydroxylamine, in the presence of a strong base, such as potassium tert-butoxide, on a nitrile of general formula (IV), ortho-substituted with a halogen atom, very preferably a fluorine atom, in a solvent such as DMF, by carrying out the process according to Scheme (14):

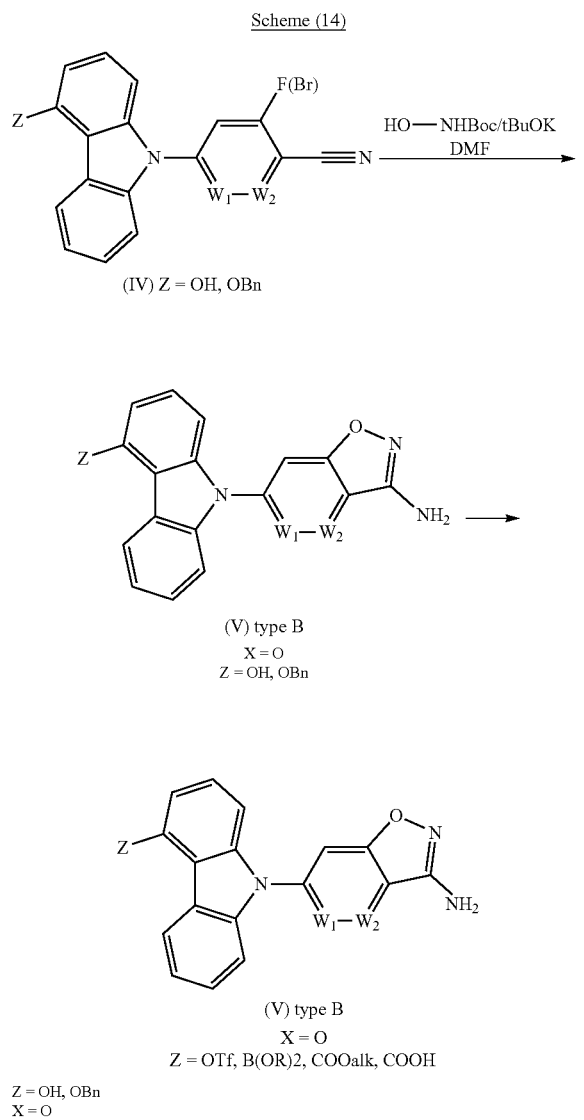

The compounds of general formula (V), in which R is of type B and X is a sulphur atom, can be prepared, advantageously in the context of the invention, through the action of sodium sulphide in a solvent such as DMSO, on a nitrile of general formula (IV), ortho-substituted with a halogen atom, very preferably a fluorine atom, followed by the action of aqueous ammonia in the presence of sodium hypochlorite, by carrying out the process according to Scheme (15), in particular under the conditions described in Biorg. Med. Chem. Lett. (2007), 17(6), 4568:

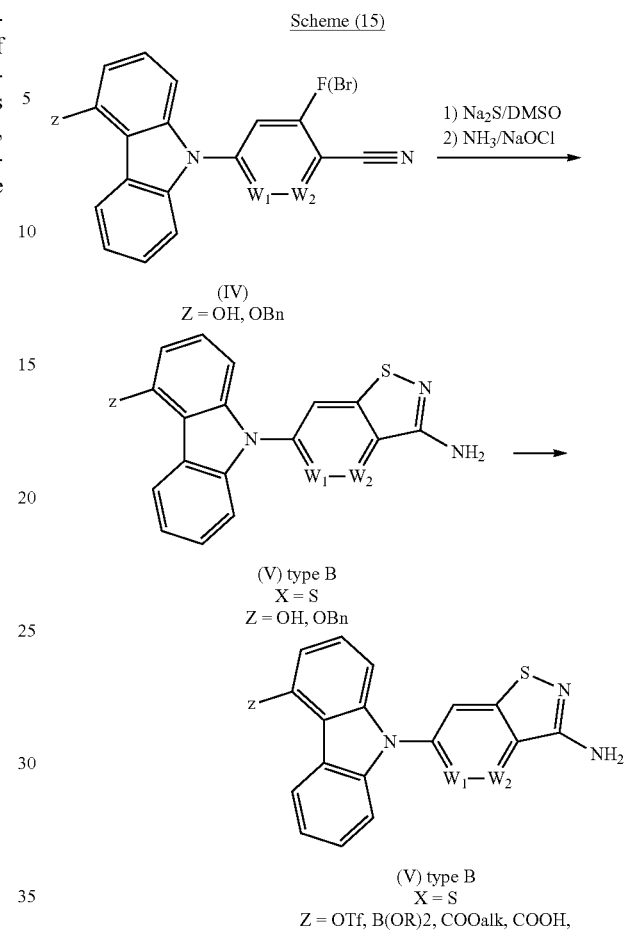

The compounds of general formula (V), in which R is of type C, can be prepared, advantageously in the context of the invention, through the action of hydroxylamine hydrochloride on a nitrile of general formula (IV), ortho-substituted with a halogen atom, very preferably a fluorine atom, by carrying out the process according to Scheme (16), in particular under the conditions described in Zeitschrift für Chemie (1984), 24(7), 254:

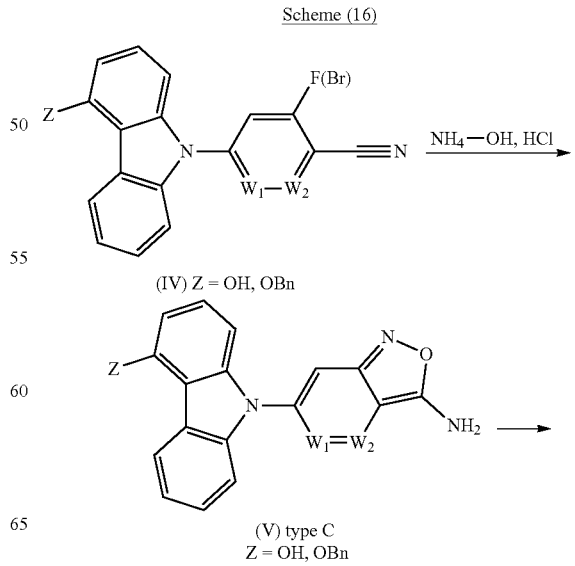

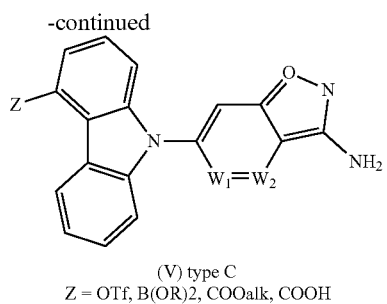

(V) type C
Z = OTf, B(OR)2, COOalk, COOH

The compounds of general formula (V), in which R is of type D, with W3 being a nitrogen atom, can be prepared, advantageously in the context of the invention, through the action of aqueous ammonia on a nitrile of general formula (IV), ortho-substituted with a halogen atom, very preferably a fluorine atom, followed by the action of a mixture of ethyl orthoformate and ammonium acetate, by carrying out the process according to Scheme (17), in particular under the conditions described in J. Het. Chem. (2006), 43(4), 913:

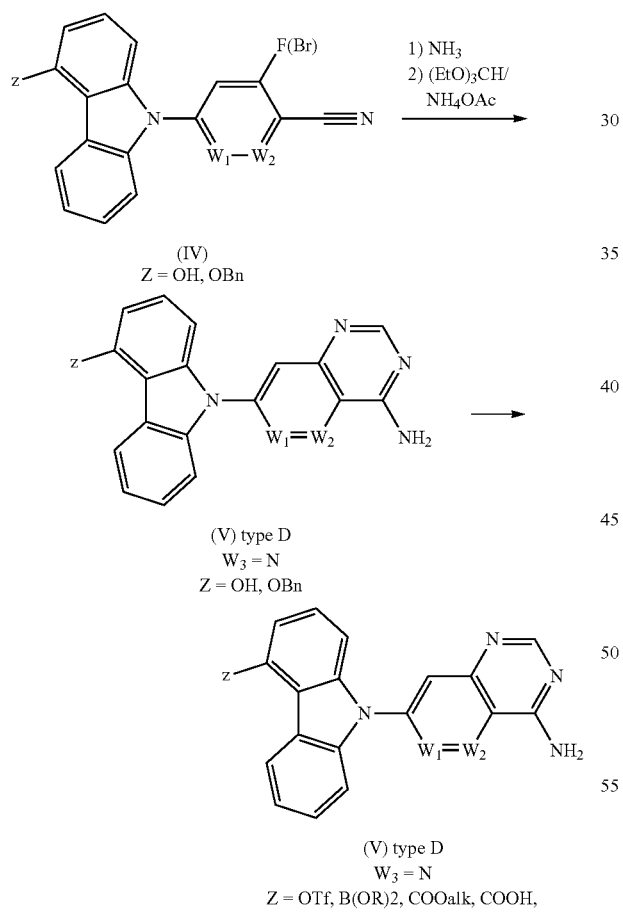

ortho-substituted with a bromine atom, so as to give an acetylenic intermediate, which is then successively treated with sodium ethoxide in ethanol, and then with a solution of hydrogen peroxide in an alkaline medium and, finally, heated in the presence of para-toluenesulphonic acid, by carrying out the process according to general Scheme (18), in particular under the conditions described in Chem. Pharm. Bull. (1986), 34, 2760.

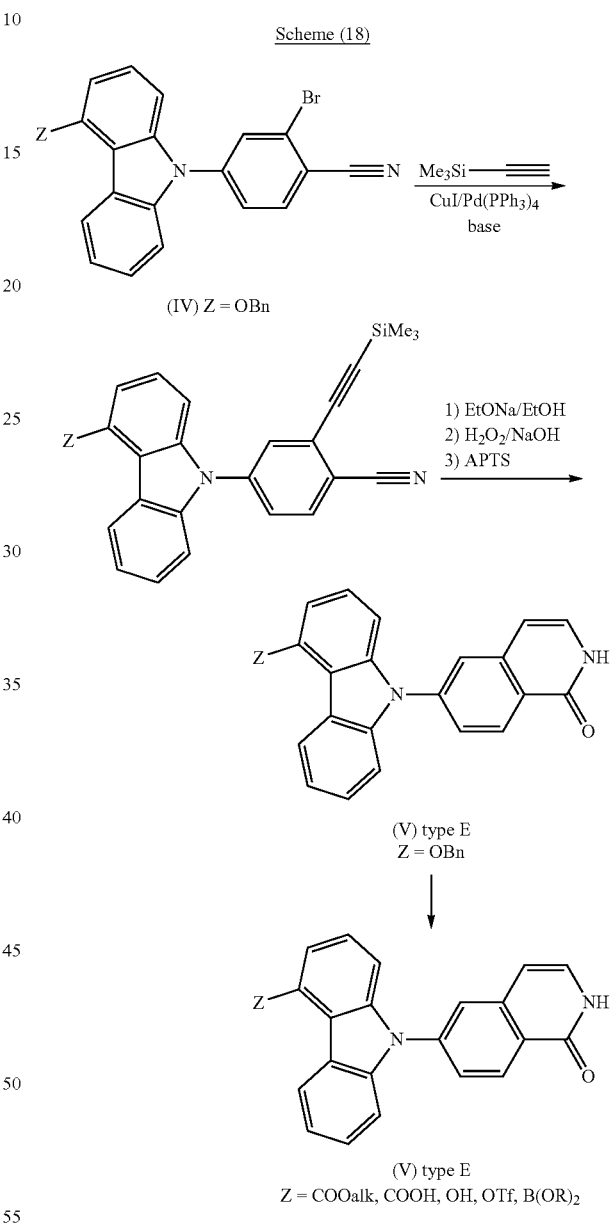

The compounds of general formula (V), in which R is of type D, with $W_1$, $W_2$ and $W_3$=CH, can be prepared, advantageously in the context of the invention, through the action of phosphorus trichloride and then of acetamide, at a temperature close to 180° in the presence of a base such as potassium carbonate, on a product of general formula (V) of type E, by carrying out the process according to Scheme (19), in particular under the conditions described in Bioorg. Med. Chem. (2006), 14(20), 6832.

The compounds of general formula (V), in which R is of type E, can be prepared, advantageously in the context of the invention, through the action of trimethylsilylacetylene, in the presence of a base, such as triethylamine or n-butylamine, in the presence of cuprous iodide and tetrakis(triphenylphosphine)palladium, on a compound of general formula (IV)

Scheme (19)

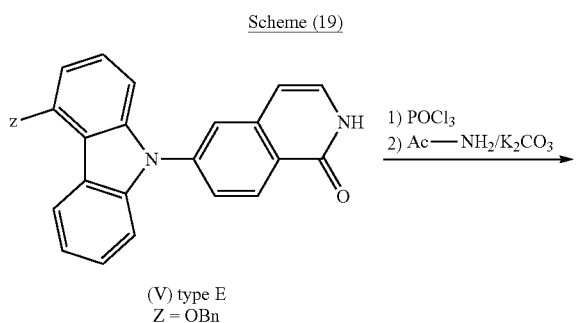

(V) type E
Z = OBn

1) POCl₃
2) Ac—NH₂/K₂CO₃ one or more radicals R1, as defined above, it is particularly advantageous according to the invention to prepare the compounds of general formula (VI) by coupling:

either a product of general formula (IV), in which Z represents a trifluoromethylsulphonyloxycarbazole radical, with a heterocyclic boronic derivative, which may be an acid or an ester, such as the methyl, n-butyl, isopropyl or pinacol ester, under the Suzuki reaction conditions, in the presence of a palladium(0) derivative as catalyst, or a product of general formula (IV) in which Z represents a boronic derivative, which may be an acid or ester, such as the methyl, n-butyl, isopropyl or pinacol ester, with a brominated or iodinated heterocyclic derivative, by carrying out the process according to Scheme (20):

Scheme (20)

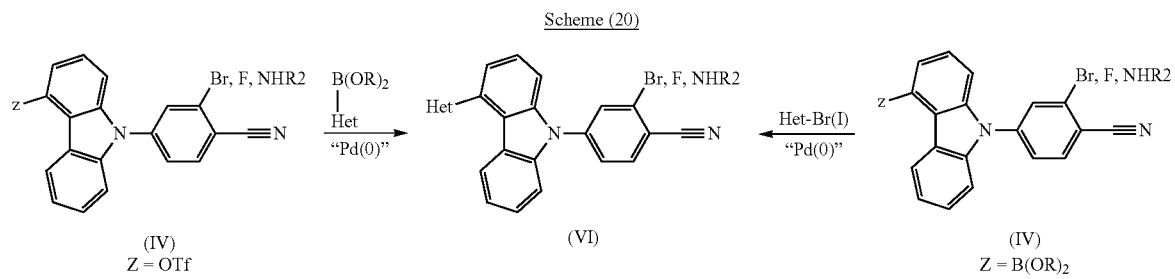

(IV)
Z = OTf (VI)

(IV)
Z = B(OR)₂

-continued

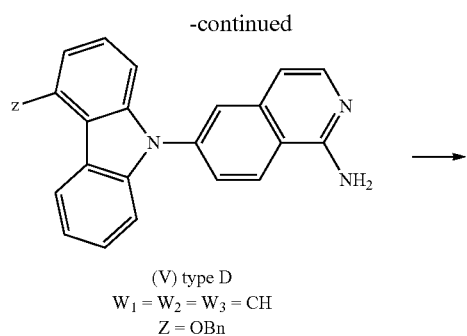

(V) type D
W₁ = W₂ = W₃ = CH
Z = OBn

More particularly, when Het is a heterocycle of benzimidazole or azabenzimidazole type, or alternatively of benzoxazole or azabenzoxazole type, or benzothiazole or azabenzothiazole type, linked via its 2-position to the 4-position of the carbazole, it is particularly advantageous to form said heterocycle by coupling a derivative of ortho-phenylenediamine or of diaminopyridine, or else of ortho-aminophenol, of ortho-aminothiophenol, or of aminohydroxypyridine or of aminomercaptopyridine which is ortho-disubstituted, with a derivative of general formula (IV) in which Z represents an acid or an ester, in particular a methyl or ethyl ester, by carrying out the process according to Scheme (21):

Scheme (21)

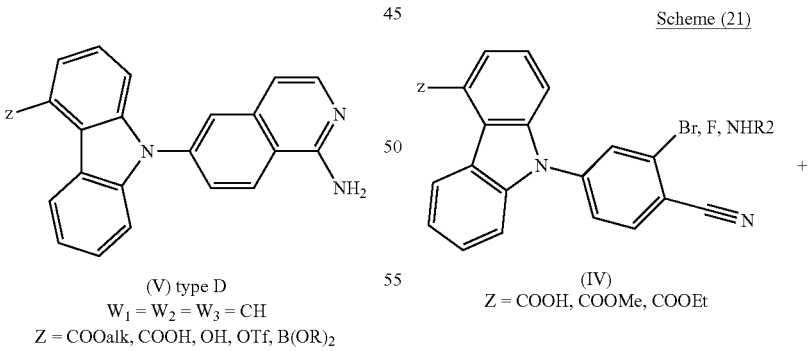

(V) type D
W₁ = W₂ = W₃ = CH
Z = COOalk, COOH, OH, OTf, B(OR)₂

(IV)
Z = COOH, COOMe, COOEt

Preparation of the Compounds of General Formula (VI)

A subject of the present invention is thus also the methods for synthesizing the products of formula (VI).

A) From Product of General Formula (IV)

More particularly, when Het does not represent a heterocyle of imidazol-2-yl, triazol-3-yl, benzimidazol-2-yl or azabenzimidazol-2-yl type, and is optionally substituted with

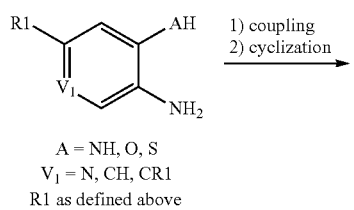

1) coupling
2) cyclization

A = NH, O, S
V₁ = N, CH, CR1
R1 as defined above

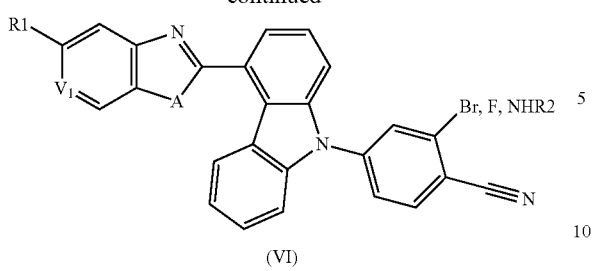

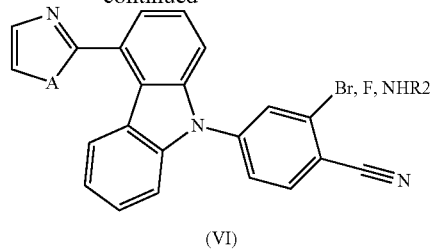

(VI)

When a product of general formula (IV) in which Z is an acid is used, it is particularly advantageous to activate this acid using a coupling agent known to those skilled in the art, such as 1-(3-dimethylaminopropyl)-3-ethylcarbodiimide hydrochloride (EDCI) in the presence of 1-hydroxybenzotriazole (HOBT), or of O-((ethoxycarbonyl)cyanomethyleneamino)-N,N, N',N'-tetramethyluronium tetrafluoroborate (TOTU).

When a product of general formula (IV) in which Z is a methyl or ethyl ester is used, it is advantageous, in the context of the invention, to carry out the process in the presence of trimethylaluminium in a halogenated organic solvent, such as dichloromethane or dichloroethane.

Various conditions for cyclization of the mixture of intermediate amides can be used in the context of the invention, such as acetic acid or a mixture of trifluoroacetic acid and trifluoroacetic anhydride. It is also particularly advantageous, in the context of the invention, to carry out this type of thermal cyclization in an acidic medium by heating in a microwave reactor.

More particularly, when said heterocycle is of the type imidazole, oxazole or thiazole, linked via its 2-position to the 4-position of the carbazole, it is particularly advantageous to form said heterocycle using an acid or an ester, by carrying out the process according to Scheme (22):

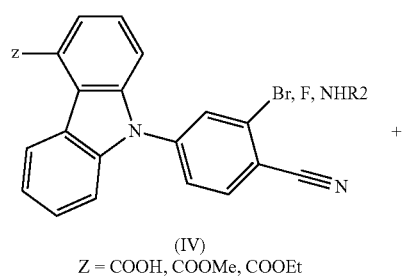

(IV)
Z = COOH, COOMe, COOEt

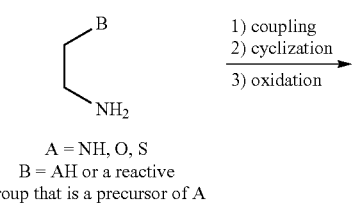

A = NH, O, S
B = AH or a reactive group that is a precursor of A 1) coupling
2) cyclization
3) oxidation In the context of the invention it is particularly advantageous to carry out the process:

1. in the case where said heterocycle is an imidazole or an imidazoline:
    using a 2-azidoethylamine, according to Tetrahedron, 47(38), 1991, 8177-94,
    using an ethylenediamine, according to Biorg. Med. Chem. Lett. 12(3), 2002, 471-75,
    using glyoxal and aqueous ammonia, according to J. Med. Chem., 46(25), 2003, 5416-27;
2. in the case where said heterocycle is an oxazole or an oxazoline:
    using a 2-azidoethanol, according to J. Org. Chem., 61(7), 1996, 2487-96,
    using a 2-aminoethanol, according to J. Med. Chem. 47(8), 2004, 1969-86 or Khim. Geterosikl. Soed. 1984(7), 881-4,
    using 2-aminoacetaldehyde diethylacetal, according to Heterocycles, 39(2), 1994, 767-78;
3. in the case where said heterocycle is a thiazole or a thiazoline:
    using a 2-chloroethylamine and Lawesson's reagent, according to Helv. Chim. Acta, 88(2), 2005, 187-95,
    using a 2-aminoethanethiol, according to J. Org. Chem. 69(3), 2004, 811-4, or Tetrahedron Lett, 41(18), 2000, 3381-4.

More generally, it is advantageous, in the context of the invention, to form the heterocycle of a product of general formula (III) using a triflate, a carboxylic acid or a carboxylic acid ester, by any one of the methods of synthesis known to those skilled in the art, such as those described in Comprehensive Organic Chemistry, by D. H. R. Barton et al. (Pergamon Press) or Advances in Heterocyclic Chemistry (Academic Press) or Heterocyclic Compounds (Wiley Intersciences).

B) From Product of General Formula (III)

More particularly, when Het does not represent a heterocycle of imidazol-2-yl, triazol-3-yl, benzimidazol-2-yl or azabenzimidazol-2-yl type, and is optionally substituted with one or more radicals R1, as defined above, it is particularly advantageous according to the invention to prepare the compounds of general formula (VI), from the products of general formula (III):

1) either by carrying out the process according to Scheme (23):
    by means of a reaction of aromatic nucleophilic substitution of 2-bromo-4-fluorobenzonitrile or of 4-bromo-5-cyano-2-fluoropyridine or of 5-bromo-2-cyano-3-fluoropyridine, in a solvent such as dimethylformamide (DMF), dimethyl sulphoxide (DMSO) or N-methylpyrrolidone (NMP), after having pretreated the carbazole derivative of general formula (III) with a strong base, for instance sodium hydride,
    optionally followed by Buchwald-Hartwig amination with an amine R2-NH₂, in which R2 is as defined above, in the presence of a base such as potassium tert-butoxide, and of a palladium(0) derivative, such as "Palladium-dppf", formed from palladium acetate and 1,1'-bis(diphenylphosphino)ferrocene, in a solvent such as toluene.

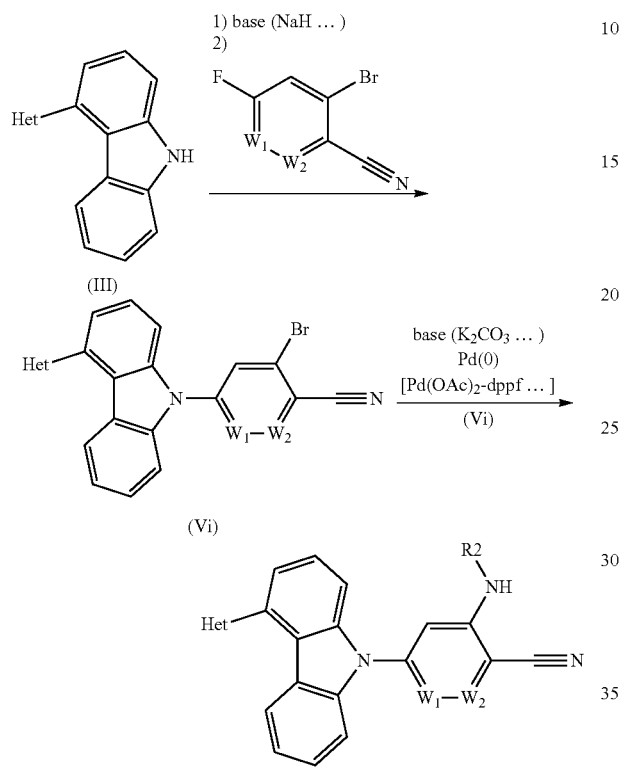

Scheme (23)

(III)

(Vi)

2) or by carrying out the process according to Scheme (24) by Buchwald-Hartwig reaction between 4-bromo-2-fluorobenzonitrile or 2-bromo-5-cyano-4-fluoropyridine or 5-bromo-2-cyano-3-fluoropyridine, and a carbazole of general formula (III), in the presence of a base such as caesium carbonate and a palladium(0) derivative, such as "Palladium-Xanthphos" formed from palladium acetate and 4,5-bis(diphenylphosphino)-9,9-dimethylxanthene, in a solvent such as dioxane, optionally followed by an aromatic nucleophilic substitution reaction with an amine R2-NH$_2$, in which R2 is as defined above, in the presence of a base such as potassium carbonate, in a solvent such as DMSO.

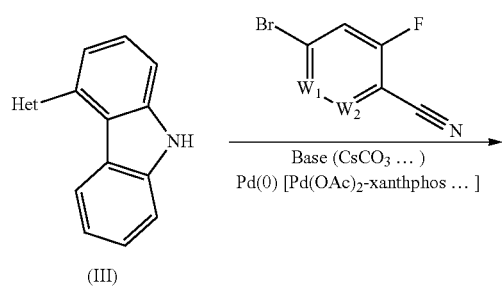

Scheme (24)

(III)

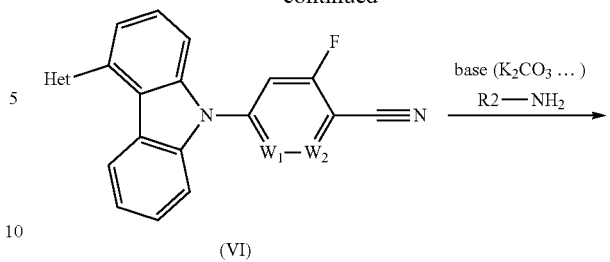

(VI)

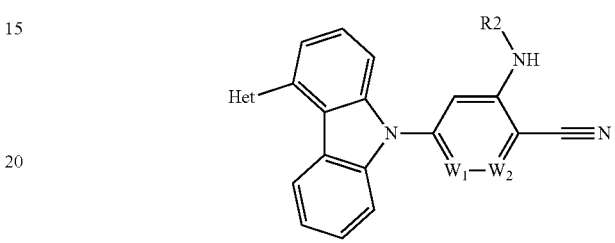

(VI)

When Het represents a heterocyle of imidazol-2-yl, triazol-3-yl, benzimidazol-2-yl or azabenzimidazol-2-yl type, and is optionally substituted with one or more radicals R1, as defined above, it is also advantageous according to the invention to prepare the compounds of general formula (VI), from the products of general formula (III), by carrying out the process according to the methods described above in Schemes (23) and (24). However, in these cases, it is advisable to protect, prior to the Buchwald-Hartwig and/or aromatic nucleophilic substitution reaction, the NH-type nitrogen of the heterocycle Het, with a protective group such as a Boc, TBDMS or SEM radical, according to any one of the methods described above or known to those skilled in the art. Said protective group will be either spontaneously cleaved during the Buchwald-Hartwig and/or aromatic nucleophilic substitution reactions, or cleaved after these reactions, using any one of the methods known to those skilled in the art.

Preparation of the Compounds of General Formula (I)

A subject of the present invention is thus also the methods for synthesizing the products of formula (I).

A) From the Products of General Formula (III)

It is particularly advantageous according to the invention to prepare the compounds of general formula (I), from the products of general formula (III), by Buchwald-Hartwig reaction between a heterocyclic carbazole derivative of general formula (III) and an aromatic derivative R—Br, R—I or R-OTf, in which R is as described above. The process is then carried out according to Scheme (25), in the presence of a base such as caesium carbonate and a palladium(0) derivative, such as "Palladium-Xanthphos", formed from palladium acetate and 4,5-bis(diphenylphosphino)-9,9-dimethylxanthene, in a solvent such as dioxane:

Scheme (25)

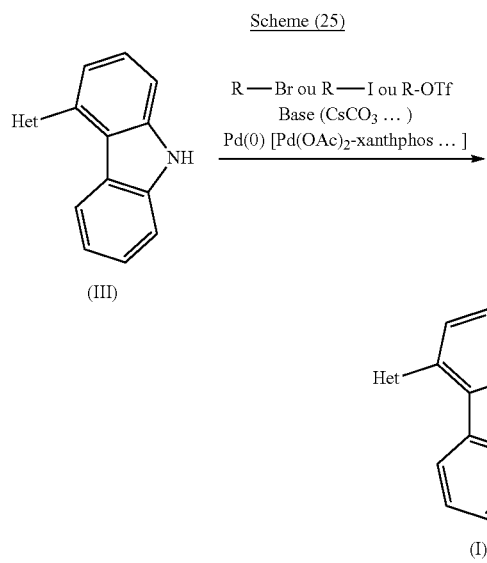

B) From the Products of General Formula (V)

More particularly, when Het does not represent a heterocycle of imidazol-2-yl, triazol-3-yl, benzimidazol-2-yl or azabenzimidazol-2-yl type, and is optionally substituted with one or more radicals R1, as defined above, it is particularly advantageous according to the invention to prepare the compounds of general formula (I) by coupling:

either a product of general formula (V), in which Z represents a trifluoromethylsulphonyloxycarbazole radical, with a heterocyclic boronic derivative, which is an acid or an ester, such as the methyl, n-butyl, isopropyl or pinacol ester, under the Suzuki reaction conditions, in the presence of a palladium (0) derivative as catalyst, or a product of general formula (V), in which Z represents a boronic derivative, which is an acid or an ester, such as the methyl, n-butyl, isopropyl or pinacol ester, with a brominated or iodinated heterocyclic derivative, by carrying out the process according to Scheme (26):

Scheme (26)

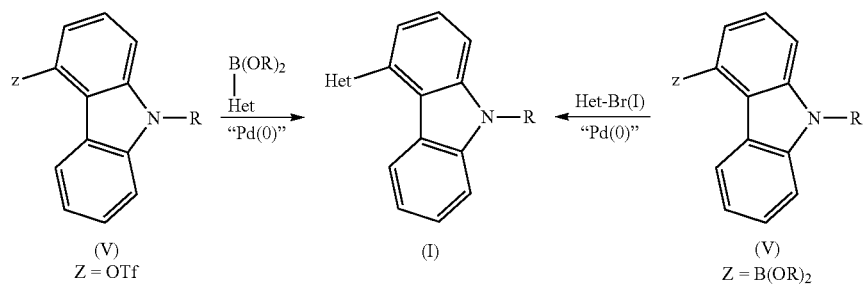

More particularly, when the heterocycle Het is of the type benzimidazole or azabenzimidazole, or alternatively of the type benzoxazole or azabenzoxazole, or benzothiazole or azabenzothiazole, linked via its 2-position to the 4-position of the carbazole, it is particularly advantageous to form said heterocycle by coupling a derivative of ortho-phenylenediamine or of diaminopyridine, or else of ortho-aminophenol, of ortho-aminothiophenol or of aminohydroxypyridine or of aminomercaptopyridine which is ortho-disubstituted, with a derivative of general formula (V) in which Z represents an acid or an ester, in particular a methyl or ethyl ester, by carrying out the process according to Scheme (27):

Scheme (27)

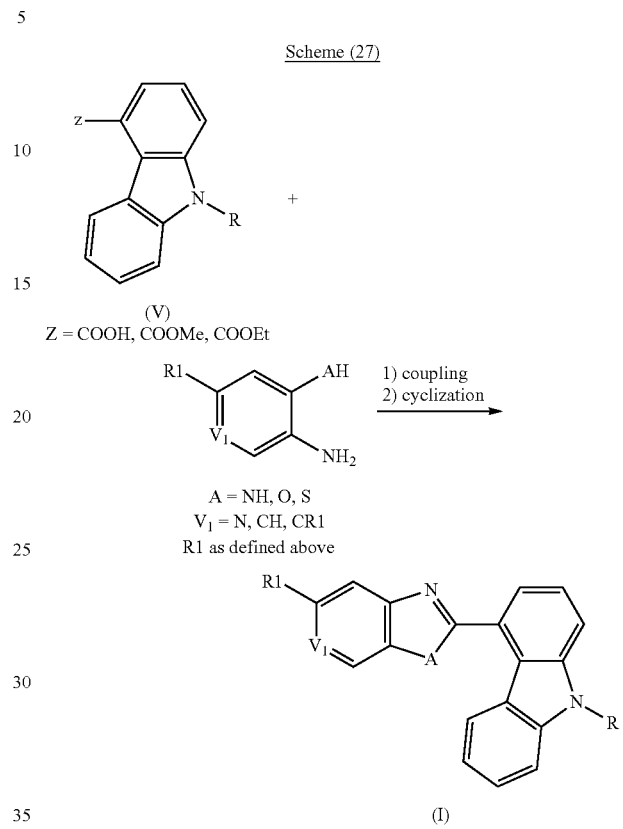

When a product of general formula (V) in which Z is an acid is used, it is particularly advantageous to activate this acid using a coupling agent known to those skilled in the art, such as 1-(3-dimethylaminopropyl)-3-ethylcarbodiimide hydrochloride (EDCI) in the presence of 1-hydroxybenzotriazole (HOBT) or of O-((ethoxycarbonyl)cyanomethyleneamino)-N,N,N',N'-tetramethyluronium tetrafluoroborate (TOTU).

When a product of general formula (V) in which Z is a methyl or ethyl ester is used, it is advantageous, in the context of the invention, to carry out the process in the presence of trimethylaluminium in a halogenated organic solvent, such as dichloromethane or dichloroethane.

Various conditions for cyclization of the mixture of intermediate amides can be used in the context of the invention, such as acetic acid or a mixture of trifluoroacetic acid and trifluoroacetic anhydride. It is also particularly advantageous, in the context of the invention, to carry out this type of thermal cyclization in an acidic medium by heating in a microwave reactor.

More particularly, when the heterocycle Het is of the type imidazole, oxazole or thiazole, linked via its 2-position to the 4-position of the carbazole, it is particularly advantageous to form said heterocycle using an acid or an ester, by carrying out the process according to Scheme (28):

Scheme (28)

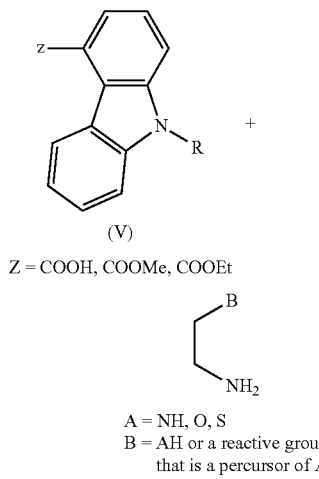

(V)
Z = COOH, COOMe, COOEt

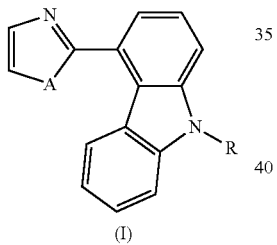

A = NH, O, S
B = AH or a reactive group that is a percursor of A 1) coupling
2) cyclization
3) oxidation (I)

In the context of the invention, it is particularly advantageous to carry out the process:
1. in the case where said heterocycle is an imidazole or an imidazoline:
   using a 2-azidoethylamine, according to Tetrahedron, 47(38), 1991, 8177-94,
   using an ethylenediamine, according to Biorg. Med. Chem. Lett. 12(3), 2002, 471-75,
   using glyoxal and aqueous ammonia, according to J. Med. Chem., 46(25), 2003, 5416-27;
2. in the case where said heterocycle is an oxazole or an oxazoline:
   using a 2-azidoethanol, according to J. Org. Chem., 61(7), 1996, 2487-96,
   using a 2-aminoethanol, according to J. Med. Chem. 47(8), 2004, 1969-86 or Khim. Geterosikl. Soed. 1984(7), 881-4,
   using 2-aminoacetaldehyde diethylacetal, according to Heterocycles, 39(2), 1994, 767-78;
3. in the case where said heterocycle is a thiazole or a thiazoline:
   using a 2-chloroethylamine and Lawesson's reagent, according to Helv. Chim. Acta, 88(2), 2005, 187-95,
   using a 2-aminoethanethiol, according to J. Org. Chem. 69(3), 2004, 811-4, or Tetrahedron Lett., 41(18), 2000, 3381-4.

More generally, it is advantageous, in the context of the invention, to form the heterocycle of a product of general formula (I) using a triflate, a carboxylic acid or a carboxylic acid ester, by means of any one of the methods of synthesis known to those skilled in the art, such as those described in Comprehensive Organic Chemistry, by D. H. R. Barton et al. (Pergamon Press) or Advances in Heterocyclic Chemistry (Academic Press) or Heterocyclic Compounds (Wiley Intersciences).

C) From a Product of General Formula (VI)

The compounds of general formula (I) in which R is of type A can be prepared by hydrolysis of the cyano radical of a compound of general formula (VI). This hydrolysis can be carried out, advantageously in the context of the invention, through the action of an aqueous solution of hydrogen peroxide in an alkaline medium in a mixture of DMSO and ethanol, according to Scheme (29):

Scheme (29)

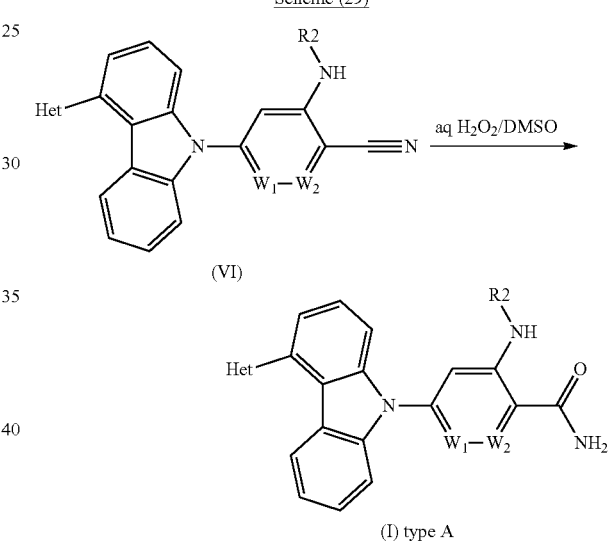

(I) type A

The compounds of general formula (I) in which R is of type B and X is an NH radical can be prepared, advantageously in the context of the invention, by means of an aromatic nucleophilic substitution reaction, followed by intramolecular cyclization, through the action of hydrazine hydrate in a polar solvent, such as n-butanol, on a nitrile of general formula (VI), ortho-substituted with a halogen atom, very preferably a fluorine atom, according to Scheme (30):

Scheme (30)

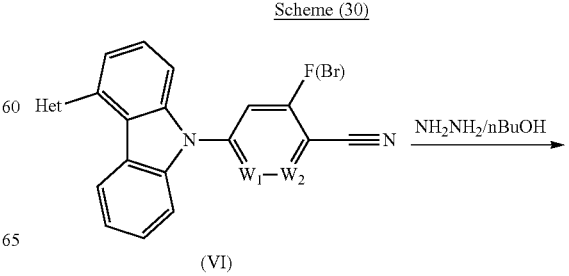

(VI)

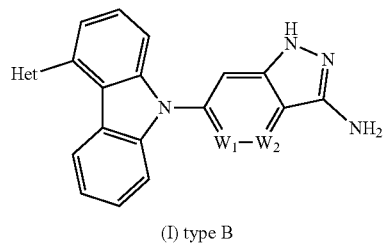

(I) type B
X = NH

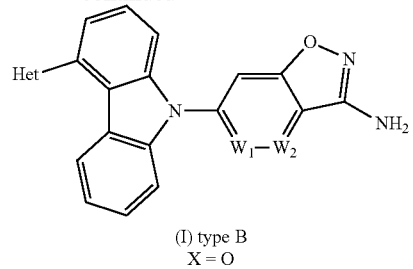

(I) type B
X = O

The compounds of general formula (I), in which R is of type B and X is an NR2 radical, with R2 as defined above, can be prepared, advantageously in the context of the invention, according to Scheme (31), through the action of a hydrazine monosubstituted with a radical R2, in a polar solvent, such as n-butanol, on a nitrile of general formula (VI), ortho-substituted with a halogen atom, very preferably a fluorine atom.

The compounds of general formula (I), in which R is of type B and X is a sulphur atom, can be prepared, advantageously in the context of the invention, through the action of sodium sulphide in a solvent such as DMSO, on a nitrile of general formula (VI), ortho-substituted with a halogen atom, very preferably a fluorine atom, followed by the action of aqueous ammonia in the presence of sodium hypochlorite, by carrying out the process according to Scheme (33), in particular under the conditions described in Biorg. Med. Chem. Lett. (2007), 17(6), 4568:

Scheme (31)

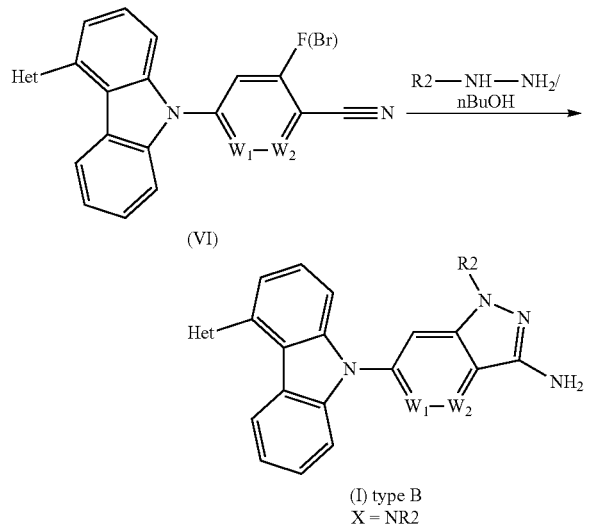

Scheme (33)

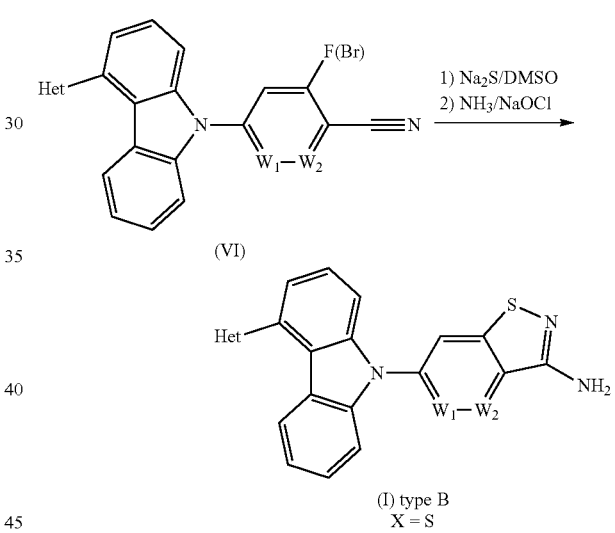

The compounds of general formula (I), in which R is of type B and X is an oxygen atom, can be prepared, advantageously in the context of the invention, through the action of an N-protected hydroxylamine, such as N-tert-butyloxycarbonylhydroxylamine, in the presence of a strong base, such as potassium tert-butoxide, on a nitrile of general formula (VI), ortho-substituted with a halogen atom, very preferably a fluorine atom, in a solvent such as DMF, by carrying out the process according to Scheme (32):

The compounds of general formula (I), in which R is of type C, can be prepared, advantageously in the context of the invention, through the action of hydroxylamine hydrochloride on a nitrile of general formula (VI), ortho-substituted with a halogen atom, very preferably a fluorine atom, by carrying out the process according to Scheme (34), in particular under the conditions described in Zeitschrift far Chemie (1984), 24(7), 254:

Scheme (32)

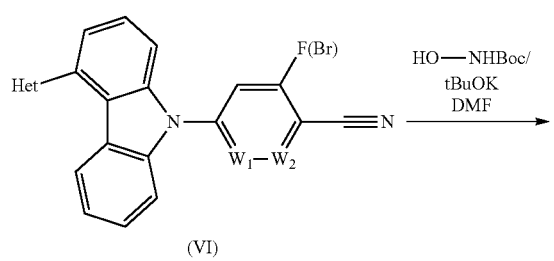

Scheme (34)

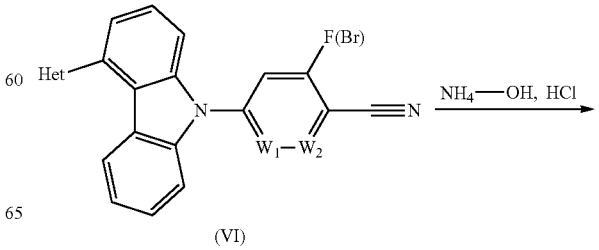

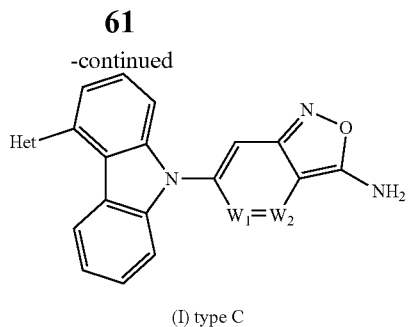

(I) type C

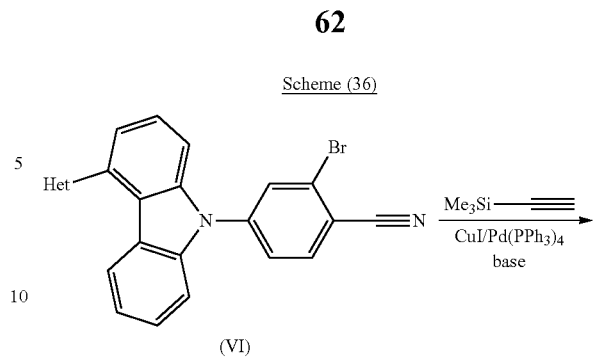

(VI)

The compounds of general formula (I), in which R is of type D, with W3 being a nitrogen atom, can be prepared, advantageously in the context of the invention, through the action of aqueous ammonia on a nitrile of general formula (VI), ortho-substituted with a halogen atom, very preferably a fluorine atom, followed by the action of a mixture of ethyl orthoformate and ammonium acetate, by carrying out the process according to Scheme (35), in particular under the conditions described in J. Het. Chem. (2006), 43(4), 913:

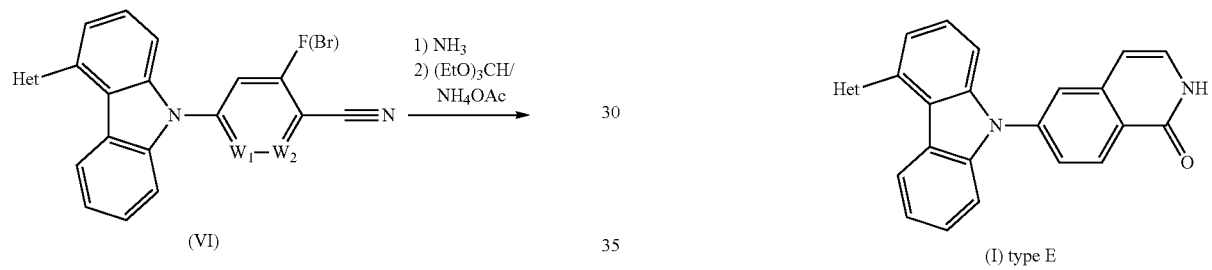

(I) type E

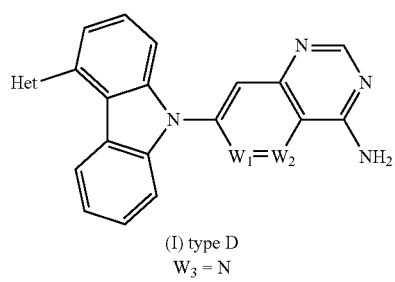

(I) type D
W₃ = N

The compounds of general formula (I), in which R is of type E, can be prepared, advantageously in the context of the invention, through the action of trimethylsilylacetylene, in the presence of a base, such as triethylamine or n-butylamine, in the presence of cuprous iodide and tetrakis(triphenylphosphine)-palladium, on a compound of general formula (VI), ortho-substituted with a bromine atom, so as to give an acetylenic intermediate, which is then successively treated with sodium ethoxide in ethanol, then with a solution of hydrogen peroxide in an alkaline medium and, finally, heated in the presence of para-toluenesulphonic acid, by carrying out the process according to general Scheme (36), in particular under the conditions described in Chem. Pharm. Bull. (1986), 34, 2760.

D) From Products of General Formula (I)

The compounds of general formula (I), in which R is of type B and X is an NR2 radical, with R2 as defined above, and in which Het does not represent a heterocycle of imidazol-2-yl, triazol-3-yl, benzimidazol-2-yl or azabenzimidazol-2-yl type, can be prepared according to Scheme (37) by N-alkylation of a product of general formula (I) of type B with X=NH. This alkylation can be carried out according to the methods known to those skilled in the art, in particular by treatment with a base such as sodium hydride, followed by the action of a halogenated derivative R2-Hal. By carrying out the process in this way, a mixture of N1- and N3-alkylated regioisomers is generally obtained, it being possible for said regioisomers to be separated using the conventional methods known to those skilled in the art.

Scheme (37)

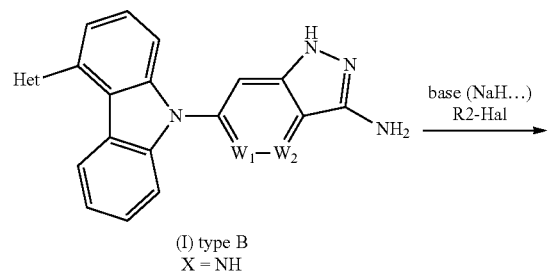

(I) type B
X = NH

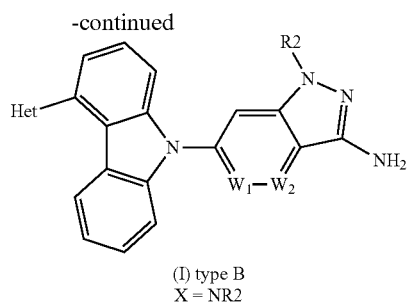

(I) type B
X = NR2

The compounds of general formula (I), in which R is of type A', and in which Y represents O—PO$_3$H$_2$, O—PO$_3$Na$_2$, O—SO$_3$H$_2$, O—SO$_3$Na$_2$, O—CH$_2$—PO$_3$H$_2$, O—CH$_2$—PO$_3$Na$_2$, O—CO-alkyl, including in particular O—CO—CH$_2$—CO$_2$tBu, O—CO—CH$_2$—NHMe, O—CO—CH$_2$—N(Me)$_2$, and the ester derivatives of amino acids of the natural or unnatural series and the ester derivatives of dipeptides or of tripeptides, and more particularly O—CO-glycine, O—CO-alanine, O—CO-serine, O—CO-lysine, O—CO-arginine, O—CO-glycine-lysine or O—CO-alanine-lysine, and n represents 2 or 3, can be prepared from the compounds of general formula (I) in which R is of type A' with Y representing OH, by carrying out the process according to Scheme (38).

Scheme (38)

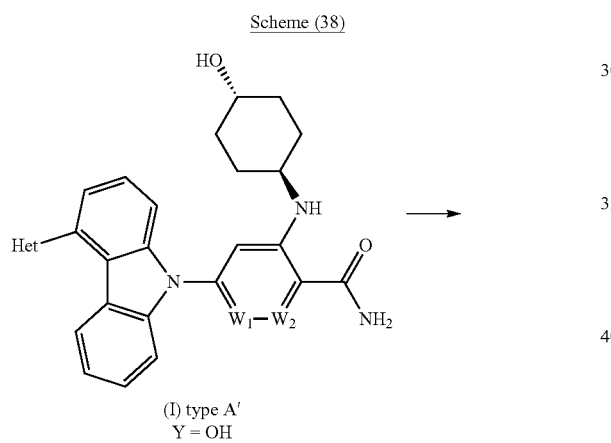

(I) type A'
Y = OH

Y = O—PO$_3$H(Na)$_2$, O—SO$_3$H(Na)$_2$,
O—CH$_2$—PO$_3$H(Na)$_2$
O—CO-alkyl,
including O—CO—CH$_2$—CO$_2$tBu,
O—CO—CH$_2$—NHMe, O—CO—CH$_2$—N(Me)$_2$
and the esters of amino acids, of dipeptides or of tripeptides The compounds of general formula (I), in which R is of type B', and in which Y represents O—PO$_3$H$_2$, O—PO$_3$Na$_2$, O—SO$_3$H$_2$, O—SO$_3$Na$_2$, O—CH$_2$—PO$_3$H$_2$, O—CH$_2$—PO$_3$Na$_2$, O—CO-alkyl, including in particular O—CO—CH$_2$—CO$_2$tBu, O—CO—CH$_2$—NHMe, O—CO—CH$_2$—N(Me)$_2$ and the ester derivatives of the amino acids of the natural or unnatural series and the ester derivatives of dipeptides or of tripeptides, and more particularly O—CO-glycine, O—CO-alanine, O—CO-serine, O—CO-lysine, O—CO-arginine, O—CO-glycine-lysine, O—CO-alanine-lysine, and n represents 2 or 3, can be prepared from the compounds of general formula (I) in which R is of type B' with Y being OH, by carrying out the process according to Scheme (39).

Scheme (39)

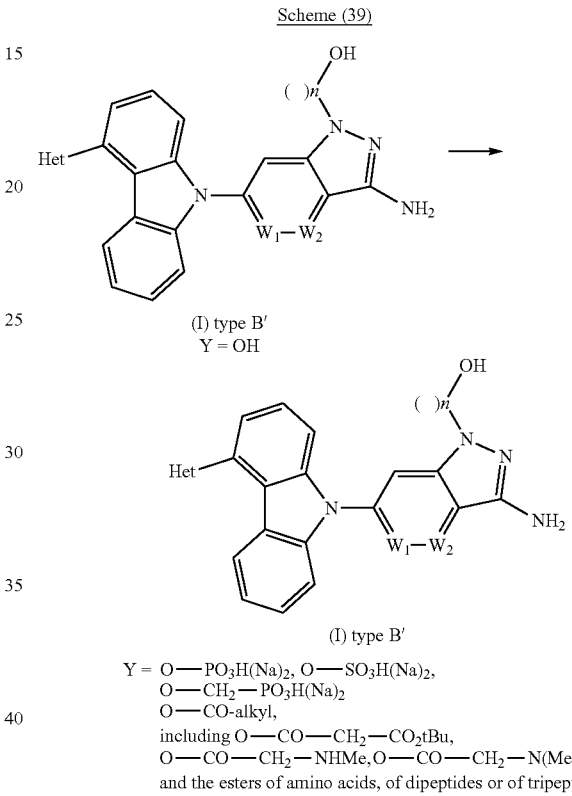

(I) type B'
Y = OH (I) type B'

Y = O—PO$_3$H(Na)$_2$, O—SO$_3$H(Na)$_2$,
O—CH$_2$—PO$_3$H(Na)$_2$
O—CO-alkyl,
including O—CO—CH$_2$—CO$_2$tBu,
O—CO—CH$_2$—NHMe, O—CO—CH$_2$—N(Me)$_2$
and the esters of amino acids, of dipeptides or of tripeptides More particularly, when Y represents a phosphate radical, in acid or salified form, the process is generally carried out through the action of di-O-benzyl- or di-O-phenylphosphoric acid chloride on a derivative of general formula (I) of type A' or B' in which Y is OH, in a solvent such as pyridine, followed by hydrogenolysis in the presence of a palladium catalyst (palladium-on-charcoal or palladium hydroxide). When the heterocyclic Het is of the type benzimidazole or azabenzimidazole or imidazole, linked via its 2-position to the 4-position of the carbazole, it may be advantageous, in the context of the invention, to protect the NH of the heterocycle in the form of N-Boc, N-TBDMS or N-SEM.

More particularly, when Y represents a sulphate radical, in acid or salified form, the process is generally carried out through the action of sulphuric anhydride—or sulphur trioxide—or of oleum—a mixture of sulphuric acid and of sulphuric anhydride—on a derivative of general formula (I) of type A' or B' in which Y is OH, in a solvent such as pyridine. When the heterocyclic Het is of the type benzimidazole or azabenzimidazole or imidazole, linked via its 2-position to the 4-position of the carbazole, it may be advantageous, in the context of the invention, to protect the NH of the heterocycle in the form of N-Boc, N-TBDMS or N-SEM.

More particularly, when Y represents a phosphonyloxymethyloxy radical, the process is generally carried out through the action of a strong base, such as sodium hydride, and then of phosphoric acid di-tert-butyl ester or of phosphoric acid chloromethyl ester on a derivative of general formula (I) of type A' or B' in which Y is OH, in a solvent such as DMF, followed by hydrolysis in an acidic medium, such as a 4N solution of hydrochloric acid. When the heterocyclic Het is of the type benzimidazole or azabenzimidazole or imidazole, linked via its 2-position to the 4-position of the carbazole, it may be advantageous, in the context of the invention, to protect the NH of the heterocycle in the form of N-Boc, N-TBDMS or N-SEM.

More particularly, when Y represents a carboxylic ester radical, the process is generally carried out through the action of a carboxylic acid, in the presence of an agent for activating the acid function, such as 1-(3-dimethylaminopropyl)-3-ethylcarbodiimide hydrochloride (EDCI), and of a base, such as 4-dimethylaminopyridine (DMAP), or of O-((ethoxycarbonyl)cyanomethyleneamino)-N,N,N',N'-tetramethyluronium tetrafluoroborate (TOTU), in a solvent such as dichloromethane. When said ester is an amino acid-derived, dipeptide-derived or tripeptide-derived ester, it is advantageous, in the context of the invention, to use an amino acid or a dipeptide-derived or tripeptide-derived acid, the amino and/or hydroxyl residue(s) of which are protected, for example in NH-Boc, NH-Fmoc or O-Su form.

The compounds of general formula (I), in which R is of type D, with $W_1$, $W_2$ and $W_3$=CH, can be prepared, advantageously in the context of the invention, through the action of phosphorus trichloride and then of acetamide, at a temperature close to 180°, in the presence of a base such as potassium carbonate, on a product of general formula (I) of type E, by carrying out the process according to Scheme (39), in particular under the conditions described in Bioorg. Med. Chem. (2006), 14(20), 6832. When the heterocyclic Het is of the type benzimidazole or azabenzimidazole or imidazole, linked via its 2-position to the 4-position of the carbazole, it may be advantageous, in the context of the invention, to protect the NH of the heterocycle in the form of N-Boc, N-TBDMS or N-SEM.

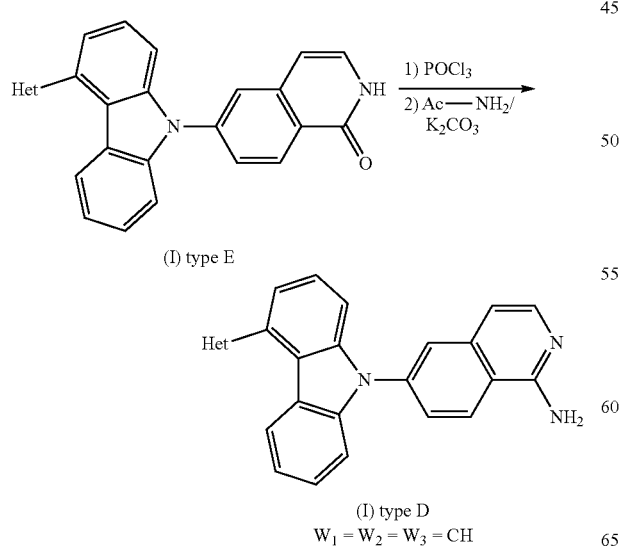

E) General Method for Synthesizing the Compounds of Formula (I) in which W1 Represents CH and W2 Represents N:

The compounds of general formula (IA), in which R represents the group below:

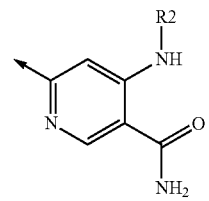

can be advantageously prepared from 4,6-dichloronicotinamide by carrying out the process:

either according to Scheme (40), using compounds of general formula (II) and 4-amino(substituted)-6-chloronicotinamides, which can be obtained by carrying out the process according to patent US 2006/027417:

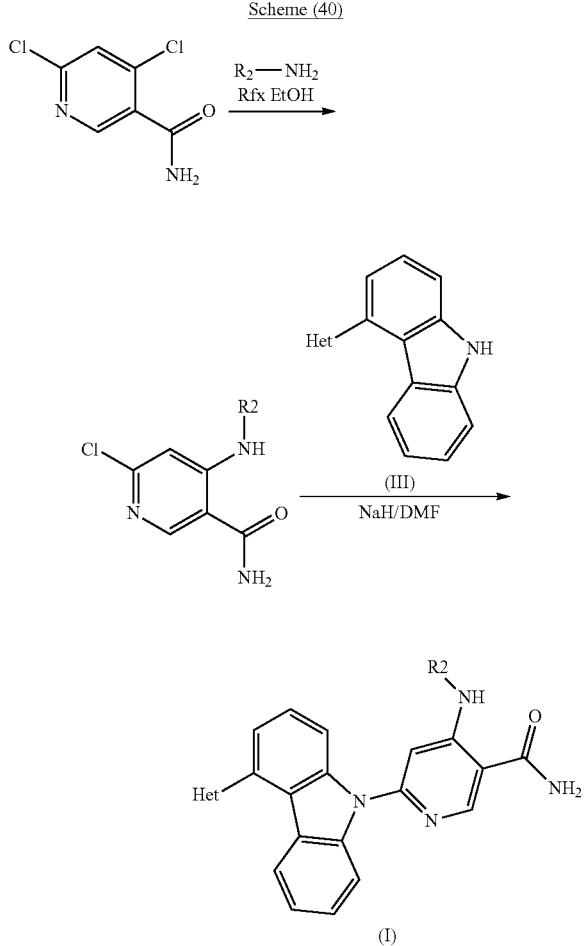

or according to Scheme 41, using compounds of general formula (VII), which can be obtained from the compounds of general formula (II) and from 4-amino(substituted)-6-chloronicotinamides, which can themselves be obtained by carrying out the process according to patent US 2006/027417:

Scheme (41)

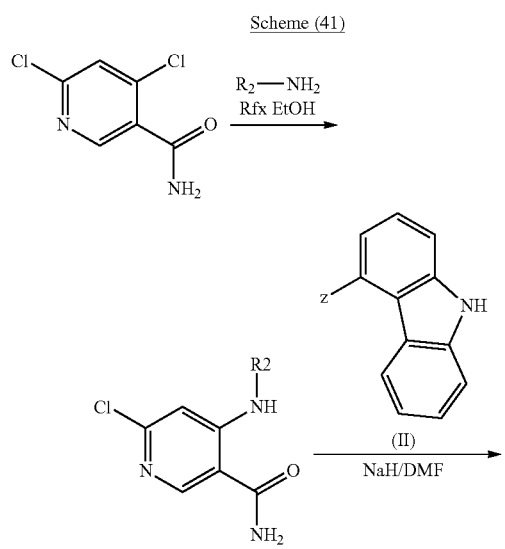

Scheme (42)

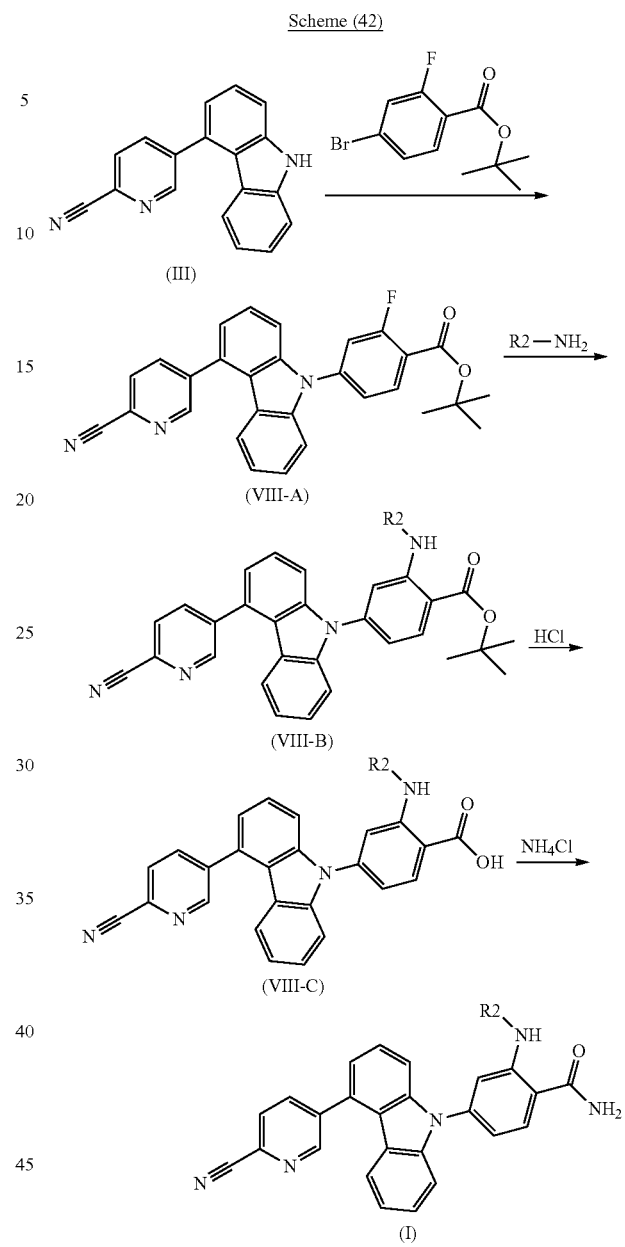

F-Method for Synthesizing the Compounds of General Formula (I) in which Het Represents a Substituted 2-Cyanopyridine Attached to the Carbazole Nucleus Via its 5-Position:

More particularly, the compounds of general formula (I) wherein R represents the group below:

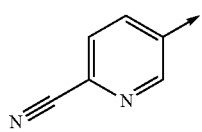

can be advantageously prepared from the compounds of general formula (III) by carrying out the process according to Scheme (42):

which implements the following successive reactions:
 a Buchwald-Hartwig reaction between the product of general formula (III), in which Het represents the 2-cyanopyridin-5-yl radical, and 4-bromo-2-fluorobenzoic acid tert-butyl ester, in the presence of a base such as caesium carbonate and a palladium(0) derivative, such as "Palladium-Xanthphos", formed from palladium acetate and 4,5-bis(diphenylphosphino)-9,9-dimethylxanthene, in a solvent such as dioxane, so as to give the compound of general formula (VIII-A),
 then an aromatic nucleophilic substitution reaction with an amine R2-NH₂, in which R2 is as defined above, in the presence of a base such as potassium carbonate, in a solvent such as DMSO, so as to give compounds of general formula (VIII-B),
 then hydrolysis of the esters of general formula (VIII-A) to acids of general formula (VIII-C), by reaction with hydrochloric acid in a solvent such as dioxane at a temperature close to 100° C., so as to give products of general formula (VIII-C), and, finally, the formation of the carbamoyl radical by coupling the acids of general formula (VIII-C), activated beforehand with (1H-benzotriazol-1-yloxy)[tris(dimethylamino)]phosphonium hexafluorophosphate (BOP) and hydroxybenzotriazole (HOBT), with ammonium chloride, in the presence of a base such as diisopropylethylamine in a solvent such as N,N-dimethylformamide.

The reactions described above can be carried out according to the conditions described in the preparation of the examples hereinafter and also according to the general methods known to those skilled in the art, in particular those described in: Comprehensive Organic Chemistry, by D. H. R. Barton et al. (Pergamon Press); Advanced Organic Chemistry, by J. Marsh (Wiley Interscience).

The products which are subjects of the present invention have advantageous pharmacological properties: it has been observed that they in particular possess inhibitory properties on the activities of chaperone proteins, and in particular on their ATPase activities.

Among these chaperone proteins, mention is in particular made of the human chaperone HSP90.

The products corresponding to general formula (I) as defined above thus have a considerable inhibitory activity on the Hsp90 chaperone.

Tests given in the experimental section hereinafter illustrate the inhibitory activity of products of the present invention with respect to such chaperone proteins.

These properties thus mean that the products of general formula (I) of the present invention can be used as medicaments in the treatment of malignant tumours.

The products of formula (I) can also be used in the veterinary field.

A subject of the invention is therefore the use, as medicaments, of the products of formula (I) as defined above.

A subject of the invention is in particular the use, as medicaments, of the products of formula (I) as defined above, the names of which are given below:

4-[4-(6-fluoro-1H-benzimidazol-2-yl)-9H-carbazol-9-yl]-2-(4-trans-hydroxycyclohexylamino)benzamide
2-(4-trans-hydroxycyclohexylamino)-4-[(4-quinolin-3-yl)-9H-carbazol-9-yl]benzamide
2-(2-diethylaminoethylamino)-4-[4-(6-fluoro-1H-benzimidazol-2-yl)-9H-carbazol-9-yl]benzamide
2-(4-trans-hydroxycyclohexylamino)-4-[4-(3H-imidazo[4,5-c]pyridin-2-yl)-9H-carbazol-9-yl]benzamide
acetic acid 4-{2-carbamoyl-5-[4-(6-fluoro-1H-benzimidazol-2-yl)-9H-carbazol-9-yl]phenylamino}cyclohexyl ester
2-cyclohexylamino-4-[4-(6-fluoro-1H-benzimidazol-2-yl)-9H-carbazol-9-yl]benzamide
4-[4-(6-fluoro-1H-benzimidazol-2-yl)-9H-carbazol-9-yl]-2-[2-(2-hydroxyethoxy)ethylamino]benzamide
4-[4-(6-fluoro-1H-benzimidazol-2-yl)-9H-carbazol-9-yl]-2-(3-hydroxypropylamino)benzamide
4-[4-(6-fluoro-1H-benzimidazol-2-yl)-9H-carbazol-9-yl]-2-(4-cis-hydroxycyclohexylamino)benzamide
2-amino-4-[4-(6-fluoro-1H-benzimidazol-2-yl)-9H-carbazol-9-yl]benzamide
4-[4-(6-fluoro-1H-benzimidazol-2-yl)-9H-carbazol-9-yl]-2-(2-pyrrolidin-1-yl-ethylamino)benzamide
6-[4-(6-fluoro-1H-benzimidazol-2-yl)-9H-carbazol-9-yl]-1H-indazol-3-ylamine 6-[4-(6-fluoro-1H-benzimidazol-2-yl)-9H-carbazol-9-yl]-1,2-benzisoxazol-3-ylamine,
3-(trans-4-hydroxycyclohexylamino)-5-[(4-quinolin-3-yl)-9H-carbazol-9-yl]pyridine-2-carboxamide
4-[4-(6-fluoro-1H-benzimidazol-2-yl)-9H-carbazol-9-yl]-2-(tetrahydro-pyran-4-ylamino)benzamide
4-[4-(6-cyanopyridin-3-yl)-9H-carbazol-9-yl]-2-[(1,2,2,6,6-pentamethylpiperidin-4-yl)amino]benzamide
aminoacetic acid 4-{[2-carbamoyl-5-(quinolin-3-yl)-9H-carbazol-9-yl]-pyridin-3-ylamino}cyclohexyl ester
4-[4-(6-cyanopyridin-3-yl)-9H-carbazol-9-yl]-2-[(8-methyl-8-azabicyclo[3.2.1]oct-3-yl)amino]benzamide
5-[4-(6-fluoro-1H-benzimidazol-2-yl)-9H-carbazol-9-yl]-3-(tetrahydropyran-4-yl)amino)pyridin-2-carboxamide
2,4-(quinolin-3-yl)-9H-carbazol-9-yl]-4-(tetrahydropyran-4-yl)-amino)pyridin-5-carboxamide
le 2-(8-methyl-8-azabicyclo[3.2.1]oct-3-yl)amino-4-[4-(quinolin-3-yl)-9H-carbazol-9-yl]benzamide
3-[(2-hydroxy-2-methylpropylamino)-5-[4-(quinolin-3-yl)-9H-carbazol-9-yl]pyridine-2-carboxamide and also the pharmaceutically acceptable addition salts with inorganic and organic acids or with inorganic and organic bases of said products of formula (I).

A subject of the invention is in particular, as medicaments, products of formula (I) as defined above:

Het is chosen from the group constituted of:

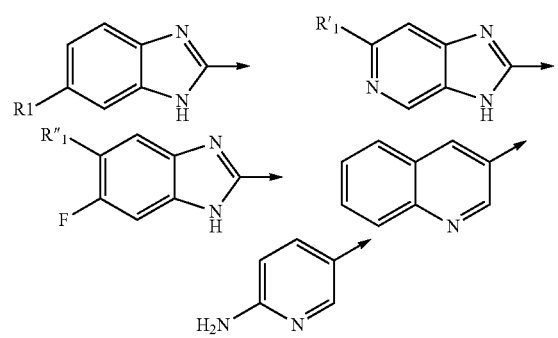

with:

R1 represents H, F, Cl, Br, CF$_3$, NO$_2$, CN, CH$_3$, OH, OCH$_3$, OCF$_3$, CO$_2$Me, CONH$_2$, CONHMe, CONH—(CH$_2$)$_3$—OMe, CONH—(CH$_2$)$_3$—N(Me)$_2$, NHC(O)Me, SO$_2$NH$_2$ or SO$_2$N(Me)$_2$;

R'1 represents H, CONH$_2$, CONHMe or OMe;

R"1 represents F, Cl, OH, OMe, CN, O—(CH$_2$)$_3$—OMe or O—(CH$_2$)$_3$—N(Me)$_2$;

and R is chosen from the group constituted of:

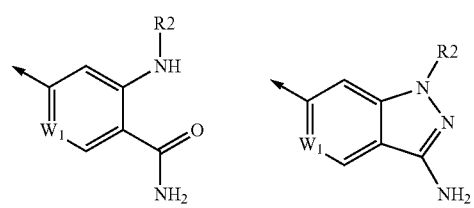

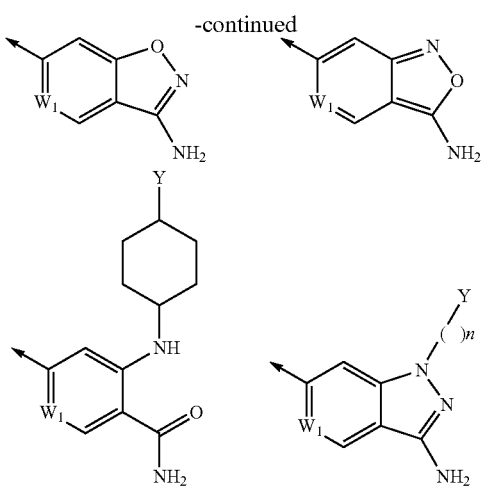

with:
R2 represents hydrogen, or ethyl substituted in the 2-position, n-propyl substituted in the 3-position or cyclohexyl trans-substituted in the 4-position with OH, SH, $NH_2$, OMe, NHMe, $N(Me)_2$, $N(Et)_2$, azetidino, oxetano, pyrrolidino, tetrahydrofurano, piperidino, tetrahydropyrano, piperazino, morpholino, homopiperidino, homopiperazino, quinuclidino, $CONH_2$ or COOH;
and Y represents OH, O—$PO_3H_2$, O—$PO_3Na_2$, O—$SO_3H_2$, O—$SO_3Na_2$, O—$CH_2$—$PO_3H_2$, O—$CH_2$—$PO_3Na_2$, O—CO—$CH_2$—$CO_2tBu$, O—CO—$CH_2$—$NH_2$ or O—CO-glycine, O—CO—$CH_2$—$N(Me)_2$, O—CO—$CH_2$—NHMe, O—CO-alanine, O—CO-serine, O—CO-lysine, O—CO—arginine, O—CO-glycine-lysine or O—CO-alanine-lysine, with n represents 2 or 3;
and also the prodrugs thereof, said products of formula (I) being in all the possible isomeric forms: tautomeric, racemic, enantiomeric and diastereoisomeric, and also the pharmaceutically acceptable addition salts with inorganic and organic acids or with inorganic and organic bases of said products of formula (I).

The products can be administered parenterally, orally, perlingually, rectally or topically.

A subject of the invention is also pharmaceutical compositions, characterized in that they contain, as active ingredient, at least one of the medicaments of general formula (I).

These compositions can be provided in the form of injectable solutions or suspensions, tablets, coated tablets, capsules, syrups, suppositories, creams, ointments and lotions. These pharmaceutical forms are prepared according to the usual methods. The active ingredient can be incorporated into excipients normally used in these compositions, such as aqueous or nonaqueous carriers, talc, gum arabic, lactose, starch, magnesium stearate, cocoa butter, fatty substances of animal or plant origin, paraffin derivatives, glycols, various wetting agents, dispersants or emulsifiers, or preserving agents.

The usual dose, which can vary according to the individual treated and the condition in question, can be, for example, from 10 mg to 500 mg per day in humans, orally.

The present invention thus relates to the use of products of formula (I) as defined above or of pharmaceutically acceptable salts of said products of formula (I), for the preparation of medicaments for inhibiting the activity of chaperone proteins, and in particular of Hsp90.

The present invention thus relates in particular to the use of products of formula (I) as defined above or of pharmaceutically acceptable salts of said products of formula (I), in which the chaperone protein is Hsp90.

The present invention thus relates to the use of products of formula (I) as defined above or of pharmaceutically acceptable salts of said products of formula (I), for the preparation of a medicament for preventing or treating a disease characterized by a disturbance of the activity of a chaperone protein of Hsp90 type, and in particular such a disease in a mammal.

The present invention relates to the use of products of formula (I) as defined above or of pharmaceutically acceptable salts of said products of formula (I), for the preparation of a medicament for preventing or treating a disease belonging to the following group: neurodegenerative diseases such as Huntington's disease, Parkinson's disease, focal cerebral ischaemia, Alzheimer's disease, multiple sclerosis and amyotrophic lateral sclerosis, malaria, *Brugia* filariasis, Bancroft's filariasis, toxoplasmosis, treatment-resistant mycoses, hepatitis B, hepatitis C, the herpes virus, dengue (or tropical flu), spinal and bulbar muscular atrophy, mesangial cell proliferation disorders, thromboses, retinopathies, psoriasis, muscle degeneration, diseases in oncology, and cancers.

The present invention thus relates to the use of products of formula (I) as defined above or of pharmaceutically acceptable salts of said products of formula (I), for the preparation of a medicament for treating diseases in oncology.

The present invention relates in particular to the use of products of formula (I) as defined above or of pharmaceutically acceptable salts of said products of formula (I), for the preparation of a medicament for treating cancers.

Among these cancers, the present invention focuses most particularly on the treatment of solid tumours and on the treatment of cancers resistant to cytotoxic agents.

The present invention thus relates in particular to the use of products of formula (I) as defined in any one of the preceding claims or of pharmaceutically acceptable salts of said products of formula (I), for the preparation of a medicament for treating cancers, among which are lung cancer, breast cancer and ovarian cancer, glioblastomas, chronic myeloid leukaemias, acute lymphoblastic leukaemias, prostate cancer, pancreatic cancer and colon cancer, metastatic melanomas, thyroid tumours and renal carcinomas.

Thus, among the main potential indications of Hsp90 inhibitors, mention may, by way of nonlimiting example, be made of:
"non small cell" lung cancers, breast cancers, ovarian cancers and glioblastomas which overexpress EGF-R or HER2;
chronic myeloid leukaemias which overexpress Bcr-Abl;
acute lymphoblastic leukaemias which overexpress Flt-3;
breast, prostate, lung, pancreatic, colon or ovarian cancers which overexpress Akt;
metastatic melanomas and thyroid tumours which overexpress the mutated form of the B-Raf protein;
androgen-dependent and androgen-independent prostate cancers;
oestrogen-dependent and oestrogen-independent breast cancers;
renal carcinomas which overexpress HIF-1a or the mutated c-met protein.

The present invention focuses even more particularly on the treatment of breast cancer, colon cancer and lung cancer.

The present invention also relates to the use of products of formula (I) as defined above or of pharmaceutically acceptable salts of said products of formula (I), for the preparation of a medicament for use in cancer chemotherapy.

As medicaments according to the present invention for use in cancer chemotherapy, the products of formula (I) according to the present invention can be used alone or in combination with chemotherapy or radiotherapy, or alternatively in combination with other therapeutic agents.

The present invention thus relates in particular to the pharmaceutical compositions as defined above containing, in addition to the active ingredients, other medicaments for anti-cancer chemotherapy.

Such therapeutic agents can be commonly used anti-tumour agents.

As examples of known protein kinase inhibitors, mention may in particular be made of butyrolactone, flavopiridol, 2-(2-hydroxyethylamino)-6-benzylamino-9-methylpurine, olomucine, Glivec and Iressa.

The products of formula (I) according to the present invention may thus also be advantageously used in combination with anti-proliferative agents: by way of examples of such anti-proliferative agents, but without however being limited to this list, mention may be made of aromatase inhibitors, anti-oestrogens, topoisomerase I inhibitors, topoisomerase II inhibitors, agents that are active on microtubules, alkylating agents, histone deacetylase inhibitors, farnesyl transferase inhibitors, COX-2 inhibitors, MMP inhibitors, mTOR inhibitors, antineoplastic antimetabolites, platinum compounds, proteasome inhibitors, such as Bortezomib, inhibitors of Histone Deactylase (HDACs), such as SAHA, and in particular inhibitors of HDAC6, compounds which bring about a reduction in protein kinase activity and also anti-angiogenic compounds, gonadorelin agonists, anti-androgens, bengamides, biphosphonates and trastuzumab.

By way of examples, mention may thus be made of anti-microtubule agents, such as taxoides, epothilones, or vinka-alkaloids, alkylating agents such as cyclophosphamide, DNA-intercalating agents such as cis-platinum and oxaliplatin, topoisomerase-interactive agents such as camptothecin and derivatives, anthracyclines such as adriamycin, antimetabolites such as 5-fluorouracil and derivatives and analogues.

The present invention therefore relates to products of formula (I) as Hsp90 chaperone inhibitors, said products of formula (I) being in all the possible isomeric forms: tautomeric, racemic, enantiomeric and diastereoisomeric, and also the pharmaceutically acceptable addition salts with inorganic and organic acids or with inorganic and organic bases of said products of formula (I), and the prodrugs thereof.

The present invention relates in particular to products of formula (I) as defined above, as Hsp90 inhibitors.

The products of formula (I) according to the present invention can be prepared by application or adaptation of known methods, and in particular of the methods described in the literature, for instance those described by R. C. Larock in: Comprehensive Organic Transformations, VCH publishers, 1989.

In the reactions described hereinafter, it may be necessary to protect reactive functional groups such as, for example, hydroxyl, amino, imino, thio or carboxyl groups, when the latter are desired in the final product but when their participation is not desired in the reactions for synthesizing the products of formula (I). Conventional protective groups can be used in accordance with the usual standard practices, such as those described, for example, by T. W. Greene and P. G. M. Wuts in "Protective Groups in Organic Chemistry" John Wiley and Sons, 1991.

The experimental section hereinafter gives non-limiting examples of starting products: other starting products can be found commercially or can be prepared according to the usual methods known to those skilled in the art.

Examples illustrating the invention: The examples of which the preparation follows illustrate the present invention without, however, limiting it.

All the examples described were characterized by proton NMR spectroscopy and by mass spectroscopy, the majority of these examples were also characterized by infrared spectroscopy.

Unless different conditions are specifically described, the LC/MS mass spectra, reported in the description of the various examples below, were carried out under the following liquid chromatography conditions:
Method A:
Column: ACQUITY BEH $C_{18}$ 1.7 µm 2.1×50 mm
Solvent: A: $H_2O$ (0.1% formic acid) B: $CH_3CN$ (0.1% formic acid)
Column temperature: 50° C.
Flow rate: 1 ml/min
Gradient (2 min): 5 to 50% B in 0.8 min; 1.2 min: 100% of B; 1.85 min 100% of B; 1.95 min 5% of B
Method B:
Column: XBridge $C_{18}$ 2.5 µm 3×50 mm
Solvent: A: $H_2O$ (0.1% formic acid) B: $CH_3CN$ (0.1% formic acid)
Column temperature: 70° C.
Flow rate: 0.9 ml/min
Gradient: 5% to 100% of B in 5.3; 5.5 min: 100% of B; 6.3 min: 5% of B
Method C:
Column: ACQUITY BEH $C_{18}$ 1.7 µm 2.1×50 mm
Solvent: A: $H_2O$ (0.1% formic acid) B: $CH_3CN$ (0.1% formic acid)
Column temperature: 70° C.
Flow rate: 0.7 ml/min
Gradient: 5% of B in 0.1 min; 5% to 95% of B in 8.3 min; 95% of B in 8.5 min; 95% to 5% B in 9.5 min; 95% of B at 12 min

EXAMPLE 1

Synthesis of 4-[4-(6-fluoro-1H-benzimidazol-2-yl)-9H-carbazol-9-yl]-2-(4-trans-hydroxycyclohexylamino)benzamide

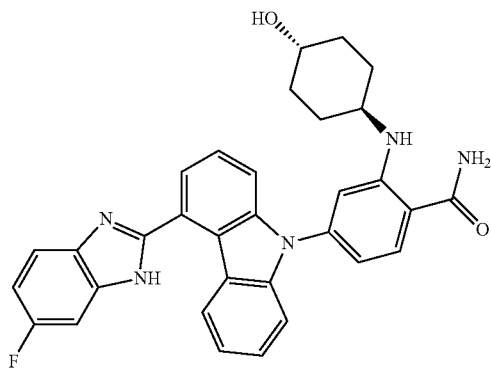

Stage 1: A mixture of 4.78 g of 4-hydroxycarbazole, 9.32 g of N-phenylbis(trifluoromethanesulphonimide) and 3.64 ml of triethylamine in 200 ml of dichloromethane is stirred for 24 hours in a 250 ml round-bottomed flask, under argon at ambient temperature. The reaction medium is evaporated to dryness under vacuum and the blackish residue is chromatographed on silica gel (40-63 µm), elution being carried out with dichloromethane. 7.07 g of 4-trifluoromethanesulphonyloxycarbazole are obtained in the form of a white solid, the characteristics of which are the following:

Melting point (Kofler bench): 90° C.

1H NMR spectrum (400 MHz, δ in ppm, DMSO-d6): 7.21 (d, J=8.0 Hz, 1H); 7.30 (t, J=8.0 Hz, 1H); 7.48 to 7.57 (m, 2H); 7.63 (m, 2H); 8.11 (d, J=8.0 Hz, 1H); 11.89 (broad s, 1H).

Mass spectrum (EI): m/z=315 (M+)

Stage 2: A mixture of 2.0 g of 4-trifluoromethanesulphonyloxycarbazole obtained according to the preceding stage, 142 mg of palladium acetate, 262 mg of 1,3-diphenylphosphinopropane and 0.88 ml of triethylamine in 35 ml of methanol and 85 ml of dimethylformamide is maintained at 50° C. for 8 hours under 2 bar of carbon monoxide, in an autoclave. After flushing with argon, the reaction medium is evaporated to dryness under vacuum and the orangey residue is chromatographed on silica gel (40-63 μm), elution being carried out with dichloromethane. 1.29 g of 9H-carbazole-4-carboxylic acid methyl ester are obtained in the form of a greenish solid, the characteristics of which are the following:

Melting point (Kofler bench): 95° C.

1H NMR spectrum (400 MHz, δ in ppm, DMSO-d6): 4.00 (s, 3H); 7.18 (m, 1H); 7.43 to 7.57 (m, 3H); 7.75 (dd, J=7.8 Hz and 1.1 Hz, 1H); 7.78 (dd, J=8.8 Hz and 1.1 Hz, 1H); 8.69 (broad d, J=8.3 Hz, 1H); 11.67 (broad s, 1H).

Mass spectrum (EI): m/z=225 (M+)

Stage 3: In a 250 ml round-bottomed flask under argon, 391 mg of a suspension of sodium hydride at 60% in petroleum jelly are added at ambient temperature, in 4 stages, in ½ hour, to a solution of 2.0 g of 9H-carbazole-4-carboxylic acid methyl ester obtained according to the preceding stage and of 1.95 g of 2-bromo-4-fluorobenzonitrile in 50 ml of dimethylformamide. The mixture is stirred at ambient temperature for 3 hours. The reaction medium is evaporated to dryness under vacuum and the residue is chromatographed on silica gel (40-63 μm), elution being carried out with a mixture of dichloromethane and cyclohexane (50:50). 3.2 g of 9-(3-bromo-4-cyanophenyl)-9H-carbazole-4-carboxylic acid methyl ester are obtained in the form of a white solid, the characteristics of which are the following:

1H NMR spectrum (400 MHz, δ in ppm, DMSO-d6): 4.03 (s, 3H); 7.36 (m, 1H); 7.47 (d, J=7.8 Hz, 1H); 7.50 to 7.60 (m, 2H); 7.72 (d, J=7.8 Hz, 1H); 7.87 (d, J=7.8 Hz, 1H); 7.91 (dd, J=8.3 Hz and 2.0 Hz, 1H); 8.26 (m, 2H); 8.75 (d, J=7.8 Hz, 1H).

Mass spectrum (LC/MS; method C): retention time Tr (min)=6.08; m/z=405 (M+).

Stage 4: In a microwave reactor, a mixture of 405 mg of 9-(3-bromo-4-cyanophenyl)-9H-carbazole-4-carboxylic acid methyl ester obtained according to the preceding stage, 461 mg of trans-4-aminocyclohexanol, 45 mg of palladium acetate, 192 mg of sodium tert-butoxide and 111 mg of 1,1'-bis(diphenylphosphino)ferrocene in 18 ml of toluene is heated at 115° C. for 30 minutes. The reaction medium is filtered through clarcel, washing being carried out with 200 ml of ethyl acetate. The filtrate is evaporated to dryness under vacuum and the residue is chromatographed on silica gel (40-63 μm), elution being carried out with a mixture of dichloromethane and methanol (97.5: 2.5). 222 mg of 9-[4-cyano-3-(4-trans-hydroxycyclohexylamino)-phenyl]-9H-carbazole-4-carboxylic acid methyl ester are obtained in the form of a brownish oil, the characteristics of which are the following:

1H NMR spectrum (400 MHz, δ in ppm, DMSO-d6): 1.21 (m, 2H); 1.41 (m, 2H); 1.78 (m, 2H); 1.91 (m, 2H); 3.32 to 3.50 (m, 2H); 4.03 (s, 3H); 4.47 (d, J=4.4 Hz, 1H); 5.88 (d, J=8.1 Hz, 1H); 6.82 (dd, J=8.3 Hz and 2.0 Hz, 1H); 7.06 (d, J=2.0 Hz, 1H); 7.32 (m, 1H); 7.42 (broad d, J=8.1 Hz, 1H); 7.48 to 7.58 (m, 2H); 7.64 to 7.68 (dd, J=8.1 Hz and 1.3 Hz, 1H); 7.75 (d, J=8.3 Hz, 1H); 7.84 (dd, J=7.5 Hz and 1.1 Hz, 1H); 8.74 (broad d, J=8.1 Hz, 1H).

Mass spectrum (LC/MS; method B): retention time Tr (min)=4.77; m/z=438 (M−H−); 440 (M+H+).

Stage 5: In a 250 ml round-bottomed flask, a mixture of 220 mg of 9-[4-cyano-3-(4-trans-hydroxycyclohexylamino)phenyl]-9H-carbazole-4-carboxylic acid methyl ester obtained according to the preceding stage and 401 μl of 2.5N sodium hydroxide in 20 ml of methanol is refluxed for 7 hours. The reaction medium is evaporated to dryness under vacuum. The residue is taken up in 20 ml of 1M hydrochloric acid and extracted with 3 times 30 ml of ethyl acetate. The combined organic phases are washed with 25 ml of a saturated solution of sodium chloride, dried over magnesium sulphate and evaporated to dryness under vacuum. The oily residue is chromatographed on silica gel (15-40 μm), elution being carried out with a mixture of dichloromethane and methanol (95:5). 157 mg of 9-[4-cyano-3-(4-trans-hydroxycyclohexylamino)phenyl]-9H-carbazole-4-carboxylic acid are obtained in the form of a beige foam, the characteristics of which are the following:

1H NMR spectrum (400 MHz, δ in ppm, DMSO-d6): 1.14 to 1.29 (m, 2H); 1.41 (m, 2H); 1.77 (m, 2H); 1.91 (m, 2H); 3.34 to 3.51 (m, 2H); 4.47 (broad d, J=4.2 Hz, 1H); 5.87 (d, J=8.3 Hz, 1H); 6.82 (dd, J=8.3 Hz and 2.0 Hz, 1H); 7.05 (d, J=2.0 Hz, 1H); 7.30 (m, 1H); 7.40 (broad d, J=8.0 Hz, 1H); 7.44 to 7.59 (m, 2H); 7.61 (dd, J=8.0 Hz and 1.1 Hz, 1H); 7.75 (d, J=8.3 Hz, 1H); 7.83 (dd, J=8.0 Hz and 1.1 Hz, 1H); 8.88 (d, J=7.8 Hz, 1H); 13.24 (broad m, 1H).

Mass spectrum (LC/MS; method A): retention time Tr (min)=0.96; m/z=424 (M−H−); 426 (M+H+).

Stage 6: In a 50 ml round-bottomed flask, a mixture of 155 mg of 9-[4-cyano-3-(4-trans-hydroxycyclohexylamino)phenyl]-9H-carbazole-4-carboxylic acid obtained according to the preceding stage, 48 mg of 4-fluoro-O-phenylenediamine, 131 mg of O-((ethoxycarbonyl)cyanomethyleneamino) N,N,N',N'-tetramethyluronium tetrafluoroborate (TOTU) and 70 μl of diisopropylethylamine in 20 ml of dimethylformamide is stirred at ambient temperature for 3.5 hours. The reaction medium is evaporated to dryness under vacuum. The residue is taken up with 40 ml of ethyl acetate. The organic phase is washed with 3 times 30 ml of a saturated solution of sodium bicarbonate and once with 30 ml of a saturated solution of sodium chloride, dried over magnesium sulphate and then evaporated to dryness under vacuum.

185 mg of 9-[4-cyano-3-(4-trans-hydroxycyclohexylamino)phenyl]-9H-carbazole-4-carboxylic acid (2-amino-4-fluorophenyl)amide are obtained in the form of a brownish foam, the characteristics of which are the following:

1H NMR spectrum (400 MHz, δ in ppm, DMSO-d6): 1.14 to 1.27 (m, 2H); 1.42 (m, 2H); 1.80 (m, 2H); 1.93 (m, 2H); 3.34 to 3.50 (m, 2H); 4.48 (d, J=4.4 Hz, 1H); 5.30 (broad s, 2H); 5.92 (d, J=8.3 Hz, 1H); 6.46 (td, J=8.4 Hz and 2.7 Hz, 1H); 6.61 (dd, J=11.2 Hz and 2.7 Hz, 1H); 6.83 (dd, J=8.3 Hz and 2.2 Hz, 1H); 7.02 (d, J=2.2 Hz, 1H); 7.26 (m, 1H); 7.38 to 7.64 (m, 6H); 7.76 (d, J=8.3 Hz, 1H); 8.32 (d, J=7.8 Hz, 1H); 9.81 (s, 1H).

Mass spectrum (LC/MS; method A): retention time Tr (min)=1.03; m/z=532 (M−H−); 534 (M+H+).

Stage 7: In a 100 ml round-bottomed flask, 185 mg of 9-[4-cyano-3-(4-trans-hydroxycyclohexylamino)phenyl]-9H-carbazole-4-carboxylic acid (2-amino-4-fluorophenyl)amide obtained according to the preceding stage, in 15 ml of glacial acetic acid, are refluxed for 1 hour. The reaction medium is evaporated to dryness under vacuum and the residue is chromatographed on silica gel (15-40 μm), elution being carried out with a mixture of dichloromethane and methanol (99:1). 121 mg of 4-[4-(6-fluoro-1H-benzimidazol-2-yl)-9H-carbazol-9-yl]-2-(4-trans-hydroxycyclohexylamino)benzonitrile are obtained in the form of a brownish foam, the characteristics of which are the following:

1H NMR spectrum (400 MHz, δ in ppm, DMSO-d6): 1.14 to 1.28 (m, 2H); 1.43 (m, 2H); 1.80 (m, 2H); 1.93 (m, 2H); 3.34 to 3.54 (m, 2H); 4.48 (d, J=4.4 Hz, 1H); 5.90 (d, J=8.3 Hz, 1H); 6.86 (dd, J=8.2 Hz and 2.0 Hz, 1H); 7.08 (d, J=2.0 Hz, 1H); 7.10 to 7.23 (m, 2H); 7.33 to 7.51 (m, 2.5H); 7.54 to 7.69 (m, 4H); 7.77 (d, J=8.3 Hz, 1H); 7.84 (dd, J=8.8 Hz and 5.1 Hz, 0.5H); 8.61 (d, J=7.8 Hz, 0.5H); 8.66 (d, J=7.8 Hz, 0.5H); 13.08 (s, 1H) (2 conformational isomers 50:50).

Mass spectrum (LC/MS; method A): retention time Tr (min)=0.98; m/z=514 (M−H−); 516 (M+H+).

Stage 8: In a 100 ml round-bottomed flask, 0.4 ml of a 30% aqueous hydrogen peroxide solution is added to a mixture of 111 mg of 4-[4-(6-fluoro-1H-benzimidazol-2-yl)-9H-carbazol-9-yl]-2-(4-trans-hydroxycyclohexylamino)benzonitrile obtained according to the preceding stage in 2 ml of ethanol and 0.8 ml of dimethyl sulphoxide and 0.4 ml of 1M sodium hydroxide and the mixture is stirred for ¼ hour at ambient temperature. 40 ml of distilled water are added and the resulting mixture is extracted with 3 times 30 ml of ethyl acetate. The combined organic phases are washed with 30 ml of a saturated solution of sodium chloride, dried over magnesium sulphate and evaporated to dryness under vacuum. The residue is chromatographed on silica gel (15-40 μm), elution being carried out with a mixture of dichloromethane and methanol (95/5).

105 mg of 4-[4-(6-fluoro-1H-benzimidazol-2-yl)-9H-carbazol-9-yl]-2-(4-trans-hydroxycyclohexylamino)benzamide are obtained in the form of a beige solid, the characteristics of which are the following:

1H NMR spectrum (400 MHz, δ in ppm, DMSO-d6): 1.16 to 1.32 (m, 4H); 1.78 (m, 2H); 1.99 (m, 2H); 3.33 (m partially masked, 1H); 3.47 (m, 1H); 4.47 (d, J=4.6 Hz, 1H); 6.70 (dd, J=8.3 Hz and 2.0 Hz, 1H); 6.88 (d, J=2.0 Hz, 1H); 7.11 to 7.22 (m, 2H); 7.27 (broad m, 1H); 7.39 to 7.50 (m, 2H), 7.50 to 7.80 (m, 5H); 7.91 (d, J=8.3 Hz, 1H); 7.96 (broad m, 1H); 8.46 (d, J=7.8 Hz, 1H); 8.65 (d, J=7.8 Hz, 1H); 13.08 (broad s, 1H).

Mass spectrum (LC/MS; method A): retention time Tr (min)=0.8; m/z=532 (M−H−); 534 (M+H+).

EXAMPLE 2

Synthesis of 2-(4-trans-hydroxycyclohexylamino)-4-[(4-quinolin-3-yl)-9H-carbazol-9-yl]benzamide

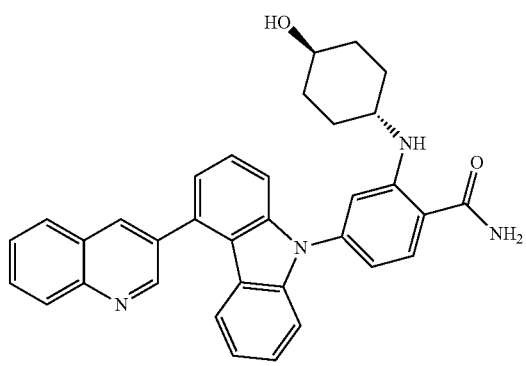

Stage 1: 78.8 mg of trifluoromethanesulphonic acid 9-H-carbazol-4-yl ester, obtained according to stage 1 of Example 1, 2.5 ml of toluene, 56.2 mg of quinolin-3-boronic acid, 55.6 mg of sodium carbonate and 57.8 mg of tetrakis(triphenylphosphine)palladium(0) are successively introduced into a 5 ml microwave reactor. After stirring for 30 seconds at ambient temperature, the reaction medium is heated, with stirring, at 115° C. for 30 minutes. After cooling to ambient temperature, the reaction medium is taken up with 5 ml of ethyl acetate and 2 ml of water. After filtration of an insoluble material and separation by settling out, the organic phase is washed twice with 2 ml of water, dried over magnesium sulphate and concentrated under reduced pressure. After purification by silica gel chromatography (15-40 μm), elution being carried out with a mixture of cyclohexane and ethyl acetate (80/20 then 70/30 by volume), 27 mg of 4-(quinolin-3-yl)-9H-carbazole are obtained in the form of a white solid, the characteristics of which are the following:

1H NMR spectrum (400 MHz, δ ppm, DMSO-d6): 6.90 (m, 1H) 7.18 (dd, J=7.5, 1.0 Hz, 1H) 7.22 (broad d, J=8.0 Hz, 1H) 7.34 (m, 1H) 7.53 (m, 2H) 7.61 (dd, J=8.3, 1.0 Hz, 1H) 7.71 (m, 1H) 7.86 (m, 1H) 8.11 (broad d, J=8.3 Hz, 1H) 8.17 (broad d, J=8.3 Hz, 1H) 8.59 (d, J=2.4 Hz, 1H) 9.13 (d, J=2.4 Hz, 1H) 11.55 (broad s, 1H).

Mass spectrum (LC/MS method A): retention time Tr (min)=0.95; MH+=295$_+$; MH_=293.

Stage 2: In a 20 ml single-necked round-bottomed flask, under argon atmosphere, 80 mg of 4-(quinolin-3-yl)-9H-carbazole, obtained according to the preceding stage, and 60 mg of 2-bromo-4-fluorobenzonitrile are dissolved in 2 ml of anhydrous dimethylformamide (DMF). 16.3 mg of sodium hydride at 60% in oil are then added, and the mixture is stirred at ambient temperature for 4 hours. After the addition of 15 ml of ethyl acetate and 3 ml of water, the organic phase is separated by settling out, washed 3 times with 3 ml of water, dried over magnesium sulphate and concentrated under reduced pressure. After purification by flash chromatography on silica gel (15-40 μm), elution being carried out with dichloromethane, 95 mg of 2-bromo-4-[(4-quinolin-3-yl)-9H-carbazol-9-yl]benzonitrile are obtained in the form of a beige lacquer, the characteristics of which are the following:

1H NMR spectrum (400 MHz, δ ppm, DMSO-d6): 7.08 (m, 1H) 7.24 (d, J=8.1 Hz, 1H) 7.36 (dd, J=6.4, 2.0 Hz, 1H) 7.43 (m, 1H) 7.49 to 7.53 (m, 1H) 7.57-7.67 (m, 2H) 7.74 (m, 1H) 7.89 (m, 1H) 7.96 (dd, J=8.3, 2.0 Hz, 1H) 8.14 (broad d, J=7.9 Hz, 1H) 8.19 (broad d, J=8.2 Hz, 1H) 8.28 (d, J=8.3 Hz, 1H) 8.30 (d, J=2.0 Hz, 1H) 8.63 (d, J=2.2 Hz, 1H) 9.14 (d, J=2.2 Hz, 1H).

Mass spectrum (LC/MS method A): retention time Tr (min)=1.22; MH+=474

Stage 3: 95 mg of 2-bromo-4-[(4-quinolin-3-yl)-9H-carbazol-9-yl]benzonitrile, obtained in the preceding stage, 92 mg of trans-4-aminocyclohexanol, 9 mg of palladium(II) acetate, 38.5 mg of potassium tert-butoxide and 3.6 ml of toluene are successively introduced into a 5 ml microwave reactor. After stirring at ambient temperature for 30 seconds, the reaction medium is heated at 115° C. for 15 minutes with stirring. After cooling, 5 ml of ethyl acetate and 3 ml of water are added. The organic phase is separated by settling out, washed twice with 2 ml of water, dried over magnesium sulphate and concentrated under reduced pressure. After purification by silica gel chromatography (15-40 μm), elution being carried out with a mixture of dichloromethane and methanol (98/2 by volume), 73 mg of 2-(4-trans-hydroxycyclohexylamino)-4-[(4-quinolin-3-yl)-9H-carbazol-9-yl]benzonitrile are obtained in the form of a beige foam, the characteristics of which are the following:

1H NMR spectrum (400 MHz, δ ppm, DMSO-d6): 1.23 (m, 2H) 1.43 (m, 2H) 1.81 (m, 2H) 1.94 (m, 2H) 3.34 to 3.54 (m, 2H) 4.49 (d, J=4.4 Hz, 1H) 5.89 (d, J=8.3 Hz, 1H) 6.89 (dd, J=8.3, 2.0 Hz, 1H) 7.04 (m, 1H) 7.10 (d, J=2.0 Hz, 1H) 7.24 (broad d, J=8.3 Hz, 1H) 7.32 (broad d, J=7.8 Hz, 1H) 7.37 to 7.48 (m, 2H) 7.54 (broad d, J=8.3 Hz, 1H) 7.60 (t, J=8.3 Hz, 1H) 7.73 (m, 1H) 7.78 (d, J=8.3 Hz, 1H) 7.89 (m, 1H) 8.13 (broad d, J=8.3 Hz, 1H) 8.19 (broad d, J=8.3 Hz, 1H) 8.62 (d, J=2.5 Hz, 1H) 9.15 (d, J=2.5 Hz, 1H).

Mass spectrum (LC/MS method A): retention time Tr (min)=1.14; MH+=509+.

Stage 4: In a 10 ml single-necked round-bottomed flask, 72 mg of 2-(4-trans-hydroxycyclohexylamino)-4-[(4-quinolin-3-yl)-9H-carbazol-9-yl]benzonitrile, obtained in the preceding stage, are dissolved in 1.2 ml of ethanol and 0.5 ml of dimethyl sulphoxide (DMSO), and then 269 μl of a 1N aqueous solution of sodium hydroxide, followed by 960 μl (2.55 mmol) of a 30% aqueous solution of hydrogen peroxide, are added successively using a syringe. After stirring for 20 minutes at ambient temperature, the reaction medium is taken up with 25 ml of ethyl acetate and 5 ml of water. The organic phase is separated by settling out, washed 3 times with 5 ml of water, dried over magnesium sulphate and concentrated under reduced pressure. After purification by crystallization from 1 ml of a mixture of dichloromethane and ethyl acetate (50/50 by volume), 71 mg of 2-(4-trans-hydroxycyclohexylamino)-4-[(4-quinolin-3-yl)-9H-carbazol-9-yl]benzamide are obtained in the form of a white powder, the characteristics of which are the following:

1H NMR spectrum (400 MHz, δ ppm, DMSO-d6): 1.25 (m, 4H) 1.79 (m, 2H) 2.00 (m, 2H) 3.33 (m, 1H) 3.47 (m, 1H) 4.47 (d, J=4.4 Hz, 1H) 6.72 (dd, J=8.3, 2.1 Hz, 1H) 6.91 (d, J=2.1 Hz, 1H) 7.03 (m, 1H) 7.19 to 7.37 (m, 3H) 7.36 to 7.46 (m, 2 H) 7.53 (broad d, J=8.2 Hz, 1H) 7.60 (t, J=8.2 Hz, 1H) 7.73 (m, 1H) 7.85 to 7.93 (m, 2H) 7.98 (broad m, 1H) 8.14 (broad d, J=8.2 Hz, 1H) 8.19 (broad d, J=8.2 Hz, 1H) 8.46 (d, J=7.8 Hz, 1H) 8.63 (d, J=2.4 Hz, 1H); 9.16 (d, J=2.4 Hz, 1H).

Mass spectrum (LC/MS method B): retention time Tr (min)=0.99; MH+=527

EXAMPLE 3

Synthesis of 2-(2-diethylaminoethylamino)-4-[4-(6-fluoro-1H-benzimidazol-2-yl)-9H-carbazol-9-yl]benzamide

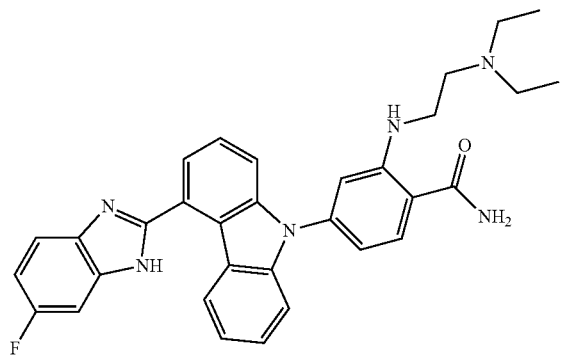

Stage 1: 0.43 g of 4-bromo-2-fluorobenzonitrile, 2.2 g of caesium carbonate, 0.12 g of 9,9-dimethyl-4,5-bis(diphenylphosphino)xanthene and 0.04 g of palladium acetate are added successively to a solution of 0.40 g of 9H-carbazole-4-carboxylic acid methyl ester, obtained according to stage 2 of Example 1, in 30 ml of dioxane under an inert argon atmosphere. The reaction mixture is refluxed for 3 hours, and then cooled, filtered and concentrated under reduced pressure. The residue is purified by silica gel chromatography, elution being carried out with a mixture of heptane and ethyl acetate (96/4 by volume), so to give 496 mg of 9-(4-cyano-3-fluorophenyl)-9H-carbazole-4-carboxylic acid methyl ester, the characteristics of which are the following:

1H NMR spectrum (400 MHz, δ in ppm, DMSO-d6): 4.03 (s, 3H) 7.36 (m, 1H) 7.47 to 7.62 (m, 3H) 7.73 to 7.79 (m, 2H) 7.87 (dd, J=7.7, 1.1 Hz, 1H) 8.02 (dd, J=10.3, 2.0 Hz, 1H) 8.26 (t, J=7.5 Hz, 1H) 8.75 (d, J=8.1 Hz, 1H).

Mass spectrum (LC/MS method A): retention time Tr (min)=1.14; MH+=345

Stage 2: 5.44 ml of a 2M solution of trimethylaluminium in toluene are added, in 5 minutes at ambient temperature, to a solution of 0.69 g of 1,2-diamino-4-fluorobenzene in 40 ml of toluene and 20 ml of tetrahydrofuran, under an argon atmosphere. After stirring at ambient temperature for 15 minutes, 1.25 g of 9-(4-cyano-3-fluorophenyl)-9H-carbazole-4-carboxylic acid methyl ester, obtained according to the preceding stage, in 20 ml of tetrahydrofuran, are added and then the mixture is refluxed for 1 hour. After a return to ambient temperature, 50 ml of water and a 2M aqueous solution of HCl are added slowly, in order to bring the pH to around 6. The aqueous phase is extracted with 100 ml of ethyl acetate, and the organic phase is then washed once with 20 ml of water, dried over magnesium sulphate and concentrated under reduced pressure. The residue obtained is dissolved in 20 ml of acetic acid and then heated at 110° C. for 1 hour. After cooling and evaporation of the solvent, 30 ml of water are added and the aqueous phase is brought to pH=8-9 by adding a saturated solution of potassium hydrogen carbonate. The crude solid obtained is purified by silica gel chromatography (15-40 μm), elution being carried out with a mixture of dichloromethane and ammonia at 7N in methanol (95/5 by volume). 0.82 g of 2-fluoro-4-[4-(6-fluoro-1H-benzimidazol-2-yl)-9H-carbazol-9-yl]benzonitrile is thus obtained, the characteristics of which are the following:

1H NMR spectrum (400 MHz, δ in ppm, DMSO-d6): 7.16 (m, 1H) 7.25 (t, J=7.6 Hz, 1H) 7.36 to 7.84 (m, 8H) 8.04 (d, J=10.3 Hz, 1H) 8.27 (t, J=7.7 Hz, 1H) 8.64 (d, J=8.3 Hz, 1H) 13.12 (broad s, 1H).

Mass spectrum (LC/MS method A): retention time Tr (min)=1.02; MH+=421+; MH−=419−.

Stage 3: 100 mg of 2-fluoro-4-[4-(6-fluoro-1H-benzimidazol-2-yl)-9H-carbazol-9-yl]benzonitrile, obtained in the preceding stage, 0.8 ml of dimethyl sulphoxide, 263 mg of potassium carbonate and 111 mg of N,N-diethylethylenediamine are introduced successively into a 2 ml microwave reactor. After stirring for 10 seconds at ambient temperature, the reaction medium is heated at 100° C. for 45 minutes with stirring. After cooling, 2 ml of ethanol, 0.4 ml of 1M sodium hydroxide and 0.4 ml of 30% aqueous hydrogen peroxide are added successively, and the mixture is stirred for ½ hour at ambient temperature. 20 ml of distilled water are added and then the resulting mixture is extracted with twice 30 ml of ethyl acetate. The combined organic phases are washed with 20 ml of a saturated solution of sodium chloride, dried over magnesium sulphate and evaporated to dryness under vacuum. The crude residue obtained is purified by silica gel chromatography (15-40 μm), elution being carried out with a mixture of dichloromethane and ammonia at 7N in methanol (95/5 by volume). 70 mg of 2-(2-diethylamino-ethylamino)-4-[4-(6-fluoro-1H-benzimidazol-2-yl)-9H-carbazol-9-yl]benzamide are thus obtained in the form of a white solid, the characteristics of which are the following:

1H NMR spectrum (400 MHz, δ in ppm, DMSO-d6): 0.95 (t, J=7.1 Hz, 6H) 2.50 (m partially masked, 4H) 2.63 (t, J=6.2

Hz, 2H) 3.15 (m, 2H) 6.74 (dd, J=8.3, 2.1 Hz, 1H) 6.84 (d, J=2.1 Hz, 1H) 7.12 to 7.21 (m, 2H) 7.25 (broad m, 1H) 7.41 to 7.87 (m, 7H) 7.90 (d, J=8.3 Hz, 1H) 7.93 (broad m, 1H) 8.47 (broad t, J=5.1 Hz, 1H) 8.62 (broad d, J=8.2 Hz, 1H); 13.09 (broad m, 1H).

Mass spectrum (LC/MS method A): retention time Tr (min)=0.68; MH+=535$_+$; MH_=533_.

EXAMPLE 4

Synthesis of 2-(4-trans-hydroxycyclohexylamino)-4-[4-(3H-imidazo[4,5-c]pyridin-2-yl)-9H-carbazol-9-yl]benzamide

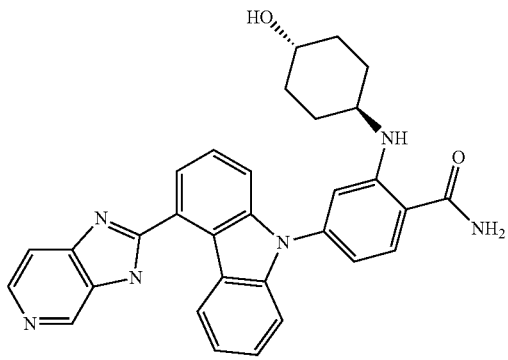

Stage 1: In a 250 ml round-bottomed flask, a mixture of 545 mg of 9-[4-cyano-3-(4-trans-hydroxycyclohexyl amino)phenyl]-9H-carbazole-4-carboxylic acid, obtained according to stage 5 of Example 1, 147 mg of 3,4-diaminopyridine, 462 mg of O-[(ethoxycarbonyl)cyanomethyleneamino]-N,N,N',N'-tetramethyluronium tetrafluoroborate (TOTU) and 245 µl of diisopropylethylamine in 75 ml of dimethylformamide is stirred at ambient temperature for 4 hours. The reaction medium is evaporated to dryness under vacuum. The residue is taken up with 100 ml of ethyl acetate. The organic phase is washed with 3 times 60 ml of a saturated solution of sodium bicarbonate and once with 60 ml of a saturated solution of sodium chloride, dried over magnesium sulphate and then evaporated to dryness under vacuum. The residue is chromatographed on silica gel (15-40 µm), elution being carried out with pure dichloromethane and then a mixture of dichloromethane and methanol (90/10 by volume). 599 mg of 9-[4-cyano-3-(4-trans-hydroxycyclohexylamino)phenyl]-9H-carbazole-4-carboxylic acid (3-aminopyridin-4-yl)amide are obtained in the form of an orangey-coloured oil, the characteristics of which are the following:

1H NMR spectrum (400 MHz, δ in ppm, DMSO-d6): 1.11 to 1.31 (m, 2H); 1.42 (m, 2H); 1.80 (m, 2H); 1.93 (m, 2H); 3.35 to 3.51 (m, 2H); 4.48 (d, J=4.4 Hz, 1H); 5.26 (broad s, 2H); 5.92 (d, J=8.1 Hz, 1H); 6.84 (dd, J=8.3 Hz and 1.9 Hz, 1H); 7.02 (d, J=1.9 Hz, 1H); 7.26 (m, 1H); 7.41 to 7.53 (m, 2H); 7.52 to 7.66 (m, 3H); 7.77 (m, 2H); 7.88 (d, J=5.4 Hz, 1H); 8.13 (s, 1H); 8.24 (d, J=8.1 Hz, 1H); 10.06 (s, 1H).

Mass spectrum (LC/MS; method A): retention time Tr (min)=0.75; m/z=515 (M−H−); 517 (M+H+).

Stage 2: In a 250 ml round-bottomed flask, 590 mg of 9-[4-cyano-3-(4-trans-hydroxycyclohexylamino)phenyl]-9H-carbazole-4-carboxylic acid (3-aminopyridin-4-yl)amide, obtained according to the preceding stage, in 50 ml of glacial acetic acid, are refluxed for 1 hour. The reaction medium is evaporated to dryness under vacuum and the residue is chromatographed on silica gel (15-40 µm), elution being carried out with a mixture of dichloromethane and methanol (99/1 then 90/10). 244 mg of 2-(4-trans-hydroxycyclohexylamino)-4-[4-(3H-imidazo[4,5-c]pyridin-2-yl)-9H-carbazol-9-yl]benzonitrile are obtained in the form of a brownish foam, the characteristics of which are the following:

1H NMR spectrum (400 MHz, δ in ppm, DMSO-d6): 1.22 (m, 2H); 1.43 (m, 2H); 1.80 (m, 2H); 1.94 (m, 2H); 3.34 to 3.53 (m, 2H); 4.48 (d, J=4.4 Hz, 1H); 5.91 (d, J=8.1 Hz, 1H); 6.87 (dd, J=8.2 Hz and 2.0 Hz, 1H); 7.09 (d, J=2.0 Hz, 1H); 7.21 (m, 1H); 7.41 to 7.52 (m, 2H); 7.59 to 7.74 (m, 4H); 7.78 (d, J=8.2 Hz, 1H); 8.41 (d, J=5.4 Hz, 1H); 8.58 (broad d, J=8.3 Hz, 1H); 9.09 (broad s, 1H); 13.40 (broad m, 11-1).

Mass spectrum (LC/MS; method A): retention time Tr (min)=0.71; m/z=497 (M−H−); 499 (M+H+).

Stage 3: In a 100 ml round-bottomed flask, 0.98 ml of 30% aqueous hydrogen peroxide is added to a mixture of 240 mg of 2-(4-trans-hydroxycyclohexylamino)-4-[4-(3H-imidazo[4,5-c]pyridin-2-yl)-9H-carbazol-9-yl]benzonitrile, obtained in the preceding stage, in 7 ml of ethanol and 3.5 ml of dimethyl sulphoxide and 0.96 ml of 1M sodium hydroxide, and the mixture is stirred for ¼ hour at ambient temperature. 40 ml of distilled water are added and the mixture is extracted with 3 times 40 ml of ethyl acetate. The combined organic phases are washed with twice 40 ml of a saturated solution of sodium chloride, dried over magnesium sulphate and evaporated to dryness under vacuum. The residue is chromatographed on silica gel (15-40 µm), elution being carried out with a mixture of dichloromethane and methanol (97/3 then 90/10). 188 mg of 2-(4-trans-hydroxycyclohexylamino)-4-[4-(3H-imidazo[4,5-c]pyridin-2-yl)-9H-carbazol-9-yl]benzamide are obtained in the form of a beige solid, the characteristics of which are the following:

1H NMR spectrum (400 MHz, δ in ppm, DMSO-d6): 1.15 to 1.31 (m, 4H); 1.78 (m, 2H); 1.99 (m, 2H); 3.21 to 3.53 (m partially masked, 2H); 4.47 (d, J=4.4 Hz, 1H); 6.70 (dd, J=8.3 Hz and 2.0 Hz, 1H); 6.89 (d, J=2.0 Hz, 1H); 7.20 (m, 1H); 7.28 (broad m, 1H); 7.39 to 7.52 (m, 2H); 7.54 to 7.76 (m, 4H); 7.91 (d, J=8.3 Hz, 1H); 7.97 (broad m, 1H); 8.41 (d, J=5.6 Hz, 1H); 8.46 (d, J=7.6 Hz, 1H); 8.59 (d, J=8.6 Hz, 1H); 9.09 (broad s, 1H); 13.40 (broad m, 1H).

Mass spectrum (LC/MS; method A): retention time Tr (min)=0.54; m/z=515 (M−H−); 517 (M+H+).

EXAMPLE 5

Synthesis of acetic acid 4-{2-carbamoyl-5-[4-(6-fluoro-1H-benzimidazol-2-yl)-9H-carbazol-9-yl]phenylamino}-trans-cyclohexyl ester

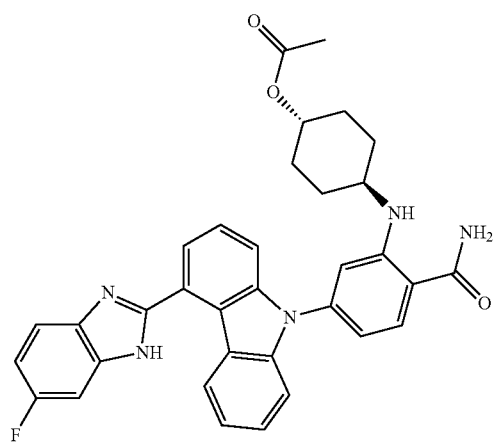

Stage 1: 2.2 g of 9-[4-cyano-3-(4-trans-hydroxycyclohexylamino)phenyl]-9H-carbazole-4-carboxylic acid (2-amino-4-fluorophenyl)amide, obtained according to stage 6 of Example 1, in 100 ml of acetic acid, are brought to reflux for 1 and half hours. After treatment as in stage 7 of Example 1, the residue is purified by silica gel chromatography (15-40 µm), elution being carried out with a mixture of dichloromethane and methanol (96/4 by volume). By recovering the first fraction eluted, 0.2 g of acetic acid 4-{2-cyano-5-[4-(6-fluoro-1H-benzimidazol-2-yl)-9H-carbazol-9-yl]phenylamino}-trans-cyclohexyl ester is obtained, after concentration, in the form of a beige solid, which is used as it is in the subsequent stage. By recovering the second fraction eluted, 1.6 g of 4-[4-(6-fluoro-1H-benzimidazol-2-yl)-9H-carbazol-9-yl]-2-(4-trans-hydroxycyclohexylamino)benzonitrile, described in stage 7 of Example 1, are obtained.

Stage 2: In a 50 ml three-necked flask, 1.36 ml of 30% aqueous hydrogen peroxide are added to a mixture of 200 mg of acetic acid 4-{2-cyano-5-[4-(6-fluoro-1H-benzimidazol-2-yl)-9H-carbazol-9-yl]phenylamino}-trans-cyclohexyl ester, obtained in the preceding stage, in 7.5 ml of ethanol and 3 ml of dimethyl sulphoxide and 0.96 ml of 1M sodium hydroxide, and the mixture is stirred for ¼ hour at ambient temperature. 40 ml of distilled water are added and the mixture is extracted with 3 times 40 ml of ethyl acetate. The combined organic phases are washed with twice 40 ml of a saturated solution of sodium chloride, dried over magnesium sulphate and evaporated to dryness under vacuum. The residue is chromatographed on silica gel (15-40 µm), elution being carried out with a mixture of dichloromethane and methanol (96/4 by volume). 170 mg of acetic acid 4-{2-carbamoyl-5-[4-(6-fluoro-1H-benzimidazol-2-yl)-9H-carbazol-9-yl]phenylamino}-trans-cyclohexyl ester are obtained in the form of an off-white solid, the characteristics of which are the following:

1H NMR spectrum (400 MHz, δ ppm, DMSO-d6): 1.25 to 1.53 (m, 4H) 1.87 (m, 2H) 1.95 (s, 3H) 2.03 (m, 2H) 3.44 (m, 1H) 4.66 (m, 1H) 6.72 (dd, J=8.3, 2.0 Hz, 1H) 6.92 (d, J=2.0 Hz, 1H) 7.04 to 7.23 (m, 2H) 7.29 (broad m, 1H) 7.39 to 7.78 (m, 7H) 7.92 (d, J=8.3 Hz, 1H) 7.99 (broad m, 1H) 8.51 (d, J=7.8 Hz, 1H) 8.65 (d, J=8.8 Hz, 1H) 13.08 (broad m, 1H).

Mass spectrum (LC/MS method A): retention time Tr (min)=0.99; MH+=576+; MH−=574−.

EXAMPLE 6

Synthesis of 2-cyclohexylamino-4-[4-(6-fluoro-1H-benzimidazol-2-yl)-9H-carbazol-9-yl]benzamide

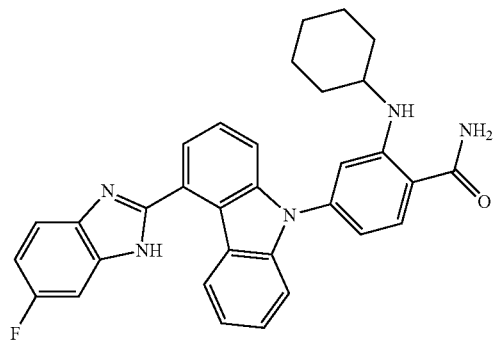

The process is carried out as in stage 3 of Example 3, but using 100 mg of 2-fluoro-4-[4-(6-fluoro-1H-benzimidazol-2-yl)-carbazol-9-yl]benzonitrile, obtained according to stage 2 of Example 3, 263 mg of potassium carbonate and 94 mg of cyclohexylamine in 0.8 ml of dimethyl sulphoxide. 0.4 ml of a 1M aqueous solution of sodium hydroxide, 0.4 ml of a 30% aqueous solution of hydrogen peroxide and 2 ml of ethanol are then added to the reaction medium. After treatment and purification as in stage 3 of Example 3, 40 mg of 2-cyclohexylamino-4-[4-(6-fluoro-1H-benzimidazol-2-yl)-9H-carbazol-9-yl]benzamide are thus obtained in the form of a white solid, the characteristics of which are the following:

1H NMR spectrum (400 MHz, δ in ppm, DMSO-d6): 1.16-1.40 (m, 5H) 1.50 (m, 1H) 1.64 (m, 2H) 1.92 (m, 2H) 3.24-3.43 (m partially masked, 1H) 6.70 (dd, J=8.3, 2.0 Hz, 1H) 6.86 (d, J=2.0 Hz, 1H) 7.10 to 7.85 (m, 10H) 7.92 (d, J=8.3 Hz, 1 H) 7.98 (broad m, 1H) 8.56 (d, J=7.8 Hz, 1H) 8.63 (d, J=7.8 Hz, 1H) 13.07 (broad m, 1H).

Mass spectrum (LC/MS method A): retention time Tr (min)=1.07; MH+=518+; MH−=516−.

EXAMPLE 7

Synthesis of 4-[4-(6-fluoro-1H-benzimidazol-2-yl)-9H-carbazol-9-yl]-2-[2-(2-hydroxyethoxy)ethylamino]benzamide

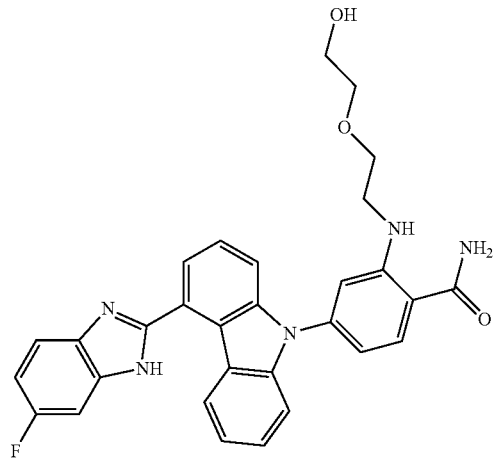

The process is carried out as in stage 3 of Example 3, but using 84 mg of 2-fluoro-4-[4-(6-fluoro-1H-benzimidazol-2-yl)-9H-carbazol-9-yl]benzonitrile, obtained according to stage 2 of Example 3, 83 mg of potassium carbonate and 421 mg of 2-(2-aminoethoxy)ethanol in 0.67 ml of dimethyl sulphoxide. 0.4 ml of a 1M aqueous solution of sodium hydroxide, 0.4 ml of a 30% aqueous solution of hydrogen peroxide and 2 ml of ethanol are then added to the reaction medium. After treatment and purification as in stage 3 of Example 3, 76 mg of 4-[4-(6-fluoro-1H-benzimidazol-2-yl)-9H-carbazol-9-yl]-2-[2-(2-hydroxyethoxy)ethylamino]benzamide are thus obtained in the form of a white solid, the characteristics of which are the following:

1H NMR spectrum (400 MHz, δ in ppm, DMSO-d6): 3.31 (m partially masked, 2H) 3.39 to 3.56 (m, 4H) 3.64 (t, J=5.6 Hz, 2H) 4.53 (t, J=5.6 Hz, 1H) 6.76 (dd, J=8.3, 2.1 Hz, 1H) 6.90 (d, J=2.1 Hz, 1H) 7.08 to 7.86 (m, 10H) 7.92 (d, J=8.3 Hz, 1 H) 7.99 (broad m, 1H) 8.54 (t, J=5.4 Hz, 1H) 8.62 (d, J=8.3 Hz, 1H) 13.08 (broad m, 1H).

Mass spectrum (LC/MS method A): retention time Tr (min)=0.78; MH+=524+; MH−=522−.

EXAMPLE 8

Synthesis of 4-[4-(6-fluoro-1H-benzimidazol-2-yl)-9H-carbazol-9-yl]-2-(3-hydroxypropylamino)benzamide

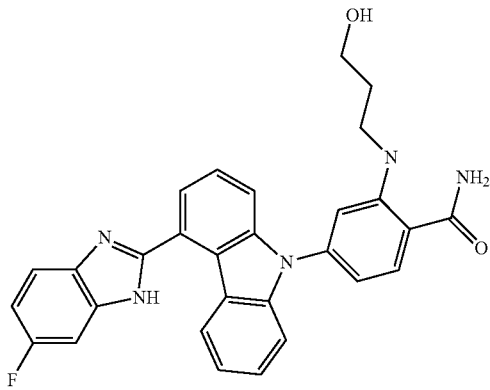

The process is carried out as in stage 3 of Example 3, but using 84 mg of 2-fluoro-4-[4-(6-fluoro-1H-benzimidazol-2-yl)-9H-carbazol-9-yl]benzonitrile, obtained according to stage 2 of Example 3, 83 mg of potassium carbonate and 300 mg of 3-amino-1-propanol in 0.67 ml of dimethyl sulphoxide. 0.4 ml of a 1M aqueous solution of sodium hydroxide, 0.4 ml of a 30% aqueous solution of hydrogen peroxide and 2 ml of ethanol are then added to the reaction medium. After treatment and purification as in stage 3 of Example 3, 85 mg of 4-[4-(6-fluoro-1H-benzimidazol-2-yl)-9H-carbazol-9-yl]-2-(3-hydroxypropylamino)benzamide are thus obtained in the form a white solid, the characteristics of which are the following:

1H NMR spectrum (400 MHz, δ in ppm, DMSO-d6): 1.73 (m, 2H) 3.19 (q, J=5.4 Hz, 2H) 3.50 (q, J=5.4 Hz, 2H) 4.49 (t, J=5.4 Hz, 1H) 6.74 (dd, J=8.3, 2.1 Hz, 1H) 6.86 (d, J=2.1 Hz, 1H) 7.08 to 7.83 (m, 9H) 7.92 (d, J=8.3 Hz, 1H) 7.99 (broad m, 1H) 8.45 (t, J=5.4 Hz, 2H) 8.62 (d, J=8.3 Hz, 1H) 13.08 (broad m, 1H).

Mass spectrum (LC/MS method A): retention time Tr (min)=0.78; MH+=494+; MH-=492-.

EXAMPLE 9

Synthesis of 4-[4-(6-fluoro-1H-benzimidazol-2-yl)-9H-carbazol-9-yl]-2-(4-cis-hydroxycyclohexylamino)benzamide

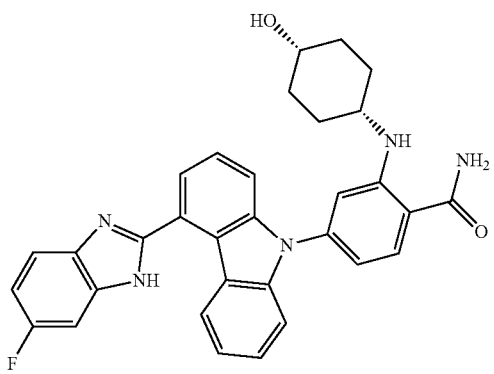

The process is carried out as in stage 3 of Example 3, but using 84 mg of 2-fluoro-4-[4-(6-fluoro-1H-benzimidazol-2-yl)-9H-carbazol-9-yl]benzonitrile, obtained according to stage 2 of Example 3, 111 mg of potassium carbonate and 607 mg of cis-4-aminocyclohexanol hydrochloride in 0.67 ml of dimethyl sulphoxide. 0.4 ml of a 1M aqueous solution of sodium hydroxide, 0.4 ml of a 30% aqueous solution of hydrogen peroxide and 2 ml of ethanol are then added to the reaction medium. After treatment and purification as in stage 3 of Example 3, 85 mg of 4-[4-(6-fluoro-1H-benzimidazol-2-yl)carbazol-9-yl]-2-(4-cis-hydroxycyclohexylamino)benzamide are thus obtained in the form of a white solid, the characteristics of which are the following:

1H NMR spectrum (400 MHz, δ in ppm, DMSO-d6): 1.44 to 1.76 (m, 8H) 3.48 (m, 1H) 3.59 (m, 1H) 4.48 (d, J=3.7 Hz, 1H) 6.71 (dd, J=8.3, 2.1 Hz, 1H) 6.86 (d, J=2.1 Hz, 1H) 7.05 to 7.86 (m, 10H) 7.93 (d, J=8.3 Hz, 1H) 7.98 (broad m, 1H) 8.62 (d, J=8.2 Hz, 1H) 8.70 (d, J=7.9 Hz, 1H) 13.08 (broad m, 1H).

Mass spectrum (LC/MS method A): retention time Tr (min)=0.86; MH+=534+; MH_=532_.

EXAMPLE 10

Synthesis of 2-amino-4-[4-(6-fluoro-1H-benzimidazol-2-yl)-9H-carbazol-9-yl]benzamide

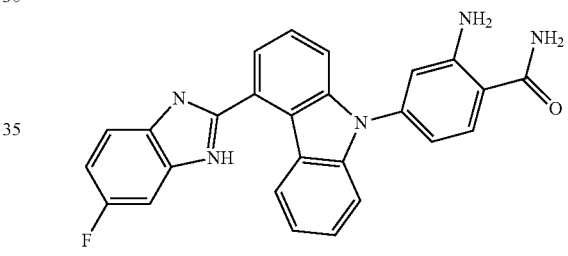

Stage 1: In a microwave reactor, a mixture of 1.015 g of 9-(3-bromo-4-cyanophenyl)-9H-carbazole-4-carboxylic acid methyl ester, obtained according to stage 3 of Example 1, 444 mg of acetamide, 71 mg of trans-N,N'-dimethylcyclohexane-1,2-diamine, 1.039 g of potassium carbonate and 95 mg of copper iodide in 20 ml of dioxane is heated at 160° C. for 1.5 hours. The reaction medium is poured into 200 ml of ethyl acetate. The organic phase is washed with 100 ml of a saturated solution of sodium bicarbonate. The aqueous phase is re-extracted with twice 100 ml of ethyl acetate. The combined organic phases are washed with twice 50 ml of a saturated solution of sodium bicarbonate and once with 100 ml of a saturated solution of sodium chloride, dried over magnesium sulphate and evaporated to dryness under vacuum. The residue is chromatographed on silica gel (40-63 μm), elution being carried out with pure dichloromethane. 520 mg of 9-(3-acetylamino-4-cyanophenyl)-9H-carbazole-4-carboxylic acid methyl ester are obtained in the form of an off-white solid, the characteristics of which are the following:

1H NMR spectrum (400 MHz, δ in ppm, DMSO-d6): 2.15 (s, 3H); 4.03 (s, 3H); 7.35 (m, 1H); 7.52 to 7.60 (m, 3H); 7.63 (dd, J=8.3 Hz and 2.0 Hz, 1H); 7.77 (d, J=7.8 Hz, 1H); 7.85 (d, J=7.8 Hz, 1H); 7.96 (d, J=2.0 Hz, 1H); 8.11 (d, J=8.3 Hz, 1H); 8.74 (d, J=7.8 Hz, 1H); 10.42 (s, 1H).

Mass spectrum (LC/MS; method A): retention time Tr (min)=1.08; m/z=382 (M–H–); 384 (M+H+).

Stage 2: In a 250 ml round-bottomed flask, a mixture of 300 mg 9-(3-acetylamino-4-cyanophenyl)-9H-carbazole-4-carboxylic acid methyl ester, obtained in the preceding stage, and 66 mg of lithium hydroxide monohydrate in 30 ml of methanol is refluxed for 2 hours. The reaction medium is evaporated to dryness under vacuum and the residue taken up with 30 ml of 1M hydrochloric acid is extracted with 3 times 30 ml of dichloromethane. The combined organic phases are washed with 30 ml of a saturated solution of sodium chloride, dried over magnesium sulphate and evaporated to dryness under vacuum. The residue is chromatographed on silica gel (15-40 μm), elution being carried out with pure dichloromethane. 113 mg of 9-(3-amino-4-cyanophenyl)-9H-carbazole-4-carboxylic acid methyl ester are obtained in the form of a white foam, the characteristics of which are the following:

1H NMR spectrum (400 MHz, δ in ppm, DMSO-d6): 4.03 (s, 3H); 6.40 (s, 2H); 6.83 (dd, J=8.3 Hz and 2.0 Hz, 1H); 7.03 (d, J=2.0 Hz, 1H); 7.32 (m, 1H); 7.46 (d, J=8.3 Hz, 1H); 7.49 to 7.58 (m, 2H); 7.70 (m, 2H); 7.84 (broad d, J=7.6 Hz, 1H); 8.73 (d, J=8.3 Hz, 1H).

Mass spectrum (LC/MS; method A): retention time Tr (min)=1.14; m/z=342 (M+H+).

Stage 3: In a 100 ml round-bottomed flask, a mixture of 113 mg of 9-(3-amino-4-cyanophenyl)-9H-carbazole-4-carboxylic acid methyl ester, obtained in the preceding stage, and 0.3 ml of 2.5M sodium hydroxide in 10 ml of methanol is refluxed. After 3.5 hours, 0.3 ml of 2.5M sodium hydroxide is added and the refluxing is continued for 5 hours in total, and then the mixture is allowed to return to ambient temperature overnight. The following day, the reaction medium is evaporated to dryness and the residue is taken up with 10 ml of 1M hydrochloric acid. The suspension is stirred at ambient temperature for ½ hour and the solid is filtered off and washed with 50 ml of distilled water. The yellow solid is chromatographed on silica gel (15-40 μm), elution being carried out with a mixture of dichloromethane and methanol (95/5). 77 mg of 9-(3-amino-4-cyanophenyl)-9H-carbazole-4-carboxylic acid are obtained in the form of a pale yellow solid, the characteristics of which are the following:

1H NMR spectrum (400 MHz, δ in ppm, DMSO-d6): 6.40 (s, 2H); 6.83 (dd, J=8.3 Hz and 2.0 Hz, 1H); 7.03 (d, J=2.0 Hz, 1H); 7.30 (td, J=7.8 Hz and 1.0 Hz, 1H); 7.44 (d, J=7.8 Hz, 1H); 7.46 to 7.56 (m, 2H); 7.65 (d, J=7.8 Hz, 1H); 7.71 (d, J=8.3 Hz, 1H); 7.83 (d, J=7.8 Hz, 1H); 8.87 (d, J=8.3 Hz, 1H); 13.37 (broad m, 1H).

Mass spectrum (LC/MS; method B): retention time Tr (min)=3.90; m/z=326 (M−H−).

Stage 4: In a 250 ml round-bottomed flask, a mixture of 77 mg of 9-(3-amino-4-cyanophenyl)-9H-carbazole-4-carboxylic acid, obtained in the preceding stage, 30 mg of 4-fluoro-O-phenylenediamine, 81 mg of O-((ethoxycarbonyl)cyanomethyleneamino)-N,N,N',N'-tetramethyluronium tetrafluoroborate (TOTU) and 43 μl of diisopropylethylamine in 10 ml of dimethylformamide is stirred at ambient temperature for 3 hours. The reaction medium is evaporated to dryness under vacuum and the residue is taken up with 75 ml of ethyl acetate and 50 ml of a saturated solution of sodium bicarbonate. The resulting product is separated by settling out and the aqueous phase is re-extracted with twice 50 ml of ethyl acetate. The combined organic phases are washed with twice 50 ml of a saturated solution of sodium chloride, dried over magnesium sulphate and evaporated to dryness under vacuum. 155 mg of a light brown solid of 9-(3-amino-4-cyanophenyl)-9H-carbazole-4-carboxylic acid (2-amino-4-fluorophenyl)amide are obtained, said product being using without further characterization in the subsequent stage.

Stage 5: In a 250 ml round-bottomed flask, a mixture of 155 mg of 9-(3-amino-4-cyanophenyl)-9H-carbazole-4-carboxylic acid (2-amino-4-fluorophenyl)amide, obtained in the preceding stage, and 10 ml of acetic acid is refluxed for 1 hour. The reaction medium is evaporated to dryness under vacuum and the residue is chromatographed twice on silica gel (15-40 μm), elution being carried out with a mixture of dichloromethane and methanol (95/5). 40 mg of 2-amino-4-[4-(6-fluoro-1H-benzimidazol-2-yl)-9H-carbazol-9-yl]benzonitrile are obtained in the form of a brownish foam, the characteristics of which are the following:

1H NMR spectrum (400 MHz, δ in ppm, DMSO-d6): 6.42 (s, 2H); 6.87 (dd, J=8.3 Hz and 2.0 Hz, 1H); 7.08 (d, J=2.0 Hz, 1H); 7.10 to 7.24 (m, 2H); 7.35 to 7.80 (broad m, 2H); 7.47 (m, 2H); 7.60 to 7.69 (m, 3H); 7.73 (d, J=8.3 Hz, 1H); 8.59 (d, J=8.3 Hz, 1H); 13.10 (broad m, 1H).

Stage 6: In a 50 ml round-bottomed flask, 0.2 ml of 30% aqueous hydrogen peroxide is added to a mixture of 40 mg of 2-amino-4-[4-(6-fluoro-1H-benzimidazol-2-yl)-9H-carbazol-9-yl]benzonitrile, obtained in the preceding stage, in 1.0 ml of ethanol and 0.4 ml of dimethyl sulphoxide and 0.2 ml of 1M sodium hydroxide, and the mixture is stirred for ¼ hour at ambient temperature. 20 ml of distilled water are added and the mixture is extracted with 3 times 30 ml of ethyl acetate. The combined organic phases are washed with 30 ml of a saturated solution of sodium chloride, dried over magnesium sulphate and evaporated to dryness under vacuum. The residue is chromatographed on silica gel (15-40 μm), elution being carried out with a mixture of dichloromethane and methanol (95/5 by volume). 24 mg of 2-amino-4-[4-(6-fluoro-1H-benzimidazol-2-yl)-9H-carbazol-9-yl]benzamide are obtained in the form of a beige solid, the characteristics of which are the following:

1H NMR spectrum (400 MHz, δ in ppm, DMSO-d6): 6.73 (dd, J=8.6 Hz and 2.2 Hz, 1H); 6.92 (s, 2H); 6.97 (d, J=2.2 Hz, 1H); 7.10 to 7.30 (m, 3H); 7.42 to 7.50 (m, 3H); 7.58 to 7.66 (m, 4H); 7.86 (d, J=8.6 Hz, 1H); 7.90 (broad m, 1H); 8.59 (d, J=8.3 Hz, 1H); 13.09 (broad m, 1H).

Mass spectrum (LC/MS; method B): retention time Tr (min)=3.41; m/z=434 (M−H−); 436 (M+H+).

EXAMPLE 11

Synthesis of 4-[4-(6-fluoro-1H-benzimidazol-2-yl)-9H-carbazol-9-yl]-2-(2-pyrrolidin-1-ylethylamino)benzamide

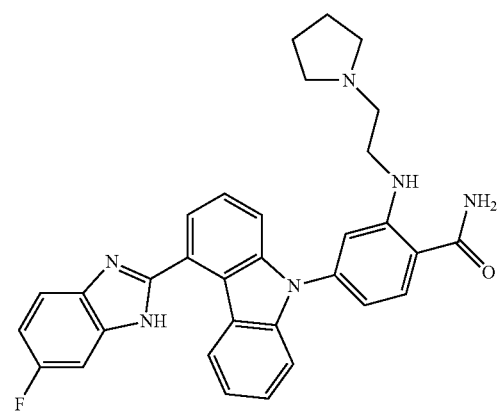

The process is carried out as in stage 3 of Example 3, but using 67 mg of 2-fluoro-4-[4-(6-fluoro-1H-benzimidazol-2-yl)carbazol-9-yl]benzonitrile, obtained in stage 2 of Example 3, 66 mg of potassium carbonate and 364 mg of N-(2-aminoethyl)pyrrolidine in 0.54 ml of dimethyl sulphoxide. 0.32 ml of a 1M aqueous solution of sodium hydroxide, 0.32 ml of a 30% aqueous solution of hydrogen peroxide and 1.6 ml of ethanol are then added to the reaction medium. After treatment and purification as in stage 3 of Example 3, 62 mg of 4-[4-(6-fluoro-1H-benzimidazol-2-yl)-9H-carbazol-9-yl]-2-(2-pyrrolidin-1-ylethylamino)benzamide are thus obtained in the form of a white solid, the characteristics of which are the following:

1H NMR spectrum (400 MHz, δ in ppm, DMSO-d6): 1.67 (m, 4H) 2.42 to 2.54 (m partially masked, 4H) 2.67 (t, J=6.5 Hz, 2H) 3.23 (m, 2H) 6.75 (dd, J=8.2, 2.1 Hz, 1H) 6.86 (d, J=2.1 Hz, 1H) 7.04 to 7.79 (m, 10H) 7.90 (d, J=8.3 Hz, 1H) 7.93 to 8.02 (broad m, 1H) 8.49 (t, J=5.4 Hz, 1H) 8.63 (d, J=8.2 Hz, 1H) 13.12 (broad m, 1 H).

Mass spectrum (LC/MS; method A): retention time Tr (min)=0.67; MH+=533+; MH_=531_.

EXAMPLE 12

Synthesis of 6-[4-(6-fluoro-1H-benzimidazol-2-yl)-9H-carbazol-9-yl]-1H-indazol-3-ylamine

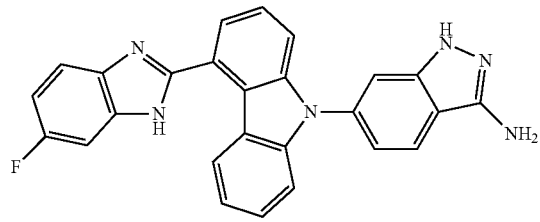

200 mg of 2-fluoro-4-[4-(6-fluoro-1H-benzimidazol-2-yl)-9H-carbazol-9-yl]benzonitrile, obtained in stage 2 of Example 3, 2 ml of n-butanol and 61 mg of hydrazine hydrate are successively introduced into a 5 ml microwave reactor. After stirring for 10 seconds at ambient temperature, the reaction medium is heated at 150° C. for 10 minutes with stirring. After cooling, a further 61 mg of hydrazine hydrate are added and the reaction medium is heated at 150° C. for a further 20 minutes with stirring. After cooling, the reaction medium is diluted with 5 ml of ethyl acetate and then the mixture is evaporated to dryness under vacuum. The crude residue obtained is purified by silica gel chromatography (15-40 μm), elution being carried out with a mixture of dichloromethane and ammonia at 7N in methanol (95/5 by volume). 60 mg of 6-[4-(6-fluoro-1H-benzimidazol-2-yl)-9H-carbazol-9-yl]-1H-indazol-3-ylamine are thus obtained in the form of an amber solid, the characteristics of which are the following:

1H NMR spectrum (400 MHz, δ in ppm, DMSO-d6): 5.54 (broad s, 2H) 7.08 (dd, J=8.5, 1.6 Hz, 1H) 7.11 to 7.23 (m, 2H) 7.32 to 7.91 (m, 9H) 7.99 (d, J=8.5 Hz, 1H) 8.64 (broad m, 1H) 11.63 (broad m, 1H).

Mass spectrum (LC/MS; method B): retention time Tr (min)=3.39; MH+=433+; MH−=431−.

EXAMPLE 13

Synthesis of 6-[4-(6-fluoro-1H-benzimidazol-2-yl)-9H-carbazol-9-yl]-1,2-benzisoxazol-3-ylamine

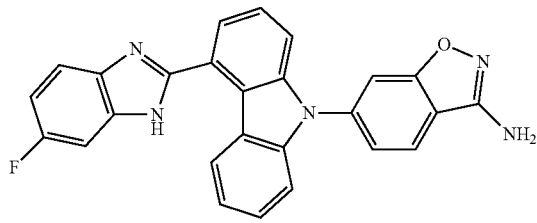

190 mg of N-Boc-hydroxylamine, 160 mg of potassium tert-butoxide and 5 ml of dimethylformamide are successively introduced into a round-bottomed flask at ambient temperature. The reaction medium is stirred for 40 minutes and then 200 mg of 2-fluoro-4-[4-(6-fluoro-1H-benzimidazol-2-yl)-9H-carbazol-9-yl]benzonitrile, obtained according to stage 2 of Example 3, are added and the mixture is stirred for 12 hours. 100 ml of a saturated aqueous solution of sodium chloride are subsequently added and the mixture is extracted with 100 ml of ethyl acetate. The organic phase is washed successively with 50 ml of water and 50 ml of a saturated aqueous solution of sodium chloride, and then dried over magnesium sulphate and evaporated to dryness under vacuum. The crude residue obtained is purified by silica gel chromatography (15-40 μm), elution being carried out with a mixture of dichloromethane and ammonia at 7N in methanol (95/5 by volume). 100 mg of 6-[4-(6-fluoro-1H-benzimidazol-2-yl)-9H-carbazol-9-yl]-1,2-benzisoxazol-3-ylamine are thus obtained in the form of an amber solid, the characteristics of which are the following:

1H NMR spectrum (400 MHz, δ in ppm, DMSO-d6): 6.61 (broad s, 2H) 7.08 to 7.19 (broad m, 1H) 7.21 (t, J=7.4 Hz, 1H) 7.36 to 7.70 (m, 7H) 7.82 (broad s, 1 H) 7.86 (broad m, 1H) 8.13 (d, J=8.5 Hz, 1H) 8.49 to 8.73 (broad m, 1H) 13.12 (broad s, 1H).

Mass spectrum (LC/MS; method A): retention time Tr (min)=0.86; MH+=434+; MH_=432_.

EXAMPLE 14

Synthesis of 2-fluoro-4-[4-(6-fluoro-1H-benzimidazol-2-yl)-9H-carbazol-9-yl]benzamide

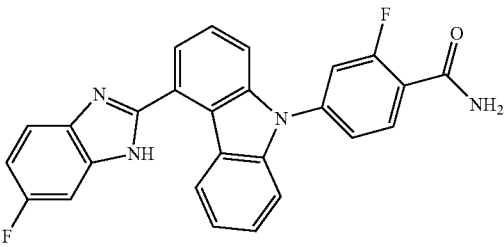

150 mg of 2-fluoro-4-[4-(6-fluoro-1H-benzimidazol-2-yl)-9H-carbazol-9-yl]benzonitrile, obtained according to stage 2 of Example 3, 1 ml of dimethyl sulphoxide, 2 ml of ethanol, 0.5 ml of 1M sodium hydroxide and 0.5 ml of 30% aqueous hydrogen peroxide are successively introduced into a round-bottomed flask and the mixture is stirred for % hour at ambient temperature. 20 ml of distilled water are added and then the suspension is filtered through sintered glass. 141 mg of 2-fluoro-4-[4-(6-fluoro-1H-benzimidazol-2-yl)-9H-carbazol-9-yl]benzamide are thus obtained in the form of a white solid, the characteristics of which are the following:

1H NMR spectrum (400 MHz, δ in ppm, DMSO-d6): 7.05-7.31 (m, 3H) 7.36-7.92 (m, 10H) 7.99 (t, J=8.2 Hz, 1H) 8.65 (d, J=8.1 Hz, 1H) 13.10 (broad m, 1H).

EXAMPLE 15

Synthesis of the tert-butyl and 4-{2-carbamoyl-5-[4-(6-fluoro-1H-benzimidazol-2-yl)-9H-carbazol-9-yl]phenylamino}cyclohexyl ester of malonic acid

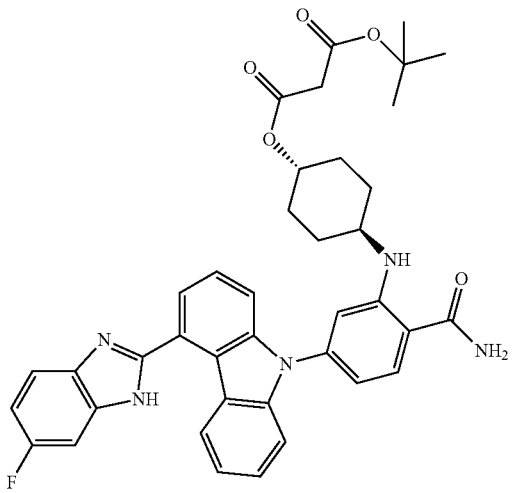

In a 50 ml three-necked flask, under an argon atmosphere, 200 mg of 4-[4-(6-fluoro-1H-benzimidazol-2-yl)-9H-carbazol-9-yl]-2-(4-trans-hydroxycyclohexylamino)benzamide, which can be obtained as in Example 1, and 0.120 g of malonic acid tert-butyl monoester are dissolved in 20 ml of dichloromethane and 2 ml of dimethylformamide. 45.8 mg of 4-dimethylaminopyridine and 144 mg of 1-(3-dimethylaminopropyl)-3-ethylcarbodiimide hydrochloride are subsequently added. The reaction medium is stirred for 20 hours at ambient temperature, and then concentrated under reduced pressure. The residue is taken up with 25 ml of water and 50 ml of a mixture of dichloromethane and methanol (9/1 by volume). The organic phase is separated by settling out, and then the aqueous phase is re-extracted twice with 50 ml of a mixture of dichloromethane and methanol (9/1 by volume). The combined organic phases are washed with 25 ml of water, dried over magnesium sulphate and concentrated to dryness under reduced pressure. The crude product thus obtained is purified by flash chromatography on 15 g of silica gel, elution being carried out with a mixture of dichloromethane and ethanol (95/5 by volume). 165 mg of tert-butyl and 4-{2-carbamoyl-5-[4-(6-fluoro-1H-benzimidazol-2-yl)-9H-carbazol-9-yl]phenylamino}cyclohexyl ester of malonic acid are thus obtained in the form of a white powder, the characteristics of which are the following:

1H NMR spectrum (400 MHz, DMSO) δ ppm: 1.30-1.56 (m, 4H) 1.37 (s, 9 H) 1.83-1.93 (m, 2H) 1.97-2.08 (m, 2H) 3.30 (s, 2H) 3.41-3.54 (m, 1H) 4.66-4.80 (m, 1H) 6.71 (dd, J=8.4, 1.6 Hz, 1H) 6.94 (d, J=1.0 Hz, 1H) 7.10-7.22 (m, 2 H) 7.30 (br. s., 1H) 7.39-7.68 (m, 7H) 7.72 (br. s., 1H) 7.92 (d, J=8.6 Hz, 1H) 8.52 (d, J=7.6 Hz, 1H) 8.66 (d, J=8.3 Hz, 1H) 13.07 (broad s, 1H).

Mass spectrum (LC/MS; method A): retention time Tr (min)=1.11; [M+H]+ m/z 676; [M+H]− m/z 674.

EXAMPLE 16

Synthesis of 2-{3-amino-6-[4-(6-fluoro-1H-benzimidazol-2-yl)-9H-carbazol-9-yl]indazol-1-yl}ethanol

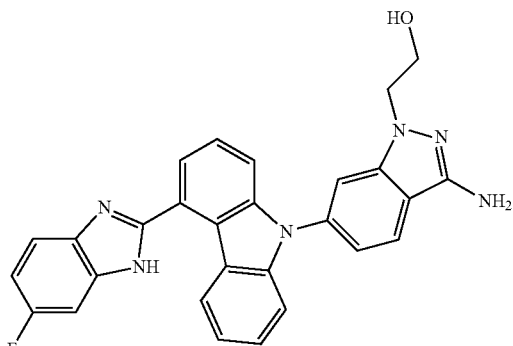

200 mg of 2-fluoro-4-[4-(6-fluoro-1H-benzimidazol-2-yl)-9H-carbazol-9-yl]benzonitrile, obtained according to stage 2 of Example 3, 2 ml of ethanol and 161 mg of 2-hydrazinoethanol are successively introduced into a 5 ml microwave reactor. After stirring for 10 seconds at ambient temperature, the reaction medium is heated at 150° C. for twice 30 minutes with stirring. After cooling, the solvent is evaporated to dryness under vacuum. The crude residue obtained is purified by silica gel chromatography (15-40 μm), elution being carried out with a mixture of dichloromethane and 7N ammonia in methanol (95/5 by volume). 60 mg of 2-{3-amino-6-[4-(6-fluoro-1H-benzimidazol-2-yl)-9H-carbazol-9-yl]indazol-1-yl}ethanol are thus obtained in the form of an off-white solid, the characteristics of which are the following:

1H NMR spectrum (400 MHz, δ in ppm, DMSO-d6): 3.74 (br. s., 2H) 4.20 (t, J=5.5 Hz, 2H) 4.76 (br. s., 1H) 5.62 (s, 2H) 7.07 (dd, J=8.3, 1.7 Hz, 1H) 7.11-7.24 (m, 2H) 7.38-7.48 (m, 2H) 7.49-7.69 (m, 5H) 7.84 (br.s., 1H) 7.96 (d, J=8.3 Hz, 1 H) 8.65 (br. s., 1H) 13.13 (broad s, 1H).

Mass spectrum (LC/MS; method A): retention time Tr (min)=0.75; MH+=477+, MH−=475−.

EXAMPLE 17

Synthesis of 2-(2-acetylaminoethylamino)-4-[4-(6-fluoro-1H-benzimidazol-2-yl)-9H-carbazol-9-yl]benzamide

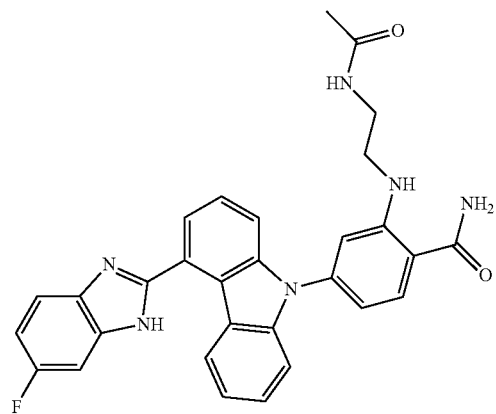

The process is carried out as in stage 3 of Example 3, but using 150 mg of 2-fluoro-4-[4-(6-fluoro-1H-benzimidazol-2-yl)-9H-carbazol-9-yl]benzonitrile, obtained according to stage 2 of Example 3, 148 mg of potassium carbonate and 810 mg of N-acetylethylenediamine in 1.2 ml of dimethyl sulphoxide. 0.4 ml of a 1M aqueous solution of sodium hydroxide, 0.4 ml of a 30% aqueous solution of hydrogen peroxide and 2 ml of ethanol are then added to the reaction medium. After treatment and purification as in stage 3 of Example 3, 72 mg of 2-(2-acetylaminoethylamino)-4-[4-(6-fluoro-1H-benzimidazol-2-yl)-9H-carbazol-9-yl]benzamide are thus obtained in the form of a white solid, the characteristics of which are the following:

1H NMR spectrum (400 MHz, δ in ppm, DMSO-d6): 1.76 (s, 3H) 3.19-3.27 (m, 4H) 6.75 (dd, J=8.1, 1.7 Hz, 1H) 6.94 (d, J=1.7 Hz, 1H) 7.09-7.23 (m, 2H) 7.31 (br. s., 1H) 7.41-7.50 (m, 2H) 7.57-7.75 (m, 5H) 7.84-8.06 (m, 3H) 8.50 (br. s., 1H) 8.62 (d, J=7.8 Hz, 1H) 13.09 (broad s, 1H).

Mass spectrum (LC/MS; method A): retention time Tr (min)=0.75; MH+=521+, MH_=519_.

EXAMPLE 18

Synthesis of 2-(2-aminoethylamino)-4-[4-(6-fluoro-1H-benzimidazol-2-yl)-9H-carbazol-9-yl]benzamide

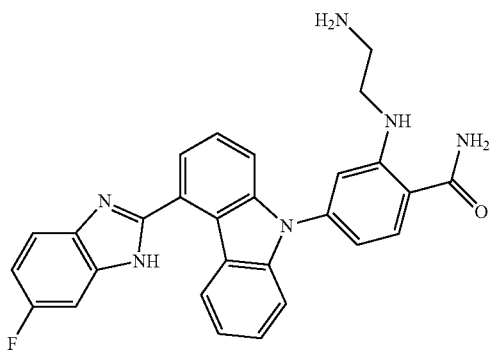

60 mg of 2-(2-acetylaminoethylamino)-4-[4-(6-fluoro-1H-benzimidazol-2-yl)-9H-carbazol-9-yl]benzamide, obtained according to Example 17, 3.4 ml of dioxane and 0.68 ml of 2M hydrochloric acid are successively introduced into a 5 ml microwave reactor. After stirring for 10 seconds at ambient temperature, the reaction medium is heated at 100° C. for twice 30 minutes with stirring. After cooling, the solvent is evaporated to dryness under vacuum. The crude residue obtained is purified by silica gel chromatography (15-40 µm), elution being carried out with a mixture of dichloromethane and 7N ammonia in methanol (90/10 by volume). 20 mg of 2-(2-aminoethylamino)-4-[4-(6-fluoro-1H-benzimidazol-2-yl)-9H-carbazol-9-yl]benzamide are thus obtained in the form of an off-white solid, the characteristics of which are the following:

1H NMR spectrum (400 MHz, δ in ppm, DMSO-d6): 2.77 (t, J=6.2 Hz, 2H) 3.14 (q, J=6.0 Hz, 2H) 6.74 (dd, J=8.3, 1.5 Hz, 1H) 6.88 (d, J=1.2 Hz, 1H) 7.10-7.35 (m, 3H) 7.38-7.85 (m, 8H) 7.87-8.04 (m, 2H) 8.50 (t, J=5.4 Hz, 1H) 8.63 (d, J=8.6 Hz, 1H).

Mass spectrum (LC/MS; method A): retention time Tr (min)=0.64; MH+=479+, MH_=477_.

EXAMPLE 19

Synthesis of 6-[4-(6-fluoro-1H-benzimidazol-2-yl)carbazol-9-yl]nicotinamide

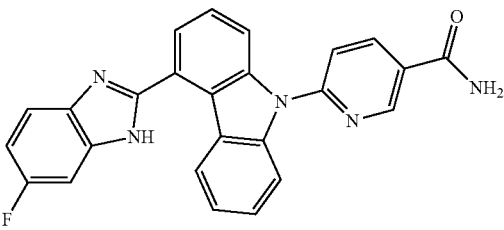

Stage 1: 0.49 g of 2-bromo-5-cyanopyridine, 2.2 g of caesium carbonate, 0.12 g of 9,9-dimethyl-4,5-bis(diphenylphosphino)xanthene and 0.04 g of palladium acetate are successively added to a solution of 0.40 g of 9H-carbazole-4-carboxylic acid methyl ester, obtained according to stage 2 of Example 1, in 30 ml of dioxane under an inert argon atmosphere. The reaction mixture is refluxed for 2 hours, and then cooled, filtered and concentrated under reduced pressure. The residue is purified by silica gel chromatography (15-40 µm), elution being carried out with a mixture of petroleum ether and dichloromethane (60/40 by volume), so as to give 376 mg of 9-(5-cyanopyridin-2-yl)-9H-carbazole-4-carboxylic acid methyl ester in the form of a yellow powder, the characteristics of which are the following:

1H NMR spectrum (400 MHz, DMSO-$d_6$) δ ppm 4.03 (s, 3H) 7.39 (t, J=8.1 Hz, 1 H) 7.51-7.64 (m, 2H) 7.84-7.92 (m, 2H) 8.04 (d, J=8.6 Hz, 1H) 8.15 (d, J=8.3 Hz, 1H) 8.61 (dd, J=8.6, 2.2 Hz, 1H) 8.70 (d, J=7.8 Hz, 1H) 9.21 (d, J=2.2 Hz, 1H).

Mass spectrum (LC/MS; method A): retention time Tr (min)=1.11; m/z=328 [M+H]+; m/z=326 [M−H]−.

Stage 2: 1.6 ml of 2M sodium hydroxide are added to a solution of 0.33 g of 9-(5-cyanopyridin-2-yl)-9H-carbazole-4-carboxylic acid methyl ester, obtained according to the preceding stage, in 30 ml of methanol, and then the mixture is heated at 60° C. for 2 hours. After a return to ambient temperature, the reaction mixture is concentrated under reduced pressure, and then 20 ml of water and a 1M aqueous solution of HCl are added in order to bring the pH to around 6. The aqueous phase is extracted with 3×100 ml of ethyl acetate, and the organic phases are then combined, dried over magnesium sulphate and concentrated under reduced pressure. 0.24 g of 9-(5-carbamoylpyridin-2-yl)-9H-carbazole-4-carboxylic acid is thus obtained in the form of a rubbery residue, the characteristics of which are the following:

1H NMR spectrum (400 MHz, DMSO-$d_6$) δ ppm 7.35 (t, J=7.7 Hz, 1H) 7.46-7.59 (m, 2H) 7.71 (br. s., 1H) 7.80 (d, J=8.3 Hz, 1H) 7.86 (d, J=7.5 Hz, 1H) 7.90 (d, J=8.3 Hz, 1H) 8.03 (d, J=8.3 Hz, 1H) 8.30 (br. s., 1H) 8.54 (dd, J=8.3, 2.4 Hz, 1H) 8.86 (d, J=7.9 Hz, 1H) 9.20 (d, J=2.2 Hz, 1H) 13.35 (broad s, 1H).

Mass spectrum (LC/MS; method A): retention time Tr (min)=0.60; m/z=332 [M+H]+; m/z=330 [M−H]−.

Stage 3: In a 50 ml round-bottomed flask, a mixture of 210 mg of 9-(5-carbamoylpyridin-2-yl)-9H-carbazole-4-carboxylic acid, obtained according to the preceding stage, 105 mg of 4-fluoro-O-phenylenediamine, 273 mg of O-((ethoxycarbonyl)cyanomethyleneamino)-N,N,N',N'-tetramethyluronium tetrafluoroborate (TOTU) and 138 µl of diisopropylethylamine in 36 ml of dimethylformamide is stirred at ambient temperature for 12 hours. 300 ml of water are added to the reaction medium and then the aqueous phase is extracted with twice 300 ml of ethyl acetate. The organic phases are combined, washed with 100 ml of a saturated solution of sodium chloride, dried over magnesium sulphate and then evaporated to dryness under vacuum. The crude residue obtained is dissolved with 8.5 ml of glacial acetic acid in a 20 ml tube reactor and heated in a microwave at 110° C. for 1 hour. After return to ambient temperature, the reaction mixture is concentrated under reduced pressure and then 10 ml of water and a 10% aqueous solution of sodium hydrogen carbonate are added in order to bring the pH to around 8. The aqueous phase is extracted with 1×100 ml of ethyl acetate and then the organic phase is concentrated under reduced pressure. The crude residue obtained is purified by silica gel chromatography (15-40 µm), elution being carried out with a mixture of dichloromethane and 7N ammonia in methanol (95/5 by volume). 110 mg of 6-[4-(6-fluoro-1H-benzimidazol-2-yl)-9H-carbazol-9-yl]nicotinamide are thus obtained in the form of an off-beige solid, the characteristics of which are the following:

1H NMR spectrum (400 MHz, δ in ppm, DMSO-d6): 7.16 (dd, J=9.8, 2.4 Hz, 1H) 7.24 (t, J=8.1 Hz, 1H) 7.41-7.58 (m, 2H) 7.58-7.79 (m, 4H) 7.84 (d, J=8.3 Hz, 1H) 7.94 (d, J=8.1 Hz, 1H) 8.01 (dd, J=8.1, 1.2 Hz, 1H) 8.30 (br. s., 1H) 8.48 (d, J=8.1 Hz, 1H) 8.56 (dd, J=8.3, 2.4 Hz, 1H) 9.22 (d, J=2.2 Hz, 1H) 13.12 (broad s, 1 H)

Mass spectrum (LC/MS; method A): retention time Tr (min)=0.69; m/z=422 (M−H−); 420 (M+H+).

EXAMPLE 20

Synthesis of 4-[4-(6-aminopyridin-3-yl)-9H-carbazol-9-yl]-2-[(4-trans-hydroxycyclohexyl)amino]benzamide

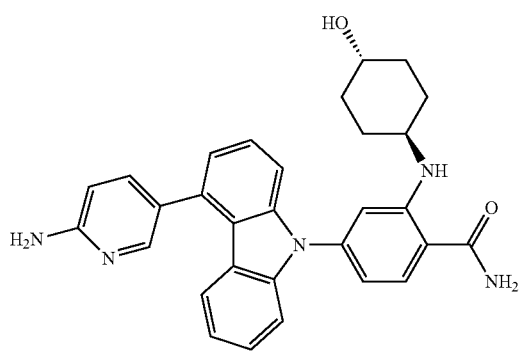

Stage 1: 1.85 g of 2-methyl propan-2-yl[5-(4,4,5,5-tetramethyl-1,3,2-dioxaborolan-2-yl)pyridin-2-yl]carbamate, 2.48 g of caesium carbonate and 70 mg of 1,1'-bis(diphenylphosphino)ferrocenepalladium(II) dichloride, as a complex with dichloromethane (1/1) [PdCl$_2$(dppf)CH$_2$Cl$_2$], are successively added, under argon, to a solution of 0.6 g of 4-trifluoromethanesulphonyloxycarbazole, obtained in stage 1 of Example 1, in a mixture of 28 ml of dioxane and 9 ml of water. The reaction mixture is refluxed for 5 hours and concentrated under reduced pressure. The brown residue is taken up in dichloromethane, treated with animal black, filtered through celite and concentrated under reduced pressure, so as to give a yellow oil which is subsequently purified by silica gel chromatography, elution being carried out with a mixture of cyclohexane and ethyl acetate (85/15 by volume). 0.39 g of 2-methylpropan-2-yl[5-(9H-carbazol-4-yl)pyridin-2-yl]carbamate is thus obtained in the form of a white solid, the characteristics of which are the following:

1H NMR spectrum (400 MHz, δ in ppm, DMSO-d6): 1.52 (s, 9H) 6.97 (m, 1 H) 7.02 (dd, J=7.5, 1.1 Hz, 1H) 7.31-7.42 (m, 2H) 7.43-7.55 (m, 3H) 7.93-8.02 (m, 2H) 8.44 (dd, J=2.3, 1.1 Hz, 1H) 9.92 (broad s, 1H) 11.47 (broad s, 1H).

Mass spectrum (LC/MS; method A): retention time Tr (min)=1.11; m/z=360 [M+H]+

Stage 2: 0.217 g of 4-bromo-2-fluorobenzonitrile, 0.9 g of caesium carbonate, 0.05 g of (9,9-dimethyl-9H-xanthene-4,5-diyl)bis(diphenylphosphane) and 0.016 g of palladium acetate are successively added, under argon, to a solution of 0.26 g of 2-methylpropan-2-yl[5-(9H-carbazol-4-yl)pyridin-2-yl]carbamate in 15 ml of dioxane. The reaction mixture is refluxed for 5 hours, cooled to ambient temperature and filtered through celite. The filtrate is concentrated under reduced pressure so as to give a brown oil which, after trituration in diisopropyl ether, gives a yellow solid which is purified by silica gel chromatography, elution being carried out with a mixture of cyclohexane and ethyl acetate (90/10 by volume). 0.11 g of 2-methylpropan-2-yl {5-[9-(4-cyano-3-fluorophenyl)-9H-carbazol-4-yl]pyridin-2-yl}carbamate is thus obtained, the characteristics of which are the following:

1H NMR spectrum (400 MHz, δ in ppm, DMSO-d6): 1.53 (s, 9H) 7.15 (m, 1 H) 7.21 (m, 1H) 7.38-7.47 (m, 2H) 7.51-7.59 (m, 3H) 7.77 (dd, J=8.4, 2.0 Hz, 1 H) 7.95-8.05 (m, 3H) 8.25 (m, 1H) 8.46 (dd, J=2.4, 1.0 Hz, 1H) 9.97 (broad s, 1H).

Mass spectrum (LC/MS; method A): retention time Tr (min)=1.26; m/z=479 [M+H]+

Stage 3: 0.095 g of potassium carbonate and 0.53 g of trans-4-aminocyclohexanol are successively added to a solution of 0.11 g of 2-methylpropan-2-yl {5-[9-(4-cyano-3-fluorophenyl)-9H-carbazol-4-yl]pyridin-2-yl}carbamate in 1 ml of dimethyl sulphoxide. The reaction mixture is heated at 90° C. for 1 hour in a microwave, and then 2.5 ml of ethanol are added, followed by 0.46 ml of a 1N solution of sodium hydroxide and 0.46 ml of 30% aqueous hydrogen peroxide. The reaction mixture is stirred at ambient temperature for 15 minutes and then diluted with distilled water. The aqueous phase is extracted twice with ethyl acetate and the combined organic phases are washed with water and a saturated solution of sodium chloride, dried over magnesium sulphate and filtered. The filtrate is concentrated under reduced pressure and the residue is purified by silica gel chromatography, elution being carried out with a mixture of cyclohexane and ethyl acetate (94/6 by volume). 0.04 g of 2-methylpropan-2-yl[5-(9-{4-carbamoyl-3-[(4-trans-hydroxycyclohexyl)amino]phenyl}-9H-carbazol-4-yl)pyridin-2-yl]carbamate is thus obtained in the form of a white solid, the characteristics of which are the following:

1H NMR spectrum (400 MHz, δ in ppm, DMSO-d6): 1.24 (m, 4H) 1.53 (s, 9 H) 1.78 (m, 2H) 1.99 (m, 2H) 3.33 (m partially masked, 1H) 3.47 (m, 1H) 4.47 (d, J=4.2 Hz, 1H) 6.69 (dd, J=8.3, 2.0 Hz, 1H) 6.87 (d, J=2.0 Hz, 1H) 7.10 (m, 1H) 7.14 (dd, J=7.2, 1.0 Hz, 1H) 7.25 (broad m, 1H) 7.35-7.48 (m, 4H) 7.52 (dd, J=8.5, 7.2 Hz, 1H) 7.89 (d, J=8.5 Hz, 1H) 7.95 (broad m, 1H) 7.99 (dd, J=8.5, 2.3 Hz, 1H) 8.03 (dd, J=8.5, 1.0 Hz, 1H) 8.45 (d, J=7.7 Hz, 1H) 8.47 (dd, J=2.3, 1.0 Hz, 1H) 9.96 (broad s, 1H).

Mass spectrum (LC/MS; method B): retention time Tr (min)=4.73; m/z=592 [M+H]+; 590 [M−H]−

Stage 4: 0.13 ml of 1N hydrochloric acid is added to a solution of 0.04 g of 2-methylpropan-2-yl 4-carbamoyl-3-[(4-trans-hydroxycyclohexyl)amino]phenyl}-9H-carbazol-4-yl)pyridin-2-yl]carbamate in 1 ml of dioxane. The reaction mixture is heated at 100° C. in a microwave for 15 minutes, and then concentrated under reduced pressure. The residue is triturated with diisopropyl ether and the solid formed is filtered off, so as to give 37 mg of 4-[4-(6-aminopyridin-3-yl)-9H-carbazol-9-yl]-2-[(4-trans-hydroxycyclohexyl)amino]benzamide hydrochloride in the form of a white solid, the characteristics of which are the following:

1H NMR spectrum (400 MHz, δ in ppm, DMSO-d6): 1.16-1.31 (m, 4H) 1.78 (m, 2H) 1.97 (m, 2H) 3.29 (m, 1H) 3.48 (m, 1H) 6.67 (dd, J=8.3, 2.2 Hz, 1H) 6.84 (d, J=2.2 Hz, 1H) 7.11-7.35 (m, 4H) 7.43-7.68 (m, 6H) 7.90 (d, J=8.3 Hz, 1H) 7.97 (broad m, 1H) 8.10-8.29 (m, 4H) 8.49 (broad m, 1H) 13.85 (broad m, 1H).

Mass spectrum (LC/MS; method B): retention time Tr (min)=2.84; m/z=492 [M+H]+; 490 [M−H]−

EXAMPLE 21

Synthesis of tert-butoxycarbonylaminoacetic acid 4-trans-{2-carbamoyl-5-[4-(6-fluoro-1H-benzimidazol-2-yl)-9H-carbazol-9-yl]phenylamino}cyclohexyl ester

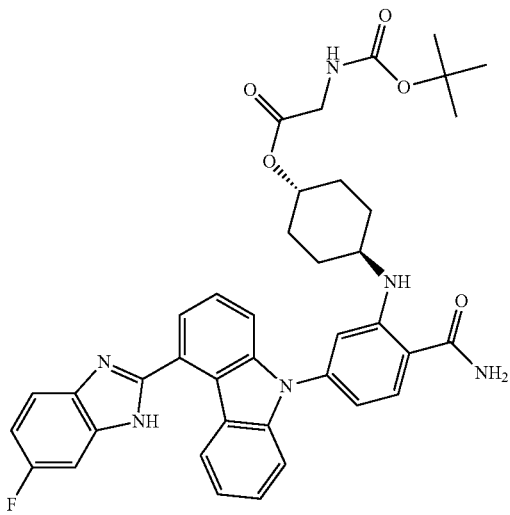

The process is carried out as in Example 15, but using 267 mg of 4-[4-(6-fluoro-1H-benzimidazol-2-yl)-9H-carbazol-9-yl]-2-(4-trans-hydroxycyclohexylamino)benzamide, which can be obtained as in Example 1, 175 mg of N-tert-butoxycarbonylglycine, 61 mg of 4-dimethylaminopyridine and 192 mg of 1-(3-dimethylaminopropyl)-3-ethylcarbodiimide hydrochloride in 50 ml of dichloromethane and 5 ml of dimethylformamide for 20 hours at 45° C. A further 175 mg of N-tert-butoxycarbonylglycine, 61 mg of 4-dimethylaminopyridine and 192 mg of 1-(3-dimethylaminopropyl)-3-ethylcarbodiimide hydrochloride are then added, and the mixture is stirred for 3 days at ambient temperature. After treatment and purification by flash chromatography, the process being carried out as in Example 15, the product then obtained is crystallized from 5 ml of diisopropyl ether. 275 mg of tert-butoxycarbonylaminoacetic acid 4-{2-carbamoyl-5-[4-(6-fluoro-1H-benzimidazol-2-yl)-9H-carbazol-9-yl]phenylamino}cyclohexyl ester are thus obtained in the form of fine light beige crystals, the characteristics of which are the following:

1H NMR spectrum (400 MHz, δ in ppm, DMSO-d6): 1.36 (s, 9H) 1.40-1.56 (m, 4H) 1.80-1.95 (m, 2H) 1.97-2.09 (m, 2H) 3.39-3.52 (m, 1H) 3.59 (d, J=6.1 Hz, 2H) 4.65-4.81 (m, 1H) 6.72 (dd, J=8.3, 1.7 Hz, 1H) 6.93 (s, 1H) 7.08-7.23 (m, 3H) 7.30 (br. s., 1H) 7.39-7.68 (m, 7H) 7.72 (br. s., 1H) 7.92 (d, J=8.3 Hz, 1H) 8.53 (d, J=7.1 Hz, 1H) 8.66 (d, J=7.8 Hz, 1H) 13.08 (br. s., 1H).

Mass spectrum (LC/MS; method A): retention time Tr (min)=1.05; [M+H]+ m/z 691; [M+H]− m/z 689

EXAMPLE 22

Synthesis of 2(S)-tert-butoxycarbonylaminopropionic acid 4-trans-{2-carbamoyl-5-[4-(6-fluoro-1H-benzimidazol-2-yl)-9H-carbazol-9-yl]phenylamino}cyclohexyl ester

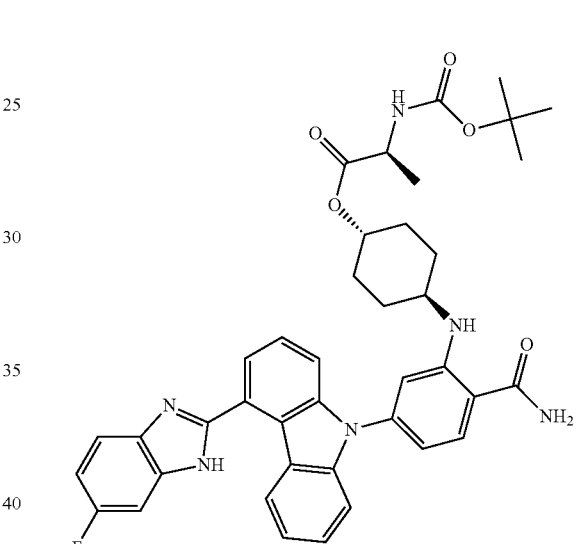

The process is carried out as in Example 15, but using 534 mg of 4-[4-(6-fluoro-1H-benzimidazol-2-yl)-9H-carbazol-9-yl]-2-(4-trans-hydroxycyclohexylamino)benzamide, which can be obtained as in Example 1, 189 mg of N-tert-butoxycarbonylalanine, 122 mg of 4-dimethylaminopyridine and 383.5 mg of 1-(3-dimethylaminopropyl)-3-ethylcarbodiimide hydrochloride in 50 ml of dichloromethane and 5 ml of dimethylformamide for 20 hours at 45° C. A further 189 mg of N-tert-butoxycarbonylalanine, 122 mg of 4-dimethylaminopyridine and 383.5 mg of 1-(3-dimethylaminopropyl)-3-ethylcarbodiimide hydrochloride are then added and the mixture is stirred for 3 days at ambient temperature. After treatment, purification by flash chromatography and crystallization, the process being carried out as in Example 16, 435 mg of 2(S)-tert-butoxycarbonylaminopropionic acid 4-trans-{2-carbamoyl-5-[4-(6-fluoro-1H-benzimidazol-2-yl)-9H-carbazol-9-yl]phenylamino}cyclohexyl ester are thus obtained in the form of fine light beige crystals, the characteristics of which are the following:

1H NMR spectrum (400 MHz, δ in ppm, DMSO-d6): 1.19 (d, J=7.3 Hz, 3H) 1.35 (s, 9H) 1.40-1.56 (m, 4H) 1.78-1.92 (m, 2H) 1.96-2.08 (m, 2H) 3.41-3.52 (m, 1H) 3.85-3.96 (m, 1H) 4.64-4.76 (m, 1H) 6.72 (dd, J=8.3, 1.7 Hz, 1H) 6.93 (s, 1H) 7.09-7.24 (m, 3H) 7.30 (br. s., 1H) 7.40-7.68 (m, 7H)

7.92 (d, J=8.3 Hz, 1H) 8.00 (br. s., 1H) 8.55 (d, J=7.1 Hz, 1H) 8.66 (d, J=7.8 Hz, 1H) 13.08 (broad s, 1H).

Mass spectrum (LC/MS; method A): retention time Tr (min)=1.08; [M+H]+ m/z 705; [M+H]− m/z 703.

EXAMPLE 23

Synthesis of 3-tert-butoxycarbonylaminopropionic acid 4-trans-{2-carbamoyl-5-[4-(6-fluoro-1H-benzimidazol-2-yl)-9H-carbazol-9-yl]phenylamino}cyclohexyl ester

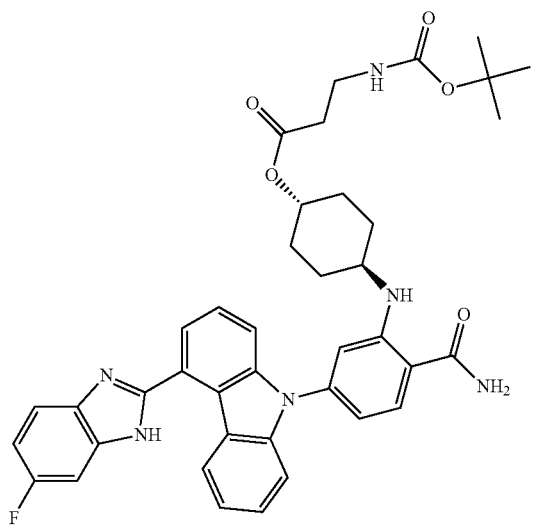

In a 250 ml three-necked flask, under an argon atmosphere, 750 mg of 4-[4-(6-fluoro-1H-benzimidazol-2-yl)-9H-carbazol-9-yl]-2-(4-trans-hydroxycyclo-hexylamino)benzamide, which can be obtained as in Example 1, and 532 mg of N-tert-butoxycarbonyl-beta-alanine are dissolved in 70 ml of dichloromethane and 14 ml of dimethylformamide. 343.5 mg of 4-dimethylaminopyridine and 923 mg of O-[(ethoxycarbonyl)cyanomethyleneamino]-N,N,N',N'-tetramethylurea (TOTU) are subsequently added, and then the mixture is stirred for 20 hours at ambient temperature. A further 750 mg of N-tert-butoxycarbonyl-beta-alanine, 343.5 mg of 4-dimethylaminopyridine and 923 mg of 0-[(ethoxycarbonyl)cyanomethyleneamino]-N,N,N',N'-tetramethylurea (TOTU) are then added, and then the mixture is stirred again for 20 hours at ambient temperature. After treatment, purification by flash chromatography and crystallization, the process being carried out as in Example 16, 725 mg of 3-tert-butoxycarbonylaminopropionic acid 4-trans-{2-carbamoyl-5-[4-(6-fluoro-1H-benzimidazol-2-yl)-9H-carbazol-9-yl]phenylamino}cyclohexyl ester are thus obtained in the form of fine light beige crystals, the characteristics of which are the following:

1H NMR spectrum (400 MHz, DMSO) δ ppm 1.33 (s, 9H) 1.37-1.51 (m, 4H) 1.83-1.92 (m, 2H) 1.97-2.07 (m, 2H) 2.36 (t, J=6.8 Hz, 2H) 3.12 (q, J=6.7 Hz, 2H) 3.38-3.52 (m, 1H) 4.61-4.78 (m, 1H) 6.72 (dd, J=8.1, 1.5 Hz, 1H) 6.74-6.83 (m, 1H) 6.91 (s, 1H) 7.10-7.22 (m, 2H) 7.30 (br. s., 1H) 7.37-7.68 (m, 7H) 7.92 (d, J=8.6 Hz, 1H) 7.99 (br. s., 1H) 8.53 (d, J=7.6 Hz, 1H) 8.64 (dd, J=19.2, 7.7 Hz, 1H) 13.08 (broad s, 1H).

Mass spectrum (LC/MS; method B): retention time Tr (min)=4.47; [M+H]+ m/z 705; [M+H]− m/z 703.

EXAMPLE 24

Synthesis of the trifluoroacetate of the 4-trans-{2-carbamoyl-5-[4-(6-fluoro-1H-benzimidazol-2-yl)-9H-carbazol-9-yl]phenylamino}cyclohexyl ester of 3-aminopropionic acid

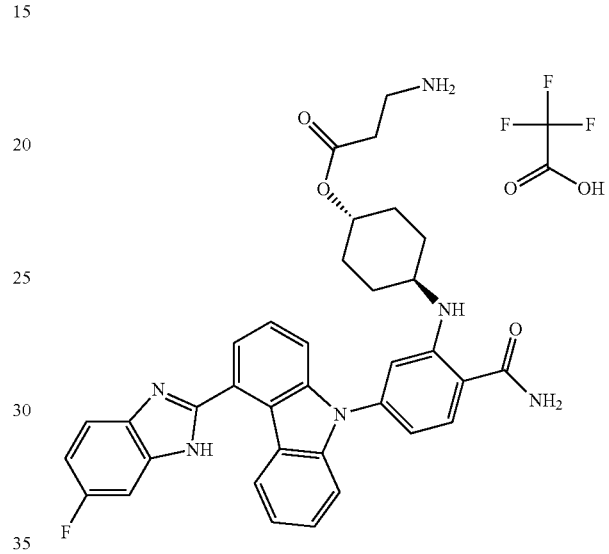

In a 50 ml single-necked round-bottomed flask, 560 mg of 3-tert-butoxycarbonylaminopropionic acid 4-trans-{2-carbamoyl-5-[4-(6-fluoro-1H-benzimidazol-2-yl)carbazol-9-yl]phenylamino}cyclohexyl ester, obtained in Example 23, are dissolved in 15 ml of dichloromethane. The solution obtained is cooled to 0° C., and then 10 ml of trifluoroacetic acid are added and the mixture is stirred at 0° C. for 2 hours. The reaction medium is concentrated under reduced pressure. The residue is then dissolved in the minimum amount of methanol (1.2 ml), and then precipitated by slow addition of 5 ml of diisopropyl ether. After stirring for 30 minutes at 0° C., the precipitate formed is spin-filter-dried, washed twice with 5 ml of diisopropyl ether and dried for 4 hours in an oven under vacuum at 50° C., in the presence of potassium hydroxide chips. 559 mg of the trifluoroacetate of the 4-trans-{2-carbamoyl-5-[4-(6-fluoro-1H-benzimidazol-2-yl)-9H-carbazol-9-yl]phenylamino}cyclohexyl ester of 3-aminopropionic acid are thus obtained in the form of an off-white powder, the characteristics of which are the following:

1H NMR spectrum (400 MHz, DMSO-d6+TFA, δ ppm): 1.38-1.59 (m, 4H) 1.89-2.01 (m, 2H) 2.03-2.14 (m, 2H) 2.59-2.69 (m, 2H) 2.98-3.11 (m, 2H) 3.44-3.57 (m, 1H) 4.73-4.83 (m, 1H) 6.83 (d, J=7.8 Hz, 1H) 7.01 (s, 1H) 7.27 (broad s, 1H) 7.52-7.63 (m, 3H) 7.67-7.93 (m, 5H) 7.97-8.09 (m, 2H).

Mass spectrum (LC/MS; method A): retention time Tr (min)=0.73; [M+H]+m/z 605; [M+H]− m/z 603

EXAMPLE 25

Synthesis of the trifluoroacetate of the 4-trans-{2-carbamoyl-5-[4-(6-fluoro-1H-benzimidazol-2-yl)-9H-carbazol-9-yl]phenylamino}cyclohexyl ester of aminoacetic acid

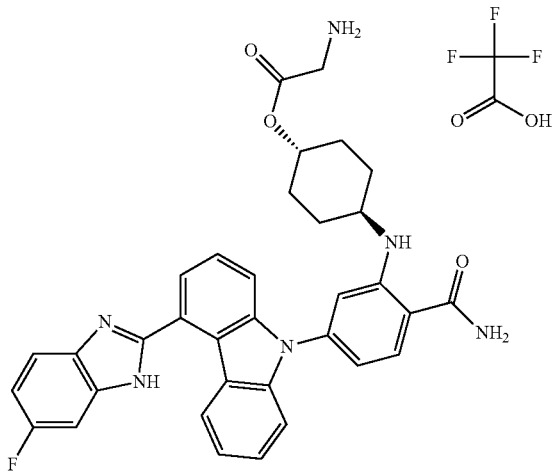

The process is carried out as in Example 24, but using 400 mg of tert-butoxycarbonylaminoacetic acid 4-trans-(2-carbamoyl-5-[4-(6-fluoro-1H-benzimidazol-2-yl)-9H-carbazol-9-yl]phenylamino]cyclohexyl ester, obtained in Example 21, in 10 ml of dichloromethane and 10 ml of trifluoroacetic acid, for 1 and a half hours at 0° C. After treatment as in Example 24, 347 mg of the trifluoroacetate of the 4-trans-{2-carbamoyl-5-[4-(6-fluoro-1H-benzimidazol-2-yl)-9H-carbazol-9-yl]phenylamino}cyclohexyl ester of aminoacetic acid are obtained in the form of a very pale yellow powder, the characteristics of which are the following:

1H NMR spectrum (400 MHz, DMSO-$d_{6+}$TFA, δ ppm): 1.37-1.63 (m, 4H) 1.89-2.01 (m, 2H) 2.02-2.15 (m, 2H) 3.45-3.57 (m, 1H) 3.78 (s, 2H) 4.82-4.94 (m, 1H) 6.79 (d, J=7.6 Hz, 1H) 6.99 (s, 1H) 7.26 (broad s, 1H) 7.49-7.62 (m, 3H) 7.67-7.92 (m, 5H) 7.94-8.10 (m, 2H).

Mass spectrum (LC/MS; method A): retention time Tr (min)=0.70; [M+H]+ m/z 591; [M+H]− m/z 589.

EXAMPLE 26

Synthesis of the trifluoroacetate of the 4-trans-{2-carbamoyl-5-[4-(6-fluoro-1H-benzimidazol-2-yl)-9H-carbazol-9-yl]phenylamino}cyclohexyl ester of 2(S)-aminopropionic acid

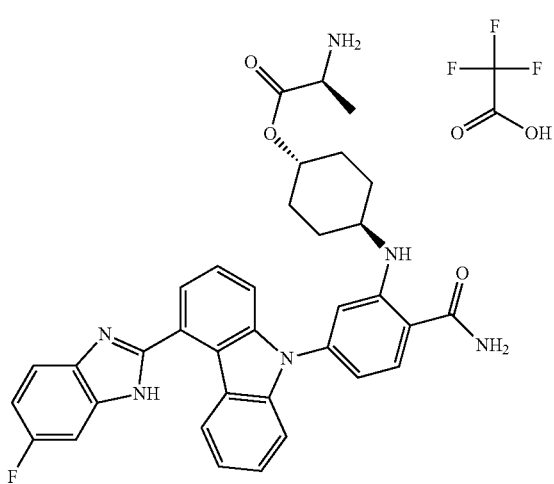

The process is carried out as in Example 24, but using 300 mg of 2(S)-tert-butoxycarbonylaminopropionic acid 4-trans-{2-carbamoyl-5-[4-(6-fluoro-1H-benzimidazol-2-yl)-9H-carbazol-9-yl]phenylamino}cyclohexyl ester, obtained in Example 22, in 7.5 ml of dichloromethane and 10 ml of trifluoroacetic acid, for 2 hours at 0° C. After treatment as in Example 24, 290 mg of the trifluoroacetate of the 4-trans-{2-carbamoyl-5-[4-(6-fluoro-1H-benzimidazol-2-yl)-9H-carbazol-9-yl]phenylamino}cyclohexyl ester of 2(S)-aminopropionic acid are obtained in the form of fine pale yellow crystals, the characteristics of which are the following:

1H NMR spectrum (400 MHz, DMSO-d6, δ ppm): 1.35 (d, J=6.8 Hz, 3H) 1.39-1.60 (m, 4H) 1.87-1.97 (m, 2H) 2.00-2.10 (m, 2H) 3.44-3.54 (m, 1H) 4.00-4.11 (m, 1H) 4.79-4.88 (m, 1H) 6.73 (d, J=8.1 Hz, 1H) 6.93 (s, 1H) 7.16-7.24 (m, 2H) 7.31 (broad s, 1H) 7.41-7.69 (m, 7H) 7.71-7.79 (m, 1H) 7.93 (d, J=8.6 Hz, 1H) 8.01 (broad s, 1H) 8.25 (broad s, 3H) 8.56 (d, J=8.1 Hz, 1H).

Mass spectrum (LC/MS; method B): retention time Tr (min)=3.14; [M+H]+ m/z 605; [M+H]− m/z 603

EXAMPLE 27

Synthesis of 2-[(4-trans-hydroxycyclohexyl)amino]-4-[4-(5-methoxypyridin-3-yl)-9H-carbazol-9-yl]benzamide

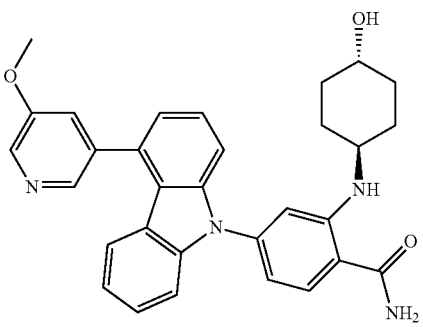

Stage 1: 0.54 g of (5-methoxypyridin-3-yl)boronic acid, 3.3 g of caesium carbonate and 93 mg of 1,1'-bis(diphenylphosphino)ferrocenepalladium(II) dichloride as a complex with dichloromethane (1/1) [PdCl$_2$(dppf)CH$_2$Cl$_2$] are successively added, under argon, to a solution of 0.8 g of 4-trifluoromethanesulphonyloxycarbazole, obtained in stage 1 of Example 1, in a mixture of 37 ml of dioxane and 12 ml of water. The reaction mixture is refluxed for 3 and a half hours, filtered through celite and concentrated under reduced pressure. The residue is subsequently purified by silica gel chromatography, elution being carried out with a mixture of cyclohexane and ethyl acetate (75/25 by volume), so as to give 0.7 g of 4-(5-methoxypyridin-3-yl)-9H-carbazole in the form of a colourless oil, the characteristics of which are the following:

1H NMR spectrum (400 MHz, δ in ppm, DMSO-d6): 3.90 (s, 3H) 6.97 (td, J=7.6, 1.0 Hz, 1H) 7.07 (dd, J=7.2, 1.1 Hz, 1H) 7.30-7.38 (m, 2H) 7.48 (dd, J=8.1, 7.2 Hz, 1H) 7.52 (d, J=8.1 Hz, 1H) 7.55-7.59 (m, 2H) 8.39 (d, J=1.9 Hz, 1H) 8.44 (d, J=2.9 Hz, 1H) 11.51 (broad s, 1H).

Mass spectrum (LC/MS; method A): retention time Tr (min)=0.77; m/z=275 [M+H]+; 273 [M−H]−

Stage 2: 0.74 g of 4-bromo-2-fluorobenzonitrile, 3.07 g of caesium carbonate, 0.172 g of (9,9-dimethyl-9H-xanthene-4,5-diyl)bis(diphenylphosphane) and 0.055 g of palladium acetate are successively added, under argon, to a solution of 0.68 g of 4-(5-methoxypyridin-3-yl)-9H-carbazole in 30 ml of dioxane. The reaction mixture is refluxed for 2 and a half hours, cooled to ambient temperature, filtered through celite and concentrated under reduced pressure. The residue is purified by silica gel chromatography, elution being carried out with a mixture of cyclohexane and ethyl acetate (80/20 by volume), so as to give 0.78 g of 2-fluoro-4-[4-(5-methoxypyridin-3-yl)-9H-carbazol-9-yl]benzonitrile in the form of a colourless oil, the characteristics of which are the following:

1H NMR spectrum (400 MHz, δ in ppm, DMSO-d6): 3.91 (s, 3H) 7.15 (m, 1 H) 7.26 (dd, J=7.1, 1.2 Hz, 1H) 7.33 (d, J=8.1 Hz, 1H) 7.44 (m, 1H) 7.51-7.63 (m, 4 H) 7.78 (dd, J=8.3, 2.0 Hz, 1H) 8.01 (dd, J=10.5, 2.0 Hz, 1H) 8.26 (m, 1H) 8.39 (d, J=2.0 Hz, 1H) 8.48 (d, J=2.9 Hz, 1H).

Mass spectrum (LC/MS; method B): retention time Tr (min)=4.72; m/z=394 [M+H]+

Stage 3: 0.316 g of potassium carbonate and 1.75 g of 4-trans-aminocyclohexanol are successively added to a solution of 0.3 g of 2-fluoro-4-[4-(5-methoxypyridin-3-yl)-9H-carbazol-9-yl]benzonitrile in 3.3 ml of dimethyl sulphoxide. The reaction mixture is heated at 90° C. for 1 hour in a microwave, and then 7.6 ml of ethanol are added, followed by 1.51 ml of a 1N solution of sodium hydroxide and 1.51 ml of 30% aqueous hydrogen peroxide. The reaction mixture is stirred at ambient temperature for 10 minutes and then diluted with distilled water. The aqueous phase is extracted twice with ethyl acetate and the combined organic phases are washed with water and a saturated solution of sodium chloride, dried over magnesium sulphate and filtered. The filtrate is concentrated under reduced pressure and the white solid obtained is purified by silica gel chromatography, elution being carried out with a mixture of dichloromethane, acetonitrile and methanol (90/5/5 by volume), so as to give 0.2 g of 2-[(4-trans-hydroxycyclohexyl)amino]-4-[4-(5-methoxypyridin-3-yl)-9H-carbazol-9-yl]benzamide in the form of a white solid, the characteristics of which are the following:

Melting point (Kofler bench): 263° C.

1H NMR spectrum (400 MHz, δ in ppm, DMSO-d6): 1.24 (m, 4H) 1.78 (m, 2 H) 1.99 (m, 2H) 3.30 (masked m, 1H) 3.48 (m, 1H) 3.91 (s, 3H) 4.47 (d, J=4.2 Hz, 1H) 6.70 (dd, J=8.4, 2.0 Hz, 1H) 6.87 (d, J=2.0 Hz, 1H) 7.09 (m, 1H) 7.19 (dd, J=7.1, 1.1 Hz, 1H) 7.26 (broad m, 1H) 7.34 (d, J=8.1 Hz, 1H) 7.38-7.45 (m, 2H) 7.48 (dd, J=8.3, 1.1 Hz, 1H) 7.54 (dd, J=8.3, 7.1 Hz, 1H) 7.61 (dd, J=2.9, 1.9 Hz, 1 H) 7.89 (d, J=8.4 Hz, 1H) 7.97 (broad m, 1H) 8.41 (d, J=1.9 Hz, 1H) 8.45 (d, J=7.7 Hz, 1H) 8.48 (d, J=2.9 Hz, 1H).

Mass spectrum (LC/MS; method B): retention time Tr (min)=3.76; m/z=507 [M+H]+; 505 [M−H]−

EXAMPLE 28

Synthesis of 5-(9-{4-carbamoyl-3-[(4-trans-hydroxycyclohexyl)amino]phenyl}-9H-carbazol-4-yl)pyridine-2-carboxamide

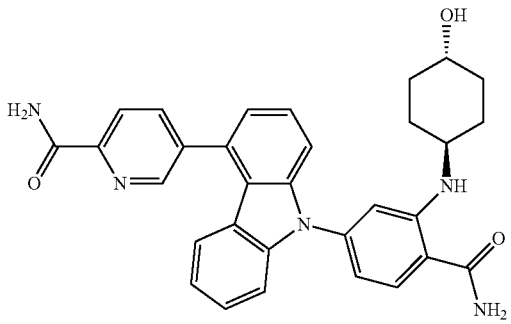

Stage 1: 0.72 g of 2-cyano-5-(4,4,5,5-tetramethyl[1,3,2]dioxaborolan-2-yl)pyridine, 3.3 g of caesium carbonate and 92 mg of 1,1'-bis(diphenyl-phosphino)ferrocenepalladium (II) dichloride as a complex with dichloromethane (1/1) [PdCl$_2$(dppf).CH$_2$Cl$_2$] are successively added, under argon, to a solution of 0.8 g of 4-trifluoromethanesulphonyloxycarbazole, obtained in stage 1 of Example 1, in a mixture of 37 ml of dioxane and 12 ml of water. The reaction mixture is refluxed for 4 hours, cooled to ambient temperature, filtered through celite and concentrated under reduced pressure. The residue is subsequently purified by silica gel chromatography, elution being carried out with a mixture of cyclohexane and ethyl acetate (85/15 by volume), so as to give 0.24 g of 5-(9H-carbazol-4-yl)pyridine-2-carbonitrile in the form of a yellow solid, the characteristics of which are the following:

1H NMR spectrum (400 MHz, δ in ppm, DMSO-d6): 6.98 (m, 1H) 7.10 (dd, J=7.2, 1.1 Hz, 1H) 7.28 (d, J=8.1 Hz, 1H) 7.38 (m, 1H) 7.48-7.56 (m, 2H) 7.63 (d, J=8.2, 1.0 Hz, 1H) 8.24 (dd, J=8.0, 1.0 Hz, 1H) 8.31 (dd, J=8.0, 2.2 Hz, 1H) 8.99 (dd, J=2.2, 1.0 Hz, 1H) 11.60 (broad s, 1H).

Mass spectrum (LC/MS; method A): retention time Tr (min)=0.99; m/z=270 [M+H]+; 268 μM−]−

Stage 2: 0.267 g of 4-bromo-2-fluorobenzonitrile, 1.1 g of caesium carbonate, 0.06 g of (9,9-dimethyl-9H-xanthene-4,5-diyl)bis(diphenylphosphane) and 0.02 g of palladium acetate are successively added, under argon, to a solution of 0.24 g of 5-(9H-carbazol-4-yl)pyridine-2-carbonitrile in 10 ml of dioxane. The reaction mixture is refluxed for 3 hours, cooled to ambient temperature, filtered through celite and concentrated under reduced pressure. The residue is purified by silica gel chromatography, elution being carried out with a mixture of cyclohexane and ethyl acetate (85/15 by volume), so as to give 0.2 g of 5-[9-(4-cyano-3-fluorophenyl)-9H-carbazol-4-yl]pyridine-2-carbonitrile in the form of an off-white solid, the characteristics of which are the following:

1H NMR spectrum (400 MHz, δ in pppm, DMSO-d6): 7.16 (m, 1H) 7.27-7.32 (m, 2H) 7.46 (m, 1H) 7.53-7.68 (m, 3H) 7.78 (dd, J=8.4, 2.0 Hz, 1H) 8.01 (dd, J=10.5, 2.0 Hz, 1H) 8.24-8.30 (m, 2H) 8.34 (d, J=7.9, 2.2 Hz, 1H) 9.01 (dd, J=2.2, 1.0 Hz, 1H)

Mass spectrum (LC/MS; method A): retention time Tr (min)=1.16; m/z=389 [M+H]+

Stage 3: 0.21 g of potassium carbonate and 1.2 g of 4-trans-aminocyclohexanol are successively added to a solution of 0.2 g of 549-(4-cyano-3-fluorophenyl)-9H-carbazol-4-yl]pyridine-2-carbonitrile in 2.2 ml of dimethyl sulphoxide. The reaction mixture is heated at 90° C. for an hour in a microwave, and then 5.1 ml of ethanol are added, followed by 1 ml of a 1N solution of sodium hydroxide and 1 ml of 30% aqueous hydrogen peroxide. The reaction mixture is stirred at ambient temperature for 5 minutes and then diluted with distilled water. The aqueous phase is extracted twice with ethyl acetate and the combined organic phases are washed with water and a saturated solution of sodium chloride, dried over magnesium sulphate and filtered. The filtrate is concentrated under reduced pressure and the off-white solid obtained is purified by silica gel chromatography, elution being carried out with a mixture of dichloromethane, acetonitrile and methanol (92/4/4 by volume) and recrystallized from ethanol, so as to give 0.13 g of 5-(9-{4-carbamoyl-3-[(4-trans-hydroxycyclohexyl)amino]phenyl}-9H-carbazol-4-yl)pyridine-2-carboxamide in the form of a white solid, the characteristics of which are the following:

Melting point (Kofler bench)>260° C.

1H NMR spectrum (400 MHz, δ in ppm, DMSO-d6): 1.24 (m, 4H) 1.78 (m, 2 H) 1.99 (m, 2H) 3.32 (m partially masked, 1H) 3.47 (m, 1H) 4.47 (d, J=4.2 Hz, 1H) 6.70 (dd, J=8.2, 1.9 Hz, 1H) 6.88 (d, J=1.9 Hz, 1H) 7.09 (m, 1H) 7.22 (dd, J=7.1, 1.2 Hz, 1H) 7.26 (broad m, 1H) 7.31 (d, J=8.1 Hz, 1H) 7.39-7.46 (m, 2H) 7.51 (dd, J=8.3, 1.0 Hz, 1H) 7.57 (dd, J=8.3, 7.1 Hz, 1H) 7.73 (broad s, 1H) 7.90 (d, J=8.1 Hz, 1H) 7.96 (broad m, 1H) 8.19-8.30 (m, 3H) 8.45 (d, J=7.7 Hz, 1H) 8.87 (dd, J=2.1, 1.1 Hz, 1H).

Mass spectrum (LC/MS; method A): retention time Tr (min)=0.81; m/z=520 [M+H]+

EXAMPLE 29

Synthesis of 2-[(4-trans-hydroxycyclohexyl)amino]-4-{4-[6-(hydroxymethyl)pyridin-3-yl]-9H-carbazol-9-yl}benzamide

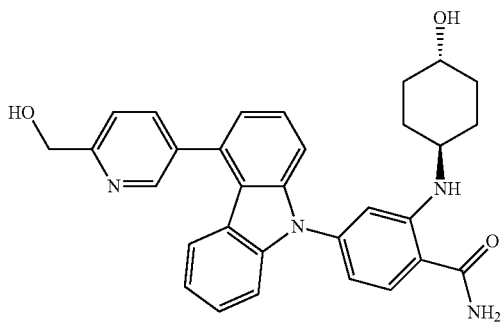

Stage 1: 0.54 g of [6-(hydroxymethyl)pyridin-3-yl]boronic acid, 3.3 g of caesium carbonate and 93 mg of 1,1'-bis(diphenylphosphino)ferrocenepalladium(II) dichloride as a complex with dichloromethane (1/1) [PdCl$_2$(dppO'CH$_2$Cl$_2$] are successively added, under argon, to a solution of 0.8 g of 4-trifluoromethanesulphonyloxycarbazole, obtained in stage 1 of Example 1, in a mixture of 37 ml of dioxane and 12 ml of water. The reaction mixture is refluxed for 5 hours, cooled to ambient temperature and concentrated under reduced pressure. The residue is subsequently taken up with a mixture of dichloromethane and ethyl acetate, treated with carbon black, filtered through celite and concentrated under reduced pressure. The residue is purified by silica gel chromatography, elution being carried out with a mixture of cyclohexane and ethyl acetate (55/45 by volume), so as to give 0.33 g of [5-(9H-carbazol-4-yl)pyridin-2-yl]methanol in the form of a colourless oil, the characteristics of which are the following:

1H NMR spectrum (400 MHz, δ in ppm, DMSO-d6): 4.71 (d, J=5.7 Hz, 2H) 5.50 (t, J=5.7 Hz, 1H) 6.95 (m, 1H) 7.03 (dd, J=7.2, 1.1 Hz, 1H) 7.31 (d, J=8.1 Hz, 1 H) 7.35 (m, 1H) 7.44-7.49 (dd, J=8.1, 7.6 Hz, 1H) 7.51 (d, J=8.1 Hz, 1H) 7.56 (dd, J=8.1, 1.1 Hz, 1H) 7.67 (broad d, J=8.1, Hz, 1H) 8.02 (dd, J=8.1, 2.4 Hz, 1H) 8.68 (dd, J=2.4, 1.0 Hz, 1H) 11.49 (broad s, 1H).

Mass spectrum (LC/MS; method A): retention time Tr (min)=0.54; m/z=275 [M+H]+; 273 [M–H]–.

Stage 2: 0.34 g of 4-bromo-2-fluorobenzonitrile, 1.4 g of caesium carbonate, 0.08 g of (9,9-dimethyl-9H-xanthene-4,5-diyl)bis(diphenylphosphane) and 25 mg of palladium acetate are successively added, under argon, to a solution of 0.31 g of [5-(9H-carbazol-4-yl)pyridin-2-yl]methanol in 15 ml of dioxane. The reaction mixture is refluxed for 4 hours, cooled to ambient temperature, filtered through celite and concentrated under reduced pressure. The residue is purified by silica gel chromatography, elution being carried out with a mixture of cyclohexane and ethyl acetate (85/15 by volume), so as to give 70 mg of 2-fluoro-4-{4-[6-(hydroxymethyl)pyridin-3-yl]-9H-carbazol-9-yl}benzonitrile in the form of a yellow solid, the characteristics of which are the following:

1H NMR spectrum (400 MHz, δ in ppm, DMSO-d6): 4.73 (d, J=5.6 Hz, 2H) 5.53 (t, J=5.6 Hz, 1H) 7.13 (m, 1H) 7.22 (m, 1H) 7.33 (d, J=8.0 Hz, 1H) 7.43 (m, 1 H) 7.52-7.60 (m, 3H) 7.70 (dd, J=8.0, 1.0 Hz, 1H) 7.78 (dd, J=8.4, 2.0 Hz, 1H) 7.99-8.06 (m, 2H) 8.25 (t, J=8.0 Hz, 1H) 8.70 (dd, J=2.0, 1.0 Hz, 1H).

Mass spectrum (LC/MS; method A): retention time Tr (min)=0.94; m/z=394 [M+H]+.

Stage 3: 73 mg of potassium carbonate and 0.4 g of 4-trans-aminocyclohexanol are successively added to a solution of 70 mg of 2-fluoro-4-{4-[6-(hydroxymethyl)pyridin-3-yl]-9H-carbazol-9-yl}benzonitrile in 2 ml of dimethyl sulphoxide. The reaction mixture is heated at 90° C. for 1 and a quarter hours in a microwave, and then 1.8 ml of ethanol are added, followed by 0.35 ml of a 1N solution of sodium hydroxide and 0.35 ml of 30% aqueous hydrogen peroxide. The reaction mixture is stirred at ambient temperature for 40 minutes and then diluted with distilled water. The aqueous phase is extracted twice with ethyl acetate and the combined organic phases are washed with water and a saturated solution of sodium chloride, dried over magnesium sulphate and filtered. The filtrate is concentrated under reduced pressure and the off-white solid obtained is purified by silica gel chromatography, elution being carried out with a mixture of dichloromethane, acetonitrile and methanol (90/5/5 by volume), and triturated in dichloromethane, so as to give 0.13 g of 2-[(4-trans-hydroxycyclohexyl)amino]-4-{4-[6-(hydroxymethyl)pyridin-3-yl]-9H-carbazol-9-yl}benzamide in the form of a white solid, the characteristics of which are the following:

1H NMR spectrum (400 MHz, δ in ppm, DMSO-d6): 1.25 (m, 4H) 1.79 (m, 2 H) 1.99 (m, 2H) 3.33 (m, 1H) 3.47 (m, 1H) 4.47 (d, J=4.4 Hz, 1H) 4.74 (d, J=5.4 Hz, 2H) 5.53 (t, J=5.4 Hz, 1H) 6.70 (dd, J=8.3, 2.0 Hz, 1H) 6.88 (d, J=2.0 Hz, 1H) 7.08 (m, 1H) 7.16 (dd, J=7.2, 1.0 Hz, 1H) 7.26 (broad m, 1H) 7.32-7.57 (m, 5H) 7.71 (d, J=8.2 Hz, 1H) 7.90 (d, J=8.4 Hz, 1H) 7.96 (broad m, 1H) 8.06 (dd, J=8.2, 2.3 Hz, 1H) 8.45 (d, J=7.8 Hz, 1H) 8.72 (dd, J=2.3, 0.9 Hz, 1H).

Mass spectrum (LC/MS; method A): retention time Tr (min)=0.67; m/z=507 [M+H]+.

EXAMPLE 30

Synthesis of 4-[4-(quinolin-3-yl)-9H-carbazol-9-yl]benzamide

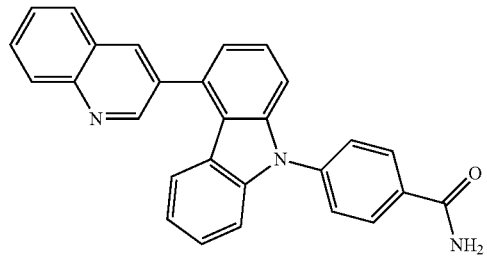

Stage 1: The process is carried out as in stage 3 of Example 2, but using 100 mg of 4-(quinolin-3-yl)-9H-carbazole, obtained in stage 2 of Example 2, 32.28 μl of 3-aminopropanol, 206 mg of caesium carbonate, 5 mg of palladium acetate and 14.6 mg of 4,5-bis(diphenylphosphino)-9,9-dimethylxanthene in 10 ml of dioxane for 2 hours at reflux. After treatment as in stage 3 of Example 1, and then purification by flash chromatography on 15 g of silica gel, elution being carried out with a mixture of cyclohexane and ethyl acetate (50/50 by volume) and the second eluted fraction being recovered, 35 mg of [4-(quinolin-3-yl)-9H-carbazol-9-yl] benzonitrile are obtained, the characteristic of which is the following:

LC/MS (method C): retention time=5.98 min.

Stage 2: By carrying out the process as in stage 4 of Example 2, but using 34 mg of the compound obtained in the preceding stage, 172 μl of a 1N solution of sodium hydroxide and 0.158 μl of a 30% aqueous solution of hydrogen peroxide, for 30 min at ambient temperature, in 1 ml of ethanol and 0.44 ml of dimethyl sulphoxide, there is obtained, after purification on a preparative silica plate, elution being carried out with a mixture of dichloromethane and methanol (80/20 by volume), 11 mg of 4-[4-(quinolin-3-yl)-9H-carbazol-9-yl] benzamide in the form of a white powder, the characteristics of which are the following:

1H NMR spectrum (400 MHz, DMSO-d6, δ ppm): 7.05 (ddd, J=8.0, 6.5, 1.6 Hz, 1H) 7.27 (d, J=8.1 Hz, 1H) 7.33 (d, J=7.1 Hz, 1H) 7.37-7.45 (m, 2H) 7.49-7.54 (m, 2H) 7.60 (dd, J=8.3, 7.3 Hz, 1H) 7.70-7.80 (m, 3H) 7.89 (t, J=8.3 Hz, 1H) 8.11-8.24 (m, 5H) 8.64 (d, J=2.0 Hz, 1H) 9.17 (d, J=2.2 Hz, 1H).

Mass spectrum (LC/MS; method A): retention time Tr (min)=1.00; m/z=414 [M+H]+

EXAMPLE 31

Synthesis of 2-(3-hydroxypropyl)amino-4-[4-(quinolin-3-yl)-9H-carbazol-9-yl]benzamide

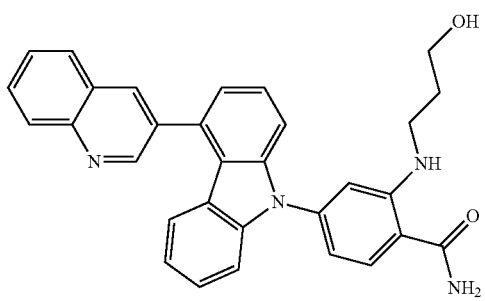

Stage 1: In a 250 ml three-necked flask, under an argon atmosphere, 1 g of 4-(quinolin-3-yl)-9H-carbazole, obtained in stage 2 of Example 2, is dissolved in 75 ml of dioxane, and then 3.32 g of caesium carbonate and 1.019 g of 4-bromo-2-fluorobenzonitrile are successively added. The reaction medium is degassed by bubbling argon for 10 minutes, and then 3.3 mg of palladium acetate and 236 mg of 4,5-bis(diphenylphosphino)-9,9-dimethylxanthene are successively added and the mixture is refluxed for 2 hours under an argon atmosphere. The reaction medium is filtered through celite, concentrated under reduced pressure, and taken up with 100 ml of water and 100 ml of ethyl acetate. The organic phase is separated by settling out and the aqueous phase is re-extracted twice with 50 ml of ethyl acetate. The combined organic phases are washed with water, dried over magnesium sulphate and concentrated under reduced pressure. The residue is purified by flash chromatography on 200 g of silica, elution being carried out with dichloromethane. 1.05 g of 2-fluoro[4-(quinolin-3-yl)-9H-carbazol-9-yl]benzonitrile are thus obtained, the characteristics of which are the following:

1H NMR spectrum (400 MHz, DMSO-d6, δ ppm): 7.08 (t, J=7.8 Hz, 1H) 7.24 (d, J=7.8 Hz, 1H) 7.36 (dd, J=6.7, 1.6 Hz, 1H) 7.43 (t, J=8.2 Hz, 1H) 7.56 (d, J=8.3 Hz, 1H) 7.59-7.67 (m, 2H) 7.73 (t, J=7.8 Hz, 1H) 7.81 (dd, J=8.3, 2.0 Hz, 1H) 7.89 (t, J=8.4 Hz, 1H) 8.04 (dd, J=10.3, 1.7 Hz, 1H) 8.13 (d, J=7.8 Hz, 1H) 8.19 (d, J=8.6 Hz, 1H) 8.27 (t, J=7.9 Hz, 1H) 8.62 (d, J=2.0 Hz, 1H) 9.14 (d, J=2.2 Hz, 1H).

Stage 2: In a 100 ml three-necked flask, 584 mg of the compound obtained in the preceding stage are dissolved in 20 ml of dimethylformamide and then 424 mg of 3-aminopropanol and 1.562 g of potassium carbonate are successively added. The mixture is heated at 140° C. for 2 hours, and then 100 ml of water and 100 ml of ethyl acetate are added. The aqueous phase is separated by settling out, and then the organic phase is re-extracted twice with 50 ml of ethyl acetate. The combined organic phases are washed with water, dried over magnesium sulphate and concentrated to dryness under reduced pressure. The residue is purified on 30 g of silica gel, elution being carried out with a mixture of cyclohexane and ethyl acetate (50/50 by volume). 565 mg of 2-(3-hydroxypropyl)amino-[4-(quinolin-3-yl)-9H-carbazol-9-yl] benzonitrile are thus obtained, the characteristic of which is the following:

LC/MS (method C): retention time=5.52 min.

Stage 3: By carrying out the process as in stage 4 of Example 2, but using 565 mg of the compound obtained in the preceding stage, 2.41 ml of a 1N solution of sodium hydroxide and 2.22 ml of a 30% aqueous solution of hydrogen peroxide, for 30 minutes at ambient temperature, in 15 ml of ethanol and 6.2 ml of dimethyl sulphoxide, there are obtained, after purification by flash chromatography on 70 g of silica, elution being carried out with a mixture of dichloromethane and methanol (95/5 by volume), 334 mg of 2-(3-hydroxypropyl)amino-4-[4-(quinolin-3-yl)-9H-carbazol-9-yl]benzamide in the form of a white powder, the characteristics of which are the following:

1H NMR spectrum (400 MHz, DMSO-d6, δ ppm): 1.74 (quin, J=6.6 Hz, 2H) 3.20 (q, J=6.6 Hz, 2H) 3.51 (q, J=6.0 Hz, 2H) 4.50 (t, J=5.1 Hz, 1H) 6.77 (dd, J=8.2, 1.8 Hz, 1H) 6.88 (d, J=1.7 Hz, 1H) 7.02 (t, J=7.6 Hz, 1H) 7.25 (d, J=8.1 Hz, 1H) 7.28 (br. s., 1H) 7.30 (dd, J=6.6, 1.7 Hz, 1H) 7.40 (t, J=7.6 Hz, 1H) 7.48 (d, J=8.3 Hz, 1H) 7.54-7.62 (m, 2H) 7.73 (t, J=7.8 Hz, 1H) 7.88 (t, J=8.3 Hz, 1H) 7.93 (d, J=8.3 Hz, 1H) 7.99 (broad s, 1H) 8.13 (d, J=7.8 Hz, 1H) 8.19 (d, J=8.3 Hz, 1H) 8.46 (t, J=5.3 Hz, 1H) 8.63 (d, J=2.0 Hz, 1H) 9.16 (d, J=2.2 Hz, 1H).

Mass spectrum (LC/MS method A): retention time Tr (min)=1.00; [M+H]+ m/z 487; [M+H] m/z 485

EXAMPLE 32

Synthesis of 2-(3-hydroxybutyl)amino-4-[4-(quinolin-3-yl)-9H-carbazol-9-yl]benzamide

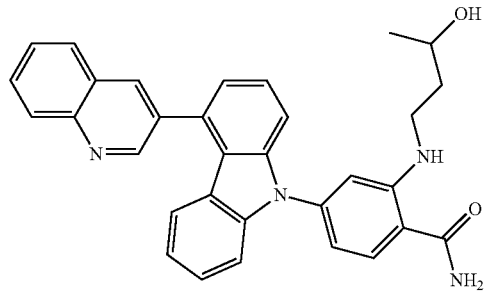

Stage 1: The process is carried out as in stage 2 of Example 31, but using 150 mg of 2-fluoro-[4-(quinolin-3-yl)-9H-carbazol-9-yl]benzonitrile, obtained in stage 2 of Example 31, 129 mg of 3-aminobutan-2-ol and 401 mg of potassium carbonate, at 140° C. for 1 hour in 5 ml of dimethylformamide. After treatment and purification by flash chromatography, under the conditions described in stage 2 of Example 31, 149 mg of 2-(3-hydroxybutyl)amino-[4-(quinolin-3-yl)-9H-carbazol-9-yl]benzonitrile are obtained, the characteristic of which is the following:

LC/MS (method C): retention time=5.48 min.

Stage 2: By carrying out the process as in stage 4 of Example 2, but using 149 mg of the compound obtained in the preceding stage, 0.62 ml of a 1N solution of sodium hydroxide and 0.568 ml of a 30% aqueous solution of hydrogen peroxide, for an hour at ambient temperature, in 3.7 ml of ethanol and 1.57 ml of dimethyl sulphoxide, there are obtained, after purification by flash chromatography on 10 g of silica, elution being carried out with a mixture of dichloromethane and methanol (97/3 by volume), 106 mg of 2-(3-hydroxybutyl)amino-4-[4-(quinolin-3-yl)-9H-carbazol-9-yl]benzamide in the form of a white powder, the characteristics of which are the following:

1H NMR spectrum (400 MHz, DMSO-$d_6$, δ ppm): 1.09 (d, J=6.1 Hz, 3H) 1.60-1.68 (m, 2H) 3.16-3.24 (m, 2H) 3.69-3.77 (m, 1H) 4.50 (d, J=4.6 Hz, 1H) 6.77 (dd, J=8.3, 1.7 Hz, 1H) 6.87 (d, J=2.0 Hz, 1H) 7.02 (t, J=7.9 Hz, 1H) 7.25 (d, J=7.8 Hz, 1H) 7.28 (broad s, 1H) 7.30 (dd, J=6.4, 1.7 Hz, 1H) 7.40 (t, J=8.1 Hz, 1H) 7.49 (d, J=8.3 Hz, 1H) 7.55-7.62 (m, 2H) 7.73 (t, J=7.9 Hz, 1H) 7.85-7.91 (m, 1 H) 7.92 (d, J=8.3 Hz, 1H) 7.97 (broad s, 1H) 8.13 (d, J=7.6 Hz, 1H) 8.19 (d, J=8.6 Hz, 1H) 8.44 (t, J=5.3 Hz, 1H) 8.63 (d, J=2.0 Hz, 1H) 9.16 (d, J=2.0 Hz, 1H).

Mass spectrum (LC/MS; method A): retention time Tr (min)=1.03; [M+H]+ m/z 501; [M+H]− m/z 499.

EXAMPLE 33

Synthesis of 2-(3-methoxypropyl)amino-4-[4-(quinolin-3-yl)-9H-carbazol-9-yl]benzamide

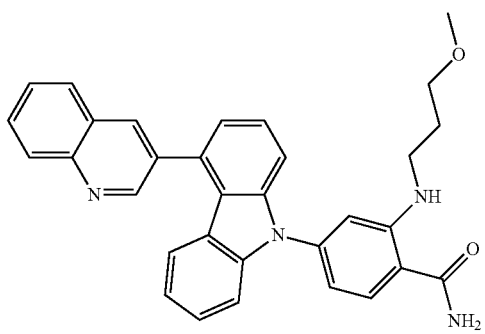

Stage 1: The process is carried out as in stage 3 of Example 3, but using 206 mg of 2-fluoro-[4-(quinolin-3-yl)-9H-carbazol-9-yl]benzonitrile, obtained in stage 1 of Example 31, 177 mg of 3-methoxypropylamine and 551 mg of potassium carbonate, at 140° C. for 1 hour, in 7 ml of dimethylformamide. After treatment as in stage 2 of Example 31, then purification by flash chromatography on silica, elution being carried out with a mixture of ethyl acetate and heptane (70/30 by volume), 190 mg of 2-(3-methoxypropyl)amino-[4-(quinolin-3-yl)-9H-carbazol-9-yl]benzonitrile are obtained, the characteristic of which is the following:

LC/MS (method C): retention time=6.02 min.

Stage 2: By carrying out the process as in stage 4 of Example 2, but using 190 mg of the compound obtained in the preceding stage, 0.787 ml of a 1N solution of sodium hydroxide and 0.724 ml of a 30% aqueous solution of hydrogen peroxide, for 1 hour at ambient temperature, in 4.8 ml of ethanol and 2 ml of dimethyl sulphoxide, they are obtained, after purification by flash chromatography on 15 g of silica, elution being carried out with a mixture of ethyl acetate and heptane (60/40 by volume), 113 mg of 2-(3-methoxypropyl)amino-4-[4-(quinolin-3-yl)-9H-carbazol-9-yl]benzamide in the form of a white powder, the characteristics of which are the following:

1H NMR spectrum (400 MHz, DMSO-d6, δ ppm): 1.82 (quin, J=6.5 Hz, 2H) 3.17-3.23 (m, 5H) 3.42 (t, J=6.2 Hz, 2H) 6.78 (dd, J=8.3, 2.0 Hz, 1H) 6.88 (d, J=2.0 Hz, 1H) 7.02 (t, J=7.9 Hz, 1H) 7.25 (d, J=8.1 Hz, 1H) 7.30 (dd, J=6.6, 1.5 Hz, 1H) 7.31 (broads, 1H) 7.40 (t, J=8.1 Hz, 1H) 7.48 (d, J=8.3 Hz, 1H) 7.54-7.62 (m, 2H) 7.73 (t, J=8.1 Hz, 1H) 7.88 (ddd, J=8.4, 7.0, 1.5 Hz, 1H) 7.93 (d, J=8.3 Hz, 1H) 7.99 (broad s, 1H) 8.14 (d, J=7.6 Hz, 1H) 8.19 (d, J=8.6 Hz, 1H) 8.48 (t, J=5.4 Hz, 1 H) 8.63 (d, J=2.0 Hz, 1H) 9.16 (d, J=2.2 Hz, 1H).

Mass spectrum (LC/MS; method A): retention time Tr (min)=1.12; [M+H]+ m/z 501.

EXAMPLE 34

Synthesis of 2-(2-carbamoylethylamino)-4-[4-(quinolin-3-yl)-9H-carbazol-9-yl]benzamide

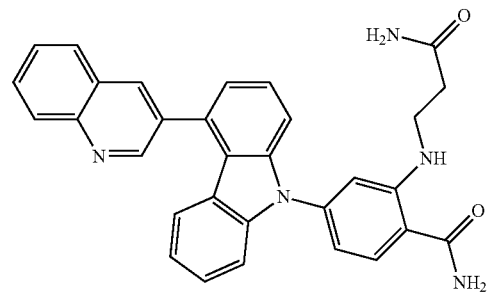

Stage 1: The process is carried out as in stage 2 of Example 31, but using 206 mg of 2-fluoro[4-(quinolin-3-yl)-9H-carbazol-9-yl]benzonitrile, obtained in stage 1 of Example 31, 248 mg of beta-alaninamide hydrochloride, 551 mg of potassium carbonate and 139 µl of triethylamine, at 140° C. for 3 hours in 7 ml of dimethylformamide. After treatment as in stage 2 of Example 31, 160 mg of a mixture are obtained, which mixture is used as it is in the subsequent stage and contains approximately 40% of 2-(2-carbamoylethylamino)-[4-(quinolin-3-yl)-9H-carbazol-9-yl]benzonitrile, the characteristic of which is the following:

LC/MS (method C): retention time=5.15 min.

Stage 2: By carrying out the process as in stage 4 of Example 2, but using 160 mg of the crude compound obtained in the preceding stage, 0.665 ml of a 1N solution of sodium hydroxide and 0.61 ml of a 30% aqueous solution of hydrogen peroxide, for 1 hour at ambient temperature, in 4 ml of ethanol and 2 ml of dimethyl sulphoxide, there are obtained, after purification by flash chromatography on 10 g of silica, elution being carried out with a mixture of dichloromethane and methanol (97/3 by volume), 34 mg of 2-(2-carboxamidoethyl)amino-4-[4-(quinolin-3-yl)-9H-carbazol-9-yl]benzamide in the form of a white powder, the characteristics of which are the following:

1H NMR spectrum (400 MHz, DMSO-d6, δ ppm): 2.38 (t, J=6.6 Hz, 2H) 3.37 (q, J=6.4 Hz, 2H) 6.78 (dd, J=8.3, 1.7 Hz, 1H) 6.83 (br. s., 1H) 6.91 (d, J=1.7 Hz, 1 H) 7.03 (t, J=7.6 Hz, 1H) 7.25 (d, J=7.8 Hz, 1H) 7.28 (br. s., 1H) 7.30 (dd, J=5.1, 3.2 Hz, 1H) 7.37 (broad s, 1H) 7.40 (t, J=8.2 Hz, 1H) 7.51 (d, J=8.3 Hz, 1H) 7.57-7.63 (m, 2H) 7.73 (t, J=7.8 Hz, 1H) 7.85-7.94 (m, 2H) 7.97 (broad s, 1H) 8.13 (d, J=7.6 Hz, 1H) 8.19 (d, J=8.3 Hz, 1H) 8.45 (t, J=5.5 Hz, 1H) 8.63 (d, J=2.0 Hz, 1H) 9.16 (d, J=2.2 Hz, 1H).

Mass spectrum (LC/MS; method A): retention time Tr (min)=1.36; [M+H]+ m/z 500; [M+H]− m/z 498.

EXAMPLE 35

Synthesis of 2(R,S)-(1-hydroxypropan-2-yl)amino-4-[4-(quinolin-3-yl)-9H-carbazol-9-yl]benzamide

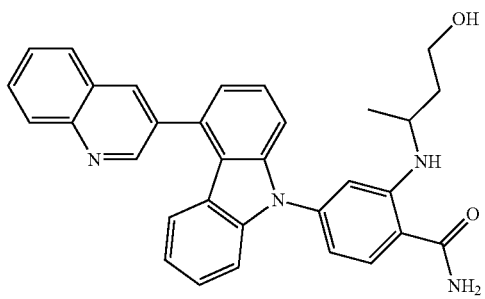

300 mg of 2-fluoro-[4-(quinolin-3-yl)-9H-carbazol-9-yl]benzonitrile, obtained in stage 1 of Example 31, 1.073 g of DL-alaninol, 296 mg of potassium carbonate and 3 ml of dimethyl sulphoxide are successively introduced into a 5 ml microwave reactor specific tube. The tube is then sealed, then heated in the microwave for 45 minutes at 100° C. After cooling to ambient temperature, 7 ml of ethanol, 1.357 ml of a 1N solution of sodium hydroxide and 1.313 ml of a 30% aqueous solution of hydrogen peroxide are successively added, and the mixture is then stirred for 5 minutes at ambient temperature. The reaction medium is run into a mixture of 50 ml of water and 50 ml of ethyl acetate. The organic phase is separated by settling out and the aqueous phase is re-extracted twice with 25 ml of ethyl acetate. The combined organic phases are washed with water, dried over sodium sulphate and concentrated to dryness under reduced pressure. The residue is purified by flash chromatography on 70 g of silica, elution being carried out with a mixture of dichloromethane and ethanol (95/5 by volume). 115 mg are thus obtained in the form of a beige powder, the characteristics of which are the following:

1H NMR spectrum (400 MHz, DMSO-d6, δ ppm): 1.16 (d, J=6.1 Hz, 3H) 3.34-3.56 (m, 3H) 4.79 (t, J=4.9 Hz, 1H) 6.72 (dd, J=8.3, 1.7 Hz, 1H) 6.91 (d, J=1.7 Hz, 1H) 7.11-7.21 (m, 2H) 7.26 (broad s, 1H) 7.44-7.47 (m, 2H) 7.48-7.56 (m, 1 H) 7.58-7.62 (m, 2H) 7.62-7.67 (m, 1H) 7.68-7.75 (m, 1H) 7.90 (d, J=8.6 Hz, 1 H) 7.95 (broad s, 1H) 8.46 (d, J=7.6 Hz, 1H) 8.65 (d, J=7.6 Hz, 1H) 13.08 (broad s, 1H).

Mass spectrum (LC/MS; method A): retention time Tr (min)=0.80; [M+H]+ m/z 494; [M+H]− m/z 492.

EXAMPLE 36

Synthesis of the trifluoroacetate of the 4-trans-{2-carbamoyl-5-[4(6-fluoro-1H-benzimidazol-2-yl)-9H-carbazol-9-yl]phenylamino}cyclohexyl ester of (S)-2,6-diaminohexanoic acid

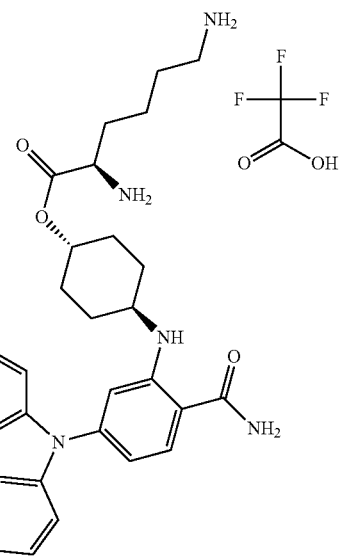

Stage 1: In a 250 ml three-necked flask, under an argon atmosphere, 534 mg of 4-[4-(6-fluoro-1H-benzimidazol-2-yl)carbazol-9-yl]-2-(4-trans-hydroxycyclohexylamino)benzamide, which can be obtained as in Example 1, and 258.5 mg of 2,6-bis-N,N'-tert-butoxycarbonyllysine are dissolved in 50 ml of dichloromethane and 10 ml of dimethylformamide. 0.349 ml of N, N-diisopropylethylamine, 244.3 mg of 4-dimethylaminopyridine and 656 mg of O-[(ethoxycarbonyl)cyanomethyleneamino]-N,N,N',N'-tetramethylurea (TOTU) are subsequently added and then the mixture is stirred for 20 hours at ambient temperature. A further 258.5 mg of 2,6-bis-N,N'-tert-butoxycarbonyllysine, 0.349 ml of N,N-diisopropylethylamine, 244.3 mg of 4-dimethylaminopyridine and 656 mg of O-[(ethoxycarbonyl)cyanomethyleneamino]-N,N,N',N'-tetramethylurea are then added and the mixture is then again stirred for 20 hours at ambient temperature. After treatment, purification by flash chromatography and crystallization, the process being carried out as in Example 16, 725 mg of (S)-2,6-bis-tert-butoxycarbonylaminohexanoic acid 4-trans-{2-carbamoyl-5-[4-(6-fluoro-1H-benzimidazol-2-yl)carbazol-9-yl]phenylamino}cyclohexyl ester are thus obtained in the form of a beige powder, the characteristic of which is the following:

Mass spectrum (LC/MS; method C): retention time=5.44 min.

Stage 2: In a 50 ml single-necked round-bottomed flask, 687 mg of the compound, obtained in the preceding stage, are dissolved in 20 ml of dichloromethane. The solution obtained is cooled to 0° C., and then 10 ml of trifluoroacetic acid are added and the mixture is stirred at 0° C. for 30 minutes and then at ambient temperature for 1 hour. The reaction medium is concentrated under reduced pressure. The residue is then taken up with 5 ml of diisopropyl ether. After stirring for 30 minutes at 0° C., the precipitate formed is spin-filter-dried, washed twice with 5 ml of diisopropyl ether and dried for 4 hours in an oven under vacuum at 50° C., in the presence of potassium hydroxide chips. 559 mg of the trifluoroacetate of the 4-trans-{2-carbamoyl-5-[4-(6-fluoro-1H-benzimidazol-2-yl)carbazol-9-yl]phenylamino}cyclohexyl ester of (S)-2,6-diaminohexanoic acid are thus obtained in the form of a light beige powder, the characteristics of which are the following:

1H NMR spectrum (400 MHz, DMSO-d6, δ ppm): 1.19-1.60 (m, 8H) 1.68-1.77 (m, 2H) 1.88-1.97 (m, 2H) 2.01-2.10 (m, 2H) 2.31 (s, 6H) 2.65-2.77 (m, 2 H) 3.43-3.48 (m, 1H) 3.91-4.00 (m, 1H) 4.80-4.91 (m, 1H) 6.74 (d, J=8.1 Hz, 1 H) 6.90 (s, 1H) 7.20 (t, J=7.8 Hz, 1H) 7.31 (broad s, 1H) 7.41-7.51 (m, 2H) 7.52-7.70 (m, 6H) 7.76 (broad s, 1H) 7.94 (d, J=8.3 Hz, 1H) 8.02 (broad s, 1H) 8.26 (broad s, 3H) 8.58 (broad s, 2H).

Mass spectrum (LC/MS; method A): retention time Tr (min)=0.60; [M+H]+ m/z 662; [M+H]– m/z 660.

EXAMPLE 37

Synthesis of 4-[4-(6-fluoro-1H-benzimidazol-2-yl)-9H-carbazol-9-yl]-2-[3(R,S)hydroxybutylamino) benzamide

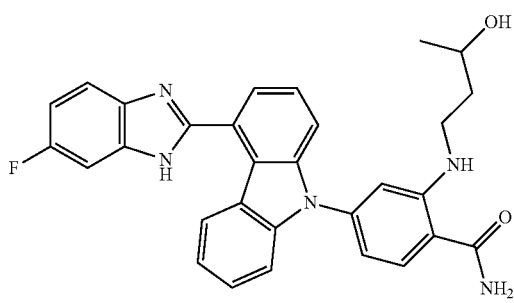

The process is carried out as in stage 3 of Example 3, but using 300 mg of 2-fluoro-4-[4-(6-fluoro-1H-benzimidazol-2-yl)-9H-carbazol-9-yl]benzonitrile, obtained according to stage 2 of Example 3, 296 mg of potassium carbonate and 1.273 g of 4-aminobutan-2(R,S)-ol in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (95/5 by volume), 270 mg of 4-[4-(6-fluoro-1H-benzimidazol-2-yl)-9H-carbazol-9-yl]-2-[3(R,S)-hydroxybutylamino]benzamide are thus obtained in the form of a beige solid, the characteristics of which are the following:

1H NMR spectrum (400 MHz, DMSO-d6, δ ppm): 1.08 (d, J=6.1 Hz, 3H) 1.57-1.71 (m, 2H) 3.13-3.24 (m, 2H) 3.66-3.77 (m, 1H) 4.49 (d, J=4.2 Hz, 1H) 6.74 (d, J=7.8 Hz, 1H) 6.85 (s, 1H) 7.10-7.23 (m, 2H) 7.28 (broad s, 1H) 7.41-7.79 (m, 7H) 7.92 (d, J=8.1 Hz, 1H) 7.98 (br. s., 1H) 8.44 (br. s., 1H) 8.62 (d, J=7.8 Hz, 1H) 13.08 (broad s, 1H).

Mass spectrum (LC/MS; method A): retention time Tr (min)=0.81; [M+H]+ m/z 508; [M+H]– m/z 506.

EXAMPLE 38

Synthesis of 4-[4-(6-fluoro-1H-benzimidazol-2-yl)-9H-carbazol-9-yl]-2-(3-methoxypropylamino)benzamide

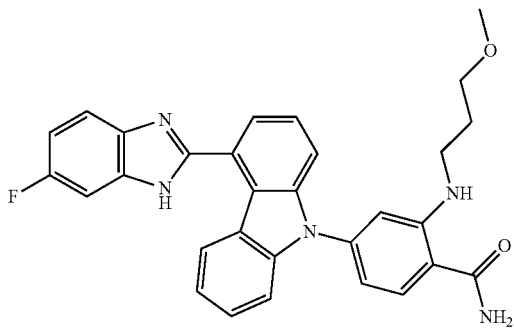

The process is carried out as in stage 3 of Example 3, but using 300 mg of 2-fluoro-4-[4-(6-fluoro-1H-benzimidazol-2-yl)-9H-carbazol-9-yl]benzonitrile, obtained according to stage 2 of Example 3, 296 mg of potassium carbonate and 1.273 g of 3-methoxypropylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (95/5 by volume), 285 mg of 4-[4-(6-fluoro-1H-benzimidazol-2-yl)-9H-carbazol-9-yl]-2-(3-methoxypropylamino)benzamide are thus obtained in the form of an off-white solid, the characteristics of which are the following:

1H NMR spectrum (400 MHz, DMSO-d6, δ ppm): 1.81 (quin, J=6.4 Hz, 2H) 3.16-3.23 (m, 5H) 3.41 (t, J=6.2 Hz, 2H) 6.75 (d, J=8.3 Hz, 1H) 6.86 (s, 1H) 7.12-7.22 (m, 2H) 7.30 (broad s, 1H) 7.46 (d, J=3.9 Hz, 1H) 7.48-7.55 (m, 1H) 7.59-7.67 (m, 4H) 7.67-7.76 (m, 1H) 7.92 (d, J=8.3 Hz, 1H) 7.99 (broad s, 1H) 8.48 (t, J=5.3 Hz, 1H) 8.63 (d, J=7.8 Hz, 1H) 13.08 (broad s, 1H).

Mass spectrum (LC/MS; method A): retention time Tr (min)=1.35; [M+H]+ m/z 508; [M+H]– m/z 506.

EXAMPLE 39

Synthesis of 4-[4-(6-fluoro-1H-benzimidazol-2-yl)-9H-carbazol-9-yl]-2-(4-hydroxybutan-3(R,S)-ylamino)benzamide

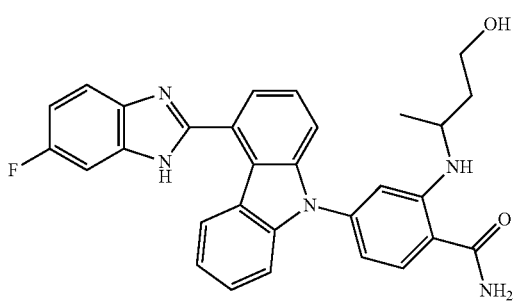

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.273 g of 3(R,S)-aminopropanol in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, then purification by flash chromatography on silica gel, elution being carried out with a mixture of dichloromethane and ethanol (95/5 by volume), followed by crystallization from 10 ml of diisopropyl ether, 165 mg of 4-[4-(6-fluoro-1H-benzimidazol-2-yl)-9H-carbazol-9-yl]-2-(4-hydroxybutan-3(R,S)-ylamino)benzamide are thus obtained in the form of a beige solid, the characteristics of which are the following:

1H NMR spectrum (400 MHz, DMSO-d6, δ ppm): 1.18 (d, J=6.1 Hz, 3H) 1.54-1.79 (m, 2H) 3.46-3.52 (m, 2H) 3.62-3.71 (m, 1H) 4.42 (t, J=4.5 Hz, 1H) 6.72 (d, J=8.1 Hz, 1H) 6.89 (s, 1H) 7.11-7.21 (m, 2H) 7.28 (broad s, 1H) 7.47 (d, J=3.9 Hz, 1H) 7.49-7.56 (m, 1H) 7.59-7.67 (m, 4H) 7.67-7.76 (m, 1H) 7.91 (d, J=8.3 Hz, 1H) 7.97 (broad s, 1H) 8.43 (d, J=7.8 Hz, 1H) 8.61 (d, J=8.3 Hz, 1H) 13.09 (broad s, 1H).

Mass spectrum (LC/MS; method A): retention time Tr (min)=1.28; [M+H]+ m/z 508; [M+H]− m/z 506

EXAMPLE 40

Synthesis of 4-[4-(6-fluoro-1H-benzimidazol-2-yl)-9H-carbazol-9-yl]-2-(2(R,S)-hydroxypropylamino)benzamide

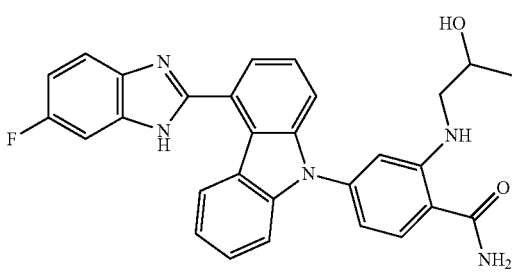

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.073 g of 1-amino-2(R,S)-propanol in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and ethanol (95/5 to 90/10 by volume), followed by crystallization from 10 ml of diisopropyl ether, 180 mg of 4-[4-(6-fluoro-1H-benzimidazol-2-yl)-9H-carbazol-9-yl]-2-(2(R,S)-hydroxypropylamino)benzamide are thus obtained in the form of a beige solid, the characteristics of which are the following:

1H NMR spectrum (400 MHz, DMSO-d6, δ ppm): 1.11 (d, J=6.1 Hz, 3H) 2.96-3.17 (m, 2H) 3.79-3.89 (m, 1H) 4.78 (d, J=4.2 Hz, 1H) 6.73 (d, J=8.3 Hz, 1 H) 6.88 (s, 1H) 7.10-7.22 (m, 2H) 7.26 (broad s, 1H) 7.46 (d, J=3.4 Hz, 1H) 7.47-7.56 (m, 1H) 7.57-7.67 (m, 4H) 7.67-7.76 (m, 1H) 7.91 (d, J=8.1 Hz, 1H) 7.96 (broad s, 1H) 8.55 (t, J=5.1 Hz, 1H) 8.63 (d, J=8.1 Hz, 1H) 13.08 (broad s, 1H).

Mass spectrum (LC/MS; method A): retention time Tr (min)=0.80; [M+H]+ m/z 494; [M+H]− m/z 492.

EXAMPLE 41

Synthesis of 2-[1-hydroxybutan-3(R,S)-ylamino]-4-[4-(quinolin-3-yl)-9H-carbazol-9-yl]benzamide

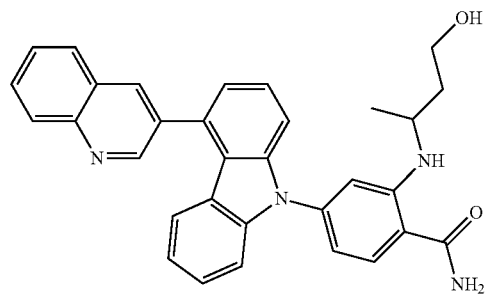

Stage 1: The process is carried out as in stage 2 of Example 31, but using 206 mg of 2-fluoro-[4-(quinolin-3-yl)-9H-carbazol-9-yl]benzonitrile, obtained in stage 1 of Example 31, 177 mg of 3(R,S)-aminobutan-1-ol and 551 mg of potassium carbonate, at 140° C. for 3 hours in 7 ml of dimethylformamide. After treatment as in stage 2 of Example 31, and then purification by flash chromatography, elution being carried out with a mixture of ethyl acetate and heptane (50/50 by volume), 110 mg of 2-[1-hydroxybutan-3(R,S)-ylamino]-4-[4-(quinolin-3-yl)-9H-carbazol-9-yl]benzonitrile are obtained, the characteristic of which is the following:

LC/MS (method C): retention time=5.46 min.

Stage 2: By carrying out the process as in stage 4 of Example 2, but using 110 mg of the crude compound obtained in the preceding stage, 0.456 ml of a 1N solution of sodium hydroxide and 0.419 ml of a 30% aqueous solution of hydrogen peroxide, for 1 hour at ambient temperature, in 2.8 ml of ethanol and 1.2 ml of dimethyl sulphoxide, there are obtained, after purification by flash chromatography on 10 g of silica, elution being carried out with a mixture of ethyl acetate and heptane (90/10 by volume), 33 mg of 2-[1-hydroxybutan-3(R,S)-ylamino]-4-[4-(quinolin-3-yl)-9H-carbazol-9-yl]benzamide in the form of a white powder, the characteristics of which are the following:

1H NMR spectrum (400 MHz, DMSO-d6, δ ppm): 1.19 (d, J=6.4 Hz, 3H) 1.55-1.79 (m, 2H) 3.45-3.53 (m, 2H) 3.62-3.71 (m, 1H) 4.42 (t, J=4.9 Hz, 1H) 6.74 (dd, J=8.3, 1.7 Hz, 1H) 6.91 (s, 1H) 7.02 (t, J=7.5 Hz, 1H) 7.25 (d, J=8.1 Hz, 1 H) 7.27 (broad s, 1H) 7.30 (dd, J=6.5, 1.6 Hz, 1H) 7.40 (t, J=7.6 Hz, 1H) 7.49 (d, J=8.3 Hz, 1H) 7.55-7.63 (m, 2H) 7.73 (t, J=7.8 Hz, 1H) 7.85-7.94 (m, 2H) 7.98 (broad s, 1H) 8.13 (d, J=7.8 Hz, 1H) 8.19 (d, J=8.6 Hz, 1H) 8.43 (d, J=7.8 Hz, 1H) 8.63 (d, J=1.7 Hz, 1H) 9.16 (d, J=2.2 Hz, 1H).

Mass spectrum (LC/MS; method A): retention time Tr (min)=1.03; [M+H]+ m/z 501; [M+H]− m/z 499

EXAMPLE 42

Synthesis of 4-[4-(6-fluoro-1H-benzimidazol-2-yl)-9H-carbazol-9-yl]-2-(2-hydroxyethylamino)benzamide

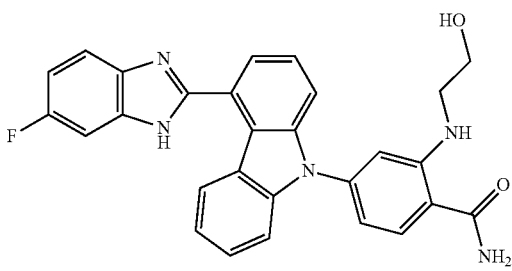

The process is carried out as in stage 3 of Example 3, but using 300 mg of 2-fluoro-4-[4-(6-fluoro-1H-benzimidazol-2-yl)-9H-carbazol-9-yl]benzonitrile, obtained according to stage 2 of Example 3, 296 mg of potassium carbonate and 0.872 g of 2-aminoethanol in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and ethanol (from 95/5 to 90/10 by volume), followed by crystallization from 10 ml of diisopropyl ether, 180 mg of 4-[4-(6-fluoro-1H-benzimidazol-2-yl)-9H-carbazol-9-yl]-2-(2-hydroxyethylamino)benzamide are thus obtained in the form of a beige solid, the characteristics of which are the following:

1H NMR spectrum (400 MHz, DMSO-d6, δ ppm): 3.18-3.50 (m, 2H) 3.60 (broad s, 2H) 4.78 (broad s, 1H) 6.75 (d, J=8.1 Hz, 1H) 6.89 (s, 1H) 7.09-7.23 (m, 2H) 7.27 (broad s, 1H) 7.40-7.55 (m, 2H) 7.57-7.78 (m, 5H) 7.91 (d, J=8.3 Hz, 1 H) 7.97 (broad s, 1H) 8.51 (s, 1H) 8.63 (d, J=7.6 Hz, 1H) 13.09 (broad s, 1H).

Mass spectrum (LC/MS; method A): retention time Tr (min)=0.76; [M+H]+ m/z 480; [M+H]– m/z 478

EXAMPLE 43

Synthesis of 2-(2-dimethylaminoethylamino)-4-[4-(6-fluoro-1H-benzimidazol-2-yl)-9H-carbazol-9-yl]benzamide

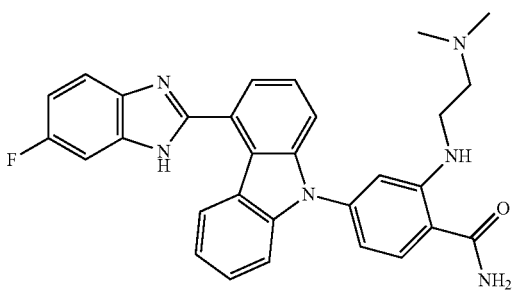

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.259 g of N,N-dimethylethylenediamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and a 7M solution of ammonia in methanol (from 95/5 to 90/10 by volume), followed by crystallization from 10 ml of diisopropyl ether, 200 mg of 2-(2-dimethylaminoethylamino)-4-[4-(6-fluoro-1H-benzimidazol-2-yl)-9H-carbazol-9-yl]benzamide are thus obtained in the form of a beige solid, the characteristics of which are the following:

1H NMR spectrum (400 MHz, DMSO-d6, δ ppm): 2.18 (s, 6H) 3.15-3.22 (m, 2H) 3.30 (masked, 2H) 6.75 (d, J=8.6 Hz, 1H) 6.85 (s, 1H) 7.10-7.21 (m, 2H) 7.25 (broad s, 1H) 7.42-7.55 (m, 2H) 7.57-7.77 (m, 5H) 7.90 (d, J=8.6 Hz, 1H) 7.96 (broad s, 1H) 8.42 (broad s, 1H) 8.62 (d, J=8.1 Hz, 1H) 13.09 (broad s, 1H).

Mass spectrum (LC/MS; method A): retention time Tr (min)=0.62; [M+H]+ m/z 507; [M+H]– m/z 505.

EXAMPLE 44

Synthesis of 4-[4-(6-fluoro-1H-benzimidazol-2-yl)-9H-carbazol-9-yl]-2-(methylcarbamoylmethylamino)benzamide

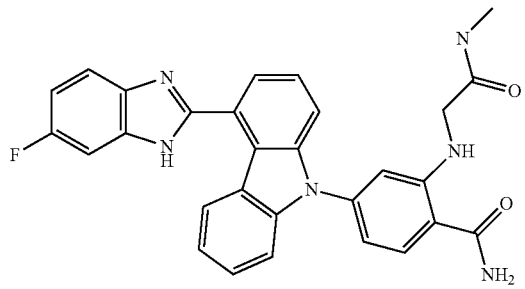

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate, 1 g of N-methylglycine hydrochloride and 820 mg of triethylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and a 7M solution of ammonia in methanol (from 95/5 to 90/10 by volume), followed by crystallization from 5 ml of ethyl acetate, 55 mg of 4-[4-(6-fluoro-1 H-benzimidazol-2-yl)-9H-carbazol-9-yl]-2-(methylcarbamoyl methyl amino)benzamide are thus obtained in the form of a beige solid, the characteristics of which are the following:

1H NMR spectrum (400 MHz, DMSO-d6, δ ppm): 2.63 (d, J=4.4 Hz, 3H) 3.81 (d, J=5.6 Hz, 2H) 6.66 (d, J=1.5 Hz, 1H) 6.84 (dd, J=8.3, 1.5 Hz, 1H) 7.12-7.22 (m, 2H) 7.31-7.39 (m, 1H) 7.42-7.50 (m, 3H) 7.55-7.78 (m, 4H) 7.87-7.92 (m, 1H) 7.94 (d, J=8.6 Hz, 1H) 8.01 (broad s, 1H) 8.59 (d, J=8.1 Hz, 1H) 8.70 (t, J=5.5 Hz, 1H) 13.08 (broad s, 1H).

Mass spectrum (LC/MS; method A): retention time Tr (min)=1.19; [M+H]+ m/z 507; [M+H]– m/z 505.

EXAMPLE 45

Synthesis of 2-[2-(1-oxypyrrolidin-1-yl)ethylamino]-4-[4-(quinolin-3-yl)-9H-carbazol-9-yl]benzamide

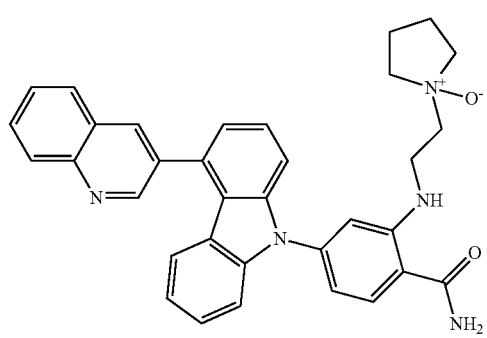

Stage 1: The process is carried out as in stage 2 of Example 31, but using 230 mg of 2-fluoro-[4-(quinolin-3-yl)-9H-carbazol-9-yl]benzonitrile, obtained in stage 1 of Example 31, 254 mg of N-(2-aminoethyl)pyrrolidine and 615 mg of potassium carbonate, at 140° C. for 3 hours in 7 ml of dimethylformamide. After treatment as in stage 2 of Example 31, 273 mg of a mixture containing predominantly 2-[2-(pyrrolidin-1-yl)ethylamino]-4-[4-(quinolin-3-yl)-9H-carbazol-9-yl]benzonitrile are obtained, which product is used as it is in the subsequent stage, and the characteristic of which is the following:

LC/MS (method C): retention time=3.98 min.

Stage 2: By carrying out the process as in stage 4 of Example 2, but using 273 mg of the crude compound obtained in the preceding stage, 1.076 ml of a 1N solution of sodium hydroxide and 0.998 ml of a 30% aqueous solution of hydrogen peroxide, for 1 hour at ambient temperature, in 2.8 ml of ethanol and 1.2 ml of dimethyl sulphoxide, there are obtained, after purification by flash chromatography on 10 g of silica, elution being carried out with a mixture of dichloromethane, methanol and a 5M aqueous solution of ammonia (90/10/1 by volume), 126 mg of 2-[2-(1-oxypyrrolidin-1-yl)ethylamino]-4-[4-(quinolin-3-yl)-9H-carbazol-9-yl]benzamide in the form of a light beige powder, the characteristics of which are the following:

1H NMR spectrum (400 MHz, DMSO-d6, δ ppm): 1.76-1.85 (m, 2H) 2.07-2.17 (m, 2H) 3.11-3.19 (m, 2H) 3.30 (broad s, 2H) 3.43 (t, J=6.2 Hz, 2H) 3.78 (q, J=5.8 Hz, 2H) 6.79 (dd, J=8.3, 1.7 Hz, 1H) 7.02 (t, J=7.5 Hz, 1H) 7.09 (d, J=1.7 Hz, 1H) 7.24 (d, J=8.1 Hz, 1H) 7.27-7.32 (m, 1H) 7.34 (broad s, 1H) 7.39 (t, J=7.3 Hz, 1H) 7.50 (d, J=8.3 Hz, 1H) 7.59 (d, J=3.9 Hz, 2H) 7.73 (t, J=7.8 Hz, 1H) 7.85-7.93 (m, 2H) 7.99 (broad s, 1H) 8.13 (d, J=7.8 Hz, 1H) 8.19 (d, J=8.6 Hz, 1H) 8.63 (d, J=2.0 Hz, 1H) 8.70 (t, J=5.7 Hz, 1H) 9.16 (d, J=2.2 Hz, 1H).

Mass spectrum (LC/MS; method A): retention time Tr (min)=0.84; [M+H]+ m/z 542; [M+H]− m/z 541.

EXAMPLE 46

Synthesis of 2-(2-ethoxyethylamino)-4-[4-(6-fluoro-1H-benzimidazol-2-yl)-9H-carbazol-9-yl]benzamide

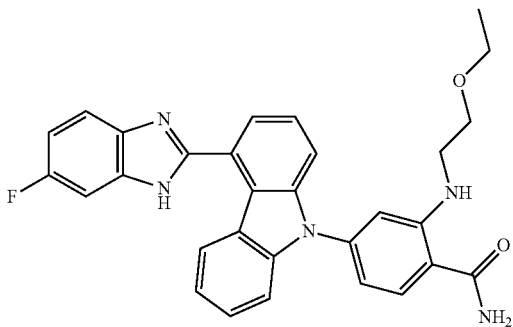

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.273 g of 2-ethoxyethylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and ethanol (from 95/5 to 90/10 by volume), followed by crystallization from 5 ml of ethyl acetate, 205 mg of 2-(2-ethoxyethylamino)-4-[4-(6-fluoro-1H-benzimidazol-2-yl)-9H-carbazol-9-yl]benzamide are thus obtained in the form of a beige solid, the characteristics of which are the following:

1H NMR spectrum (400 MHz, DMSO-d6, δ ppm): 1.12 (t, J=7.1 Hz, 3H) 3.30-3.33 (m, 2H) 3.48 (q, J=6.8 Hz, 2H) 3.58 (t, J=5.4 Hz, 2H) 6.76 (dd, J=8.2, 1.8 Hz, 1H) 6.90 (d, J=1.7 Hz, 1H) 7.11-7.21 (m, 2H) 7.29 (broad s, 1H) 7.41-7.55 (m, 3 H) 7.56-7.81 (m, 4H) 7.92 (d, J=8.3 Hz, 1H) 7.98 (broad s, 1H) 8.55 (t, J=5.4 Hz, 1 H) 8.62 (d, J=7.6 Hz, 1H) 13.08 (broad s, 1H).

Mass spectrum (LC/MS; method A): retention time Tr (min)=1.37; [M+H]+ m/z 508; [M+H]− m/z 506.

EXAMPLE 47

Synthesis of 2-(2-carbamoylethylamino)-4-[4-(6-fluoro-1H-benzimidazol-2-yl)-9H-carbazol-9-yl]benzamide

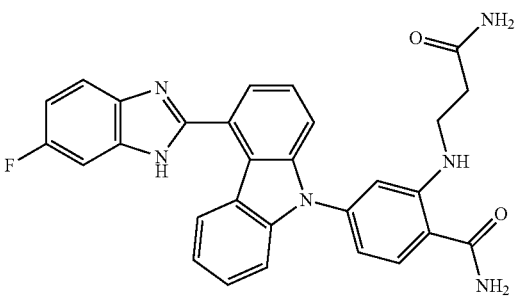

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate, 1.779 g of beta-alanineamide hydrochloride and 1.445 g of triethylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with mixtures of dichloromethane and ethanol (from 95/5 to 90/10 by volume), followed by crystallization from 10 ml of diisopropyl ether, 200 mg of 2-(2-carbamoylethylamino)-4-[4-(6-fluoro-1H-benzimidazol-2-yl)-9H-carbazol-9-yl]benzamide are thus obtained in the form of a beige solid, the characteristics of which are the following:

1H NMR spectrum (400 MHz, DMSO-$d_6$, δ ppm): 2.38 (t, J=6.6 Hz, 2H) 3.36 (q, J=6.3 Hz, 2H) 6.76 (dd, J=8.3, 1.5 Hz, 1H) 6.82 (broad s, 1H) 6.89 (d, J=1.5 Hz, 1H) 7.12-7.22 (m, 2H) 7.27 (broad s, 1H) 7.36 (broad s, 1H) 7.43-7.54 (m, 3H) 7.54-7.81 (m, 4H) 7.92 (d, J=8.3 Hz, 1H) 7.97 (broad s, 1H) 8.44 (t, J=5.5 Hz, 1H) 8.61 (d, J=7.8 Hz, 1H) 13.07 (broad s, 1H).

Mass spectrum (LC/MS; method A): retention time Tr (min)=0.72; [M+H]+ m/z 507; [M+H]– m/z 505.

EXAMPLE 48

Synthesis of 4-[4-(6-fluoro-1H-benzimidazol-2-yl)-9H-carbazol-9-yl]-2-[(furan-2-ylmethyl)amino]benzamide

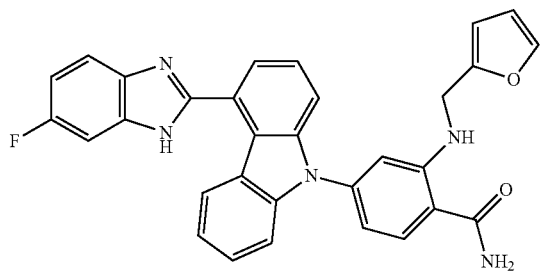

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.387 g of furfurylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (96/4 by volume), followed by crystallization from 10 ml of diisopropyl ether, 160 mg of 4-[4-(6-fluoro-1H-benzimidazol-2-yl)-9H-carbazol-9-yl]-2-[(furan-2-ylmethyl)amino]benzamide are thus obtained in the form of a beige solid, the characteristics of which are the following:

1H NMR spectrum (400 MHz, DMSO-$d_6$, δ ppm): 4.46 (d, J=5.9 Hz, 2H) 6.29 (d, J=3.2 Hz, 1H) 6.45-6.50 (m, 1H) 6.81 (dd, J=8.2, 1.8 Hz, 1H) 7.00 (d, J=1.7 Hz, 1H) 7.11-7.22 (m, 2H) 7.34-7.79 (m, 9H) 7.94 (d, J=8.6 Hz, 1H) 8.03 (br. s., 1H) 8.59 (d, J=8.1 Hz, 1H) 8.82 (t, J=5.9 Hz, 1H) 13.07 (broad s, 1H).

Mass spectrum (LC/MS; method A): retention time Tr (min)=0.96; [M+H]+ m/z 516; [M+H]– m/z 514.

EXAMPLE 49

Synthesis of 4-[4-(6-cyanopyridin-3-yl)-9H-carbazol-9-yl]-2-[(4-trans-hydroxycyclohexyl)amino]benzamide

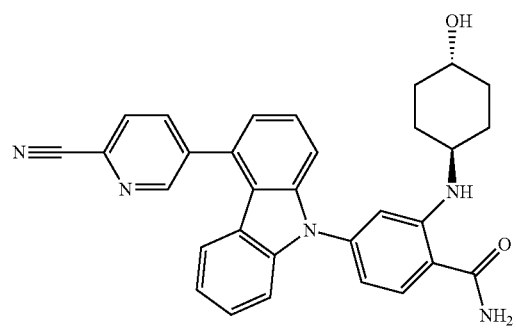

Stage 1: 0.63 g of 2-methylpropan-2-yl 4-bromo-2-fluorobenzoate, 1.88 g of caesium carbonate, 0.11 g of (9,9-dimethyl-9H-xanthene-4,5-diyl)bis(diphenylphosphane) and 0.03 g of palladium acetate are successively added, under argon, to a solution of 0.41 g of 5-(9H-carbazol-4-yl)pyridine-2-carbonitrile, obtained in stage 1 of Example 28, in 20 ml of dioxane. The reaction mixture is refluxed for 4 and a half hours, cooled to ambient temperature, filtered through celite and concentrated under reduced pressure. The residue is purified by silica gel chromatography, elution being carried out with a mixture of cyclohexane and ethyl acetate (90/10 by volume), so as to give 0.48 g of 2-methylpropan-2-yl 4-[4-(6-cyanopyridin-3-yl)-9H-carbazol-9-yl]-2-fluorobenzoate in the form of a light brown oil, the characteristics of which are the following:

1H NMR spectrum (400 MHz, δ in ppm, DMSO-d6): 1.60 (s, 9H) 7.15 (t, J=7.8 Hz, 1H) 7.27 (dd, J=6.9, 1.2 Hz, 1H) 7.31 (d, J=7.8 Hz, 1H) 7.45 (t, J=7.8 Hz, 1H) 7.52 (d, J=7.8 Hz, 1H) 7.56-7.65 (m, 3H) 7.74 (dd, J=11.4, 1.7 Hz, 1H) 8.13 (t, J=8.3 Hz, 1H) 8.29 (d, J=8.1 Hz, 1H) 8.34 (dd, J=8.1, 2.2 Hz, 1H) 9.02 (d, J=2.2 Hz, 1H)

Mass spectrum (LC/MS; method B): retention time Tr (min)=5.81; m/z=464 [M+H]+.

Stage 2: 0.3 g of potassium carbonate and 1.68 g of 4-trans-aminocyclohexanol are successively added to a solution of 0.34 g of 2-methylpropan-2-yl 4-[4-(6-cyanopyridin-3-yl)-9H-carbazol-9-yl]-2-fluorobenzoate in 6 ml of dimethyl sulphoxide. The reaction mixture is heated at 90° C. for 2 hours in a microwave, and then diluted with distilled water. The aqueous phase is extracted twice with ethyl acetate and the combined organic phases are washed with water and a saturated solution of sodium chloride, dried over magnesium sulphate and concentrated to dryness under reduced pressure. The residue is purified by silica gel chromatography, elution being carried out with a mixture of cyclohexane and ethyl acetate (75/25 by volume), so as to give 0.15 g of 2-methylpropan-2-yl 4-[4-(6-cyanopyridin-3-yl)-9H-carbazol-9-yl]-2-[(trans-4-hydroxycyclohexyl)amino]benzoate in the form of a white solid, the characteristics of which are the following:

1H NMR spectrum (400 MHz, δ in ppm, DMSO-d6): 1.20-1.35 (m, 4H) 1.55-1.85 (m, 3H) 1.59 (s, 9H) 2.01 (m, 1H) 3.30-3.52 (m, 2H) 4.50 (d, J=4.3 Hz, 1H) 6.75 (dd, J=8.5, 2.2 Hz, 1H) 6.99 (d, J=2.2 Hz, 1H) 7.11 (ddd, J=8.2, 6.9, 2.2 Hz, 1H) 7.23 (dd, J=6.9, 2.2 Hz, 1H) 7.31 (d, J=8.3 Hz, 1H) 7.40-7.48 (m, 2H) 7.52-7.61 (m, 2H) 7.85 (dd, J=8.2 Hz, 1H) 8.04 (d, J=8.5 Hz, 1H) 8.29 (d, J=7.9 Hz, 1H) 8.34 (dd, J=7.9, 2.0 Hz, 1H) 9.02 (broad d, J=2.0 Hz, 1H).

Mass spectrum (LC/MS; method B): retention time Tr (min)=5.95; m/z=559 [M+H]+.

Stage 3: 1.5 ml of 1N hydrochloric acid are added to a solution of 0.14 g of 2-methyl propan-2-yl 4-[4-(6-cyanopyridin-3-yl)-9H-carbazol-9-yl]-2-[(4-trans-hydroxycyclohexyl)amino]benzoate in 5 ml of dioxane. The reaction mixture is heated at 100° C. in a microwave for 1 hour and 50 minutes and then concentrated under reduced pressure. The residue is triturated with diisopropyl ether and the solid formed is filtered, so as to give 100 mg of 4-[4-(6-cyanopyridin-3-yl)-9H-carbazol-9-yl]-2-[(4-trans-hydroxycyclohexyl)amino]benzoic acid in the form of a white solid, the characteristics of which are the following:

1H NMR spectrum (400 MHz, δ in ppm, DMSO-d6): 1.27 (m, 4H) 1.79 (m, 2 H) 2.01 (m, 2H) 3.39 (m, 1H) 3.48 (m, 1H) 4.48 (d, J=4.3 Hz, 1H) 6.72 (broad d, J=8.3 Hz, 1H) 6.94 (broad s, 1H) 7.11 (m, 1H) 7.23 (m, 1H) 7.32 (d, J=8.0 Hz, 1H) 7.40-7.50 (m, 2H) 7.53-7.61 (m, 2H) 8.07 (d, J=8.3 Hz, 1H) 8.19 (broad m, 1H) 8.29 (d, J=8.2 Hz, 1H) 8.35 (dd, J=8.2, 2.4 Hz, 1H) 9.03 (d, J=2.4 Hz, 1H) 12.79 (broad m, 1H)

Mass spectrum (LC/MS; method B): retention time Tr (min)=4.56; m/z=503 [M+H]+; 501 [M+H]−.

Stage 4: 132 mg of (1H-benzotriazol-1-yloxy)[tris(dimethylamino)]phosphonium hexafluorophosphate (BOP), 40 mg of hydroxybenzotriazole (HOBT), 21 mg of ammonium chloride and 0.13 ml of diisopropylethylamine are successively added to a solution of 100 mg of 4-[4-(6-cyanopyridin-3-yl)-9H-carbazol-9-yl]-2-[(4-trans-hydroxycyclohexyl) amino]benzoic acid in 10 ml of N,N-dimethylformamide. The reaction mixture is stirred at ambient temperature for 4 and a half hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of dichloromethane, acetonitrile and methanol (96/2/2 by volume), and triturated in diisopropyl ether, so as to give 35 mg of 4-[4-(6-cyanopyridin-3-yl)-9H-carbazol-9-yl]-2-[(4-trans-hydroxycyclohexyl)amino]benzamide in the form of a white solid, the characteristics of which are the following:

Melting point (Buchi melting point B-545)=274° C.

1H NMR spectrum (400 MHz, δ in ppm, DMSO-d6): 1.24 (m, 4H) 1.78 (m, 2 H) 1.98 (m, 2H) 3.30 (m partially masked, 1H) 3.46 (m, 1H) 4.48 (d, J=4.2 Hz, 1H) 6.69 (dd, J=8.6, 1.9 Hz, 1H) 6.88 (d, J=1.9 Hz, 1H) 7.11 (m, 1H) 7.23 (d, J=7.0 Hz, 1H) 7.27 (broad m, 1H) 7.32 (d, J=8.2 Hz, 1H) 7.44 (m, 2H) 7.51-7.61 (m, 2H) 7.90 (d, J=8.4 Hz, 1H) 7.97 (broad m, 1H) 8.29 (d, J=7.9 Hz, 1H) 8.35 (dd, J=7.9, 2.0 Hz, 1H) 8.45 (d, J=7.7 Hz, 1H) 9.03 (broad s, 1H).

Mass spectrum (LC/MS; method A): retention time Tr (min)=0.99; m/z=502 [M+H]+; 500 [M−H]−.

EXAMPLE 50

Synthesis of 4-[4-(6-fluoro-1H-benzimidazol-2-yl)-9H-carbazol-9-yl]-2-[(furan-3-ylmethyl)amino]benzamide

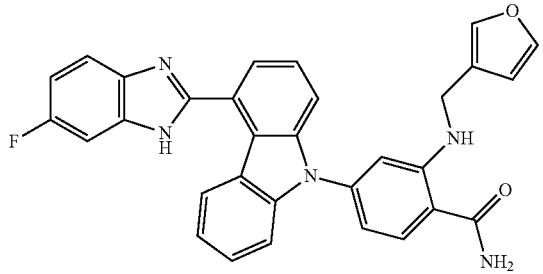

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.387 g of 3-furylmethylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (96/4 by volume), followed by crystallization from 5 ml of ethyl acetate, 220 mg of 4-[4-(6-fluoro-1H-benzimidazol-2-yl)-9H-carbazol-9-yl]-2-[(furan-3-ylmethyl)amino]benzamide are thus obtained in the form of a beige solid, the characteristics of which are the following:

1H NMR spectrum (400 MHz, DMSO-$d_6$, δ ppm): 4.27 (d, J=5.4 Hz, 2H) 6.48 (s, 1H) 6.79 (d, J=8.1 Hz, 1H) 6.91 (s, 1H) 7.10-7.21 (m, 2H) 7.29-7.76 (m, 10H) 7.93 (d, J=8.3 Hz, 1H) 8.01 (broad s, 1H) 8.59 (d, J=7.8 Hz, 1H) 8.70 (t, J=5.3 Hz, 1 H) 13.09 (broad s, 1H).

Mass spectrum (LC/MS; method A): retention time Tr (min)=0.95; m/z=516 [M+H]+; 514 [M−H]−.

EXAMPLE 51

Synthesis of 4-[4-(6-fluoro-1H-benzimidazol-2-yl)-9H-carbazol-9-yl]-2-[(2H-pyrazol-3-ylmethyl)amino]benzamide

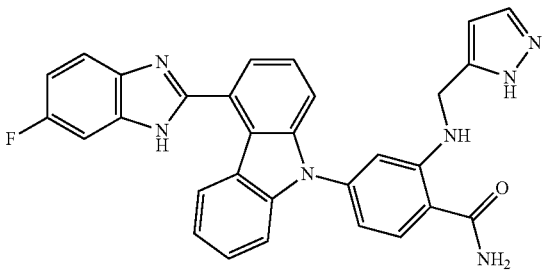

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.387 g of 2H-pyrazol-3-ylmethylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 2 ml of ethyl acetate, 50 mg of 4-[4-(6-fluoro-1H-benzimidazol-2-yl)-9H-carbazol-9-yl]-2-[(2H-pyrazol-3-ylmethyl)amino]benzamide are thus obtained in the form of a beige solid, the characteristics of which are the following:

1H NMR spectrum (400 MHz, DMSO-$d_6$, δ ppm): 4.38 (broad s, 2H) 6.19 (s, 1H) 6.77 (d, J=6.1 Hz, 1H) 6.95 (s, 1H) 7.11-7.22 (m, 2H) 7.28-8.10 (m, 11H) 8.55 (s, 1H) 8.80 (t, J=5.5 Hz, 1H) 12.63 (broad s, 1H) 13.07 (broad s, 1H).

Mass spectrum (LC/MS; method A): retention time Tr (min)=0.78; m/z=516 [M+H]+; 514 [M−H]−.

EXAMPLES 52 AND 53

Synthesis of 4-[4-(6-fluoro-1H-benzimidazol-2-yl)-9H-carbazol-9-yl]-2-(2-hydroxy-1-hydroxymethylethylamino)benzamide and of 2-(2-amino-1-hydroxymethylethyloxy)-4-[4-(6-fluoro-1H-benzimidazol-2-yl)-9H-carbazol-9-yl]benzamide

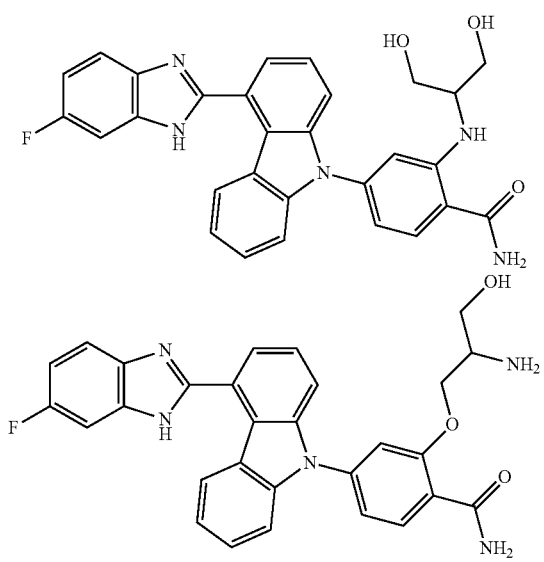

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.301 g of 2-amino-1,3-propanediol in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. The reaction medium is treated as in stage 3 of Example 3. The residue obtained is purified by preparative HPLC on a Whelk 01 SS chiral column (10 µM, 250×4.6 mm), elution being carried out with a mobile phase consisting of a mixture of heptane, ethanol, methanol and triethylamine (30/60/10/0.1 by volume).

By concentrating the first eluted fraction (retention time=4.19 min), 18.1 mg of 4-[4-(6-fluoro-1H-benzimidazol-2-yl)-9H-carbazol-9-yl]-2-(2-hydroxy-1-hydroxymethylethylamino)benzamide, Example 52, are obtained in the form of a white foam, the characteristics of which are the following:

1H NMR spectrum (400 MHz, DMSO-$d_6$+TFA, δ ppm): 3.39-3.45 (m, 1H) 3.49-3.58 (m, 4H) 6.74 (dd, J=8.1, 1.7 Hz, 1H) 7.00 (d, J=1.7 Hz, 1H) 7.23 (ddd, J=8.1, 5.7, 2.3 Hz, 1H) 7.51-7.59 (m, 3H) 7.66 (d, J=8.1 Hz, 1H) 7.72-7.77 (m, 2 H) 7.81-7.87 (m, 2H) 7.91 (d, J=8.3 Hz, 1H) 8.01 (dd, J=8.8, 4.4 Hz, 1H).

Mass spectrum (LC/MS; method C): retention time Tr (min)=3.22; m/z=510 [M+H]+; 508 [M−H]−.

By concentrating the second eluted fraction (retention time=9.36 min), 45.3 mg of 2-(2-amino-1-hydroxymethylethyloxy)-4-[4-(6-fluoro-1H-benzimidazol-2-yl)-9H-carbazol-9-yl]benzamide, Example 53, are obtained in the form of a white foam, the characteristics of which are the following:

1H NMR spectrum (400 MHz, DMSO-$d_6$, δ ppm): 1.94 (broad s, 2H) 3.06-3.17 (m, 1H) 3.39-3.50 (m, 2H) 4.05 (dd, J=10, 5 Hz, 1H) 4.20 (dd, J=10, 5 Hz, 1 H) 4.71 (t, J=5.3 Hz, 1H) 7.08-7.26 (m, 2H) 7.31 (dd, J=8.2, 1.8 Hz, 1H) 7.36-7.44 (m, 2H) 7.44-7.52 (m, 2H) 7.57-7.70 (m, 4H) 7.79-7.90 (m, 1H) 8.12 (d, J=8.1 Hz, 1H) 8.17 (broad s, 1H) 8.65 (dd, J=19.9, 7.9 Hz, 1H) 13.09 (broad s, 1H).

Mass spectrum (LC/MS; method C): retention time Tr (min)=2.77; m/z=510 [M+H]+; 508 [M−H]−.

EXAMPLE 54

Synthesis of 4-[4-(6-fluoro-1H-benzimidazol-2-yl)carbazol-9-yl]-2-[3(S)-methoxypropylamino]benzamide

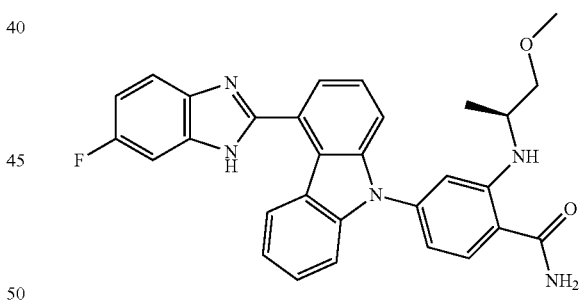

The process is carried out as in stage 3 of Example 3, but using 300 mg of 2-fluoro-4-[4-(6-fluoro-1H-benzimidazol-2-yl)carbazol-9-yl]benzonitrile, obtained according to stage 3 of Example 3, 296 mg of potassium carbonate and 1.273 g of 1-methoxy-2(S)-propylamine in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. The reaction medium is treated as in stage 2 of Example 3. The residue obtained is purified by preparative HPLC on a Chiralpak AD silica column (20 µm, 250×4.6 mm), elution being carried out with a mixture of heptane, ethanol and trifluoroacetic acid (80/20/0.1 by volume). 155 mg of 4-[4-(6-fluoro-1H-benzimidazol-2-yl)carbazol-9-yl]-2-[3(S)-methoxypropylamino]benzamide are thus obtained in the form of a white foam, the characteristics of which are the following:

1H NMR spectrum (400 MHz, DMSO-d$_6$+TFA, δ ppm): 1.18 (d, J=6.4 Hz, 3H) 3.29 (s, 3H) 3.37-3.41 (m, 2H) 3.68-3.78 (m, 1H) 6.76 (dd, J=8.2, 1.8 Hz, 1H) 6.94 (d, J=1.5 Hz, 1H) 7.10-7.24 (m, 2H) 7.42-7.50 (m, 3H) 7.57-7.68 (m, 4H) 7.92 (d, J=8.3 Hz, 1H) 8.57 (d, J=7.6 Hz, 1H).

Mass spectrum (LC/MS; method A): retention time Tr (min)=0.93; m/z=508 [M+H]+; 506 [M–H]–.

EXAMPLE 55

Synthesis of 4-[4-(2-aminopyrimidin-5-yl)-9H-carbazol-9-yl]-2-[(4-trans-hydroxycyclohexyl)amino]benzamide hydrochloride

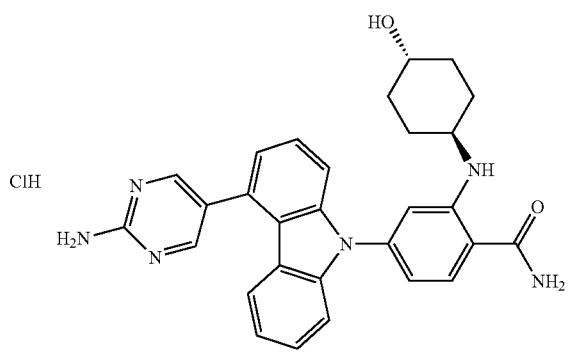

Stage 1: 2.72 g (12.4 mmol) of di-tert-butyl dicarbonate and 6.6 mg (0.54 mmol) of 4-dimethylaminopyridine are successively added to a solution of 1.2 g of 2-amino-[4-(4,4,5,5-tetramethyl-1,3,2-dioxaborolan-2-yl)pyrimidine in 50 ml of dichloromethane. The reaction mixture is stirred at ambient temperature for 15 hours, poured into distilled water and then extracted with dichloromethane. The organic phase is subsequently washed with water and with a saturated solution of sodium chloride, dried over magnesium sulphate and concentrated under reduced pressure. The residue is triturated with diisopropyl ether, so as to give 1.7 g of bis(2-methylpropan-2-yl) [5-(4,4,5,5-tetramethyl-1,3,2-dioxaborolan-2-yl)pyrimidin-2-yl]imidodicarbonate in the form of a white solid, the characteristics of which are the following:

1H NMR spectrum (400 MHz, δ in ppm, DMSO-d6): 1.32 (s, 12H) 1.40 (s, 18 H) 8.93 (s, 2H).

Mass spectrum (EI): m/z=421 (M+).

Stage 2: 1.7 g of 2-methylpropan-2-yl[5-(4,4,5,5-tetramethyl-1,3,2-dioxaborolan-2-yl)pyrimidin-2-yl]biscarbamate, obtained in the preceding stage, 3.72 g of caesium carbonate and 100 mg of bis(diphenylphosphino)ferrocenepalladium (II) dichloride as a complex with dichloromethane (1/1) [PdCl$_2$(dppf).CH$_2$Cl$_2$] are successively added, under argon, to a solution of 0.96 g of 4-trifluoromethanesulphonyloxycarbazole, obtained in stage 1 of Example 1, in a mixture of 36 ml of dioxane and 12 ml of water. The reaction mixture is refluxed for 4 hours, cooled to ambient temperature, filtered through celite and concentrated under reduced pressure. The brown residue is purified by silica gel chromatography, elution being carried out with a mixture of cyclohexane and ethyl acetate (85/15 by volume). 0.56 g of 2-methylpropan-2-yl[5-(9H-carbazol-4-yl)pyrimidin-2-yl]biscarbamate is thus obtained in the form of a white solid, the characteristics of which are the following:

1H NMR spectrum (400 MHz, δ in ppm, DMSO-d6): 1.46 (s, 18H) 6.92 (m, 1 H) 7.14 (d, J=7.4 Hz, 1H) 7.21 (d, J=8.1 Hz, 1H) 7.39 (m, 1H) 7.49-7.57 (m, 2H) 7.64 (dd, J=8.1, 1.0 Hz, 1H) 9.11 (s, 2H) 11.62 (broad s, 1H).

Mass spectrum (LC/MS; method A): retention time Tr (min)=1.16; m/z=461 [M+H]+; 459 [M–H]–.

Stage 3: 0.325 g of 4-bromo-2-fluorobenzonitrile, 1.3 g of caesium carbonate, 75 mg of (9,9-dimethyl-9H-xanthene-4,5-diyl)bis(diphenylphosphane) and 24 mg of palladium acetate are successively added, under argon, to a solution of 0.5 g of 2-methylpropan-2-yl[5-(9H-carbazol-4-yl)pyrimidin-2-yl]biscarbamate in 30 ml of dioxane. The reaction mixture is refluxed for 6 hours, cooled to ambient temperature, filtered through celite and concentrated under reduced pressure. The residue is purified by silica gel chromatography, elution being carried out with a mixture of cyclohexane and ethyl acetate (80/20 by volume). 0.51 g of 2-methylpropan-2-yl {5-[9-(4-cyano-3-fluorophenyl)-9H-carbazol-4-yl}pyrimidin-2-yl]biscarbamate is thus obtained, the characteristics of which are the following:

1H NMR spectrum (400 MHz, δ in ppm, DMSO-d6): 1.47 (s, 18H) 7.10 (m, 1 H) 7.23 (d, J=8.0 Hz, 1H) 7.34 (dd, J=7.2, 1.1 Hz, 1H) 7.48 (m, 1H) 7.55-7.69 (m, 3H) 7.78 (dd, J=8.3, 2.0 Hz, 1H) 8.02 (dd, J=10.2, 2.0 Hz, 1H) 8.27 (t, J=8.0 Hz, 1 H) 9.15 (s, 2H).

Mass spectrum (LC/MS; method A): retention time Tr (min)=1.26; m/z=580 [M+H]+.

Stage 4: 0.18 g of potassium carbonate and 1.01 g of 4-trans-aminocyclohexanol are successively added to a solution of 0.25 g of 2-methylpropan-2-yl {{5-[9-(4-cyano-3-fluorophenyl)-9H-carbazol-4-yl]pyrimidin-2-yl}biscarbamate in 6 ml of dimethyl sulphoxide. The reaction mixture is heated at 90° C. for 1 hour and 15 minutes in a microwave, and then 4.5 ml of ethanol are added, followed by 0.86 ml of a 1N solution of sodium hydroxide and 0.86 ml of 30% aqueous hydrogen peroxide. The reaction mixture is stirred at ambient temperature for an hour and then diluted with distilled water. The aqueous phase is extracted twice with ethyl acetate and the combined organic phases are washed with water and a saturated solution of sodium chloride, dried over magnesium sulphate and concentrated under reduced pressure. The residue is purified by silica gel chromatography, elution being carried out with a mixture of dichloromethane, acetonitrile and methanol (92/4/4 by volume). 0.1 g of 2-methylpropan-2-yl[5-(9-{4-carbamoyl-3-[(4-trans-hydroxycyclohexyl)amino]phenyl}-9H-carbazol-4-yl)pyrimidin-2-yl]carbamate is thus obtained in the form of a white solid, the characteristics of which are the following:

1H NMR spectrum (400 MHz, δ in ppm, DMSO-d6): 1.24 (m, 4H) 1.52 (s, 9H) 1.78 (m, 2H) 1.99 (m, 2H) 3.30 (masked m, 1H) 3.46 (m, 1H) 4.47 (d, J=4.6 Hz, 1H) 6.69 (dd, J=8.3, 2.0 Hz, 1H) 6.87 (d, J=2.0 Hz, 1H) 7.14 (m, 1H) 7.20 (dd, J=7.1, 1.0 Hz, 1H) 7.26 (broad m, 1H) 7.41-7.45 (m, 3H) 7.4 (dd, J=8.6, 1.0 Hz, 1 H) 7.55 (dd, J=8.6, 7.1 Hz, 1H) 7.89 (d, J=8.6 Hz, 1H) 7.95 (broad m, 1H) 8.44 (d, J=8.4 Hz, 1H) 8.86 (s, 2H) 10.29 (broad s, 1H).

Mass spectrum (LC/MS; method A): retention time Tr (min)=1.00; m/z=593 [M+H]+.

Stage 5: 0.32 ml of 1N hydrochloric acid is added to a solution of 0.1 g (0.17 mmol) of 2-methylpropan-2-yl[5-(9-{4-carbamoyl-3-[(4-trans-hydroxy-cyclohexyl)amino]phenyl}-9H-carbazol-4-yl)pyrimidin-2-yl]carbamate in 1.3 ml of dioxane. The reaction mixture is heated at 100° C. in a microwave for 15 minutes and then concentrated under reduced pressure. The residue is triturated with diisopropyl ether and the solid formed is filtered off, so as to give 87 mg of 4-[4-(2-aminopyrimidin-5-yl)-9H-carbazol-9-yl]-2-[(4- trans-hydroxycyclohexyl)amino]benzamide hydrochloride in the form of a white solid, the characteristics of which are the following:

1H NMR spectrum (400 MHz, δ in ppm, DMSO-d6): 1.24 (m, 4H) 1.78 (m, 2H) 1.98 (m, 2H) 3.33 (m, 1H) 3.50 (masked m, 1H) 6.68 (dd, J=8.5, 2.0 Hz, 1H) 6.86 (d, J=2.0 Hz, 1H) 7.13-7.19 m, 2H) 7.27 (broad m, 1H) 7.41-7.46 (m, 2H) 7.51 (t, J=8.0 Hz, 1H) 7.61 (d, J=8.0 Hz, 1H) 7.89 (d, J=8.5 Hz, 1H) 7.96 (broad m, 1H) 8.60 (s, 1H).

Mass spectrum (LC/MS; method A): retention time Tr (min)=0.73; m/z=493 [M+H]+.

EXAMPLE 56

Synthesis of 4-[4-(2-aminopyrimidin-5-yl)-9H-carbazol-9-yl]-2-[(3-hydroxypropyl)amino]benzamide hydrochloride

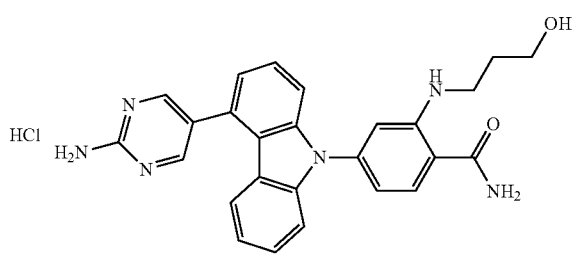

Stage 1: 0.18 g of potassium carbonate and 0.64 g of 3-amino-1-propanol are successively added to a solution of 0.25 g of 2-methylpropan-2-yl {{5-[9-(4-cyano-3-fluorophenyl)-9H-carbazol-4-yl]pyrimidin-2-yl}biscarbamate, obtained in stage 3 of Example 55, in 6 ml of dimethyl sulphoxide. The reaction mixture is heated at 90° C. for 1 hour and 15 minutes in a microwave, and then 4.5 ml of ethanol are added, followed by 0.86 ml of a 1N solution of sodium hydroxide and 0.86 ml of 30% aqueous hydrogen peroxide. The reaction mixture is stirred at ambient temperature for 1 hour and then diluted with distilled water. The aqueous phase is extracted twice with ethyl acetate and the combined organic phases are washed with water and a saturated solution of sodium chloride, dried over magnesium sulphate and filtered. The filtrate is concentrated under reduced pressure and the residue is purified by silica gel chromatography, elution being carried out with a mixture of dichloromethane, acetonitrile and methanol (92/4/4 by volume). 0.15 g of 2-methylpropan-2-yl[5-(9-{4-carbamoyl-3-[(3-hydroxypropyl)amino]phenyl}-9H-carbazol-4-yl)pyrimidin-2-yl]biscarbamate is thus obtained in the form of a white solid, the characteristics of which are the following:

1H NMR spectrum (400 MHz, δ in ppm, DMSO-d6): 1.52 (s, 9H) 1.72 (m, 2H) 3.18 (m, 2H) 3.49 (m, 2H) 4.48 (t, J=5.1 Hz, 1H) 6.73 (dd, J=8.4, 2.1 Hz, 1H) 6.84 (d, J=2.1 Hz, 1. H) 7.14 (m, 1H) 7.20 (m, 1H) 7.27 (broad m, 1H) 7.39-7.58 (m, 5H) 7.91 (d, J=8.5 Hz, 1H) 7.98 (broad m, 1H) 8.44 (t, J=5.7 Hz, 1H) 8.86 (s, 2 H) 10.29 (broad s, 1H).

Mass spectrum (LC/MS; method A): retention time Tr (min)=0.11; m/z=553 [M+H]+.

Stage 2: 0.51 ml of 1N hydrochloric acid is added to a solution of 0.15 g of 2-methylpropan-2-yl[5-(9-{4-carbamoyl-3-[(3-hydroxypropyl)amino]phenyl}-9H-carbazol-4-yl)pyrimidin-2-yl]biscarbamate in 2 ml of dioxane. The reaction mixture is heated at 100° C. in a microwave for 15 minutes and then concentrated under reduced pressure. The residue is triturated with diisopropyl ether and the solid formed is filtered off, so as to give 130 mg of 4-[4-(2-aminopyrimidin-5-yl)-9H-carbazol-9-yl]-2-[(3-hydroxypropyl)amino]benzamide hydrochloride in the form of a white solid, the characteristics of which are the following:

1H NMR spectrum (400 MHz, δ in ppm, DMSO-d6): 1.72 (m, 2H) 3.18 (t, J=6.9 Hz, 2H) 3.50 (masked m, 2H) 6.73 (dd, J=8.3, 2.0 Hz, 1H) 6.83 (d, J=2.0 Hz, 1H) 7.11-7.20 (m, 2H) 7.29 (broad m, 1H) 7.38-7.56 (m, 4H) 7.60 (d, J=8.1 Hz, 1H) 7.91 (d, J=8.4 Hz, 1H) 7.98 (broad m, 1H) 8.58 (s, 2H).

Mass spectrum (LC/MS; method A): retention time Tr (min)=0.70; m/z=453 [M+H]+.

EXAMPLE 57

Synthesis of 4-[4-(6-fluoro-1H-benzimidazol-2-yl)-9H-carbazol-9-yl]-2-[(1H-imidazoly-4-yl)methylamino]benzamide

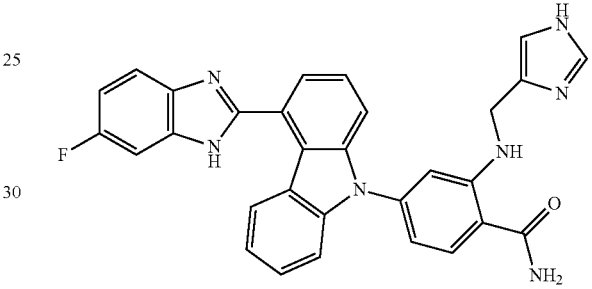

Stage 1: The process is carried out as in stage 2 of Example 31, but using 300 mg of 2-fluoro-4-[4-(6-fluoro-1H-benzimidazol-2-yl)-9H-carbazol-9-yl]benzonitrile, obtained in stage 3 of Example 3, 121.4 mg of (1H-imidazol-4-yl)methylamine hydrochloride, 789 mg of potassium carbonate and 289 mg of triethylamine, at 140° C. for 3 hours in 7 ml of dimethylformamide. After treatment as in stage 2 of Example 2, 421 mg of a mixture are obtained, said mixture being used as it is in the subsequent stage and containing predominantly 4-[4-(6-fluoro-1H-benzimidazol-2-yl)-9H-carbazol-9-yl]-2-[(1H-imidazol-4-yl)methylamino]benzontrile, the characteristic of which is the following:

LC/MS (method C): retention time=3.23 min.

Stage 2: By carrying out the process as in stage 4 of Example 2, but using 421 mg of the crude compound obtained in the preceding stage, 1.816 ml of a 1N solution of sodium hydroxide and 1.668 ml of a 30% aqueous solution of hydrogen peroxide, for 10 minutes at ambient temperature, in 10 ml of ethanol and 4 ml of dimethyl sulphoxide, there are obtained, after purification by flash chromatography on 15 g of silica, elution being carried out with mixtures of dichloromethane, methanol and 5M aqueous ammonia (80/20/1 then 75/25/1 by volume), 33 mg of 4-[4-(6-fluoro-1H-benzimidazol-2-yl)-9H-carbazol-9-yl]-2-[(1H-imidazol-4-yl)methylamino]benzamide in the form of a beige powder, the characteristics of which are the following:

1H NMR spectrum (400 MHz, DMSO-d$_6$, δ ppm): 3.64 (s, 2H) 7.13 (t, J=10.8 Hz, 1H) 7.19-7.25 (m, 1H) 7.32 (s, 1H) 7.43-7.89 (m, 14H) 8.03 (broad s, 1H) 8.72 (d, J=8.1 Hz, 1H).

Mass spectrum (LC/MS; method C): retention time Tr (min)=2.70; m/z=516 [M+H]+; m/z=514 [M−H]−.

EXAMPLE 58

Synthesis of 3-(4-trans-hydroxycyclohexylamino)-5-[(4-quinolin-3-yl)-9H-carbazol-9-yl]pyridine-2-carboxamide

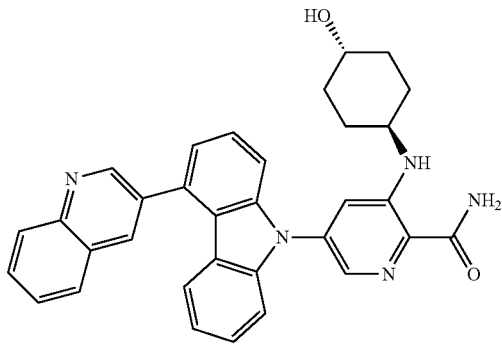

Stage 1: In a 20 ml round-bottomed flask, 60 mg of sodium hydride dispersed at 60% in oil are added, under argon in small amounts, to a mixture of 500 mg of 4-(quinolin-3-yl)-9H-carbazole obtained according to stage 1 of Example 2 and 262 mg of 2-cyano-3,5-difluoropyridine dissolved in 6 ml of anhydrous dimethylformamide. The reaction medium is subsequently stirred at ambient temperature for 3 hours and then 262 mg of 2-cyano-3,5-difluoropyridine and 60 mg of sodium hydride dispersed at 60% in oil are added. The reaction medium is stirred at ambient temperature overnight under argon, and then poured into distilled water containing a small amount of sodium chloride. The aqueous phase is extracted twice with ethyl acetate, and the combined organic phases are washed with a saturated solution of sodium chloride, dried over magnesium sulphate and evaporated to dryness under vacuum. The residue is chromatographed on silica gel (15-40 μm), elution being carried out with a gradient of dichloromethane and diisopropyl ether (from 99/1 to 90/10 by volume). 483 mg of a mixture of positional isomers are obtained, said mixture being separated by silica gel chromatography (15-40 μm), elution being carried out with a gradient of ethyl acetate and heptane (90/10 to 80/20 by volume). 129 mg of 3-fluoro-5-[(4-quinolin-3-yl)-9H-carbazol-9-yl]pyridine-2-carbonitrile are obtained in the form of a white solid, the characteristics of which are the following:

1H NMR spectrum (400 MHz, δ in ppm, DMSO-d6): 7.11 (t, J=7.3 Hz, 1H); 7.25 (d, J=7.8 Hz, 1H); 7.39 (d, J=6.6 Hz, 1H); 7.44 (t, J=8.2 Hz, 1H); 7.61 (d, J=7.6 Hz, 1H); 7.65 (d, J=7.3 Hz, 1H); 7.70 (d, J=8.3 Hz, 1H); 7.74 (t, J=7.5 Hz, 1H); 7.89 (t, J=8.3 Hz, 1H); 8.14 (d, J=7.8 Hz, 1H); 8.19 (d, J=8.6 Hz, 1H); 8.63 (d, J=2.0 Hz, 1H); 8.70 (dd, J=9.8 and 2.0 Hz, 1H); 9.07 (s, 1H); 9.13 (d, J=2.2 Hz, 1H).

Mass spectrum (LC/MS method A): retention time Tr (min)=1.16; [M+H]+=415.

251 mg of the 5-fluoro-3-[(4-quinolin-3-yl)-9H-carbazol-9-yl]pyridine-2-carbonitrile isomer are also obtained.

Stage 2: 127 mg of 3-fluoro-5-(4-quinolin-3-yl-carbazol-9-yl)pyridine-2-carbonitrile, obtained according to the preceding stage, 706 mg of 4-trans-aminocyclohexanol, 127 mg of potassium carbonate and 1.5 ml of dimethyl sulphoxide are successively introduced into a 2 ml microwave reactor. After stirring for 30 seconds at ambient temperature, the reaction medium is heated at 100° C. for 45 minutes with stirring. After cooling, the mixture is transferred into a 25 ml round-bottomed flask and 3 ml of ethanol, 0.58 ml of 1N sodium hydroxide and 0.57 ml of 30% aqueous hydrogen peroxide are successively added at ambient temperature under argon. After stirring at ambient temperature for 30 minutes, the reaction medium is poured into distilled water and the aqueous phase is extracted 3 times with ethyl acetate. The combined organic phases are washed with a saturated solution of sodium chloride, dried over magnesium sulphate and evaporated to dryness under vacuum. The residue is chromatographed on silica gel (15-40 μm), elution being carried out with a gradient of dichloromethane and methanol (from 99/1 to 95/5 by volume). After combining and evaporation of the advantageous fractions, the solid is made into a paste in diisopropyl ether, filtered, washed with pentane and dried under vacuum. 81 mg of 3-(4-trans-hydroxycyclohexylamino)-5-[4-quinolin-3-yl]-9H-carbazol-9-yl]pyridine-2-carboxamide are obtained in the form of an off-white solid, the characteristics of which are the following:

1H NMR spectrum (400 MHz, δ in ppm, DMSO-d6): 1.21 to 1.36 (m, 4H); 1.75 to 1.84 (m, 2H); 1.97 to 2.04 (m, 2H); 3.44 to 3.53 (m, 2H); 4.51 (broad s, 1H); 7.05 (t, J=8.1 Hz, 1H); 7.26 (d, J=8.1 Hz, 1H); 7.33 (d, J=7.1 Hz, 1H); 7.39 to 7.47 (m, 2H); 7.50 to 7.57 (m, 3H); 7.58 to 7.65 (m, 1H); 7.74 (t, J=7.5 Hz, 1H); 7.89 (t, J=8.1 Hz, 1H); 7.99 (d, J=1.7 Hz, 1H); 8.11 to 8.16 (m, 2H); 8.19 (d, J=8.3 Hz, 1H); 8.62 (d, J=1.7 Hz, 1H); 8.74 (d, J=8.1 Hz, 1H); 9.15 (d, J=2.2 Hz, 1H).

Mass spectrum (LC/MS; method A): retention time Tr (min)=1.07; [M+H]+=528.

EXAMPLE 59

Synthesis of 4-[4-(6-fluoro-1H-benzimidazol-2-yl)-9H-carbazol-9-yl]-2-(tetrahydropyran-4-ylamino)benzamide

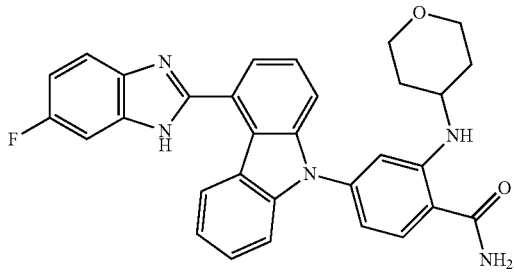

The process is carried out as in stage 3 of Example 3, but using 300 mg of 2-fluoro-4-[4-(6-fluoro-1H-benzimidazol-2-yl)carbazol-9-yl]benzonitrile, obtained according to stage 2 of Example 3, 296 mg of potassium carbonate and 1.444 g of 4-aminotetrahydropyran in 3 ml of dimethyl sulphoxide. 1.357 ml of a 1M aqueous solution of sodium hydroxide, 1.313 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (97/3 by volume), followed by crystallization from 2 ml of ethyl acetate, 150 mg of 4-[4-(6-fluoro-1H-benzimidazol-2-yl)-9H-carbazol-9-yl]-2-(tetrahydropyran-4-ylamino)benzamide are thus obtained in the form of a beige solid, the characteristics of which are the following:

1H NMR spectrum (400 MHz, DMSO-$d_6$, δ ppm): 1.35-1.50 (m, 2H) 1.89-1.97 (m, 2H) 3.36-3.46 (m, 2H) 3.56-3.68 (m, 1H) 3.80 (dt, J=11.6, 3.8 Hz, 2H) 6.73 (dd, J=8.3, 1.7 Hz, 1H) 6.96 (d, J=1.7 Hz, 1H) 7.10-7.23 (m, 2H) 7.32 (broad s, 1H) 7.37-7.67 (m, 6H) 7.67-7.78 (m, 1H) 7.93 (d, J=8.3 Hz, 1H) 8.01 (broad s, 1H) 8.58 (d, J=7.6 Hz, 1H) 8.66 (d, J=8.3 Hz, 1H) 13.08 (broad s, 1H).

Mass spectrum (LC/MS; method C): retention time Tr (min)=3.83; [M+H]+=520; [M−H]−=518.

EXAMPLE 60

Synthesis of 4-[4-(6-fluoro-1H-benzimidazol-2-yl)-9H-carbazol-9-yl]-2-(3-methoxypropoxy)benzamide

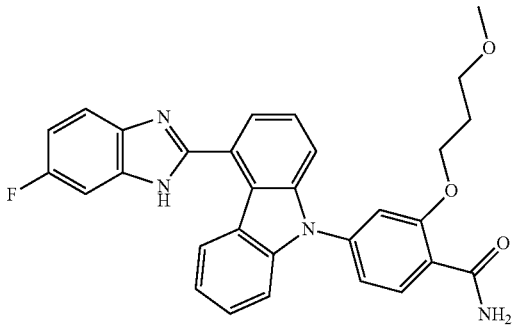

Stage 1: In a 25 ml three-necked flask, under an argon atmosphere, 1.257 g of 3-methoxypropanol are dissolved in 10 ml of dimethylformamide, and then 228.5 mg of sodium hydride at 60% in oil are added and the mixture is stirred for 30 minutes at ambient temperature once no more gas is seen to be given off. 300 mg of 2-fluoro-4-[4-(6-fluoro-1H-benzimidazol-2-yl)-9H-carbazol-9-yl]benzonitrile, obtained in stage 3 of Example 3, are then added and the mixture is again stirred for 30 minutes at ambient temperature. The reaction medium is run into 200 ml of water and extracted 3 times with 50 ml of ethyl acetate. The combined organic phases are washed with a saturated aqueous solution of sodium chloride, dried over magnesium sulphate and concentrated to dryness under reduced pressure. The residue obtained is stirred into 2 ml of diisopropyl ether, and the crystals formed are spin-filter-dried and washed with diisopropyl ether. 300 mg of a mixture are thus obtained, said mixture being used as it is in the subsequent stage and containing very predominantly 4-[4-(6-fluoro-1H-benzimidazol-2-yl)-9H-carbazol-9-yl]-2-(3-methoxypropoxy)benzonitrile, the characteristic of which is the following:

LC/MS (method C): retention time=4.93 min.

Stage 2: By carrying out the process as in stage 4 of Example 2, but using 450 mg of crude compound, identical to that obtained in the preceding stage, 1.742 ml of a 1N solution of sodium hydroxide and 1.6686 ml of a 30% aqueous solution of hydrogen peroxide, for 15 minutes at ambient temperature, in 9 ml of ethanol and 4 ml of dimethyl sulphoxide, there are obtained, after purification by crystallization from 15 ml of diisopropyl ether, 345 mg of 414-(6-fluoro-1H-benzimidazol-2-yl)-9H-carbazol-9-yl]-2-(3-methoxypropoxy)benzamide in the form of a beige powder, the characteristics of which are the following:

1H NMR spectrum (400 MHz, DMSO-$d_6$, δ ppm): 2.00-2.10 (m, 2H) 3.24 (s, 3H) 3.53 (t, J=4.9 Hz, 2H) 4.26 (t, J=4.8 Hz, 2H) 7.10-7.25 (m, 2H) 7.31 (d, J=7.8 Hz, 1H) 7.40 (s, 1H) 7.43-7.56 (m, 3H) 7.57-7.76 (m, 5H) 7.88 (broad s, 1H) 8.15 (d, J=7.8 Hz, 1H) 8.66 (d, J=7.6 Hz, 1H) 13.06 (broad s, 1H).

Mass spectrum (LC/MS; method C): retention time Tr (min)=3.82; [M+H]+=509; [M−H]−=507.

EXAMPLE 61

Synthesis of 4-[4-(6-fluoro-1H-benzimidazol-2-yl)-9H-carbazol-9-yl]-2-(3-hydroxy-3-methylbutylamino)benzamide

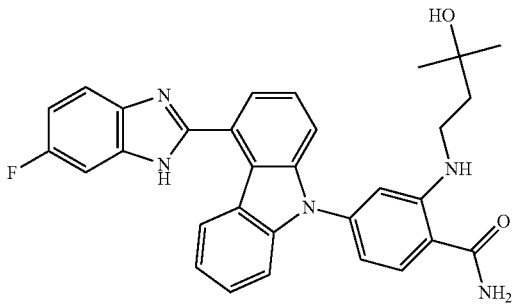

The process is carried out as in stage 3 of Example 3, but using 155.6 mg of 2-fluoro-4-[4-(6-fluoro-1H-benzimidazol-2-yl)-9H-carbazol-9-yl]benzonitrile, obtained according to stage 2 of Example 3, 153.4 mg of potassium carbonate, 1.033 g of 4-amino-2-methylbutan-2-ol hydrochloride and 0.749 g of triethylamine in 2 ml of dimethyl sulphoxide. 0.703 ml of a 1M aqueous solution of sodium hydroxide, 0.681 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 5 ml of ethyl acetate, 185 mg of 4-[4-(6-fluoro-1H-benzimidazol-2-yl)-9H-carbazol-9-yl]-2-(3-hydroxy-3-methylbutylamino)benzamide are thus obtained in the form of a beige solid, the characteristics of which are the following:

1H NMR spectrum (400 MHz, DMSO-$d_6$, δ ppm): 1.11 (s, 6H) 1.71 (t, J=7.8 Hz, 2H) 3.16-3.23 (m, 2H) 4.26 (s, 1H) 6.74 (dd, J=8.3, 1.5 Hz, 1H) 6.86 (d, J=1.7 Hz, 1H) 7.11-7.22 (m, 2H) 7.29 (broad s, 1H) 7.44-7.57 (m, 3H) 7.58-7.67 (m, 3 H) 7.68-7.75 (m, 1H) 7.92 (d, J=8.3 Hz, 1H) 7.98 (broad s, 1H) 8.40 (t, J=4.9 Hz, 1 H) 8.62 (d, J=8.3 Hz, 1H) 13.08 (broad s, 1H).

Mass spectrum (LC/MS; method C): retention time Tr (min)=3.70; [M+H]+=522; [M−H]−=520.

EXAMPLE 62

Synthesis of 4-[4-(6-fluoro-1H-benzimidazol-2-yl)-9H-carbazol-9-yl]-2-(2-fluoroethylamino)benzamide

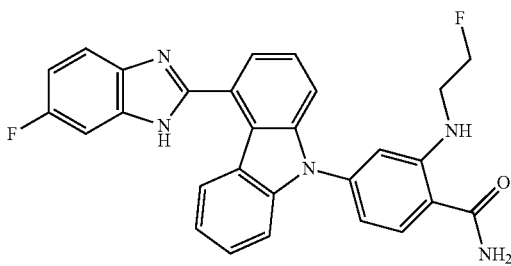

The process is carried out as in stage 3 of Example 3, but using 500 mg of 2-fluoro-4-[4-(6-fluoro-1H-benzimidazol-2-yl)-9H-carbazol-9-yl]benzonitrile, obtained according to stage 2 of Example 3, 493 mg of potassium carbonate, 1.78 g of 2-fluoroethylamine hydrochloride and 1.805 g of triethylamine in 5 ml of dimethyl sulphoxide. 2.26 ml of a 1M aqueous solution of sodium hydroxide, 2.19 ml of a 30% aqueous solution of hydrogen peroxide and 10 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 1 ml of ethyl acetate, 390 mg of 4-[4-(6-fluoro-1H-benzimidazol-2-yl)-9H-carbazol-9-yl]-2-(2-fluoroethylamino)benzamide are thus obtained in the form of a beige solid, the characteristics of which are the following:

1H NMR spectrum (400 MHz, DMSO-$d_6$, δ ppm): 3.51 (dq, J=27.9, 5.1 Hz, 2 H) 4.61 (dt, J=47.7, 4.6 Hz, 2H) 6.80 (dd, J=8.3, 2.0 Hz, 1H) 6.97 (d, J=2.0 Hz, 1H) 7.10-7.21 (m, 2H) 7.35 (broad s, 1H) 7.39 (dd, J=8.8, 2.4 Hz, 1H) 7.45-7.48 (m, 2 H) 7.57-7.66 (m, 3H) 7.84 (dd, J=8.8, 4.9 Hz, 1H) 7.94 (d, J=8.3 Hz, 1H) 8.03 (broad s, 1H) 8.58-8.70 (m, 2H) 13.08 (broad s, 1H).

Mass spectrum (LC/MS; method A): retention time Tr (min)=0.87; [M+H]+=482; [M−H]−=480.

EXAMPLE 63

Synthesis of 4-[4-(quinolin-3-yl)-9H-carbazol-9-yl]-2-(4-hydroxy-3(R,S)-methylbutylamino)benzamide

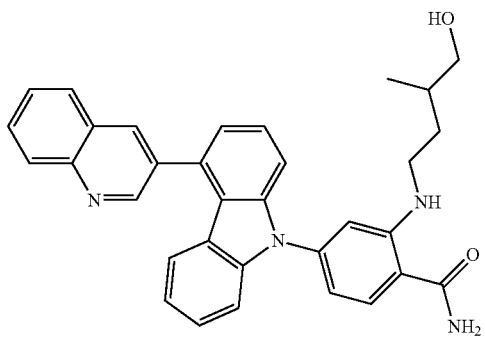

The process is carried out as in stage 2 of Example 3, but using 300 mg of 2-fluoro-4-[4-(quinolin-3-yl)-9H-carbazol-9-yl]benzonitrile, obtained according to stage 1 of Example 32, 301 mg of potassium carbonate and 1.50 g of 4-amino-2(R,S)-methylbutanol in 3 ml of dimethyl sulphoxide. 1.38 ml of a 1M aqueous solution of sodium hydroxide, 1.336 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 5 ml of ethyl acetate, 225 mg of 4-[4-(quinolin-3-yl)-9H-carbazol-9-yl]-2-(4-hydroxy-3(R,S)-methylbutylamino)benzamide are thus obtained in the form of a beige solid, the characteristics of which are the following:

1H NMR spectrum (400 MHz, DMSO-$d_6$, δ ppm): 0.87 (d, J=6.6 Hz, 3H) 1.31-1.43 (m, 1H) 1.58-1.68 (m, 1H) 1.70-1.80 (m, 1H) 3.10-3.22 (m, 2H) 3.24-3.28 (m, 2H) 4.44 (t, J=5.4 Hz, 1H) 6.77 (dd, J=8.3, 1.7 Hz, 1H) 6.88 (d, J=1.7 Hz, 1 H) 7.02 (t, J=7.6 Hz, 1H) 7.25 (d, J=8.1 Hz, 1H) 7.28 (broad s, 1H) 7.30 (dd, J=5.9, 2.2 Hz, 1H) 7.40 (t, J=7.8 Hz, 1H) 7.49 (d, J=8.3 Hz, 1H) 7.56-7.63 (m, 2H) 7.73 (t, J=7.6 Hz, 1H) 7.88 (t, J=8.3 Hz, 1H) 7.93 (d, J=8.3 Hz, 1H) 7.98 (broad s, 1H) 8.14 (d, J=8.1 Hz, 1H) 8.19 (d, J=8.6 Hz, 1H) 8.43 (t, J=5.0 Hz, 1H) 8.63 (d, J=2.0 Hz, 1H) 9.16 (d, J=2.0 Hz, 1H).

Mass spectrum (LC/MS; method A): retention time Tr (min)=1.07; [M+H]+=515; [M−H]−=513.

EXAMPLE 64

Synthesis of 2-(2-hydroxy-2-cyclopentylethylamino)-4-[4-(quinolin-3-yl)-9H-carbazol-9-yl]benzamide

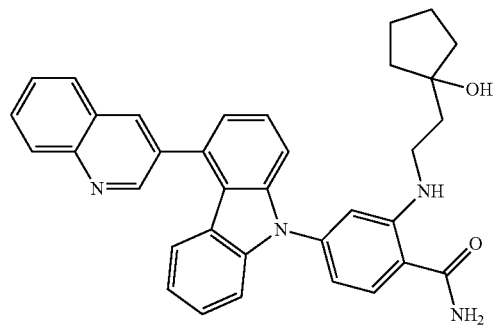

Stage 1: The process is carried out as in stage 2 of Example 31, but using 300 mg of 2-fluoro-4-[4-(quinolin-3-yl)-9H-carbazol-9-yl]benzonitrile, obtained according to stage 1 of Example 32, 375 mg of 1-(2-aminoethyl)cyclopentanol and 803 mg of potassium carbonate, at 140° C. for 3 hours in 10 ml of dimethylformamide. After treatment as in stage 2 of Example 31, 537 mg of a mixture are obtained, said mixture being used as it is in the subsequent stage and containing predominantly 2-(2-hydroxy-2-cyclopentylethylamino)-4-[4-(qui nolin-3-yl)-9H-carbazol-9-yl]benzonitrile, the characteristic of which is the following:

LC/MS (method C): retention time=5.87 min.

Stage 2: By carrying out the process as in stage 4 of Example 2, but using the crude compound obtained in the preceding stage, 2.054 ml of a 1N solution of sodium hydroxide and 1.89 ml of a 30% aqueous solution of hydrogen peroxide, for 1 hour at ambient temperature, in 13.6 ml of ethanol and 5.7 ml of dimethyl sulphoxide, there are obtained, after purification by flash chromatography on 30 g of silica, elution being carried out with a mixture of dichloromethane and ethanol (97/3 by volume), 246 mg of 2-(2-hydroxy-2-cyclopentylethylamino)-4-[4-(quinolin-3-yl)-9H-carbazol-9-yl]benzamide in the form of a beige powder, the characteristics of which are the following:

1H NMR spectrum (400 MHz, DMSO-$d_6$, δ ppm): 1.40-1.71 (m, 8H) 1.81-1.85 (m, 2H) 3.21-3.29 (m, 2H) 4.14 (s, 1H) 6.76 (dd, J=8.3, 2.0 Hz, 1H) 6.88 (d, J=1.7 Hz, 1H) 7.03 (t, J=8.1 Hz, 1H) 7.25 (d, J=7.8 Hz, 1H) 7.28 (broad s, 1H) 7.30 (dd, J=6.4, 2.0 Hz, 1H) 7.40 (t, J=8.3 Hz, 1H) 7.49 (d, J=8.1 Hz, 1H) 7.55-7.62 (m, 2H) 7.73 (t, J=8.1 Hz, 1H) 7.86-7.91 (m, 1H) 7.92 (d, J=8.3 Hz, 1H) 7.97 (broad s, 1H) 8.13 (d, J=8.3 Hz, 1H) 8.19 (d, J=8.3 Hz, 1H) 8.42 (t, J=5.4 Hz, 1H) 8.63 (d, J=2.2 Hz, 1H) 9.16 (d, J=2.4 Hz, 1H).

Mass spectrum (LC/MS; method A): retention time Tr (min)=1.3; m/z=541 [M+H]+; m/z=539 [M−H]−.

EXAMPLE 65

Synthesis of 2-[2-(4-hydroxy-1-methylpiperidin-4-yl)ethylamino]-4-[4-(quinolin-3-yl)-9H-carbazol-9-yl]benzamide

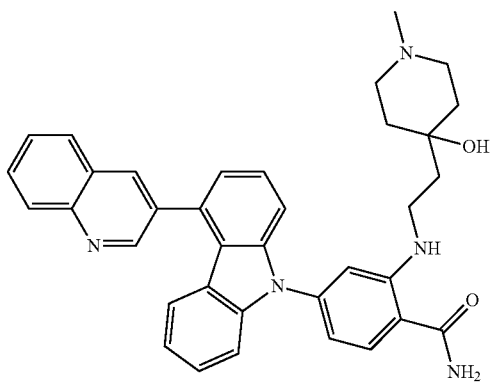

Stage 1: The process is carried out as in stage 2 of Example 31, but using 300 mg of 2-fluoro-4-[4-(quinolin-3-yl)-9H-carbazol-9-yl]benzonitrile, obtained according to stage 1 of Example 31, 460 mg of 4-(2-aminoethyl)-1-methylpiperidin-4-ol and 803 mg of potassium carbonate, at 140° C. for 3 hours in 10 ml of dimethylformamide. After treatment as in stage 2 of Example 31, 487 mg of a mixture are obtained, said mixture being used as it is in the subsequent stage and containing predominantly 2-[2-(4-hydroxy-1-methylpiperidin-4-yl)ethylamino]-4-[4-(quinolin-3-yl)-9H-carbazol-9-yl]benzonitrile, the characteristic of which is the following:

LC/MS (method C): retention time=3.77 min.

Stage 2: By carrying out the process as in stage 4 of Example 2, but using the crude compound obtained in the preceding stage, 1.768 ml of a 1N solution of sodium hydroxide and 1.625 ml of a 30% aqueous solution of hydrogen peroxide, for 1 hour at ambient temperature, in 11.7 ml of ethanol and 4.9 ml of dimethyl sulphoxide, there are obtained, after purification by flash chromatography on 25 g of silica, elution being carried out with mixtures of dichloromethane and 7M ammonia in methanol (96/4 then 90/10 then 80/20 by volume), 130 mg of 2-[2-(4-hydroxy-1-methylpiperidin-4-yl)ethylamino]-4-[4-(quinolin-3-yl)-9H-carbazol-9-yl]benzamide in the form of a white powder, the characteristics of which are the following:

1H NMR spectrum (400 MHz, DMSO-$d_6$, δ ppm): 1.44-1.52 (m, 4H) 1.67-1.75 (m, 2H) 2.10 (s, 3H) 2.17-2.25 (m, 2H) 2.28-2.36 (m, 2H) 3.18-3.26 (m, 2H) 4.11 (s, 1H) 6.76 (dd, J=8.3, 2.0 Hz, 1H) 6.89 (d, J=2.0 Hz, 1H) 7.02 (t, J=8.1 Hz, 1H) 7.25 (d, J=8.1 Hz, 1H) 7.28 (broad s, 1H) 7.30 (dd, J=6.5, 1.6 Hz, 1H) 7.40 (t, J=8.2 Hz, 1H) 7.48 (d, J=8.3 Hz, 1H) 7.54-7.63 (m, 2H) 7.73 (t, J=8.1 Hz, 1H) 7.85-7.91 (m, 1H) 7.92 (d, J=8.3 Hz, 1H) 7.98 (broad s, 1H) 8.13 (d, J=7.8 Hz, 1 H) 8.19 (d, J=8.3 Hz, 1H) 8.38 (t, J=5.1 Hz, 1H) 8.63 (d, J=2.0 Hz, 1H) 9.16 (d, J=2.2 Hz, 1H).

Mass spectrum (LC/MS; method A): retention time Tr (min)=0.81; m/z=570 [M+H]+; m/z=568 [M−H]−.

EXAMPLE 66

Synthesis of 2-[(3-hydroxypropyl)amino]-4-[4-(5-methoxypyridin-3-yl)-9H-carbazol-9-yl]benzamide

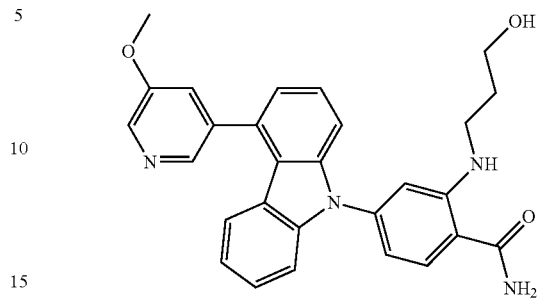

0.85 g of potassium carbonate and 3.14 ml of 3-amino-1-propanol are successively added to a solution of 0.81 g of 2-fluoro-4-[4-(5-methoxypyridin-3-yl)-9H-carbazol-9-yl]benzonitrile obtained in stage 2 of Example 27, in 7 ml of dimethyl sulphoxide. The reaction mixture is heated at 90° C. for 1 hour and 20 minutes in a microwave, and then 20.9 ml of ethanol are added, followed by 4 ml of a 1N solution of sodium hydroxide and 4 ml of 30% aqueous hydrogen peroxide. The reaction mixture is stirred at ambient temperature for 2 hours and then diluted with distilled water. The aqueous phase is extracted twice with ethyl acetate and the combined organic phases are washed with water and a saturated solution of sodium chloride, dried over magnesium sulphate and concentrated under reduced pressure. The white solid obtained is purified by trituration in diisopropyl ether, so as to give 0.45 g of 2-[(3-hydroxypropyl)amino]-4-[4-(5-methoxypyridin-3-yl)-9H-carbazol-9-yl]benzamide in the form of a white solid, the characteristics of which are the following:

Melting point (Kofler bench): 198° C.

1H NMR spectrum (400 MHz, DMSO-d6): 1.73 (m, 2H) 3.19 (m, 2 H) 3.50 (m, 2H) 3.91 (s, 3H) 4.48 (t, J=5.3 Hz, 1H) 6.74 (dd, J=8.4, 2.0 Hz, 1H) 6.84 (d, J=2.0 Hz, 1H) 7.09 (m, 1H) 7.19 (m, 1H) 7.28 (broad m, 1H) 7.34 (d, J=8.2 Hz, 1H) 7.41 (m, 1H) 7.47 (d, J=8.1 Hz, 1H) 7.49-7.57 (m, 2H) 7.61 (dd, J=2.9, 1.9 Hz, 1H) 7.91 (d, J=8.3 Hz, 1H) 7.98 (broad m, 1H) 8.41 (d, J=1.9 Hz, 1H) 8.44 (t, J=5.3 Hz, 1H) 8.48 (d, J=2.9 Hz, 1H)

Mass spectrum (LC/MS; method A): retention time Tr (min)=0.84; m/z=467 [M+H]+.

EXAMPLE 67

Synthesis of 4-{4-[5-(benzyloxy)pyridin-3-yl]-9H-carbazol-9-yl}-2-[(4-trans-hydroxycyclohexyl)amino]benzamide

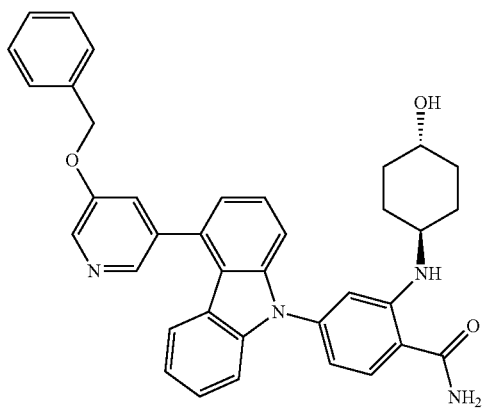

Stage 1: 1.91 g of 3-bromo-5-benzyloxypyridine, under argon, are added to a solution of 2 ml of triisopropyl borate in a mixture of 12 ml of toluene and 3 ml of tetrahydrofuran. The solution is cooled to −70° C. and then 5.42 ml of n-butyl-lithium (1.6N in hexane) are added dropwise. The reaction medium is stirred for 3 hours, and brought back to −20° C., and 7.23 ml of 2N hydrochloric acid are added dropwise. The reaction mixture is left to return to ambient temperature and poured into distilled water. The aqueous phase is extracted with ethyl acetate, and then the organic phase is washed with a saturated solution of sodium chloride, dried over magnesium sulphate and concentrated under reduced pressure, so as to give 0.21 g of [5-(benzyloxy)pyridin-3-yl]boronic acid in the form of a white powder (adapted from Wenjie Li et al. *An Improved Protocol for the Preparation of* 3-*Pyridyl- and Some Arylboronic Acids J. Org. Chem.*, (2002), 67(15), 5394-5397), the characteristics of which are the following:

Mass spectrum (LC/MS; method A): retention time Tr (min)=0.44; m/z=230 [M+H]+; 228 [M+H]−.

Stage 2: 1.63 g of [5-(benzyloxy)pyridin-3-yl]boronic acid, 6.4 g of caesium carbonate and 0.182 g of 1,1′-bis(diphenylphosphino)ferrocenepalladium(II) dichloride as a complex with dichloromethane (1/1) [PdCl$_2$(dppf).CH$_2$Cl$_2$] are successively added, under argon, to a solution of 1.57 g of 4-trifluoromethanesulphonyloxycarbazole, obtained in stage 1 of Example 1, in a mixture of 71 ml of dioxane and 24 ml of water. The reaction mixture is refluxed for 5 hours, filtered through celite and concentrated under reduced pressure. The residue is subsequently purified by silica gel chromatography, elution being carried out with a mixture of cyclohexane and ethyl acetate (80/20 by volume), so as to give 1.4 g of 4-[5-(benzyloxy)pyridin-3-yl]-9H-carbazole in the form of a pale yellow oil, the characteristics of which are the following:

1H NMR spectrum (400 MHz, δ in ppm, DMSO-d6): 5.27 (s, 2H) 6.94 (m, 1 H) 7.05 (dd, J=7.3, 1.1 Hz, 1H) 7.28 (d, J=8.2 Hz, 1H) 7.31-7.53 (m, 8H) 7.56 (dd, J=8.1, 1.1 Hz, 1H) 7.66 (dd, J=3.0, 1.9 Hz, 1H) 8.39 (d, J=1.9 Hz, 1H) 8.50 (d, J=3.0 Hz, 1H) 11.51 (broad s, 1H).

Mass spectrum (LC/MS; method A): retention time Tr (min)=1.05; m/z=351 [M+H]+.

Stage 3: 1.08 g of 4-bromo-2-fluorobenzonitrile, 4.48 g of caesium carbonate, 0.25 g of (9,9-dimethyl-9H-xanthene-4,5-diyl)bis(diphenylphosphane) and 0.08 g of palladium acetate are successively added, under argon, to a solution of 1.27 g of 4-[5-(benzyloxy)pyridin-3-yl]-9H-carbazole in 100 ml of dioxane. The reaction mixture is refluxed for 2 and a half hours, cooled to ambient temperature, filtered through celite and concentrated under reduced pressure. The residue is purified by silica gel chromatography, elution being carried out with a mixture of cyclohexane and ethyl acetate (80/20 by volume), so as to give 1.1 g of 4-{4-[5-(benzyloxy)pyridin-3-yl]-9H-carbazol-9-yl}-2-fluorobenzonitrile in the form of a colourless oil, the characteristics of which are the following:

1H NMR spectrum (400 MHz, δ in ppm, DMSO-d6): 5.29 (s, 2H) 7.12 (m, 1 H) 7.24 (dd, J=7.0, 1.3 Hz, 1H) 7.29 (d, J=8.1 Hz, 1H) 7.32-7.62 (m, 9H) 7.68 (dd, J=2.9, 1.9 Hz, 1H) 7.78 (dd, J=8.4, 2.1 Hz, 1H) 8.01 (dd, =10.4, 2.1 Hz, 1H) 8.25 (m, 1H) 8.39 (d, J=1.9 Hz, 1H) 8.55 (d, J=2.9 Hz, 1H).

Mass spectrum (LC/MS; method A): retention time Tr (min)=1.22; m/z=470 [M+H]+.

Stage 4: 0.47 g of potassium carbonate and 2.6 g (22 mmol) of 4-trans-aminocyclohexanol are successively added to a solution of 0.55 g of 4-{4-[5-(benzyloxy)pyridin-3-yl]-9H-carbazol-9-yl}-2-fluorobenzonitrile in 6 ml of dimethyl sulphoxide. The reaction mixture is heated at 90° C. for 1 hour 20 minutes in a microwave, and then 11.5 ml of ethanol are added, followed by 2.2 ml of a 1N solution of sodium hydroxide and 2.2 ml of 30% aqueous hydrogen peroxide. The reaction mixture is stirred at ambient temperature for 1 hour and then diluted with distilled water. The aquoeus phase is extracted twice with ethyl acetate and the combined organic phases are washed with water and a saturated solution of sodium chloride, dried over magnesium sulphate and filtered. The filtrate is concentrated under reduced pressure and the white solid obtained is purified by silica gel chromatography, elution being carried out with a mixture of dichloromethane and methanol (97/3), so as to give 0.3 g of 4-{4-[5-(benzyloxy)pyridin-3-yl]-9H-carbazol-9-yl}-2-[(4-trans-hydroxycyclohexyl)amino]benzamide in the form of a white solid, the characteristics of which are the following:

1H NMR spectrum (400 MHz, δ in ppm, DMSO-d6): 1.24 (m, 4H) 1.78 (m, 2 H) 1.99 (m, 2H) 3.33 (m partially masked, 1H) 3.47 (m, 1H) 4.47 (d, J=4.3 Hz, 1H) 5.29 (s, 2H) 6.69 (dd, J=8.4, 2.0 Hz, 1H) 6.87 (d, J=2.0 Hz, 1H) 7.06 (m, 1H) 7.17 (dd, J=7.2, 1.1 Hz, 1H) 7.30-7.58 (m, 11H) 7.69 (dd, J=2.9, 1.9 Hz, 1H) 7.89 (d, J=8.5 Hz, 1H) 7.96 (broad m, 1H) 8.41 (d, J=1.9 Hz, 1H) 8.45 (d, J=8.4 Hz, 1H) 8.55 (d, J=2.9 Hz, 1H).

Mass spectrum (LC/MS; method A): retention time Tr (min)=1.06; m/z=583 [M+H]+.

EXAMPLE 68

Synthesis of 4-{4-[5-(benzyloxy)pyridin-3-yl]-9H-carbazol-9-yl}-2-[(3-hydroxypropyl)amino]benzamide

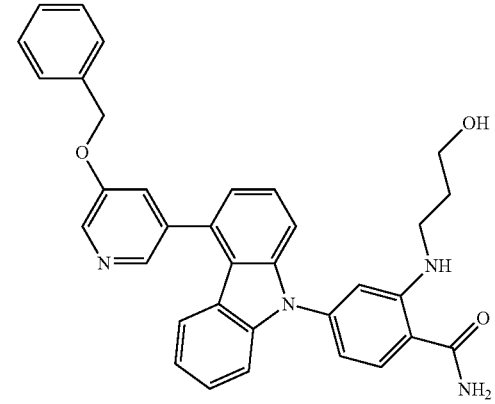

0.47 g of potassium carbonate and 1.7 g of 3-amino-1-propanol are successively added to a solution of 0.55 g of 4-{4-[5-(benzyloxy)pyridin-3-yl]-9H-carbazol-9-yl}-2-fluorobenzonitrile, obtained in stage 3 of Example 67, in 6 ml of dimethyl sulphoxide. The reaction mixture is heated at 90° C. for 1 hour 20 minutes in a microwave, and then 11.5 ml of ethanol are added, followed by 2.2 ml of a 1N solution of sodium hydroxide and 2.2 ml of 30% aqueous hydrogen peroxide. The reaction mixture is stirred at ambient temperature for 1 hour and then diluted with distilled water. The aqueous phase is extracted twice with ethyl acetate and the combined organic phases are washed with water and a saturated solution of sodium chloride, dried over magnesium sulphate and concentrated under reduced pressure, and the residue is triturated with dichloromethane and diisopropyl ether, so as to give 0.29 g of 4-{4-[5-(benzyloxy)pyridin-3-yl]-9H-carbazol-9-yl}-2-[(3-hydroxypropyl)amino]benzamide in the form of a white solid, the characteristics of which are the following:

Melting point (Kofler bench): 168° C.

1H NMR spectrum (400 MHz, δ in ppm, DMSO-d6): 1.73 (m, 2H) 3.19 (m, 2 H) 3.50 (m, 2H) 4.48 (t, J=5.2 Hz, 1H) 5.29 (s, 2H) 6.74 (dd, J=8.4, 2.0 Hz, 1H) 6.84 (d, J=2.0 Hz, 1H) 7.06 (m, 1H) 7.17 (m, 1H) 7.20-7.57 (m, 11H) 7.70 (dd, J=2.9, 1.8 Hz, 1H) 7.91 (d, J=8.4 Hz, 1H) 7.96 (broad m, 1H) 8.41 (d, J=1.8 Hz, 1 H) 8.44 (t, J=5.4 Hz, 1H) 8.54 (d, J=2.9 Hz, 1H).

Mass spectrum (LC/MS; method A): retention time Tr (min)=1.05; m/z=543 [M+H]+; 541 [M−H]−.

EXAMPLE 69

Synthesis of 2-[(3-hydroxypropyl)amino]-4-{4-[6-(trifluoromethyl)pyridin-3-yl]-9H-carbazol-9-yl}benzamide

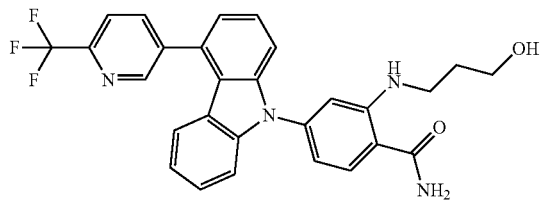

Stage 1: 0.96 g of [2-trifluoromethylpyridin-5-yl]boronic acid, 4.55 g of caesium carbonate and 0.13 g of 1,1'-bis(diphenylphosphino)ferrocenepalladium(II) dichloride as a complex with dichloromethane (1/1) [PdCl₂(dppf).CH₂Cl₂] are successively added, under argon, to a solution of 1.1 g of 4-trifluoromethanesulphonyloxycarbazole, obtained in stage 1 of Example 1, in a mixture of 50 ml of dioxane and 17 ml of water. The reaction mixture is refluxed for 5 hours, filtered through celite and concentrated under reduced pressure. The residue is subsequently purified by silica gel chromatography, elution being carried out with a mixture of cyclohexane and ethyl acetate (85/15 by volume) so as to give 0.54 g of 4-[6-(trifluoromethyl)pyridin-3-yl]-9H-carbazole in the form of a pale yellow oil, the characteristics of which are the following:

1H NMR spectrum (400 MHz, δ in ppm, DMSO-d6): 6.98 (d, J=7.1 Hz, 1H) 7.11 (dd, J=7.1, 1.0 Hz, 1H) 7.26 (d, J=8.1 Hz, 1H) 7.37 (t, J=8.2 Hz, 1H) 7.49-7.57 (m, 2H) 7.63 (dd, J=8.1, 1.0 Hz, 1H) 8.12 (d, J=7.8 Hz, 1H) 8.34 (dd, J=8.1, 1.7 Hz, 1H) 9.00 (d, J=2.0 Hz, 1H) 11.59 (broad s, 1H).

Mass spectrum (LC/MS; method A): retention time Tr (min)=1.11; m/z=313 [M+H]+; 311 [M−H]−.

Stage 2: 0.52 g of 4-bromo-2-fluorobenzonitrile, 2.14 g of caesium carbonate, 0.12 g of (9,9-dimethyl-9H-xanthene-4,5-diyl)bis(diphenylphosphane) and 39 mg of palladium acetate are successively added, under argon, to a solution of 0.54 g of 4-[6-(trifluoromethyl)pyridin-3-yl]-9H-carbazole in 50 ml of dioxane. The reaction mixture is refluxed for 6 hours, cooled to ambient temperature, filtered through celite and concentrated under reduced pressure. The residue is purified by silica gel chromatography, elution being carried out with a mixture of cyclohexane and ethyl acetate (96/4 by volume) so as to give 0.37 g of 2-fluoro-4-{4-[6-(trifluoromethyl)pyridin-3-yl]-9H-carbazol-9-yl}benzonitrile in the form of a white powder, the characteristics of which are the following:

Mass spectrum (LC/MS; method B): retention time Tr (min)=5.44; m/z=432 [M+H]+.

Stage 3: 0.17 g of potassium carbonate and 0.64 ml of 3-amino-1-propanol are successively added to a solution of 0.18 g of 2-fluoro-4-{4-[6-(trifluoromethyl)pyridin-3-yl]-9H-carbazol-9-yl}benzonitrile in 2 ml of dimethyl sulphoxide. The reaction mixture is heated at 90° C. for 1 hour 20 minutes in a microwave, and then 4.2 ml of ethanol are added, followed by 0.8 ml of a 1N solution of sodium hydroxide and 0.8 ml of 30% aqueous hydrogen peroxide. The reaction mixture is stirred at ambient temperature for 2 hours and then diluted with distilled water. The aqueous phase is extracted twice with ethyl acetate and the combined organic phases are washed with water and a saturated solution of sodium chloride, dried over magnesium sulphate and concentrated under reduced pressure. The white solid obtained is purified by silica gel chromatography, elution being carried out with a mixture of dichloromethane, acetonitrile and methanol (96/2/2 by volume) so as to give 24 mg of 2-[(3-hydroxypropyl)amino]-4-{4-[6-(trifluoromethyl)pyridin-3-yl]-9H-carbazol-9-yl}benzamide in the form of a white solid, the characteristics of which are the following Melting point (Kofler bench): 180° C.

1H NMR spectrum (400 MHz, δ in ppm, DMSO-d6): 1.73 (quin, J=6.5 Hz, 2H) 3.15-3.22 (m, 2H) 3.50 (d, J=6.1 Hz, 2H) 4.48 (t, J=5.1 Hz, 1H) 6.74 (dd, J=8.3, 2.0 Hz, 1H) 6.85 (d, J=2.0 Hz, 1H) 7.07-7.13 (m, 1H) 7.24 (dd, J=5.3, 3.1 Hz, 1H) 7.25 (broad s, 1H) 7.29 (d, J=8.1 Hz, 1H) 7.39-7.50 (m, 2H) 7.56-7.59 (m, 2H) 7.91 (d, J=8.3 Hz, 1H) 7.97 (broad s, 1H) 8.15 (d, J=7.6 Hz, 1H) 8.38 (dd, J=7.9, 1.8 Hz, 1H) 8.45 (t, J=5.0 Hz, 1H) 9.04 (d, J=2.0 Hz, 1H).

Mass spectrum (LC/MS; method A): retention time Tr (min)=1.09; m/z=505 [M+H]+; 503 [M+H]−.

EXAMPLE 70

Synthesis of 4-[4-(6-fluoro-1H-benzimidazol-2-yl)-9H-carbazol-9-yl]-2-[2-(4-hydroxy-1-methylpiperidin-4-yl)ethylamino]benzamide

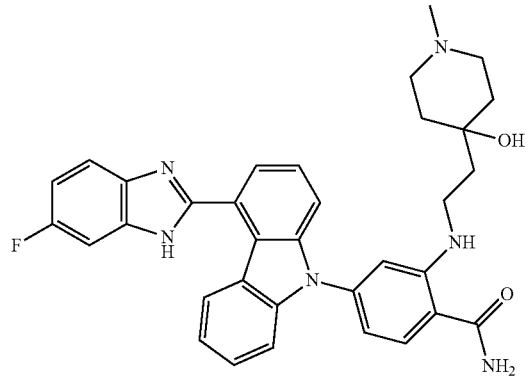

Stage 1: The process is carried out as in stage 2 of Example 31, but using 300 mg of 2-fluoro-4-[4-(6-fluoro-1H-benzimidazol-9-yl)-9H-carbazol-9-yl]benzonitrile, obtained according to stage 2 of Example 3, 452 mg of 4-(2-aminoethyl)-1-methylpiperidin-4-ol and 789 mg of potassium carbonate, at 140° C. for 3 hours in 10 ml of dimethylformamide. After treatment as in stage 2 of Example 31, 527 mg of a mixture are obtained, said mixture being used as it is in the subsequent stage and containing predominantly 4-[4-(6-fluoro-1H-benzimidazol-2-yl)-9H-carbazol-9-yl]-2-[2-(4-hydroxy-1-methylpiperidin-4-yl)ethylamino]benzonitrile, the characteristic of which is the following:

LC/MS (method C): retention time=3.41 min.

Stage 2: By carrying out the process as in stage 4 of Example 2, using the crude compound obtained in the preceding stage, 1.886 ml of a 1N solution of sodium hydroxide and 1.733 ml of a 30% aqueous solution of hydrogen peroxide, for 1 hour at ambient temperature, in 13.3 ml of ethanol and 5.6 ml of dimethyl sulphoxide, there are obtained, after purification by flash chromatography on 25 g of silica, elution being carried out with a mixture of dichloromethane and 7M ammonia in methanol (90/10 by volume), 80 mg of 4-[4-(6-fluoro-1H-benzimidazol-2-yl)-9H-carbazol-9-yl]-2-[2-(4-hydroxy-1-methylpiperidin-4-yl)ethylamino]benzamide in the form of a white powder, the characteristics of which are the following:

1H NMR spectrum (400 MHz, DMSO-$d_6$, δ ppm): 1.43-1.52 (m, 4H) 1.70 (t, J=7.8 Hz, 2H) 2.10 (s, 3H) 2.16-2.26 (m, 2H) 2.28-2.37 (m, 2H) 3.18-3.25 (m, 2 H) 4.11 (s, 1H) 6.74 (dd, J=8.3, 2.0 Hz, 1H) 6.87 (d, J=2.0 Hz, 1H) 7.09-7.22 (m, 2 H) 7.24-7.44 (m, 1H) 7.46 (d, J=3.9 Hz, 2H) 7.57-7.68 (m, 4H) 7.78-8.02 (m, 2 H) 7.91 (d, J=8.3 Hz, 1H) 8.38 (t, J=5.1 Hz, 1H) 8.63 (broad s, 1H) 13.08 (broad s, 1H).

Mass spectrum (LC/MS; method C): retention time Tr (min)=2.92; m/z=577 [M+H]+; m/z=575 [M−H]−.

EXAMPLE 71

Synthesis of 4-[4-(6-fluoro-1H-benzimidazol-2-yl)-9H-carbazol-9-yl]-2-[2-(1-hydroxycyclopentyl)ethylamino]benzamide

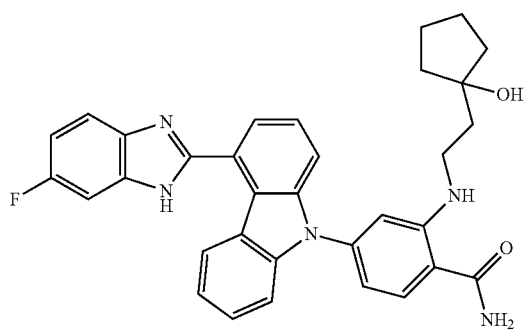

Stage 1: The process is carried out as in stage 2 of Example 31, but using 300 mg of 2-fluoro-4-[4-(6-fluoro-1H-benzimidazol-9-yl)-9H-carbazol-9-yl]benzonitrile, obtained according to stage 2 of Example 3, 92.5 mg of 1-(2-aminoethyl)cyclopentanol and 789 mg of potassium carbonate, at 140° C. for 3 hours in 10 ml of dimethylformamide. After treatment as in stage 2 of Example 31, 581 mg of a mixture are obtained, said mixture being used as it is in the subsequent stage and containing predominantly 4-[4-(6-fluoro-1H-benzimidazol-2-yl)-9H-carbazol-9-yl]-2-[2-(1-hydroxycyclopentyl)ethylamino]benzonitrile, the characteristic of which is the following:

LC/MS (method C): retention time=4.82 min.

Stage 2: By carrying out the process as in stage 4 of Example 2, but using the crude compound obtained in the preceding stage, 2.12 ml of a 1N solution of sodium hydroxide and 1.95 ml of a 30% aqueous solution of hydrogen peroxide, for 1 hour at ambient temperature, in 15 ml of ethanol and 6.3 ml of dimethyl sulphoxide, there are obtained, after purification by flash chromatography on 25 g of silica, elution being carried out with a mixture of dichloromethane and ethanol (94/6 by volume), 112 mg of 4-[4-(6-fluoro-1H-benzimidazol-2-yl)-9H-carbazol-9-yl]-2,2-(1-hydroxycyclopentyl)ethylamino]benzamide in the form of a white powder, the characteristics of which are the following:

1H NMR spectrum (400 MHz, DMSO-$d_6$, δ ppm): 1.39-1.70 (m, 8H) 1.82 (t, J=7.6 Hz, 2H) 3.20-3.28 (m, 2H) 4.12 (s, 1H) 6.74 (dd, J=8.3, 2.0 Hz, 1H) 6.86 (d, J=2.0 Hz, 1H) 7.10-7.22 (m, 2H) 7.23-7.42 (m, 1H) 7.46 (d, J=3.4 Hz, 2H) 7.57-7.67 (m, 4H) 7.83 (broad s, 1H) 7.92 (d, J=8.3 Hz, 1H) 7.96 (broad s, 1H) 8.42 (t, J=5.3 Hz, 1H) 8.62 (broad s, 1H) 13.08 (broad s, 1H).

Mass spectrum (LC/MS; method C): retention time Tr (min)=3.96; m/z=548 [M+H]+; m/z=546 [M−H]−.

EXAMPLE 72

Synthesis of 2-(3-hydroxy-3-methylbutylamino)-4-[4-(quinolin-3-yl)-9H-carbazol-9-yl]benzamide

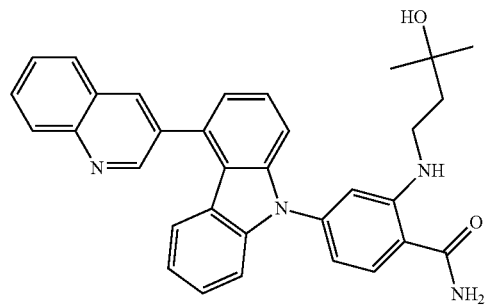

The process is carried out as in stage 2 of Example 3, but using 153 mg of 2-fluoro-4-[4-(quinolin-3-yl)-9H-carbazol-9-yl]benzonitrile, obtained according to stage 1 of Example 32, 153.4 mg of potassium carbonate, 1.033 g of 5-aminopentan-2-ol and 0.749 g of triethylamine in 2 ml of dimethyl sulphoxide. 0.703 ml of a 1M aqueous solution of sodium hydroxide, 0.681 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 5 ml of ethyl acetate, 165 mg of 2-(3-hydroxy-3-methylbutylamino)-4-[4-(quinolin-3-yl)-9H-carbazol-9-yl]benzamide are thus obtained in the form of a beige solid, the characteristics of which are the following:

1H NMR spectrum (400 MHz, DMSO-$d_6$, δ ppm): 1.11 (s, 6H) 1.66-1.77 (m, 2H) 3.16-3.25 (m, 2H) 4.28 (s, 1H) 6.76 (d, J=7.8 Hz, 1H) 6.88 (s, 1H) 7.02 (t, J=7.3 Hz, 1H) 7.25 (d, J=7.6 Hz, 1H) 7.28 (broad s, 1H) 7.30 (d, J=5.6 Hz, 1H) 7.37-7.43 (m, 1H) 7.49 (d, J=7.8 Hz, 1H) 7.55-7.62 (m, 2H) 7.73 (t, J=7.1 Hz, 1

H) 7.85-7.94 (m, 2H) 7.97 (broad s, 1H) 8.14 (d, J=8.8 Hz, 1H) 8.19 (d, J=8.1 Hz, 1H) 8.39 (t, J=4.4 Hz, 1H) 8.63 (s, 1H) 9.16 (s, 1H).

Mass spectrum (LC/MS; method A): retention time Tr (min)=1.06; m/z=515 [M+H]+; m/z=513 [M−H]−.

EXAMPLE 73

Synthesis of 2-[(4-trans-hydroxycyclohexyl)amino]-4-[4-(5-hydroxypyridin-3-yl)-9H-carbazol-9-yl]benzamide

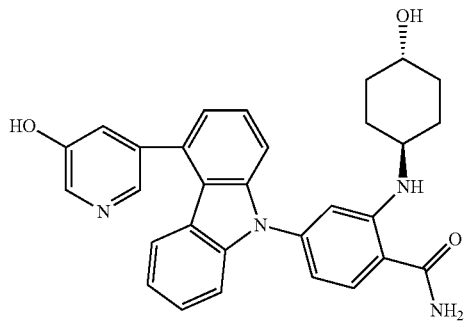

0.19 g of 4-{4-[5-(benzyloxy)pyridin-3-yl]-9H-carbazol-9-yl}-2-[(4-trans-hydroxycyclohexyl)amino]benzamide, obtained in stage 4 of Example 67, and 0.16 g of ammonium formate are successively added to a suspension of 5.2 mg of palladium-on-charcoal, 10%, in 5 ml of methanol. The reaction mixture is refluxed for 2 hours and then filtered through celite and washed with methanol. The filtrate is concentrated under reduced pressure and purified by silica gel chromatography, elution being carried out with a mixture of dichloromethane and methanol (95/5 by volume) so as to give 94 mg of 2-[(4-trans-hydroxycyclohexyl)amino]-4-[4-(5-hydroxypyridin-3-yl)-9H-carbazol-9-yl]benzamide in the form of a white solid, the characteristics of which are the following:

1H NMR spectrum (400 MHz, δ in ppm, DMSO-d6): 1.15-1.32 (m, 4H) 1.78 (br. s., 2H) 1.99 (broad s, 2H) 3.33 (broad s, 1H) 3.47 (broad s, 1H) 4.47 (d, J=3.9 Hz, 1H) 6.70 (dd, J=8.3, 2.0 Hz, 1H) 6.89 (d, J=1.7 Hz, 1H) 7.09 (ddd, J=8.1, 5.7, 2.6 Hz, 1H) 7.14 (d, J=7.1 Hz, 1H) 7.26 (broad s, 1H) 7.33-7.55 (m, 6H) 7.89 (d, J=8.3 Hz, 1H) 7.96 (broad s, 1H) 8.24 (s, 1H) 8.30 (d, J=2.2 Hz, 1H) 8.45 (d, J=7.6 Hz, 1H) 10.41 (broad s, 1H).

Mass spectrum (LC/MS; method B): retention time Tr (min)=3.06; m/z=493 [M+H]+; 491 [M+H]−.

EXAMPLE 74

Synthesis of 2-[(4-trans-hydroxycyclohexyl)amino]-4-{4-[6-(trifluoromethyl)pyridin-3-yl]-9H-carbazol-9-yl}benzamide

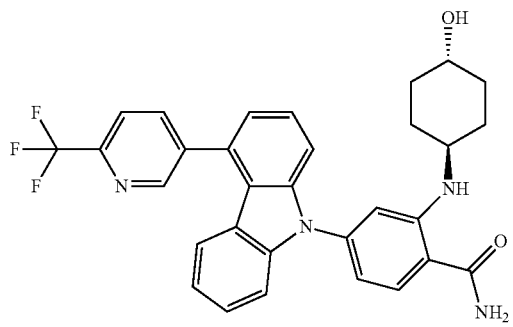

0.17 g of potassium carbonate and 0.96 g of 4-trans-aminocyclohexanol are successively added to a solution of 0.18 g of 2-fluoro-4-{4-[6-(trifluoromethyl)pyridin-3-yl]-9H-car-bazol-9-yl}benzonitrile, obtained in stage 2 of Example 69, in 2 ml of dimethyl sulphoxide. The reaction mixture is heated at 90° C. for 1 hour 20 minutes in a microwave, and then 4.2 ml of ethanol are added, followed by 0.8 ml of a 1N solution of sodium hydroxide and 0.8 ml of 30% aqueous hydrogen peroxide. The reaction mixture is stirred at ambient temperature for 2 hours and then diluted with distilled water. The aqueous phase is extracted twice with ethyl acetate and the combined organic phases are washed with water and a saturated solution of sodium chloride, dried over magnesium sulphate and concentrated under reduced pressure. The white solid obtained is purified by silica gel chromatography, elution being carried out with a mixture of dichloromethane, acetonitrile and methanol (95/2.5/2.5 by volume) so as to give 21 mg of 2-[(4-trans-hydroxycyclohexyl)amino]-4-{4-[6-(trifluoromethyl)pyridin-3-yl]-9H-carbazol-9-yl}benzamide in the form of a white solid, the characteristics of which are the following:

1H NMR spectrum (400 MHz, δ in ppm, DMSO-d6): 1.17-1.32 (m, 4H) 1.78 (broad s, 2H) 1.99 (br. s., 2H) 3.32 (broad s, 1H) 3.47 (br. s., 1H) 4.47 (d, J=4.4 Hz, 1H) 6.70 (dd, J=8.3, 2.0 Hz, 1H) 6.89 (d, J=1.7 Hz, 1H) 7.11 (ddd, J=8.1, 4.9, 3.2 Hz, 1H) 7.24 (dd, J=7.1, 1.2 Hz, 1H) 7.27 (broad s, 1H) 7.30 (d, J=8.1 Hz, 1H) 7.42-7.46 (m, 2H) 7.50-7.62 (m, 2H) 7.90 (d, J=8.3 Hz, 1H) 7.97 (broad s, 1H) 8.16 (d, J=8.3 Hz, 1H) 8.38 (dd, J=7.9, 1.8 Hz, 1H) 8.45 (d, J=7.6 Hz, 1H) 9.04 (d, J=2.0 Hz, 1H).

Mass spectrum (LC/MS; method A): retention time Tr (min)=1.10; m/z=545 [M+H]+; 543 [M+H]−.

EXAMPLE 75

Synthesis of 4-[4-(6-fluoro-1H-benzimidazol-2-yl)-9H-carbazol-9-yl]-2-(3-fluoropropylamino)benzamide

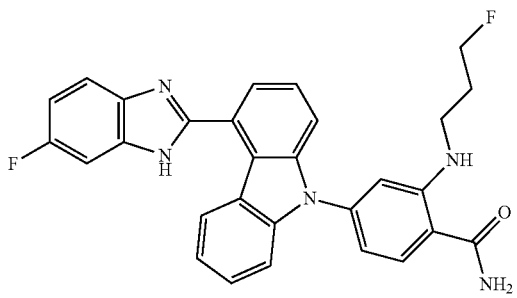

The process is carried out as in stage 3 of Example 3, but using 200 mg of 2-fluoro-4-[4-(6-fluoro-1H-benzimidazol-2-yl)-carbazol-9-yl]benzonitrile, obtained according to stage 2 of Example 3, 197.3 mg of potassium carbonate, 1.081 g of 3-fluoropropylamine hydrochloride and 0.963 g of triethylamine in 2 ml of dimethyl sulphoxide. 0.904 ml of a 1M aqueous solution of sodium hydroxide, 0.875 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 2 ml of ethyl acetate, 175 mg of 4-[4-(6-fluoro-1H-benzimidazol-2-yl)-carbazol-9-yl]-2-(3-fluoropropylamino)benzamide are thus obtained in the form of an off-white solid, the characteristics of which are the following:

Mass spectrum (LC/MS; method A): retention time Tr (min)=0.92; m/z=496 [M+H]+; m/z=494 [M−H]−.

EXAMPLE 76

Synthesis of 2-(3-fluoropropylamino)-4-[4-(quinolin-3-yl)-9H-carbazol-9-yl]benzamide

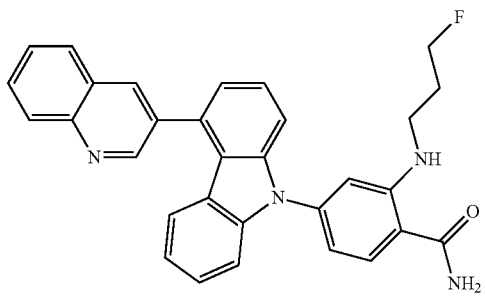

The process is carried out as in stage 3 of Example 3, but using 196.8 mg of 2-fluoro-4-[4-(quinolin-3-yl)-9H-carbazol-9-yl]benzonitrile, obtained according to stage 1 of Example 32, 197.3 mg of potassium carbonate, 1.081 g of 3-fluoropropylamine hydrochloride and 0.963 g of triethylamine in 2 ml of dimethyl sulphoxide. 0.904 ml of a 1M aqueous solution of sodium hydroxide, 0.875 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 1 ml of ethyl acetate, 185 mg of 2-(3-fluoropropylamino)-4-[4-(quinolin-3-yl)-9H-carbazol-9-yl]benzamide are thus obtained in the form of an off-white solid, the characteristics of which are the following:

1H NMR spectrum (400 MHz, DMSO-$d_6$) δ ppm 1.88-2.07 (m, 2H) 3.23-3.35 (m, 2H) 4.55 (dt, J=47.4, 5.9 Hz, 2H) 6.79 (dd, J=8.3, 2.0 Hz, 1H) 6.91 (d, J=1.7 Hz, 1H) 7.02 (t, J=7.9 Hz, 1H) 7.25 (d, J=7.8 Hz, 1H) 7.30 (dd, J=6.6, 1.7 Hz, 1H) 7.33 (br. s., 1H) 7.40 (t, J=8.2 Hz, 1H) 7.48 (d, J=8.1 Hz, 1H) 7.54-7.62 (m, 2H) 713 (ddd, J=8.1, 7.0, 1.1 Hz, 1H) 7.88 (ddd, J=8.4, 6.9, 1.3 Hz, 1H) 7.94 (d, J=8.3 Hz, 1H) 8.00 (broad s, 1H) 8.14 (d, J=7.8 Hz, 1H) 8.19 (d, J=8.3 Hz, 1H) 8.52 (t, J=5.6 Hz, 1H) 8.63 (d, J=2.2 Hz, 1H) 9.15 (d, J=2.2 Hz, 1H).

Mass spectrum (LC/MS; method A): retention time Tr (min)=1.12; m/z=489 [M+H]+; m/z=487 [M−H]−.

EXAMPLE 77

Synthesis of 2-(2-fluoroethylamino)-4-[4-(quinolin-3-yl)-9H-carbazol-9-yl]benzamide

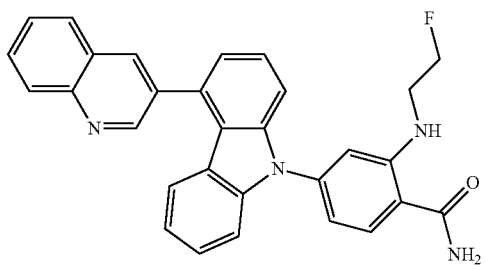

The process is carried out as in stage 2 of Example 3, but using 196.8 mg of 2-fluoro-4-[4-(quinolin-3-yl)-9H-carbazol-9-yl]benzonitrile, obtained according to stage 1 of Example 32, 197.3 mg of potassium carbonate, 0.948 g of 2-fluoroethylamine hydrochloride and 0.963 g of triethylamine in 2 ml of dimethyl sulphoxide. 0.904 ml of a 1M aqueous solution of sodium hydroxide, 0.875 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 1 ml of ethyl acetate, 165 mg of 2-(2-fluoroethylamino)-4-[4-(quinolin-3-yl)-9H-carbazol-9-yl]benzamide are thus obtained in the form of an off-white solid, the characteristics of which are the following:

1H NMR spectrum (400 MHz, DMSO-$d_6$) δ ppm 3.52 (dq, J=27.9, 5.1 Hz, 2 H) 4.61 (dt, J=47.7, 4.6 Hz, 2H) 6.82 (dd, J=8.3, 2.0 Hz, 1H) 6.99 (d, J=1.7 Hz, 1H) 7.02 (t, J=7.8 Hz, 1H) 7.25 (d, J=7.8 Hz, 1H) 7.30 (dd, J=5.9, 2.2 Hz, 1H) 7.35 (broad s, 1H) 7.40 (t, J=8.3 Hz, 1H) 7.49 (d, J=8.3 Hz, 1H) 7.54-7.64 (m, 2H) 7.73 (t, J=7.1 Hz, 1H) 7.88 (ddd, J=8.4, 7.0, 1.5 Hz, 1H) 7.95 (d, J=8.3 Hz, 1H) 8.03 (broad s, 1H) 8.14 (d, J=7.6 Hz, 1H) 8.19 (d, J=8.6 Hz, 1H) 8.62 (d, J=2.0 Hz, 1H) 8.67 (t, J=5.6 Hz, 1H) 9.15 (d, J=2.2 Hz, 1H).

EXAMPLE 78

Obtaining a library of [4-(quinolin-3-yl)-9H-carbazol-9-yl]-arylcarboxamides—application to the synthesis of 5-[4-(quinolin-3-yl)-9H-carbazol-9-yl]pyridin-2-amide

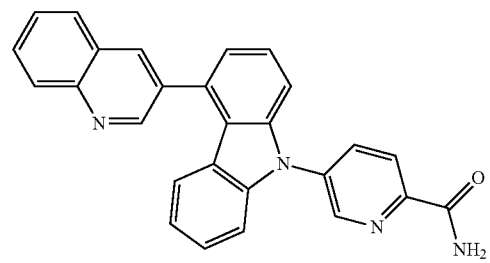

A library of 40 various [4-(quinolin-3-yl)-9H-carbazol-9-yl]-arylcarboxamide type derivatives can be prepared according to the scheme below,

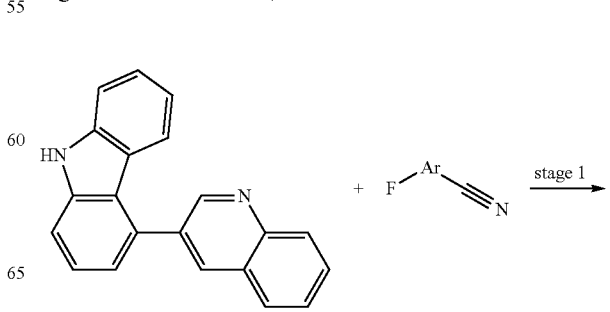

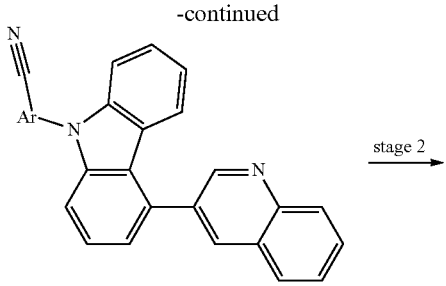

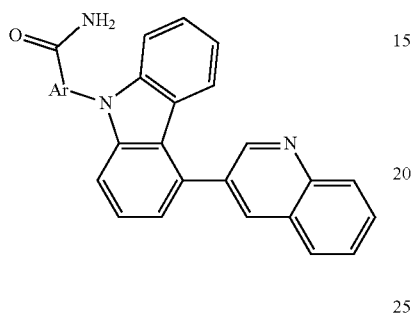

and by carrying out the procedure according to the following protocol:

Stage 1: In a 250 ml three-necked flask, under an argon atmosphere, 800 mg of sodium hydride at 60% in oil are stirred in 10 ml of heptane for 5 minutes, and then the mixture is allowed to separate by settling out for 15 minutes. The supernatant is removed with a pipette. 80 ml of anhydrous dimethylformamide are then added, followed, portionwise over 30 minutes, by 2.944 g of 4-(quinolin-3-yl)-9H-carbazole, obtained in stage 1 of Example 2. The reaction medium is stirred until no more hydrogen gas is given off. The solution obtained is divided up into 40 identical samples of 2 ml, which are each transferred into a 5 ml tube reactor. 0.25 mmol of a different aryl fluoride is added, under an argon atmosphere, to each tube. The tube reactors are septum-sealed, and then heated overnight at 60° C. 0.1 ml of trifluoroacetic acid is then added to each tube reactor. The 40 reaction media obtained are extracted, in parallel, by adding 20 ml of ethyl acetate, washing 10 ml of a 5% aqueous solution of sodium hydrogen carbonate, drying over a magnesium sulphate cartridge, and evaporating to dryness under reduced pressure. The 40 residues thus obtained are purified by supercritical chromatography in parallel, so as to give 40 [4-(quinolin-3-yl)-9H-carbazol-9-yl]arylnitriles, used in stage 2.

Stage 2: The 40 arylnitriles, obtained in stage 1, are transferred into forty 5 ml tube reactors, where they are dissolved in 3 ml of a mixture of ethanol and dimethyl sulphoxide (2/1 by volume). 0.25 ml of a 2N aqueous solution of sodium hydroxide and 0.5 ml of a 30-35% aqueous solution of hydrogen peroxide are then added to each tube reactor. After stirring for 1 hour at ambient temperature, the 40 reaction media are extracted in parallel by adding 20 ml of ethyl acetate, washing with 10 ml of a 10% aqueous solution of sodium chloride, drying over a magnesium sulphate cartridge and evaporating to dryness under reduced pressure. 40 [4-(quinolin-3-yl)-9H-carbazol-9-yl]arylcarboxamides are thus obtained.

Example 78 is prepared within this library, and 37.2 mg of 5-[4-(quinolin-3-yl)-9H-carbazol-9-yl]pyridin-2-amide, Example 78, are thus obtained in the form of a light beige powder, the characteristics of which are the following:

1H NMR spectrum (DMSO, 500 MHz, δ ppm): 9.20 (d, J=2.3 Hz, 1H), 9.02 (m, 1H), 8.68 (d, J=2.3 Hz, 1H), 8.39 (m, 2H), 8.32 (s, 1H), 8.22 (d, J=8.7 Hz, 1H), 8.17 (d, J=8.7 Hz, 1H), 7.91 (td, J=8.7, 1.4 Hz, 1H), 7.85 (s, 1H), 7.76 (m, 1H), 7.62 (dt, J=8.7, 7.6 Hz, 1H), 7.56 (d, 8.1 Hz, 1H), 7.45 (d, 8.1 Hz, 1H), 7.42 (m, 1H), 7.36 (dm, J=7.5 Hz, 1H), 7.26 (d, J=8.1 Hz, 1H), 7.01 (m, 1H).

EXAMPLE 79

Synthesis of 4-[4-(6-fluoro-1H-benzimidazol-2-yl)-9H-carbazol-9-yl]-2-[2-(pyridin-2-yl)ethylamino]benzamide

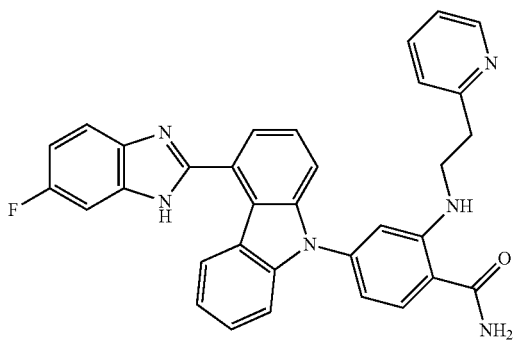

The process is carried out as in stage 3 of Example 3, but using 250 mg of 2-fluoro-4-[4-(6-fluoro-1H-benzimidazol-2-y0-9H-carbazol-9-yl]benzonitrile, obtained according to stage 2 of Example 3, 247.6 mg of potassium carbonate and 1.454 g of 2-(2-aminoethyl)pyridine in 2.5 ml of dimethyl sulphoxide. 1.131 ml of a 1M aqueous solution of sodium hydroxide, 1.094 ml of a 30% aqueous solution of hydrogen peroxide and 6 ml of ethanol are then added to the reaction medium. After treatment as in stage 3 of Example 3, and then purification by flash chromatography on silica gel, elution being carried out with mixtures of dichloromethane and ethanol (from 96/4 to 94/6 by volume), followed by crystallization from 5 ml of diisopropyl ether, 261 mg of 4-[4-(6-fluoro-1H-benzimidazol-2-yl)-9H-carbazol-9-yl]-2-[2-(pyridin-2-yl)ethylamino]benzamide are thus obtained in the form of a beige solid, the characteristics of which are the following:

TLC on silica gel: Rf=0.27 (dichloromethane/ethanol 95/5).

1H NMR spectrum (400 MHz, DMSO-$d_6$, δ ppm): 3.05 (t, J=6.8 Hz, 2H) 3.54 (q, J=6.6 Hz, 2H) 6.75 (dd, J=8.2, 1.6 Hz, 1H) 6.93 (d, J=1.7 Hz, 1H) 7.11-7.22 (m, 3H) 7.27 (broad s, 1H) 7.31 (d, J=7.6 Hz, 1H) 7.42-7.55 (m, 3H) 7.57-7.80 (m, 5 H) 7.91 (d, J=8.3 Hz, 1H) 7.96 (broad s, 1H) 8.43 (d, J=4.2 Hz, 1H) 8.54 (t, J=5.4 Hz, 1H) 8.62 (d, J=8.1 Hz, 1H) 13.08 (broad s, 1H).

Mass spectrum (LC/MS; method A): retention time Tr (min)=0.68; m/z=541 [M+H]+; m/z=539 [M−H]−.

EXAMPLE 80

Synthesis of 4-[4-(quinolin-3-yl)-9H-carbazol-9-yl]-2-[2-(pyridin-2-yl)ethylamino]benzamide

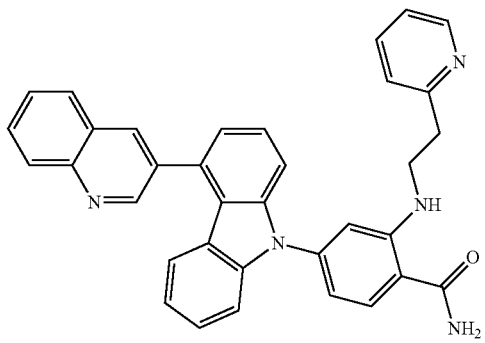

The process is carried out as in stage 3 of Example 3, but using 250 mg of 2-fluoro-4-[4-(quinolin-3-yl)-9H-carbazol-9-yl]benzonitrile, obtained according to stage 1 of Example 32, 250.7 mg of potassium carbonate and 1.477 g of 2-(2-aminoethyl)pyridine in 2.5 ml of dimethyl sulphoxide. 1.149 ml of a 1M aqueous solution of sodium hydroxide, 1.111 ml of a 30% aqueous solution of hydrogen peroxide and 6 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 5 ml of diisopropyl ether, 167 mg of 4-[4-(quinolin-3-yl)-9H-carbazol-9-yl]-2-[2-(pyridin-2-yl)ethylamino]benzamide are thus obtained in the form of white crystals, the characteristics of which are the following:

TLC on silica gel: Rf=0.29 (dichloromethane/ethanol 95/5).

1H NMR spectrum (400 MHz, DMSO-$d_6$, δ ppm): 3.06 (t, J=6.8 Hz, 2H) 3.51-3.59 (m, 2H) 6.78 (dd, J=8.3, 2.0 Hz, 1H) 6.95 (d, J=2.0 Hz, 1H) 7.03 (t, J=8.1 Hz, 1H) 7.19 (ddd, J=7.5, 4.9, 1.1 Hz, 1H) 7.23-7.35 (m, 4H) 7.40 (t, J=8.3 Hz, 1H) 7.49 (d, J=8.3 Hz, 1H) 7.55-7.62 (m, 2H) 7.68 (td, J=7.6, 1.8 Hz, 1H) 7.73 (t, J=8.1 Hz, 1H) 7.85-7.93 (m, 2H) 7.96 (broad s, 1H) 8.14 (d, J=7.6 Hz, 1H) 8.19 (d, J=8.3 Hz, 1H) 8.44 (ddd, J=4.9, 1.7, 1.0 Hz, 1H) 8.54 (t, J=5.5 Hz, 1H) 8.63 (d, J=1.7 Hz, 1H) 9.16 (d, J=2.2 Hz, 1H).

Mass spectrum (LC/MS; method A): retention time Tr (min)=0.88; m/z=534 [M+H]+.

EXAMPLE 81

Synthesis of 4-[4-(6-fluoro-1H-benzimidazol-2-yl)-9H-carbazol-9-yl]-2-[(pyridin-2-ylmethyl)amino]benzamide

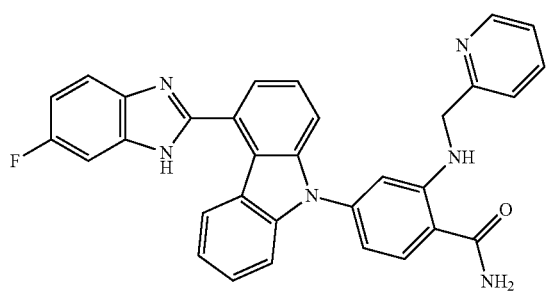

The process is carried out as in stage 3 of Example 3, but using 150 mg of 2-fluoro-4-[4-(6-fluoro-1H-benzimidazol-2-yl)-carbazol-9-yl]benzonitrile, obtained according to stage 2 of Example 3, 148 mg of potassium carbonate and 0.772 g of 2-(aminomethyl)pyridine in 2 ml of dimethyl sulphoxide. 0.678 ml of a 1M aqueous solution of sodium hydroxide, 0.656 ml of a 30% aqueous solution of hydrogen peroxide and 3 ml of ethanol are then added to the reaction medium. After treatment as in stage 3 of Example 3, and then purification by flash chromatography on silica gel, elution being carried out with mixtures of dichloromethane and a 7M solution of ammonia in methanol (from 95/5 to 80/20 by volume), followed by crystallization from 2 ml of ethyl acetate, 75 mg of 4-[4-(6-fluoro-1H-benzimidazol-2-yl)-9H-carbazol-9-yl]-2-[(pyridin-2-ylmethyl)amino]benzamide are thus obtained in the form of a beige solid, the characteristics of which are the following:

1H NMR spectrum (400 MHz, DMSO-$d_6$, δ ppm): 4.55 (d, J=5.9 Hz, 2H) 6.74 (d, J=1.5 Hz, 1H) 6.79 (dd, J=8.3, 1.7 Hz, 1H) 7.09-7.21 (m, 3H) 7.30-7.43 (m, 5H) 7.49 (t, J=7.8 Hz, 1H) 7.56-7.65 (m, 2H) 7.80-7.87 (m, 2H) 7.94 (d, J=8.3 Hz, 1H) 8.03 (broad s, 1H) 8.47-8.57 (m, 2H) 9.09 (t, J=6.0 Hz, 1H) 13.06 (broad s, 1H).

Mass spectrum (LC/MS; method A): retention time Tr (min)=0.73; m/z=527 [M+H]+; m/z=525 [M−H]−.

EXAMPLE 82

Synthesis of 4-[4-(6-fluoro-1H-benzimidazol-2-yl)-9H-carbazol-9-yl]-2-[2-(1H-imidazol-1-yl)ethylamino]benzamide

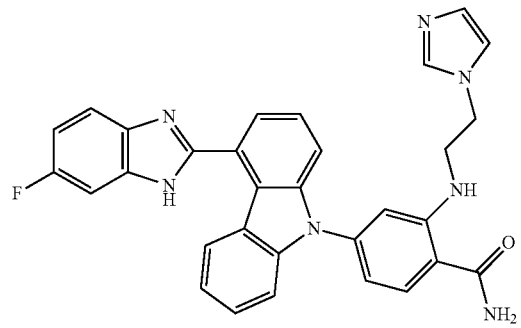

The process is carried out as in stage 3 of Example 3, but using 150 mg of 2-fluoro-4-[4-(6-fluoro-1H-benzimidazol-2-yl)carbazol-9-yl]benzonitrile, obtained according to stage 2 of Example 3, 148 mg of potassium carbonate, 1.314 g of 2-(1H-imidazol-1-yl)ethylamine dihydrochloride and 1.445 g of triethylamine in 2 ml of dimethyl sulphoxide. 0.678 ml of a 1M aqueous solution of sodium hydroxide, 0.656 ml of a 30% aqueous solution of hydrogen peroxide and 3 ml of ethanol are then added to the reaction medium. After treatment as in stage 3 of Example 3, and then purification by flash chromatography on silica gel, elution being carried out with a mixture of dichloromethane and ethanol (90/10 by volume), followed by crystallization from 2 ml of ethyl acetate, 130 mg of 4-[4-(6-fluoro-1H-benzimidazol-2-yl)-9H-carbazol-9-yl]-2-[2-(1H-imidazol-1-yl)ethylamino]benzamide are thus obtained in the form of a beige solid, the characteristics of which are the following:

1H NMR spectrum (400 MHz, DMSO-d$_6$, δ ppm): 3.56 (q, J=5.4 Hz, 2H) 4.20 (t, J=5.6 Hz, 2H) 6.77 (d, J=8.3 Hz, 1H) 6.86 (s, 1H) 6.95 (s, 1H) 7.12-7.22 (m, 3 H) 7.33 (broad s, 1H) 7.45 (broad s, 2H) 7.57-7.67 (m, 5H) 7.82 (broad s, 1H) 7.92 (d, J=7.8 Hz, 1H) 8.01 (broad s, 1H) 8.56-8.66 (m, 2H) 13.08 (br. s., 1H).

Mass spectrum (LC/MS; method C): retention time Tr (min)=2.91; m/z=530 [M+H]+; m/z=528 [M−H]−.

EXAMPLE 83

Synthesis of 4-[4-(6-fluoro-1H-benzimidazol-2-yl)-9H-carbazol-9-yl]-2-[(2,2,6,6-tetramethyl-1H-piperidin-4-ylamino]benzamide

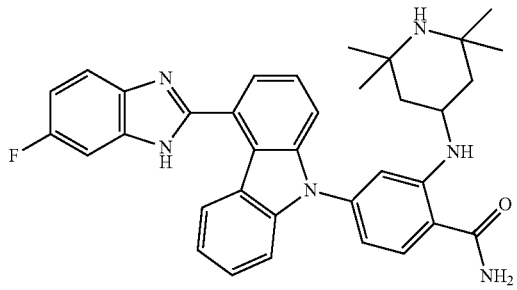

The process is carried out as in stage 3 of Example 3, but using 250 mg of 2-fluoro-4-[4-(6-fluoro-1H-benzimidazol-2-yl)-carbazol-9-yl]benzonitrile, obtained according to stage 2 of Example 3, 247.6 mg of potassium carbonate and 1.86 g of 4-amino-2,2,6,6-tetramethylpiperidine in 2.5 ml of dimethyl sulphoxide in a microwave for 1 hour 30 minutes at 110° C. 1.131 ml of a 1M aqueous solution of sodium hydroxide, 1.094 ml of a 30% aqueous solution of hydrogen peroxide and 6 ml of ethanol are then added to the reaction medium. After treatment as in stage 3 of Example 3, and then purification by flash chromatography on silica gel, elution being carried out with a mixture of dichloromethane and ammonia in a 7M solution in methanol (95/5 by volume), followed by crystallization from 10 ml of diisopropyl ether, 142 mg of 4-[4-(6-fluoro-1H-benzimidazol-2-yl)-9H-carbazol-9-yl]-2-(2,2,6,6-tetramethyl-1H-piperidin-4-ylamino]benzamide are thus obtained in the form of fine ecru crystals, the characteristics of which are the following:

TLC on silica gel: Rf=0.43 (dichloromethane/7M ammonia in methanol 90/10).

1H NMR spectrum (400 MHz, DMSO-d$_6$, δ ppm): 1.02-1.08 (m, 14H) 1.95 (d, J=10.0 Hz, 2H) 3.72-3.83 (m, 1H) 6.80 (d, J=8.1 Hz, 1H) 6.95 (s, 1H) 7.11-7.23 (m, 2H) 7.29 (broad s, 1H) 7.43-7.56 (m, 3H) 7.58-7.78 (m, 4H) 7.93 (d, J=8.3 Hz, 1H) 7.99 (broad s, 1H) 8.36 (d, J=7.3 Hz, 1H) 8.59 (d, J=7.8 Hz, 1H) 13.08 (broad s, 1H).

Mass spectrum (LC/MS; method A): retention time Tr (min)=0.69; m/z=575 [M+H]+; m/z=573 [M−H]−.

EXAMPLE 84

Synthesis of 4-[4-(quinolin-3-yl)-9H-carbazol-9-yl]-2-(2,2,6,6-tetramethyl-1H-piperidin-4-ylamino]benzamide

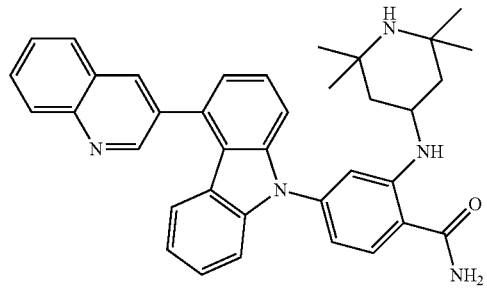

The process is carried out as in stage 3 of Example 3, but using 250 mg of 2-fluoro-4-[4-(quinolin-3-yl)carbazol-9-yl]benzonitrile, obtained according to stage 1 of Example 32, 251 mg of potassium carbonate and 1.891 g of 4-amino-2,2,6,6-tetramethylpiperidine in 2.5 ml of dimethyl sulphoxide. 1.15 ml of a 1M aqueous solution of sodium hydroxide, 1.113 ml of a 30% aqueous solution of hydrogen peroxide and 6 ml of ethanol are then added to the reaction medium. After treatment as in stage 3 of Example 3, and then purification by flash chromatography on silica gel, elution being carried out with a mixture of dichloromethane and ammonia in a 7M solution in methanol (96/4 by volume), followed by crystallization from 10 ml of diisopropyl ether, 306 mg of 4-[4-(quinolin-3-yl)-9H-carbazol-9-yl]-2-(2,2,6,6-tetramethyl-1H-piperidin-4-ylamino]benzamide are thus obtained in the form of fine ecru crystals, the characteristics of which are the following:

TLC on silica gel: Rf=0.13 (dichloromethane/7M ammonia in methanol 95/5).

1H NMR spectrum (400 MHz, DMSO-d$_6$, δ ppm): 1.04-1.10 (m, 14H) 1.96 (dd, J=12.0, 2.4 Hz, 2H) 3.73-3.85 (m, 1H) 6.81 (dd, J=8.3, 1.5 Hz, 1H) 6.99 (s, 1 H) 7.03 (t, J=7.5 Hz, 1H) 7.25 (d, J=8.1 Hz, 1H) 7.28 (broad s, 1H) 7.31 (d, J=6.8 Hz, 1H) 7.41 (t, J=7.8 Hz, 1H) 7.53-7.67 (m, 3H) 7.73 (t, J=7.7 Hz, 1H) 7.88 (t, J=8.2 Hz, 1H) 7.94 (d, J=8.3 Hz, 1H) 7.98 (broad s, 1H) 8.13 (d, J=7.8 Hz, 1H) 8.19 (d, J=8.6 Hz, 1H) 8.37 (d, J=7.6 Hz, 1H) 8.63 (d, J=1.7 Hz, 1H) 9.16 (d, J=2.2 Hz, 1H).

Mass spectrum (LC/MS; method C): retention time Tr (min)=3.50; m/z=568 [M+H]+; m/z=566 [M−H]−.

EXAMPLE 85

Synthesis of 4-[4-(6-fluoro-1H-benzimidazol-2-yl)-9H-carbazol-9-yl]-2-(1,2,2,6,6-pentamethyl-1H-piperidin-4-ylamino]benzamide

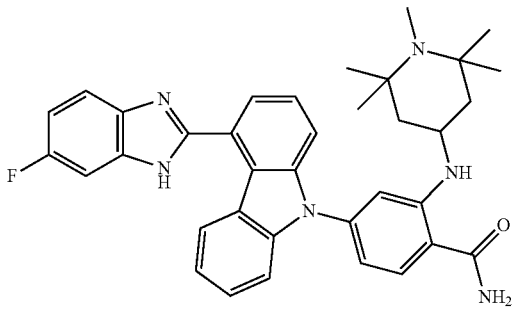

The process is carried out as in stage 3 of Example 3, but using 150 mg of 2-fluoro-4-[4-(6-fluoro-1H-benzimidazol-2-yl)-carbazol-9-yl]benzonitrile, obtained according to stage 2 of Example 3, 148 mg of potassium carbonate and 0.486 g of 4-amino-1,2,2,6,6-pentamethylpiperidine in 1.5 ml of dimethyl sulphoxide, in a microwave for 1 hour 30 minutes at 110° C. 0.678 ml of a 1M aqueous solution of sodium hydroxide, 0.656 ml of a 30% aqueous solution of hydrogen peroxide and 3.5 ml of ethanol are then added to the reaction medium. After treatment as in stage 3 of Example 3, and then purification by flash chromatography on silica gel, elution being carried out with a gradient of mixtures of dichloromethane and ethanol (from 95/5 to 85/15 by volume), followed by crystallization from 10 ml of diisopropyl ether, 56.5 mg of 4-[4-(6-fluoro-1H-benzimidazol-2-yl)-9H-carbazol-9-yl]-2-(1,2,2,6,6-pentamethyl-1H-piperidin-4-ylamino]benzamide are thus obtained in the form of fine ecru crystals, the characteristics of which are the following:

TLC on silica gel: Rf=0.09 (dichloromethane/ethanol 90/10).

1H NMR spectrum (400 MHz, DMSO-d$_6$+TFA, δ ppm): 1.35 (s, 6H) 1.48 (s, 6 H) 1.73 (t, J=12.5 Hz, 2H) 2.32 (d, J=12.7 Hz, 2H) 2.75 (s, 3H) 4.09 (t, J=11.7 Hz, 1 H) 6.92 (d, J=8.3 Hz, 1H) 7.20 (s, 1H) 7.27 (t, J=7.6 Hz, 1H) 7.54-7.61 (m, 2H) 7.64-7.81 (m, 4H) 7.88 (d, J=7.8 Hz, 1H) 7.95 (d, J=7.3 Hz, 1H) 8.01-8.08 (m, 2 H).

Mass spectrum (LC/MS; method A): retention time Tr (min)=0.74; m/z=589 [M+H]+; m/z=587 [M−H]−.

EXAMPLE 86

Synthesis of 2-[(pyridin-2-ylmethyl)amino]-4-[4-(quinolin-3-yl)-9H-carbazol-9-yl]benzamide

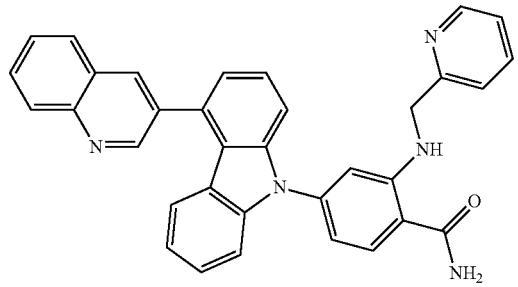

The process is carried out as in stage 3 of Example 3, but using 150 mg of 2-fluoro-4-[4-(quinolin-3-yl)carbazol-9-yl]benzonitrile, obtained according to stage 1 of Example 32, 150.5 mg of potassium carbonate and 0.785 g of 2-(aminomethyl)pyridine in 2 ml of dimethyl sulphoxide. 0.69 ml of a 1M aqueous solution of sodium hydroxide, 0.667 ml of a 30% aqueous solution of hydrogen peroxide and 3 ml of ethanol are then added to the reaction medium. After treatment as in stage 3 of Example 3, and then purification by flash chromatography on silica gel, elution being carried out with a mixture of dichloromethane and ammonia as a 7M solution in methanol (from 90/10 to 80/20 by volume), followed by crystallization from 1 ml of ethyl acetate and 3 ml of diisopropyl ether, 95 mg of 2-[(pyridin-2-ylmethyl)amino]-4-[4-(quinolin-3-yl)-9H-carbazol-9-yl]benzamide are thus obtained in the form of a beige solid, the characteristics of which are the following:

1H NMR spectrum (400 MHz, DMSO-d$_6$, δ ppm): 4.56 (d, J=5.9 Hz, 2H) 6.75 (d, J=1.7 Hz, 1H) 6.81 (dd, J=8.3, 2.0 Hz, 1H) 6.99 (t, J=7.6 Hz, 1H) 7.17-7.22 (m, 2H) 7.24-7.31 (m, 3H) 7.33-7.37 (m, 1H) 7.37 (broad s, 1H) 7.41 (d, J=7.8 Hz, 1 H) 7.47 (dd, J=8.3, 7.3 Hz, 1H) 7.72 (t, J=8.1 Hz, 1H) 7.80-7.91 (m, 2H) 7.94 (d, J=8.3 Hz, 1H) 8.03 (broad s, 1H) 8.12 (d, J=7.6 Hz, 1H) 8.18 (d, J=8.6 Hz, 1H) 8.52 (d, J=4.9 Hz, 1H) 8.61 (d, J=2.0 Hz, 1H) 9.10 (t, J=6.1 Hz, 1H) 9.13 (d, J=2.4 Hz, 1H).

Mass spectrum (LC/MS; method A): retention time Tr (min)=0.93; m/z=520 [M+H]+; m/z=518 [M−H]−.

EXAMPLE 87

Synthesis of 2-[2-(1H-imidazol-1-yl)ethylamino]-4-[4-(quinolin-3-yl)-9H-carbazol-9-yl]benzamide

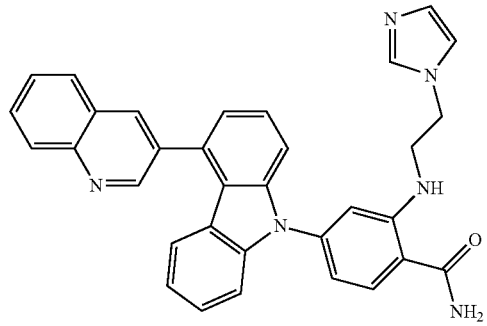

The process is carried out as in stage 3 of Example 3, but using 150 mg of 2-fluoro-4-[4-(quinolin-3-yl)carbazol-9-yl]benzonitrile, obtained according to stage 1 of Example 32, 150.5 mg of potassium carbonate, 1.336 g of 2-(1H-imidazol-1-yl)ethylamine dihydrochloride in 2 ml of dimethyl sulphoxide. 0.69 ml of a 1M aqueous solution of sodium hydroxide, 0.667 ml of a 30% aqueous solution of hydrogen peroxide and 3 ml of ethanol are then added to the reaction medium. After treatment as in stage 3 of Example 3, and then purification by flash chromatography on silica gel, elution being carried out with a mixture of dichloromethane and ethanol (90/10 by volume), followed by crystallization from 1 ml of ethyl acetate and 3 ml of diisopropyl ether, 130 mg of 2-[2-(1H-imidazol-1-yl)ethylamino]-4-[4-(quinolin-3-yl)-9H-carbazol-9-yl]benzamide are thus obtained in the form of a beige solid, the characteristics of which are the following:

1H NMR spectrum (400 MHz, DMSO-d$_6$, δ ppm): 3.53-3.60 (m, 2H) 4.21 (t, J=6.1 Hz, 2H) 6.80 (dd, J=8.2, 1.8 Hz, 1H) 6.87 (s, 1H) 6.98 (d, J=2.0 Hz, 1H) 7.03 (t, J=7.9 Hz, 1H) 7.19 (s, 1H) 7.25 (d, J=8.1 Hz, 1H) 7.30 (dd, J=6.8, 1.2 Hz, 1H) 7.34 (broad s, 1H) 7.40 (t, J=8.1 Hz, 1H) 7.48 (d, J=8.1 Hz, 1H) 7.54-7.63 (m, 3H) 7.73 (t, J=8.1 Hz, 1H) 7.89 (ddd, J=8.4, 7.0, 1.2 Hz, 1H) 7.93 (d, J=8.3 Hz, 1H) 8.01 (broad s, 1H) 8.14 (d, J=7.8 Hz, 1H) 8.19 (d, J=8.6 Hz, 1H) 8.60 (t, J=5.9 Hz, 1H) 8.62 (d, J=2.2 Hz, 1H) 9.15 (d, J=2.2 Hz, 1H).

Mass spectrum (LC/MS; method A): retention time Tr (min)=0.81; m/z=523 [M+H]+; m/z=521 [M−H]−.

EXAMPLE 88

Synthesis of (1,2,2,6,6-pentamethyl-1H-piperidin-4-ylamino]-4-[4-(quinolin-3-yl)-9H-carbazol-9-yl]-2-benzamide

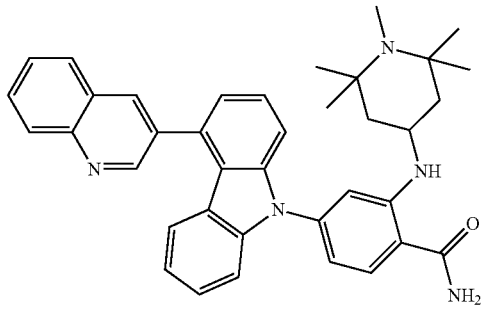

The process is carried out as in stage 3 of Example 3, but using 147.6 mg of 2-fluoro-4-[4-(quinolin-3-yl)carbazol-9-yl]benzonitrile, obtained according to stage 1 of Example 32, 148 mg of potassium carbonate and 0.486 g of 4-amino-1,2,2,6,6-pentamethylpiperidine in 1.5 ml of dimethyl sulphoxide, in a microwave for 1 hour and 30 minutes at 110° C. 0.678 ml of a 1M aqueous solution of sodium hydroxide, 0.656 ml of a 30% aqueous solution of hydrogen peroxide and 3.5 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 10 ml of diisopropyl ether, 61.9 mg of (1,2,2,6,6-pentamethyl-1H-piperidin-4-ylamino]-4-[4-(quinolin-3-yl)-9H-carbazol-9-yl]-2-benzamide are thus obtained in the form of fine off-white crystals, the characteristics of which are the following:

TLC on silica gel: Rf=0.21 (dichloromethane/ethanol 95/5).

1H NMR spectrum (400 MHz, DMSO-$d_6$, δ ppm): 0.96 (s, 6H) 1.12 (s, 6H) 1.27 (t, J=10.8 Hz, 2H) 1.97 (d, J=10.3 Hz, 2H) 2.16 (s, 3H) 3.61-3.76 (m, 1H) 6.82 (d, J=8.3 Hz, 1H) 6.99 (s, 1H) 7.03 (t, J=7.6 Hz, 1H) 7.25 (d, J=8.3 Hz, 1H) 7.28 (broad s, 1H) 7.31 (d, J=6.8 Hz, 1H) 7.40 (t, J=7.6 Hz, 1H) 7.53-7.67 (m, 3H) 7.73 (t, J=7.6 Hz, 1H) 7.88 (t, J=7.6 Hz, 1H) 7.94 (d, J=8.8 Hz, 1H) 7.99 (broad s, 1 H) 8.13 (d, J=8.3 Hz, 1H) 8.19 (d, J=8.3 Hz, 1H) 8.36 (d, J=7.3 Hz, 1H) 8.63 (s, 1H) 9.15 (d, J=1.5 Hz, 1H).

Mass spectrum (LC/MS; method A): retention time Tr (min)=0.88; m/z=582 [M+H]+.

EXAMPLE 89

Synthesis of 4-[4-(6-fluoro-1H-benzimidazol-2-yl)-9H-carbazol-9-yl]-2-(3(R,S)-hydroxycyclohexyl-1(R,S)-amino)benzamide

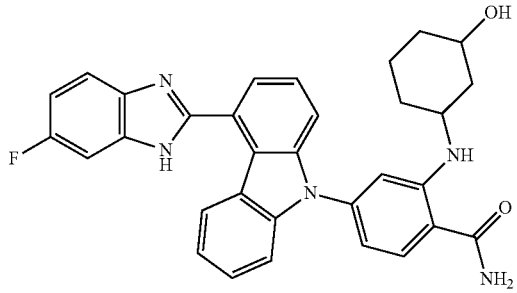

The process is carried out as in stage 3 of Example 3, but using 200 mg of 2-fluoro-4-[4-(6-fluoro-1H-benzimidazol-2-yl)carbazol-9-yl]benzonitrile, obtained according to stage 2 of Example 3, 263 mg of potassium carbonate and 0.658 g of 3(R,S)-aminocyclohexan-1(R,S)-ol in 4.7 ml of dimethyl sulphoxide, in a microwave for 1 hour and 30 minutes at 110° C. 0.952 ml of a 1M aqueous solution of sodium hydroxide, 0.875 ml of a 30% aqueous solution of hydrogen peroxide and 9.5 ml of ethanol are then added to the reaction medium. After treatment as in stage 3 of Example 3, and then purification by flash chromatography on silica gel, elution being carried out with a gradient of mixtures of dichloromethane and ethanol (from 94/6 to 92/8 by volume), followed by crystallization from 10 ml of diisopropyl ether, 98.7 mg of 4-[4-(6-fluoro-1H-benzimidazol-2-yl)-9H-carbazol-9-yl]-2-(3(R,S)-hydroxycyclohexyl-1(R,S)-amino)benzamide are thus obtained in the form of fine ecru crystals, the characteristics of which are the following:

TLC on silica gel: Rf=0.11 (dichloromethane/ethanol 95/50).

1H NMR spectrum (400 MHz, DMSO-$d_6$+TFA, δ ppm): 1.10-1.29 (m, 2H) 1.63-1.85 (m, 4H) 1.93-2.26 (m, 2H) 3.35-3.47 (m, 1H) 3.73-3.92 (m, 1H) 6.82-6.89 (m, 1H) 6.93-7.01 (m, 1H) 7.26 (ddd, J=8.0, 5.8, 2.3 Hz, 1H) 7.52-7.61 (m, 3H) 7.67-7.90 (m, 5H) 7.98-8.06 (m, 2H).

Mass spectrum (LC/MS; method A): retention time Tr (min)=0.85; m/z=534 [M+H]+; m/z=532 [M−H]−.

EXAMPLE 90

Synthesis of 4-[4-(6-fluoro-1H-benzimidazol-2-yl)-9H-carbazol-9-yl]-2-(2-hydroxy-2-methylpropylamino)benzamide

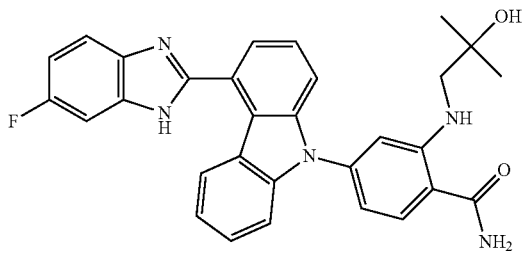

The process is carried out as in stage 3 of Example 3, but using 150 mg of 2-fluoro-4-[4-(6-fluoro-1H-benzimidazol-2-yl)carbazol-9-yl]benzonitrile, obtained according to stage 2 of Example 3, 148 mg of potassium carbonate and 0.477 g of 1-amino-2-methylpropan-2-ol in 2 ml of dimethyl sulphoxide, in a microwave for 1 hour and 15 minutes at 115° C. 0.678 ml of a 1M aqueous solution of sodium hydroxide, 0.656 ml of a 30% aqueous solution of hydrogen peroxide and 3 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 1 ml of ethyl acetate and 4 ml of diisopropyl ether, 85 mg of 4-[4-(6-fluoro-1H-benzimidazol-2-yl)-9H-carbazol-9-yl]-2-(2-hydroxy-2-methylpropylamino)benzamide are thus obtained in the form of a beigey-ecru solid, the characteristics of which are the following:

1H NMR spectrum (400 MHz, DMSO-$d_6$, δ ppm): 1.17 (s, 6H) 3.04 (d, J=5.4 Hz, 2H) 4.52 (s, 1H) 6.71 (dd, J=8.3, 2.0 Hz, 1H) 6.89 (d, J=2.0 Hz, 1H) 7.10-7.21 (m, 2H) 7.25 (broad s, 1H) 7.34-7.53 (m, 3H) 7.57-7.67 (m, 3H) 7.84 (dd, J=8.6, 5.1 Hz, 1H) 7.90 (d, J=8.3 Hz, 1H) 7.96 (broad s, 1H) 8.58-8.69 (m, 2H) 13.08 (broad s, 1H).

Mass spectrum (LC/MS; method A): retention time Tr (min)=0.84; m/z=508 [M+H]+; m/z=506 [M−H]−.

EXAMPLE 91

Synthesis of (2-hydroxy-2-methylpropylamino)-4-[4-(quinolin-3-yl)-9H-carbazol-9-yl]-2-benzamide

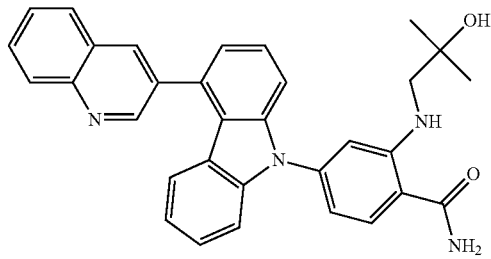

The process is carried out as in stage 3 of Example 3, but using 150 mg of 2-fluoro-4-[4-(quinolin-3-yl)-9H-carbazol-9-yl]benzonitrile, obtained according to stage 1 of Example 32, 155.5 mg of potassium carbonate and 0.485 g of 1-amino-2-methylpropan-2-ol in 2 ml of dimethyl sulphoxide, in a microwave at 100° C. for 1 hour.

0.69 ml of a 1M aqueous solution of sodium hydroxide, 0.667 ml of a 30% aqueous solution of hydrogen peroxide and 3 ml of ethanol are then added to the reaction medium. After treatment as in stage 3 of Example 3, and then purification by flash chromatography on silica gel, elution being carried out with mixtures of dichloromethane and ammonia in a 7M solution in methanol (from 95/5 to 80/20 by volume), followed by crystallization from 1 ml of ethyl acetate and 4 ml of diisopropyl ether, 155 mg of (2-hydroxy-2-methylpropylamino)-4-[4-(quinolin-3-yl)-9H-carbazol-9-yl]-2-benzamide are thus obtained in the form of fine ecru crystals, the characteristics of which are the following:

1H NMR spectrum (400 MHz, DMSO-d$_6$, δ ppm): 1.17 (s, 6H) 3.05 (d, J=5.4 Hz, 2H) 4.52 (s, 1H) 6.73 (dd, J=8.2, 1.8 Hz, 1H) 6.91 (d, J=1.7 Hz, 1H) 7.02 (t, J=7.5 Hz, 1H) 7.25 (d, J=8.1 Hz, 1H) 7.27 (broad s, 1H) 7.30 (dd, J=6.8, 1.2 Hz, 1 H) 7.39 (t, J=7.6 Hz, 1H) 7.46 (d, J=8.3 Hz, 1H) 7.53-7.62 (m, 2H) 7.73 (t, J=8.1 Hz, 1H) 7.86-7.92 (m, 1H) 7.96 (broad s, 1H) 8.14 (d, J=7.6 Hz, 1H) 8.19 (d, J=8.6 Hz, 1H) 8.60-8.65 (m, 2H) 9.15 (d, J=2.2 Hz, 1H).

Mass spectrum (LC/MS; method A): retention time Tr (min)=1.06; m/z=501 [M+H]+; m/z=499 [M−H]−.

EXAMPLE 92

Synthesis of 4-[4-(6-fluoro-1H-benzimidazol-2-yl)-9H-carbazol-9-yl]-2-[(oxazol-4-ylmethyl)amino]benzamide

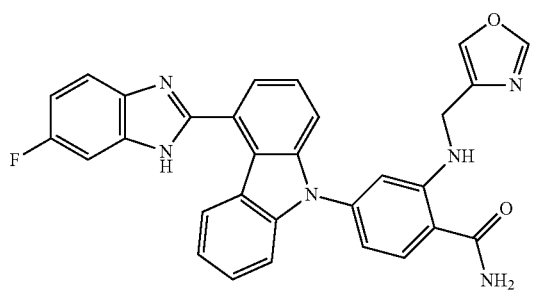

The process is carried out as in stage 3 of Example 3, but using 195 mg of 2-fluoro-4-[4-(6-fluoro-1H-benzimidazol-2-yl)carbazol-9-yl]benzonitrile, obtained according to stage 2 of Example 3, 256.5 mg of potassium carbonate, 499.5 mg of oxazol-4-ylmethylamine hydrochloride and 187.8 mg of triethylamine in 4 ml of dimethyl sulphoxide, in a microwave for 1 hour and 30 minutes at 115° C. 0.928 ml of a 1M aqueous solution of sodium hydroxide, 0.853 ml of a 30% aqueous solution of hydrogen peroxide and 8 ml of ethanol are then added to the reaction medium. After treatment as in stage 3 of Example 3, and then purification by flash chromatography on silica gel, elution being carried out with a gradient of mixtures of dichloromethane and ethanol (from 97/3 to 92/8 by volume), followed by crystallization from 10 ml of diisopropyl ether, 111 mg of 4-[4-(6-fluoro-1H-benzimidazol-2-yl)-9H-carbazol-9-yl]-2-[(oxazol-4-ylmethyl)amino]benzamide are thus obtained in the form of a pale yellow powder, the characteristics of which are the following:

TLC on silica gel: Rf=0.31 (dichloromethane/ethanol 95/5)

1H NMR spectrum (400 MHz, DMSO-d$_6$, δ ppm): 4.34 (s, 2H) 6.78 (dd, J=8.1, 1.7 Hz, 1H) 6.98 (d, J=1.5 Hz, 1H) 7.09-7.19 (m, 2H) 7.34-7.74 (m, 9H) 7.90-7.95 (m, 2H) 8.27 (s, 1H) 8.54 (d, J=7.8 Hz, 1H) 8.68 (broad s, 1H) 12.83 (broad s, 1H).

Mass spectrum (LC/MS; method A): retention time Tr (min)=0.82; m/z=517 [M+H]+; m/z=515 [M−H]−.

EXAMPLE 93

Synthesis of 4-[4-(6-fluoro-1H-benzimidazol-2-yl)-9H-carbazol-9-yl]-2-{[(1(R,S), 2(R,S)-2-hydroxycyclohexylmethyl)amino}benzamide

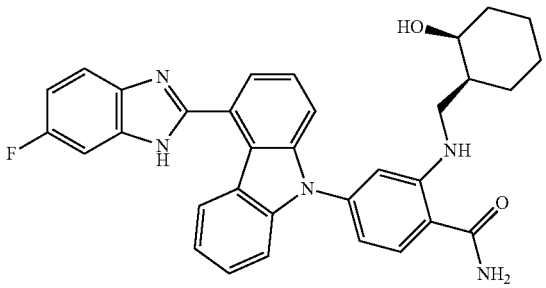

The process is carried out as in stage 3 of Example 3, but using 160 mg of 2-fluoro-4-[4-(6-fluoro-1H-benzimidazol-2-yl)-9H-carbazol-9-yl]benzonitrile, obtained according to stage 2 of Example 3, 210 mg of potassium carbonate, 504 mg of cis-2-aminomethylcyclohexan-1-ol hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a gradient of mixtures of dichloromethane and ethanol (from 95/5 to 92/8 by volume), followed by crystallization from 10 ml of diisopropyl ether, 165 mg of 4-[4-(6-fluoro-1H-benzimidazol-2-yl)-9H-carbazol-9-yl]-2-{[(1(R,S), 2(R,S)-2-hydroxy-cyclo-hexylmethyl)amino}benzamide are thus obtained in the form of fine ecru crystals, the characteristics of which are the following:

TLC on silica gel: Rf=0.19 (dichloromethane/ethanol 95/5)

1H NMR spectrum (400 MHz, DMSO-d$_6$, δ ppm): 1.18-1.73 (m, 9H) 2.90-3.22 (m, 2H) 3.82 (broad s, 1H) 4.41 (d, J=2.9 Hz, 1H) 6.74 (d, J=8.1 Hz, 1H) 6.83 (s, 1H) 7.11-7.23 (m, 2H) 7.31 (broad s, 1H) 7.39-7.68 (m, 6H) 7.84 (broad s, 1 H) 7.92 (d, J=8.3 Hz, 1H) 8.01 (broad s, 1H) 8.54 (t, J=4.9 Hz, 1H) 8.63 (broad s, 1 H) 10.22 (broad s, 1H).

Mass spectrum (LC/MS; method A): retention time Tr (min)=0.96; m/z=548 [M+H]+; m/z=546 [M−H]−.

EXAMPLE 94

Synthesis of 2-[(oxazol-4-ylmethyl)amino]-4-[4-(quinolin-3-yl)-9H-carbazol-9-yl]benzamide

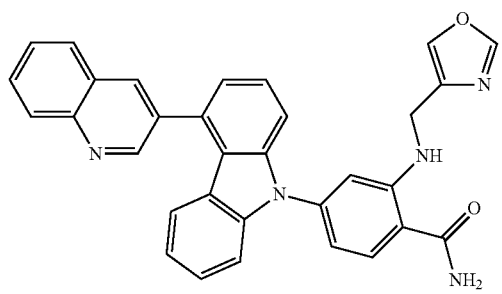

The process is carried out as in stage 3 of Example 3, but using 165.4 mg of 2-fluoro-4-[4-(quinolin-3-yl)-9H-carbazol-9-yl]benzonitrile, obtained according to stage 1 of Example 32, 221 mg of potassium carbonate, 431 mg of oxazol-4-ylmethylamine hydrochloride and 324 mg of triethylamine in 3.5 ml of dimethyl sulphoxide, in a microwave for 1 hour and 30 minutes at 115° C. 0.8 ml of a 1M aqueous solution of sodium hydroxide, 0.735 ml of a 30% aqueous solution of hydrogen peroxide and 7 ml of ethanol are then added to the reaction medium. After treatment as in stage 3 of Example 3, and then purification by flash chromatography on silica gel, elution being carried out with a mixture of dichloromethane and ethanol (96/4 by volume), followed by crystallization from 10 ml of diisopropyl ether, 36 mg of 2-[(oxazol-4-ylmethyl)amino]-4-[4-(quinolin-3-yl)-9H-carbazol-9-yl]benzamide are thus obtained in the form of a pale yellow powder, the characteristics of which are the following:

TLC on silica gel: Rf=0.21 (dichloromethane/ethanol 95/5)

1H NMR spectrum (400 MHz, DMSO-d$_6$+TFA, δ ppm): 4.39 (s, 2H) 6.86 (d, J=8.1 Hz, 1H) 6.99 (s, 1H) 7.06 (t, J=7.2 Hz, 1H) 7.40-7.50 (m, 4H) 7.58-7.66 (m, 2H) 7.96-8.03 (m, 2H) 8.07 (t, J=7.5 Hz, 1H) 8.26 (t, J=7.6 Hz, 1H) 8.37 (s, 1 H) 8.44 (d, J=8.3 Hz, 1H) 8.49 (d, J=8.3 Hz, 1H) 9.56 (s, 1H) 9.80 (s, 1H).

Mass spectrum (LC/MS; method C): retention time Tr (min)=4.38; m/z=510 [M+H]+.

EXAMPLE 95

Synthesis of 2-{[(1(R,S),2(R,S)-2-hydroxycyclohexylmethyl)-amino}-4-[4-(quinolin-3-yl)-9H-carbazol-9-yl]benzamide

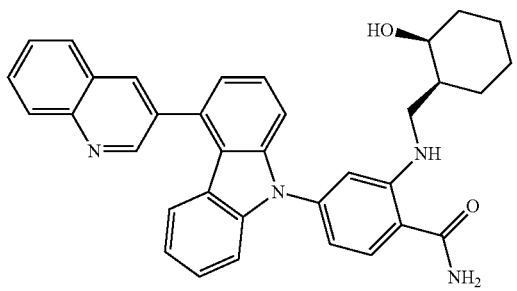

The process is carried out as in stage 3 of Example 3, but using 157 mg of 2-fluoro-4-[4-(quinolin-3-yl)-9H-carbazol-9-yl]benzonitrile, obtained according to stage 1 of Example 32, 210 mg of potassium carbonate, 504 mg of cis-2-aminomethylcyclohexan-1-ol hydrochloride and 308 mg of triethylamine in 2.5 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 5 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 10 ml of diisopropyl ether, 127 mg of 2-{[(1(R,S),2(R,S)-2-hydroxycyclohexylmethyl)amino}-4-[4-(quinolin-3-yl)-9H-carbazol-9-yl]benzamide are thus obtained in the form of a pale yellow powder, the characteristics of which are the following:

TLC on silica gel: Rf=0.17 (dichloromethane/ethanol 95/5)

1H NMR spectrum (400 MHz, DMSO-d$_6$+TFA, δ ppm): 1.16-1.79 (m, 9H) 2.93-3.27 (m, 2H) 3.85 (broad s, 1H) 6.81 (d, J=7.6 Hz, 1H) 6.88 (s, 1H) 7.07 (t, J=6.7 Hz, 1H) 7.38-7.59 (m, 4H) 7.68 (s, 2H) 7.96 (d, J=7.8 Hz, 1H) 8.06 (t, J=6.6 Hz, 1H) 8.25 (t, J=7.5 Hz, 1H) 8.42 (d, J=8.6 Hz, 1H) 8.48 (d, J=7.6 Hz, 1H) 9.52 (s, 1H) 9.77 (s, 1H).

Mass spectrum (LC/MS; method C): retention time Tr (min)=4.89; m/z=541 [M+H]+; m/z=539 [M−H]−.

EXAMPLE 96

Synthesis of 4-[4-(6-fluoro-1H-benzimidazol-2-yl)-9H-carbazol-9-yl]-2-[1(R,S),2(R,S)-2-hydroxymethylcyclohexyl-1-amino])benzamide

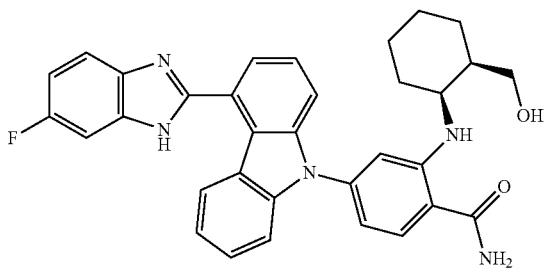

The process is carried out as in stage 3 of Example 3, but using 160 mg of 2-fluoro-4-[4-(6-fluoro-1H-benzimidazol-2-yl)carbazol-9-yl]benzonitrile, obtained according to stage 2 of Example 3, 210 mg of potassium carbonate, 504 mg of cis-2-hydroxymethylcyclohexanamine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 10 ml of diisopropyl ether, 110 mg of 4-[4-(6-fluoro-1H-benzimidazol-2-yl)-9H-carbazol-9-yl]-2-[1(R,S),2(R,S)-2-hydroxymethylcyclohexyl-1-amino]benzamide are thus obtained in the form of fine light beige crystals, the characteristics of which are the following:

TLC on silica gel: Rf=0.10 (dichloromethane/ethanol 95/5).

1H NMR spectrum (400 MHz, DMSO-$d_6$, δ ppm): 1.12-1.88 (m, 9H) 3.21-3.34 (m, 2H) 3.87 (d, J=4.9 Hz, 1H) 4.45 (t, J=5.0 Hz, 1H) 6.70 (d, J=8.3 Hz, 1H) 6.94 (s, 1H) 7.06-7.23 (m, 2H) 7.30 (broad s, 1H) 7.37-7.52 (m, 2H) 7.58-7.72 (m, 4H) 7.85 (dd, J=8.8, 4.9 Hz, 1H) 7.93 (d, J=8.3 Hz, 1H) 8.03 (broad s, 1H) 8.62 (dd, J=19.8, 8.1 Hz, 1H) 8.93 (d, J=8.6 Hz, 1H) 13.12 (s, 1H).

Mass spectrum (LC/MS; method A): retention time Tr (min)=0.93; m/z=548 [M+H]+; m/z=546 [M−H]−.

EXAMPLE 97

Synthesis of 4-[4-(6-fluoro-1H-benzimidazol-2-yl)-9H-carbazol-9-yl]-2-[1 (S,R),2(R,S)-2-hydroxymethylcyclohexyl-1-amino])benzamide

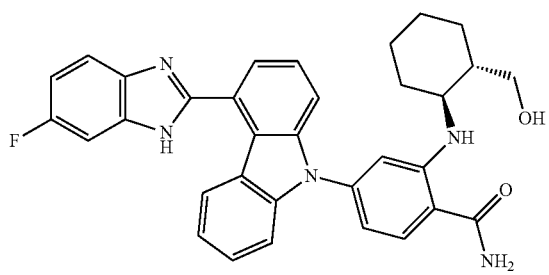

The process is carried out as in stage 3 of Example 3, but using 160 mg of 2-fluoro-4-[4-(6-fluoro-1H-benzimidazol-2-yl)carbazol-9-yl]benzonitrile, obtained according to stage 2 of Example 3, 210 mg of potassium carbonate, 504 mg of trans-2-hydroxymethylcyclohexanamine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and ethanol (96/4 by volume), followed by crystallization from 10 ml of diisopropyl ether, 99 mg of 4-[4-(6-fluoro-1H-benzimidazol-2-yl)-9H-carbazol-9-yl]-2-[1 (S,R),2(R,S)-2-hydroxymethylcyclohexyl-1-amino]benzamide are thus obtained in the form of shiny ecru crystals, the characteristics of which are the following:

TLC on silica gel: Rf=0.10 (dichloromethane/ethanol 95/5).

1H NMR spectrum (400 MHz, DMSO-$d_6$, δ ppm): 1.11-1.32 (m, 4H) 1.37-1.51 (m, 1H) 1.50-1.73 (m, 2H) 1.81 (d, J=6.8 Hz, 1H) 2.02 (d, J=12.7 Hz, 1H) 3.24-3.48 (masked m, 2H) 3.49-3.60 (m, 1H) 4.43 (t, J=4.9 Hz, 1H) 6.68 (d, J=8.8 Hz, 1H) 6.91 (s, 1H) 7.05-7.25 (m, 2H) 7.24-7.51 (m, 3H) 7.54-7.73 (m, 4H) 7.76-7.96 (m, 2H) 8.01 (broad s, 1H) 8.45-8.74 (m, 2H) 13.11 (broad s, 1H).

Mass spectrum (LC/MS; method A): retention time Tr (min)=0.94; m/z=548 [M+H]+; m/z=546 [M−H]−.

EXAMPLE 98

Synthesis of 2-{(R)-(1-azabicyclo[2.2.2]oct-3-yl)amino}-4-[4-(6-fluoro-1H-benzimidazol-2-yl)-9H-carbazol-9-yl]benzamide

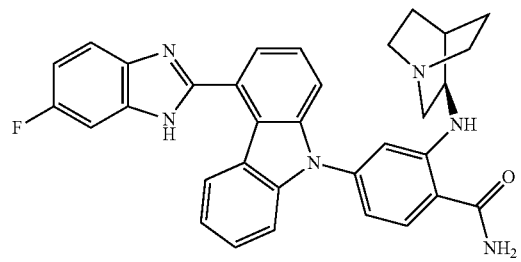

The process is carried out as in stage 3 of Example 3, but using 160 mg of 2-fluoro-4-[4-(6-fluoro-1H-benzimidazol-2-yl)carbazol-9-yl]benzonitrile, obtained according to stage 2 of Example 3, 210 mg of potassium carbonate, 806 mg of (R)-(+)-3-aminoquinuclidine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and a 7M solution of ammonia in methanol (95/5 by volume), followed by crystallization from 10 ml of diisopropyl ether, 67 mg of 2-{(R)-(1-azabicyclo[2.2.2]oct-3-yl)amino}-4-[4-(6-fluoro-1H-benzimidazol-2-yl)-9H-carbazol-9-yl]benzamide are thus obtained in the form of an ecru foam, the characteristics of which are the following:

TLC on silica gel: Rf=0.13 (dichloromethane/7M ammonia in methanol 95/5).

1H NMR spectrum (400 MHz, DMSO-$d_6$, δ ppm): 1.32-1.68 (m, 3H) 1.75 (broad s, 1H) 1.90 (broad s, 1H) 2.45 (d, J=12.7 Hz, 1H) 2.54-2.87 (m, 4H) 3.11-3.28 (m, 1H) 3.54 (broad s, 1H) 6.59-6.88 (m, 2H) 7.19 (t, J=7.1 Hz, 2H) 7.25-7.51 (m, 3H) 7.53-7.74 (m, 4H) 7.72-8.01 (m, 2H) 8.06 (broad s, 1H) 8.64 (broad s, 1H) 8.97 (d, J=6.6 Hz, 1H) 13.14 (broad s, 1H).

Mass spectrum (LC/MS; method A): retention time Tr (min)=0.67; m/z=545 [M+H]+; m/z=543 μM−H]−.

EXAMPLE 99

Synthesis of 2-{(S)-(1-azabicyclo[2.2.2]oct-3-yl)amino}-4-[4-(6-fluoro-1H-benzimidazol-2-yl)-9H-carbazol-9-yl]benzamide

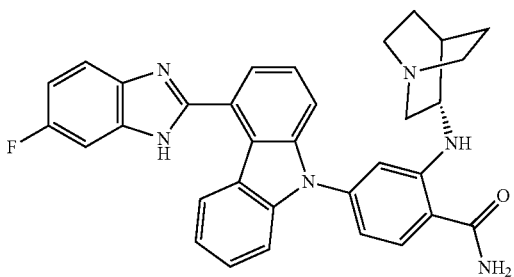

The process is carried out as in stage 3 of Example 3, but using 160 mg of 2-fluoro-4-[4-(6-fluoro-1H-benzimidazol-2-yl)carbazol-9-yl]benzonitrile, obtained according to stage 2 of Example 3, 210 mg of potassium carbonate, 806 mg of (S)-(−)-3-aminoquinuclidine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and a 7M solution of ammonia in methanol (95/5 by volume), followed by crystallization from 10 ml of diisopropyl ether, 42 mg of 2-{(S)-(1-azabicyclo[2.2.2]oct-3-yl)amino}-4-[4-(6-fluoro-1H-benzimidazol-2-yl)-9H-carbazol-9-yl]benzamide are thus obtained in the form of an ecru powder, the characteristics of which are the following:

TLC on silica gel: Rf=0.13 (dichloromethane/7M ammonia in methanol 95/5)

Mass spectrum (LC/MS; method A): retention time Tr (min)=0.66; m/z=545 [M+H]+; m/z=543 [M−H]−.

EXAMPLE 100

Synthesis of 2-[1(R,S),2(R,S)-2-hydroxymethylcyclohexyl-1-amino]-4-[4-(quinolin-3-2-yl)-9H-carbazol-9-yl]benzamide

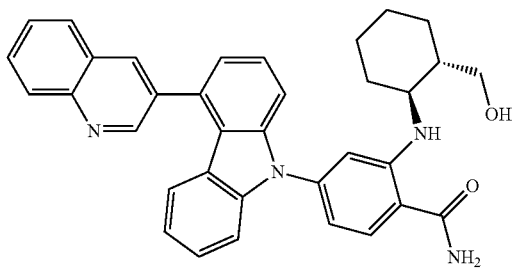

The process is carried out as in stage 3 of Example 3, but using 157 mg of 2-fluoro-4-[4-(6-fluoro-1H-benzimidazol-2-yl)carbazol-9-yl]benzonitrile, obtained according to stage 1 of Example 32, 210 mg of potassium carbonate, 504 mg of trans-2-hydroxymethylcyclohexanamine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 10 ml of diisopropyl ether, 100.5 mg of 2-[1(R,S),2(R,S)-2-hydroxymethyl-cyclohexyl-1-amino]-4-[4-(quinolin-3-2-yl)-9H-carbazol-9-yl]benzamide are thus obtained in the form of an off-white powder, the characteristics of which are the following:

TLC on silica gel: Rf=0.20 (dichloromethane/ethanol 95/5)

1H NMR spectrum (400 MHz, DMSO-$d_6$, δ ppm): 1.09-1.35 (m, 4H) 1.34-1.52 (m, 1H) 1.51-1.73 (m, 2H) 1.73-1.89 (m, 1H) 1.94-2.10 (m, 1H) 3.41-3.63 (masked m, 3H) 4.45 (broad s, 1H) 6.70 (d, J=8.3 Hz, 1H) 6.93 (broad s, 1H) 6.97-7.09 (m, 1H) 7.25-7.36 (m 4H) 7.57 (m, 3H) 7.74 (t, J=7.5 Hz, 1H) 7.82-7.95 (m, 2H) 8.01 (broad s, 1H) 8.14 (d, J=8.3 Hz, 1H) 8.19 (d, J=8.3 Hz, 1H) 8.58 (d, J=7.6 Hz, 1H) 8.64 (broad s, 1H) 9.16 (broad s, 1H).

Mass spectrum (LC/MS; method C): retention time Tr (min)=4.83; m/z=541 [M+H]+; m/z=539 [M−H]−.

EXAMPLE 101

Synthesis of 2-[1(S,R),2(R,S)-2-hydroxymethylcyclohexyl-1-amino]-4-[4-(quinolin-3-2-yl)-9H-carbazol-9-yl]benzamide The process is carried out as in stage 3 of Example 3, but using 157 mg of 2-fluoro-4-[4-(6-fluoro-1H-benzimidazol-2-yl)-9H-carbazol-9-yl]benzonitrile, obtained according to stage 1 of Example 32, 210 mg of potassium carbonate, 504 mg of cis-2-hydroxymethylcyclohexanamine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and ethanol (95/5 by volume), followed by crystallization from 10 ml of diisopropyl ether, 93 mg of 2-[1(S,R),2(R,S)-2-hydroxymethylcyclohexyl-1-amino]-4-[4-(quinolin-3-2-yl)-9H-carbazol-9-yl]benzamide are thus obtained in the form of an off-white powder, the characteristics of which are the following:

TLC on silica gel: Rf=0.20 (dichloromethane/ethanol 95/5)

1H NMR spectrum (400 MHz, DMSO-$d_6$, δ ppm): 1.20-1.88 (m, 9H) 3.23-3.33 (masked m, 2H) 3.88 (d, J=4.4 Hz, 1H) 4.46 (t, J=5.0 Hz, 1H) 6.72 (d, J=8.1 Hz, 1H) 6.96 (s, 1H) 7.03 (t, J=7.6 Hz, 1H) 7.19-7.36 (m, 3H) 7.40 (t, J=7.7 Hz, 1 H) 7.50 (d, J=8.3 Hz, 1H) 7.55-7.64 (m, 2H) 7.67-7.81 (m, 1H) 7.89 (t, J=7.7 Hz, 1H) 7.93 (d, J=8.6 Hz, 1H) 8.03 (broad s, 1H) 8.14 (d, J=8.1 Hz, 1H) 8.19 (d, J=8.6 Hz, 1H) 8.64 (d, J=1.7 Hz, 1H) 8.94 (d, J=8.6 Hz, 1H) 9.16 (d, J=2.0 Hz, 1H).

Mass spectrum (LC/MS; method C): retention time Tr (min)=4.77; m/z=541 [M+H]+; m/z=539 [M−H]−.

EXAMPLE 102

Synthesis of [4-(6-fluoro-1H-benzimidazol-2-yl)-9H-carbazol-9-yl]-2-[(4-hydroxy-1-methylpiperidin-4-ylmethyl)amino]benzamide

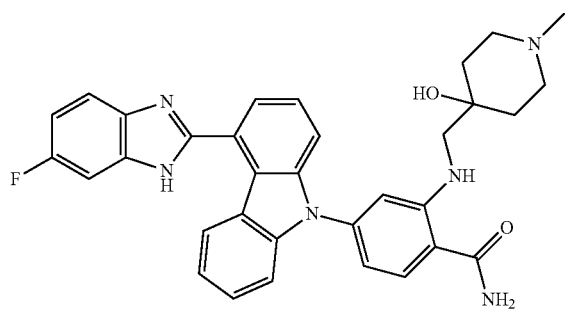

The process is carried out as in stage 3 of Example 3, but using 150 mg of 2-fluoro-4-[4-(6-fluoro-1H-benzimidazol-2-yl)-9H-carbazol-9-yl]benzonitrile, obtained according to stage 2 of Example 3, 148 mg of potassium carbonate and 412 mg of 4-aminomethyl-1-methylpiperidin-4-ol in 1.5 ml of dimethyl sulphoxide, in a microwave for 1 hour and 30 minutes at 115° C. 0.678 ml of a 1M aqueous solution of sodium hydroxide, 0.656 ml of a 30% aqueous solution of hydrogen peroxide and 3.6 ml of ethanol are then added to the reaction medium. After treatment as in stage 3 of Example 3, and then purification by flash chromatography on silica gel, elution being carried out with a mixture of dichloromethane and a 7M solution of ammonia in methanol (95/5 by volume), 3 mg of [4-(6-fluoro-1H-benzimidazol-2-yl)-9H-carbazol-9-yl]-2-[(4-hydroxy-1-methylpiperidin-4-ylmethyl)amino]benzamide are thus obtained in the form of a white powder, the characteristic of which is the following:

Mass spectrum (LC/MS; method C): retention time Tr (min)=4.48; m/z=562 [M+H]+; m/z=560 [M−H]−.

EXAMPLE 103

Synthesis of 2-[(4-hydroxy-1-methylpiperidin-4-ylmethyl)-amino]-[4-(quinolin-3-yl)-9H-carbazol-9-yl]benzamide

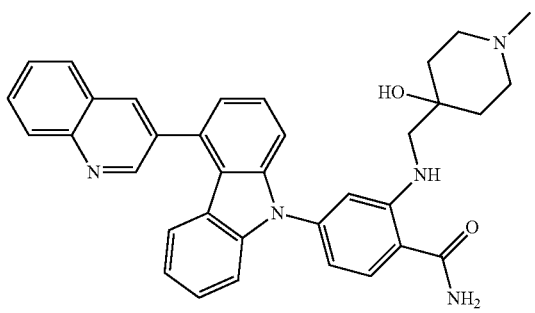

The process is carried out as in stage 3 of Example 3, but using 147.6 mg of 2-fluoro-4-[4-(quinolin-3-yl)-9H-carbazol-9-yl]benzonitrile, obtained according to stage 1 of Example 32, 148 mg of potassium carbonate and 412 mg of 4-aminomethyl-1-methylpiperidin-4-ol in 1.5 ml of dimethyl sulphoxide, in a microwave for 1 hour and 30 minutes at 115° C. 0.678 ml of a 1M aqueous solution of sodium hydroxide, 0.656 ml of a 30% aqueous solution of hydrogen peroxide and 3.6 ml of ethanol are then added to the reaction medium. After treatment as in stage 3 of Example 3, and then purification by flash chromatography on silica gel, elution being carried out with a mixture of dichloromethane and a 7M solution of ammonia in methanol (95/5 by volume), 15 mg of 2-[(4-hydroxy-1-methylpiperidin-4-ylmethyl)amino]-[4-(quinolin-3-yl)-9H-carbazol-9-yl]benzamide are thus obtained in the form of a white powder, the characteristics of which are the following:

Mass spectrum (LC/MS; method C): retention time Tr (min)=3.33; m/z=556 [M+H]+; m/z=554 [M−H]−.

EXAMPLE 104

Synthesis of 4-[4-(6-fluoro-1H-benzimidazol-2-yl)-9H-carbazol-9-yl]-2-[(pyridin-3-ylmethyl)amino]benzamide

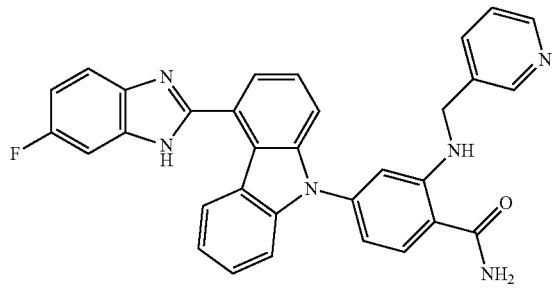

The process is carried out as in stage 3 of Example 3, but using 168.2 mg of 2-fluoro-4-[4-(6-fluoro-1H-benzimidazol-2-yl)-9H-carbazol-9-yl]benzonitrile, obtained according to stage 2 of Example 3, 166 mg of potassium carbonate and 346 mg of 3-(aminomethyl)pyridine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), 35 mg of 414-(6-fluoro-1H-benzimidazol-2-yl)-9H-carbazol-9-yl]-2-[(pyridin-3-ylmethyl)-amino]benzamide are thus obtained in the form of a white powder, the characteristics of which are the following:

1H NMR spectrum (300 MHz, DMSO-$d_6$, δ ppm): 4.54 (d, J=5.6 Hz, 2H) 6.66-6.88 (m, 2H) 6.99-7.21 (m, 3H) 7.25 (d, J=8.2 Hz, 1H) 7.33 (t, J=7.7 Hz, 1H) 7.37-7.56 (m, 4H) 7.61 (d, J=7.3 Hz, 1H) 7.64-7.79 (m, 2H) 7.95 (d, J=8.4 Hz, 1H) 8.05 (broad s, 1H) 8.51-8.62 (m, 3H) 8.97 (t, J=6.3 Hz, 1H) 13.05 (broad s, 1 H).

Mass spectrum (LC/MS method A): retention time Tr (min)=0.68; [M+H]+m/z 527; [M+H]− m/z 525.

EXAMPLE 105

Synthesis of 2-[(pyridin-3-ylmethyl)amino]-4-[4-(quinolin-3-yl)-9H-carbazol-9-yl]benzamide

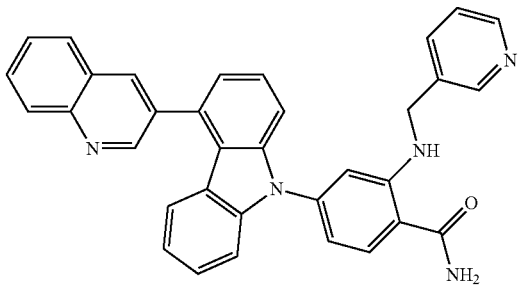

The process is carried out as in stage 3 of Example 3, but using 165.4 mg of 2-fluoro-4-[4-(quinolin-3-yl)-9H-carbazol-9-yl]benzonitrile, obtained according to stage 1 of Example 32, 166 mg of potassium carbonate and 346 mg of 3-(aminomethyl)pyridine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), 98 mg of 2-[(pyridin-3-ylmethyl)amino]-4-[4-(quinolin-3-yl)-9H-carbazol-9-yl]benzamide are thus obtained in the form of a white powder, the characteristics of which are the following:

1H NMR spectrum (300 MHz, DMSO-$d_6$, δ ppm): 4.55 (d, J=6.0 Hz, 2H) 6.73-6.86 (m, 2H) 6.98 (t, J=7.5 Hz, 1H) 7.09-7.32 (m, 5H) 7.33-7.52 (m, 3H) 7.64-7.80 (m, 2H) 7.88 (t, J=7.7 Hz, 1H) 7.95 (d, J=8.4 Hz, 1H) 8.05 (broad s, 1H) 8.12 (d, J=7.8 Hz, 1H) 8.18 (d, J=8.7 Hz, 1H) 8.50-8.58 (m, 2H) 8.60 (d, J=1.6 Hz, 1H) 8.98 (t, J=6.0 Hz, 1H) 9.12 (d, J=2.2 Hz, 1H)

Mass spectrum (LC/MS method A): retention time Tr (min)=0.85; [M+H]+ m/z 520; [M+H]− m/z 518.

EXAMPLE 106

Synthesis of 4-[4-(6-fluoro-1H-benzimidazol-2-yl)-9H-carbazol-9-yl]-2-[2-(pyridin-3-yl)ethylamino]benzamide

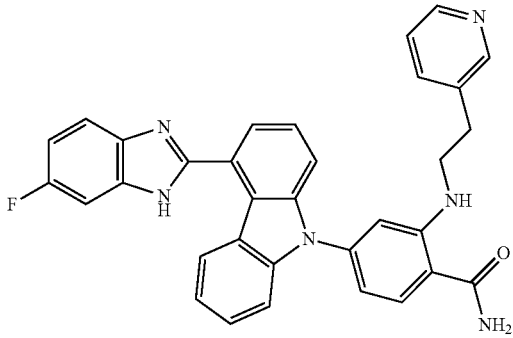

The process is carried out as in stage 3 of Example 3, but using 168.2 mg of 2-fluoro-4-[4-(6-fluoro-1H-benzimidazol-2-yl)-9H-carbazol-9-yl]benzonitrile, obtained according to stage 2 of Example 3, 166 mg of potassium carbonate and 391 mg of 3-(2-aminoethyl)pyridine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), 70 mg of 4-[4-(6-fluoro-1H-benzimidazol-2-yl)-9H-carbazol-9-yl]-2-[2-(pyridin-3-yl)-ethylamino]benzamide are thus obtained in the form of a white powder, the characteristics of which are the following:

1H NMR spectrum (400 MHz, DMSO-$d_6$, δ ppm): 2.94 (t, J=7.0 Hz, 2H) 3.41-3.50 (m, 2H) 6.79 (dd, J=8.3, 1.7 Hz, 1H) 6.97 (d, J=1.7 Hz, 1H) 7.03 (t, J=7.6 Hz, 1 H) 7.25 (d, J=7.8 Hz, 1H) 7.27-7.33 (m, 2H) 7.36 (br. s., 1H) 7.40 (t, J=7.7 Hz, 1 H) 7.49 (d, J=8.1 Hz, 1H) 7.54-7.63 (m, 2H) 7.66-7.78 (m, 2H) 7.89 (t, J=7.6 Hz, 1H) 7.93 (d, J=8.3 Hz, 1H) 8.03 (broad s, 1H) 8.14 (d, J=8.1 Hz, 1H) 8.19 (d, J=8.6 Hz, 1H) 8.41 (dd, J=4.6, 1.5 Hz, 1H) 8.50 (d, J=2.0 Hz, 1H) 8.59 (t, J=5.5 Hz, 1H) 8.64 (d, J=2.2 Hz, 1H) 9.16 (d, J=2.2 Hz, 1H).

Mass spectrum (LC/MS method A): retention time Tr (min)=0.87; [M+H]+ m/z 534; [M+H]− m/z 532.

EXAMPLE 107

Synthesis of 2-[2-(pyridin-3-yl)ethylamino]-4-[4-(quinolin-3-yl)-9H-carbazol-9-yl]benzamide

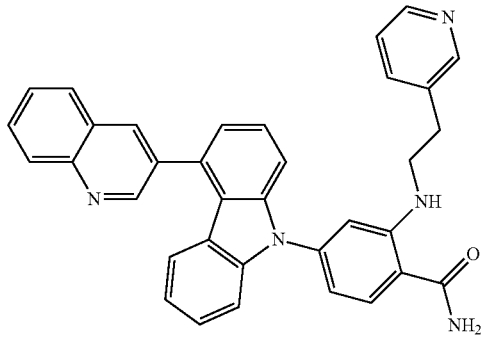

The process is carried out as in stage 3 of Example 3, but using 165.4 mg of 2-fluoro-4-[4-(quinolin-3-yl)-9H-carbazol-9-yl]benzonitrile, obtained according to stage 1 of Example 32, 166 mg of potassium carbonate and 346 mg of 3-(2-aminoethyl)pyridine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and ethanol (95/5 by volume), 84 mg of 2-[2-(pyridin-3-yl)-ethylamino]-4-[4-(quinolin-3-yl)-9H-carbazol-9-yl]benzamide are thus obtained in the form of a white powder, the characteristics of which are the following:

1H NMR spectrum (400 MHz, DMSO-$d_6$, δ ppm): 2.93 (t, J=6.8 Hz, 2H) 3.44 (q, J=6.8 Hz, 2H) 6.77 (dd, J=8.1, 1.2 Hz, 1H) 6.95 (d, J=1.2 Hz, 1H) 7.07-7.25 (m, 2H) 7.30 (dd, J=7.8, 4.6 Hz, 1H) 7.36 (broad s, 1H) 7.47 (d, J=3.7 Hz, 2H) 7.56-7.73 (m, 5H) 7.79 (broad s, 1H) 7.93 (d, J=8.3 Hz, 1H) 8.03 (broad s, 1H) 8.41 (d, J=4.6 Hz, 1H) 8.49 (d, J=1.7 Hz, 1H) 8.59 (t, J=5.5 Hz, 1H) 8.64 (d, J=7.1 Hz, 1H) 13.13 (broad s, 1H).

Mass spectrum (LC/MS method A): retention time Tr (min)=0.70; [M+H]+ m/z 541; [M+H]− m/z 539.

EXAMPLE 108

Synthesis of 2-((R)-(1-azabicyclo[2.2.2]oct-3-yl)amino)-4-[4-(quinolin-3-yl)-9H-carbazol-9-yl]benzamide

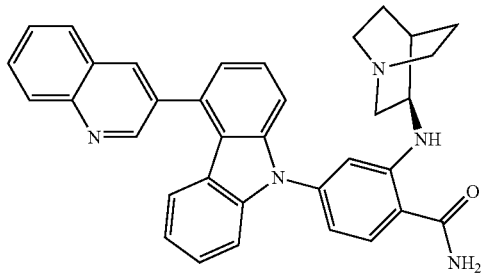

The process is carried out as in stage 3 of Example 3, but using 157.4 mg of 2-fluoro-4-[4-(6-fluoro-1H-benzimidazol-2-yl)carbazol-9-yl]benzonitrile, obtained according to stage 2 of Example 3, 210 mg of potassium carbonate, 806 mg of (R)-(+)-3-aminoquinuclidine hydrochloride and 308 mg of triethylamine in 3.2 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 6.5 ml of ethanol are then added to the reaction medium. After treatment as in stage 3 of Example 3, and then purification by flash chromatography on silica gel, elution being carried out with a mixture of dichloromethane and a 7M solution of ammonia in methanol (95/5 by volume), followed by crystallization from 10 ml of diisopropyl ether, 61.5 mg of 2-{(R)-(1-azabicyclo[2.2.2]oct-3-yl)amino}-4-[4-(quinolin-3-yl)-9H-carbazol-9-yl]benzamide are thus obtained in the form of an ecru powder, the characteristics of which are the following:

TLC on silica gel: Rf=0.12 (dichloromethane/7M ammonia in methanol 95/5).

1H NMR spectrum (400 MHz, DMSO-$d_6$, δ ppm): 1.36-1.65 (m, 3H) 1.69-1.84 (m, 1H) 1.92 (broad s, 1H) 2.40-2.46 (m, 1H) 2.56-2.85 (m, 3H) 3.14-3.29 (m, 2H) 3.54 (broad s, 1H) 6.70-6.85 (m, 2H) 7.02 (t, J=7.6 Hz, 1H) 7.19-7.35 (m, 3H) 7.36-7.49 (m, 2H) 7.50-7.63 (m, 2H) 7.73 (t, J=7.5 Hz, 1H) 7.89 (t, J=7.6 Hz, 1H) 7.95 (d, J=8.3 Hz, 1H) 8.02 (broad s, 1H) 8.14 (d, J=7.8 Hz, 1H) 8.19 (d, J=8.3 Hz, 1H) 8.62 (s, 1H) 8.95 (d, J=6.8 Hz, 1H) 9.15 (d, J=2.0 Hz, 1H)

Mass spectrum (LC/MS method A): retention time Tr (min)=0.82; [M+H]+ m/z 538.

EXAMPLE 109

Synthesis of 2-(3(R,S)-hydroxycyclohexyl-1(R,S)-amino)-4-[4-(quinolin-3-yl)-9H-carbazol-9-yl]benzamide

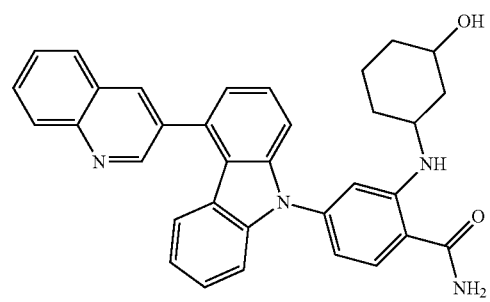

The process is carried out as in stage 3 of Example 3, but using 157 mg of 2-fluoro-4-[4-(quinolin-3-yl)-9H-carbazol-9-yl]benzonitrile, obtained according to stage 1 of Example 32, 210 mg of potassium carbonate and 0.525 g of 3(R,S)-aminocyclohexan-1(R,S)-ol in 3.8 ml of dimethyl sulphoxide, in a microwave for 1 hour and 30 minutes at 115° C. 0.76 ml of a 1M aqueous solution of sodium hydroxide, 0.7 ml of a 30% aqueous solution of hydrogen peroxide and 7.5 ml of ethanol are then added to the reaction medium. After treatment as in stage 3 of Example 3, and then purification by flash chromatography on silica gel, elution being carried out with a mixture of dichloromethane and ethanol (94/6 by volume), followed by crystallization from 10 ml of diisopropyl ether, 137 mg of 2-(3(R,S)-hydroxycyclohexyl-1(R,S)-amino)-4-[4-(quinolin-3-yl)-9H-carbazol-9-yl]benzamide, as an approximately 70/30 mixture of two diastereoisomers, are thus obtained in the form of an off-white powder, the characteristics of which are the following:

TLC on silica gel: Rf=0.14 (dichloromethane/ethanol 96/4).

1H NMR spectrum (400 MHz, DMSO-$d_6$, δ ppm): 1.32-1.82 (m, 4H) 1.96 (d, J=11.7 Hz, 2H) 2.20 (d, J=11.2 Hz, 2H) 3.33-3.49 (m, 1H) 3.70-3.88 (m, 1H) 4.43-4.60 (m, 1H) 6.73 (d, J=8.3 Hz, 1H) 6.89 (d, J=10.5 Hz, 1H) 7.02 (t, J=7.3 Hz, 1H) 7.16-7.34 (m, 3H) 7.36-7.48 (m, 2H) 7.48-7.56 (m, 1H) 7.60 (t, J=7.7 Hz, 1 H) 7.73 (t, J=7.6 Hz, 1H) 7.80-7.95 (m, 2H) 7.98 (broad s, 1H) 8.13 (d, J=8.1 Hz, 1 H) 8.19 (d, J=8.3 Hz, 1H) 8.36-8.69 (m, 2H) 9.16 (s, 1H)

Mass spectrum (LC/MS method A): retention time Tr (min)=1.05; [M+H]+ m/z 527.

EXAMPLE 110

Synthesis of 4-[4-(6-fluoro-1H-benzimidazol-2-yl)-9H-carbazol-9-yl]-2-[(1-methyl-1H-imidazol-4-yl)methylamino]benzamide

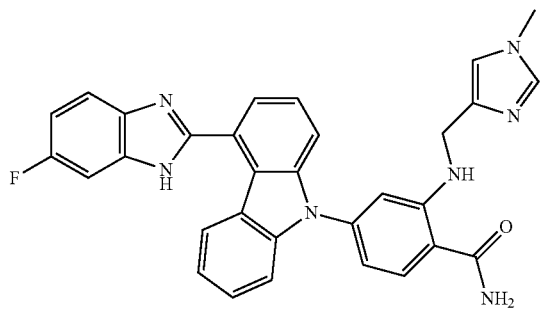

The process is carried out as in stage 3 of Example 3, but using 160 mg of 2-fluoro-4-[4-(6-fluoro-1H-benzimidazol-2-yl)-9H-carbazol-9-yl]benzonitrile, obtained according to stage 2 of Example 3, 210 mg of potassium carbonate and 338.5 mg of (1-methyl-1H-imidazol-4-yl)methylamine in 3.3 ml of dimethyl sulphoxide, in a microwave for 1 hour and 30 minutes at 115° C. 0.76 ml of a 1M aqueous solution of sodium hydroxide, 0.70 ml of a 30% aqueous solution of hydrogen peroxide and 6.6 ml of ethanol are then added to the reaction medium. After treatment as in stage 3 of Example 3, and then purification by flash chromatography on silica gel, elution being carried out with a mixture of dichloromethane and ethanol (95/5 by volume), 78 mg of 4-[4-(6-fluoro-1H-benzimidazol-2-yl)-9H-carbazol-9-yl]-2-[(1-methyl-1H-imidazol-4-yl)methylamino]benzamide are thus obtained in the form of an ecru powder, the characteristics of which are the following:

1H NMR spectrum (400 MHz, DMSO-$d_6$, δ ppm): 3.64 (s, 3H) 4.22 (d, J=5.1 Hz, 2H) 6.76 (dd, J=8.3, 2.0 Hz, 1H) 6.96 (d, J=2.0 Hz, 1H) 6.99 (s, 1H) 7.07-7.49 (m, 5H) 7.52 (s, 1H) 7.54-7.69 (m, 4H) 7.73-8.07 (m, 3H) 8.49-8.62 (m, 1H) 8.69 (t, J=5.3 Hz, 1H) 13.08 (broad s, 1H)

Mass spectrum (LC/MS method A): retention time Tr (min)=0.64; [M+H]+ m/z 530; [M+H]− m/z 528.

EXAMPLE 111

Synthesis of 4-[4-(6-fluoro-1H-benzimidazol-2-yl)-9H-carbazol-9-yl]-2-[(1-hydroxycyclopentan-1-yl)methylamino]benzamide

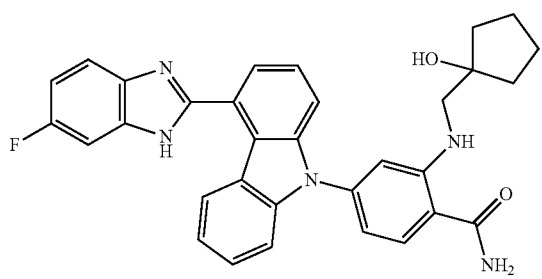

The process is carried out as in stage 3 of Example 3, but using 160 mg of 2-fluoro-4-[4-(6-fluoro-1H-benzimidazol-2-yl)-9H-carbazol-9-yl]benzonitrile, obtained according to stage 2 of Example 3, 210 mg of potassium carbonate and 351 mg of 1-(aminomethyl)cyclopentan-1-ol in 3.3 ml of dimethyl sulphoxide, in a microwave for 1 hour and 30 minutes at 115° C. 0.76 ml of a 1M aqueous solution of sodium hydroxide, 0.70 ml of a 30% aqueous solution of hydrogen peroxide and 6.6 ml of ethanol are then added to the reaction medium. After treatment as in stage 3 of Example 3, and then purification by flash chromatography on silica gel, elution being carried out with a mixture of dichloromethane and methanol (95/5 by volume), 14.4 mg of 4-[4-(6-fluoro-1H-benzimidazol-2-yl)-9H-carbazol-9-yl]-2-[(1-hydroxycyclopentan-1-yl)methylamino]benzamide are thus obtained in the form of an ecru powder, the characteristics of which are the following:

1H NMR spectrum (400 MHz, DMSO-$d_6$, δ ppm): 1.43-1.79 (m, 8H) 3.14 (d, J=5.1 Hz, 2H) 4.48 (s, 1H) 6.71 (dd, J=8.2, 1.8 Hz, 1H) 6.88 (d, J=1.7 Hz, 1H) 7.00-7.34 (m, 3H) 7.35-7.76 (m, 7H) 7.77-8.00 (m, 2H) 8.50-8.74 (m, 2H) 13.08 (broad s, 1H)

Mass spectrum (LC/MS method A): retention time Tr (min)=0.92; [M+H]+ m/z 534; [M+H]− m/z 532.

EXAMPLE 112

Synthesis of 4-[4-(6-cyanopyridin-3-yl)-9H-carbazol-9-yl]-2-[(3-hydroxypropyl)amino]benzamide

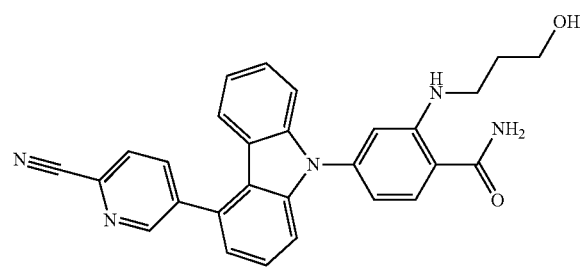

Stage 1: 0.9 g of potassium carbonate and 3.3 ml of 3-amino-1-propanol are successively added to a solution of 1 g of 2-methylpropan-2-yl 4-[4-(6-cyanopyridin-3-yl)-9H-carbazol-9-yl]-2-fluorobenzoate, obtained in stage 1 of Example 49, in 8 ml of dimethyl sulphoxide. The reaction mixture is heated at 90° C. for 1 and a half hours in a microwave, and then diluted with distilled water. The aqueous phase is washed twice with ethyl acetate and the combined organic phases are washed with water and a saturated solution of sodium chloride, dried over magnesium sulphate and filtered. The residue is purified by silica gel chromatography, elution being carried out with a mixture of cyclohexane and ethyl acetate (70/30 by volume), so as to give 0.7 g of 2-methylpropan-2-yl 4-[4-(6-cyanopyridin-3-yl)-9H-carbazol-9-yl]-2-[(3-hydroxypropyl)-amino]benzoate in the form of a yellow oil, the characteristics of which are the following:

1H NMR spectrum (400 MHz, δ in ppm, DMSO-d6): 1.60 (s, 9H) 1.76 (quin, J=6.4 Hz, 2H) 3.23-3.30 (m, 2H) 3.47-3.54 (m, 2H) 4.59 (t, J=5.0 Hz, 1H) 6.80 (dd, J=8.3, 2.0 Hz, 1H) 6.95 (d, J=2.0 Hz, 1H) 7.08-7.15 (m, 1H) 7.24 (dd, J=6.5, 1.8 Hz, 1H) 7.31 (d, J=8.1 Hz, 1H) 7.44 (td, J=7.7, 1.2 Hz, 1H) 7.51 (d, J=8.1 Hz, 1 H) 7.55-7.63 (m, 2H) 7.94 (t, J=5.4 Hz, 1H) 8.05 (d, J=8.3 Hz, 1H) 8.30 (dd, J=7.1, 1.0 Hz, 1H) 8.35 (dd, J=8.1, 2.2 Hz, 1H) 9.03 (dd, J=2.1, 0.9 Hz, 1H)

Mass spectrum (LC/MS; method A): retention time Tr (min)=1.27; m/z=519 [M+H]+.

Stage 2: 8 ml of 1N hydrochloric acid are added to a solution of 0.7 g of 2-methylpropan-2-yl 4-[4-(6-cyanopyridin-3-yl)-9H-carbazol-9-yl]-2-[(3-hydroxypropyl)amino] benzoate in 10 ml of dioxane. The reaction mixture is heated at 100° C. in a microwave for 2 hours and then concentrated under reduced pressure. The residue is purified by silica gel chromatography, elution being carried out with a mixture of dichloromethane and methanol (96/4 by volume), so as to give 190 mg of 4-[4-(6-cyanopyridin-3-yl)-9H-carbazol-9-yl]-2-[(3-hydroxypropyl)amino]benzoic acid in the form of a pale yellow powder the characteristics of which are the following:

1H NMR spectrum (400 MHz, δ in ppm, DMSO-d6): 1.75 (quin, J=6.4 Hz, 2H) 3.20-3.27 (m, 2H) 3.48-3.55 (m, 2H) 4.52 (t, J=4.9 Hz, 1H) 6.77 (dd, J=8.3, 2.0 Hz, 1H) 6.92 (d, J=2.0 Hz, 1H) 7.11 (td, J=7.8, 0.7 Hz, 1H) 7.23 (dd, J=6.7, 1.6 Hz, 1H) 7.31 (d, J=7.8 Hz, 1H) 7.44 (td, J=7.7, 1.0 Hz, 1H) 7.51 (d, J=8.3 Hz, 1H) 7.55-7.63 (m, 2H) 8.08 (d, J=8.3 Hz, 1H) 8.20 (broad s, 1H) 8.28 (d, J=8.1 Hz, 1H) 8.35 (dd, J=8.1, 2.2 Hz, 1H) 9.03 (dd, J=2.2, 0.7 Hz, 1H)

Mass spectrum (LC/MS; method A): retention time Tr (min)=1.05; m/z=463 [M+H]+; 461 [M+H]−.

Stage 3: 260 mg of (1H-benzotriazol-1-yloxy)[tris(dimethylamino)]phosphonium hexafluorophosphate (BOP), 79 mg of hydroxybenzotriazole (HOBT), 41 mg (0.8 mmol) of ammonium chloride and 0.26 ml of diisopropylethylamine are successively added to a solution of 180 mg of 4-[4-(6-cyanopyridin-3-yl)-9H-carbazol-9-yl]-2-[(3-hydroxypropyl)amino]benzoic acid in 10 ml of N,N-dimethylformamide. The reaction mixture is stirred at ambient temperature for 4 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of dichloromethane and methanol (96/4 by volume), and triturated in diisopropyl ether, so as to give 60 mg of 4-[4-(6-cyanopyridin-3-yl)-9H-carbazol-9-yl]-2-[(3-hydroxypropyl)amino]benzamide in the form of a white solid, the characteristics of which are the following:

Melting point (Buchi melting point B-545)=204° C.

1H NMR spectrum (400 MHz, δ in ppm, DMSO-d6): 1.72 (quin, J=6.5 Hz, 2H) 3.15-3.22 (m, 2H) 3.46-3.53 (m, 2H) 4.48 (t, J=5.0 Hz, 1H) 6.74 (dd, J=8.3, 1.7 Hz, 1H) 6.84 (d, J=1.7 Hz, 1H) 7.07-7.14 (m, 1H) 7.22 (dd, J=5.0, 3.5 Hz, 1H) 7.30 (broad s., 1H) 7.31 (d, J=7.8 Hz, 1H) 7.40-7.50 (m, 2H) 7.55-7.59 (m, 2H) 7.91 (d, J=8.3 Hz, 1H) 7.98 (broad s, 1H) 8.28 (d, J=7.6 Hz, 1H) 8.35 (dd, J=8.1, 2.2 Hz, 1H) 8.45 (t, J=5.1 Hz, 1H) 9.03 (d, J=1.5 Hz, 1H)

Mass spectrum (LC/MS; method A): retention time Tr (min)=0.97; m/z=462 [M+H]+; 460 [M−H]−.

EXAMPLE 113

Synthesis of 4-[4-(quinolin-3-yl)-9H-carbazol-9-yl]-2-(tetrahydropyran-4-yl)amino)benzamide

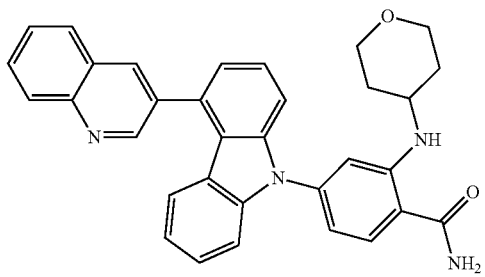

The process is carried out as in stage 3 of Example 3, but using 150 mg of 2-fluoro-4-[4-(quinolin-3-yl)-9H-carbazol-9-yl]benzonitrile, obtained according to stage 1 of Example 32, 150.5 mg of potassium carbonate, 0.500 g (3.63 mmol) of 4-aminotetrahydropyran hydrochloride and 0.367 g of triethylamine in 1.5 ml of dimethyl sulphoxide, in a microwave for 1 hour and 30 minutes at 115° C. 0.69 ml of a 1M aqueous solution of sodium hydroxide, 0.667 ml of a 30% aqueous solution of hydrogen peroxide and 3.5 ml of ethanol are then added to the reaction medium. After treatment as in stage 3 of Example 3, and then purification by flash chromatography on silica gel, elution being carried out with a mixture of dichloromethane and ethanol (97/3 by volume), followed by crystallization from 2 ml of diisopropyl ether, 65 mg of 4-[4-(quinolin-3-yl)-9H-carbazol-9-yl]-2-(tetrahydropyran-4-yl)amino)benzamide are thus obtained in the form of a beige powder, the characteristics of which are the following:

1H NMR spectrum (400 MHz, DMSO-$d_6$, δ ppm): 1.36-1.50 (m, 2H) 1.95 (d, J=10.8 Hz, 2H) 3.41 (t, J=9.8 Hz, 2H) 3.62-3.70 (m, 1H) 3.81 (dt, J=11.9, 3.9, 3.8 Hz, 2H) 6.76 (dd, J=8.3, 2.0 Hz, 1H) 6.98 (d, J=1.7 Hz, 1H) 7.02 (ddd, J=8.0, 6.8, 1.6 Hz, 1H) 7.25 (d, J=7.8 Hz, 1H) 7.30 (d, J=6.6 Hz, 1H) 7.33 (broad s, 1H) 7.36-7.46 (m, 2H) 7.50 (d, J=7.3 Hz, 1H) 7.58 (d, J=7.1 Hz, 1H) 7.73 (t, J=7.6 Hz, 1H) 7.88 (t, J=7.7 Hz, 1H) 7.94 (d, J=8.3 Hz, 1H) 8.01 (broad s, 1H) 8.14 (d, J=8.1 Hz, 1 H) 8.19 (d, J=8.3 Hz, 1H) 8.58 (d, J=7.3 Hz, 1H) 8.62 (d, J=2.2 Hz, 1H) 9.15 (d, J=2.2 Hz, 1H).

Mass spectrum (LC/MS; methode A): retention time Tr (min)=1.09; m/z=513 [M+H]+.

EXAMPLE 114

Synthesis of 4-[4-(6-fluoro-1H-benzimidazol-2-yl)-9H-carbazol-9-yl]-2-[(1-hydroxycyclopropan-1-yl)methylamino]benzamide

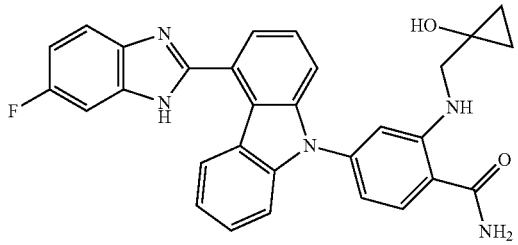

The process is carried out as in stage 3 of Example 3, but using 168.2 mg of 2-fluoro-4-[4-(6-fluoro-1H-benzimidazol-2-yl)-9H-carbazol-9-yl]benzonitrile, obtained according to stage 2 of Example 3, 165.8 mg of potassium carbonate and 279 mg of 1-(aminomethyl)cyclopropan-1-ol in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and methanol (95/5 by volume), 26 mg of 4-[4-(6-fluoro-1H-benzimidazol-2-yl)-9H-carbazol-9-yl]-2-[(1-hydroxycyclopropan-1-yl)methylamino]benzamide are thus obtained in the form of a pale yellow powder, the characteristics of which are the following:

1H NMR spectrum (400 MHz, DMSO-$d_6$, δ ppm): 0.39-0.55 (m, 2H) 0.56-0.72 (m, 2H) 3.23 (d, J=5.6 Hz, 1H) 5.41 (s, 1H) 6.73 (dd, J=8.3, 1.7 Hz, 1H) 6.89 (d, J=2.0 Hz, 1H) 7.02-7.32 (m, 3H) 7.33-7.82 (m, 7H) 7.84-8.06 (m, 2H) 8.57-8.70 (m, 2H) 13.07 (s, 1H).

EXAMPLE 115

Synthesis of 4-[4-(6-fluoro-1H-benzimidazol-2-yl)-9H-carbazol-9-yl]-2-[(1-methyl-1H-pyrazol-4-yl)methylamino]benzamide

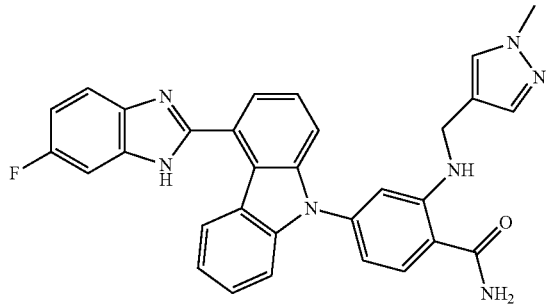

The process is carried out as in stage 3 of Example 3, but using 168.2 mg of 2-fluoro-4-[4-(6-fluoro-1H-benzimidazol-2-yl)-9H-carbazol-9-yl]benzonitrile, obtained according to stage 2 of Example 3, 165.8 mg of potassium carbonate and 356 mg of 4-aminomethyl-1-methyl-1H-pyrazole in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and methanol (95/5 by volume), 95 mg of 4-[4-(6-fluoro-1H-benzimidazol-2-yl)-9H-carbazol-9-yl]-2-[(1-methyl-1H-pyrazol-4-yl)methylamino]benzamide are thus obtained in the form of a pale yellow powder, the characteristics of which are the following:

1H NMR spectrum (400 MHz, DMSO-$d_6$, δ ppm): 3.82 (s, 3H) 4.24 (d, J=4.9 Hz, 2H) 6.77 (dd, J=8.3, 2.0 Hz, 1H) 6.89 (d, J=1.7 Hz, 1H) 7.09-7.21 (m, 2H) 7.24-7.39 (m, 3H) 7.43 (t, J=8.2 Hz, 1H) 7.46-7.54 (m, 2H) 7.57 (t, J=7.8 Hz, 1H) 7.60-7.80 (m, 3H) 7.87-8.07 (m, 2H) 8.56-8.65 (m, 2H) 13.07 (broad s, 1H).

Mass spectrum (LC/MS; method A): retention time Tr (min)=0.82; m/z=530 [M+H]+; m/z=528 [M−H]−.

EXAMPLE 116

Synthesis of 5-[4-(quinolin-3-yl)-9H-carbazol-9-yl]-3-(tetrahydropyran-4-yl)amino)pyridin-2-carboxamide

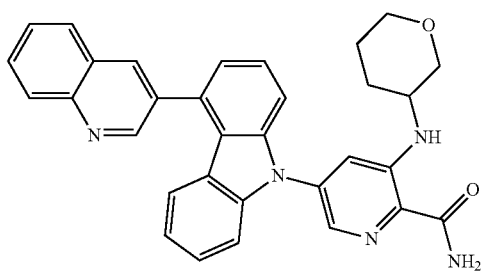

Stage 1: 200 mg of 2-cyano-3,5-difluoropyridine, 236 mg of 4-aminotetrahydropyran hydrochloride, 395 mg of potassium carbonate and 173.4 mg of triethylamine in 3 ml of dimethyl sulphoxide are introduced into a 5 ml microwave tube reactor. The mixture is then heated in a microwave for 1 hour at 115° C. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. After purification by flash chromatography on 25 g of silica gel, elution being carried out with mixtures of ethyl acetate and heptane (40/60 then 60/40 by volume), and the first eluted product being recovered, 80 mg of 2-cyano-5-fluoro-3-(tetrahydropyran-4-yl)aminopyridine are thus obtained in the form of an ecru powder, the characteristics of which are the following:

1H NMR spectrum (500 MHz, DMSO-$d_6$) δ ppm 1.55-1.68 (m, 2H) 1.78 (dd, J=12.5, 2.2 Hz, 2H) 3.40 (td, J=11.7, 1.5 Hz, 2H) 3.56-3.69 (m, 1H) 3.87 (dd, J=11.5, 2.7 Hz, 2H) 6.48 (d, J=7.8 Hz, 1H) 7.40 (dd, J=12.0, 2.2 Hz, 1H) 7.89 (d, J=2.4 Hz, 1H).

150 mg of 2-cyano-3-fluoro-5-(tetrahydropyran-4-yl)aminopyridine are also isolated, by recovering the second eluted product.

Stage 2: In a 25 ml three-necked flask, under an argon atmosphere, 98 mg of 4-(quinolin-3-yl)-9H-carbazole, obtained according to stage 1 of Example 2, are dissolved in 5 ml of dimethylformamide. 20 mg of sodium hydride at 60% in oil are then added and the mixture is stirred for 30 minutes at ambient temperature and then 30 minutes at 30° C. 81 mg of 2-cyano-5-fluoro-3-(tetrahydropyran-4-yl)aminopyridine, obtained in the preceding stage, are then added and the mixture is heated at 50° C. overnight. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. After purification by flash chromatography on 15 g of silica gel, elution being carried out with a gradient of mixtures of ethyl acetate and heptane (30/70 to 50/50 by volume), 95 mg of are thus obtained in the form of an ecru powder, the characteristic of which is the following:

LC/MS (method C): retention time=5.28 min.

Stage 3: 95 mg of 5-[4-(quinolin-3-yl)-9H-carbazol-9-yl]-3-(tetrahydropyran-4-yl)aminopyridinecarbonitrile, obtained in the preceding stage, are dissolved in 1 ml of dimethyl sulphoxide and 2.5 ml of ethanol, and then 0.384 ml of a 1M aqueous solution of sodium hydroxide and 0.352 ml of a 30% aqueous solution of hydrogen peroxide are successively added. After stirring for 1 hour at ambient temperature, the reaction medium is run into 50 ml of water and 50 ml of ethyl acetate. The aqueous phase is re-extracted twice with 25 ml of ethyl acetate. The combined organic phases are washed with water, dried over sodium sulphate and concentrated under reduced pressure. After purification by flash chromatography on 10 g of silica gel, elution being carried out with a mixture of dichloromethane and methanol (98/2 by volume), followed by crystallization from 2 ml of diethyl ether, 64 mg of 5-[4-(quinolin-3-yl)-9H-carbazol-9-yl]-3-(tetrahydropyran-4-yl)amino)pyridin-2-carboxamide are thus obtained in the form of a beige powder, the characteristics of which are the following:

1H NMR spectrum (400 MHz, DMSO-$d_6$, δ ppm): 1.38-1.53 (m, 2H) 1.96 (d, J=12.5 Hz, 2H) 3.39-3.48 (m, 2H) 3.66-3.79 (m, 1H) 3.83 (dt, J=11.5, 3.5 Hz, 2 H) 6.99-7.09 (m, 1H) 7.26 (d, J=8.1 Hz, 1H) 7.33 (d, J=6.8 Hz, 1H) 7.37-7.47 (m, 2H) 7.52 (d, J=8.3 Hz, 1H) 7.56-7.65 (m, 3H) 7.74 (t, J=7.6 Hz, 1H) 7.89 (td, J=7.6, 1.3 Hz, 1H) 8.03 (d, J=2.0 Hz, 1H) 8.09-8.24 (m, 3H) 8.62 (d, J=2.0 Hz, 1H) 8.87 (d, J=7.8 Hz, 1H) 9.15 (d, J=2.2 Hz, 1H).

Mass spectrum (LC/MS; method A): retention time Tr (min)=1.11; m/z=514 [M+H]+.

EXAMPLE 117

Synthesis of 4-[4-(6-fluoro-1H-benzimidazol-2-yl)-9H-carbazol-9-yl]-2-[(1-methyl-1H-imidazol-4-yl)ethylamino]benzamide

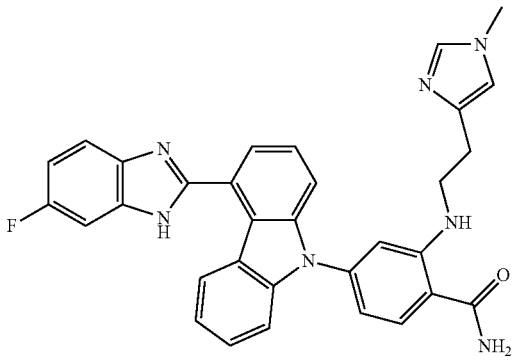

The process is carried out as in stage 3 of Example 3, but using 168.2 mg of 2-fluoro-4-[4-(6-fluoro-1H-benzimidazol-2-yl)-9H-carbazol-9-yl]benzonitrile, obtained according to stage 2 of Example 3, 165.8 mg of potassium carbonate, 517 mg of 2-(1-methyl-1H-imidazol-4-yl)ethylamine hydrochloride and 324 mg of triethylamine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on 10 g of silica gel, elution being carried out with a mixture of dichloromethane and methanol (95/5 by volume), 34 mg of 4-[4-(6-fluoro-1H-benzimidazol-2-y0-9H-carbazol-9-yl]-2-[(1-methyl-1H-imidazol-4-yl)ethylamino]benzamide are thus obtained in the form of a white solid, the characteristics of which are the following:

1H NMR spectrum (400 MHz, DMSO-d$_6$, δ ppm): 2.72 (t, J=7.0 Hz, 2H) 3.31-3.35 (masked m, 2H) 3.74 (s, 3H) 6.76 (dd, J=8.2, 1.8 Hz, 1H) 6.88 (d, J=2.0 Hz, 1 H) 7.09-7.22 (m, 2H) 7.24-7.38 (m, 2H) 7.39-7.56 (m, 4H) 7.56-7.81 (m, 4H) 7.93 (d, J=8.3 Hz, 1H) 7.99 (broad s, 1H) 8.53 (t, J=5.1 Hz, 1H) 8.63 (d, J=8.3 Hz, 1 H) 13.08 (broad s, 1H).

Mass spectrum (LC/MS; method A): retention time Tr (min)=0.86; m/z=544 [M+H]+; m/z=542 [M−H]−.

EXAMPLE 118

Synthesis of 4-[4-(6-fluoro-1H-benzimidazol-2-yl)-9H-carbazol-9-yl]-2-[2(R,S)-hydroxymethylcyclopentan-1(S,R)-amino]benzamide

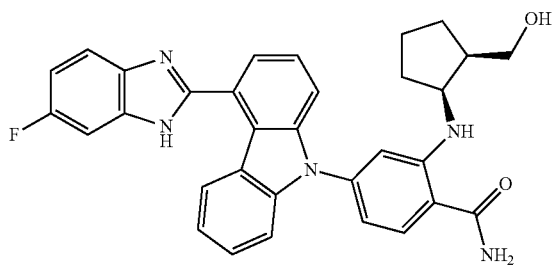

The process is carried out as in stage 3 of Example 3, but using 150 mg of 2-fluoro-4-[4-(6-fluoro-1H-benzimidazol-2-yl)-9H-carbazol-9-yl]benzonitrile, obtained according to stage 2 of Example 3, 148 mg of potassium carbonate and 493 mg of cis-(2-aminocyclopentyl)methanol in 2 ml of dimethyl sulphoxide, in a microwave for 1 hour and 15 minutes at 115° C. 0.678 ml of a 1M aqueous solution of sodium hydroxide, 0.656 ml of a 30% aqueous solution of hydrogen peroxide and 3 ml of ethanol are then added to the reaction medium. After treatment as in stage 3 of Example 3, and then purification by flash chromatography on silica gel, elution being carried out with a mixture of dichloromethane and methanol (95/5 by volume), and then crystallization from 1 ml of ethyl acetate, 75 mg of 4-[4-(6-fluoro-1H-benzimidazol-2-yl)-9H-carbazol-9-yl]-2-[2(R,S)-hydroxymethylcyclopentane-1(S,R)-amino]benzamide are thus obtained in the form of a beige solid, the characteristics of which are the following:

1H NMR spectrum (400 MHz, DMSO-d$_6$+TFA, δ ppm): 1.29-1.96 (m, 6H) 2.14-2.29 (m, 1H) 3.44-3.62 (m, 2H) 3.87-3.99 (m, 1H) 6.83 (d, J=8.6 Hz, 1H) 7.03 (s, 1H) 7.26 (t, J=7.6 Hz, 1H) 7.45-8.10 (m, 10H).

Mass spectrum (LC/MS; method A): retention time Tr (min)=0.89; m/z=534 [M+H]+; m/z=532 [M−H]−.

EXAMPLE 119

Synthesis of 2-[(1-methyl-1H-pyrazol-4-yl)methylamino]-4-[4-(quinolin-3-yl)-9H-carbazol-9-yl]benzamide

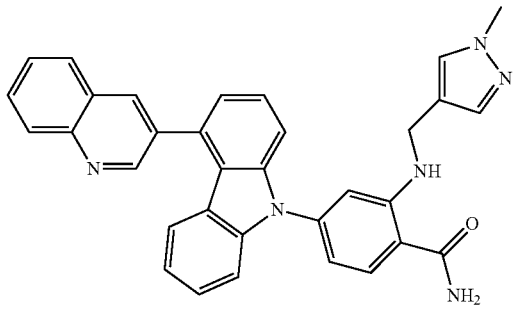

The process is carried out as in stage 3 of Example 3, but using 165.4 mg of 2-fluoro-4-[4-(quinolin-3-yl)-9H-carbazol-9-yl]benzonitrile, obtained according to stage 1 of Example 32, 165.8 mg of potassium carbonate and 356 mg of 4-aminomethyl-1-methyl-1H-pyrazole in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on 10 g of silica gel, elution being carried out with a mixture of dichloromethane and methanol (95/5 by volume), 2-[(1-methyl-1H-pyrazol-4-yl)methylamino]-4-[4-(quinolin-3-yl)-9H-carbazol-9-yl]benzamide is thus obtained in the form of a white powder, the characteristics of which are the following:

1H NMR spectrum (400 MHz, DMSO-d$_6$+TFA, δ ppm): 3.86 (s, 3H) 4.29 (s, 2H) 6.85 (dd, J=8.2, 2.1 Hz, 1H) 6.92 (d, J=1.7 Hz, 1H) 6.99-7.11 (m, 1H) 7.35-7.46 (m, 5H) 7.50-7.57 (m, 1H) 7.58-7.69 (m, 2H) 7.98 (d, J=8.1 Hz, 1H) 8.05 (t, J=7.7 Hz, 1H) 8.24 (t, J=8.3 Hz, 1H) 8.42 (d, J=8.3 Hz, 1H) 8.47 (d, J=8.6 Hz, 1H) 9.49 (d, J=1 Hz, 1H) 9.74 (d, J=1.5 Hz, 1H).

Mass spectrum (LC/MS; method A): retention time Tr (min)=1.03; m/z=523 [M+H]+.

EXAMPLE 120

Synthesis of 2-[(1-methyl-1H-imidazol-4-yl)ethylamino]-4-[4-(quinolin-3-yl)-9H-carbazol-9-yl]benzamide

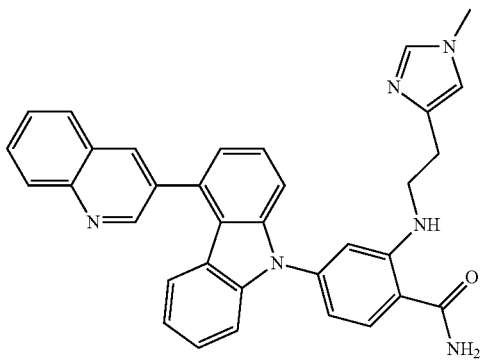

The process is carried out as in stage 3 of Example 3, but using 165.4 mg of 2-fluoro-4-[4-(quinolin-3-yl)-9H-carbazol-9-yl]benzonitrile, obtained according to stage 1 of Example 32, 165.8 mg of potassium carbonate, 517 mg of 2-(1-methyl-1H-imidazol-4-yl)ethylamine hydrochloride and 324 mg of triethylamine in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on 10 g of silica gel, elution being carried out with a mixture of dichloromethane and methanol (95/5 by volume), 49 mg of 2-[(1-methyl-1H-imidazol-4-yl)ethylamino]-4-[4-(quinolin-3-yl)-9H-carbazol-9-yl]benzamide are thus obtained in the form of a white solid, the characteristics of which are the following:

1H NMR spectrum (400 MHz, DMSO-$d_6$, δ ppm): 2.73 (t, J=6.7 Hz, 2H) 3.30-3.34 (masked m, 2H) 3.75 (s, 3H) 6.78 (dd, J=8.3, 1.7 Hz, 1H) 6.90 (d, J=2.0 Hz, 1 H) 6.95-7.08 (m, 1H) 7.25 (d, J=8.1 Hz, 1H) 7.27-7.33 (m, 3H) 7.40 (ddd, J=8.3, 7.2, 1 Hz, 1H) 7.45-7.51 (m, 1H) 7.51 (s, 1H) 7.54-7.64 (m, 3H) 7.68-7.78 (m, 1 H) 7.80-8.06 (m, 3H) 8.14 (d, J=7.6 Hz, 1H) 8.19 (d, J=8.8 Hz, 1H) 8.54 (t, J=4.9 Hz, 1H) 8.63 (d, J=1.7 Hz, 1H).

Mass spectrum (LC/MS; method A): retention time Tr (min)=1.06; m/z=537 [M+H]+; m/z=535 μM−H]−.

EXAMPLE 121

Synthesis of 4-[4-(quinolin-3-yl)-9H-carbazol-9-yl]-2-[(1-hydroxycyclopropan-1-yl)methylamino]benzamide

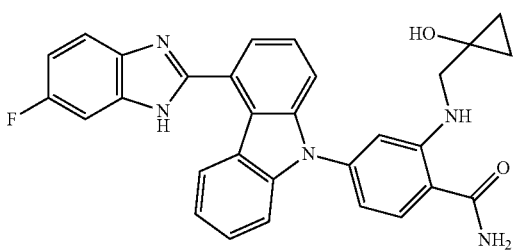

The process is carried out as in stage 3 of Example 3, but using 165.4 mg of 2-fluoro-4-[4-(quinolin-3-yl)-9H-carbazol-9-yl]benzonitrile, obtained according to stage 2 of Example 3, 165.8 mg of potassium carbonate and 279 mg of 1-(aminomethyl)cyclopropan-1-ol in 1.7 ml of dimethyl sulphoxide, in a microwave for 1 hour and 30 minutes at 115° C. 0.76 ml of a 1M aqueous solution of sodium hydroxide, 0.735 ml of a 30% aqueous solution of hydrogen peroxide and 4 ml of ethanol are then added to the reaction medium. After treatment as in stage 3 of Example 3, and then purification by flash chromatography on silica gel, elution being carried out with a mixture of dichloromethane and methanol (95/5 by volume), 11 mg of 4-[4-(quinolin-3-yl)-9H-carbazol-9-yl]-2-[(1-hydroxycyclopropan-1-yl)methylamino]benzamide are thus obtained in the form of a pale yellow powder, the characteristics of which are as follows:

Mass spectrum (LC/MS; method A): retention time Tr (min)=1.04; m/z=499 [M+H]−; m/z=497 [M−H]−.

EXAMPLE 122

Synthesis of 3-[1,2,2,6,6-pentamethylpiperidin-4-yl)amino]-5-[4-(quinolin-3-yl)-9H-carbazol-9-yl]pyridin-2-carboxamide

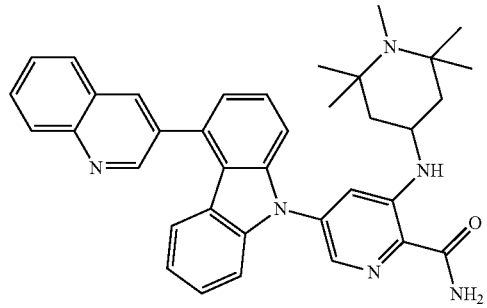

Stage 1: 682 mg of 2-cyano-3,5-difluoropyridine, 995 mg of 4-amino-1,2,2,6,6-pentamethylpiperidine and 1.346 mg of potassium carbonate in 10 ml of dimethyl sulphoxide are introduced into a 20 ml microwave tube reactor. The mixture is then heated in the microwave for 1 hour at 115° C. The reaction medium is run into 100 ml of water and 100 ml of ethyl acetate. The aqueous phase is re-extracted twice with 50 ml of ethyl acetate. The combined organic phases are washed with water and then with a saturated aqueous solution of sodium chloride, dried over sodium sulphate and concentrated under reduced pressure. After purification by flash chromatography on 70 g of silica gel, elution being carried out with a mixture of dichloromethane, methanol and 4N aqueous ammonia (99/1/0.8 by volume), and the first eluted product being recovered, 290 mg of 2-cyano-5-fluoro-3-(1,2,2,6,6-pentamethylpiperidin-4-yl)aminopyridine are thus obtained in the form of an ecru powder, the characteristics of which are the following:

1H NMR spectrum (400 MHz, DMSO-$d_6$) δ ppm 1.07 (s, 6H) 1.08 (s, 6H) 1.46 (t, J=12.1 Hz, 2H) 1.73 (dd, J=12.5, 3.5 Hz, 2H) 2.18 (s, 3H) 3.70-3.82 (m, 1 H) 6.27 (d, J=8.6 Hz, 1H) 7.18 (dd, J=11.8, 2.4 Hz, 1H) 7.89 (d, J=2.4 Hz, 1H).

Stage 2: In a 25 ml three-necked flask, under an argon atmosphere, 102 mg of 4-(quinolin-3-yl)-9H-carbazole, obtained according to stage 1 of Example 2, are dissolved in 5.5 ml of dimethylformamide. 21 mg of sodium hydride at 60% in oil are then added and the mixture is stirred for 30 minutes at ambient temperature and then 30 minutes at 30° C.

100.6 mg of 2-cyano-5-fluoro-3-(1,2,2,6,6-pentamethylpiperidin-4-yl)aminopyridine, obtained in the preceding stage, are then added and the mixture is heated at 50° C. overnight. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. 191 mg of a mixture containing predominantly 3-(1,2,2,6,6-pentamethylpiperidin-4-ylamino)-5-[4-(quinolin-3-yl)-9H-carbazol-9-yl]pyridinecarbonitrile are thus obtained in the form of a beige powder, used as it is in the subsequent stage and the characteristic of which is the following:

LC/MS (method C): retention time=3.68 min.

Stage 3: 190 mg of 3-(1,2,2,6,6-pentamethylpiperidin-4-ylamino)-5-[4-(quinolin-3-yl)-9H-carbazol-9-yl]pyridinecarbonitrile, obtained in the preceding stage, are dissolved in 2 ml of dimethyl sulphoxide and 5 ml of ethanol, and then 0.673 ml of a 1M aqueous solution of sodium hydroxide and 0.618 ml of a 30% aqueous solution of hydrogen peroxide are successively added. After stirring for 1 hour at ambient temperature, the reaction medium is run into 50 ml of water and 50 ml of ethyl acetate. The aqueous phase is re-extracted twice with 25 ml of ethyl acetate. The combined organic phases are washed with water, dried over sodium sulphate and concentrated under reduced pressure. After purification by flash chromatography on 15 g of silica gel, elution being carried out with a mixture of dichloromethane, methanol and 4N aqueous ammonia (93/7/0.5 by volume), 89 mg of 3-[1,2,2,6,6-pentamethylpiperidin-4-yl)amino]-5-[4-(quinolin-3-yl)-9H-carbazol-9-yl]pyridin-2-carboxamide are thus obtained in the form of a beige powder, the characteristics of which are the following:

1H NMR spectrum (400 MHz, DMSO-$d_6$, δ ppm): 0.98 (s, 6H) 1.12 (s, 6H) 1.30 (t, J=12.0 Hz, 2H) 1.96 (d, J=11.2 Hz, 2H) 2.17 (s, 3H) 3.70-3.87 (m, 1H) 7.06 (t, J=7.6 Hz, 1H) 7.26 (d, J=8.1 Hz, 1H) 7.34 (d, J=6.6 Hz, 1H) 7.42 (t, J=7.8 Hz, 1H) 7.50-7.68 (m, 5H) 7.73 (t, J=7.9 Hz, 1H) 7.89 (t, J=7.6 Hz, 1H) 8.10 (d, J=2.0 Hz, 1H) 8.11-8.17 (m, 2H) 8.19 (d, J=8.3 Hz, 1H) 8.54-8.66 (m, 2H) 9.15 (d, J=2.2 Hz, 1H).

Mass spectrum (LC/MS; method A): retention time Tr (min)=0.89; m/z=583 [M+H]+.

EXAMPLE 123

Synthesis of 4-{(2-carbamoyl-5-[4-(quinolin-3-yl)-9H-carbazol-9-yl]phenylamino}piperidine-1-carboxylic acid tert-butyl ester Stage 1: The process is carried out as in stage 3 of Example 3, but using 300 mg of 2-fluoro-4-[4-(quinolin-3-yl)-9H-carbazol-9-yl]benzonitrile, obtained according to stage 1 of Example 31, 2.035 g of 4-amino-1-tert-butoxycarbonylpiperidine and 301 mg of potassium carbonate, in 3 ml of dimethyl sulphoxide at 110° C. for 1 hour 15 minutes. After treatment as in stage 3 of Example 3, and then purification by flash chromatography on silica gel, elution being carried out with a mixture of dichloromethane and ethanol (99/1 by volume), 330 mg of 4-{2-cyano-5-[4-(quinolin-3-yl)-9H-carbazol-9-yl]phenylamino}piperidine-1-carboxylic acid tert-butyl ester are obtained in the form of a beige solid, the characteristic of which is the following:

LC/MS (method C): retention time=6.22 min.

Stage 2: By carrying out the process as in stage 4 of Example 2, but using 400 mg of 4-{2-cyano-5-[4-(quinolin-3-yl)-9H-carbazol-9-yl]phenylamino}piperidine-1-carboxylic acid tert-butyl ester, obtained according to the preceding stage, 1.28 ml of a 1N solution of sodium hydroxide and 1.24 ml of a 30% aqueous solution of hydrogen peroxide, for 5 minutes at ambient temperature, in 6.5 ml of ethanol and 4 ml of dimethyl sulphoxide, there are obtained, after purification by flash chromatography on silica gel, elution being carried out with a mixture of dichloromethane and ethanol (95/5 by volume), 300 mg of 4-{2-carbamoyl-5-[4-(quinolin-3-yl)-9H-carbazol-9-yl]phenylamino}piperidine-1-carboxylic acid tert-butyl ester in the form of a white powder, the characteristics of which are the following:

1H NMR spectrum (400 MHz, DMSO-$d_6$, δ ppm): 1.24-1.37 (m, 2H) 1.39 (s, 9H) 1.88-1.98 (m, 2H) 2.89-3.07 (m, 2H) 3.56-3.68 (m, 1H) 3.75 (d, J=12.7 Hz, 2H) 6.68-6.80 (m, J=10.3 Hz, 1H) 6.98 (d, J=1.5 Hz, 1H) 7.02 (t, J=8.1 Hz, 1H) 7.25 (d, J=8.3 Hz, 1H) 7.30 (d, J=6.8 Hz, 1H) 7.33 (broad s, 1H) 7.36-7.48 (m, 2H) 7.49-7.55 (m, 1H) 7.55-7.63 (m, 1H) 7.73 (t, J=7.6 Hz, 1H) 7.89 (t, J=7.7 Hz, 1H) 7.93 (d, J=8.3 Hz, 1H) 8.01 (broad s, 1H) 8.14 (d, J=7.8 Hz, 1H) 8.19 (d, J=8.3 Hz, 1H) 8.59 (d, J=8.1 Hz, 1H) 8.62 (d, J=1.7 Hz, 1H) 9.15 (d, J=2.2 Hz, 1H).

Mass spectrum (LC/MS; method A): retention time Tr (min)=1.21; m/z=612 [M+H]+; m/z=610 [M+H]+.

EXAMPLE 124

Synthesis of 2-(piperidin-4-ylamino)-4-[4-(quinolin-3-yl)-9H-carbazol-9-yl]benzamide hydrochloride

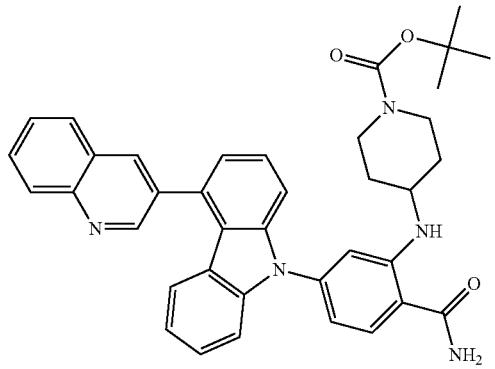

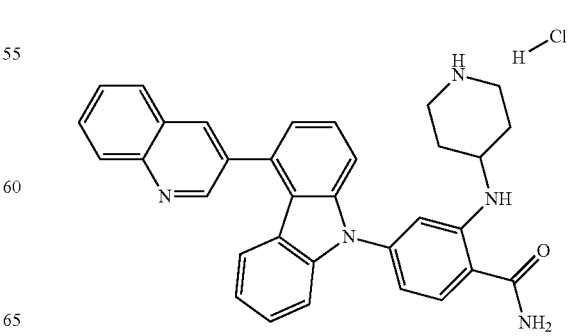

In a 25 ml three-necked flask, 370 mg of 4-{2-carbamoyl-5-[4-(quinolin-3-yl)-9H-carbazol-9-yl]phenylamino}piperidine-1-carboxylic acid tert-butyl ester, obtained as in Example 123, are dissolved in 3 ml of dioxane, and then 2.845 of a 4M solution of hydrochloric acid in dioxane are added and the mixture is stirred overnight at ambient temperature. The precipitate formed is spin-dried over sintered glass and washed successively with 5 ml of dichloromethane and 5 ml of diisopropyl ether. After drying in an oven under vacuum at 50° C., 320 mg of 2-(piperidin-4-ylamino)-4-[4-(quinolin-3-yl)-9H-carbazol-9-yl]benzamide hydrochloride are thus obtained in the form of a pale yellow solid, the characteristics of which are the following:

1H NMR spectrum (400 MHz, DMSO-$d_6$, δ ppm): 1.53-1.73 (m, 2H) 2.12 (d, J=13.4 Hz, 2H) 2.81-3.05 (m, 2H) 3.23 (d, J=13.2 Hz, 2H) 3.73 (t, J=10.0 Hz, 1H) 6.79 (d, J=8.3 Hz, 1H) 6.96-7.10 (m, 2H) 7.20-7.49 (m, 5H) 7.51-7.68 (m, 2H) 7.87 (t, J=7.2 Hz, 1H) 7.97 (d, J=8.3 Hz, 1H) 8.04 (t, J=7.7 Hz, 1H) 8.10 (broad s, 1 H) 8.28 (d, J=8.3 Hz, 1H) 8.34 (d, J=8.3 Hz, 1H) 8.84 (broad s, 1H) 8.97 (broad s, 2 H) 9.36 (s, 1H).

Mass spectrum (LC/MS; method C): retention time Tr (min)=3.35; m/z=512 [M+H]+; m/z=510 [M+H]+.

EXAMPLE 125

Synthesis of 4-[4-(6-cyanopyridin-3-yl)-9H-carbazol-9-yl]-2-[(3-hydroxy-3-methylbutyl)amino]benzamide

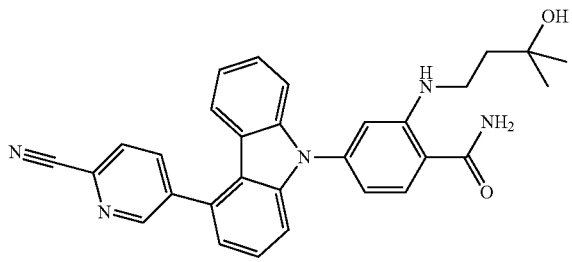

Stage 1: 0.26 g of potassium carbonate and 1.35 g of 4-amino-2-methylbutan-2-ol are successively added to a solution of 0.22 g of 2-methylpropan-2-yl 4-[4-(6-cyanopyridin-3-yl)-9H-carbazol-9-yl]-2-fluorobenzoate, obtained in stage 1 of Example 49, in 8 ml of dimethyl sulphoxide. The reaction mixture is heated at 90° C. for 1 hour and 20 minutes in a microwave, and then diluted with distilled water. The aqueous phase is extracted twice with ethyl acetate and the combined organic phases are washed with water and a saturated solution of sodium chloride, dried over magnesium sulphate and concentrated to dryness under reduced pressure. The residue is purified by silica gel chromatography, elution being carried out with a mixture of cyclohexane and ethyl acetate (80/20 by volume), so as to give 0.17 g of 2-methylpropan-2-yl 4-[4-(6-cyanopyridin-3-yl)-9H-carbazol-9-yl]-2-[(3-hydroxy-3-methylbutyl)amino]benzoate in the form of a yellow oil, the characteristics of which are the following:

1H NMR spectrum (400 MHz, δ in ppm, DMSO-d6): 1.12 (s, 6H) 1.59 (s, 9H) 1.70-1.78 (m, 2H) 3.23-3.29 (m, 2H) 4.32 (s, 1H) 6.78 (dd, J=8.3, 2.0 Hz, 1H) 6.95 (d, J=2.0 Hz, 1H) 7.11 (td, J=8.1, 0.7 Hz, 1H) 7.23 (dd, J=6.6, 1.5 Hz, 1H) 7.31 (d, J=8.1 Hz, 1H) 7.44 (td, J=7.8, 1.2 Hz, 1H) 7.51 (d, J=8.3 Hz, 1H) 7.55-7.63 (m, 2H) 7.91 (t, J=5.1 Hz, 1H) 8.04 (d, J=8.6 Hz, 1H) 8.28 (d, J=7.3 Hz, 1H) 8.34 (dd, J=8.1, 2.2 Hz, 1H) 9.02 (d, J=2.0 Hz, 1H).

Mass spectrum (LC/MS; method A): retention time Tr (min)=1.32; m/z=547 [M+H]+.

Stage 2: 1.6 ml of 1N hydrochloric acid are added to a solution of 0.15 g of 2-methylpropan-2-yl 4-[4-(6-cyanopyridin-3-yl)-9H-carbazol-9-yl]-2-[(3-hydroxy-3-methylbutyl)amino]benzoate in 8 ml of dioxane. The reaction mixture is heated at 100° C. in a microwave for 2 hours and then concentrated under reduced pressure. The residue is purified by silica gel chromatography, elution being carried out with a mixture of dichloromethane and methanol (97/3 by volume), so as to give 20 mg of 4-[4-(6-cyanopyridin-3-yl)-9H-carbazol-9-yl]-2-[(3-hydroxy-3-methylbutyl)amino]benzoic acid in the form of a pale yellow powder, the characteristics of which are the following:

1H NMR spectrum (400 MHz, δ in ppm, DMSO-d6): 1.11 (s, 6H) 1.69-1.76 (m, 2H) 3.20-3.26 (m, 2H) 4.28 (s, 1H) 6.73 (d, J=8.8 Hz, 1H) 6.88 (s, 1H) 7.11 (td, J=7.8, 0.7 Hz, 1H) 7.23 (dd, J=6.6, 1.5 Hz, 1H) 7.31 (d, J=8.1 Hz, 1H) 7.44 (td, J=8.3, 1.0 Hz, 1H) 7.51 (d, J=8.1 Hz, 1H) 7.55-7.63 (m, 2H) 8.07 (d, J=8.6 Hz, 1 H) 8.28 (dd, J=8.1, 0.7 Hz, 1H) 8.35 (dd, J=7.8, 2.2 Hz, 1H) 9.03 (dd, J=2.1, 0.9 Hz, 1H).

Mass spectrum (LC/MS; method A): retention time Tr (min)=1.09; m/z=491 [M+H]+.

Stage 3: 108 mg of (1H-benzotriazol-1-yloxy)[tris(dimethylamino)]phosphonium hexafluorophosphate (BOP), 33 mg of hydroxybenzotriazole (HOBT), 17 mg of ammonium chloride and 0.1 ml of diisopropylethylamine are successively added to a solution of 80 mg of 4-[4-(6-cyanopyridin-3-yl)-9H-carbazol-9-yl]-2-[(3-hydroxy-3-methylbutyl)amino]benzoic acid in 10 ml of N,N-dimethylformamide. The reaction mixture is stirred at ambient temperature for 12 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of dichloromethane and methanol (96/4 by volume), so as to give 18 mg of 4-[4-(6-cyanopyridin-3-yl)-9H-carbazol-9-yl]-2-[(3-hydroxy-3-methylbutyl)amino]benzamide in the form of a white solid, the characteristics of which are the following:

1H NMR spectrum (400 MHz, δ in ppm, DMSO-d6): 1.10 (s, 6H) 1.66-1.74 (m, 2H) 3.15-3.22 (m, 2H) 4.26 (s, 1H) 6.73 (dd, J=8.2, 2.1 Hz, 1H) 6.85 (d, J=2.0 Hz, 1H) 7.11 (ddd, J=8.1, 6.8, 1.0 Hz, 1H) 7.23 (t, J=4.2 Hz, 1H) 7.32 (d, J=7.8 Hz, 1H) 7.43 (ddd, J=8.3, 6.8, 1.0 Hz, 1H) 7.48 (d, J=8.3 Hz, 1H) 7.58 (d, J=4.2 Hz, 2H) 7.66 (broad s, 1H) 7.90 (d, J=8.3 Hz, 1H) 7.95 (broad s, 1H) 8.28 (dd, J=8.1, 0.7 Hz, 1H) 8.35 (dd, J=7.8, 2.0 Hz, 1H) 8.38 (t, J=5.0 Hz, 1H) 9.03 (dd, J=2.2, 1.0 Hz, 1H).

Mass spectrum (LC/MS; method B): retention time Tr (min)=4.36; m/z=490 [M+H]+; 488 [M-H]-.

EXAMPLE 126

Synthesis of 4-[4-(6-cyanopyridin-3-yl)-9H-carbazol-9-yl]-2-(tetrahydro-2H-pyran-4-ylamino)benzamide

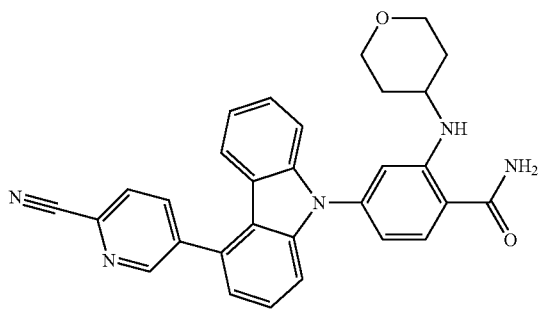

Stage 1: 0.95 g of potassium carbonate and 4.62 g of 4-aminotetrahydropyran are successively added to a solution of 1.06 g of 2-methylpropan-2-yl 4-[4-(6-cyanopyridin-3-yl)-9H-carbazol-9-yl]-2-fluorobenzoate, obtained in stage 1 of Example 49, in 8 ml of dimethyl sulphoxide. The reaction mixture is heated at 90° C. for 3 hours in a microwave, and then diluted with distilled water. The aqueous phase is washed twice with ethyl acetate and the combined organic phases are washed with water and a saturated solution of sodium chloride, dried over magnesium sulphate and filtered. The residue is purified by silica gel chromatography, elution being carried out with a mixture of cyclohexane and ethyl acetate (85/15 by volume), so as to give 0.5 g of 2-methylpropan-2-yl 4-[4-(6-cyanopyridin-3-yl)-9H-carbazol-9-yl]-2-(tetrahydro-2H-pyran-4-ylamino)benzoate in the form of a white foam, the characteristics of which are the following:

1H NMR spectrum (400 MHz, $\delta$ in ppm, DMSO-d6): 1.42-1.54 (m, 2H) 1.60 (s, 9H) 1.92-2.01 (m, 2H) 3.36-3.45 (m, 2H) 3.65-3.76 (m, 1H) 3.78-3.86 (m, 2 H) 6.78 (dd, J=8.6, 2.0 Hz, 1H) 7.07 (d, J=2.0 Hz, 1H) 7.11 (ddd, J=8.1, 5.4, 2.6 Hz, 1H) 7.23 (dd, J=6.8, 1.2 Hz, 1H) 7.31 (d, J=8.1 Hz, 1H) 7.40-7.47 (m, 2H) 7.51-7.61 (m, 2H) 7.92 (d, J=7.8 Hz, 1H) 8.06 (d, J=8.6 Hz, 1H) 8.28 (dd, J=8.1, 0.7 Hz, 1H) 8.33 (dd, J=8.1, 2.2 Hz, 1H) 9.01 (dd, J=2.1, 0.9 Hz, 1H).

Mass spectrum (LC/MS; method A): retention time Tr (min)=1.34; m/z=545 [M+H]+.

Stage 2: 5 ml of 1N hydrochloric acid are added to a solution of 0.47 g of 2-methylpropan-2-yl 4-[4-(6-cyanopyridin-3-yl)-9H-carbazol-9-yl]-2-(tetrahydro-2H-pyran-4-ylamino)benzoate in 4 ml of dioxane. The reaction mixture is heated at 100° C. in a microwave for 2 hours and then concentrated under reduced pressure. The residue is purified twice by silica gel chromatography, elution being carried out successively with a mixture of dichloromethane and methanol (98/2 by volume) and then with a mixture of cyclohexane and ethyl acetate (50/50 by volume), so as to give 150 mg of 4-[4-(6-cyanopyridin-3-yl)-9H-carbazol-9-yl]-2-(tetrahydro-2H-pyran-4-ylamino)benzoic acid in the form of a yellow powder, the characteristics of which are the following:

1H NMR spectrum (400 MHz, $\delta$ in ppm, DMSO-d6): 1.38-1.49 (m, 2H) 1.90-1.98 (m, 2H) 3.36-3.46 (m, 2H) 3.61 (broad s, 1H) 3.77-3.86 (m, 2H) 6.67 (d, J=7.8 Hz, 1H) 6.87 (s, 1H) 7.09 (ddd, J=8.0, 5.1, 3.1 Hz, 1H) 7.21 (dd, J=6.8, 1.2 Hz, 1H) 7.31 (d, J=7.8 Hz, 1H) 7.41-7.45 (m, 2H) 7.50-7.60 (m, 2H) 8.11 (d, J=8.3 Hz, 1H) 8.28 (dd, J=7.8, 0.5 Hz, 1H) 8.34 (dd, J=8.1, 2.2 Hz, 1H) 9.02 (dd, J=2.2, 0.7 Hz, 1H).

Mass spectrum (LC/MS; method A): retention time Tr (min)=1.11; m/z=489 [M+H]+; 487 [M−H]−.

Stage 3: 0.2 g of (1H-benzotriazol-1-yloxy)[tris(dimethylamino)]phosphonium hexafluorophosphate (BOP), 62 mg of hydroxybenzotriazole (HOBT), 33 mg of ammonium chloride and 0.25 ml of diisopropylethylamine are successively added to a solution of 0.15 g of 4-[4-(6-cyanopyridin-3-yl)-9H-carbazol-9-yl]-2-(tetrahydro-2H-pyran-4-ylamino)benzoic acid in 20 ml of N,N-dimethylformamide. The reaction mixture is stirred at ambient temperature for 12 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of cyclohexane and ethyl acetate (70/30 by volume), so as to give 100 mg of 4-[4-(6-cyanopyridin-3-yl)-9H-carbazol-9-yl]-2-(tetrahydro-2H-pyran-4-ylamino)benzamide in the form of a white solid, the characteristics of which are the following:

Melting point (Buchi melting point B-545)=256° C.

1H NMR spectrum (400 MHz, $\delta$ in ppm, DMSO-d6): 1.37-1.47 (m, 2H) 1.89-1.97 (m, 2H) 3.37-3.44 (m, 2H) 3.57-3.67 (m, 1H) 3.76-3.83 (m, 2H) 6.73 (dd, J=8.3, 2.0 Hz, 1H) 6.95 (d, J=1.7 Hz, 1H) 7.07-7.13 (m, 1H) 7.22 (dd, J=7.1, 1.0 Hz, 1H) 7.30 (broad s, 1H) 7.32 (d, J=7.8 Hz, 1H) 7.41-7.45 (m, 2H) 7.50-7.61 (m, 2H) 7.92 (d, J=8.3 Hz, 1H) 8.00 (broad s, 1H) 8.28 (dd, J=8.1, 0.7 Hz, 1H) 8.34 (dd, J=8.1, 2.2 Hz, 1H) 8.58 (d, J=7.8 Hz, 1H) 9.02 (dd, J=2.2, 1.0 Hz, 1H).

Mass spectrum (LC/MS; method A): retention time Tr (min)=1.05; m/z=488 [M+H]+; 486 [M−H]−.

EXAMPLE 127

Synthesis of 4-[4-(6-cyanopyridin-3-yl)-9H-carbazol-9-yl]-2-[(1,2,2,6,6-pentamethylpiperidin-4-yl)amino]benzamide

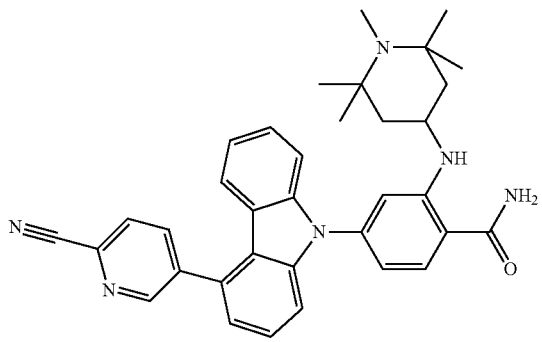

Stage 1: 0.95 g of potassium carbonate and 7.8 ml of 4-amino-1,2,2,6,6-pentamethylpiperidine are successively added to a solution of 1.06 g of 2-methylpropan-2-yl 4-[4-(6-cyanopyridin-3-yl)-9H-carbazol-9-yl]-2-fluorobenzoate, obtained in stage 1 of Example 49, in 8 ml of dimethyl sulphoxide. The reaction mixture is heated at 90° C. for 2 hours and 15 minutes in a microwave, and then diluted with distilled water. The aqueous phase is extracted twice with ethyl acetate and the combined organic phases are washed with water and a saturated solution of sodium chloride and dried over magnesium sulphate. The residue is purified by silica gel chromatography, elution being carried out with a mixture of dichloromethane and methanol (97/3 by volume), so as to give 0.8 g of 2-methylpropan-2-yl 4-[4-(6-cyanopyridin-3-yl)-9H-carbazol-9-yl]-2-[(1,2,2,6,6-pentamethylpiperidin-4-yl)amino]benzoate in the form of a yellow oil, the characteristics of which are the following:

1H NMR spectrum (400 MHz, $\delta$ in ppm, DMSO-d6): 0.95 (s, 6H) 1.13 (s, 6H) 1.32 (t, J=11.0 Hz, 2H) 1.59 (s, 9H) 1.99 (d, J=11.7 Hz, 2H) 2.16 (s, 3H) 3.77 (broad s, 1H) 6.85 (dd, J=8.4, 1.6 Hz, 1H) 7.05 (s, 1H) 7.12 (td, J=8.1, 1.0 Hz, 1H) 7.24 (dd, J=7.2, 0.9 Hz, 1H) 7.31 (d, J=7.8 Hz, 1H) 7.44 (ddd, J=8.3, 7.2, 1.1 Hz, 1 H) 7.54-7.61 (m, 2H) 7.67 (dd, J=8.3, 0.7 Hz, 1H) 7.74 (d, J=7.1 Hz, 1H) 8.06 (d, J=8.3 Hz, 1H) 8.28 (dd, J=7.8, 0.7 Hz, 1H) 8.34 (dd, J=8.1, 2.2 Hz, 1H) 9.02 (dd, J=2.1, 0.9 Hz, 1H).

Mass spectrum (LC/MS; method B): retention time Tr (min)=4.30; m/z=614 [M+H]+.

Stage 2: 7.7 ml of 1N hydrochloric acid are added to a solution of 0.79 g of 2-methylpropan-2-yl 4-[4-(6-cyanopyridin-3-yl)-9H-carbazol-9-yl]-2-[(1,2,2,6,6-pentamethylpiperidin-4-yl)amino]benzoate in 5 ml of dioxane. The reaction mixture is heated at 100° C. in a microwave for 2 hours and then concentrated under reduced pressure. The residue is purified by silica gel chromatography, elution being carried out with a mixture of dichloromethane and methanol (95/5 by volume), so as to give 280 mg of 4-[4-(6-cyanopyridin-3-yl)-9H-carbazol-9-yl]-2-[(1,2,2,6,6-pentamethylpiperidin-4-yl)amino]benzoic acid in the form of a pale yellow powder, the characteristics of which are the following:

1H NMR spectrum (400 MHz, δ in ppm, DMSO-d6): 1.22 (broad s, 6H) 1.36 (broad s, 6H) 1.70 (broad s, 2H) 2.09-2.22 (m, 2H) 2.56 (broad s, 3H) 3.97 (broad s, 1H) 6.80 (d, J=8.1 Hz, 1H) 7.08-7.14 (m, 2H) 7.23 (dd, J=7.1, 0.7 Hz, 1H) 7.32 (d, J=8.1 Hz, 1H) 7.44 (td, J=8.6, 1.0 Hz, 1H) 7.55-7.61 (m, 2H) 7.68 (d, J=8.3 Hz, 1H) 8.12 (d, J=8.6 Hz, 1H) 8.28 (dd, J=7.8, 0.7 Hz, 1H) 8.35 (d, J=8.1, 2.2 Hz, 1H) 9.02 (dd, J=2.1, 0.9 Hz, 1H).

Mass spectrum (LC/MS; method B): retention time Tr (min)=3.66; m/z=558 [M+H]+; 556 [M+H]−.

Stage 3: 330 mg of (1H-benzotriazol-1-yloxy)[tris(dimethylamino)]phosphonium hexafluorophosphate (BOP), 100 mg of hydroxybenzotriazole (HOBT), 54 mg of ammonium chloride and 0.41 ml of diisopropylethylamine are successively added to a solution of 280 mg of 4-[4-(6-cyanopyridin-3-yl)-9H-carbazol-9-yl]-2-[(1,2,2,6,6-pentamethylpiperidin-4-yl)amino]benzoic acid in 30 ml of N,N-dimethylformamide. The reaction mixture is stirred at ambient temperature for 12 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of dichloromethane, acetonitrile and methanol (85/7.5/7.5 by volume), so as to give 60 mg of 4-[4-(6-cyanopyridin-3-yl)-9H-carbazol-9-yl]-2-[(1,2,2,6,6-pentamethylpiperidin-4-yl)amino]benzamide in the form of a white solid, the characteristics of which are the following:

1H NMR spectrum (400 MHz, δ in ppm, DMSO-d6): 0.94 (s, 6H) 1.11 (s, 6H) 1.26 (t, J=11.4 Hz, 2H) 1.91-1.99 (m, 2H) 2.15 (s, 3H) 3.67 (broad s, 1H) 6.78 (dd, J=8.2, 1.8 Hz, 1H) 6.95 (d, J=2.0 Hz, 1H) 7.11 (td, J=7.8, 0.7 Hz, 1H) 7.23 (dd, J=7.2, 0.9 Hz, 1H) 7.29 (broad s, 1H) 7.31 (d, J=7.8 Hz, 1H) 7.44 (ddd, J=8.4, 7.3, 0.9 Hz, 1H) 7.53-7.61 (m, 2H) 7.65 (dd, J=8.6, 0.7 Hz, 1H) 7.92 (d, J=8.6 Hz, 1H) 7.97 (broad s, 1H) 8.28 (dd, J=8.1, 0.7 Hz, 1H) 8.35 (dd, J=8.1, 2.2 Hz, 1H) 8.36 (broad s, 1H) 9.02 (dd, J=2.1, 0.9 Hz, 1H).

Mass spectrum (LC/MS; method A): retention time Tr (min)=0.84; m/z=557 [M+H]+; 555 [M−H]−.

EXAMPLE 128

Synthesis of aminoacetic acid 4-trans-{[2-carbamoyl-5-(quinolin-3-yl)-9H-carbazol-9-yl]pyridin-3-ylamino}cyclohexyl ester

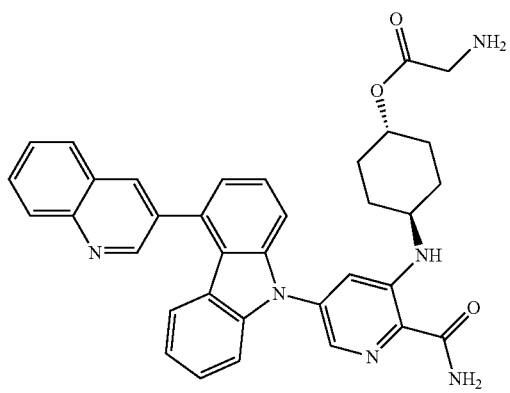

Stage 1: 500 mg of 2-cyano-3,5-difluoropyridine, 493 mg of trans-4-aminocyclohexanol and 987 mg of potassium carbonate in 7.5 ml of dimethyl sulphoxide are introduced into a 5 ml microwave tube reactor. The mixture is then heated in the microwave for 1 hour at 115° C. The reaction medium is run into 100 ml of water and 100 ml of ethyl acetate. The aqueous phase is re-extracted twice with 50 ml of ethyl acetate. The combined organic phases are washed with water and then with a saturated aqueous solution of sodium chloride, dried over sodium sulphate and concentrated under reduced pressure. After purification by flash chromatography on 40 g of silica gel, elution being carried out with a mixture of ethyl acetate and cyclohexane (50/50 by volume), and the first eluted product being recovered, 309 mg of 2-cyano-5-fluoro-3-(4-trans-hydroxycyclohexylamino)pyridine are thus obtained in the form of a white powder, the characteristics of which are the following:

TLC on silica gel: Rf=0.20 (ethyl acetate/cyclohexane 50/50).

1H NMR spectrum (400 MHz, DMSO-$d_6$, d ppm): 1.20-1.47 (m, 4H) 1.75-1.89 (m, 4H) 3.32-3.45 (m, 2H) 4.54 (d, J=4.4 Hz, 1H) 6.23 (d, J=8.1 Hz, 1H) 7.30 (dd, J=12.1, 2.3 Hz, 1H) 7.85 (d, J=2.4 Hz, 1H).

Stage 2: In a 50 ml three-necked flask, under an argon atmosphere, 338.5 mg of 4-(quinolin-3-yl)-9H-carbazole, obtained according to stage 1 of Example 2, are dissolved in 20 ml of dimethylformamide. 69 mg of sodium hydride at 60% in oil are then added and the mixture is stirred for 30 minutes at ambient temperature and then 30 minutes at 50° C. 297.6 mg of 2-cyano-5-fluoro-3-(4-trans-hydroxycyclohexylamino)pyridine, obtained in the preceding stage, are then added, at 50° C., and the mixture is heated at 80° C. for 2 hours. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. 580 mg of a mixture containing very predominantly 3-(4-trans-hydroxycyclohex-1-ylamino)-5-[4-(quinolin-3-yl)-9H-carbazol-9-yl]pyridinecarbonitrile are thus obtained in the form of a beige powder, which is used as it is in the subsequent stage and the characteristic of which is the following:

LC/MS (method C): retention time=4.92 min.

Stage 3: 575 mg of 3-(4-trans-hydroxycyclohex-1-ylamino)-5-[4-(quinolin-3-yl)-9H-carbazol-9-yl]pyridinecarbonitrile, obtained in the preceding stage, are dissolved in 6 ml of dimethyl sulphoxide and 15 ml of ethanol, and then 2.25 ml of a 1M aqueous solution of sodium hydroxide and 2.07 ml of a 30% aqueous solution of hydrogen peroxide are successively added. After stirring for 5 minutes at ambient temperature, the reaction medium is run into 100 ml of water and 100 ml of ethyl acetate. The aqueous phase is re-extracted 3 times with 25 ml of ethyl acetate. The combined organic phases are washed with water, dried over sodium sulphate and concentrated under reduced pressure. After purification by flash chromatography on 50 g of silica gel, elution being carried out with a mixture of dichloromethane and ethanol (95/5 by volume), 512 mg of 3-(4-trans-hydroxycyclohexyl)amino]-5-[4-(quinolin-3-yl)-9H-carbazol-9-yl]pyridine-2-carboxamide, already described in Example 58 but using a different synthetic pathway, are thus obtained in the form of an off-white powder, the characteristic of which is the following:

LC/MS (method C): retention time=4.84 min.

Stage 4: The process is carried out as in Example 23, but using 180 mg of 3-(4-trans-hydroxycyclohexyl)amino]-5-[4-(quinolin-3-yl)-9H-carbazol-9-yl]pyridin-2-carboxamide, obtained in the preceding stage, 119.5 mg of N-tert-butoxycarbonylglycine, 83.3 mg of 4-dimethylaminopyridine and 224 mg of O-[(ethoxycarbonyl)cyanomethyleneamino]-N,N,N',N'-tetramethylurea (TOTU) in 17 ml of dichloromethane and 3 ml of dimethylformamide, for 20 hours at ambient temperature. 1119.5 mg of N-tert-butoxycarbonylglycine, 83.3 mg of 4-dimethylaminopyridine and 224 mg of O-[(ethoxycarbonyl)cyanomethyleneamino]-N,N,N',N'-tetramethylurea (TOTU) are then again added and the mixture is stirred for 6 hours at 40° C. After treatment and purification by flash chromatography on 70 g of silica gel, elution being carried out with a gradient of mixtures of dichloromethane and ethanol (from 100/0 to 97/3 by volume), 223 mg of tert-butoxycarbonylaminoacetic acid 4-trans-{2-carbamoyl-5-[4-(quinolin-3-yl)-9H-carbazol-9-yl]phenylamino}cyclohexyl ester are thus obtained in the form of a beige powder, the characteristic of which is the following:

LC/MS (method C): retention time Tr (min)=5.51 min.

Stage 5: The process is carried out as in Example 25, but using 215 mg of tert-butoxycarbonylaminoacetic acid 4-trans-{2-carbamoyl-5-[4-(quinolin-3-yl)-9H-carbazol-9-yl]phenylamino}cyclohexyl ester, obtained in the preceding stage, in 5.4 ml of dichloromethane and 5.4 ml of trifluoroacetic acid, for 1 hour at ambient temperature. After concentration under reduced pressure, the residue is dissolved in 20 ml of ethyl acetate and washed with a saturated solution of sodium hydrogen carbonate, and then with water. After drying over magnesium sulphate, and concentration to approximately 1 ml, the crystals formed are spin-dried over sintered glass and washed twice with 1 ml of diisopropyl ether. 139 mg of aminoacetic acid 4-trans-{[2-carbamoyl-5-(quinolin-3-yl)-9H-carbazol-9-yl]pyridin-3-ylamino}cyclohexyl ester are thus obtained in the form of fine light beige crystals, the characteristics of which are the following:

TLC on silica gel: Rf=0.6 (dichloromethane/7M ammonia in methanol 90/10).

1H NMR spectrum (400 MHz, DMSO-$d_6$, δ ppm): 1.34-1.58 (m, 4H) 1.91 (d, J=12.2 Hz, 2H) 2.05 (d, J=10.8 Hz, 2H) 3.24-3.29 (m, 2H) 3.49-3.61 (m, 1H) 4.68-4.79 (m, 1H) 7.06 (t, J=8.1 Hz, 1H) 7.27 (d, J=7.8 Hz, 1H) 7.34 (d, J=7.3 Hz, 1H) 7.38-7.48 (m, 2H) 7.49-7.66 (m, 4H) 7.74 (t, J=7.3 Hz, 1H) 7.90 (td, J=7.7, 1.2 Hz, 1H) 8.01 (d, J=2.0 Hz, 1H) 8.10-8.23 (m, 3H) 8.62 (d, J=2.0 Hz, 1H) 8.80 (d, J=7.8 Hz, 1H) 9.15 (d, J=2.4 Hz, 1H).

Mass spectrum (LC/MS method A): retention time Tr (min)=0.88; [M+H]+=585.

EXAMPLE 129

Synthesis of 3-(2-fluoroethylamino)-5-[4-(quinolin-3-yl)-9H-carbazol-9-yl]pyridine-2-carboxamide

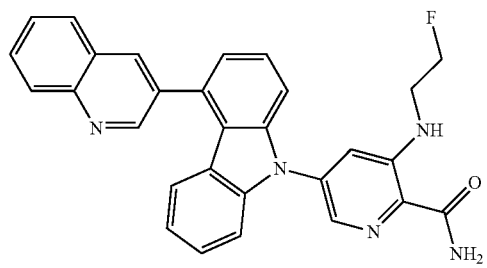

Stage 1: 500 mg of 2-cyano-3,5-difluoropyridine, 426 mg of 2-fluoroethylamine hydrochloride, 987 mg of potassium carbonate and 433 mg of triethylamine in 10 ml of dimethyl sulphoxide are introduced into a 20 ml microwave tube reactor. The mixture is then heated in the microwave for 1 and a half hours at 115° C. The reaction medium is run into 100 ml of water and 100 ml of ethyl acetate. The aqueous phase is re-extracted twice with 50 ml with ethyl acetate. The combined organic phases are washed with water and then with a saturated aqueous solution of sodium chloride, dried over sodium sulphate and concentrated under reduced pressure. After purification by flash chromatography on 70 g of silica gel, elution being carried out with a mixture of ethyl acetate and cyclohexane (30/70 by volume), and the first eluted product being recovered, 125 mg of 2-cyano-5-fluoro-3-(2-fluoroethylamino)pyridine are thus obtained in the form of a white powder, the characteristics of which are the following:

1H NMR spectrum (400 MHz, DMSO-$d_6$) δ ppm 3.55 (dq, J=26.0, 5.0, 5.0 Hz, 2H) 4.57 (dd, J=47.4, 5.0 Hz, 2H) 6.91 (broad s, 1H) 7.33 (dd, J=12.0, 2.2 Hz, 1H) 7.90 (d, J=2.4 Hz, 1H).

400 mg of 2-cyano-3-fluoro-5-(2-fluoroethylamino)pyridine are isolated by recovering the second eluted product.

Stage 2: In a 25 ml three-necked flask, under an argon atmosphere, 192.8 mg of 4-(quinolin-3-yl)-9H-carbazole, obtained according to stage 1 of Example 2, are dissolved in 10 ml of dimethylformamide. 32 mg of sodium hydride at 60% in oil are then added and the mixture is stirred for 30 minutes at ambient temperature. 120 mg of 2-cyano-5-fluoro-3-(2-fluoroethylamino)pyridine, obtained in the preceding stage, are then added and the mixture is heated at 50° C. overnight. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. After purification by flash chromatography on silica gel, elution being carried out with dichloromethane, 150 mg of a mixture are thus obtained, said mixture being used as it is in the subsequent stage and containing approximately 35% of 3-(2-fluoroethylamino)-5-[4-(quinolin-3-yl)-9H-carbazol-9-yl]pyridinecarbonitrile, the characteristic of which is the following:

LC/MS (method C): retention time=5.23 min, and 65% of starting 4-(quinolin-3-yl)-9H-carbazole.

Stage 3: 160 mg of the mixture obtained in the preceding stage are dissolved in 2 ml of dimethyl sulphoxide and 4 ml of ethanol, and then 0.233 ml of a 1M aqueous solution of sodium hydroxide and 0.225 ml of a 30% aqueous solution of hydrogen peroxide are successively added. After stirring for 5 minutes at ambient temperature, the reaction medium is run into 50 ml of water and 50 ml of ethyl acetate. The aqueous phase is re-extracted twice with 50 ml of ethyl acetate. The combined organic phases are washed with water, dried over sodium sulphate and concentrated under reduced pressure. After purification by flash chromatography on 15 g of silica gel, elution being carried out with a mixture of dichloromethane and ethanol (94/6 by volume), 35 mg of 3-(2-fluoroethylamino)-5-[4-(quinolin-3-yl)-9H-carbazol-9-yl]pyridine-2-carboxamide are thus obtained in the form of a beige powder, the characteristics of which are the following:

1H NMR spectrum (400 MHz, DMSO-d$_6$, δ ppm): 3.62 (dq, J=27.9, 5.0 Hz, 2H) 4.63 (dt, J=47.7, 5.0 Hz, 2H) 7.06 (t, J=7.5 Hz, 1H) 7.25 (d, J=8.1 Hz, 1H) 7.33 (dd, J=6.4, 2.0 Hz, 1H) 7.41 (t, J=7.1 Hz, 1H) 7.50 (d, J=8.1 Hz, 1H) 7.54-7.65 (m, 4H) 7.74 (t, J=7.6 Hz, 1H) 7.89 (t, J=7.7 Hz, 1H) 8.08 (d, J=2.0 Hz, 1H) 8.11-8.22 (m, 3H) 8.62 (d, J=1.7 Hz, 1H) 8.97 (t, J=5.0 Hz, 1H) 9.15 (d, J=2.2 Hz, 1H).

Mass spectrum (LC/MS method A): retention time Tr (min)=1.10; [M+H]+=476.

EXAMPLES 130 AND 131

Separation of the enantiomers of 4-[4-(6-fluoro-1H-benzimidazol-2-yl)-9H-carbazol-9-yl]-2-[1(S,R),2(R,S)-2-hydroxymethylcyclohexyl-1-amino])benzamide

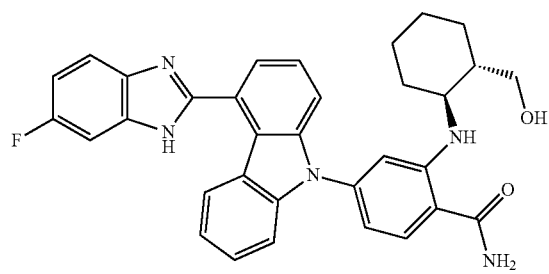

80 mg of the product obtained in Example 97 are resolved in a Chiralpack T304 20 µm 700 g silica column, elution being carried out at 150 ml/min with a mixture of heptane, ethanol and trifluoroacetic acid (90/10/0.1 as mixtures).

When the first eluted product is recovered, 33 mg of the dextrorotatory enantiomer of 4-[4-(6-fluoro-1H-benzimidazol-2-yl)-9H-carbazol-9-yl]-2-[1(S,R),2(R,S)-2-hydroxymethylcyclohexyl-1-amino])benzamide are obtained in the form of a beige solid, the characteristics of which are the following:

optical rotation: $\alpha_{589}^{20}$=+30°+/−1.1° (C=0.26% in methanol).

analytical HPLC (Chiralpak T304 20 µm column; 6×250 mm; 90/10/0.1 heptane/ethanol/TFA at 1 ml/min): retention time=23 min.

1H NMR spectrum (400 MHz, DMSO-d$_6$+ TFA, δ ppm): 1.23-1.39 (m, 4H) 1.43-1.54 (m, 1H) 1.56-1.70 (m, 2H) 1.76-1.88 (m, 1H) 1.98-2.09 (m, 1H) 3.25-3.36 (m, 1H) 3.42-3.60 (m, 2H) 6.75 (dd, J=8.3, 2.0 Hz, 1H) 6.98 (d, J=1.7 Hz, 1H) 7.22-7.29 (m, 1H) 7.52-7.63 (m, 3H) 7.69 (d, J=8.1 Hz, 1H) 7.71-7.79 (m, 2 H) 7.82-7.91 (m, 2H) 7.96 (d, J=8.3 Hz, 1H) 8.04 (dd, J=9.0, 4.4 Hz, 1H).

Mass spectrum (LC/MS; method A): retention time Tr (min)=0.94; [M+H]+=548; [M−H]−=546.

When the second eluted product is recovered, 32 mg of the laevorotatory enantiomer of 4-[4-(6-fluoro-1H-benzimidazol-2-yl)-9H-carbazol-9-yl]-2-[1(S,R),2(R,S)-2-hydroxymethylcyclohexyl-1-amino])benzamide are obtained in the form of a beige solid, the characteristics of which are the following:

optical rotation: $\alpha_{589}^{20}$=−18°+/−0.9° (C=0.3% in methanol).

analytical HPLC (Chiralpak T304 20 µm column; 6×250 mm; 90/10/0.1 heptane/ethanol/TFA at 1 ml/min): retention time=42.5 min.

1H NMR spectrum (400 MHz, DMSO-d$_6$, δ ppm): 1.17-1.35 (m, 4H) 1.44 (broad s, 1H) 1.51-1.69 (m, 2H) 1.72-1.87 (m, 1H) 2.02 (d, J=10.3 Hz, 1H) 3.20-3.28 (masked, 1H) 3.37-3.60 (m, 2H) 4.38 (t, J=4.4 Hz, 1H) 6.67 (dd, J=8.3, 2.0 Hz, 1H) 6.91 (d, J=2.0 Hz, 1H) 7.08-7.21 (m, 2H) 7.25 (br. s., 1H) 7.41-7.47 (m, 2 H) 7.52-7.69 (m, 5H) 7.90 (d, J=8.6 Hz, 1H) 7.97 (br. s., 1H) 8.56 (d, J=8.6 Hz, 1H) 8.62 (dd, J=19.8, 8.6 Hz, 1H) 13.09 (br. s., 1H).

Mass spectrum (LC/MS; method A): retention time Tr (min)=0.94; [M+H]+=548; [M−H]−=546.

EXAMPLE 132

Synthesis of 5-[4-(quinolin-3-yl)-9H-carbazol-9-yl]-3-(2,2,6,6-tetramethylpiperidin-4-ylamino)pyridine-2-carboxamide

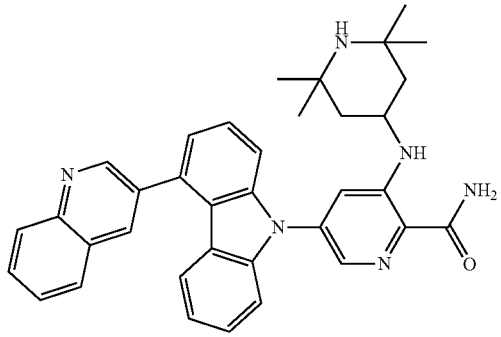

The 5-[4-(quinolin-3-yl)-9H-carbazol-9-yl]-3-(2,2,6,6-tetramethylpyperidin-4-ylamino)pyridine-2-carboxamide is obtained by carrying out the process as in Example 122, but using 4-(quinolin-3-yl)-9H-carbazole, obtained according to stage 1 of Example 2, and 5-fluoro-3-(1,2,2,6,6-tetramethylpiperidin-4-ylamino)pyridine-2-carbonitrile, itself obtained by carrying out the process as for the 5-fluoro-3-(1,2,2,6,6-tetramethylpiperidin-4-ylamino)pyridine-2-carbonitrile in stage 1 of Example 122, according to the scheme below:

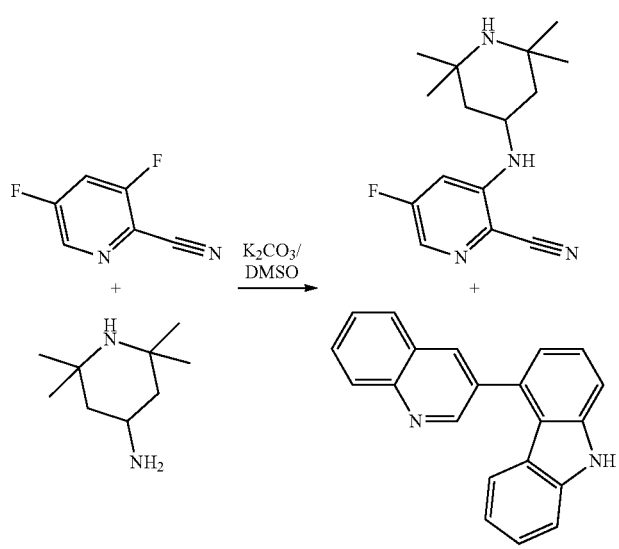
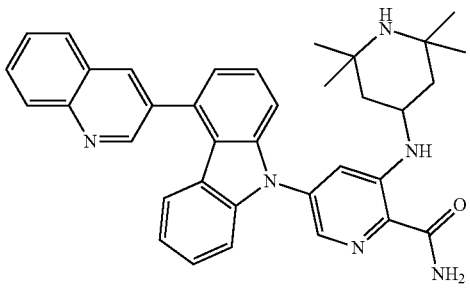

EXAMPLE 133

Synthesis of 3-[(2-pyridin-2-yl)ethylamino)-5-[4-(quinolin-3-yl)-9H-carbazol-9-yl]pyridine-2-carboxamide

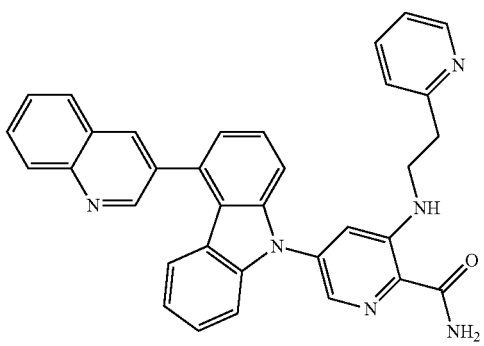

Stage 1: 841 mg of 2-cyano-3,5-difluoropyridine, 880 mg of 2-(2-aminoethyl)pyridine and 1.658 g of potassium carbonate in 12.5 ml of dimethyl sulphoxide are introduced into a 20 ml microwave tube reactor. The mixture is then heated in a microwave for 1 and a half hours at 115° C. The reaction medium is run into 100 ml of water and 100 ml of ethyl acetate. The aqueous phase is re-extracted twice with 50 ml of ethyl acetate. The combined organic phases are washed with water and then with a saturated aqueous solution of sodium chloride, dried over sodium sulphate and concentrated under reduced pressure. After purification by flash chromatography on 70 g of silica gel, elution being carried out with a mixture of ethyl acetate and cyclohexane (40/60 by volume), and the first eluted product being recovered, 549 mg of 2-cyano-5-fluoro-3-(2-pyridin-2-ylethylamino)pyridine are thus obtained in the form of a beige powder, the characteristics of which are the following:

1H NMR spectrum (400 MHz, DMSO-$d_6$, δ ppm): 3.02 (t, J=7.1 Hz, 2H) 3.57 (q, J=6.8 Hz, 2H) 6.94 (broad s, 1H) 7.15-7.27 (m, 2H) 7.33 (d, J=7.8 Hz, 1H) 7.71 (td, J=7.6, 1.8 Hz, 1H) 7.86 (d, J=2.4 Hz, 1H) 8.51 (d, J=4.9 Hz, 1H).

Stage 2: In a 50 ml three-necked flask under an argon atmosphere, 236.5 mg of 4-(quinolin-3-yl)-9H-carbazole, obtained according to stage 1 of Example 2, are dissolved in 20 ml of dimethylformamide. 48 mg of sodium hydride at 60% in oil are then added and the mixture is stirred for 30 minutes at 50° C. 213 mg of 2-cyano-5-fluoro-3-(2-pyridin-2-ylethylamino)pyridine, obtained in the preceding stage, are then added and the mixture is heated at 80° C. for 4 hours. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. 420 mg of a mixture are thus obtained, said mixture being used as it is in the subsequent stage and containing predominantly 3-[(2-pyridin-2-yl)ethylamino)-5-[4-(quinolin-3-yl)-9H-carbazol-9-yl]pyridin-2-carbonitrile, the characteristic of which is the following:

LC/MS (method C): retention time=4.55 min.

Stage 3: 300 mg of the mixture obtained in the preceding stage are dissolved in 3.3 ml of dimethyl sulphoxide and 8 ml of ethanol, and then 1.25 ml of 1M aqueous solution of sodium hydroxide and 1.15 ml of a 30% aqueous solution of hydrogen peroxide are successively added. After stirring for 5 minutes at ambient temperature, the reaction medium is run into 50 ml of water and 50 ml of ethyl acetate. The aqueous phase is re-extracted twice with 50 ml of ethyl acetate. The combined organic phases are washed with water, dried over sodium sulphate and concentrated under reduced pressure. After purification by flash chromatography on 35 g of silica gel, elution being carried out with a mixture of dichloromethane and ethanol (96/4 by volume), and then crystallization from 5 ml of diisopropyl ether, 128 mg of 3-[(2-pyridin-2-yl)ethylamino)-5-[4-(quinolin-3-yl)-9H-carbazol-9-yl]pyridin-2-carboxamide are thus obtained in the form of an off-white powder, the characteristics of which are the following:

TLC on silica gel: Rf=0.21 (dichloromethane/ethanol 95/5).

1H NMR spectrum (400 MHz, DMSO-d6) δ ppm 3.08 (t, J=6.6 Hz, 2H) 3.64 (q, J=5.8 Hz, 2H) 7.06 (t, J=7.6 Hz, 1H) 7.19 (dd, J=6.2, 5.0 Hz, 1H) 7.26 (d, J=7.8 Hz, 1H) 7.34 (d, J=7.3 Hz, 2H) 7.42 (t, J=7.7 Hz, 1H) 7.46-7.65 (m, 5H)

7.65-7.78 (m, 2H) 7.89 (t, J=7.5 Hz, 1H) 8.04 (s, 1H) 8.07-8.17 (m, 2H) 8.19 (d, J=8.6 Hz, 1H) 8.45 (d, J=4.4 Hz, 1H) 8.63 (s, 1H) 8.84 (br. s., 1H) 9.16 (s, 1H).

Mass spectrum (LC/MS; method B): retention time Tr (min)=3.83; m/z=535 [M+H]+.

EXAMPLE 134

Synthesis of 4-[4-(6-cyanopyridin-3-yl)-9H-carbazol-9-yl]-2-[(2-fluoroethyl)amino]benzamide

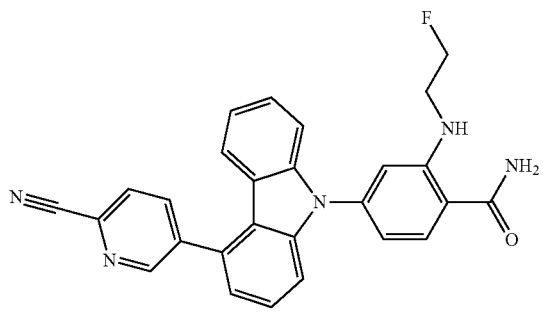

Stage 1: 4.83 g of potassium carbonate and 3 g (40 mmol) of 2-fluoroethylamine are successively added to a solution of 0.7 g of 2-methylpropan-2-yl 4-[4-(6-cyanopyridin-3-yl)-9H-carbazol-9-yl]-2-fluorobenzoate, obtained in stage 1 of Example 49, in 5 ml of dimethyl sulphoxide. The reaction mixture is heated at 90° C. for 2 hours and 50 minutes in a microwave, and then diluted with distilled water. The aqueous phase is washed twice with ethyl acetate and the combined organic phases are washed with water and a saturated solution of sodium chloride, dried over magnesium sulphate and concentrated to dryness under reduced pressure. The residue is purified by silica gel chromatography, elution being carried out with dichloromethane, so as to give 0.15 g of 2-methylpropan-2-yl 4-[4-(6-cyanopyridin-3-yl)-9H-carbazol-9-yl]-2-[(2-fluoroethyl)amino]benzoate in the form of a white powder, the characteristics of which are the following:

1H NMR spectrum (400 MHz, δ in ppm, DMSO-d6): 1.60 (s, 9H) 3.59 (dq, J=28.4, 5.4 Hz, 2H) 4.64 (dt, J=47.9, 4.9 Hz, 2H) 6.84 (dd, J=8.6, 2.0 Hz, 1H) 7.06 (d, J=2.0 Hz, 1H) 7.11 (t, J=6.6 Hz, 1H) 7.23 (dd, J=6.7, 1.3 Hz, 1H) 7.31 (d, J=8.1 Hz, 1H) 7.43 (t, J=7.3 Hz, 1H) 7.51 (d, J=7.8 Hz, 1H) 7.54-7.63 (m, 2H) 8.07 (d, J=8.6 Hz, 1H) 8.12 (t, J=5.7 Hz, 1H) 8.28 (d, J=7.8 Hz, 1H) 8.34 (dd, J=8.1, 2.0 Hz, 1H) 9.02 (d, J=2.0 Hz, 1H).

Mass spectrum (LC/MS; method A): retention time Tr (min)=1.32; m/z=507 [M+H]+.

Stage 2: 1.54 ml of 1N hydrochloric acid are added to a solution of 0.13 g of 2-methylpropan-2-yl 4-[4-(6-cyanopyridin-3-yl)-9H-carbazol-9-yl]-2-[(2-fluoroethyl)amino]benzoate in 6 ml of dioxane. The reaction mixture is heated at 100° C. in a microwave for 2 hours and then concentrated under reduced pressure. The residue is purified by silica gel chromatography, elution being carried out with a mixture of dichloromethane and methanol (97/3 by volume), so as to give 40 mg of 4-[4-(6-cyanopyridin-3-yl)-9H-carbazol-9-yl]-2-[(2-fluoroethyl)amino]benzoic acid in the form of an off-white powder, the characteristics of which are the following:

1H NMR spectrum (400 MHz, δ in ppm, DMSO-d6): 3.45-3.63 (m, 2H) 4.62 (dt, J=47.9, 4.6 Hz, 2H) 6.70-6.84 (m, 1H) 6.96 (s, 1H) 7.10 (t, J=7.6 Hz, 1H) 7.22 (dd, J=7.5, 0.9 Hz, 1H) 7.31 (d, J=8.1 Hz, 1H) 7.40-7.46 (m, 1H) 7.51 (d, J=8.6 Hz, 1H) 7.54-7.63 (m, 2H) 8.10 (d, J=8.6 Hz, 1H) 8.28 (d, J=7.8 Hz, 1H) 8.35 (dd, J=8.1, 2.0 Hz, 1H) 9.03 (d, J=2.2 Hz, 1H).

Mass spectrum (LC/MS; method B): retention time Tr (min)=4.76; m/z=451 [M+H]+; 449 [M+H]−.

Stage 3: 58 mg of (1H-benzotriazol-1-yloxy)[tris(dimethylamino)]phosphonium hexafluorophosphate (BOP), 18 mg of hydroxybenzotriazole (HOBT), 9 mg of ammonium chloride and 0.07 ml of diisopropylethylamine are successively added to a solution of 40 mg of 4-[4-(6-cyanopyridin-3-yl)-9H-carbazol-9-yl]-2-[(2-fluoroethyl)amino]benzoic acid in 30 ml of N,N-dimethylformamide. The reaction mixture is stirred at ambient temperature for 2 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a mixture of dichloromethane, acetonitrile and methanol (96/2/2 by volume), so as to gve 30 mg of 4-[4-(6-cyanopyridin-3-yl)-9H-carbazol-9-yl]-2-[(2-fluoroethyl)amino]benzamide in the form of a white solid, the characteristics of which are the following:

1H NMR spectrum (400 MHz, δ in ppm, DMSO-d6): 3.50 (dq, J=27.9, 5.4 Hz, 2H) 4.60 (dt, J=47.9, 4.9 Hz, 2H) 6.79 (dd, J=8.1, 1.7 Hz, 1H) 6.96 (d, J=1.5 Hz, 1 H) 7.10 (td, J=7.3, 1.0 Hz, 1H) 7.20-7.25 (m, 1H) 7.31 (d, J=8.3 Hz, 1H) 7.35 (broad s, 1H) 7.40-7.51 (m, 2H) 7.55-7.59 (m, 2H) 7.93 (d, J=8.3 Hz, 1H) 8.02 (broad s, 1H) 8.28 (d, J=7.8 Hz, 1H) 8.34 (dd, J=7.8, 2.4 Hz, 1H) 8.66 (t, J=5.6 Hz, 1H) 9.02 (d, J=2.0 Hz, 1H).

Mass spectrum (LC/MS; method A): retention time Tr (min)=1.06; m/z=450 [M+H]+; 448 [M−H]−.

EXAMPLE 135

Synthesis of 4-[4-(6-cyanopyridin-3-yl)-9H-carbazol-9-yl]-2-[(8-methyl-8-azabicyclo[3.2.1]oct-3-yl)amino]benzamide

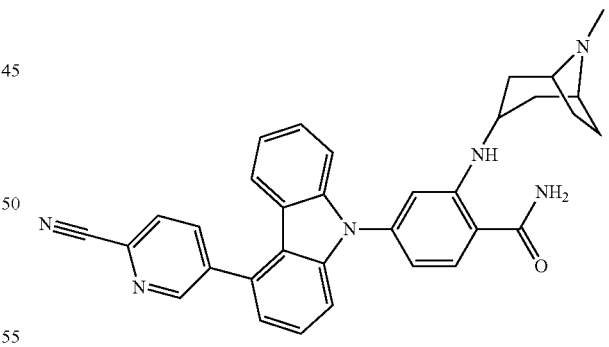

Stage 1: 0.89 g of potassium carbonate and 6 g of 8-methyl-8-azabicyclo[3.2.1]octan-3-amine are successively added to a solution of 1 g of 2-methylpropan-2-yl 4-[4-(6-cyanopyridin-3-yl)-9H-carbazol-9-yl]-2-fluorobenzoate, obtained in stage 1 of Example 49, in 8 ml of dimethyl sulphoxide. The reaction mixture is heated at 100° C. for 1 hour and 40 minutes in a microwave, and then diluted with distilled water. The aqueous phase is extracted twice with ethyl acetate and the combined organic phases are washed with water and a saturated solution of sodium chloride, dried over magnesium sulphate and concentrated to dryness under reduced pressure.

The residue is purified by silica gel chromatography, elution being carried out with a mixture of dichloromethane and methanol (92/8 as mixtures), so as to give 0.34 g of 2-methylpropan-2-yl 4-[4-(6-cyanopyridin-3-yl)-9H-carbazol-9-yl]-2-[(8-methyl-8-azabicyclo[3.2.1]oct-3-yl)amino]benzoate in the form of a white powder, the characteristics of which are the following:

1H NMR spectrum (400 MHz, δ in ppm, DMSO-d6): 1.60 (s, 9H) 1.62-1.67 (m, 2H) 1.86-1.93 (m, 2H) 2.01-2.12 (m, 4H) 2.17 (s, 3H) 3.07 (s, 2H) 3.65-3.72 (m, 1H) 6.74-6.80 (m, 2H) 7.11 (td, J=7.8, 1.2 Hz, 1H) 7.23 (dd, J=4.4, 3.7 Hz, 1H) 7.30 (d, J=8.1 Hz, 1H) 7.40-7.46 (m, 1H) 7.48 (d, J=8.1 Hz, 1H) 7.56-7.60 (m, 2H) 8.05 (d, J=9.0 Hz, 1H) 8.28 (dd, J=7.8, 0.7 Hz, 1H) 8.34 (m, J=7.8, 2.0 Hz, 1H) 8.44 (d, J=6.6 Hz, 1H) 9.02 (dd, J=2.2, 1.0 Hz, 1H).

Mass spectrum (LC/MS; method B): retention time Tr (min)=4.30; m/z=584 [M+H]+.

Stage 2: 3.49 ml of 1N hydrochloric acid are added to a solution of 340 mg of 2-methylpropan-2-yl 4-[4-(6-cyanopyridin-3-yl)-9H-carbazol-9-yl]-2-[(8-methyl-8-azabicyclo[3.2.1]oct-3-yl)amino]benzoate in 6 ml of dioxane. The reaction mixture is heated at 100° C. in a microwave for 2 hours and then concentrated under reduced pressure. The residue is purified by trituration with diisopropyl ether, so as to give 330 mg of 4-[4-(6-cyanopyridin-3-yl)-9H-carbazol-9-yl]-2-[(8-methyl-8-azabicyclo[3.2.1]oct-3-yl)amino]benzoic acid hydrochloride in the form of a pale yellow powder, the characteristics of which are the following:

1H NMR spectrum (400 MHz, δ in ppm, DMSO-d6): 2.05-2.14 (m, 2H) 2.19-2.44 (m, 6H) 2.70 (d, J=4.9 Hz, 3H) 3.80-3.95 (m, 3H) 6.85 (dd, J=8.6, 2.0 Hz, 1 H) 6.93 (d, J=1.7 Hz, 1H) 7.12 (t, J=7.5 Hz, 1H) 7.24 (dd, J=6.8, 1.0 Hz, 1H) 7.31 (d, J=8.1 Hz, 1H) 7.43 (t, J=7.8 Hz, 1H) 7.49-7.66 (m, 3H) 8.14 (d, J=8.8 Hz, 1H) 8.29 (d, J=7.6 Hz, 1H) 8.33 (dd, J=7.8, 2.2 Hz, 1H) 8.72 (d, J=6.6 Hz, 1H) 9.01 (d, J=2.1 Hz, 1H) 9.70 (broad s, 1H) 13.04 (broad s, 1H).

Mass spectrum (LC/MS; method A): retention time Tr (min)=0.87; m/z=528 [M+H]+; 526 [M+H]−.

Stage 3: 390 mg of (1H-benzotriazol-1-yloxy)[tris(dimethylamino)]phosphonium hexafluorophosphate (BOP), 120 mg of hydroxybenzotriazole (HOBT), 60 mg of ammonium chloride and 0.48 ml of diisopropylethylamine are successively added to a solution of 330 mg of 4-[4-(6-cyanopyridin-3-yl)-9H-carbazol-9-yl]-2-[(8-methyl-8-azabicyclo[3.2.1] oct-3-yl)amino]benzoic acid in 10 ml of N,N-dimethylformamide. The reaction mixture is stirred at ambient temperature for 4 hours and then diluted with distilled water and extracted with ethyl acetate. The organic phase is subsequently washed with distilled water and a saturated solution of sodium chloride, dried over magnesium sulphate, filtered and concentrated under reduced pressure. The residue is purified by silica gel chromatography, elution being carried out with a gradient of methanol in dichloromethane, so as to give 107 mg of a solid which is taken up with dichloromethane and washed successively with a 1M solution of potassium monophosphate, a saturated solution of sodium bicarbonate and a saturated solution of sodium chloride, dried over magnesium sulphate, filtered and concentrated under reduced pressure, so as to give 15 mg of 4-[4-(6-cyanopyridin-3-yl)-9H-carbazol-9-yl]-2-[(8-methyl-8-azabicyclo[3.2.1]oct-3-yl)amino]benzamide in the form of a white solid, the characteristics of which are the following:

1H NMR spectrum (400 MHz, δ in ppm, DMSO-d6): 1.61 (d, J=14.2 Hz, 2H) 1.86-2.09 (m, 6H) 2.16 (s, 3H) 3.04 (s, 2H) 3.53-3.66 (m, 1H) 6.66 (d, J=2.0 Hz, 1H) 6.71 (dd, J=8.1, 2.0 Hz, 1H) 7.10 (ddd, J=8.1, 6.5, 1.7 Hz) 7.22 (dd, J=6.1, 2.2 Hz, 1H) 7.31 (d, J=8.1 Hz, 1H) 7.39-7.49 (m, 2H) 7.53-7.59 (m, 2H) 7.93 (d, J=8.3 Hz, 1H) 8.28 (dd, J=7.8, 0.7 Hz, 1H) 8.34 (dd, J=8.1, 2.2 Hz, 1H) 9.02 (dd, J=2.1, 0.9 Hz, 1H) 9.08 (d, J=7.3 Hz, 1H).

Mass spectrum (LC/MS; method A): retention time Tr (min)=0.80; m/z=527 [M+H]+.

EXAMPLE 136

Synthesis of 5-[4-(6-fluoro-1H-benzimidazol-2-yl)-9H-carbazol-9-yl]-3-(tetrahydropyran-4-yl)amino) pyridine-2-carboxamide

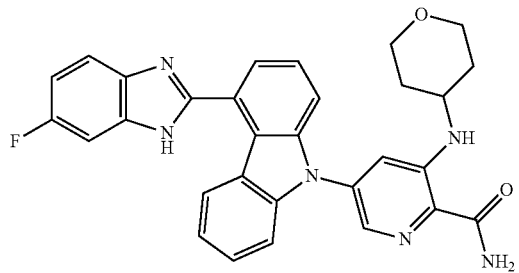

Stage 1: In a 25 ml three-necked flask under an argon atmosphere, 172 mg of 9H-carbazole-4-carboxylic acid methyl ester, obtained according to stage 1 of Example 3, are dissolved in 5.5 ml of dimethylformamide. 45.9 mg of sodium hydride at 60% in oil are then added and the mixture is stirred for 30 minutes at ambient temperature and then 30 minutes at 50° C. 169 mg of 2-cyano-5-fluoro-3-(tetrahydropyran-4-yl)-aminopyridine, obtained according to stage 1 of Example 116, are subsequently added and the mixture is heated at 50° C. overnight. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. After purification by flash chromatography on 20 g of silica gel, elution being carried out with a mixture of dichloromethane and acetonitrile (95/5 by volume), 120 mg of 1H-1-[3-(tetrahydropyran-4-yl)amino-2-carbamoylpyridin-5-yl]carbazole-4-carboxylic acid methyl ester are thus obtained in the form of an ecru powder, the characteristic of which is the following:

Mass spectrum (LC/MS; method A): retention time Tr (min)=1.10; m/z=427 [M+H]+.

Stage 2: In a 25 ml three-necked flask under an argon atmosphere, 53.2 mg of 1,2-diamino-4-fluorobenzene are dissolved in 4 ml of toluene and 2 ml of tetrahydrofuran, and then 0.422 ml of a 2M solution of trimethylaluminium in toluene is added dropwise and the mixture is stirred for 15 minutes at ambient temperature. A solution of 120 mg of 1H-1-[3-(tetrahydropyran-4-yl)amino-2-carbamoylpyridin-5-yl]carbazole-4-carboxylic acid methyl ester, obtained in the preceding stage, in 2 ml of toluene is then added dropwise. The reaction medium is refluxed for 3 hours. After cooling to ambient temperature, 10 ml of water and a few drops of a 1M aqueous solution of hydrochloric acid are added so as to bring the mixture to pH 4-5, and then the mixture is extracted 3 times with 10 ml of ethyl acetate. The combined organic phases are washed with water, dried over magnesium sulphate and concentrated under reduced pressure. 165 mg of the mixture of the regioisomers of 1H-1-[3-(tetrahydropyran-4-yl)amino-2-carbamoylpyridin-5-yl]carbazole-4-carboxylic acid 1,2-diamino-4-fluorobenzene amides are thus obtained, said mixture being used as it is in the subsequent stage.

Stage 3: 165 mg of the mixture obtained in the preceding stage and 2 ml of acetic acid are introduced into a 5 ml microwave tube reactor. The mixture is then heated successively for 45 minutes at 100° C. and then 1 and a half hours at 120° C. and, finally, 30 minutes at 150° C. After concentration of the acetic acid under reduced pressure, the residue is taken up with 20 ml of water and 20 ml of ethyl acetate, and then a saturated aqueous solution of sodium hydrogen carbonate is added so as to bring the pH to 7-8. The organic phase is separated by settling out and the aqueous phase is re-extracted twice with 20 ml of ethyl acetate. The combined organic phases are washed with water, dried over sodium sulphate and concentrated under reduced pressure. After purification by flash chromatography on 15 g of silica, elution being carried out with a mixture of heptane and ethyl acetate (55/45 by volume), 18 mg of 5-[4-(6-fluoro-1H-benzimidazol-2-yl)-9H-carbazol-9-yl]-3-(tetrahydropyran-4-yl)amino)pyridine-2-carboxamide are thus obtained in the form of an ecru powder, the characteristics of which are the following:

1H NMR spectrum (400 MHz, DMSO-$d_6$, δ ppm): 1.37-1.52 (m, 2H) 1.95 (d, J=15.2 Hz, 2H) 3.37-3.46 (m, 2H) 3.65-3.78 (m, 1H) 3.78-3.89 (m, 2H) 7.17 (broad s, 1H) 7.23 (t, J=7.6 Hz, 1H) 7.36-7.53 (m, 3H) 7.54-7.73 (m, 5H) 7.85 (broad s, 1H) 8.00 (d, J=2.0 Hz, 1H) 8.21 (br. s., 1H) 8.74 (broad s, 1H) 8.88 (d, J=7.8 Hz, 1H) 13.14 (broad s, 1H).

Mass spectrum (LC/MS; method A): retention time Tr (min)=0.91; m/z=521 [M+H]+; m/z=519 [M−H]−.

EXAMPLE 137

Synthesis of 2-[4-(quinolin-3-yl)-9H-carbazol-9-yl]-4-(tetrahydropyran-4-yl)amino)pyridine-5-carboxamide

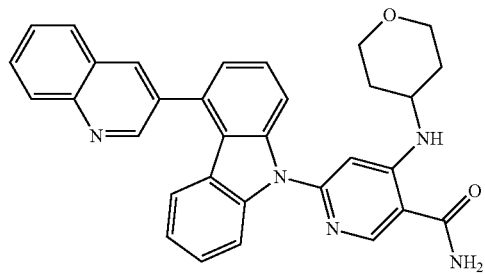

Stage 1: In a 25 ml single-necked round-bottomed flask, 300 mg of 4,6-dichloronicotinamide are dissolved in 4.5 ml of ethanol and 4.5 ml of dimethylacetamide, and then 238 mg of 4-aminotetrahydropyran hydrochloride and 711 mg of diisopropylethylamine are added. The mixture is then heated overnight at 60° C. After concentration under reduced pressure, the residue is extracted with dichloromethane, washed with water, dried over magnesium sulphate and concentrated under reduced pressure. After purification by flash chromatography on 25 g of silica, elution being carried out with a mixture of ethyl acetate and heptane (85/15 by volume), 132.5 mg of 6-chloro-4-(tetrahydropyran-4-yl)aminonicotinamide are obtained, the characteristic of which is the following:

1H NMR spectrum (400 MHz, DMSO-$d_6$, δ ppm): 1.32-1.46 (m, 2H) 1.88 (d, J=11.2 Hz, 2H) 3.47 (td, J=11.2, 2.2 Hz, 2H) 3.66-3.77 (m, 1H) 3.82 (dt, J=11.7, 3.6 Hz, 2H) 6.82 (s, 1H) 7.45 (broad s, 1H) 8.07 (broad s, 1H) 8.41 (s, 1H) 8.86 (d, J=8.1 Hz, 1H).

Stage 2: In a 25 ml three-necked flask under a nitrogen atmosphere, 80 mg of 6-chloro-4-(tetrahydropyran-4-yl)aminonicotinamide, obtained in the preceding stage, and 184.3 mg of 4-(quinolin-3-yl)-9H-carbazole, obtained according to stage 1 of Example 2, are dissolved in 7 ml of dioxane, and then argon is bubbled into the solution for 10 minutes, with preheating at around 50° C. 306 mg of caesium carbonate, 7 mg (31 μmol) of palladium acetate and 22 mg of 4,5-bis (diphenylphosphino)-9,9-dimethylxanthene are then successively added and the mixture is heated at 90° C. for 3 hours under an argon atmosphere. After cooling, the reaction medium is diluted with 20 ml of ethyl acetate, and the insoluble material is filtered through celite and rinsed twice with 10 ml of ethyl acetate. The combined filtrates are washed with water, dried over magnesium sulphate and concentrated under reduced pressure. After purification by flash chromatography on 25 g of silica, elution being carried out with a gradient of mixtures of dichloromethane and methanol (from 98/2 to 95/5 by volume), 11.8 mg of 2-[4-(quinolin-3-yl)-9H-carbazol-9-yl]-4-(tetrahydropyran-4-yl)amino)pyridine-5-carboxamide. are obtained in the form of an off-white powder, the characteristics of which are the following:

1H NMR spectrum (400 MHz, DMSO-$d_6$, δ ppm): 1.32-1.46 (m, 2H) 1.88 (d, J=11.2 Hz, 2H) 3.47 (td, J=11.2, 2.2 Hz, 2H) 3.66-3.77 (m, 1H) 3.82 (dt, J=11.7, 3.6 Hz, 2H) 6.82 (s, 1H) 7.45 (broad s, 1H) 8.07 (broad s, 1H) 8.41 (s, 1H) 8.86 (d, J=8.1 Hz, 1H).

Mass spectrum (LC/MS; method A): retention time Tr (min)=0.95; m/z=514 [M+H]+; m/z=512 [M−H]−.

EXAMPLE 138

Synthesis of 2-(8-methyl-8-azabicyclo[3.2.1]oct-3-yl)amino-4-[4-(quinolin-3-yl)-9H-carbazol-9-yl]benzamide

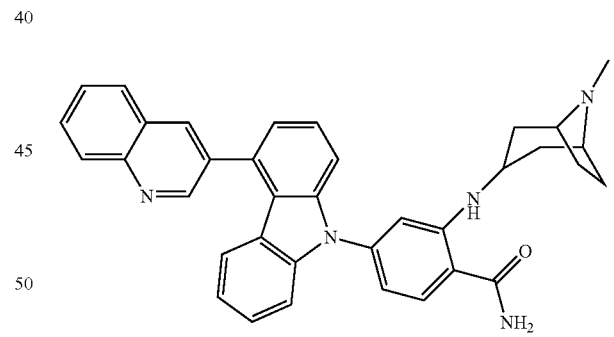

The process is carried out as in stage 3 of Example 3, but using 300 mg of 2-fluoro-4-[4-(quinolin-3-yl)-9H-carbazol-9-yl]benzonitrile, obtained according to stage 1 of Example 32, 301 mg of potassium carbonate and 3 g of 8-methyl-8-azabicyclo[3.2.1]octan-3-amine in 1.7 ml of dimethyl sulphoxide, in a microwave for 1 hour and 15 minutes at 115° C. 1.38 ml (1.38 mmol) of a 1M aqueous solution of sodium hydroxide, 1.33 ml (13 mmol) of a 30% aqueous solution of hydrogen peroxide and 8 ml of ethanol are then added to the reaction medium. After treatment as in stage 3 of Example 3, and then purification by flash chromatography on 10 g of silica gel, elution being carried out with a mixture of dichloromethane and ammonia in a 7M solution in methanol (97/3 by volume), 150 mg of 2-(8-methyl-8-azabicyclo[3.2.1]oct- 3-yl)amino-4-[4-(quinolin-3-yl)-9H-carbazol-9-yl]benzamide are thus obtained in the form of an off-white solid, the characteristics of which are the following:

1H NMR spectrum (400 MHz, DMSO-$d_6$, δ ppm): 1.62 (d, J=13.4 Hz, 2H) 1.88-2.11 (m, 6H) 2.16 (s, 3H) 3.04 (broad s, 2H) 3.61 (q, J=6.5 Hz, 1H) 6.69 (s, 1H) 6.74 (dd, J=8.4, 1.3 Hz, 1H) 7.02 (t, J=7.5 Hz, 1H) 7.24 (d, J=8.1 Hz, 1H) 7.29 (d, J=6.6 Hz, 1H) 7.33 (broad s, 1H) 7.39 (t, J=7.6 Hz, 1H) 7.47 (d, J=8.1 Hz, 1H) 7.51-7.63 (m, 2H) 7.73 (t, J=7.5 Hz, 1H) 7.88 (t, J=7.7 Hz, 1H) 7.95 (d, J=8.3 Hz, 1H) 8.00 (broad s, 1H) 8.13 (d, J=7.8 Hz, 1H) 8.19 (d, J=8.3 Hz, 1H) 8.62 (d, J=1.7 Hz, 1H) 9.09 (d, J=7.1 Hz, 1H) 9.15 (d, J=2.0 Hz, 1H).

Mass spectrum (LC/MS; method A): retention time Tr (min)=0.82; m/z=552 [M+H]+−.

EXAMPLE 139

Synthesis of 3-[(2-hydroxy-2-methylpropylamino)-5-[4-(quinolin-3-yl)-9H-carbazol-9-yl]pyridine-2-carboxamide

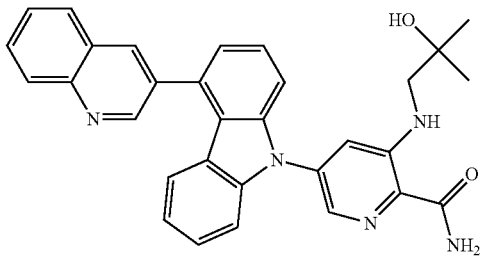

Stage 1: 1.8 g of 2-cyano-3,5-difluoropyridine, 1.375 g of 2-(2-aminoethyl)pyridine and 3.552 g of potassium carbonate in 27 ml of dimethyl sulphoxide are introduced into a 20 ml microwave tube reactor by means of three successive identical operations. The mixture is then heated in a microwave for 1 hour at 115° C. The reaction medium is run into 100 ml of water and 200 ml of ethyl acetate. The aqueous phase is re-extracted twice with 250 ml of ethyl acetate. The combined organic phases are washed with water and then with a saturated aqueous solution of sodium chloride, dried over sodium sulphate and concentrated under reduced pressure. After purification by flash chromatography on 200 g of silica gel, elution being carried out with a mixture of ethyl acetate and cyclohexane (50/50 by volume), and the first eluted product being recovered, 768 mg of 2-cyano-5-fluoro-3-(2-hydroxy-2-methylpropylamino)pyridine are thus obtained in the form of a beige powder, the characteristic of which is the following:

1H NMR spectrum (400 MHz, DMSO-$d_6$, δ ppm): 1.14 (s, 6H) 3.16 (d, J=5.9 Hz, 2H) 4.67 (s, 1H) 6.21 (broad s, 1H) 7.36 (dd, J=12.0, 2.4 Hz, 1H) 7.86 (d, J=2.4 Hz, 1H).

Stage 2: In a 50 ml three-necked flask under an argon atmosphere, 338.5 mg of 4-(quinolin-3-yl)-9H-carbazole, obtained according to stage 1 of Example 2, are dissolved in 20 ml of dimethylformamide. 69 mg of sodium hydride at 60% in oil are then added and the mixture is stirred for 30 minutes at 50° C. 265 mg of 2-cyano-5-fluoro-3-(2-hydroxy-2-methylpropylamino)pyridine, obtained in the preceding stage, are then added and the mixture is heated at 80° C. for 2 hours. The reaction medium is taken up with 50 ml of ethanol and concentrated to dryness under reduced pressure. The brown oil obtained is purified by flash chromatography on 30 g of silica, elution being carried out with a mixture of dichloromethane and ethanol (95/5 by volume). 419 mg of a mixture are thus obtained, said mixture being used as it is in the subsequent stage and containing very predominantly 3-[(2-hydroxy-2-methylpropylamino)-5-[4-(quinolin-3-yl)-9H-carbazol-9-yl]pyridin-2-carbonitrile, the characteristic of which is the following:

LC/MS (method C): retention time=5.39 min.

Stage 3: 415 mg of the mixture obtained in the preceding stage are dissolved in 4.5 ml of dimethyl sulphoxide and 11 ml of ethanol, and then 1.71 ml of a 1M aqueous solution of sodium hydroxide and 1.58 ml of a 30% aqueous solution of hydrogen peroxide are successively added. After stirring for 15 minutes at ambient temperature, the reaction medium is run into 50 ml of water and 50 ml of ethyl acetate. The aqueous phase is re-extracted twice with 50 ml of ethyl acetate. The combined organic phases are washed with water, dried over sodium sulphate and concentrated under reduced pressure. After successive crystallizations from 20 ml of diisopropyl ether and then from 5 ml of ethyl acetate, 401 mg of 3-[(2-hydroxy-2-methylpropylamino)-5-[4-(quinolin-3-yl)-9H-carbazol-9-yl]pyridine-2-carboxamide are thus obtained in the form of a pale yellow foam, the characteristics of which are the following:

1H NMR spectrum (400 MHz, DMSO-$d_6$, δ ppm): 1.18 (s, 6H) 3.16 (d, J=5.6 Hz, 2H) 4.58 (s, 1H) 7.05 (t, J=7.6 Hz, 1H) 7.26 (d, J=8.1 Hz, 1H) 7.33 (dd, J=7.1, 1.2 Hz, 1H) 7.41 (t, J=7.7 Hz, 1H) 7.48 (d, J=8.1 Hz, 1H) 7.51 (broad s, 1H) 7.54-7.63 (m, 3H) 7.74 (t, J=7.6 Hz, 1H) 7.89 (ddd, J=8.4, 7.0, 1.5 Hz, 1H) 8.00 (d, J=2.0 Hz, 1H) 8.11 (broad s, 1H) 8.14 (dd, J=8.4, 0.9 Hz, 1H) 8.19 (d, J=8.6 Hz, 1H) 8.62 (d, J=2.2 Hz, 1H) 8.97 (t, J=5.7 Hz, 1H) 9.15 (d, J=2.2 Hz, 1H).

Mass spectrum (LC/MS; method A): retention time Tr (min)=1.08; m/z=502 [M+H]+−.

EXAMPLE 140

Synthesis of dimethylaminoacetic acid 4-trans-{2-carbamoyl-5-[4(6-fluoro-1H-benzimidazol-2-yl)carbazol-9-yl]phenylamino}cyclohexyl ester

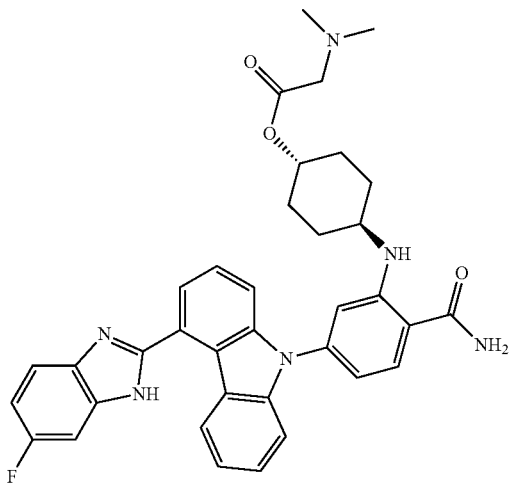

The process is carried out as in Example 15, but using 100 mg of 4-[4-(6-fluoro-1H-benzimidazol-2-yl)carbazol-9-yl]-2-(4-trans-hydroxycyclohexyl-amino)benzamide, which can be obtained as in Example 1, 38.7 mg of N,N-dimethylglycine, 23 mg of 4-dimethylaminopyridine and 71.9 mg of 1-(3-dimethylaminopropyl)-3-ethylcarbodiimide hydrochloride in 10 ml of dichloromethane and 2 ml of dimethylformamide for 20 hours at 45° C. After treatment as in Example 15, then purification by flash chromatography, elution being carried out with a mixture of dichloromethane and ethanol acetate (95/5 as mixtures), and then crystallization from 5 ml of diisopropyl ether, 75 mg of dimethylaminoacetic acid 4-trans-{2-carbamoyl-544(6-fluoro-1H-benzimidazol-2-yl)carbazol-9-yl]phenylamino}cyclohexyl ester are obtained in the form of an off-white solid, the characteristics of which are the following:

1H NMR spectrum (400 MHz, DMSO-$d_6$+TFA, δ ppm): 1.37-1.68 (m, 4H) 1.98 (d, J=10.3 Hz, 2H) 2.09 (d, J=10.3 Hz, 2H) 2.86 (s, 6H) 3.48-3.58 (m, 1H) 4.18 (s, 2H) 4.79-5.10 (m, 1H) 6.80 (dd, J=8.3, 1.7 Hz, 1H) 6.99 (d, J=1.7 Hz, 1H) 7.15-7.35 (m, 1H) 7.47-7.63 (m, 3H) 7.66-7.81 (m, 3H) 7.83 (dd, J=7.6, 1.5 Hz, 1H) 7.88 (dd, J=8.4, 2.3 Hz, 1H) 7.99 (d, J=8.3 Hz, 1H) 8.04 (dd, J=8.9, 4.5 Hz, 1H).

Mass spectrum (LC/MS; method A): retention time Tr (min)=0.73; m/z=619 [M+H]+; 617 [M+H]−.

EXAMPLE 141

Synthesis of 2-[(3-hydroxypropyl)amino]-4-[4-(5-hydroxypyridin-3-yl)-9H-carbazol-9-yl]benzamide

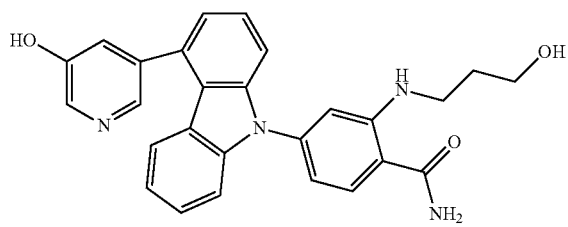

0.3 g of 4-[(445-(benzyloxy)pyridin-3-yl]-9H-carbazol-9-yl}-2-[(3-hydroxypropyl)amino]benzamide, obtained in Example 67, and 0.28 g of ammonium formate are successively added to a suspension of 8.8 mg of palladium-on-charcoal, 10%, in 8 ml of methanol. The reaction mixture is refluxed for 2 and a half hours and then filtered through celite and washed with methanol. The filtrate is concentrated under reduced pressure and washed successively with diethyl ether, dichloromethane and water, and then taken up in a dichloromethane/methanol mixture and concentrated under vacuum, so as to give 20 mg of 2-[(3-hydroxypropyl)amino]-4-[4-(5-hydroxypyridin-3-yl)-9H-carbazol-9-yl]benzamide in the form of a white solid, the characteristics of which are the following:

1H NMR spectrum (400 MHz, δ in ppm, DMSO-d6): 1.73 (quin, J=6.4 Hz, 2H) 3.15-3.22 (m, 2H) 3.46-3.54 (m, 2H) 4.49 (t, J=5.1 Hz, 1H) 6.74 (dd, J=8.4, 1.8 Hz, 1H) 6.85 (d, J=1.0 Hz, 1H) 7.05-7.11 (m, 1H) 7.14 (dd, J=5.7, 2.1 Hz, 1H) 7.27 (broad s, 1H) 7.33-7.55 (m, 6H) 7.91 (d, J=8.3 Hz, 1H) 7.97 (broad s, 1H) 8.24 (s, 1H) 8.30 (d, J=2.4 Hz, 1H) 8.44 (t, J=5.3 Hz, 1H) 10.22 (broad s, 1H).

Mass spectrum (LC/MS; method A): retention time Tr (min)=0.61; m/z=453 [M+H]+; 451 [M+H]−.

EXAMPLE 142

Synthesis of 2-[4-(quinolin-3-yl)-9H-carbazol-9-yl]-4-(4-trans-hydroxycyclohexylamino)pyridine-5-carboxamide

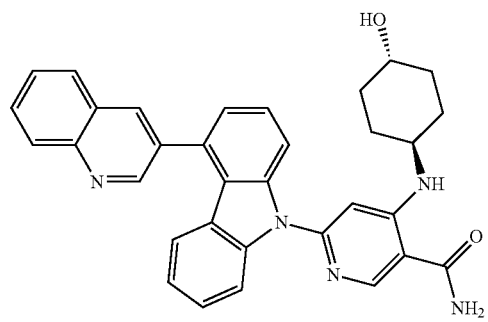

Stage 1: In a 50 ml single-necked round-bottomed flask, 500 mg of 4,6-dichloronicotinamide are dissolved in 7.5 ml of ethanol and 7.5 ml of dimethylacetamide, and then 663 mg of trans-4-aminocyclohexanol are added. The mixture is then heated overnight at 60° C. After concentration under reduced pressure, 360 mg of 6-chloro-4-(4-trans-hydroxycyclohexyl)aminonicotinamide are obtained, the characteristic of which is the following:

1H NMR spectrum (400 MHz, DMSO-$d_6$) δ ppm 1.09-1.42 (m, 4H) 1.79 (dd, J=13.1, 2.8 Hz, 2H) 1.91 (dd, J=12.8, 2.6 Hz, 2H) 3.38-3.52 (m, 2H) 4.56 (d, J=3.9 Hz, 1H) 6.73 (s, 1H) 7.41 (broad s, 1H) 8.03 (broad s, 1H) 8.38 (s, 1H) 8.76 (d, J=7.8 Hz, 1H).

Stage 2: In a 25 ml three-necked flask, under a nitrogen atmosphere, 150 mg of 6-chloro-4-(4-trans-hydroxycyclohexyl)aminonicotinamide and 327 g of 4-(quinolin-3-yl)-9H-carbazole, obtained according to stage 1 of Example 2, are dissolved in 13 ml of dioxane, and then argon is bubbled into the solution for 10 minutes, with preheating at around 50° C. 544 mg of caesium carbonate, 12.5 mg of palladium acetate and 39 mg of 4,5-bis(diphenylphosphino)-9,9-dimethylxanthene are then successively added and the mixture is heated at 90° C. for 3 hours under an argon atmosphere. After cooling, the reaction medium is diluted with 20 ml of ethyl acetate, and the insoluble material is filtered off through celite and rinsed twice with 10 ml of ethyl acetate. The combined filtrates are washed with water, dried over magnesium sulphate and concentrated under reduced pressure. After purification by flash chromatography on 70 g of silica, elution being carried out with a mixture of dichloromethane and methanol (96/4 by volume), 20 mg of 2-[4-(quinolin-3-yl)-9H-carbazol-9-yl]-4-(4-trans-hydroxycyclohexylamino)pyridine-5-carboxamide are obtained in the form of an off-white powder, the characteristics of which are the following:

1H NMR spectrum (400 MHz, DMSO-$d_6$) δ ppm 1.26-1.39 (m, 4H) 1.76-1.86 (m, 2H) 1.97-2.07 (m, 2H) 3.44-3.56 (m, 2H) 4.52 (d, J=4.2 Hz, 1H) 6.97 (s, 1H) 7.04 (t, J=7.5 Hz, 1H) 7.21 (d, J=7.8 Hz, 1H) 7.32 (d, J=7.3 Hz, 1H) 7.41 (t, J=7.6 Hz, 1H) 7.47 (broad s, 1H) 7.61 (t, J=8.3 Hz, 1H) 7.70-7.79 (m, 2H) 7.80-7.93 (m, 2H) 8.10 (broad s, 1H) 8.14 (d, J=8.1 Hz, 1H) 8.19 (d, J=8.6 Hz, 1H) 8.62 (d, J=1.7 Hz, 1H) 8.78 (s, 1H) 8.96 (d, J=8.1 Hz, 1H) 9.14 (d, J=2.2 Hz, 1H).

Mass spectrum (LC/MS; method A): retention time Tr (min)=0.83; m/z=526 [M+H]+.

EXAMPLE 143

Synthesis of 5-[4-(6-fluoro-1H-benzimidazol-2-yl)-9H-carbazol-9-yl]-3-(4-trans-hydroxycyclohexylamino)pyridine-2-carboxamide

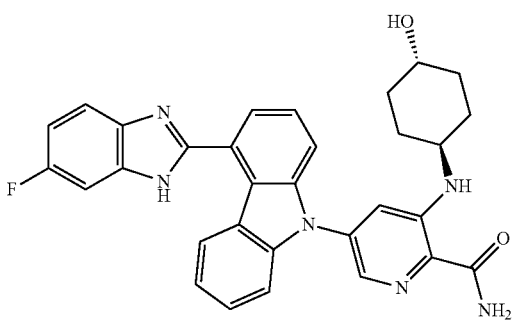

Stage 1: In a 50 ml three-necked flask, under an argon atmosphere, 676 mg of 9H-carbazole-4-carboxylic acid methyl ester, obtained according to stage 1 of Example 3, are dissolved in 50 ml of dimethylformamide. 180 mg of sodium hydride at 60% in oil are then added and the mixture is stirred for 30 minutes at ambient temperature and then 30 minutes at 50° C. 706 mg of 2-cyano-5-fluoro-3-(4-trans-hydroxycyclohexyl)aminopyridine, obtained according to stage 1 of Example 128, are then added and the mixture is heated at 60-65° C. for 6 hours. The reaction medium is run into 50 ml of water and 50 ml of ethyl acetate. The aqueous phase is re-extracted twice with 25 ml of ethyl acetate. The combined organic phases are washed with water and then with a saturated aqueous solution of sodium chloride, dried over sodium sulphate and concentrated under reduced pressure. After purification by successive flash chromatographies on 200 and then 80 g of silica gel, elution being carried out with gradients of mixtures of dichloromethane and acetonitrile (from 95/5 to 90/10 by volume), 454 mg of 1H-1-[3-(4-trans-hydroxycyclohexyl)amino-2-carbamoylpyridin-5-yl]carbazole-4-carboxylic acid methyl ester are thus obtained in the form of a colourless gum, the characteristics of which are the following:

TLC on silica gel: Rf=0.25 (dichloromethane/acetonitrile 9/1).

Mass spectrum (LC/MS; method C): retention time Tr (min)=4.47; m/z=441 [M+H]+.

Stage 2: In a 100 ml three-necked flask, under an argon atmosphere, 195 mg of 1,2-diamino-4-fluorobenzene are dissolved in 15 ml of toluene and 10 ml of tetrahydrofuran, and then 1.55 ml of a 2M solution of trimethylaluminium in toluene are added dropwise and the mixture is stirred for 15 minutes at ambient temperature. A solution of 454 mg of 1H-1-[3-(4-trans-hydroxycyclohexyl)amino-2-carbamoylpyridin-5-yl]carbazole-4-carboxylic acid methyl ester, obtained in the preceding stage, in 5 ml of toluene, is then added dropwise. The reaction medium is refluxed for 3 hours. After cooling to ambient temperature, 50 ml of water and a few drops of a 1M aqueous solution of hydrochloric acid are added so as to bring the pH to 4-5, and then the mixture is extracted 3 times with 50 ml of ethyl acetate. The combined organic phases are washed with water, dried over magnesium sulphate and concentrated under reduced pressure. After purification by flash chromatography on 30 g of silica, elution being carried out with a mixture of dichloromethane, methanol and 4M aqueous ammonia (96/4/1 by volume), 120 mg of the mixture of the regioisomers of 1H-1-[3-(4-trans-hydroxycyclohexyl)amino-2-carbamoylpyridin-5-yl]carbazole-4-carboxylic acid 1,2-diamino-4-fluorobenzene amides are obtained, the characteristic of which is the following:

Mass spectrum (LC/MS; method C): retention time Tr (min)=5.59; m/z=534 [M+H]+.

Stage 3: 120 mg (0.224 mmol) of the mixture of regioisomers obtained in the preceding stage and 1.5 ml of acetic acid are introduced into a 5 ml microwave tube reactor. The mixture is then heated twice for 30 minutes at 100° C. After concentration of the acetic acid under reduced pressure, the residue is taken up with 20 ml of water and 20 ml of ethyl acetate, and then a saturated aqueous solution of sodium hydrogen carbonate is added so as to bring the pH to 7-8. The organic phase is separated by settling out and the aqueous phase is re-extracted twice with 20 ml of ethyl acetate. The combined organic phases are washed with water, dried over sodium sulphate and concentrated under reduced pressure. 144 mg of 5-[4-(6-fluoro-1 H-benzimidazol-2-yl)-9H-carbazol-9-yl]-3-(4-trans-hydroxycyclohexylamino)pyridine-2-carbonitrile are thus obtained in the form of a beige powder, used as it is in the subsequent stage.

Stage 4: 144 mg of 5-[4-(6-fluoro-1H-benzimidazol-2-yl)-9H-carbazol-9-yl]-3-(4-trans-hydroxycyclohexylamino)pyridine-2-carbonitrile, obtained in the preceding stage, are dissolved in 1.5 ml of dimethyl sulphoxide and 3.7 ml of ethanol, and then 0.56 ml of a 1N aqueous solution of sodium hydroxide and 0.51 ml of a 30% aqueous solution of hydrogen peroxide are successively added. After stirring for 40 minutes at ambient temperature, 50 ml of water and 50 ml of ethyl acetate are added. The aqueous phase is re-extracted twice with 25 ml of ethyl acetate. The combined organic phases are washed with water, dried over magnesium sulphate and concentrated under reduced pressure. After purification by flash chromatography on 10 g of silica, elution being carried out with a mixture of dichloromethane and methanol (95/5 by volume), 80.6 mg of 544-(6-fluoro-1H-benzimidazol-2-yl)-9H-carbazol-9-yl]-3-(4-trans-hydroxycyclohexylamino)pyridine-2-carboxamide are obtained in the form of an ecru powder, the characteristics of which are the following:

1H NMR spectrum (400 MHz, DMSO-$d_6$) δ ppm 1.19-1.36 (m, 4H) 1.71-1.86 (m, 2H) 1.94-2.07 (m, 2H) 3.38-3.53 (m, 2H) 4.49 (d, J=3.9 Hz, 1H) 7.10-7.19 (m, 1H) 7.22 (t, J=7.6 Hz, 1H) 7.42 (d, J=8.1 Hz, 1H) 7.48 (t, J=7.7 Hz, 1H) 7.51-7.60 (m, 4H) 7.62 (t, J=7.7 Hz, 1H) 7.66-7.71 (m, 1H) 7.73 (broad s, 1H) 7.96 (d, J=2.0 Hz, 1H) 8.13 (broad s, 1H) 8.71 (d, J=8.3 Hz, 1H) 8.75 (d, J=7.8 Hz, 1H) 13.09 (broad s, 1H).

Mass spectrum (LC/MS; method A): retention time Tr (min)=0.84; m/z=535 [M+H]+; m/z=533 [M−H]−.

EXAMPLE 144

Synthesis of 4-[4-(quinolin-3-yl)-9H-carbazol-9-yl]-2-(exo-7-oxabicyclo[2.2.1]hept-2-ylamino)benzamide

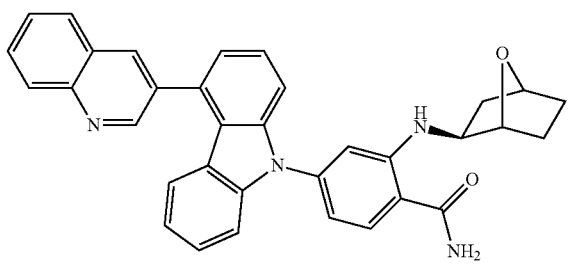

Stage 1: Exo N-benzyloxycarbonyl-7-oxabicyclo[2.2.1]hept-2-ylamine is prepared by carrying out the process as described by P. Spurr et al., WO 2008/154043, for the synthesis of exo N-ethoxycarbonyl-7-oxabicyclo[2.2.1]hept-2-ylamine, with ethanol being replaced with benzyl alcohol during the Curtius reaction used in the final stage. 3.21 g of exo N-benzyloxycarbonyl-7-oxabicyclo[2.2.1]hept-2-ylamine are thus obtained in the form of a thick, dark yellow oil, the characteristics of which are the following:

Mass spectrum (LC/MS; method B): retention time Tr (min)=3.42; MH+=248

Stage 2: 3.81 g of exo N-benzyloxycarbonyl-7-oxabicyclo[2.2.1]hept-2-ylamine, 0.82 g of palladium-on-charcoal at 10% and 40 ml of ethanol are successively introduced into an autoclave, and then the reaction medium is hydrogenated under 2 bar at 25° C. for 16 h with stirring. The mixture is subsequently filtered through Clarcel and the solid is washed with ethanol. The filtrate is concentrated to dryness under reduced pressure and the crude residue obtained is purified by chromatography on a 30 g cartridge of silica gel (15-40 μm), elution being carried out with a mixture of chloroform, methanol and 28% aqueous ammonia (55/6/1 by volume), at a flow rate of 40 ml/min. 647 mg of 2-exo-7-oxabicyclo[2.2.1]heptanamine are thus obtained in the form of a yellow liquid, the characteristics of which are the following:

Mass spectrum (LC/MS; method A): retention time Tr (min)=0.11; MH+=114+

Stage 3: 210 mg of 2-fluoro-4-[4-(quinolin-3-yl)-9H-carbazol-9-yl]benzonitrile, obtained according to stage 1 of Example 32, 2.1 ml of dimethyl sulphoxide, 211 mg of potassium carbonate and 460 mg of 2-exo-7-oxabicyclo[2.2.1]heptanamine, obtained in the preceding stage, are successively introduced into a 5 ml microwave reactor. After stirring for 1 minute at ambient temperature, the reaction medium is heated at 115° C. under microwave radiation for 90 minutes with stirring. After cooling, 5 ml of ethanol, 0.97 ml of 1M sodium hydroxide and 0.93 ml of 30% aqueous hydrogen peroxide are successively added and the mixture is stirred for 5 minutes at ambient temperature. 20 ml of distilled water are added and then the mixture is extracted with 3 times 25 ml of ethyl acetate. The combined organic phases are washed with a saturated solution of sodium chloride, dried over magnesium sulphate and concentrated to dryness under vacuum. The crude residue obtained is purified by chromatography on a 70 g cartridge of silica gel (15-40 μm), elution being carried out with a mixture of dichloromethane and ethanol (97/3 by volume), and then with a mixture of chloroform, methanol and 28% aqueous ammonia (12/3/0.5 by volume), at a flow rate of 50 ml/min. 250 mg of a yellow liquid are thus obtained, said liquid being repurified by chromatography on a 25 g cartridge of silica gel (15-40 μm), elution being carried out with a mixture of dichloromethane and ethanol (97/3 by volume), at a flow rate of 20 ml/min. The product obtained is triturated in 4 ml of diisopropyl ether, filtered, spin-dried, and then dried in an oven under vacuum (40° C., 20 mbar) for 2 hours. 189 mg of 4-[4-(quinolin-3-yl)-9H-carbazol-9-yl]-2-(exo-7-oxabicyclo[2.2.1]hept-2-ylamino)benzamide are thus obtained in the form of a pale yellow powder, the characteristics of which are the following:

1H NMR spectrum (400 MHz, δ in ppm, DMSO-d6): 1.31-1.59 (m, 5H) 2.04 (dd, J=12.3, 7.5 Hz, 1H) 3.64 (td, J=7.1, 2.9 Hz, 1H) 4.40 (d, J=4.6 Hz, 1H) 4.60 (t, J=4.5 Hz, 1H) 6.81 (dd, J=8.2, 1.8 Hz, 1H) 6.85 (d, J=1.7 Hz, 1H) 7.03 (t, J=7.6 Hz, 1H) 7.25 (d, J=8.1 Hz, 1H) 7.30 (dd, J=6.1, 2.0 Hz, 1H) 7.33 (broad s, 1H) 7.41 (t, J=8.1 Hz, 1H) 7.50 (d, J=8.1 Hz, 1H) 7.54-7.64 (m, 2H) 7.73 (t, J=7.5 Hz, 1H) 7.89 (ddd, J=8.3, 7.0, 1.3 Hz, 1H) 7.93 (d, J=8.3 Hz, 1H) 8.00 (broad s, 1H) 8.14 (d, J=7.6 Hz, 1H) 8.19 (d, J=8.3 Hz, 1H) 8.45 (d, J=7.3 Hz, 1H) 8.63 (d, J=2.0 Hz, 1H) 9.16 (d, J=2.0 Hz, 1H).

Mass spectrum (LC/MS; method A): retention time Tr (min)=1.12; MH+=525.

EXAMPLE 145

Synthesis of 5-[4-(6-fluoro-1H-benzimidazol-2-yl)-9H-carbazol-9-yl]-2-(1,2,2,6,6-pentamethylpiperidin-4-ylamino)pyridine-2-carboxamide

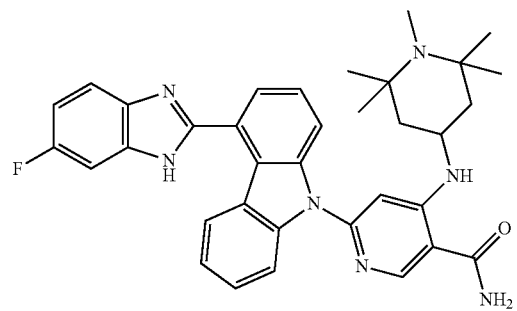

5-[4-(6-Fluoro-1H-benzimidazol-2-yl)-9H-carbazol-9-yl]-2-(1,2,2,6,6-pentamethylpiperidin-4-ylamino)pyridine-2-carboxamide is obtained by carrying out the process as in Example 143, but using 9H-carbazole-4-carboxylic acid methyl ester, obtained according to stage 1 of Example 3, and 5-fluoro-3-(1,2,2,6,6-pentamethylpiperidin-4-ylamino)pyridine-2-carbonitrile, obtained according to stage 1 of Example 132, according to the scheme below:

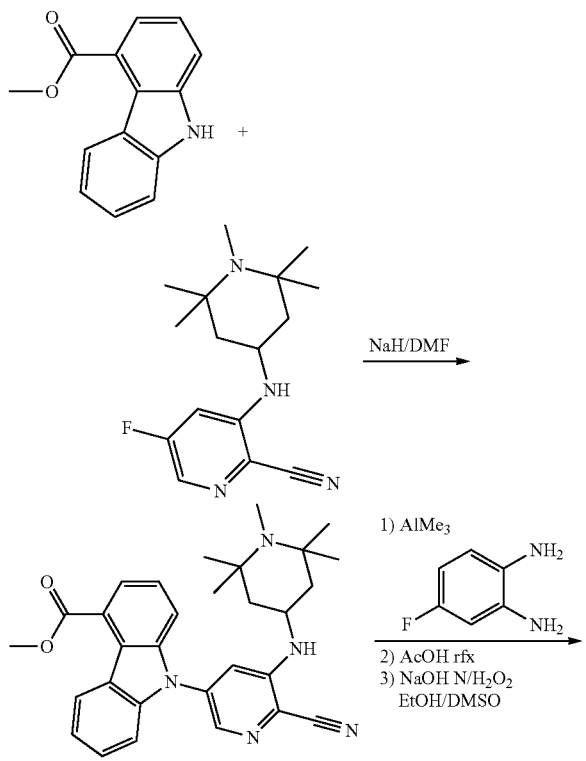

211
-continued

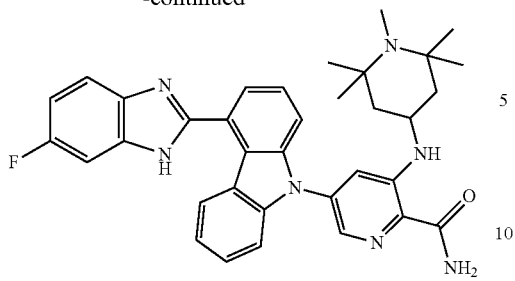

EXAMPLE 146

Synthesis of 4-(1,2,2,6,6-pentamethylpiperidin-4-ylamino)-2-[4-(quinolin-3-yl)-9H-carbazol-9-yl]pyridine-5-carboxamide

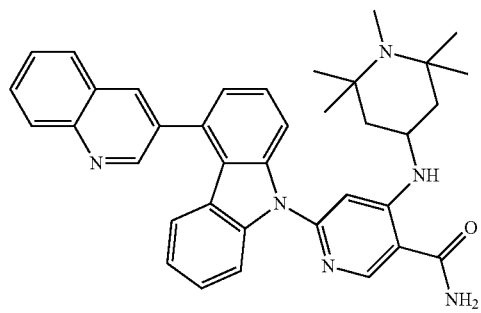

4-(1,2,2,6,6-Pentamethylpiperidin-4-ylamino)-2-[4-(quinolin-3-yl)-9H-carbazol-9-yl]pyridine-5-carboxamide is obtained by carrying out the process as in Example 142, but using 4-(quinolin-3-yl)-9H-carbazole, obtained according to stage 1 of Example 2, and 1,2,2,6,6-pentamethylpiperidine-4-amine and 4,6-dichloronicotinamide, according to the scheme below:

212

EXAMPLE 147

Synthesis of 4-(2-hydroxy-2-methylpropylamino)-2-[4-(quinolin-3-yl)-9H-carbazol-9-yl]pyridine-5-carboxamide

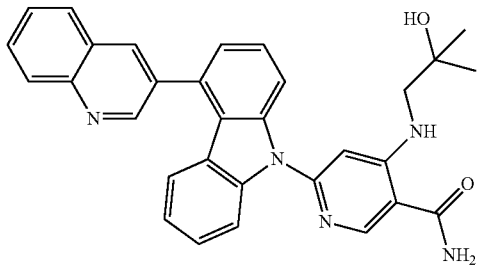

4-(2-Hydroxy-2-methylpropylamino)-2-[4-(quinolin-3-yl)-9H-carbazol-9-yl]pyridine-5-carboxamide is obtained by carrying out the process as in Example 142, but using 4-(quinolin-3-yl)-9H-carbazole, obtained according to stage 1 of Example 2, and 1-amino-2-methylpropan-2-ol and 4,6-dichloronicotinamide, according to the scheme below:

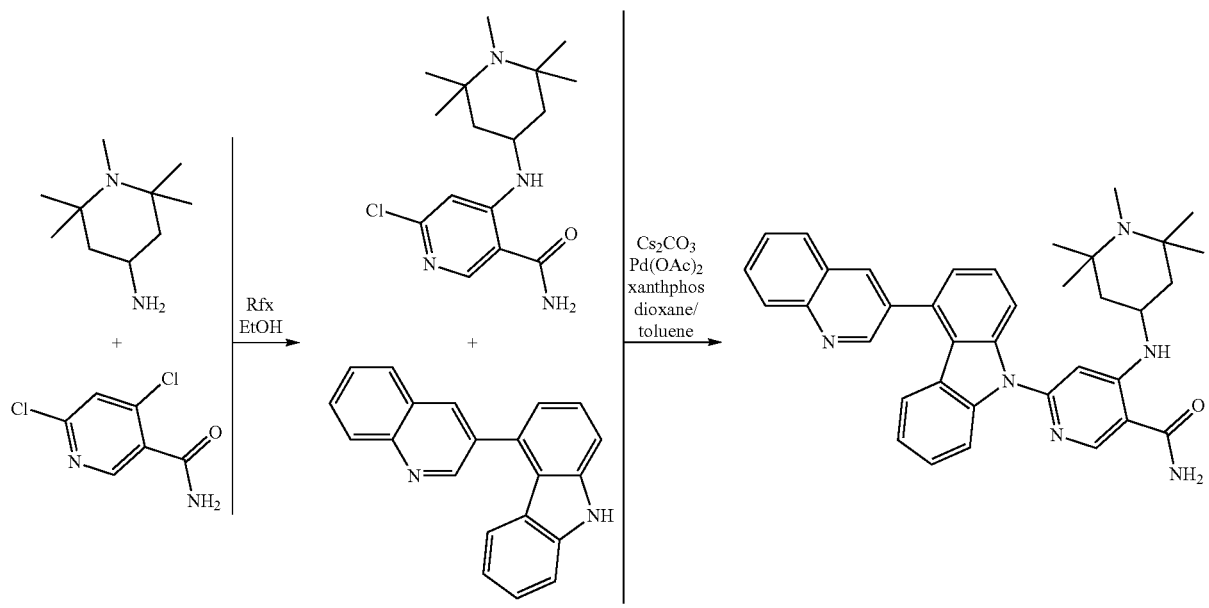

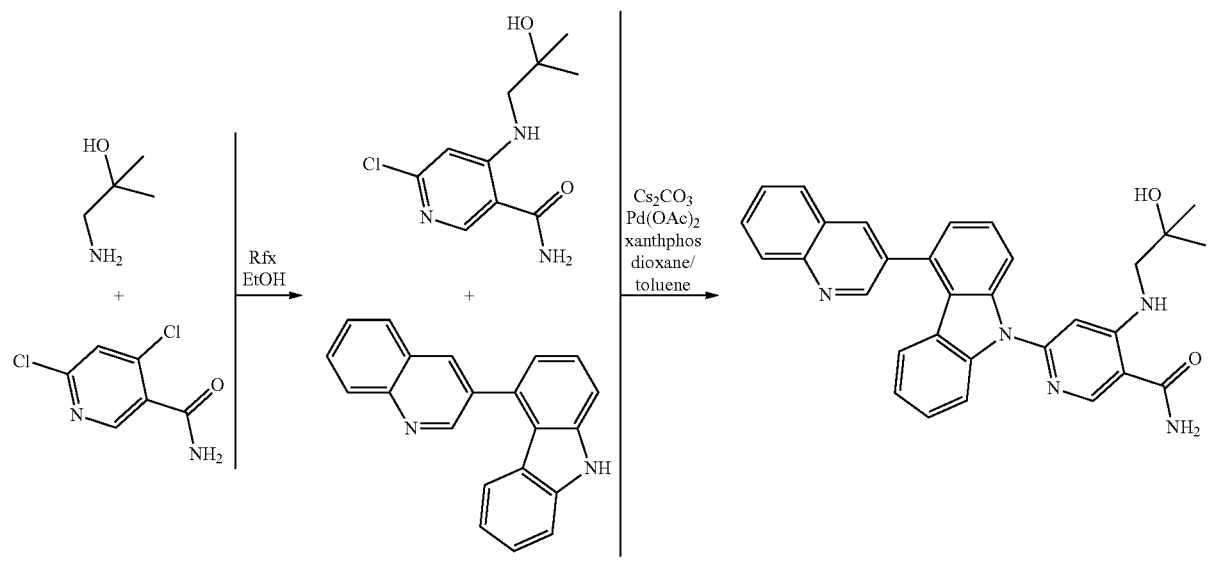

EXAMPLE 148

Synthesis of 2-[(8-methyl-8-azabicyclo[3.2.1]oct-3-yl)amino]-4-[4-(6-fluoro-1H-benzimidazol-2-yl)-9H-carbazol-9-yl]benzamide

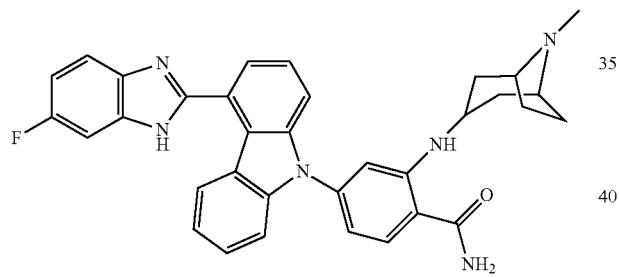

2-[(8-Methyl-8-azabicyclo[3.2.1]oct-3-yl)amino]-4-[4-(6-fluoro-1H-benzimidazol-2-yl)-9H-carbazol-9-yl]benzamide is obtained by carrying out the process as in stage 3 of Example 3, but using 2-fluoro-4-[4-(6-fluoro-1H-benzimidazol-2-yl)carbazol-9-yl]benzonitrile, obtained according to stage 2 of Example 3, and (8-methyl-8-azabicyclo[3.2.1]oct-3-yl)amine, according to the scheme below:

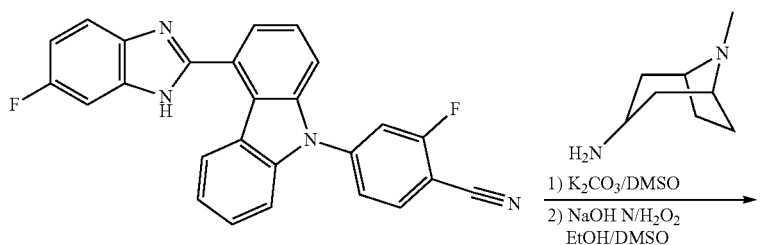

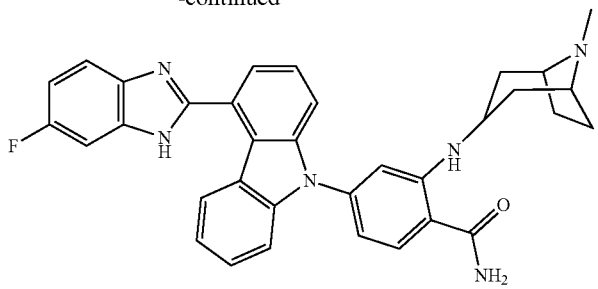

EXAMPLE 149

Pharmaceutical Composition

Tablets corresponding to the following formula were prepared:
Product of Example 12 . . . 0.2 g
Excipient for a tablet with a final weight of . . . 1 g
(details of the excipient: lactose, talc, starch, magnesium stearate).

EXAMPLE 150

Pharmaceutical Composition

Tablets corresponding to the following formula were prepared:
Product of Example 7 . . . 0.2 g
Excipient for a tablet with a final weight of . . . 1 g
(details of the excipient: lactose, talc, starch, magnesium stearate).

The present invention also comprises all the pharmaceutical compositions prepared with any product of formula (I) according to the present invention.

Biological Tests for Biologically Characterizing the Products of the Invention:

1) Biochemical Activity:

The biochemical activity of the compounds can in particular be evaluated by means of the "Hsp82/ATPase" test described below:

The inorganic phosphate released during the hydrolysis of ATP by the ATPase activity of Hsp82 is quantified by the malachite green method. In the presence of this reagent, formation of the inorganic phosphate-molybdate-malachite green complex, which absorbs at a wavelength of 620 nm, occurs.

The products to be evaluated are incubated in a reaction volume of 30 µl, in the presence of 1 µM Hsp82 and of 250 µM of substrate (ATP) in a buffer composed of 50 mM Hepes-NaOH (pH 7.5), 1 mM DTT, 5 mM $MgCl_2$ and 50 mM KCl at 37° C. for 60 min. In parallel, an inorganic phosphate range of between 1 and 40 µM is made up in the same buffer. The ATPase activity is then revealed by adding 60 µl of biomol green reagent (Tebu). After incubation at ambient temperature for 20 min, the absorbance of the various wells is measured using a microplate reader at 620 nm. The inorganic phosphate concentration of each sample is then calculated from the standard curve. The ATPase activity of Hsp82 is expressed as concentration of inorganic phosphate produced in 60 minutes. The effect of the various products tested is expressed as percentage inhibition of the ATPase activity.

The formation of ADP due to the ATPase activity of Hsp82 was used to develop another method for evaluating the enzyme activity of this enzyme by application of an enzymatic coupling system involving pyruvate kinase (PK) and lactate dehydrogenase (LDH). In this kinetic-type spectrophotometric method, PK catalyses the formation of ATP and of pyruvate from phosphoenol pyruvate (PEP) and the ADP produced by Hsp82. The pyruvate formed, which is a substrate for LDH, is subsequently converted to lactate in the presence of NADH. In this case, the decrease in the NADH concentration, measured through the decrease in absorbance at the wavelength of 340 nm, is proportional to the concentration of ADP produced by Hsp82.

The products tested are incubated in a reaction volume of 100 µl of buffer composed of 100 mM Hepes-NaOH (pH 7.5), 5 mM $MgCl_2$, 1 mM DTT, 150 mM KCl, 0.3 mM NADH, 2.5 mM PEP and 250 µM ATP. This mixture is preincubated at 37° C. for 30 minutes before the addition of 3.77 units of LDH and 3.77 units of PK. The reaction is initiated by addition of the product to be evaluated, in varying concentrations, and of Hsp82, at the concentration of 1 µM. The enzymatic activity of Hsp82 is then measured continuously, in a microplate reader, at 37° C., at the wavelength of 340 nm. The initial rate of the reaction is obtained by measuring the slope of the tangent to the origin of the curve recorded. The enzymatic activity is expressed in µM of ADP formed per minute. The effect of the various products tested is expressed as percentage inhibition of the ATPase activity according to the codification below:

A: $IC_{50} < 1$ µM
B: $1$ µM $< IC_{50} < 10$ µM

2) Cellular Activity:

The cellular activity of the compounds can in particular be evaluated by means of the phenotypic "SKBr3/HER2" cell test described below:

The SKBr3 mammalian adenocarcinoma cells, overexpressing the Her2 tyrosine kinase receptor, originate from the ATCC (HTB-30) and are cultured in McCoy's 5A medium supplemented with 10% FBS and 1% L-glutamine.

The cells are seeded in 12-well plates at a proportion of 125 000 cells per well in 1 ml of complete medium. The following day, the products are added at varying concentrations. After incubation for 24 h, the cells are trypsinized, washed with PBS and incubated with 100 ng of anti-Her2 antibody coupled to PE (Phycoerythrin) (BD 340552) for 30 minutes at 4° C. in the dark. The fluorescence due to the expression of the Her2 receptor at the surface of the cells is then read using a FACS Calibur flow cytometer (Becton-Dickinson). The percentage inhibition of Her2 expression as a function of the concentrations of product tested is fitted by the nonlinear regression technique (XLfit, equation 205) in order to measure an $IC_{50}$ for each product.

The activity of the products is codified as follows:
A: $IC_{50} < 1$ µM
B: $1$ µM $< IC_{50} < 10$ µM The summarizing table below gives the biochemical and cellular activities of representative compounds of the invention.

Table of Results

| Ex | Structure | Hsp82 ATPase IC$_{50}$ μM | SKBR$_3$ HER2 IC$_{50}$ μM |
|---|---|---|---|
| 1 | 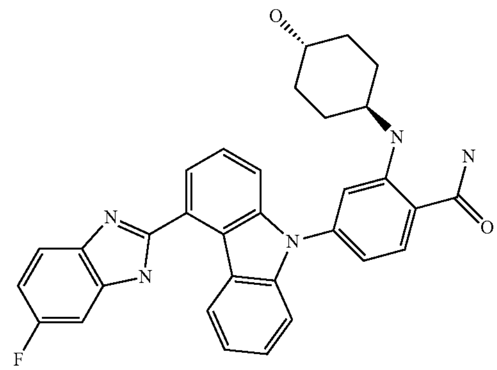 | A | A |
| 2 | 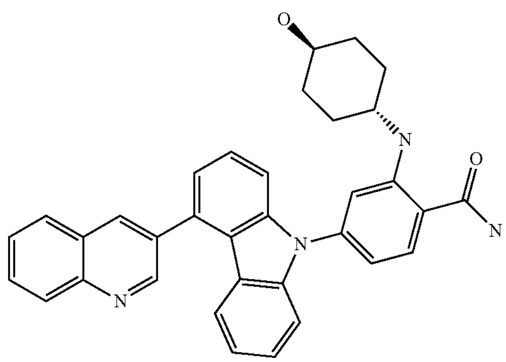 | A | A |
| 3 | 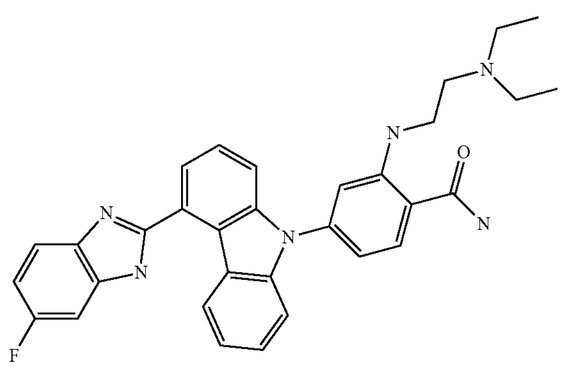 | A | A |
| 4 | 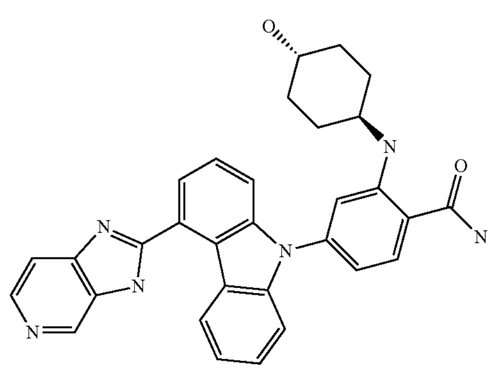 | A | A |

-continued
| Ex | Structure | Hsp82 ATPase IC$_{50}$ μM | SKBR$_3$ HER2 IC$_{50}$ μM |
|---|---|---|---|
| 5 | 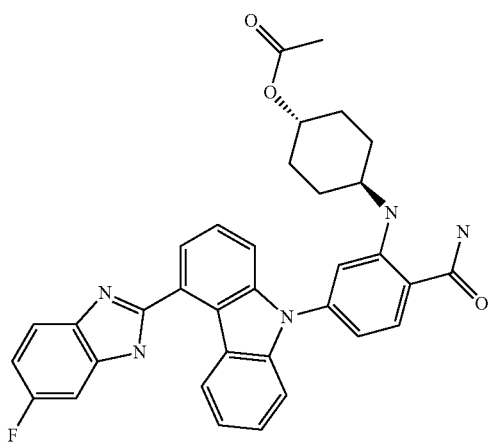 | B | A |
| 6 | 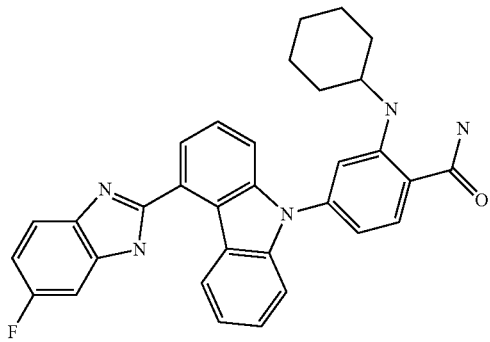 | B | A |
| 7 | 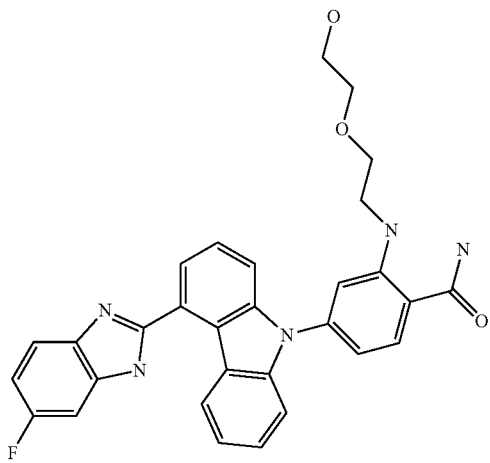 | A | A |

-continued
| Ex | Structure | Hsp82 ATPase IC$_{50}$ μM | SKBR$_3$ HER2 IC$_{50}$ μM |
|---|---|---|---|
| 8 | 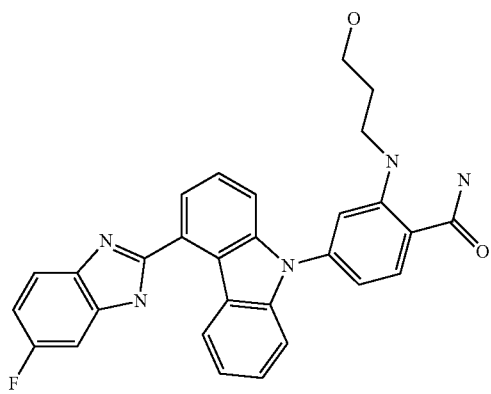 | A | A |
| 9 | 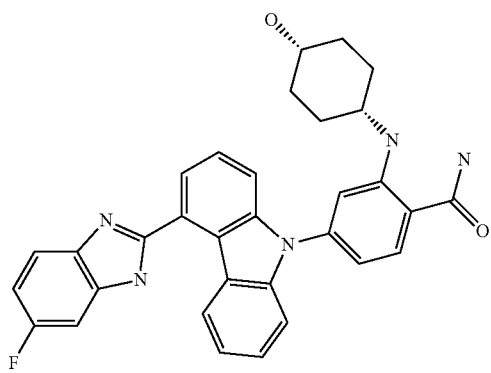 | B | A |
| 10 | 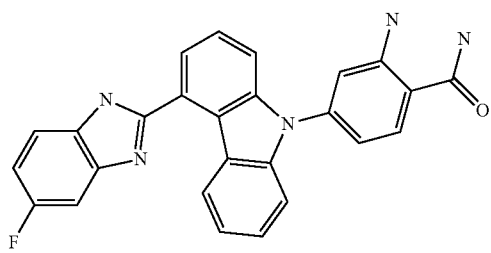 | A | B |
| 11 | 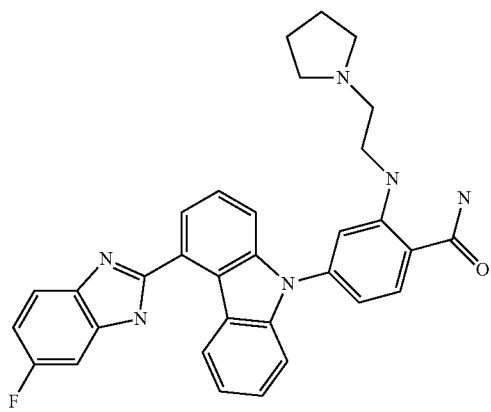 | A | A |

-continued

| Ex | Structure | Hsp82 ATPase IC$_{50}$ μM | SKBR$_3$ HER2 IC$_{50}$ μM |
|---|---|---|---|
| 12 | 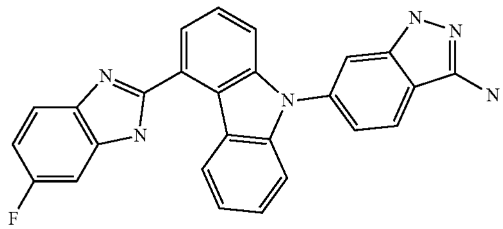 | B | B |
| 13 | 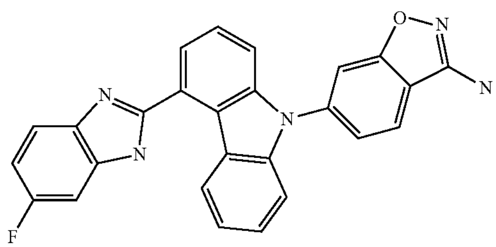 | B | B |
| 14 | 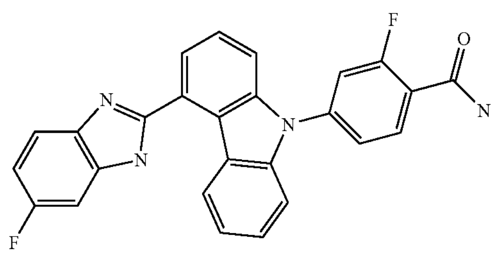 | B | A |
| 15 | 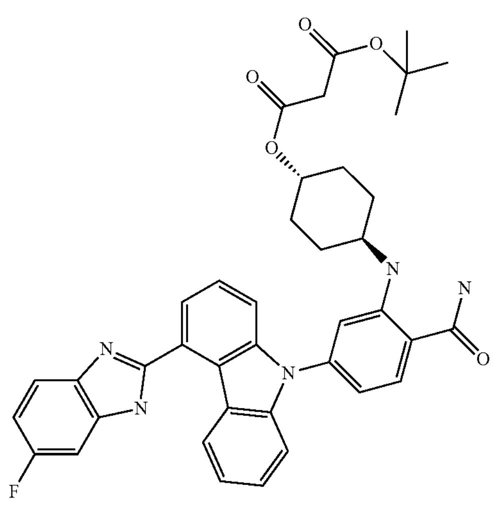 | B | A |
| 16 | 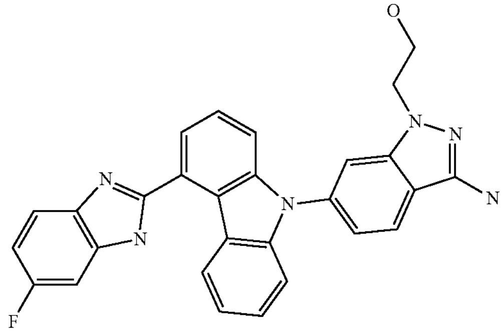 | B | B |

-continued
| Ex | Structure | Hsp82 ATPase IC$_{50}$ μM | SKBR$_3$ HER2 IC$_{50}$ μM |
|---|---|---|---|
| 17 | 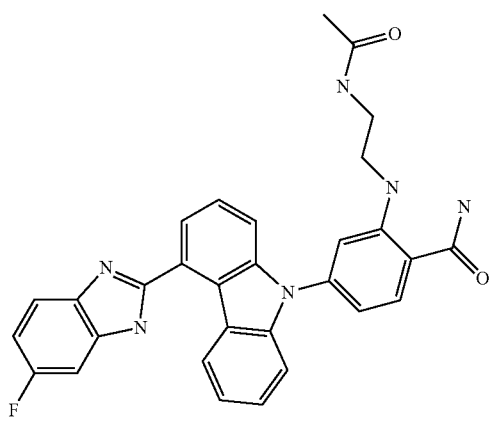 | A | A |
| 18 | 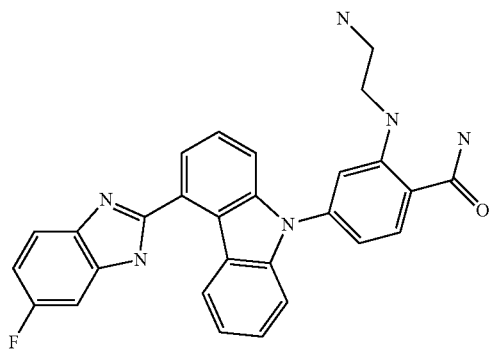 | A | B |
| 19 | 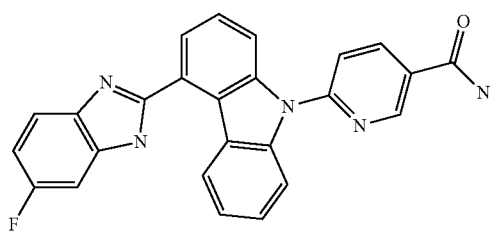 | B | B |
| 20 | 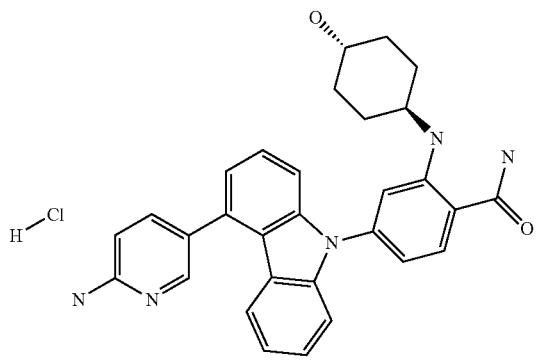 | A | A |

-continued
| Ex | Structure | Hsp82 ATPase IC$_{50}$ μM | SKBR$_3$ HER2 IC$_{50}$ μM |
|---|---|---|---|
| 21 | 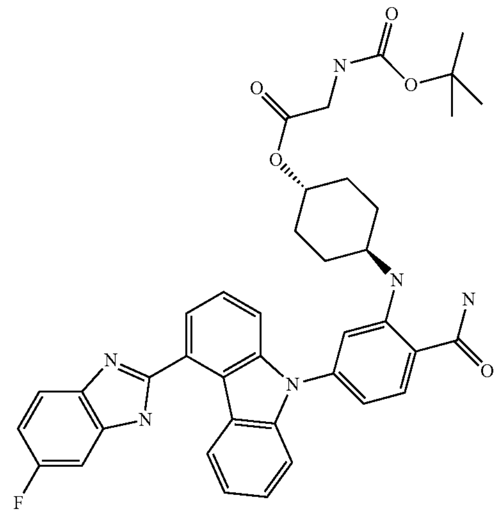 | B | A |
| 22 | Chiral | B | A |
| 23 | 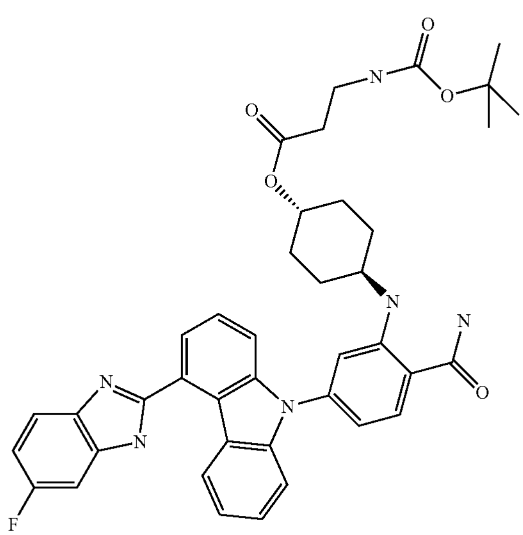 | B | A |
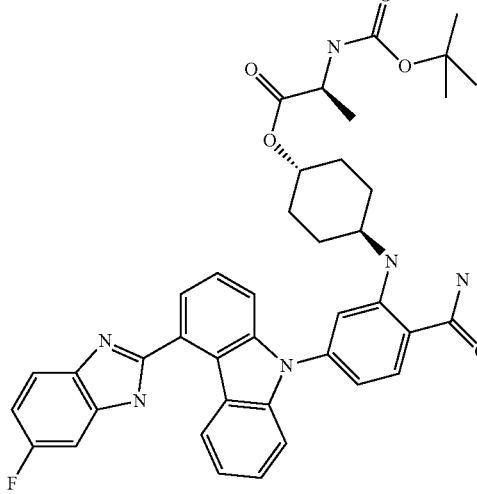
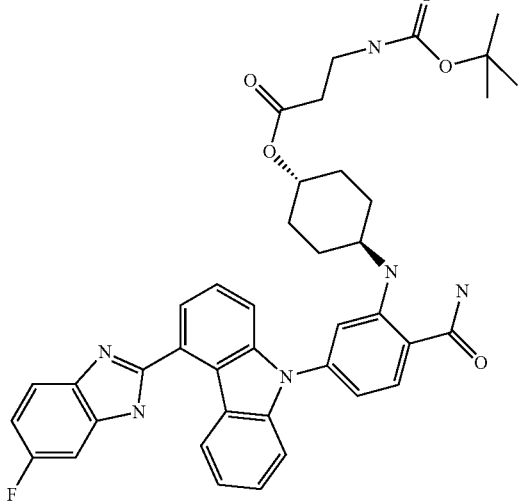

-continued

| Ex | Structure | Hsp82 ATPase IC$_{50}$ μM | SKBR$_3$ HER2 IC$_{50}$ μM |
|---|---|---|---|
| 24 | 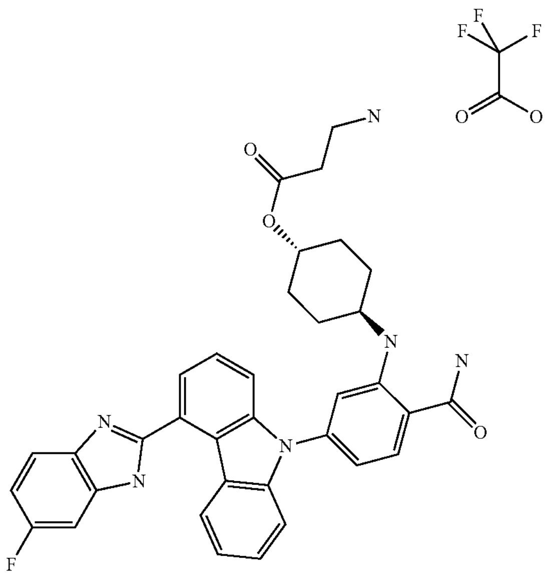 | B | A |
| 25 | 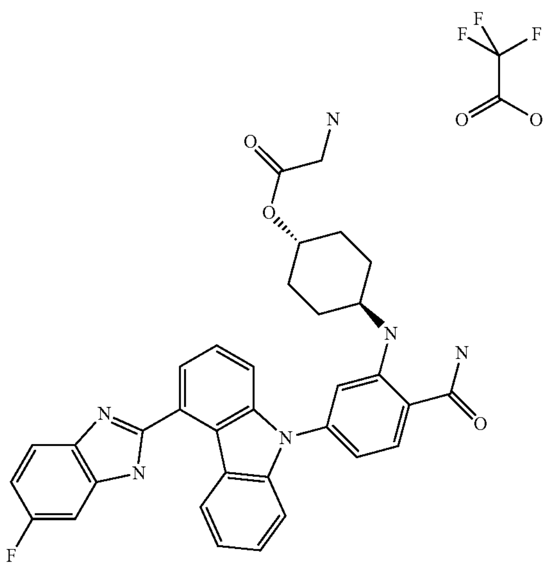 | B | A |
| 26 | Chiral | A | A |

-continued
| Ex | Structure | Hsp82 ATPase IC$_{50}$ μM | SKBR$_3$ HER2 IC$_{50}$ μM |
|---|---|---|---|
| 27 | 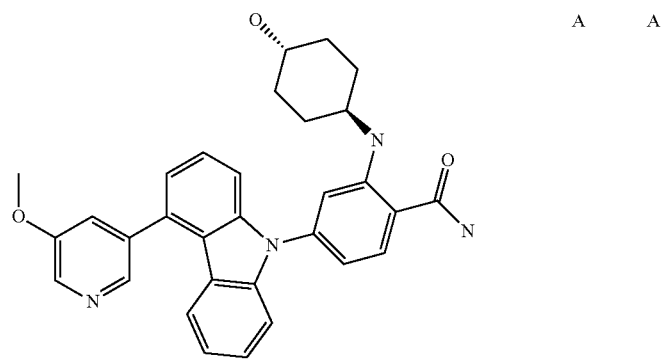 | A | A |
| 28 | 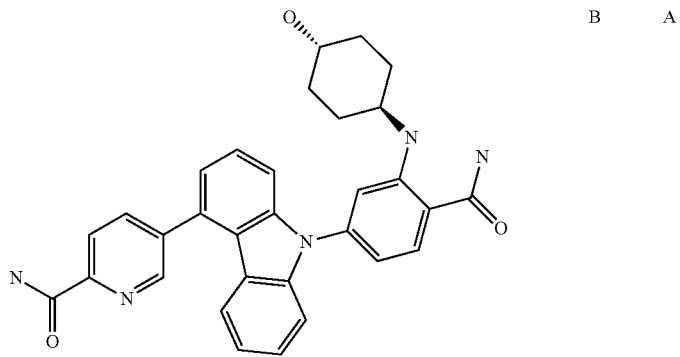 | B | A |
| 29 | 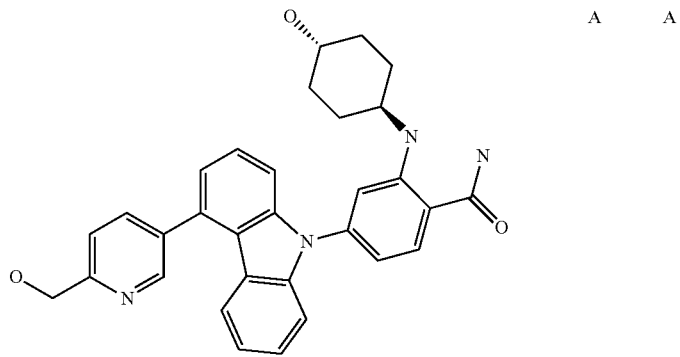 | A | A |
| 30 | 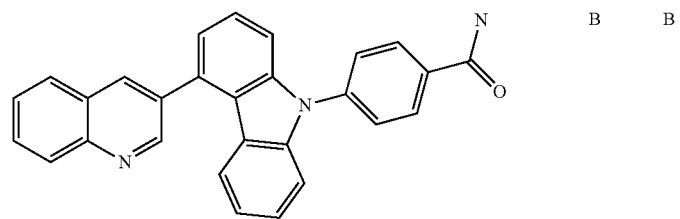 | B | B |

-continued
| Ex | Structure | Hsp82 ATPase IC$_{50}$ μM | SKBR$_3$ HER2 IC$_{50}$ μM |
|---|---|---|---|
| 31 | 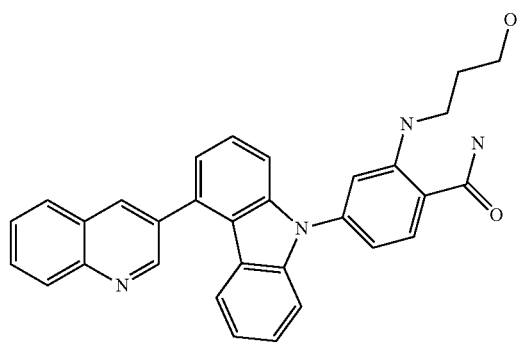 | A | A |
| 32 | 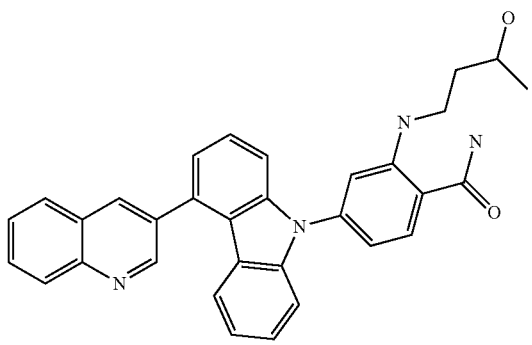 | A | A |
| 33 | 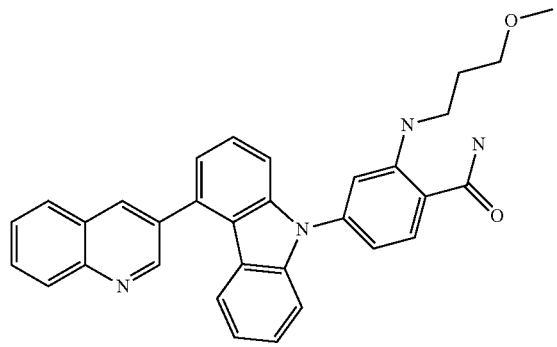 | A | A |
| 34 | 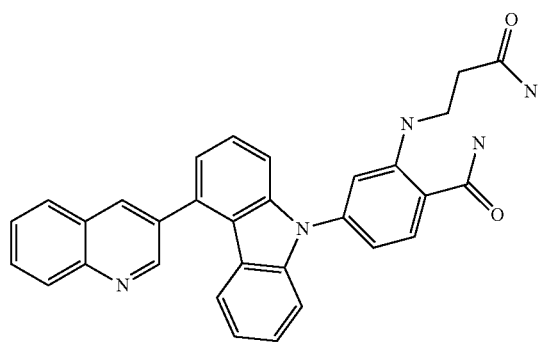 | A | A |

| Ex | Structure | Hsp82 ATPase IC$_{50}$ μM | SKBR$_3$ HER2 IC$_{50}$ μM |
|---|---|---|---|
| 35 | 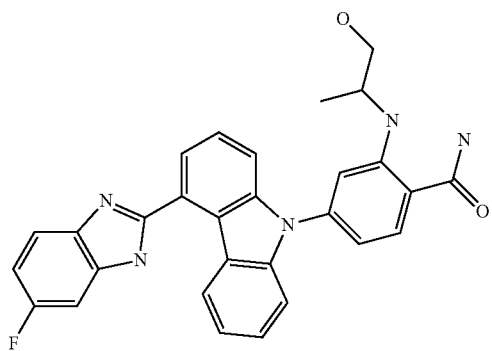 | A | A |
| 36 | 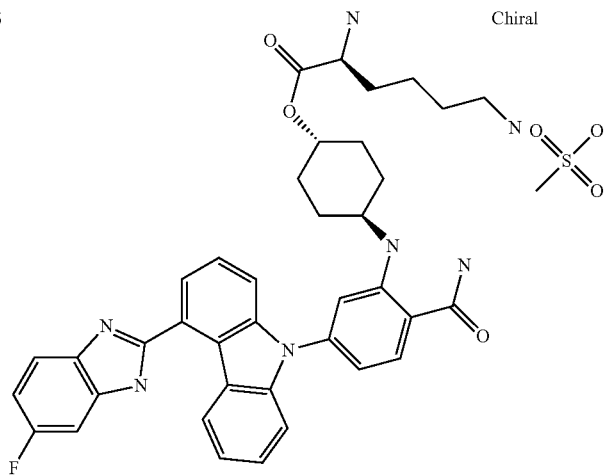 Chiral | A | A |
| 37 | 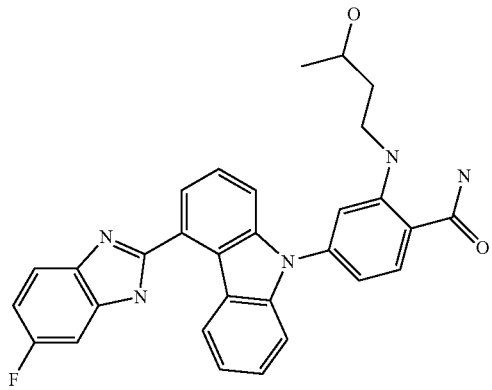 | A | A |

-continued

| Ex | Structure | Hsp82 ATPase IC$_{50}$ μM | SKBR$_3$ HER2 IC$_{50}$ μM |
|---|---|---|---|
| 38 | 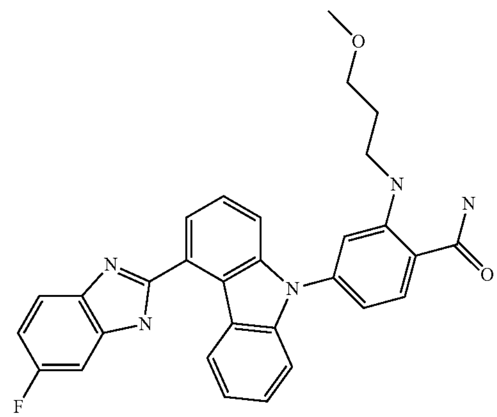 | A | A |
| 39 | 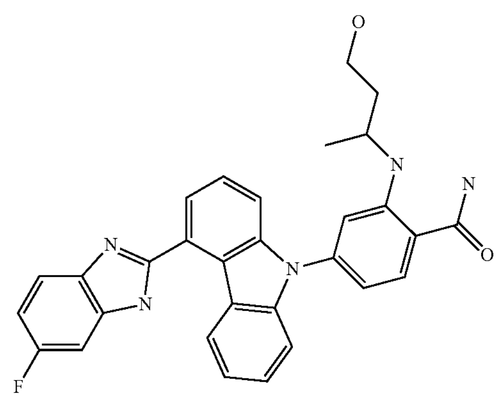 | A | A |
| 40 | 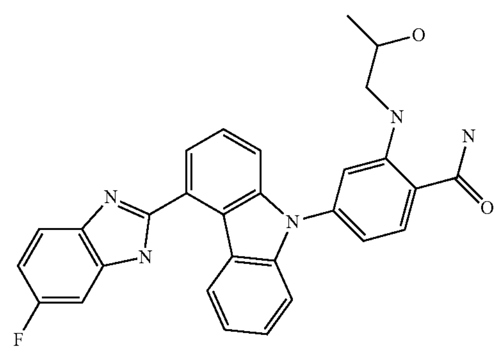 | A | A |
| 41 | 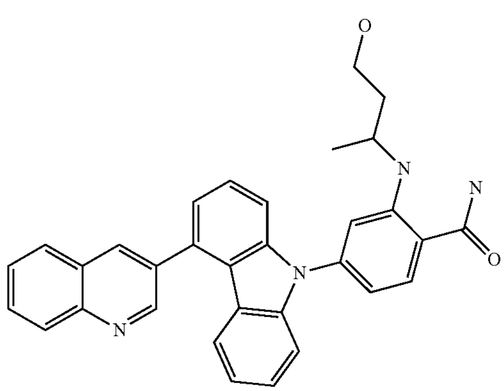 | A | A |

-continued

| Ex | Structure | Hsp82 ATPase IC$_{50}$ μM | SKBR$_3$ HER2 IC$_{50}$ μM |
|---|---|---|---|
| 42 | 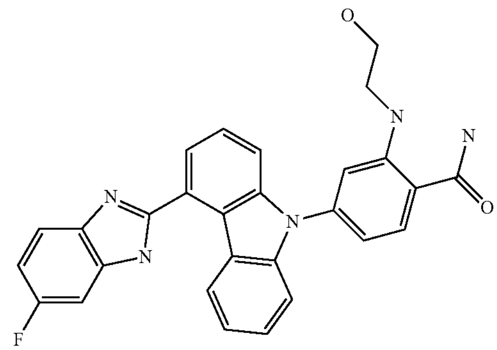 | A | A |
| 43 | 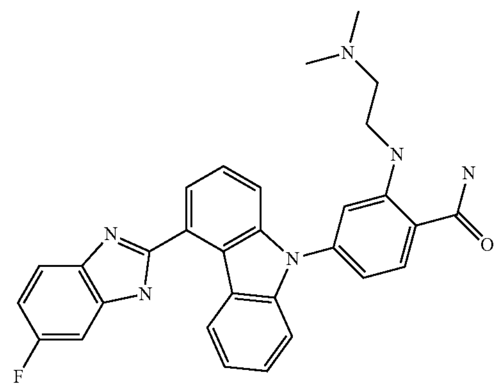 | A | A |
| 44 | 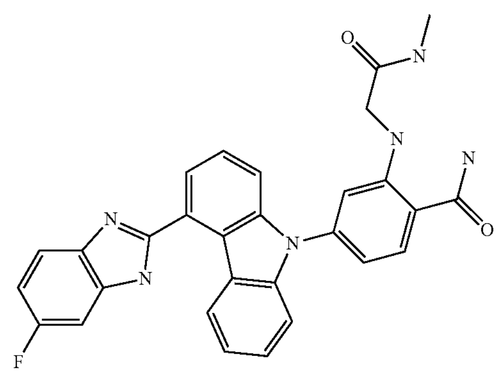 | B | A |
| 45 | 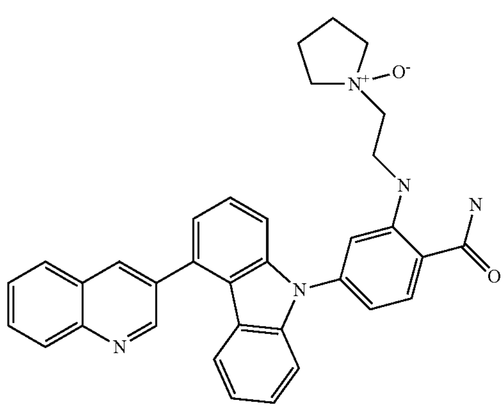 | A | A |

-continued

| Ex | Structure | Hsp82 ATPase IC$_{50}$ μM | SKBR$_3$ HER2 IC$_{50}$ μM |
|---|---|---|---|
| 46 | 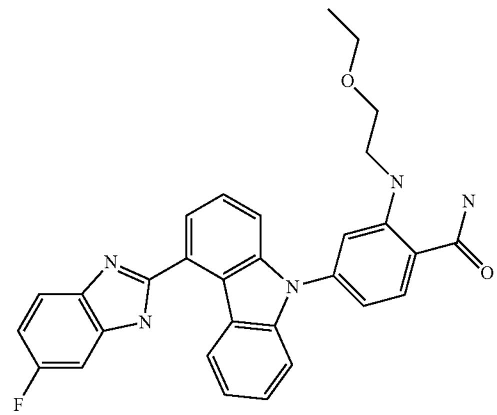 | B | A |
| 47 | 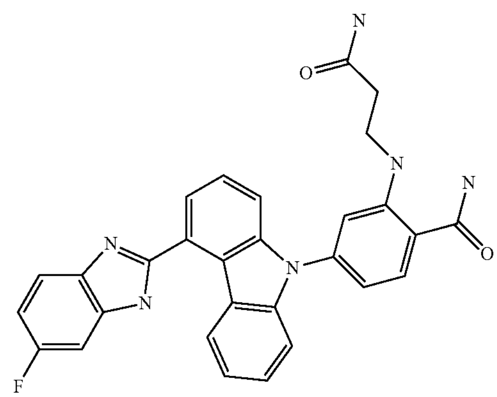 | A | A |
| 48 | 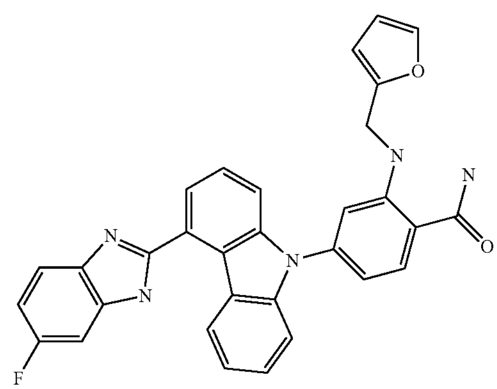 | B | A |
| 49 | 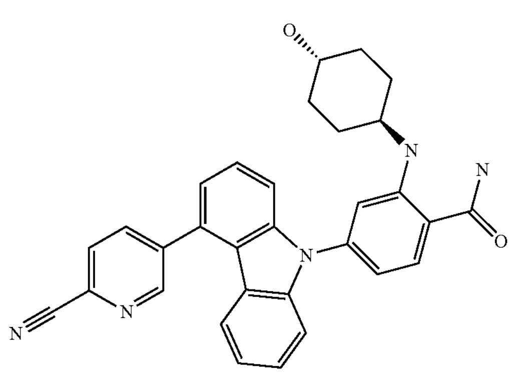 | A | A |

-continued
| Ex | Structure | Hsp82 ATPase IC$_{50}$ μM | SKBR$_3$ HER2 IC$_{50}$ μM |
|---|---|---|---|
| 50 | 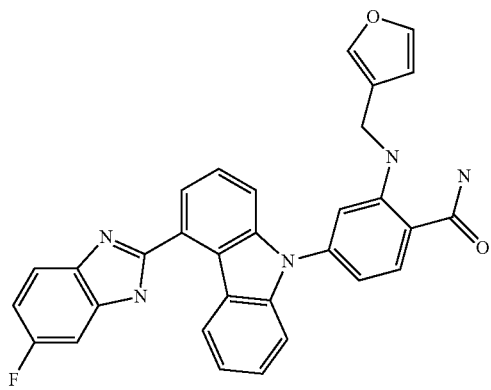 | B | A |
| 51 | 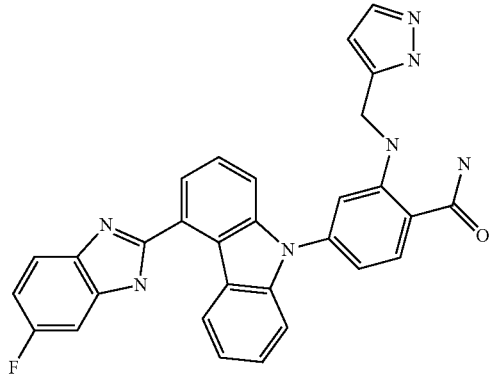 | B | A |
| 52 | 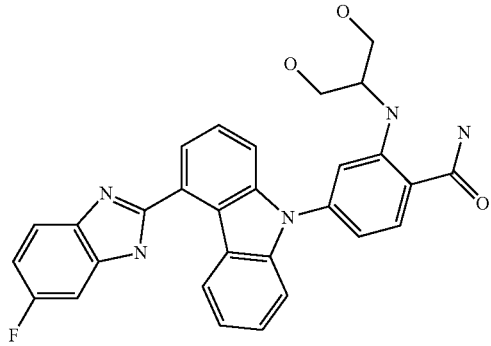 | A | A |
| 53 | 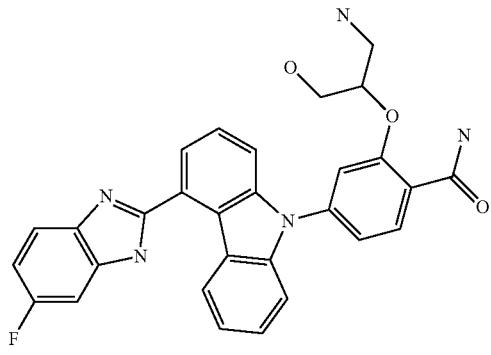 | B | B |

-continued

| Ex | Structure | Hsp82 ATPase IC$_{50}$ μM | SKBR$_3$ HER2 IC$_{50}$ μM |
|---|---|---|---|
| 54 | Chiral | A | A |
| 55 | 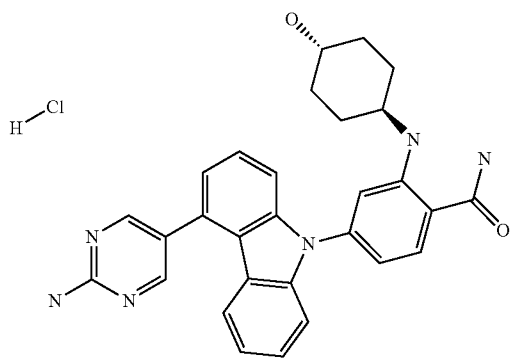 | A | A |
| 56 | 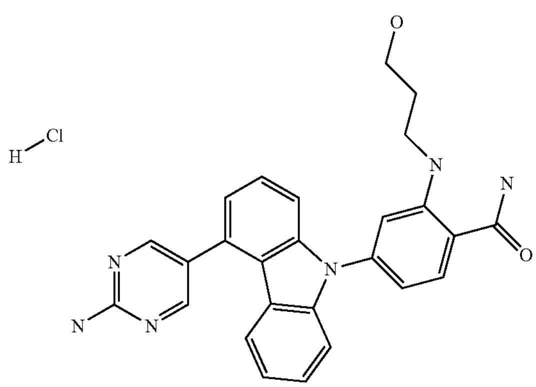 | A | nd |
| 57 | 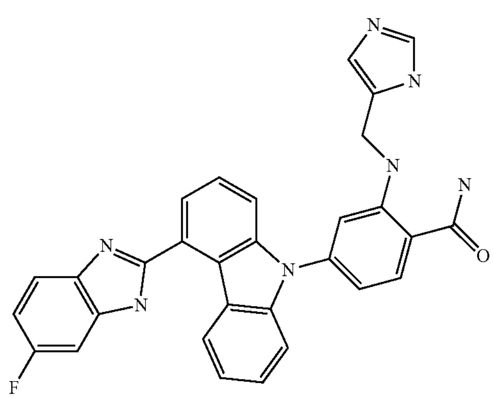 | B | B |

-continued

| Ex | Structure | Hsp82 ATPase IC$_{50}$ μM | SKBR$_3$ HER2 IC$_{50}$ μM |
|---|---|---|---|
| 58 | 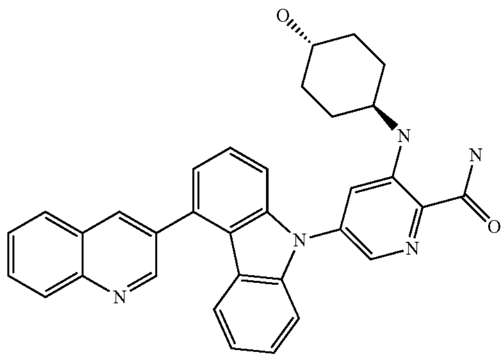 | A | A |
| 59 | 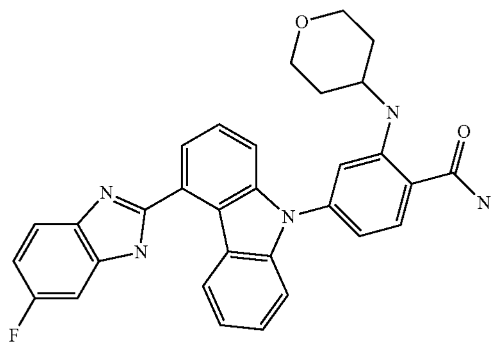 | A | A |
| 60 | 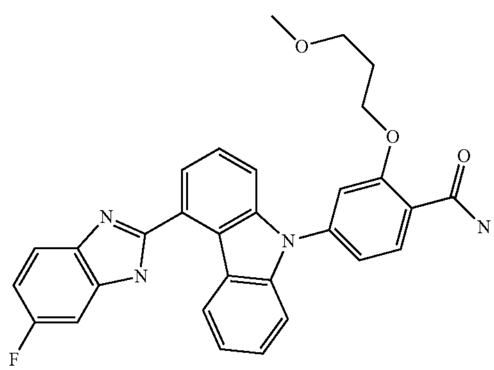 | nd | B |
| 61 | 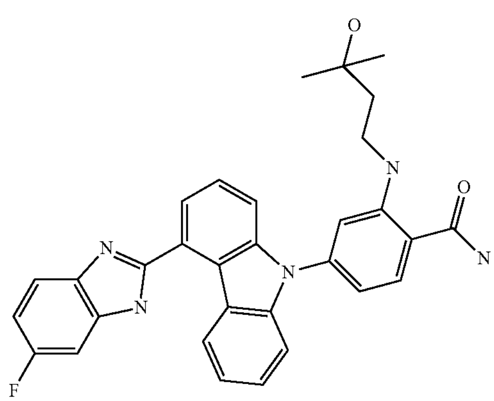 | B | A |

-continued
| Ex | Structure | Hsp82 ATPase IC$_{50}$ μM | SKBR$_3$ HER2 IC$_{50}$ μM |
|---|---|---|---|
| 62 | 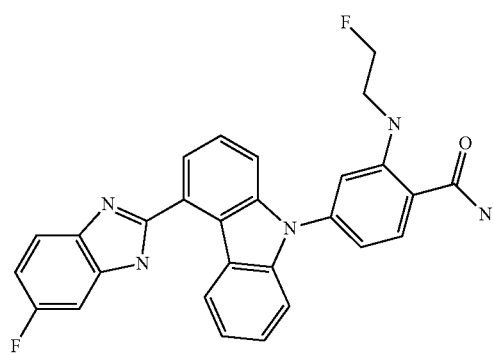 | A | A |
| 63 | 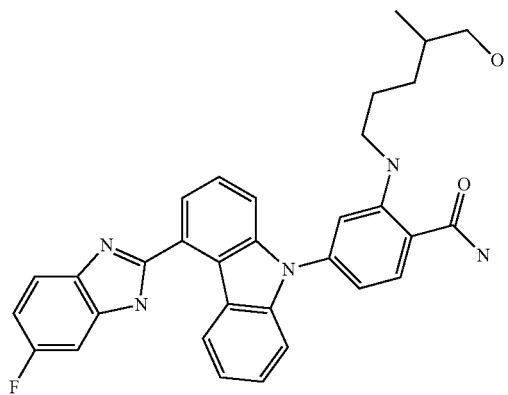 | A | A |
| 64 | 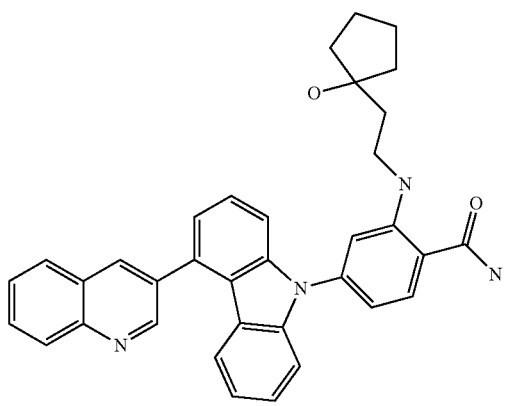 | A | A |

-continued

| Ex | Structure | Hsp82 ATPase IC₅₀ µM | SKBR₃ HER2 IC₅₀ µM |
|---|---|---|---|
| 65 | 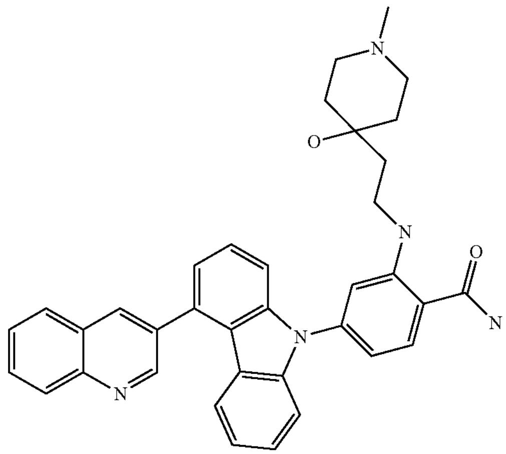 | A | A |
| 66 | 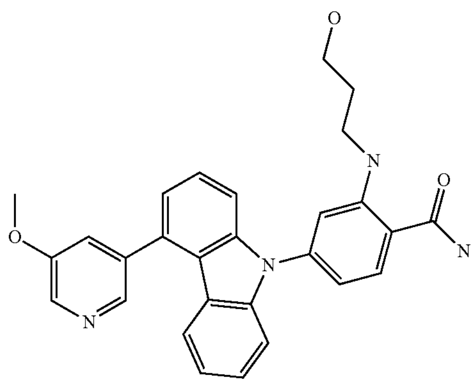 | A | B |
| 67 | 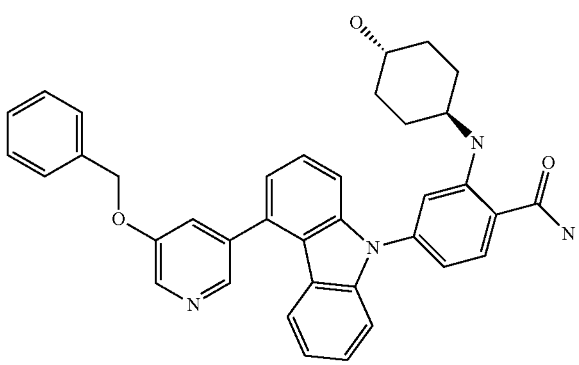 | B | B |
| 68 | 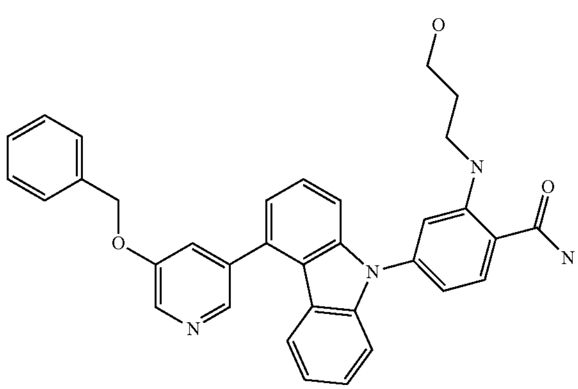 | B | B |

-continued
| Ex | Structure | Hsp82 ATPase IC$_{50}$ μM | SKBR$_3$ HER2 IC$_{50}$ μM |
|---|---|---|---|
| 69 | 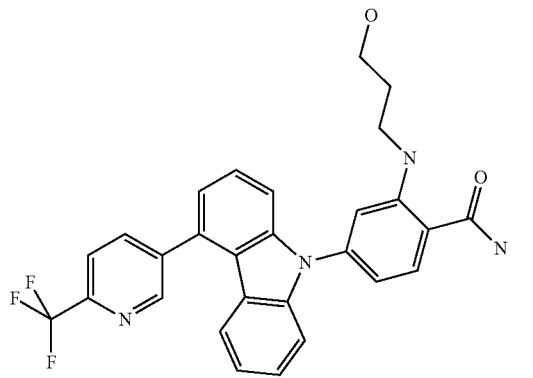 | B | B |
| 70 | 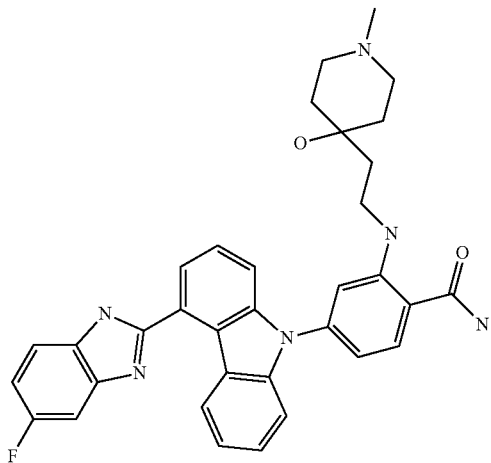 | nd | A |
| 71 | 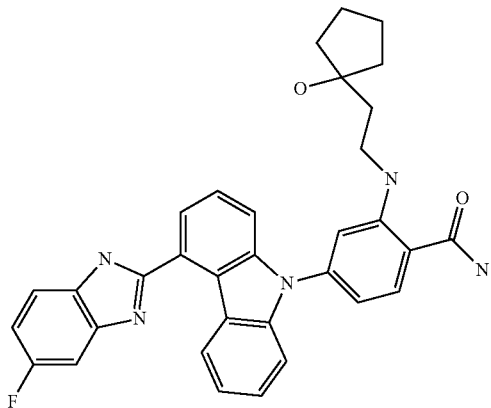 | nd | A |

-continued

| Ex | Structure | Hsp82 ATPase IC₅₀ μM | SKBR₃ HER2 IC₅₀ μM |
|---|---|---|---|
| 72 | 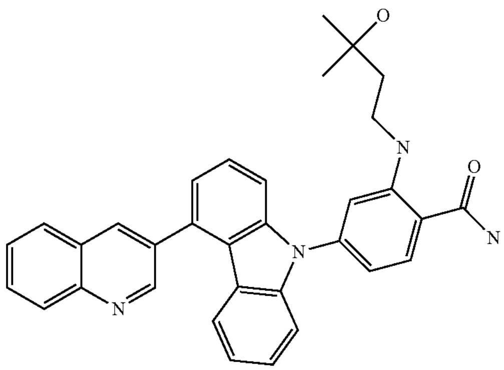 | nd | A |
| 73 | 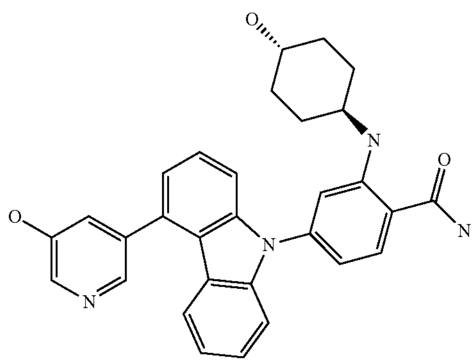 | nd | A |
| 74 | 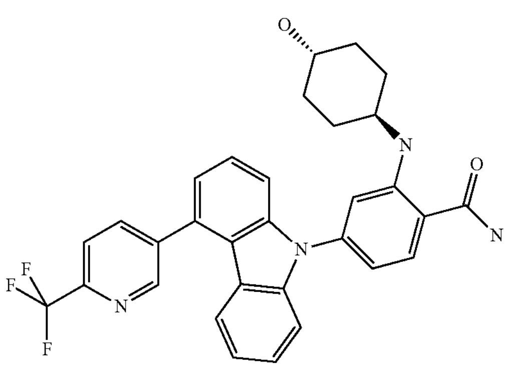 | nd | B |
| 75 | 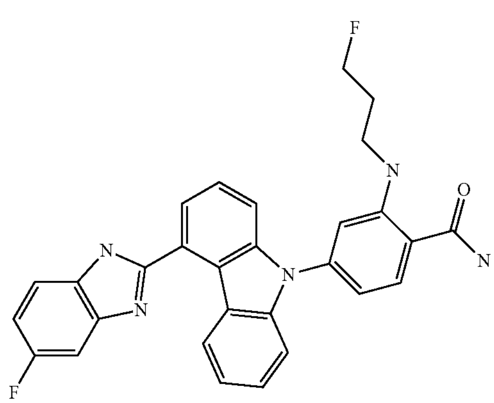 | nd | A |

-continued

| Ex | Structure | Hsp82 ATPase IC$_{50}$ μM | SKBR$_3$ HER2 IC$_{50}$ μM |
|---|---|---|---|
| 76 | 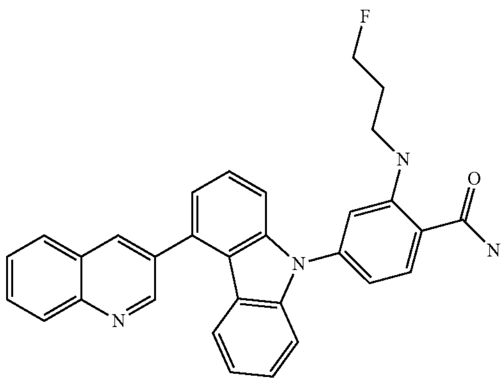 | nd | A |
| 77 | 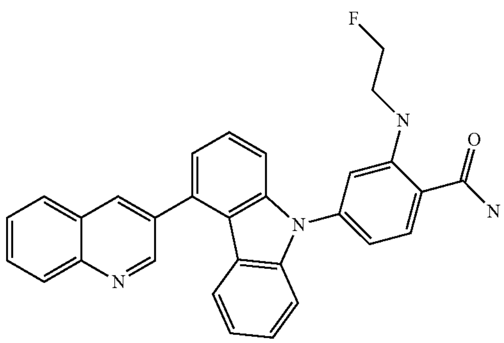 | nd | A |
| 78 | 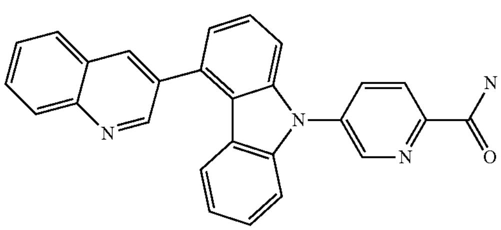 | nd | B |
| 79 | 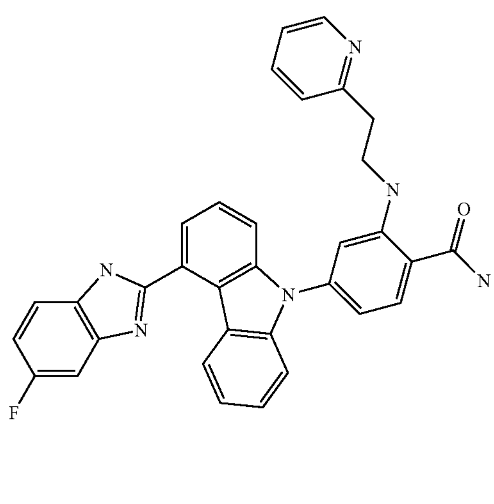 | nd | A |

| Ex | Structure | Hsp82 ATPase IC$_{50}$ μM | SKBR$_3$ HER2 IC$_{50}$ μM |
|---|---|---|---|
| 80 | 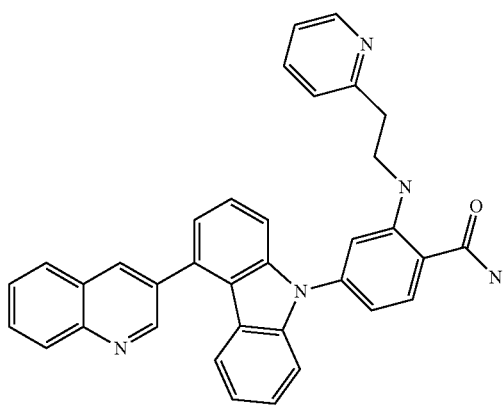 | nd | A |
| 81 | 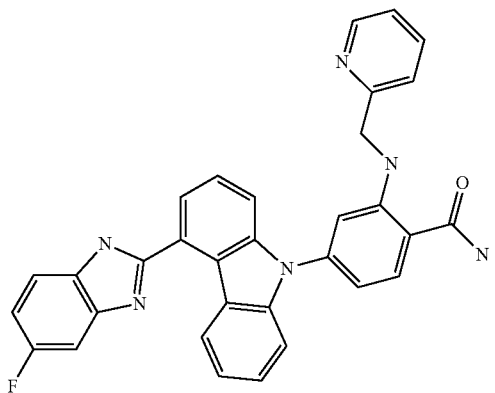 | nd | A |
| 82 | 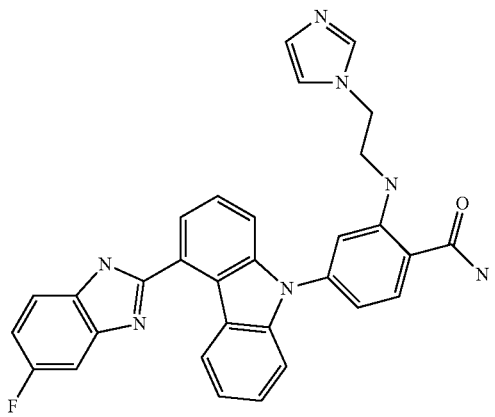 | nd | A |

-continued
| Ex | Structure | Hsp82 ATPase IC$_{50}$ μM | SKBR$_3$ HER2 IC$_{50}$ μM |
|---|---|---|---|
| 83 | 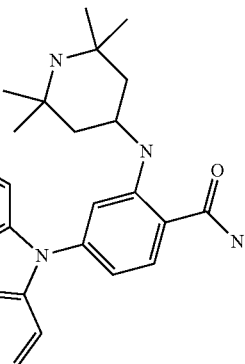 | nd | A |
| 84 | 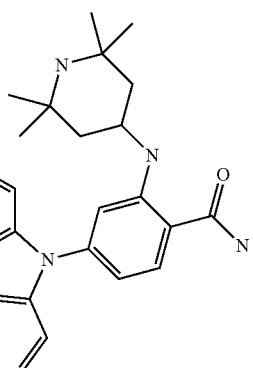 | nd | A |
| 85 | 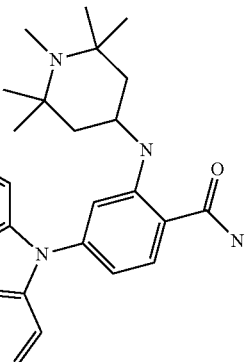 | nd | A |
| 86 | 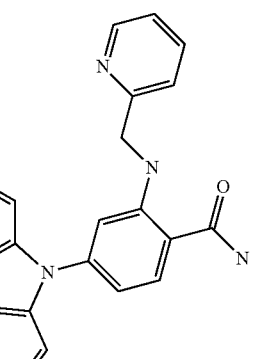 | nd | A |

-continued

| Ex | Structure | Hsp82 ATPase IC$_{50}$ μM | SKBR$_3$ HER2 IC$_{50}$ μM |
|---|---|---|---|
| 87 | 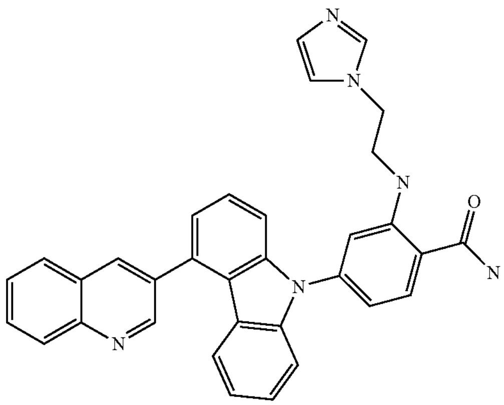 | nd | A |
| 88 | 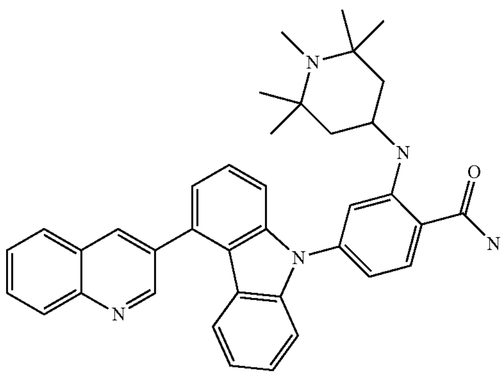 | nd | A |
| 89 | 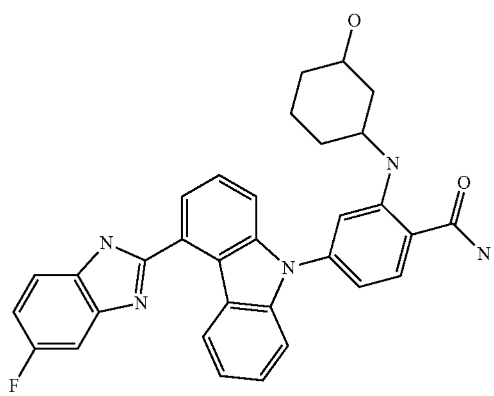 | nd | A |
| 90 | 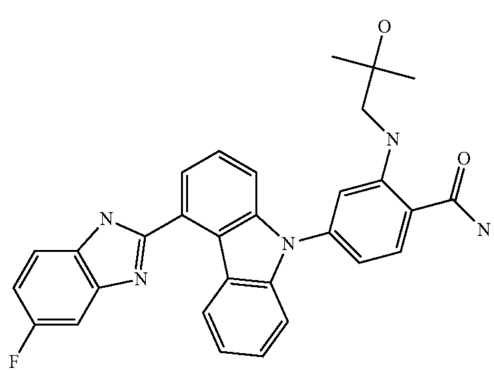 | nd | A |

-continued

| Ex | Structure | Hsp82 ATPase IC$_{50}$ µM | SKBR$_3$ HER2 IC$_{50}$ µM |
|---|---|---|---|
| 91 | 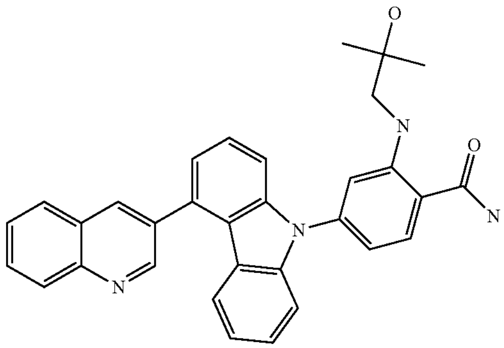 | nd | A |
| 92 | 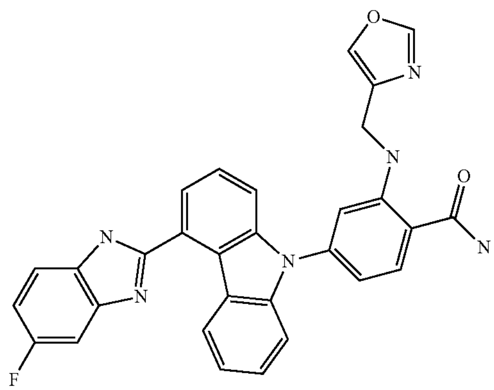 | nd | A |
| 93 | 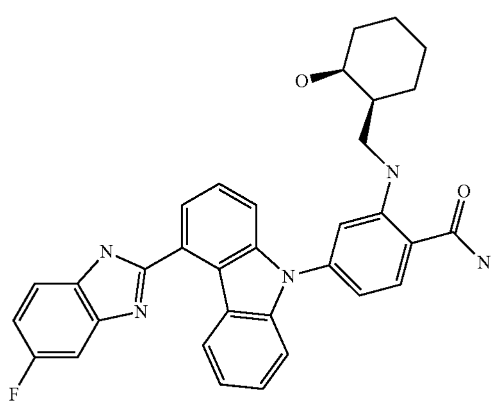 | nd | A |
| 94 | 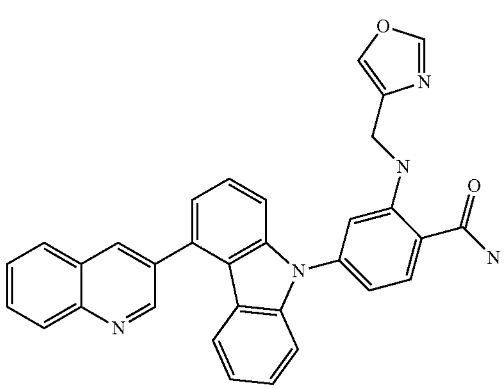 | nd | A |

-continued
| Ex | Structure | Hsp82 ATPase IC$_{50}$ μM | SKBR$_3$ HER2 IC$_{50}$ μM |
|---|---|---|---|
| 95 | 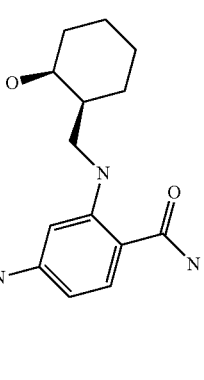 | nd | A |
| 96 | 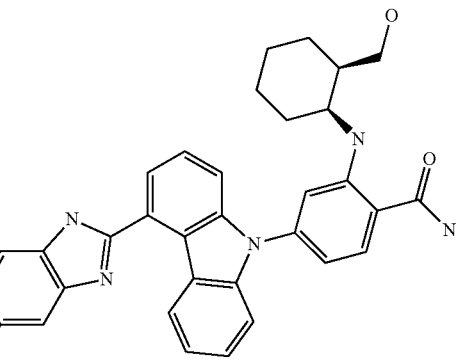 | nd | A |
| 97 | 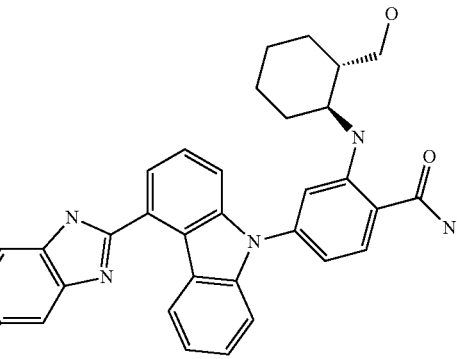 | nd | A |
| 98 | 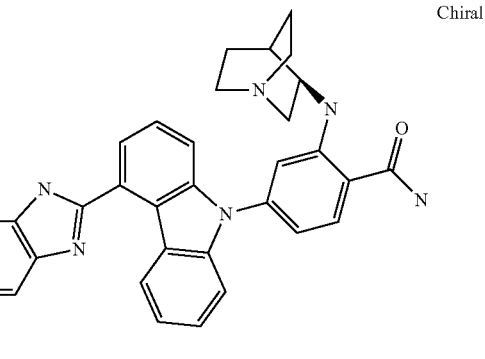 Chiral | nd | A |

-continued
| Ex | Structure | Hsp82 ATPase IC$_{50}$ μM | SKBR$_3$ HER2 IC$_{50}$ μM |
|---|---|---|---|
| 99 | 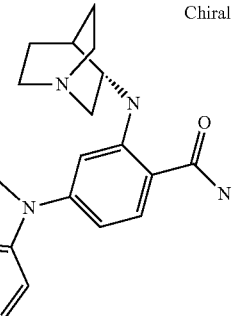 Chiral | nd | A |
| 100 | 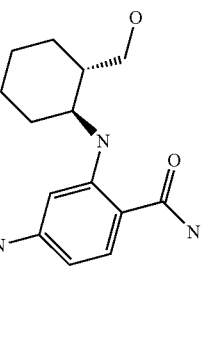 | nd | A |
| 101 | 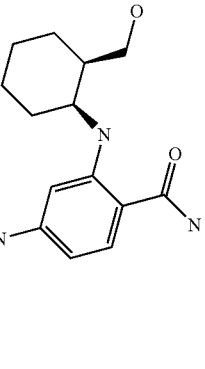 | nd | A |
| 102 | 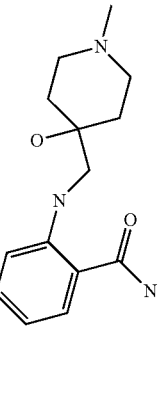 | nd | B |

-continued
| Ex | Structure | Hsp82 ATPase IC$_{50}$ μM | SKBR$_3$ HER2 IC$_{50}$ μM |
|---|---|---|---|
| 103 | 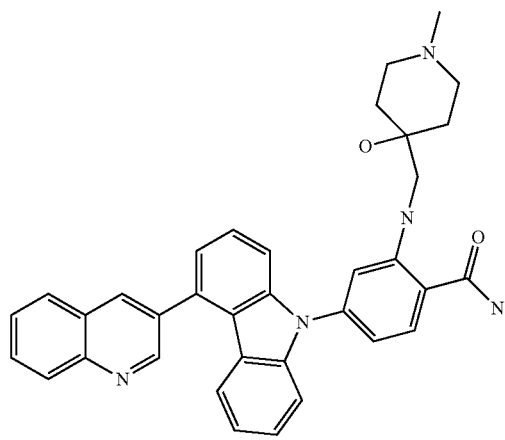 | nd | A |
| 104 | 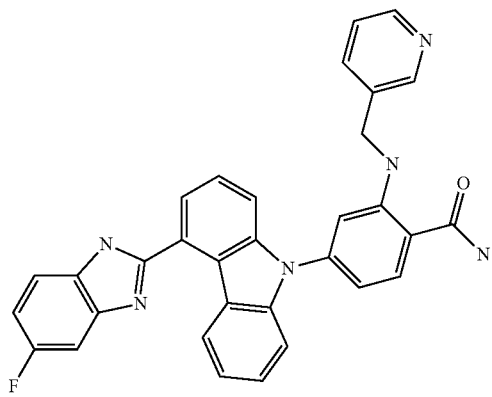 | nd | A |
| 105 | 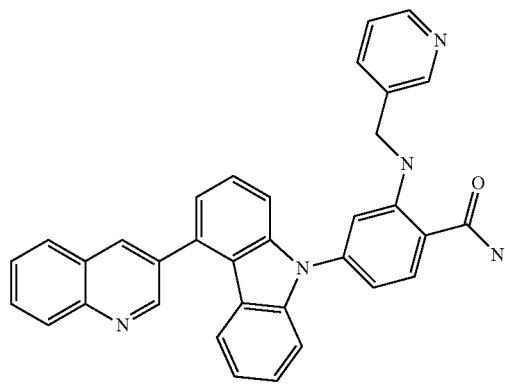 | nd | A |

-continued

| Ex | Structure | Hsp82 ATPase IC$_{50}$ μM | SKBR$_3$ HER2 IC$_{50}$ μM |
|---|---|---|---|
| 106 | 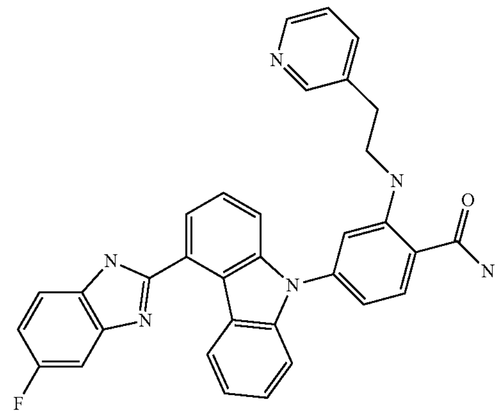 | nd | A |
| 107 | 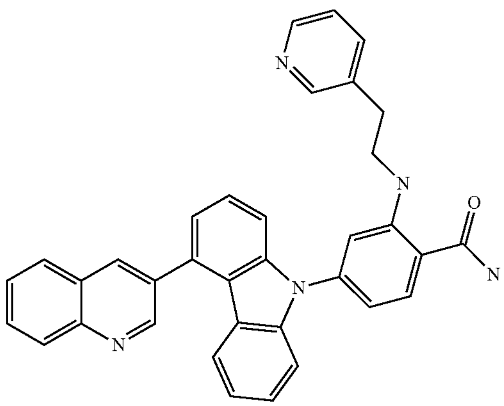 | nd | A |
| 108 | Chiral | nd | A |
| 109 | 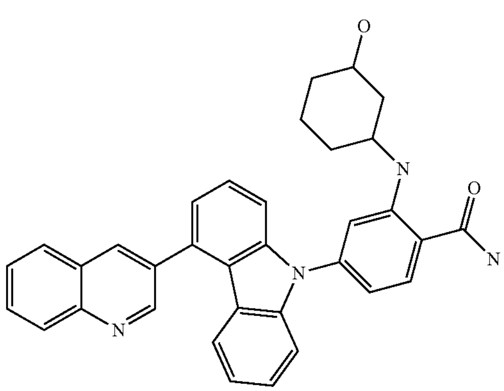 | nd | A |

-continued

| Ex | Structure | Hsp82 ATPase IC$_{50}$ μM | SKBR$_3$ HER2 IC$_{50}$ μM |
|---|---|---|---|
| 110 | 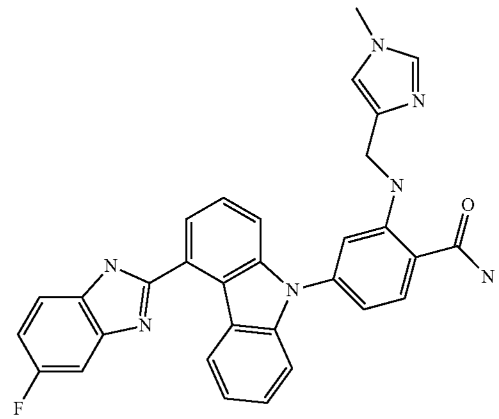 | nd | A |
| 111 | 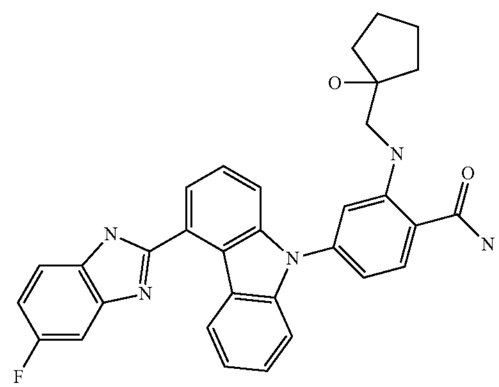 | nd | A |
| 112 | 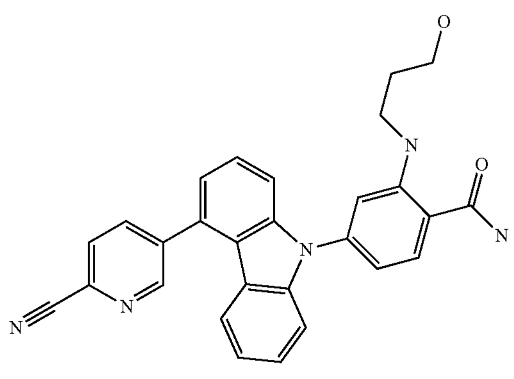 | nd | A |
| 113 | 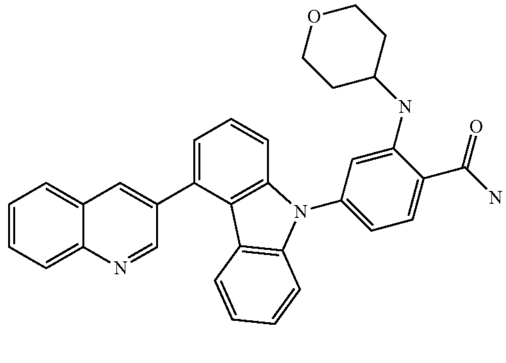 | nd | A |

-continued

| Ex | Structure | Hsp82 ATPase IC$_{50}$ μM | SKBR$_3$ HER2 IC$_{50}$ μM |
|---|---|---|---|
| 114 | 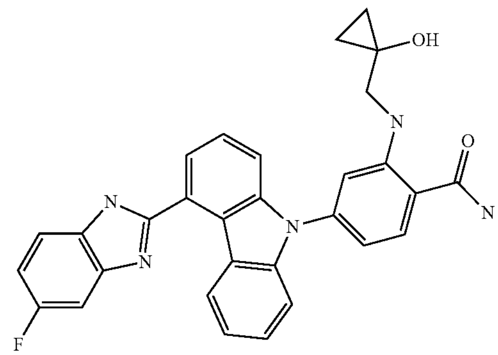 | nd | A |
| 115 | 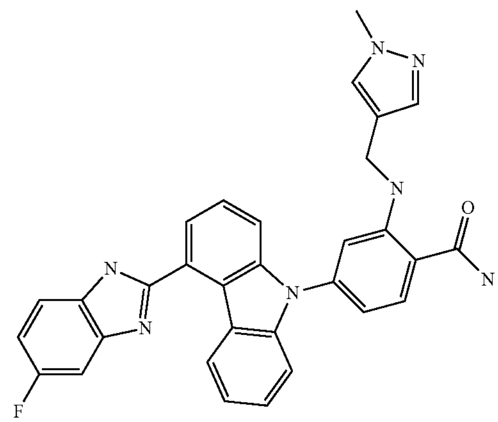 | nd | A |
| 116 | 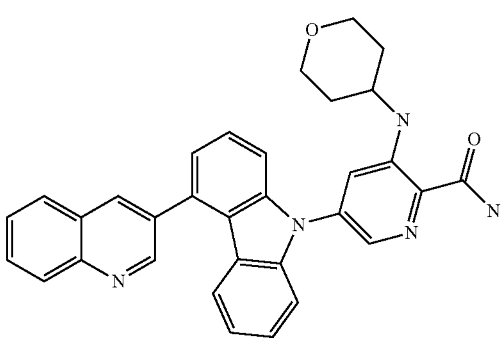 | nd | A |
| 117 | 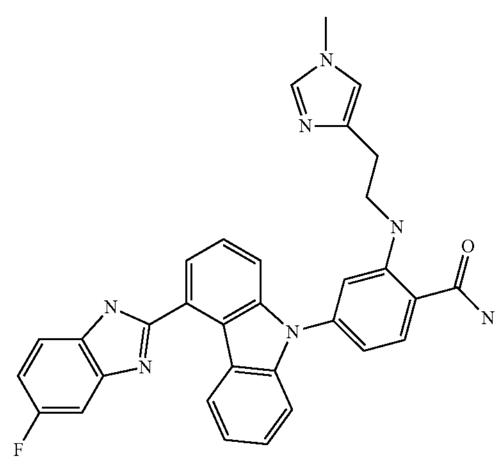 | nd | A |

-continued

| Ex | Structure | Hsp82 ATPase IC$_{50}$ μM | SKBR$_3$ HER2 IC$_{50}$ μM |
|---|---|---|---|
| 118 | 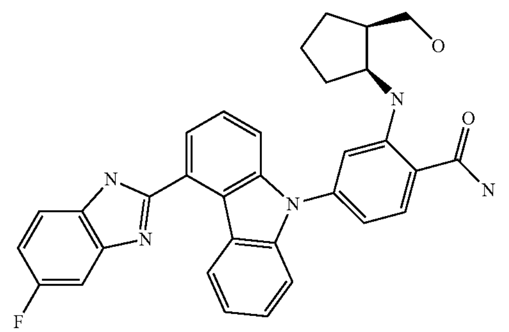 | nd | A |
| 119 | 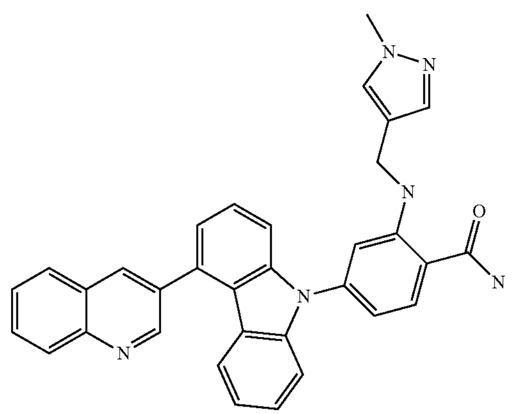 | nd | A |
| 120 | 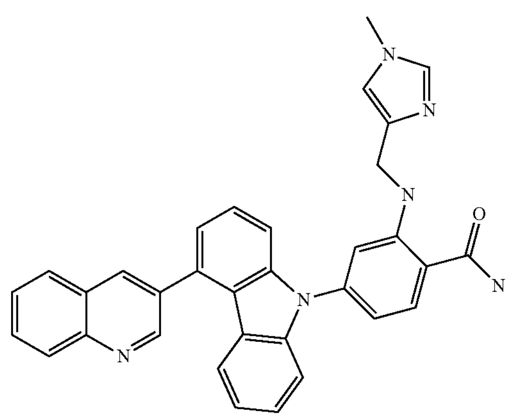 | nd | A |
| 121 | 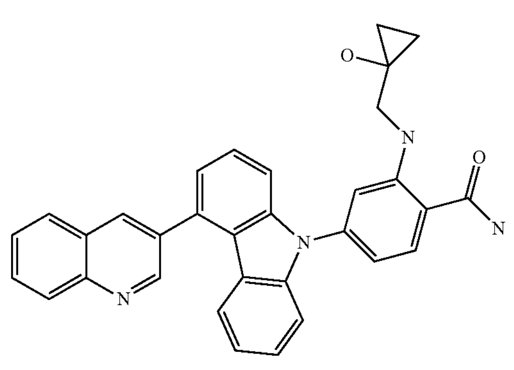 | nd | A |

-continued
| Ex | Structure | Hsp82 ATPase IC$_{50}$ μM | SKBR$_3$ HER2 IC$_{50}$ μM |
|---|---|---|---|
| 122 | 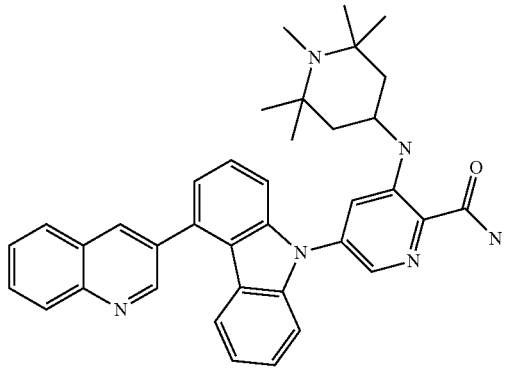 | nd | A |
| 123 | 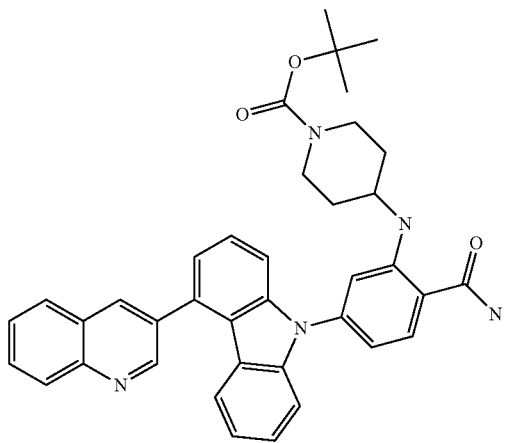 | nd | B |
| 124 | 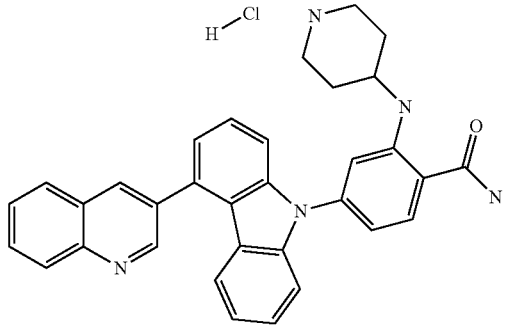 | nd | A |
| 125 | 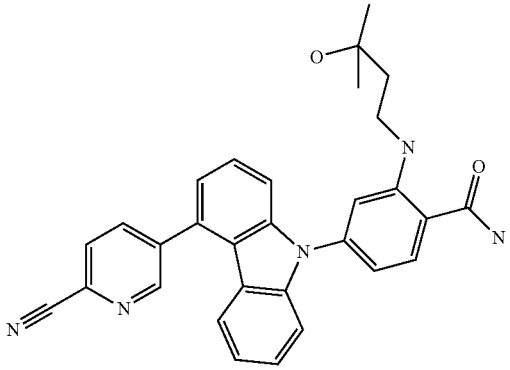 | nd | A |

-continued

| Ex | Structure | Hsp82 ATPase IC$_{50}$ μM | SKBR$_3$ HER2 IC$_{50}$ μM |
|---|---|---|---|
| 126 | 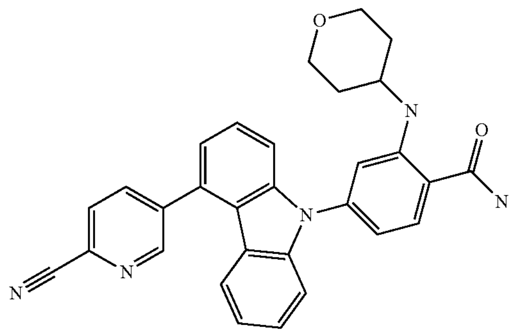 | nd | A |
| 127 | 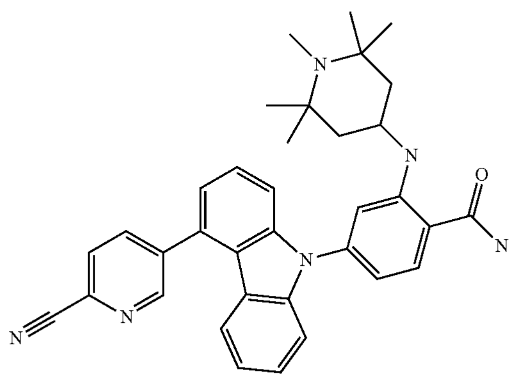 | nd | A |
| 128 | 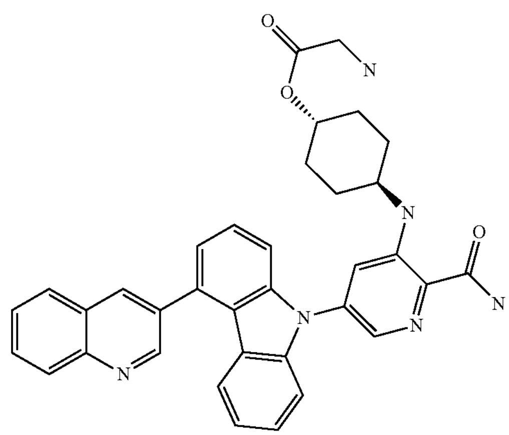 | nd | A |
| 129 | 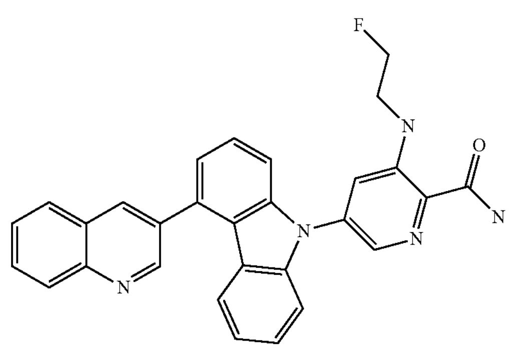 | nd | A |

-continued

| Ex | Structure | Hsp82 ATPase IC$_{50}$ μM | SKBR$_3$ HER2 IC$_{50}$ μM |
|---|---|---|---|
| 130 | 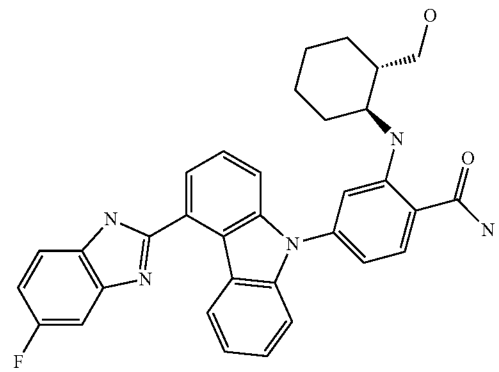 | nd | A |
| 131 | 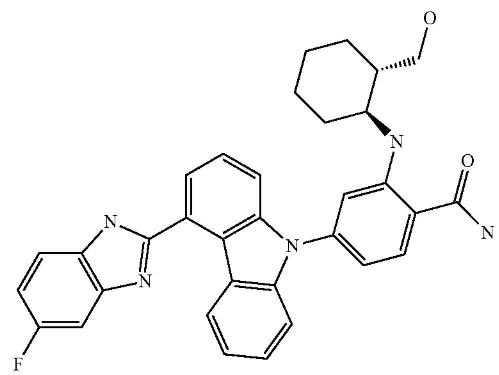 | nd | A |
| 132 | 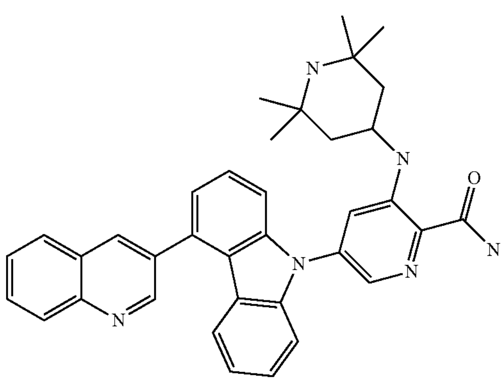 | nd | B |
| 133 | 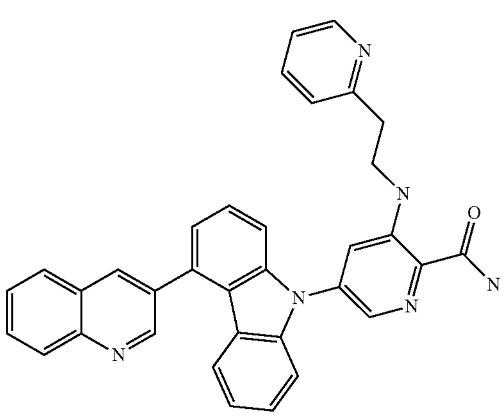 | nd | A |

-continued
| Ex | Structure | Hsp82 ATPase IC$_{50}$ μM | SKBR$_3$ HER2 IC$_{50}$ μM |
|---|---|---|---|
| 134 | 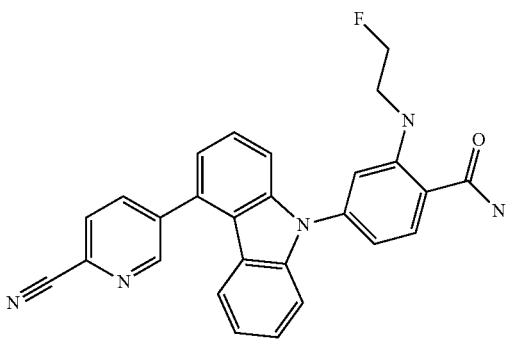 | nd | A |
| 135 | 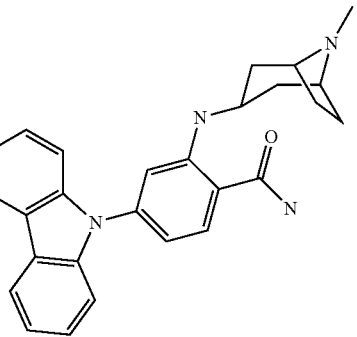 | nd | A |
| 136 | 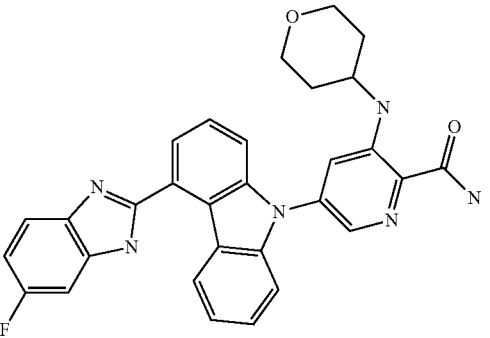 | nd | A |
| 137 | 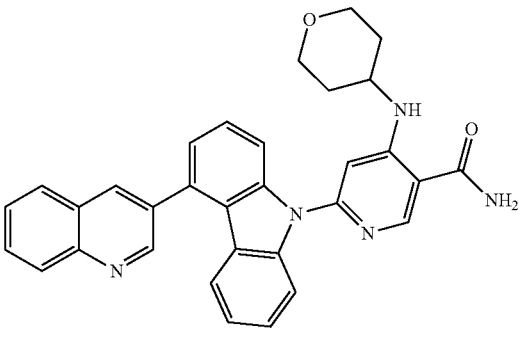 | nd | A |

-continued
| Ex | Structure | Hsp82 ATPase IC$_{50}$ μM | SKBR$_3$ HER2 IC$_{50}$ μM |
|---|---|---|---|
| 138 | 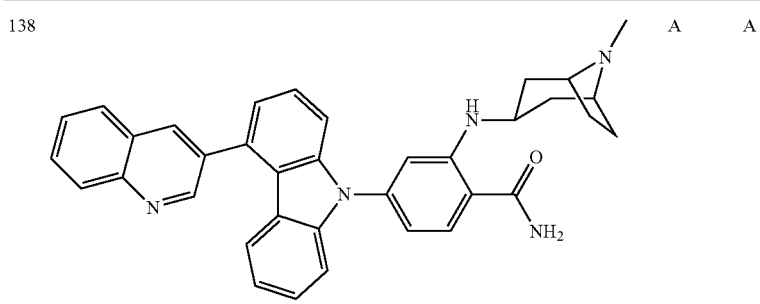 | A | A |
| 139 | 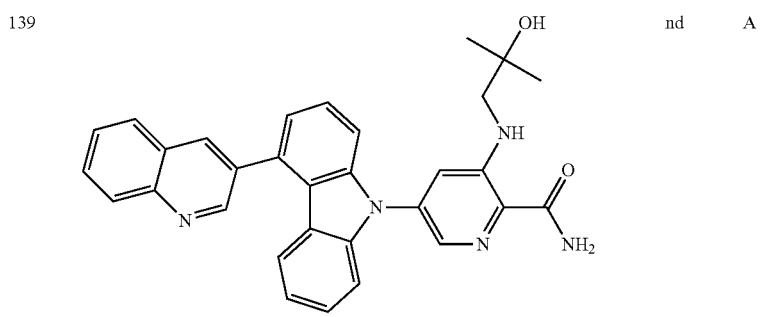 | nd | A |
| 140 | 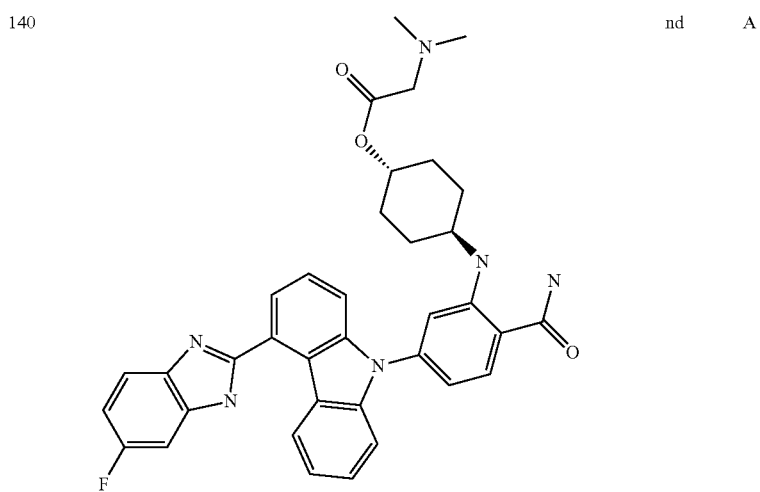 | nd | A |
| 141 | 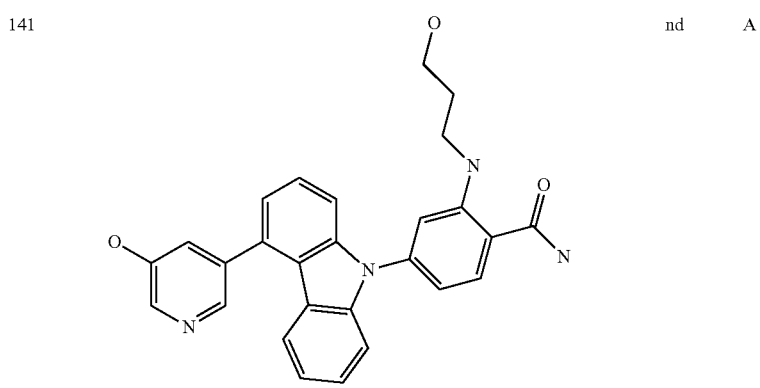 | nd | A |

-continued
| Ex | Structure | Hsp82 ATPase IC$_{50}$ μM | SKBR$_3$ HER2 IC$_{50}$ μM |
|---|---|---|---|
| 142 | 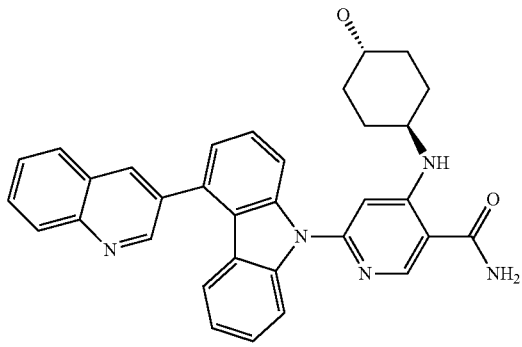 | ND | A |
| 143 | 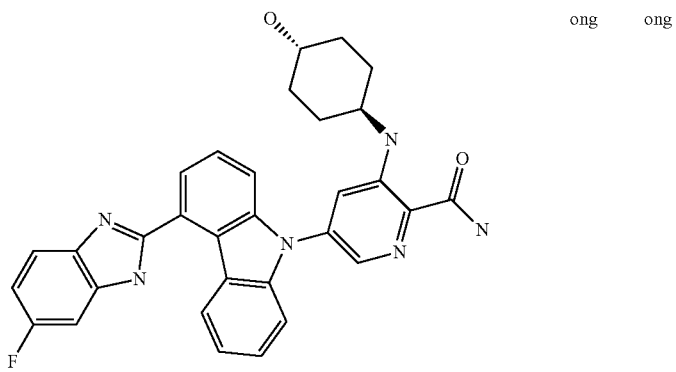 | ong | ong |
| 144 | 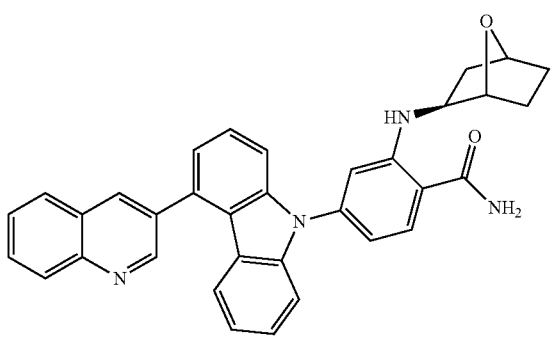 | | |
| 145 | 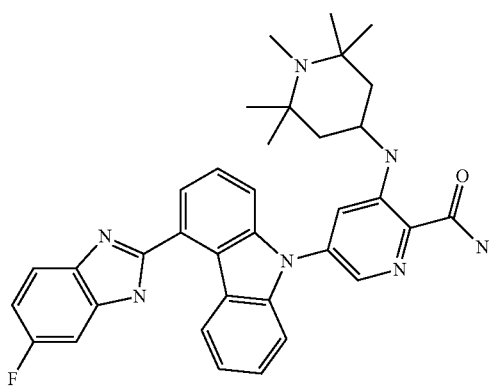 | | |

| Ex | Structure | Hsp82 ATPase IC$_{50}$ μM | SKBR$_3$ HER2 IC$_{50}$ μM |
|---|---|---|---|
| 146 | 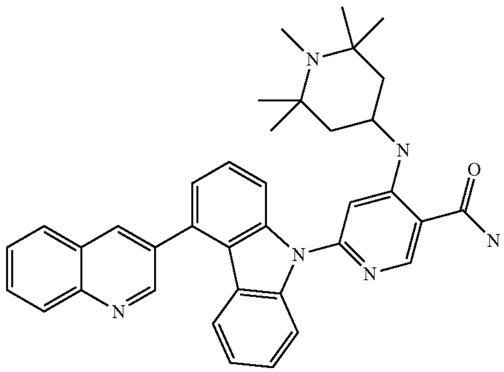 | | |
| 147 | 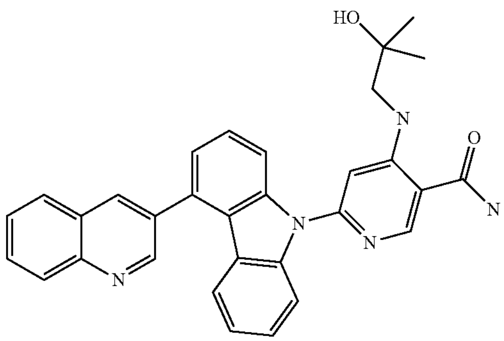 | | |
| 148 | 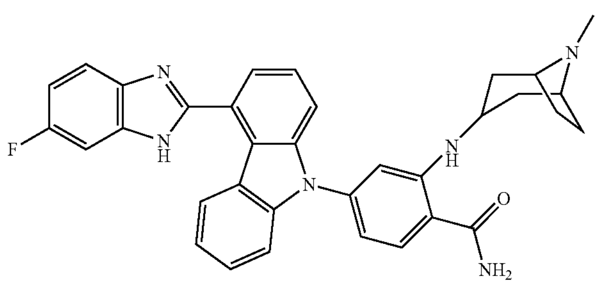 | | |
The invention claimed is:
1. A compound according to formula (I)
in which:
Het is selected from:
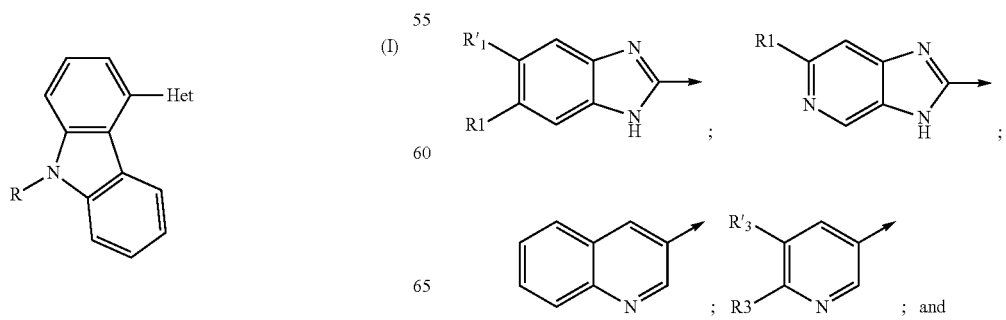

-continued

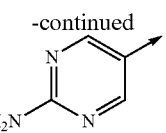

in which one of R'3 and R3 represents a hydrogen atom and the other is selected from —NH₂, —CN, —CH₂—OH, —CF₃, —OH, —O—CH₂-phenyl, —O—CH₃ and —CO—NH₂;

R is selected from:

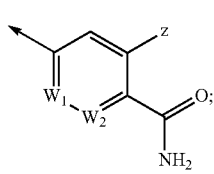
(A')

R1 and R'1 are independently selected from: H, halogen, CF₃, cyano, alkyl, hydroxyl, amino, alkoxy, phenylalkoxy, carboxamide, wherein said alkyl and alkoxy radicals are optionally and independently substituted with one or more radicals selected from halogen and hydroxyl;

W1 and W2 are independently CH or N;

Z is selected from a hydrogen atom, halogen atom, —O—R2 radical, and —NH—R2 radical, wherein:

R2 is selected from a hydrogen atom, $C_1$-$C_6$ alkyl radical, $C_3$-$C_8$ cycloalkyl radical, and $C_3$-$C_{10}$ heterocycloalkyl radical, which is monocyclic or bicyclic wherein said alkyl, cycloalkyl, and heterocycloalkyl radicals are optionally and independently substituted with one or more radicals selected from:

halogen, hydroxyl, amino, carboxamide (CONH₂), carboxyl, and heterocycloalkyl selected from piperidino, tetrahydropyrano, pyrrolidino; quinuclidino, cycloalkyl, heteroaryl, CO—NH(alkyl), —O—CO-alkyl, —NH—CO-alkyl, alkyl, alkoxy, and dialkylamino, wherein said alkyl and alkoxy radicals are optionally substituted with a hydroxyl, amino, dialkylamino, CO₂alkyl, NHCO₂alkyl; wherein said cyclic, cycloalkyl, heterocycloalkyl, and heteroaryl radicals are optionally and independently substituted with one or more radicals selected from hydroxyl, alkyl, and amino radicals;

or an addition salt thereof formed with an inorganic or organic acid or with an inorganic or organic base.

2. A compound according to claim 1, wherein:

Het is selected from:

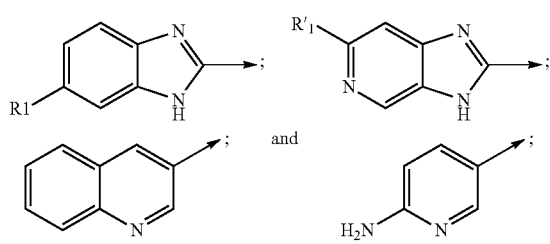

R is:

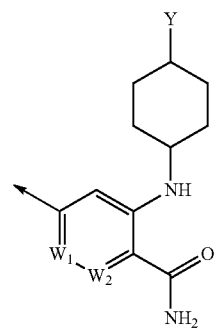

R1 is selected from H, F, Cl, Br, CH₃, and OH;
R'1 is H;
W1 and W2 are selected from CH and N, provided that at least one of W1 and W2 is CH; and
Y is selected from OH, O—CO—CH₂—CO₂tBU, O—CO—CH₂—NH₂, and O—CO—CH₂—N(Me)₂.

3. A compound according to claim 1, wherein:

Het is selected from:

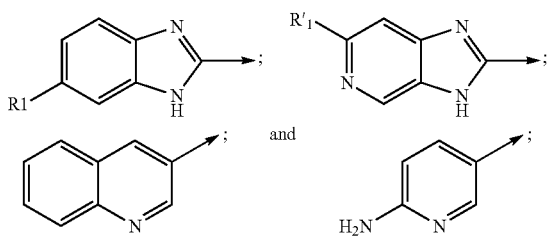

R1 is selected from H, F, Cl, Br, CH₃, and OH;
R'1 is H;
and R is selected from:

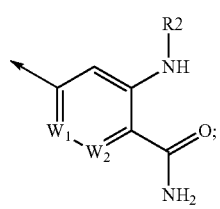

W1 and W2 are selected from CH and N, provided that at least one of W1 and W2 is CH;
R2 is selected from hydrogen, ethyl substituted in the 2-position with a substituent, and n-propyl substituted in the 3-position with a substituent, wherein said substituent is selected from OH, NH₂, OMe, N(Me)₂, and CONH₂; and
Y is selected from OH, O—CO—CH₂—CO₂tBu, O—CO—CH₂—NH₂, and O—CO—CH₂—N(Me)₂.

4. A compound according to claim 1, wherein said compound is selected from:
4-[4-(6-fluoro-1H-benzimidazo 1-2-yl)-9H-carbazol-9-yl]-2-(4-trans-hydroxycyclohexylamino)benzamide;
2-(4-trans-hydroxycyclohexylamino)-4-[(4-quinolin-3-yl)-9H-carbazol-9-yl]benzamide;
2-(2-diethylaminoethylamino)-4-[4-(6-fluoro-1H-benzimidazol-2-yl)-9H-carbazol-9-yl]benzamide;

2-(4-trans-hydroxycyclohexylamino)-4-[4-(3H-imidazo[4,5-c]pyridin-2-yl)carbazol-9-yl]benzamide;
acetic acid 4-{2-carbamoyl-5-[4-(6-fluoro-1H-benzimidazol-2-yl)-9H-carbazol-9-yl]phenylamino}cyclohexyl ester;
2-cyclohexylamino-4-[4-(6-fluoro-1H-benzimidazol-2-yl)-9H-carbazol-9-yl]benzamide;
4-[4-(6-fluoro-1H-benzimidazol-2-yl)-9H-carbazol-9-yl]-2-[2-(2-hydroxyethoxy)ethylamino]benzamide;
[[−]]4-[4-(6-fluoro-1H-benzimidazol-2-yl)-9H-carbazol-9-yl]-2-(3-hydroxypropylamino)benzamide;
4-[4-(6-fluoro-1H-benzimidazol-2-yl)-9H-carbazol-9-yl]-2-(4-cis-hydroxycyclohexylamino)benzamide;
2-amino-4-[4-(6-fluoro-1H-benzimidazol-2-yl)-9,4-carbazol-9-yl]benzamide;
4-[4-(6-fluoro-1H-benzimidazol-2-yl)-9H-carbazol-9-yl]-2-(2-pyrrolidin-1-ylethylamino)benzamide;
3-(trans-4-hydroxycyclohexylamino)-5-[(4-quinolin-3-yl)-9H-carbazol-9-yl)pyridine-2-carboxamide;
4-[4-(6-fluoro-1H-benzimidazol-2-yl)-9H-carbazol-9-yl]-2-(tetrahydro-pyran-4-ylamino)benzamide;
4-[4-(6-cyanopyridin-3-yl)-9,1-carbazol-9-yl]-2-[(1,2,2,6,6-pentamethylpiperidin-4-yl)amino]benzamide;
aminoacetic acid 4-{[2-carbamoyl-5-(quinolin-3-yl)-9H-carbazol-9-yl]pyridin-3-ylamino}cyclohexyl ester;
4-[4-(6-cyanopyridin-3-yl)-9H-carbazol-9-yl]-2-[(8-methyl-8-azabicyclo[3.2.1]oct-3-yl)amino]benzamide;
5-[4-(6-fluoro-1H-benzimidazol-2-yl)-9H-carbazol-9-yl]-3-(tetrahydropyran-4-yl)amino)pyridine-2-carboxamide;
2-[4-(quinolin-3-yl)-9H-carbazol-9-yl]-4-(tetrahydropyran-4-yl)-amino)pyridine-5-carboxamide;
2-(8-methyl-8-azabicyclo[3.2.1]oct-3-yl)amino-4-[4-(quinolin-3-yl)-9H-carbazol-9-yl]benzamide; and
3-[(2-hydroxy-2-methylpropylamino)-5-[4-(quinolin-3-yl)-9H-carbazol-9-yl]pyridine-2-carboxamide.

5. A pharmaceutical composition comprising a compound according to claim 1 or a pharmaceutically acceptable salt thereof and a pharmaceutically acceptable excipient.

6. A pharmaceutical composition comprising a compound according to claim 3 or a pharmaceutically acceptable salt thereof and a pharmaceutically acceptable excipient.

7. A pharmaceutical composition comprising a compound according to claim 4 or a pharmaceutically acceptable salt thereof and a pharmaceutically acceptable excipient.

8. A pharmaceutical composition according to claim 5, 6, or 7, further comprising an active ingredient for anticancer chemotherapy.

* * * * *